US012351836B2

(12) United States Patent
Wolfe et al.

(10) Patent No.: US 12,351,836 B2
(45) Date of Patent: Jul. 8, 2025

(54) MICROHOMOLOGY MEDIATED REPAIR OF MICRODUPLICATION GENE MUTATIONS

(71) Applicant: UNIVERSITY OF MASSACHUSETTS, Boston, MA (US)

(72) Inventors: Scot A Wolfe, Winchester, MA (US); Charles P Emerson, Jr., Lyndon, VT (US); Sukanya Iyer, Marlborough, MA (US); Sneha Suresh, Dracut, MA (US); Christian Mueller, Concord, MA (US); Jennifer Chen, Kingston (CA); Dongsheng Guo, Shrewsbury, MA (US); Oliver King, Somerville, MA (US)

(73) Assignee: UNIVERSITY OF MASSACHUSETTS, Westborough, MA (US)

( * ) Notice: Subject to any disclaimer, the term of this patent is extended or adjusted under 35 U.S.C. 154(b) by 1066 days.

(21) Appl. No.: 17/051,632

(22) PCT Filed: May 3, 2019

(86) PCT No.: PCT/US2019/030576

§ 371 (c)(1),
(2) Date: Oct. 29, 2020

(87) PCT Pub. No.: WO2019/213504

PCT Pub. Date: Nov. 7, 2019

(65) Prior Publication Data

US 2021/0230568 A1 Jul. 29, 2021

Related U.S. Application Data

(60) Provisional application No. 62/823,173, filed on Mar. 25, 2019, provisional application No. 62/667,201, filed on May 4, 2018.

(51) Int. Cl.
*C12N 9/22* (2006.01)
*A61K 35/76* (2015.01)
*A61K 38/00* (2006.01)

(52) U.S. Cl.
CPC ................ *C12N 9/22* (2013.01); *A61K 35/76* (2013.01); *A61K 38/00* (2013.01); *C12N 2310/20* (2017.05); *C12N 2800/80* (2013.01)

(58) Field of Classification Search
None
See application file for complete search history.

(56) References Cited

U.S. PATENT DOCUMENTS 5,705,188 A 1/1998 Junichi et al. ................ 424/450
2018/0243446 A1* 8/2018 Cohn .................. C12N 15/907

FOREIGN PATENT DOCUMENTS

WO WO 97/30731 8/1997
WO WO-2017147056 A1 * 8/2017 ........... C12N 15/102
WO WO 2017/193029 11/2017

OTHER PUBLICATIONS

Lattanzi et al. Correction of the Exon 2 Duplication in DMD Myoblasts by a Single CRISPR/Cas9 System. Molecular Therapy: Nucleic Acids vol. 7 Jun. 2017 (Year: 2017).*

Wulan Deng et al.: "Casfish: CRISPR/Cas9-mediated in situ labeling of genomic loci in fixed cells", Proceedings of The National Academy of Sciences, vol. 112, No. 38, Aug. 31, 2015 (Aug. 31, 2015), pp. 11870-11875.

Supplementary European search report for Application No. 19 79 5866, mailed Jan. 20, 2022.

Ata, et al., "Toward Precision Molecular Surgery: Robust, Selective Induction of Microhomology-Mediated End Joining in Vivo." bioRxiv:291187 (2018A).

Auton, et al., "A Global Reference for Human Genetic Variation." *Nature*, 526(7571):68-74 (2015).

Bae, et al., "Microhomology-Based Choice of Cas9 Nuclease Target Sites." *Nat Methods*, 11(7):705-706 (2014).

Benson "Tandem Repeats Finder: A Program to Analyze DNA Sequences." *Nucleic Acids Res*, 27(2):573-580 (1999).

Bertz, et al., "The Titin-Telethonin Complex is a Directed, Superstable Molecular Bond in the Muscle Z-Disk." *Proc Natl Acad Sci U S A*, 106(32):13307-133310 (2009).

Blankenberg, et al., "Manipulation of Fastq Data with Galaxy." *Bioinformatics*, 26(14):1783-1785 (2010).

Bolukbasi, et al., "Orthogonal Cas9-Cas9 Chimeras Provide a Versatile Platform for Genome Editing." *Nat Commun*, 9(1):4856 (2018).

Brantly, et al., "Pulmonary Function and High-Resolution CT Findings in Patients with an Inherited Form of Pulmonary Fibrosis, Hermansky-Pudlak Syndrome, Due to Mutations in HPS-1." *Chest*, 117(1):129-136 (2000).

(Continued)

*Primary Examiner* — Jennifer Dunston
*Assistant Examiner* — Tiffany Nicole Grooms
(74) *Attorney, Agent, or Firm* — Medlen & Carroll, LLP

(57) ABSTRACT

The present invention is directed to the filed of gene therapy. In particular, compositions and methods are disclosed that repair gene microduplication mutations by reversion to a wild type sequence. For example, the creation of a double stranded break by a programmable nuclease protein within a microduplication induces the microhomology mediated end joining DNA repair pathway that in the process of DNA repair removes the microduplication mutation and restores the wild type sequence.

6 Claims, 33 Drawing Sheets
(3 of 33 Drawing Sheet(s) Filed in Color)
Specification includes a Sequence Listing.

(56) References Cited

OTHER PUBLICATIONS

Brinkman, et al., "Easy Quantitative Assessment of Genome Editing by Sequence Trace Decomposition." *Nucleic Acids Res*, 42(22):e168 (2014).
Caron, et al., "A Human Pluripotent Stem Cell Model of Facioscapulohumeral Muscular Dystrophy-Affected Skeletal Muscles." *Stem Cells Transl Med*, 5(9):1145-1161 (2016).
Chirmule, et al., "Immune Responses to Adenovirus and Adeno-Associated Virus in Humans." *Gene Ther*, 6(9):1574-1583 (1999).
Cong, et al., "Multiplex Genome Engineering Using CRISPR/CAS Systems." *Science*, 339(6121):819-823 (2013).
Daya and Berns "Gene Therapy Using Adeno-Associated Virus Vectors." *Clin Microbiol Rev*, 21(4):583-593 (2008).
Deyle and Russell "Adeno-Associated Virus Vector Integration." *Curr Opin Mol Ther*, 11(4):442-447 (2009).
Doudna and Charpentier "Genome Editing. The New Frontier of Genome Engineering with CRISPR-Cas9." *Science*, 346(6213):1258096 (2014).
Dutta, et al., "Microhomology-Mediated End Joining is Activated in Irradiated Human Cells Due to Phosphorylation-Dependent Formation of the Xrccl Repair Complex." *Nucleic Acids Res*, 45(5):2585-2599 (2017).
Edraki, et al., "A Compact, High-Accuracy Cas9 with a Dinucleotide Pam for In vivo Genome Editing." *Mol Cell*, 73(4):714-726 e714 (2019).
El-Chemaly and Young, "Hermansky-Pudlak Syndrome." *Clin Chest Med*, 37(3):505-511 (2016).
Esvelt, et al., "Orthogonal Cas9 Proteins for RNA-Guided Gene Regulation and Editing." *Nat Methods*, 10(11):1116-1121 (2013).
Fernandes and Shapiro, "Tay-Sachs Disease." *Arch Neurol*, 61(9):1466-1468 (2004).
Fu, et al., "Improving Crispr-Cas Nuclease Specificity Using Truncated Guide RNA s." *Nat Biotechnol*, 32(3):279-284 (2014).
Genomes Project, et al., "A Global Reference for Human Genetic Variation." *Nature*, 526(7571):68-74 (2015).
Grieger and Samulski "Adeno-Associated Virus as a Gene Therapy Vector: Vector Development, Production and Clinical Applications." *Adv Biochem Eng Biotechnol*, 99:119-145 (2005).
Hernandez, et al., "Latent Adeno-Associated Virus Infection Elicits Humoral but Not Cell-Mediated Immune Responses in a Nonhuman Primate Model." *J Virol*, 73(10):8549-8558 (1999).
Hindorff, et al., "Potential Etiologic and Functional Implications of Genome-Wide Association Loci for Human Diseases and Traits." *Proc Natl Acad Sci U S A*, 106(23):9362-9367 (2009).
Hisano, et al., "Precise in-Frame Integration of Exogenous DNA Mediated by Crispr/Cas9 System in Zebrafish." *Sci Rep*, 5:8841 (2015).
Hu, et al., "Evolved Cas9 Variants with Broad Pam Compatibility and High DNA Specificity." *Nature*, 556(7699):57-63 (2018).
Jinek, et al., "A Programmable Dual-RNA-Guided DNA Endonuclease in Adaptive Bacterial Immunity." *Science*, 337(6096):816-821 (2012).
Kearns, et al., "Cas9 Effector-Mediated Regulation of Transcription and Differentiation in Human Pluripotent Stem Cells." *Development*, 141(1):219-223 (2014).
Kim, et al., "In Vivo Genome Editing with a Small Cas9 Orthologue Derived from Campylobacter Jejuni." *Nat Commun*, 8:14500 (2017).
Kim, et al., "Microhomology-Assisted Scarless Genome Editing in Human Ipscs." *Nat Commun*, 9(1):939 (2018).
Kleinstiver, et al., "Engineered Crispr-Cas9 Nucleases with Altered Pam Specificities." *Nature*, 523(7561):481-485 (2015).
Koboldt, et al., "Varscan 2: Somatic Mutation and Copy Number Alteration Discovery in Cancer by Exome Sequencing." *Genome Res*, 22(3):568-576 (2012).
Komor, et al., "Crispr-Based Technologies for the Manipulation of Eukaryotic Genomes." *Cell*, 168(1-2):20-36 (2017).
Kosicki, et al., "Repair of Double-Strand Breaks Induced by Crispr-Cas9 Leads to Large Deletions and Complex Rearrangements." *Nat Biotechnol*, 36(8):765-771 (2018).
Kotin, et al., "Site-Specific Integration by Adeno-Associated Virus." *Proc Natl Acad Sci U S A*, 87(6):2211-2215 (1990).
Landrum, et al., "Clinvar: Improving Access to Variant Interpretations and Supporting Evidence." *Nucleic Acids Res*, 46(D1):D1062-D1067 (2018).
Lek, et al., "Analysis of Protein-Coding Genetic Variation in 60,706 Humans." *Nature*, 536(7616):285-291 (2016).
Li, et al., "The Sequence Alignment/Map Format and Samtools." *Bioinformatics*, 25(16):2078-2079 (2009).
Li "Exploring Single-Sample Snp and Indel Calling with Whole-Genome De Novo Assembly." *Bioinformatics*, 28(14):1838-1844 (2012).
Li "Minimap2: Pairwise Alignment for Nucleotide Sequences." *Bioinformatics*, 34(18):3094-3100 (2018).
Maguire, et al., "Safety and Efficacy of Gene Transfer for Leber's Congenital Amaurosis." *N Engl J Med*, 358(21):2240-2248 (2008).
McVeyLee "MMEJ Repair of Double-Strand Breaks (Director's Cut): Deleted Sequences and Alternative Endings." *Trends Genet*, 24(11):529-538 (2008).
Moreira, et al., "Limb-Girdle Muscular Dystrophy Type 2g is Caused by Mutations in the Gene Encoding the Sarcomeric Protein Telethonin." *Nat Genet*, 24(2):163-166 (2000).
Nigro and Savarese, "Genetic Basis of Limb-Girdle Muscular Dystrophies: The 2014 Update." *Acta Myol*, 33(1):1-12 (2014).
Obenchain, et al., "Variantannotation: A Bioconductor Package for Exploration and Annotation of Genetic Variants." *Bioinformatics*, 30(14):2076-2078 (2014).
Oh, et al., "Positional Cloning of a Gene for Hermansky-Pudlak Syndrome, a Disorder of Cytoplasmic Organelles." *Nat Genet*, 14(3):300-306 (1996).
Ponnazhagan, et al., "Adeno-Associated Virus 2-Mediated Gene Transfer in Vivo: Organ-Tropism and Expression of Transduced Sequences in Mice." *Gene*, 190(1):203-210 (1997).
Richmond, et al., "Melanocytes Derived from Patients with Hermansky-Pudlak Syndrome Types 1, 2, and 3 Have Distinct Defects in Cargo Trafficking." *J Invest Dermatol*, 124(2):420-427 (2005).
Rittié and Fisher, "Isolation and Culture of Skin Fibroblasts." *Methods Mol Med*, 117:83-98 (2005).
Robinson, et al., "Integrative Genomics Viewer." *Nat Biotechnol*, 29(1):24-26 (2011).
Sakuma, et al., "Mmej-Assisted Gene Knock-in Using Talens and Crispr-Cas9 with the Pitch Systems." *Nat Protoc*, 11(1):118-133 (2016).
Sfeir and Symington, "Microhomology-Mediated End Joining: A Back-up Survival Mechanism or Dedicated Pathway?". *Trends Biochem Sci*, 40(11):701-714 (2015).
Sharma, et al., "Homology and Enzymatic Requirements of Microhomology-Dependent Alternative End Joining." *Cell Death Dis*, 6(3):e1697 (2015).
Shen, et al., "Predictable and Precise Template-Free Crispr Editing of Pathogenic Variants." *Nature*, 563(7733):646-651 (2018).
Stadler, et al., "Establishment of Clonal Myogenic Cell Lines from Severely Affected Dystrophic Muscles—Cdk4 Maintains the Myogenic Population." *Skelet Muscle*, 1(1):12 (2011).
Surosky, et al., "Adeno-Associated Virus Rep Proteins Target DNA Sequences to a Unique Locus in the Human Genome." *J Virol*, 71(10):7951-7959 (1997).
Suzuki, et al., "In Vivo Genome Editing via Crispr/Cas9 Mediated Homology-Independent Targeted Integration." *Nature*, 540(7631):144-149 (2016).
Tan, et al., "Unified Representation of Genetic Variants." *Bioinformatics*, 31(13):2202-2204 (2015).
Van Overbeek, et al., "DNA Repair Profiling Reveals Nonrandom Outcomes at Cas9-Mediated Breaks." *Mol Cell*, 63(4):633-646 (2016).
Wang, et al., "Parp-1 and Ku Compete for Repair of DNA Double Strand Breaks by Distinct Nhej Pathways." *Nucleic Acids Res*, 34(21):6170-6182 (2006).
Zetsche, et al., "Cpfl is a Single RNA Guided Endonuclease of a Class 2 Crispr-Cas System." *Cell*, 163(3):759-771 (2015).
Zhang, et al., "Pear: A Fast and Accurate Illumina Paired-End Read Merger." *Bioinformatics*, 30(5):614-620 (2014).
Christensen, et al., "Localization of Surfactant Protein-D in the Rheumatoid Synovial Membrane." *Apmis*, 126(1):9-13 (2018).

(56) References Cited

OTHER PUBLICATIONS

Finelli, et al., "Fish Characterisation of an Identical (16)(P11.2p12.2) Tandem Duplication in Two Unrelated Patients with Autistic Behaviour." *J Med Genet*, 41(7):e90 (2004).
Iyer, et al., "Precise Therapeutic Gene Correction by a Simple Nuclease-Induced Double-Stranded Break." *Nature*, 568(7753):561-565 (2019).
Lattanzi, et al., "Correction of the Exon 2 Duplication in Dmd Myoblasts by a Single Crispr/Cas9 System." *Mol Ther Nucleic Acids*, 7:11-19 (2017).
Oh, et al., "Mutation Analysis of Patients with Hermansky-Pudlak Syndrome: A Frameshift Hot Spot in the HPS Gene and Apparent Locus Heterogeneity." *Am J Hum Genet*, 62(3):593-598 (1998).
Ata, et al., "Robust Activation of Microhomology-Mediated End Joining for Precision Gene Editing Applications." *PLOS Genetics*, 14(9):e1007652 (2018).

* cited by examiner

**Exon 1 telethonin (*TCAP*) – LGMD2G**

8 bp duplication in exon 1

SEQ ID: 1012
ATGGCTACCTCAGAGCTGAGCTGCGAGGTGTCGAGGTGTCGGAGGAGAAC
TGTGAGCGCCGGGAGGCCTTCTGGGCAGAATGGAAGGATCTGACACTGTC
CACACGGCCCGAGGAGGG

SpCas9 target site (Watson)

SEQ ID: 1013
AGCTGAGCTGCGAGGTG•TCGAGGTGT

**Exon 15 (*HPS1*) - Hermansky-Pudlak Syndrome**

SEQ ID: 1014
GCTGCTCCAGGCATGTGGGAAGCTGAAGCGGCAGCTCTGCGCCATCTACC
GGCTGAACTTTCTGACCACAGCCCCCAGCAGGGGAGGCCCCCAGCAGGGG
AGGCCCACACCTGCCCCAGCACCTGCAGGACCAAGTGCAGAGGCTCATGC
G

SpCas9 Target site (Watson)

SEQ ID: 1015
CCAGCAGGGGAGGCCCCC•AGCAGGGGAGGCCC

FIG. 2

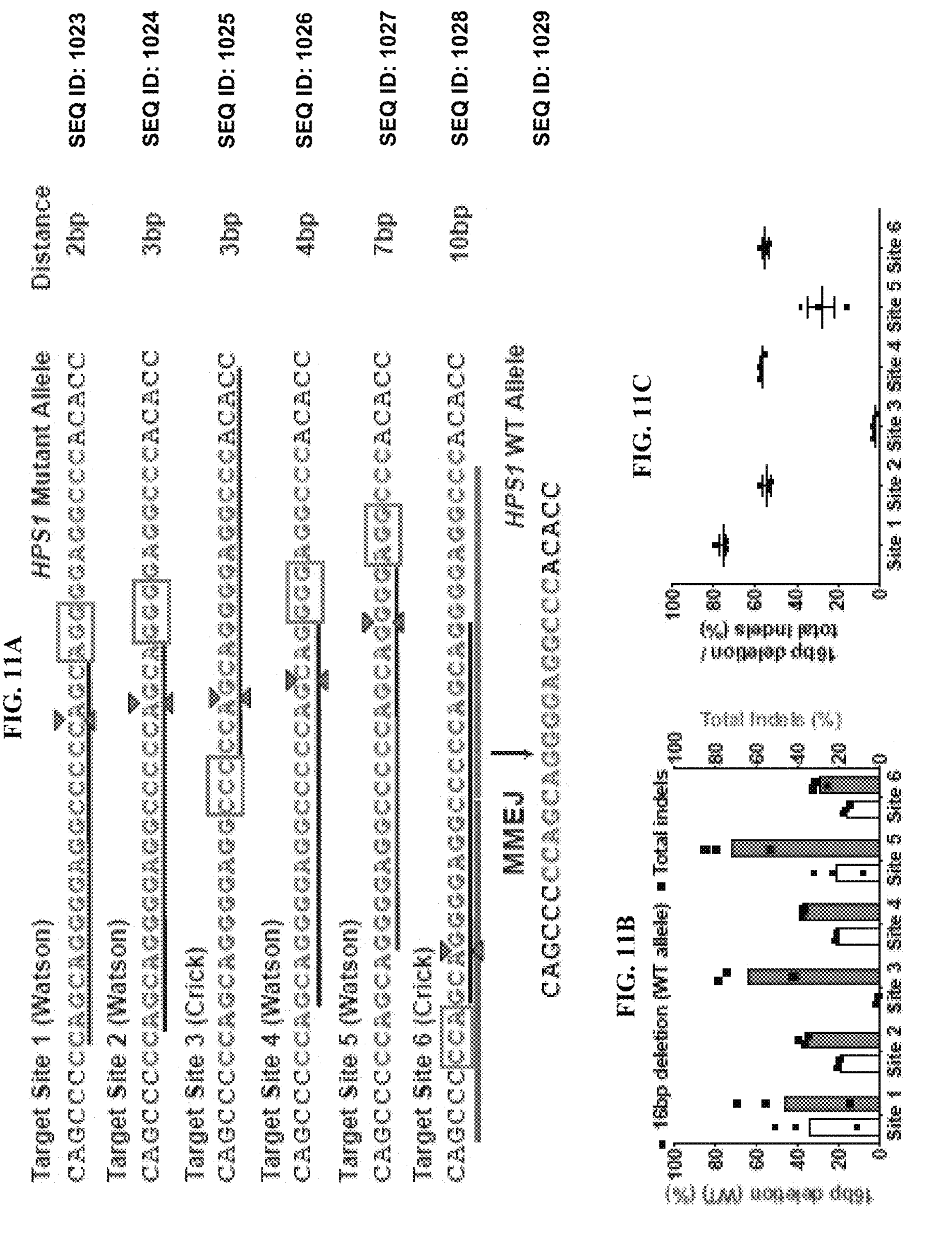

| | | Distance | |
|---|---|---|---|
| | HPS1 Mutant Allele | | |
| Target Site 1 (Watson) | CAGCCCCCAGCCAGGGGGAGCCAGGAGGGCCCACACC | 2bp | SEQ ID: 1023 |
| Target Site 2 (Watson) | CAGCCCCCAGCCAGGGGGAGCCAGGAGGGCCCACACC | 3bp | SEQ ID: 1024 |
| Target Site 3 (Crick) | CAGCCCCCAGCCAGGGGGAGCCAGGAGGGCCCACACC | 3bp | SEQ ID: 1025 |
| Target Site 4 (Watson) | CAGCCCCCAGCCAGGGGGAGCCAGGAGGGCCCACACC | 4bp | SEQ ID: 1026 |
| Target Site 5 (Watson) | CAGCCCCCAGCCAGGGGGAGCCAGGAGGGCCCACACC | 7bp | SEQ ID: 1027 |
| Target Site 6 (Crick) | CAGCCCCCAGCCAGGGGGAGCCAGGAGGGCCCACACC | 10bp | SEQ ID: 1028 |

MMEJ

HPS1 WT Allele

CAGCCCCCAGCCAGGGGGAGCCCCACACC   SEQ ID: 1029

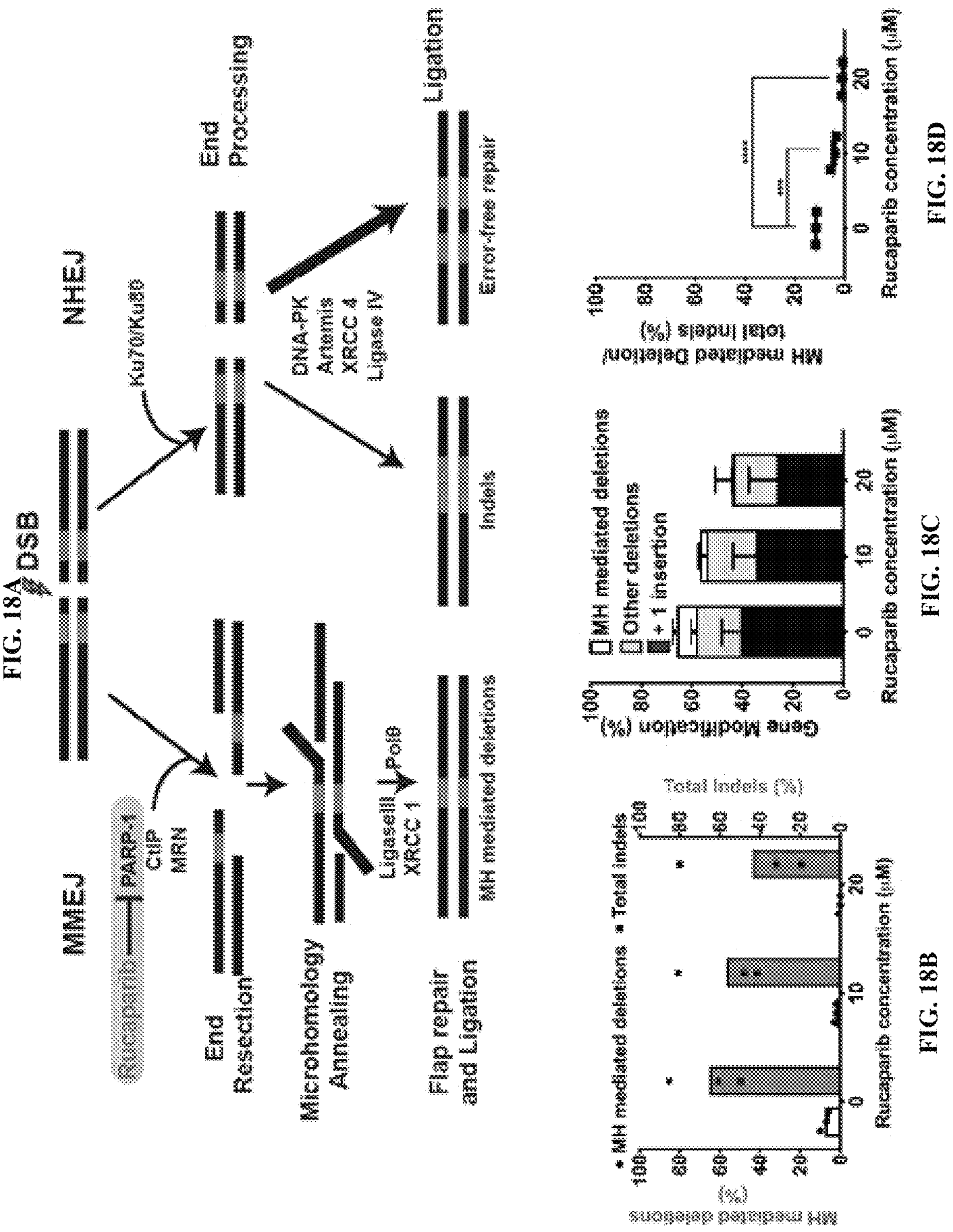
FIG. 18A
DSB
MMEJ
NHEJ
PARP-1
CtIP
MRN
End Resection
Microhomology Annealing
Ligase III
XRCC 1
Polθ
Flap repair and Ligation
MH mediated deletions
Ku70/Ku80
End Processing
DNA-PK
Artemis
XRCC 4
Ligase IV
Indels
Error-free repair
Ligation
MH mediated deletions (%)
Total indels (%)
MH mediated deletions
Total indels
Rucaparib concentration (μM)
FIG. 18B
Gene Modification (%)
MH mediated deletions
Other deletions
+ 1 insertion
Rucaparib concentration (μM)
FIG. 18C
MH mediated Deletion/ total indels (%)
Rucaparib concentration (μM)
FIG. 18D

FIG. 20C

| Indel observed | Sequence observed | Alleles present (%) | |
|---|---|---|---|
| MH mediated del | AGCTGAGCTG--------CGAGGTGTCGGAGGAGAACTGTGA | 67.70 | SEQ ID: 1078 |
| del | AGCTGAGCTGCGAG--GTCGAGGTGTCGGAGGAGAACTGTGA | 7.63 | SEQ ID: 1079 |
| del | AGCTGAGCTGCGAGGT-----------------GAACTGTGA | 6.09 | SEQ ID: 1080 |
| Unedited | AGCTGAGCTGCGAGGTGTCGAGGTGTCGGAGGAGAACTGTGA | 3.92 | SEQ ID: 1081 |
| ins | AGCTGAGCTGCGAGGTGTtCGAGGTGTCGGAGGAGAACTGTGA | 3.92 | SEQ ID: 1082 |
| ins | AGCTGAGCTGCGAGGTGTgtCGAGGTGTCGGAGGAGAACTGTGA | 3.75 | SEQ ID: 1083 |
| del | AGCTGAGCTGCGAGGT-TCGAGGTGTCGGAGGAGAACTGTGA | 2.86 | SEQ ID: 1084 |
| del | AGCTGAGCTGCGAG---TCGAGGTGTCGGAGGAGAACTGTGA | 1.27 | SEQ ID: 1085 |
| del | AGCTGAGCTGCGAGGTGT-------TCGGAGGAGAACTGTGA | 1.15 | SEQ ID: 1086 |
| del | AGCTGAGCTGC------TCGAGGTGTCGGAGGAGAACTGTGA | 0.98 | SEQ ID: 1087 |
| del | AGCTGAGCTGCGA--------------GGAGGAGAACTGTGA | 0.74 | SEQ ID: 1088 |

| Indel observed | Sequence observed | Alleles present (%) | |
|---|---|---|---|
| MH mediated del | AGCTGAGCTG--------CGAGGTGTCGGAGGAGAACTGTGA | 45.11 | SEQ ID: 1089 |
| Unedited | AGCTGAGCTGCGAGGTGTCGAGGTGTCGGAGGAGAACTGTGA | 26.17 | SEQ ID: 1090 |
| del | AGCTGAGCTGCGAGG--TCGAGGTGTCGGAGGAGAACTGTGA | 7.05 | SEQ ID: 1091 |
| ins | AGCTGAGCTGCGAGGTGTtCGAGGTGTCGGAGGAGAACTGTGA | 6.23 | SEQ ID: 1092 |
| del | AGCTGAGCTGCGAGGT-----------------GAACTGTGA | 3.04 | SEQ ID: 1093 |
| del | AGCTGAGCTGCGAGGTGT-------TCGGAGGAGAACTGTGA | 2.67 | SEQ ID: 1094 |
| ins | AGCTGAGCTGCGAGGTGTgtCGAGGTGTCGGAGGAGAACTGTGA | 2.46 | SEQ ID: 1095 |
| del | AGCTGAGCTGCGAGGT-TCGAGGTGTCGGAGGAGAACTGTGA | 2.41 | SEQ ID: 1096 |
| del | AGCTGAGCTGC------TCGAGGTGTCGGAGGAGAACTGTGA | 2.34 | SEQ ID: 1097 |
| del | AGCTGAGCTGCGA---GTCGAGGTGTCGGAGGAGAACTGTGA | 1.70 | SEQ ID: 1098 |
| del | AGCTGAGCTGCGA--------------GGAGGAGAACTGTGA | 0.80 | SEQ ID: 1099 |

FIG. 20D

MICROHOMOLOGY MEDIATED REPAIR OF MICRODUPLICATION GENE MUTATIONS

CROSS-REFERENCE TO RELATED APPLICATIONS

This application is a U.S. national stage filing under 35 U.S.C. § 371 of and claims priority to, international application No. PCT/US19/30576, filed May 3, 2019, currently pending, which claims priority under 35 U.S.C. § 119 (e) to U.S. Provisional Application Ser. No. 62/823,173, filed Mar. 25, 2019, and which claims priority under 35 U.S.C. § 119 (e) to U.S. Provisional Application Ser. No. 62/667,201, filed May 4, 2018, each of which is herein incorporated by reference in its entirety.

A Sequence Listing has been submitted in an ASCII text file named "19351 sequencelrg" created on Feb. 24, 2021, consisting of 196,567 bytes, the entire content of which is herein incorporated by reference.

FIELD OF THE INVENTION

The present invention is directed to the field of gene therapy. In particular, compositions and methods are disclosed that repair gene microduplication mutations by reversion to a wild type sequence. For example, the creation of a double stranded break within a microduplication by a programmable nuclease protein induces the microhomology mediated end joining DNA repair pathway that in the process of DNA repair removes the microduplication mutation and restores the wild type sequence.

BACKGROUND

Genome editing by programmable nuclease systems has revolutionized biological research and is rapidly moving towards many clinical applications. In most instances, the successful repair of an aberrant gene to correct a disease entails precise correction of the genetic sequence typically via the Homology Directed Repair (HDR) pathway. This pathway requires not only the use of a programmable nuclease to generate a double-strand break (DSB) at the locus to initiate DNA repair, but also the delivery of exogenous donor DNA to precisely re-write the genomic sequence To date, HDR is inefficient in most cell types, particularly in post-mitotic differentiated cell types such as neurons and muscle [Suzuki, K. et al. In vivo genome editing via CRISPR/Cas9 mediated homology-independent targeted integration. *Nature* 540, 144-149 (2016).], which are the affected tissues in many devastating genetic disorders. This barrier significantly limits the clinical efficacy of the current generation of nuclease-based gene repair tools.

What is needed in the art are compositions and methods that can safely and efficiently target disease-causing microduplication mutations within a genome and cure the disease by reverting the microduplication mutation to a wild type sequence.

SUMMARY

The present invention is directed to the filed of gene therapy. In particular, compositions and methods are disclosed that repair gene microduplication mutations by reversion to a wild type sequence. For example, the creation of a double stranded break within a microduplication by a programmable nuclease protein induces the microhomology mediated end joining DNA repair pathway that in the process of DNA repair removes the microduplication mutation and restores the wild type sequence.

In one embodiment, the present invention contemplates a programmable nuclease having sequence-specific DNA-binding affinity for a target gene or genomic locus, wherein said target gene or genomic locus comprises a microduplication mutation. In one embodiment, said nuclease further comprises a protospacer adjacent motif binding domain having said sequence-specific DNA-binding affinity for said target gene or genomic locus protospacer adjacent motif sequence. In one embodiment, the nuclease includes, but is not limited to, a Class II CRISPR single effector nuclease, a Cas9 nuclease, a Cas12 nuclease, a zinc finger nuclease and/or a transcription activator-like effector nuclease. In one embodiment, a duplicate sequence of the microduplication mutation has a length of between 1-40 nucleotides. In one embodiment, a duplicate sequence of the microduplication mutation has a length of greater than 40 nucleotides.

In one embodiment, the present invention contemplates a method, comprising; i) a subject comprising a target gene or genomic locus having a microduplication mutation; and ii) a pharmaceutical formulation comprising a programmable nuclease, the nuclease having sequence-specific DNA-binding affinity for a region that contains said microduplication mutation of the target gene or genomic locus; and b) administering said pharmaceutical formulation to the patient under conditions such that the microduplication mutation is replaced with a wild type sequence of the target gene or genomic locus. In one embodiment, said wild type sequence replacement comprises a correction through DNA repair. In one embodiment, the DNA repair correction is performed without assistance of an exogenously supplied donor DNA. In one embodiment, said nuclease further comprises a protospacer adjacent motif binding domain having said DNA-binding specificity for said target gene or genomic locus protospacer adjacent motif sequence. In one embodiment, the target gene includes, but is not limited to, TCAP, HPS1, HEXA, DOK7 and/or RAX2. In one embodiment, the subject further exhibits at least one symptom of a disease caused by the target gene microduplication mutation. In one embodiment, the disease includes, but is not limited to limb-girdle muscular dystrophy 2G, Hermanksy-Pudlak syndrome, Tay-Sachs Disease, familial limb-girdle myasthenia and/or cone-rod dystrophy 11. In one embodiment, administering further reduces the at least one symptom of the disease. In one embodiment, the nuclease includes, but is not limited to, a Class II CRISPR single effector nuclease, a Cas9 nuclease, a Cas12 nuclease, a zinc finger nuclease and/or a transcription activator-like effector nuclease. In one embodiment, the pharmaceutical formulation comprises an adeno-associated virus encoding said programmable nuclease.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but also plural entities and also includes the general class of which a specific example may be used for illustration. The terminology herein may be used to describe specific embodiments of the invention, but their usage does not delimit the invention, except as outlined in the claims.

The term "about" as used herein, in the context of any of any assay measurements refers to +/−5% of a given measurement.

As used herein, the term "CRISPRs" or "Clustered Regularly Interspaced Short Palindromic Repeats" refers to an acronym for DNA loci that contain multiple, short, direct repetitions of base sequences. Each repetition contains a series of bases followed by the same series in reverse and then by 30 or so base pairs known as "spacer DNA". The spacers are short segments of DNA from a virus and may serve as a 'memory' of past exposures to facilitate an adaptive defense against future invasions (PMID 25430774).

As used herein, the term "Cas" or "CRISPR-associated (cas)" refers to genes often associated with CRISPR repeat-spacer arrays (PMID 25430774).

As used herein, the term "Cas9" refers to a nuclease from Type II CRISPR systems, an enzyme specialized for generating double-strand breaks in DNA, with two active cutting sites (the HNH and RuvC domains), one for each strand of the double helix. Jinek combined tracrRNA and spacer RNA into a "single-guide RNA" (sgRNA) molecule that, mixed with Cas9, could find and cleave DNA targets through Watson-Crick pairing between the guide sequence within the sgRNA and the target DNA sequence (PMID 22745249).

As used herein, the term "catalytically active Cas9" refers to an unmodified Cas9 nuclease comprising full nuclease activity.

The term "nickase" as used herein, refers to a nuclease that cleaves only a single DNA strand, either due to its natural function or because it has been engineered to cleave only a single DNA strand. Cas9 nickase variants that have either the RuvC or the HNH domain mutated provide control over which DNA strand is cleaved and which remains intact (Jinek, et al. 2012 (PMID 22745249) and Cong, et al. 2013 (PMID 23287718)).

As used herein, the term "Cas12" (or Cpf1) refers to a nuclease from Type V CRISPR systems, an enzyme specialized for generating double-strand breaks in DNA, with one active cutting sites (the RuvC domain), that cuts both DNA strands. Zetsche demonstrated that when programmed with its crRNA Cas12 (Cpf1), could find and cleave DNA targets through Watson-Crick pairing between the guide sequence within the crRNA and the target DNA sequence (PMID 26422227).

The term, "trans-activating crRNA", "tracrRNA" as used herein, refers to a small trans-encoded RNA. For example, CRISPR/Cas (clustered, regularly interspaced short palindromic repeats/CRISPR-associated proteins) constitutes an RNA-mediated defense system, which protects against viruses and plasmids. This defensive pathway has three steps. First a copy of the invading nucleic acid is integrated into the CRISPR locus. Next, CRISPR RNAs (crRNAs) are transcribed from this CRISPR locus. The crRNAs are then incorporated into effector complexes, where the crRNA guides the complex to the invading nucleic acid and the Cas proteins degrade this nucleic acid. There are several pathways of CRISPR activation, one of which requires a tracrRNA, which plays a role in the maturation of crRNA. TracrRNA is complementary to base pairs with a pre-crRNA forming an RNA duplex. This is cleaved by RNase III, an RNA-specific ribonuclease, to form a crRNA/tracrRNA hybrid. This hybrid acts as a guide for the endonuclease Cas9, which cleaves the invading nucleic acid.

The term "nuclease" as used herein, refers to any protein comprising a pre-determined sequence of amino acids that bind to a specific nucleotide sequence and create a double stranded break. Such nucleases can include, but are not limited to, a Class II CRISPR single effector nuclease, a Cas9 nuclease, a Cas12 nuclease (also known as Cpf1), a zinc finger nuclease (ZFN) protein and/or a transcription activator-like effector nuclease (TALEN). For example, a Class II CRISPR single effector nuclease and/or a Cas9 nuclease may be assembled into a CRISPR complex.

The term "protospacer adjacent motif" (or PAM) as used herein, refers to a DNA sequence that may be required for a Cas9/sgRNA to form an R-loop to interrogate a specific DNA sequence through Watson-Crick pairing of its guide RNA with the genome.

The term "protospacer adjacent motif recognition domain" as used herein, refers to a nuclease C-terminus amino acid sequence having specific DNA-binding specificity to a target gene PAM sequence.

The term "target gene" as used herein, refers to a specific genomic region, usually comprising at least one allele, whose dysfunction is associated with a disease. For example, a target gene may have a microduplication mutation that is a causative factor for a disease. A microduplication can be composed of a tandem repeat. Tandem repeats in DNA are a pattern of one or more nucleotides that are repeated and the repetitions are directly adjacent to each other.

As used herein, the term "sgRNA" refers to single guide RNA used in conjunction with CRISPR associated systems (Cas). sgRNAs are a fusion of crRNA and tracrRNA and contain nucleotides of sequence complementary to the desired target site (Jinek, et al. 2012 (PMID 22745249)). Watson-Crick pairing of the sgRNA with the target site permits R-loop formation, which in conjunction with a functional PAM permits DNA cleavage or in the case of nuclease-deficient Cas9 allows binds to the DNA at that locus.

The term "patient" or "subject", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "affinity" as used herein, refers to any attractive force between substances or particles that causes them to enter into and remain in chemical combination. For example, an inhibitor compound that has a high affinity for a receptor will provide greater efficacy in preventing the receptor from interacting with its natural ligands, than an inhibitor with a low affinity.

As used herein, the term "orthogonal" refers to targets that are non-overlapping, uncorrelated, or independent. For example, if two orthogonal Cas9 isoforms were utilized, they would employ orthogonal sgRNAs that only program one of the Cas9 isoforms for DNA recognition and cleavage (Esvelt, et al. 2013 (PMID 24076762)). For example, this would allow one Cas9 isoform (e.g. *S. pyogenes* Cas9 or spCas9) to function as a nuclease programmed by a sgRNA that may be specific to it, and another Cas9 isoform (e.g. *N. meningitidis* Cas9 or nmCas9) to operate as a nuclease dead Cas9 that provides DNA targeting to a binding site through its PAM specificity and orthogonal sgRNA. Other Cas9s include *S. aureus* Cas9 or SaCas9 and *A. naeslundii* Cas9 or AnCas9.

The term "truncated" as used herein, when used in reference to either a polynucleotide sequence or an amino acid sequence means that at least a portion of the wild type sequence may be absent. In some cases truncated guide sequences within the sgRNA or crRNA may improve the editing precision of Cas9 (Fu, et al. 2014 (PMID 24463574)).

The term "base pairs" as used herein, refer to specific nucleobases (also termed nitrogenous bases), that are the building blocks of nucleotide sequences that form a primary structure of both DNA and RNA. Double stranded DNA may be characterized by specific hydrogen bonding patterns, base pairs may include, but are not limited to, guanine-cytosine and adenine-thymine) base pairs.

The term "genomic locus" or "target gene" as used herein, refers to any pre-determined nucleotide sequence capable of binding to a Cas9 protein contemplated herein. The target may include, but may be not limited to, a nucleotide sequence complementary to a programmable DNA binding domain or an orthogonal Cas9 protein programmed with its own guide RNA, a nucleotide sequence complementary to a single guide RNA, a protospacer adjacent motif recognition sequence, an on-target binding sequence and an off-target binding sequence.

The term "on-target binding sequence" as used herein, refers to a subsequence of a specific genomic target that may be completely complementary to a programmable DNA binding domain and/or a single guide RNA sequence.

The term "off-target binding sequence" as used herein, refers to a subsequence of a specific genomic target that may be partially complementary to a programmable DNA binding domain and/or a single guide RNA sequence.

The term "cleavage" or "break" as used herein, may be defined as the generation of a break in the DNA. This could be either a single-stranded break or a double-stranded break depending on the type of nuclease that may be employed.

As used herein, the term "edit", "editing" or "edited" refers to a method of altering a nucleic acid sequence of a polynucleotide (e.g., for example, a wild type naturally occurring nucleic acid sequence or a mutated naturally occurring sequence) by selective deletion of a specific genomic target or the specific inclusion of new sequence through the use of an exogenously supplied DNA template. Such a specific genomic target includes, but may be not limited to, a chromosomal region, mitochondrial DNA, a gene, a promoter, an open reading frame or any nucleic acid sequence.

The term "delete", "deleted", "deleting" or "deletion" as used herein, may be defined as a change in either nucleotide or amino acid sequence in which one or more nucleotides or amino acid residues, respectively, are, or become, absent.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "C-A-G-T," may be complementary to the sequence "A-C-T-G." Complementarity can be "partial" or "total." "Partial" complementarity may be where one or more nucleic acid bases may be not matched according to the base pairing rules. "Total" or "complete" complementarity between nucleic acids may be where each and every nucleic acid base may be matched with another base under the base pairing rules. The degree of complementarity between nucleic acid strands has significant effects on the efficiency and strength of hybridization between nucleic acid strands. This may be of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence which may be partially complementary, i.e., "substantially homologous," to a nucleic acid sequence may be one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This may be not to say that conditions of low stringency are such that non-specific binding may be permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

The terms "homology" and "homologous" as used herein in reference to amino acid sequences refer to the degree of identity of the primary structure between two amino acid sequences. Such a degree of identity may be detected in a portion of each amino acid sequence, or along the entire length of the amino acid sequence. Two or more amino acid sequences that are "substantially homologous" may have at least 50% identity, preferably at least 75% identity, more preferably at least 85% identity, most preferably at least 95%, or 100% identity.

An oligonucleotide sequence which may be a "homolog" may be defined herein as an oligonucleotide sequence which exhibits greater than or equal to 50% identity to a sequence, when sequences having a length of 100 bp or larger are compared.

As used herein, the term "gene" means the deoxyribonucleotide sequences comprising the coding region of a structural gene and including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogeneous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

The term "gene of interest" as used herein, refers to any pre-determined gene for which deletion may be desired.

The term "allele" as used herein, refers to any one of a number of alternative forms of the same gene or same genetic locus.

The term "protein" as used herein, refers to any of numerous naturally occurring extremely complex substances (as an enzyme or antibody) that consist of amino acid residues joined by peptide bonds, contain the elements carbon, hydrogen, nitrogen, oxygen, usually sulfur. In general, a protein comprises amino acids having an order of magnitude within the hundreds.

The term "peptide" as used herein, refers to any of various amides that are derived from two or more amino acids by combination of the amino group of one acid with the carboxyl group of another and are usually obtained by partial hydrolysis of proteins. In general, a peptide comprises amino acids having an order of magnitude within the tens.

The term "polypeptide", refers to any of various amides that are derived from two or more amino acids by combination of the amino group of one acid with the carboxyl group of another and are usually obtained by partial hydrolysis of proteins. In general, a polypeptide comprises amino acids having an order of magnitude within the tens or larger.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "an isolated nucleic acid", as used herein, refers to any nucleic acid molecule that has been removed from its natural state (e.g., removed from a cell and may be, in a preferred embodiment, free of other genomic nucleic acid).

The terms "amino acid sequence" and "polypeptide sequence" as used herein, are interchangeable and to refer to a sequence of amino acids.

As used herein the term "portion" when in reference to a protein (as in "a portion of a given protein") refers to fragments of that protein. The fragments may range in size from four amino acid residues to the entire amino acid sequence minus one amino acid.

The term "portion" when used in reference to a nucleotide sequence refers to fragments of that nucleotide sequence. The fragments may range in size from 5 nucleotide residues to the entire nucleotide sequence minus one nucleic acid residue.

As used herein, the term "hybridization" may be used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) may be impacted by such factors as the degree of complementarity between the nucleic acids, stringency of the conditions involved, the $T_m$ of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., Co t or Rot analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "$T_m$" may be used in reference to the "melting temperature." The melting temperature may be the temperature at which a population of double-stranded nucleic acid molecules becomes half dissociated into single strands. As indicated by standard references, a simple estimate of the $T_m$ value may be calculated by the equation: $T_m$=81.5+0.41 (% G+C), when a nucleic acid may be in aqueous solution at 1M NaCl. Anderson et al., "Quantitative Filter Hybridization" In: *Nucleic Acid Hybridization* (1985). More sophisticated computations take structural, as well as sequence characteristics, into account for the calculation of $T_m$.

As used herein the term "stringency" may be used in reference to the conditions of temperature, ionic strength, and the presence of other compounds such as organic solvents, under which nucleic acid hybridizations are conducted. "Stringency" typically occurs in a range from about $T_m$ to about 20° C. to 25° C. below $T_m$. A "stringent hybridization" can be used to identify or detect identical polynucleotide sequences or to identify or detect similar or related polynucleotide sequences. For example, when fragments are employed in hybridization reactions under stringent conditions the hybridization of fragments which contain unique sequences (i.e., regions which are either non-homologous to or which contain less than about 50% homology or complementarity) are favored. Alternatively, when conditions of "weak" or "low" stringency are used hybridization may occur with nucleic acids that are derived from organisms that are genetically diverse (i.e., for example, the frequency of complementary sequences may be usually low between such organisms).

As used herein, the terms "restriction endonucleases" and "restriction enzymes" refer to bacterial enzymes, each of which cut double-stranded DNA at or near a specific nucleotide sequence.

DNA molecules are said to have "5' ends" and "3' ends" because mononucleotides are reacted to make oligonucleotides in a manner such that the 5' phosphate of one mononucleotide pentose ring may be attached to the 3' oxygen of its neighbor in one direction via a phosphodiester linkage. Therefore, an end of an oligonucleotide may be referred to as the "5' end" if its 5' phosphate may be not linked to the 3' oxygen of a mononucleotide pentose ring. An end of an oligonucleotide may be referred to as the "3' end" if its 3' oxygen may be not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "an oligonucleotide having a nucleotide sequence encoding a gene" means a nucleic acid sequence comprising the coding region of a gene, i.e. the nucleic acid sequence which encodes a gene product. The coding region may be present in a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the terms "nucleic acid molecule encoding", "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "bind", "binding", or "bound" as used herein, includes any physical attachment or close association, which may be permanent or temporary. Generally, an interaction of hydrogen bonding, hydrophobic forces, van der Waals forces, covalent and ionic bonding etc., facilitates physical attachment between the molecule of interest and the analyte being measuring. The "binding" interaction may be brief as in the situation where binding causes a chemical reaction to occur. That may be typical when the binding component may be an enzyme and the analyte may be a substrate for the enzyme. Reactions resulting from contact between the binding agent and the analyte are also within the definition of binding for the purposes of the present invention.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 2 presents exemplary sequences of microduplication targets within a TCAP gene and a HSP1 gene. The microduplicated sequences in each exon are highlighted with and without boxes. The target sites for SpCas9 are shown below each sequence with the GG PAM element in bold and the spacer (guide) sequence underlined. The position of the DSB in the sequence is indicated by a "."

FIG. 10A: Schematic of MMEJ-based pathway for repair of a microduplication. A DSB at the centre of a microduplication (reptition) is expected to initiate 5' end resection to expose the microhomologies on each side. These repeats anneal with each other and are repaired via the MMEJ pathway to yield the wild-type (WT) sequence.

FIG. 10B: The pathogenic 8-bp microduplication within TCAP (bold grey text) with the SpyCas9 protospacer-adjacent motif (PAM) sequence in the box and the protospacer sequence underlined. A SpyCas9-induced DSB (carets) is expected to drive MMEJ repair to revert the mutant allele to the wild-type sequence (grey text).

FIG. 10C: Percentage of 8-bp deletion (white bars) and total indels (grey bars) resulting from SpyCas9 RNP treatment of LGMD2G iPSCs homozygous for the 8-bp microduplication or wild-type iPSCs. Bars denote mean and dots indicate individual data points. n=3 biological replicates.

FIG. 10D: Genotype analysis of 22 LGMD2G iPSC clones after treatment with SpyCas9 RNPs. Hypo, hypomorphic allele.

FIG. 10E: Percentage of 8-bp deletion (white bars) and total indels (grey bars) resulting from SpyCas9 treatment of myoblasts derived from patient-derived LGMD2G iPSCs. Bars denote mean and dots indicate individual data points. n=3 biological replicates.

FIG. 11A-C shows that MMEJ-based repair efficiently and precisely corrects HPS1 allele containing 16-bp microduplication.

FIG. 11A: The 16-bp microduplication repeats are shown in bold grey and grey text. For six SpyCas9 guides targeting the microduplication, the PAM sequence is demarcated in the box and the protospacer sequence is underlined. A DSB (carets with distance from the repeat centre indicated) is expected to drive reversion to the wild-type sequence (grey text). Sequence underlined with grey bold lines in target site 6 indicates an alternate 16-bp microhomology within this repeat.

FIG. 11B: Percentage of 16-bp deletions (white) and total indels (grey) for guides shown in a based on UMI-based Illumina sequencing. Bars denote mean and dots indicate individual data points. n=3 biological replicates.

FIG. 11C: Percentage of wild-type reverted alleles (16-bp deletion) among all alleles with insertions or deletions (indels) from b. Mean±s.e.m., dots indicate individual data points. n=3 biological replicates.

FIG. 12A: Experimental design. HPS1 B-LCL cells were treated with rucaparib 24 h before and after electroporation with SpyCas9 RNPs targeting the HPS1 locus and collected for subsequent UMI-based Illumina sequencing[15].

FIG. 12B: Percentage of microhomology (MH)-mediated deletion (white) and total indels (grey) in cells treated with SpyCas9 in the presence of 0, 10 or 20 μM rucaparib, measured by UMI-based Illumina deep sequencing. Bars denote mean and dots indicate individual data points. n=3 biological replicates.

FIG. 12C: Percentage of microhomology-mediated deletion alleles among all other alleles with indels from FIG. 12B. Mean=s.e.m., dots indicate individual data points. n=3 biological replicates. **** P=0.00003, unpaired two tailed t-test.

FIG. 12D: Left, alignment of resulting sequences observed by Illumina sequencing upon SpyCas9 RNP treatment of HPS1 B-LCL cells. Right, heatmap showing percentage of alleles generated by SpyCas9 for cells exposed to 0, 10 or 20 μM rucaparib. Gradient scale indicates the percentage occurrence of that sequence.

FIG. 13A: Non-pathogenic endogenous microduplications ranging in size from 4 bp to 36 bp. Microduplication repeats are shown as bold text. The SpyCas9 PAM sequence is shown in the box on the right and the LbaCas12a PAM sequence is shown in the off center light grey box. Anticipated DSBs produced by SpyCas9 and LbaCas12a are denoted by grey and white carets, respectively.

FIG. 13B: Percentage of microhomology-mediated deletion (white) and total indels (grey) produced at each endogenous site following SpyCas9 treatment, calculated using UMI-based Illumina sequencing. Bars denote mean and dots indicate individual data points. n=3 biological replicates.

FIG. 13C: Percentage of microhomology-mediated deletions (white) and total indels (grey) produced at three endogenous sites when treated with SpyCas9 or LbaCas12a. Bars denote mean and dots indicate individual data points. n=3 biological replicates.

FIG. 18A-E presents exemplary data showing the effect of rucaparib on the profile of microhomology-mediated deletion products at AAVS1 locus in patient-derived HPS1 B-LCL cells.

FIG. 18A: Schematic of two prominent DNA double-strand break repair pathways. A DSB can be repaired through various pathways that produce different DNA sequence end-products. The NHEJ pathway is the dominant DSB repair pathway in most cells. The MMEJ pathway uses end-resection to discover small homologies on each side of the break that can be used to template the fusion of the broken ends. PARP-1 regulates DSB flux through the MMEJ pathway. Treatment of cells with rucaparib—an inhibitor of PARP-1—attenuates DSB flux down the MMEJ repair pathway.

FIG. 18B: Percentage of microhomology-mediated deletions (white) and total indels (grey) resulting from SpyCas9 treatment of cells in the presence of 0, 10 and 20 μM rucaparib. Bars show mean and dots show individual data points from three biological replicates based on UMI-based Illumina deep sequencing.

FIG. 18C: Percentage of 1-bp insertions (black), microhomology mediated deletions (white) and other deletions (grey) produced by SpyCas9 RNP with a sgRNA targeting the AAVS1 locus with the addition of increasing amounts of rucaparib. Mean±s.e.m. from three biological replicates based on UMI-based Illumina deep sequencing.

FIG. 18D: Percentage of microhomology-mediated deletions out of total indels in cells treated with SpyCas9 in the presence of rucaparib. Mean±s.e.m., dots represent individual data points from three biological replicates. P values determined using two-tailed unpaired t-test. * P=0.0004, ** $P=6.5\times10^{-7}$.

FIG. 18E: Left, alignment of allele sequences obtained from deep sequencing analysis from samples treated with SpyCas9 RNP in the presence of different rucaparib concentrations. Microhomologies present at the AAVS1 locus are shown in by grey. Microhomology-mediated deletion is indicated by two-toned text. The carets indicate site of DSB created by SpyCas9. Inserted bases (ins) are shown in lower case, deleted bases (del) are shown as black dashes. Right, heatmap depicting the percentage of alleles generated after SpyCas9 treatment of cells in the presence of different concentrations of rucaparib (0, 10 or 20 μM). The grey colour gradient scale indicates the percentage of occurrence of that sequence. Heatmap represents mean values from a total of three independent biological replicates.

FIG. 19A: Percentage of microhomology-mediated deletions out of total indels at endogenous sites in cells treated with SpyCas9 and LbaCas12a. Mean±s.e.m., dots represent individual data points from three biological replicates.

FIG. 19B: Schematic of endogenous site containing a 24-bp microduplication for SpyCas9 target sites 1-3. The 24-bp microduplication repeats are shown. The PAM sequence is outlined and the protospacer sequence is underlined. The carets indicate the site of DSB.

FIG. 19C: Percentage of alleles with 24-bp deletion (white) and total indels (grey) for all three guides from TIDE analysis. Guide 3 produces primarily 23-bp deletions, but not 24-bp deletions, probably because it recuts the collapsed DNA sequence. Bars shows the mean from n=3 biological repeats, individual data points are represented by dots.

FIG. 19D: Proportion of the 24-bp deletion out of total indels as individual data points (dots), with mean±s.e.m. n=3 biological repeats.

FIG. 19E: Schematic of endogenous site containing a 27-bp microduplication for SpyCas9 target sites 1 and 2.

FIG. 19F: Percentage of alleles with 27-bp deletion (white) and total indels (grey) for both guides from UMI-based Illumina deep sequencing. Bars show the mean from n=3 biological repeats, individual data points are represented by dots.

FIG. 19G: Proportion of the 27-bp deletion out of total indels as individual data points (dots) with mean±s.e.m. n=3 biological replicates.

FIG. 20A-D presents exemplary data showing indel populations resulting from SpyCas9 editing at the TCAP locus.

FIG. 20A: Indel percentages resulting from SpyCas9 RNP treatment in patient-derived iPSCs homozygous for the 8-bp microduplication or in wild-type iPSCs. Mean±s.e.m. from three biological replicates.

FIG. 20B: Breakdown of indel classes resulting from SpyCas9 treatment of myoblasts derived from patient-derived LGMD2G iPSCs. Mean=s.e.m. from three biological replicates.

FIG. 20C: Sequence alignment of the edited alleles resulting from SpyCas9 RNP treatment of LGMD2G iPSCs. Grey text indicates DNA repeats that constitute the microduplication, and collapse is indicated by underlined text. Dashes indicate deleted bases and lower case text indicates inserted bases. Data are from one biological replicate out of three independent biological replicates.

FIG. 20D: Sequence alignment of the edited alleles resulting from SpyCas9 RNP treatment of myoblasts derived from patient-derived LGMD2G iPSCs. Data are from one biological replicate out of three independent biological replicates.

FIG. 21A: Percentage of gene modification observed from PacBio sequencing (one replicate from FIG. 10C out of three biological replicates). black, alleles containing the 8-bp deletion; grey, other small indels (≤100 bp); light grey, large insertions (0.14%, not visible on the graph); white, large deletions (>100 bp).

FIG. 21B: IGV graphs depicting representative reads obtained for unedited (top) and edited (bottom) LGMD2G iPSCs, spanning a genomic region of about 2,035 bp surrounding the TCAP target site. The carat indicates the 8-bp deletion site. Data represent one replicate out of three independent biological replicates.

FIG. 23A: Contour plots from a representative flow cytometry assay to detect telethonin expression in healthy control cells ($TCAP^{+/+}$), patient cells ($TCAP^{-/-}$), and SpyCas9-treated homozygous and heterozygous iPS clone-derived myoblasts differentiated for 10 days in culture. Plots are representative of three independent replicates.

FIG. 23B: Histograms from a representative flow cytometry assay to detect telethonin expression. Left, overlay of anti-telethonin antibody staining for four representative samples for different TCAP genotypes. Right, comparison between patient cells and healthy control cells, and SpyCas9-treated homozygous and heterozygous iPS clone-derived myoblasts differentiated for 10 days in culture. Histograms are representative of three independent replicates.

FIG. 23C: Cells were selected by removing cell debris first as shown by gate P1, and then single cells were selected from P1 by removing clustered cells as shown by gate P2. The cells in gate P2 were used for flow analysis. Plots are representative of one biological replicate.

FIG. 23D: Average percentage of telethonin-expressing cells from two technical replicates of three biological replicates. Error bars indicate s.e.m (n=6) and circles represent individual data points. P values (0.33 for patient versus heterozygous and 0.04 for patient versus homozygous clones) were calculated by two-sided Student's t-test.

FIG. 23E: Western blot showing validation of anti-telethonin antibody (Santa Cruz Biotechnology). Human muscle lysate and lysate from HEK293T cells transfected with haemagglutinin-tagged-telethonin expression construct were separated on an SDS 4-12% acrylamide gradient gel and the resulting blot was probed with anti-telethonin antibody.

FIG. 25A: Target site 1.

FIG. 25B: Target site 2.

FIG. 25C: Target site 3.

FIG. 25D: Target site 4.

FIG. 25E: Target site 5.

FIG. 25F: Target site 6.

FIG. 26A: Number of insertion variants of length >1 bp that are annotated as Pathogenic or Pathogenic/likely pathogenic in ClinVar. Variants are binned by length, with all those of length 40 bp or greater combined. The insertions (grey) are stratified into progressively finer categories: duplications (red); 'simple' duplications (described in text, orange); and the subset of these observed at least once in gnomAD exome/genome databases (green).

FIG. 26B: Number of insertion variants of length >1 bp that are observed at least once in the 'coding' regions of the gnomAD exome/genome databases. As above, insertions (grey) are stratified into progressively finer categories: duplications (red); 'simple' duplications (orange); the subset of these listed in ClinVar (cyan); and the subset annotated as Pathogenic or Pathogenic/likely pathogenic in Clin Var (green). Cyan and green bars are not visible at this resolution.

DETAILED DESCRIPTION OF THE INVENTION

The present invention is directed to the field of gene therapy. In particular, compositions and methods are disclosed that repair gene microduplication mutations by reversion to a wild type sequence. For example, the creation of double stranded breaks by a nuclease protein induces the microhomology mediated end joining DNA repair pathway that corrects the microduplication back to the wild type sequence without the assistance of an exogenously supplied donor DNA.

In one embodiment, the present invention contempates a subset of disease-causing alleles within the human population that are the product of small duplications (microduplications of 1 to 40 base pairs) within a gene sequence. These alleles occur in human subpopulations with substantial frequencies and result in rare diseases such as Limb Girdle Muscular Dystrophy 2G (LGMD2G) [Nigro, V. & Savarese, M. Genetic basis of limb-girdle muscular dystrophies: the 2014 update. *Acta Myol* 33, 1-12 (2014)], Tay-Sachs Disease [Fernandes Filho, J. A. & Shapiro, B. E. Tay-Sachs disease. *Arch. Neurol.* 61, 1466-1468 (2004).], and Hermansky-Pudlak syndrome (HPS) [El-Chemaly, S. & Young, L. R. Hermansky-Pudlak Syndrome. *Clin. Chest Med.* 37, 505-511 (2016).] among others (Table 1).

Figure 8:
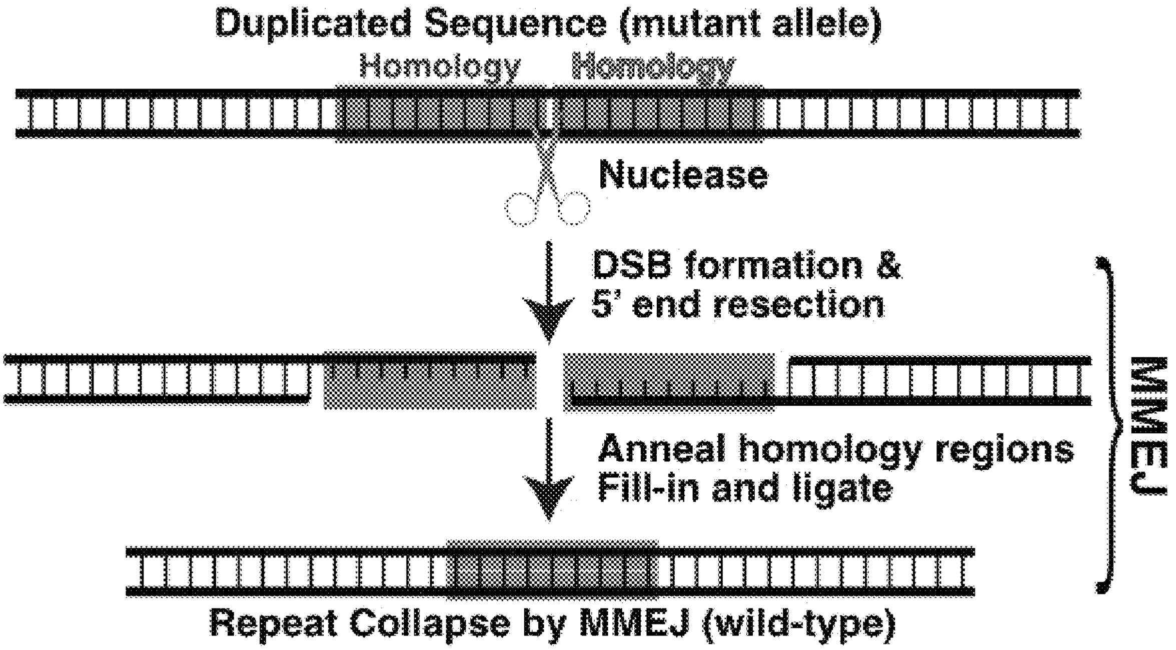
FIG. 8 presents an overview of duplicated repeat collapse by MMEJ-mediated DNA repair pathways. A nuclease targeted near the center of the duplicated segment can lead to the collapse of the duplication. As disclosed herein, the present method targets this collapse and restores the wild-type sequence.

In one embodiment, the present invention contemplates a method demonstrating that disease-causing microduplications can be reverted to the wild-type sequence simply through the generation of a DSB near the center of the duplication, enabling development of simplified Cas9-based therapeutic interventions tailored to each disorder. Our discovery was based initially on the theoretical idea that a nuclease-generated DSB would harness a common cellular DNA repair pathway-microhomology mediated end joining (MMEJ). Sfeir et al., "Microhomology-Mediated End Joining: A Back-up Survival Mechanism or Dedicated Pathway?" *Trends Biochem Sci* 40:701-714 (2015). MMEJ utilizes small regions of sequence homology on each side of the break to collapse the DNA sequence. See, FIG. 8. The idea of microhomology collapse of sequences has been observed in programmable nuclease editing data for some time. Bae et al., "Microhomology-based choice of Cas9 nuclease target sites" *Nature Methods* 11:705-706 (2014). However, the realization that it could be applied to disease correction to achieve highly efficient reversion to the wild-type sequence has not been described.

The data presented herein demonstrates a successful, efficient correction of disease-causing alleles in patient-derived cell lines harboring microduplications including, but not limited to, TCAP (LGMD2G) and HPS1 (HPS). The data shows that this correction can be successfully performed in iPSC, stem cell progenitor cells and adult somatic cells, opening up multiple route for the delivery of a nuclease-based therapy. Based on a computational analysis of human allele variants described herein, more than 100 diseases have been identified that should be amenable to this type of genetic correction. As the introduced nuclease is programmed to target a mutant DNA sequence, the reverted wild-type sequence is not a substrate, and thus should be stable even in the presence of the nuclease. Furthermore, microhomolgy-mediated correction does not require a DNA cassette to regenerate the wild-type sequence, only the transient delivery of the nuclease (e.g. Cas9 and its sgRNA) to target the locus. The demonstrated high rate of correction for these two distinct genetic disorders suggests that our correction approach will have broad application to a wide variety of important genetic disorders associated with microduplications for which there are no therapeutics currently available, providing patients with a definitive cure.

Although it is not necessary to understand the mechanism of an invention, it is believed that targeting a double strand break to a microduplication can cause the collapse of the microduplication back to the wild-type sequence with high efficiency and that this might be used to correct disease alleles without the need for a DNA repair template.

Current programmable nuclease-based methods (for example, CRISPR-Cas9) for precise correction of a disease-causing genetic mutation harness the homology-directed repair pathway. However, this repair process requires co-delivery of an exogenous DNA donor to recode the sequence and can be inefficient in many cell types. In some embodiments, the present invention contemplates disease-causing frameshift mutations resulting from microduplications which can be efficiently reverted to the wild-type sequence simply by generating a double-stranded break near the centre of the duplication. It has been demonstrated herein using patient-derived cell lines: for example, limb-girdle muscular dystrophy 2G (LGMD2G)[1], Hermansky-Pudlak syndrome type 1 (HPS1)[2] and Tay-Sachs Disease. Clonal analysis of inducible pluripotent stem cells (iPSCs) from the LGMD2G cell line, which contain a mutation in TCAP, treated with the *Streptococcus pyogenes* Cas9 (SpyCas9) nuclease revealed that about 80% contained at least one wild-type TCAP allele; this correction also restored TCAP expression in LGMD2G iPSC-derived myotubes. SpyCas9 also efficiently corrected the genotype of an HPS1 patient-derived B-lymphoblastoid cell line. Inhibition of polyADP-ribose polymerase 1 (PARP-1) suppressed the nuclease-mediated collapse of the microduplication to the wild-type sequence, confirming that precise correction is mediated by the microhomology-mediated end joining (MMEJ) pathway. Analysis of editing by SpyCas9 and Lachnospiraceae bacterium ND2006 Cas12a (LbaCas12a) at non-pathogenic 4-36-base pair microduplications within the genome indicates that the correction strategy is broadly applicable to a wide range of microduplication lengths and can be initiated by a variety of nucleases. Finally, LbaCas12a was employed to achieve precise correction of the four base pair duplication in HEXA Tay-Sachs patient-derived B-lymphoblastoid cell line. The simplicity, reliability and efficacy of this MMEJ-based therapeutic strategy should permit the development of nuclease-based gene correction therapies for a variety of diseases that are associated with microduplications.

I. Double Stranded Deoxyribonucleotide Break Repair Mechanisms

Figures 10A, 10B, 10C, 10D, 10E:
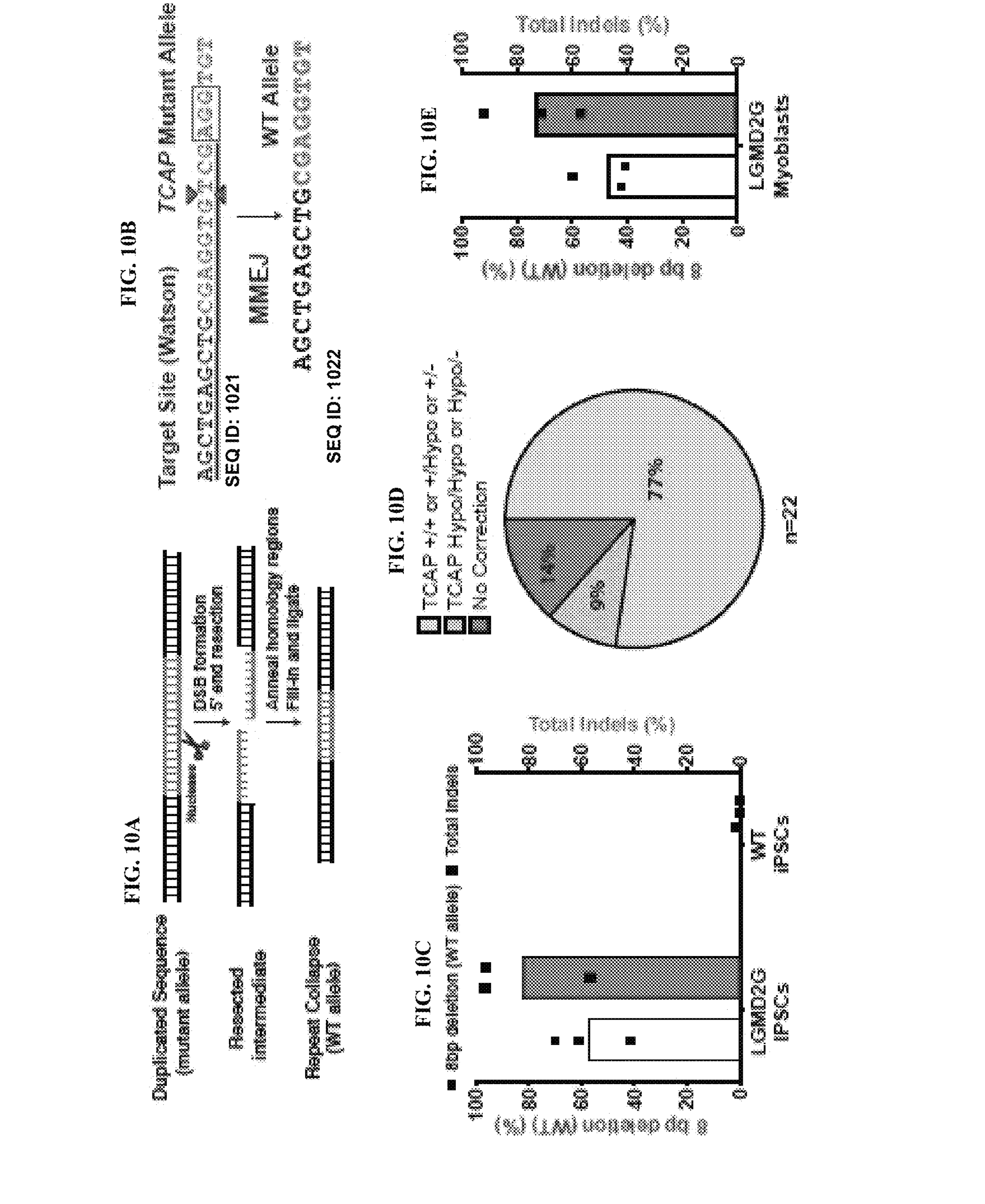
FIG. 10A-E shows that MMEJ-based repair efficiently and precisely corrects TCAP allele containing an 8-bp duplication.

MMEJ is an error-prone double-stranded break (DSB) DNA repair pathway that uses regions of microhomology (2-25 bp) on each side of a DSB to define the boundaries at which DNA segments are rejoined[3]. This mutagenic process generates deletions that result in the loss of one of the repeat sequences and the intervening region. See FIG. 10A and FIG. 18. Hallmarks of MMEJ repair on DNA products generated through editing of programmable nucleases have been observed in a variety of cell types and their effect on gene inactivation rates has been appreciated[4,5]. The MMEJ pathway has also been harnessed for the targeted insertion of exogenous donor DNAs in mammalian cells and zebrafish and frog embryos[6,7]. Herein, a nuclease-based therapeutic approach is described that harnesses the MMEJ pathway to precisely correct frameshift mutations resulting from microduplications (e.g., tandem duplications). It was reasoned that MMEJ-based repair of a programmable nuclease-induced DSB near the centre of a disease-causing microduplication would achieve precise reversion to the wild-type genomic sequence. This strategy might be an effective alternative to homology-directed repair-based gene correction approaches and would not require co-delivery of a donor DNA. Furthermore, the reverted wild-type sequence would no longer be complementary to the single-guide RNA (sgRNA) targeting the microduplication, leading to stable correction even in the presence of Cas9 nuclease.

To evaluate the efficacy of the presently contemplated MMEJ-based correction strategy, LGMD2G and HPS1 were selected as exemplary diseases that affect different human tissues and whose causes include pathogenic microduplications of different lengths. Both of these diseases are autosomal recessive disorders that are represented at modest frequencies in different human subpopulations and currently have no treatments. One of the disease alleles identified in LGMD2G patients features an 8-bp duplication in exon 1 of TCAP, a mutation that is found in the East Asian population at a frequency of approximately 1 in 1,000 alleles. TCAP encodes the telethonin protein, a 19-kDa cardiac and striated muscle-specific structural protein located in the Z-disc of sarcomeres that links titin proteins to stabilize the contractile apparatus for muscle contraction[8]. Homozygous or compound heterozygous inactivating mutations in TCAP manifest as severe muscle atrophy and cardiomyopathy that typically develop during late adolescence into early adulthood[1,9].

Figure 1:
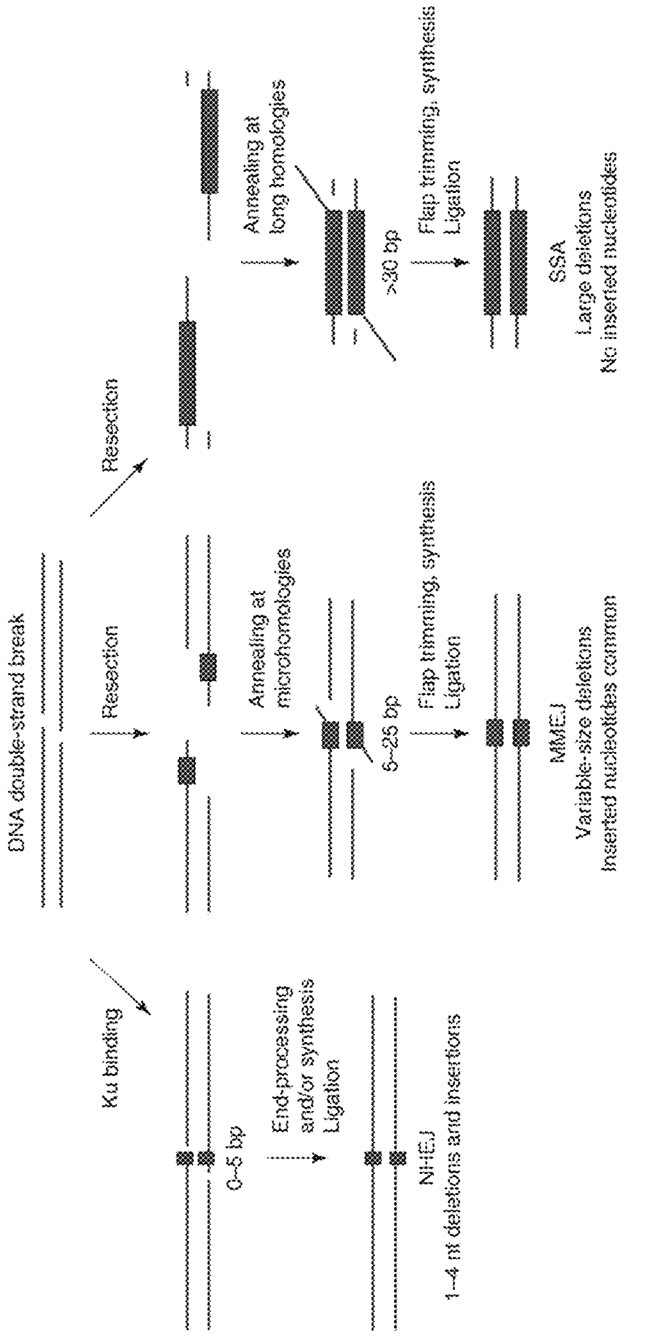
FIG. 1 shows an overview of several naturally occurring mutagenic DNA repair pathways. Microhomology Mediated End Joining (MMEJ) mediated repair is the center pathway involving a 5' end resection and annealing of homologous sequences.

The double strand breaks (DSBs) that are generated within the genomes of eukaryotic systems are potentially repaired by a number of different DNA-damage response pathways such as canonical non-homologous end joining (cNHEJ), homologous recombination (HR), and alternate non-homologous end joining (aNHEJ). McVey et al., "MMEJ repair of double-strand breaks (director's cut): deleted sequences and alternative endings" *Trends in Genetics* 24:529-538 (2008). cNHEJ is a precise repair pathway where ends are rejoined and typically reconstitute the original DNA sequence. HR uses a DNA template with homology to sequences flanking the DSB to copy a homologous sequence to repair the broken site. aNHEJ is a mutation prone process that utilizes resection of 5' ends of the DSB to complete the repair. The Microhomology Mediated End Joining (MMEJ) pathway involves rejoining the DNA ends using short regions of homology on each side of the break (e.g., usually >2 bases) where the intervening sequence is deleted. See, FIG. 1.

When artificial nucleases are introduced into the cell to target the genome, the DSBs that are generated are likely to proceed down the cNHEJ pathway where they are precisely repaired, which restores the existing nuclease target sequence, whether wild type or mutated. Eventually, however, mutations are inevitably generated that disrupt the target site. Sequencing information on these deletions suggests that in many instances the resulting deletion mutations are generated by MMEJ, due to the sequence scars that contain microhomologies that are both sides of the break. Analysis of Cas9 nuclease DNA target sequences suggests that there is a correlation between the efficiency of collapse and the length of the microhomology on each side of the break. Bae et al., "Microhomology-based choice of Cas9 nuclease target sites" *Nature Methods* 11:705-706 (2014).

Figure 18E:
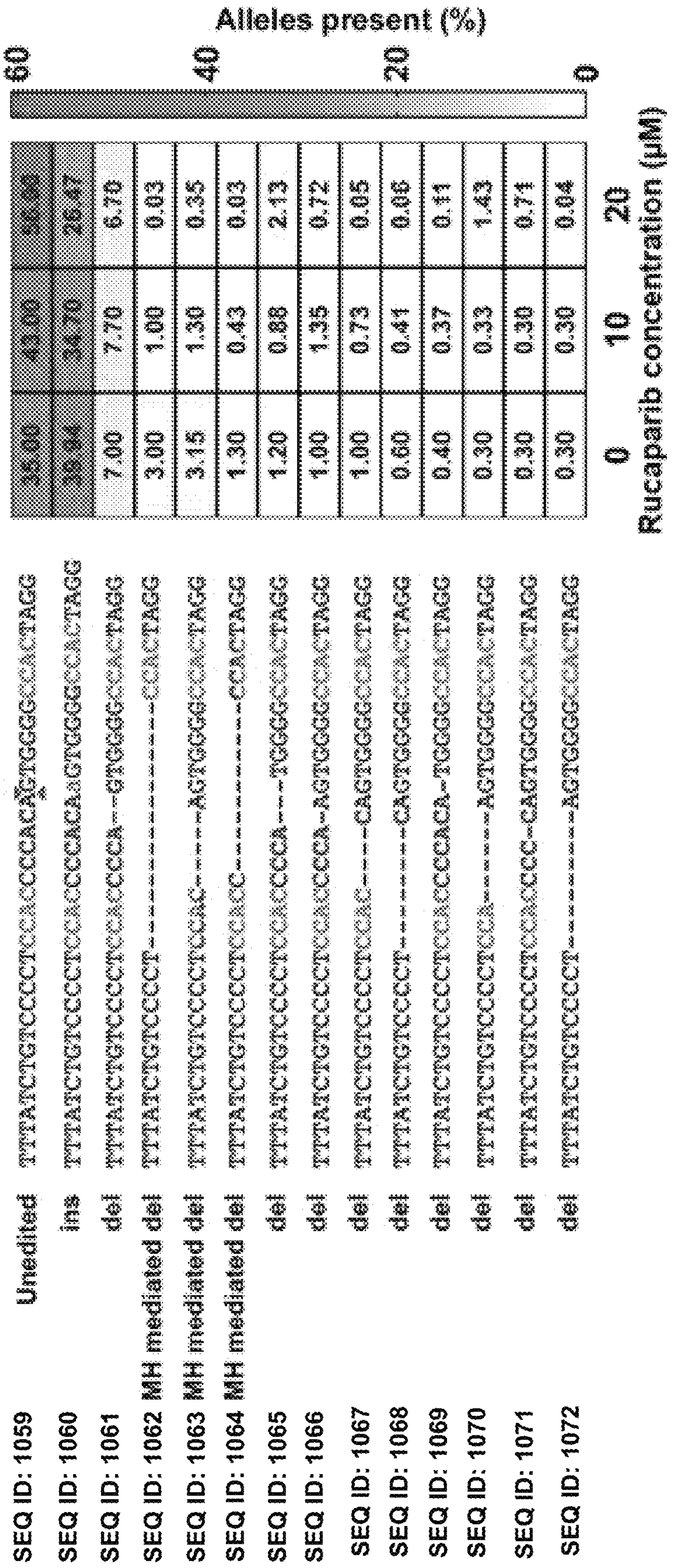

DSBs at most genomic sites are repaired primarily through the NHEJ pathway, which can produce small insertions or deletions during imprecise repair (for example, AAVS1). 28 See, FIG. 18. The data presented herein, which span DSBs in twelve sequences, indicate that microduplications are preferentially repaired via the MMEJ pathway, which yields predictable and efficient collapse. For this class of pathogenic mutations, precise repair via the MMEJ pathway provides a favourable alternative to homology-directed repair, which is inefficient in many cell types[29]. Consistent with the present findings, MMEJ-mediated repair was recently used to efficiently correct the pathogenic microduplication associated with HPS130. Although the use of allele frequencies from gnomAD can help to prioritize potential targets for MMEJ-based repair, this underestimates the extent of genetic diseases-particularly dominant ones-caused by microduplications.

II. Microhomology Mediated End Joining Disease Mutation Repair

To test the generality of the presently contemplated MMEJ-based repair approach and the range of sequence lengths over which duplication collapse is efficient, editing products generated by SpyCas9 targeting endogenous microduplications within the human genome were evaluated.

Figure 13A:
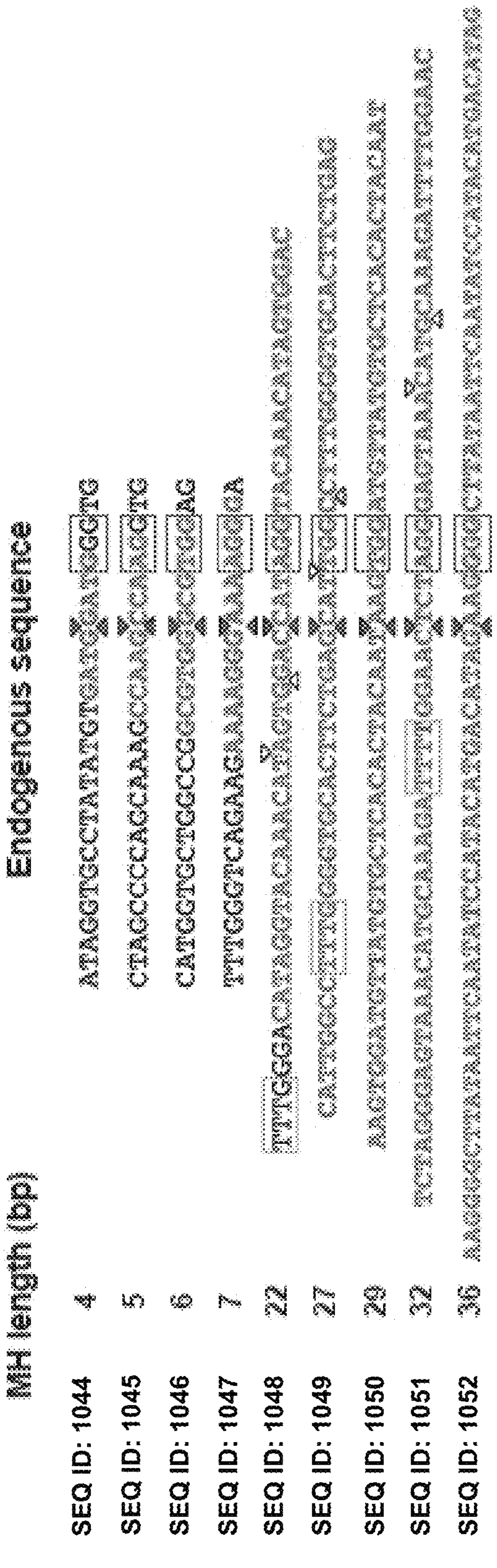
FIG. 13A-C presents exemplary data showing that MMEJ-based approach efficiently achieves precise collapse of endogenous microduplications across various repeat lengths.
Figure 13B:
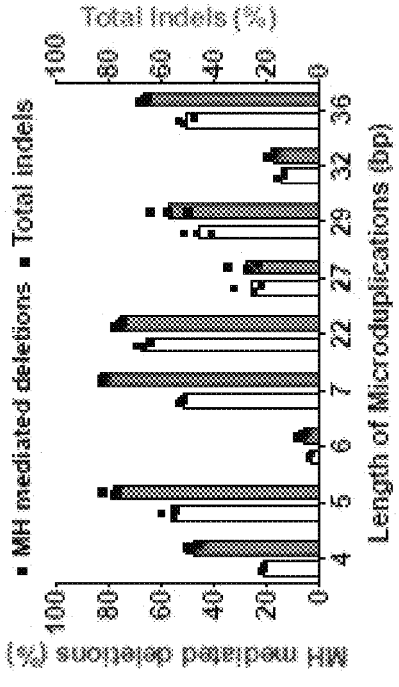
Figure 19A:
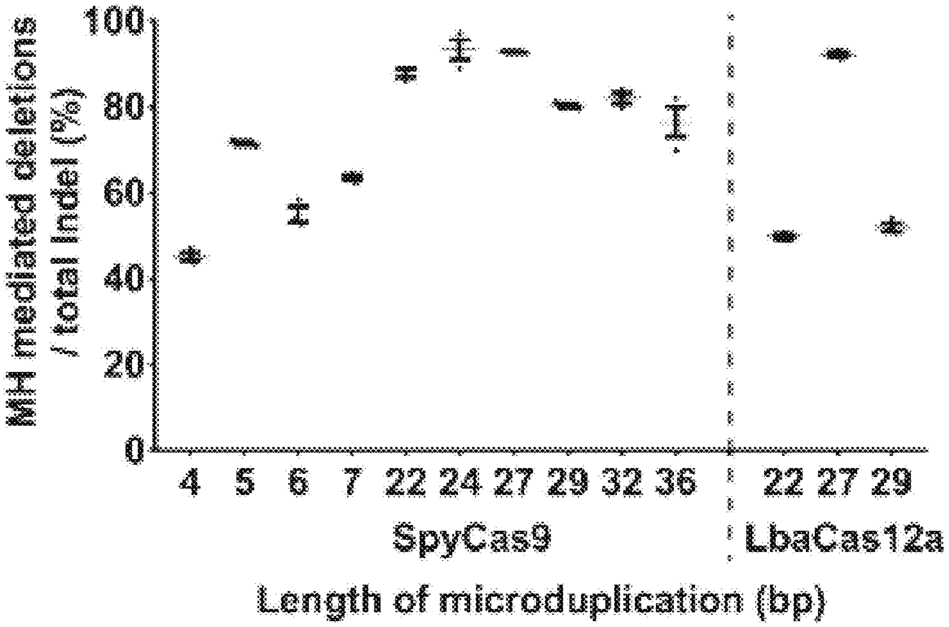
FIG. 19A-G presents exemplary data showing gene editing with SpyCas9 and LbCas12a at endogenous microduplications.
Figure 19B:
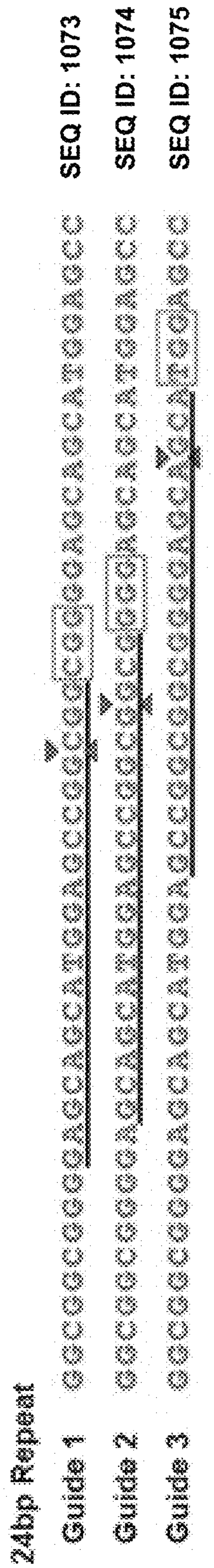
Figure 19C:
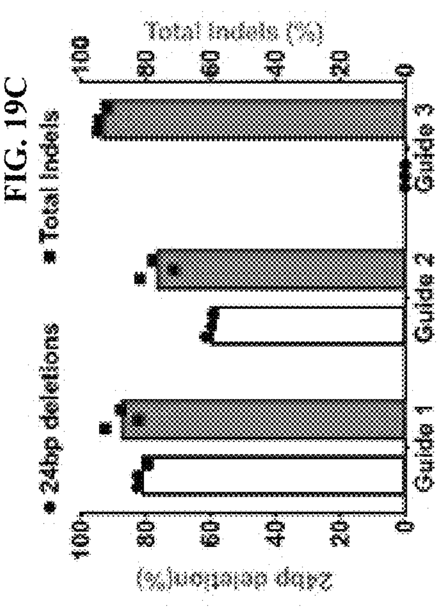
Figure 19D:
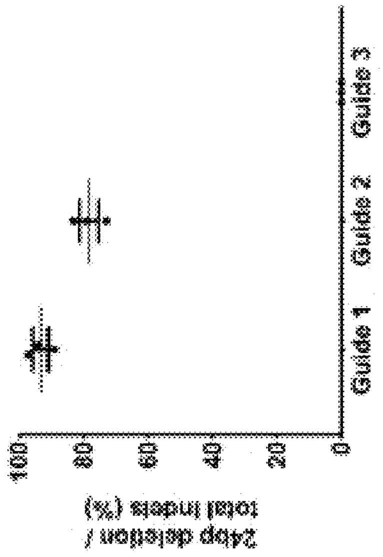
Figure 19E:
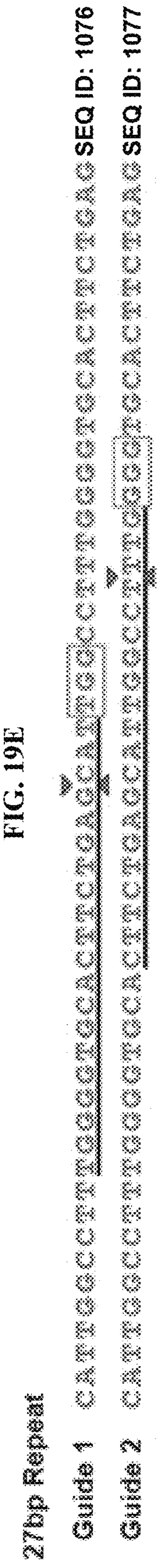
Figure 19F:
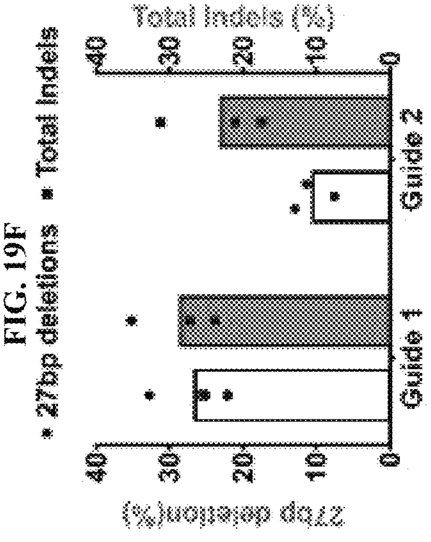
Figure 19G:
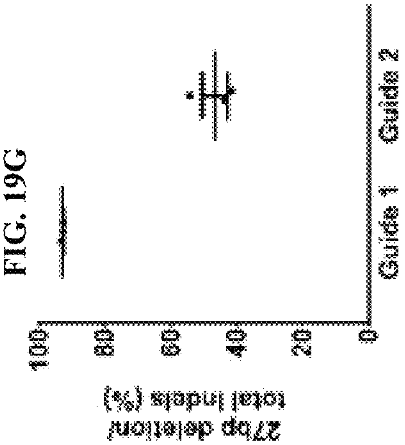

A bioinformatic analysis was performed to identify non-pathogenic, unique endogenous microduplications ranging from 4 bp to 36 bp in length in the human genome. See, FIG. 13A. The efficiency of microduplication collapse resulting from a SpyCas9 produced DSB at the centre of the microduplications in HEK 293T cells at these sites was examined. Although the bulk editing rate varied across these target sites, it was consistently found that duplication collapse was the major end-product within the edited alleles (ranging from 45% to 93%), regardless of the microduplication length. See, FIG. 13B and FIG. 19A. Consistent with the analysis at an HPS1 locus, a decrease in the duplication collapse efficiency was observed for 24- and 27-bp-long microduplications as cut sites were moved away from the centre. See, FIG. 19B-19G.

Figure 13C:
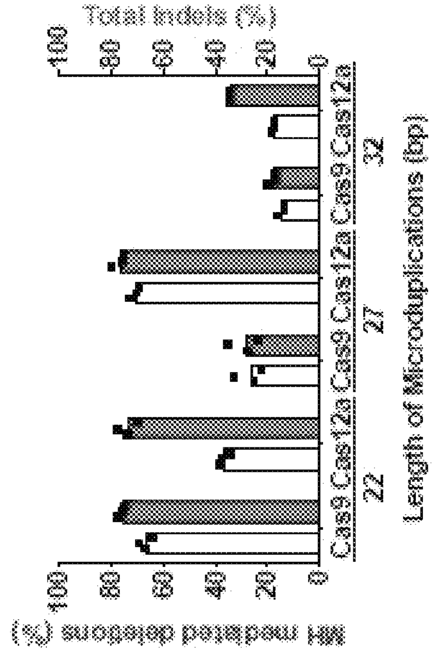
Figure 14:
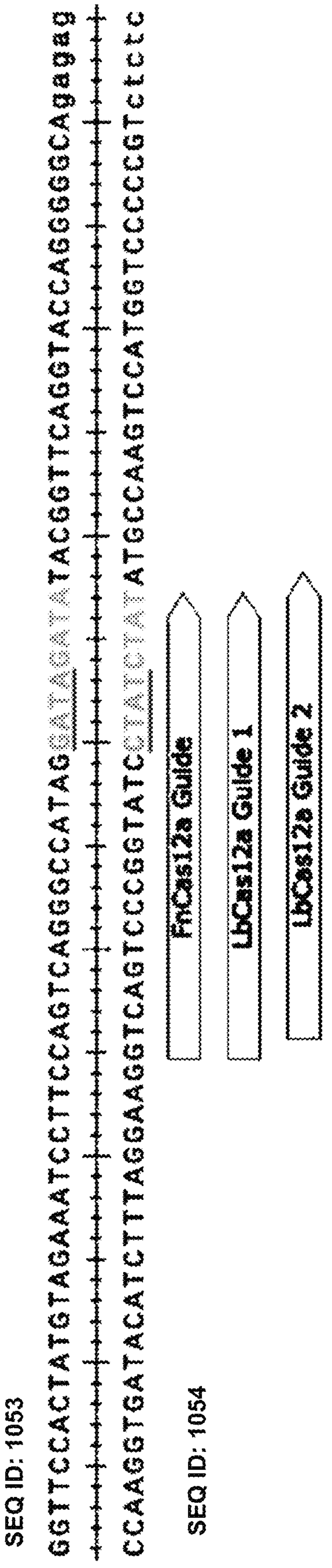
FIG. 14 show the disease-causing GATA microduplication (grey underlined-grey tandem segment) in the Tay-Sachs HEXA gene.
Figure 15:
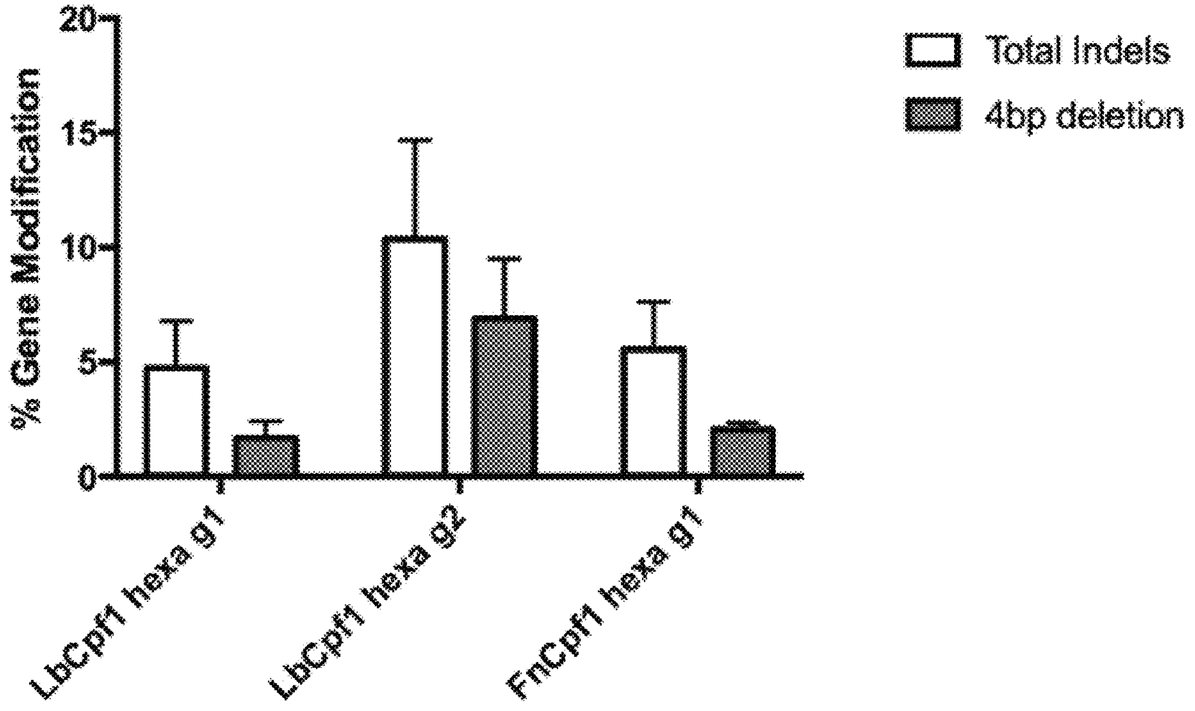
FIG. 15 presents exemplary data showing indel/deletion ratios subsequent to HEXA gene editing with Cas12a RNPs in a Tay-Sachs patient-derived B-EBV cells with a Cas9: sgRNA concentration ratio of 60 pmol protein to 120 pmol guide RNA.
Figure 16:
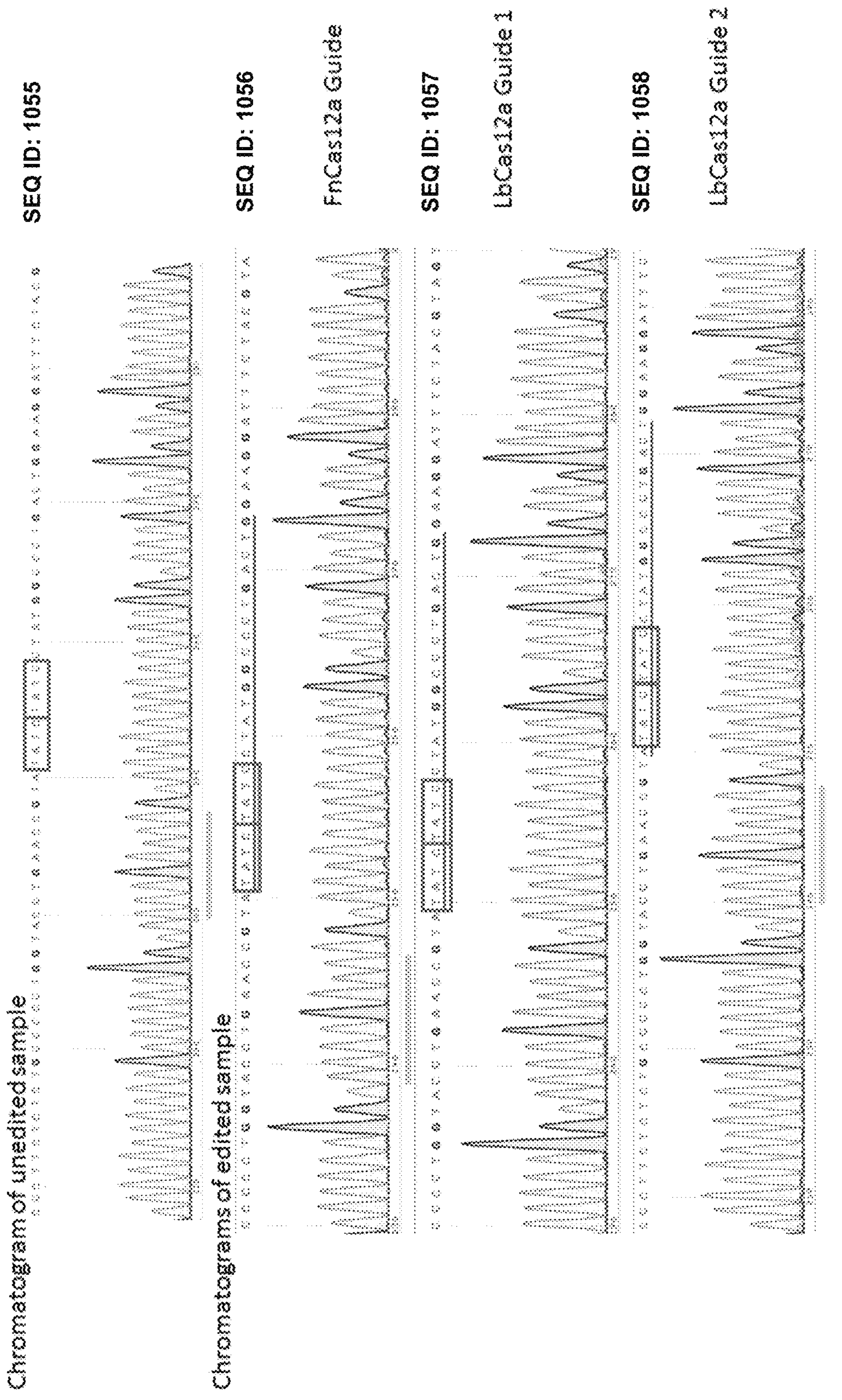
FIG. 16 presents exemplary data showing representative sequence chromatograms of the edited HEXA genes, where sequencing is on the complementary strand.
Figure 17:
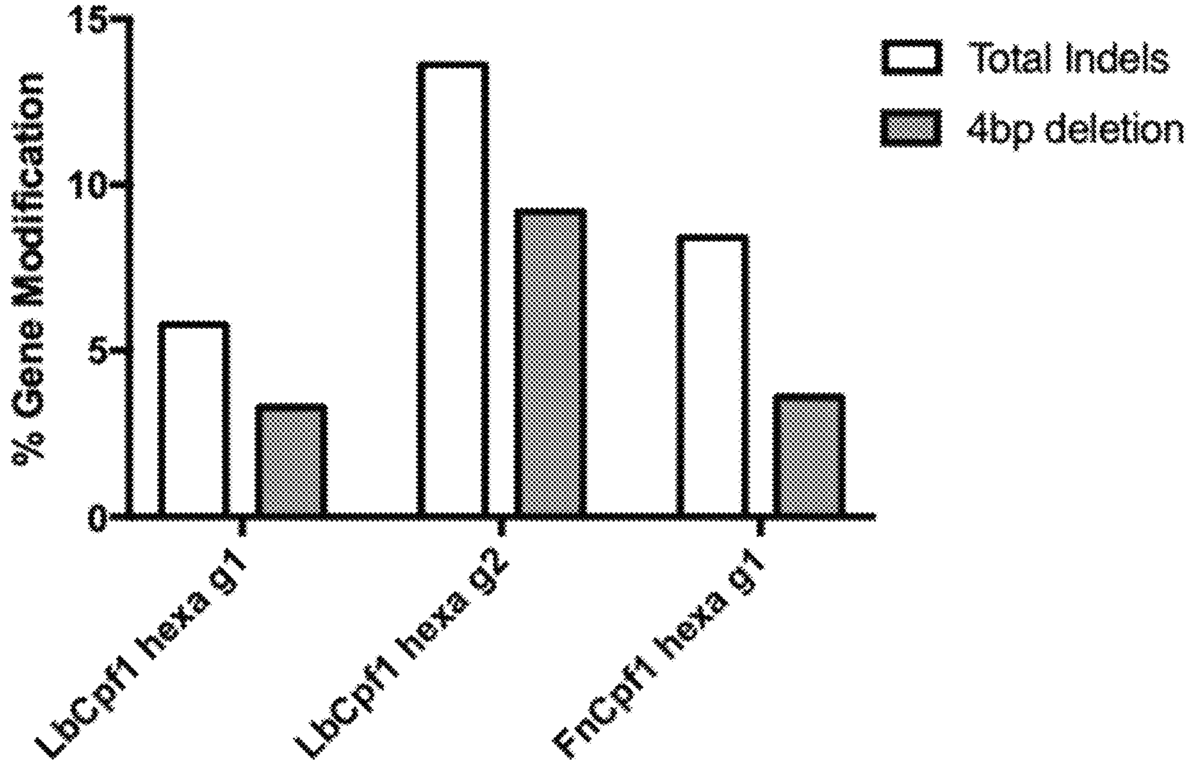
FIG. 17 presents exemplary data showing indel/deletion ratios subsequent to HEXA gene editing with Cas12a RNPs in a Tay-Sachs patient-derived B-EBV cells with a Cas9: sgRNA concentration ratio of 90 pmol protein to 180 pmol guide RNA.

Whereas SpyCas9 generates blunt DSBs, the type V CRISPR-Cas nuclease Cas12a generates DSBs with 5' overhangs[19]. It was then investigated whether LbaCas12a-generated breaks might be preferentially repaired by a resection-dependent pathway such as MMEJ by comparing the efficiency of microduplication collapse engendered by SpyCas9 and LbaCas12a nucleases at three endogenous sites. Efficient repeat collapse (50-90% of edited alleles) could be achieved with LbaCas12a at all three of these sites, with efficiencies similar to those of SpyCas9. See, FIG. 13C and FIG. 19A. In addition, LbaCas12a could drive repeat collapse for the four base pair duplication in HEXA that is associated with Tay-Sachs Disease. See, FIGS. 14-17. Overall, these data demonstrate that the MMEJ-based editing approach can be used to efficiently collapse microduplications up to lengths of at least 36 bp using either Cas9 or Cas12a programmable nucleases.

Recently, an algorithm has been developed to more reliably predict target loci that would be predisposed to generate a more homogeneous mutant allele population through MMEJ. Ata et al., "Toward Precision Molecular Surgery: Robust, Selective Induction of Microhomology-mediated End Joining in vivo" BioRxiv, (posted online Mar. 28, 2018). Thus, the goal of this algorithm was to identify sites in genes where the generation of a double strand break (DSB) will be repaired through the use of microhomologies on each side of the break to collapse the DNA sequence such that it is out-of-frame with regards to its translation and thus will not produce a functional protein. Termed the "MENTHU" algorithm, it appears primarily to be a way of post-processing predictions generated from an earlier reported algorithm (Bae et al., nature.com/articles/nmeth.3015 (2014)) to improve the prediction for when a DSB will be repaired by MMEJ in a fairly homogeneous way. This is useful if one wants to do precision genome editing, whereas Bae et al were considering the blunter application of making (any) out-of-frame deletions for gene knock-out.

The Ata et al. paper invites users to access this algorithm to facilitate the scanning of reference wild-type genes using Genbank IDs or RefSeq IDs to identify sites that will collapse primarily through a single MMEJ event down to a specific sequence. genesculpt.org/menthu/. The Ata et al. algorithm is designed for the primary application of making knockouts in model organisms, e.g. the source-code repository for MENTHU has the subtitle "MENTHU knockout site recommender". Consequently, Ata et al. discloses making mutants in zebrafish embryos through the injection of a programmable nuclease (TALENs or SpCas9), and then analyzing the resulting genetic products and phenotypes of these mutant animals.

Although the MENTHU algorithm appears to be set up to analyze genes, in principle any DNA sequence can be evaluated, e.g. with variant alleles and flanking sequence, but this is user dependent—not a function of the algorithm. In addition, most of the known pathogenic variant alleles that are duplications cause frame-shifts, and the algorithm is not set up to define going from an out-of-frame sequence to an in-frame sequence, let alone restoring the wild-type sequence.

In some embodiments, the present invention contemplates an alternative method that is focused on capturing abutting duplications within the ExAC database or gnomAD databases—a database of variants identified in whole-genome and whole-exome sequencing data aggregated from many large-scale projects (and subsuming the earlier ExAC exome-only database)—that may be suitable for MMEJ repair. Importantly, the basic representation of variants in gnomAD lists the genomic position, reference (REF) sequence starting at that position, and alternate (ALT) sequence starting at that position; it is not typically readily apparent if a variant is a duplication, as typically only the base immediately preceding an insertion is used as the reference allele, whereas to establish whether the inserted sequence is a duplication requires examining more of the flanking regions (e.g. the HEXA duplication has REF=G, ALT=GGATA, where only a single copy of the duplication is present). See, Tables 5 and 6 Furthermore, the gnomAD webpages and downloadable vcf files are not compatible with the MENTHU program in their raw form: the webpages for variants show surrounding genomic reference sequence only as a PNG graphic (not in text form) or via links to the UCSC genome browser for the reference genome; the vcf files sometime indicate when variants are duplications in the HGVSc fields added by Ensembl VEP, but again these files do not directly provide sequence of the duplication (both reference-copy and extra inserted copy) together with enough genomic flanking sequence to use for identifying cleavage sites that would be suitable for MMEJ. This alternative technology rebuilt the surrounding genomic sequence and identified common positions for nuclease cleavage around these duplications that could be tested to achieve collapse of the duplication and restore the wild-type sequence. Never is this concept mentioned in the MENTHU manuscript or algorithm.

In addition, the present invention—unlike the Ata et al. algorithm captures allele frequencies that allow the prioritization of potential targets based on the associated diseases, where the information on pathogenicity is extracted from the Clin Var database and combined with gnomAD and 1000 Genome Project phase 3 databases to determine how common the variants are overall and in specific human subpopulations.

Thus, the embodiments contemplated herein represent a completely novel analysis of a human genome variant database to extract information of disease alleles that may be amenable to gene correction by replacing microduplication mutations sequences with their requisite wild type sequences via an MMEJ strategy.

III. Gene Microduplication Diseases

There are a number of diseases that have causative alleles within the human population that are associated with microduplications within the genome. See, Table 1.

TABLE 1

Exemplary Disease alleles associated with microduplications

| SEQ ID | Disease | locus | duplication | dbSNP ID | clin Var ID | gnomAD allele frequency |
|---|---|---|---|---|---|---|
| 144 | LGMD2G | TCAP | CGAGGTGT | rs778568339 | ND | 8.126e−5 |
| 145 | HPS | HPS1 | CCAGCAGGGGAGGCCC | rs281865163 | 5277 | 2.845e−5 |

TABLE 1-continued

Exemplary Disease alleles associated with microduplications

| SEQ ID | Disease | locus | duplication | dbSNP ID | clin Var ID | gnomAD allele frequency |
|---|---|---|---|---|---|---|
| 146 | Tay-Sachs | HEXA | GATA | rs387906309 | 3889 | 0.0008041 |
| 147 | familial limb-girdle myasthenia | DOK7 | GCCT | rs764365793 | 1273 | 0.0006367 |
| 148 | Cone-rod dystrophy 11 | RAX2 | CCCGGG | rs549932754 | 1242 | 0.0007684 |

There are likely to be many more microduplications that are associated with diseases. But most disease phenotypes have not been linked to a specific microduplication. For example, ~90% GWAS disease-associated SNPs are found in non-coding sequences, though which variants are themselves causal, as opposed to being in linkage disequilibrium with causal variants, is in many cases not yet known. Hindorff et al., "Potential etiologic and functional implications of genome-wide association loci for human diseases and traits" *Proceedings of the National Academy of Sciences* 106:9362-9367 (2009). In addition, repeat expansion diseases (e.g., Huntington's disease, ALS [C9ORF72], etc.) could be thought of as extended microduplications as well.

In one embodiment, the present invention contemplates a method for reverting a gene comprising a nucleotide micro-duplication mutation to a wild-type sequence. In one embodiment, the method comprises generating a DSB near the center of the nucleotide microduplication. In one embodiment, the nucleotide microduplication causes a disease. In one embodiment, the DSB is created by targeting a nuclease to the nucleotide microduplication center. In one embodiment, the nuclease includes, but is not limited to Cas9, CRISPR, Cas12 (Cpf1), zinc finger nucleases and/or TALEN. Although it is not necessary to understand the mechanism of an invention, it is believed that since the nuclease is targeting a mutated sequence, once the mutation reversion to a wild type sequence has occurred, the repaired target sequence would no longer be recognized by the nuclease, and thus remains a wild type sequence in the presence of the repairing nuclease. It is further believed that a correction DNA cassette is not needed for an MMEJ repair back to the wild-type sequence, only the nuclease (e.g. Cas9) and a targeting moiety having affinity for the mutant locus (e.g. sgRNA).

The data presented herein describes successful correction of disease causing alleles in patient-derived cell lines harboring microduplications in TCAP and HPS1. A high rate of correction is achieved in patient cells lines through the delivery of a nuclease suggesting that nuclease-induced MMEJ repair of microduplications within a genome can be programmed for other gene microduplication targets causing other diseases (e.g. HEXA-Tay-Sachs syndrome, other diseases in Table 1) leading to cures for these diseases.

A. TCAP and HSP1 Microduplication Repair

The site-specific nuclease, *S. pyogenes* Cas9 (SpCas9) was used in the following therapeutic gene editing method. Jinek et al., "A programmable dual-RNA-guided DNA endonuclease in adaptive bacterial immunity" *Science* 337:816-821 (2012). Nonetheless, it is contemplated herein that similar results can be obtained using any Cas9 (or CRISPR), a Cpf1 nuclease or any other programmable nuclease system including, but not limited to, zinc finger nucleotide (ZFN), TALEN, mega-TAL or meganuclease all of which can be targeted to a gene microduplication sequence. The data presented herein show two different proof-of-principle targets (TCAP and HSP1) that may have therapeutic value. Both of these diseases are associated with substantial morbidity, and no curative therapies are currently available.

The mutant TCAP allele contains an 8 base duplication that leads to an out of frame coding sequence. UCSC: genome.ucsc.edu/cgi-bin/hgTracks?db=hg19&highlight=hg19. chr17%3A37821635-37821635&position=chr17%3A37821610-37821660. This TCAP allele has a frequency of ~1 in 1000 in the east Asian population. gnomad.broadinstitute.org/variant/17-37821635-G-GCGAGGTGT. Individuals with homozygous inactivating mutations in TCAP have Limb Girdle Muscular Dystrophy 2G (LGMD2G).

The mutant HPS1 allele contains a 16 bp duplication that leads to an out of frame coding sequence. gnomad.broadinstitute.org/variant/10-100183554-T-TGGGCCTCCCCTGCTGG (SEQ ID NO: 149). This allele has a frequency of ~1 in 21 in populations within Puerto Rico. MPH, S. E.-C. M. & MD, L. R. Y. Hermansky-Pudlak Syndrome 1-7 (2017). Individuals with homozygous inactivating mutations in HPS1 have Hermanksy-Pudlak syndrome (HPS1).

Figure 9:
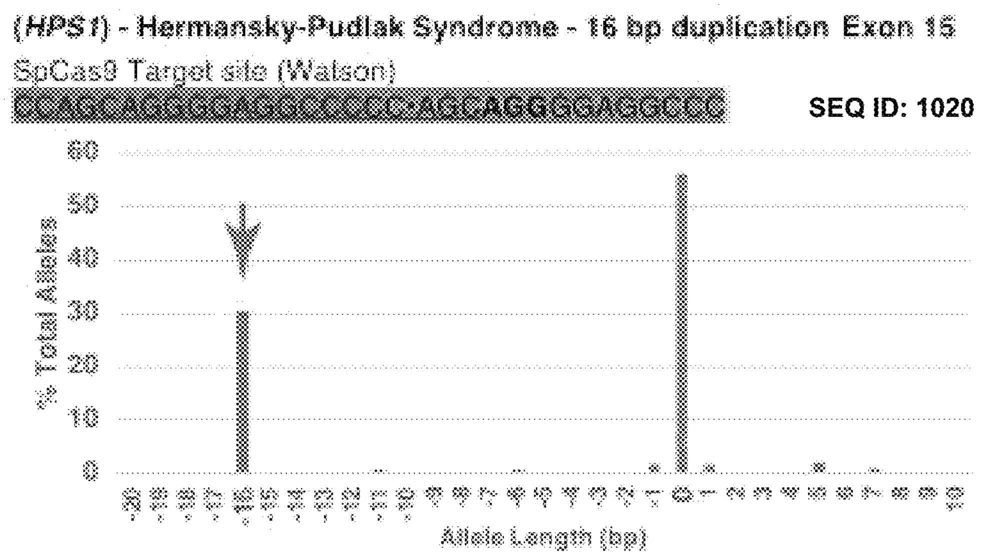
FIG. 9 presents exemplary data showing that a mutant HPS1 allele contains a 16 bp duplication (annotation as in FIG. 2).

B-EBV cells were obtained from a patient that contains a homozygous 16 bp microduplication in the HPS1 gene with SpCas9 by nucleofection. ICE (similar to TIDE[16]) analysis of sanger sequence chromatogram from SpCas9 treated HPS1 B-EBV cells. The estimated mutagenesis rate is 41% with 30% of the alleles containing a 16 bp deletion (red arrow), which is a reversion to the wild-type sequence. Zero (x-axis) is no change in the length or composition of the 16 bp microduplication. See, FIG. 9.

Figure 3:
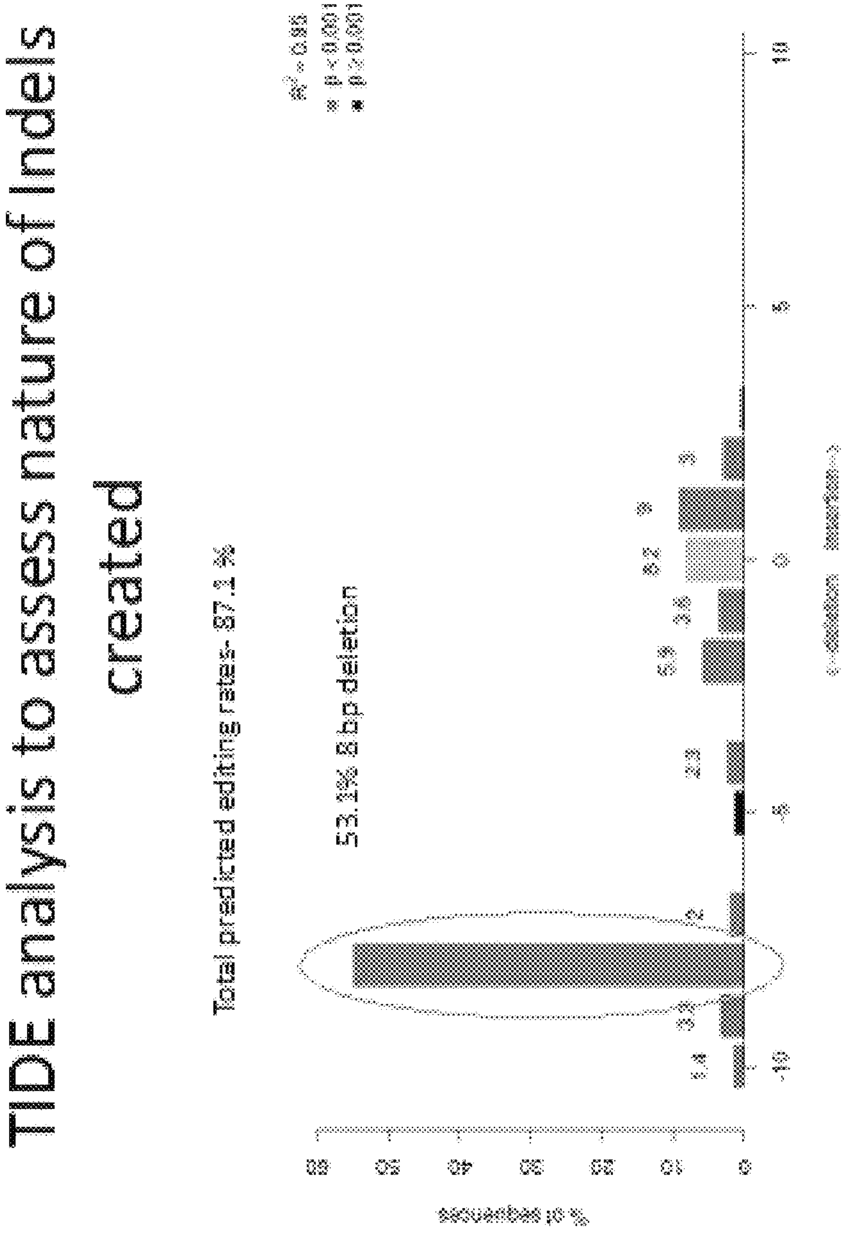
FIG. 3 presents exemplary data of a TIDE analysis of sanger sequence chromatogram from SpCas9 treated LGMD2G iPSCs. The estimated mutagenesis rate is 87% with 53% of the alleles containing an 8 bp deletion (oval), which would be consistent with a reversion to the WT sequence.

Patient-derived cells were obtained to test the potential for a nuclease targeting these deletions to revert the duplicated mutant allele. For TCAP, iPSCs were derived from fibroblasts from an individual that is a homozygous carrier of the 8 bp duplication. See, FIG. 3. For HPS1, B-EBV cells were purchased from Coriell generated from a patient that is homozygous for the 16 bp duplication in HPS1 [GM14606]. For the nuclease system, a 3×NLS-SpCas9 protein was used complemented with sgRNAs (Synthego) for the target sequences. See, Table 2.

TABLE 2

| Guide Sequences in sgRNAs targeting duplications | | |
|---|---|---|
| SEQ ID NO: | Microduplication locus | SpCas9 Guide sequence |
| 150 | TCAP | AGCTGAGCTGCGAGGTGTCG |
| 151 | HPS1 | CAGCAGGGGAGGCCCCCAGC |

Figure 4:
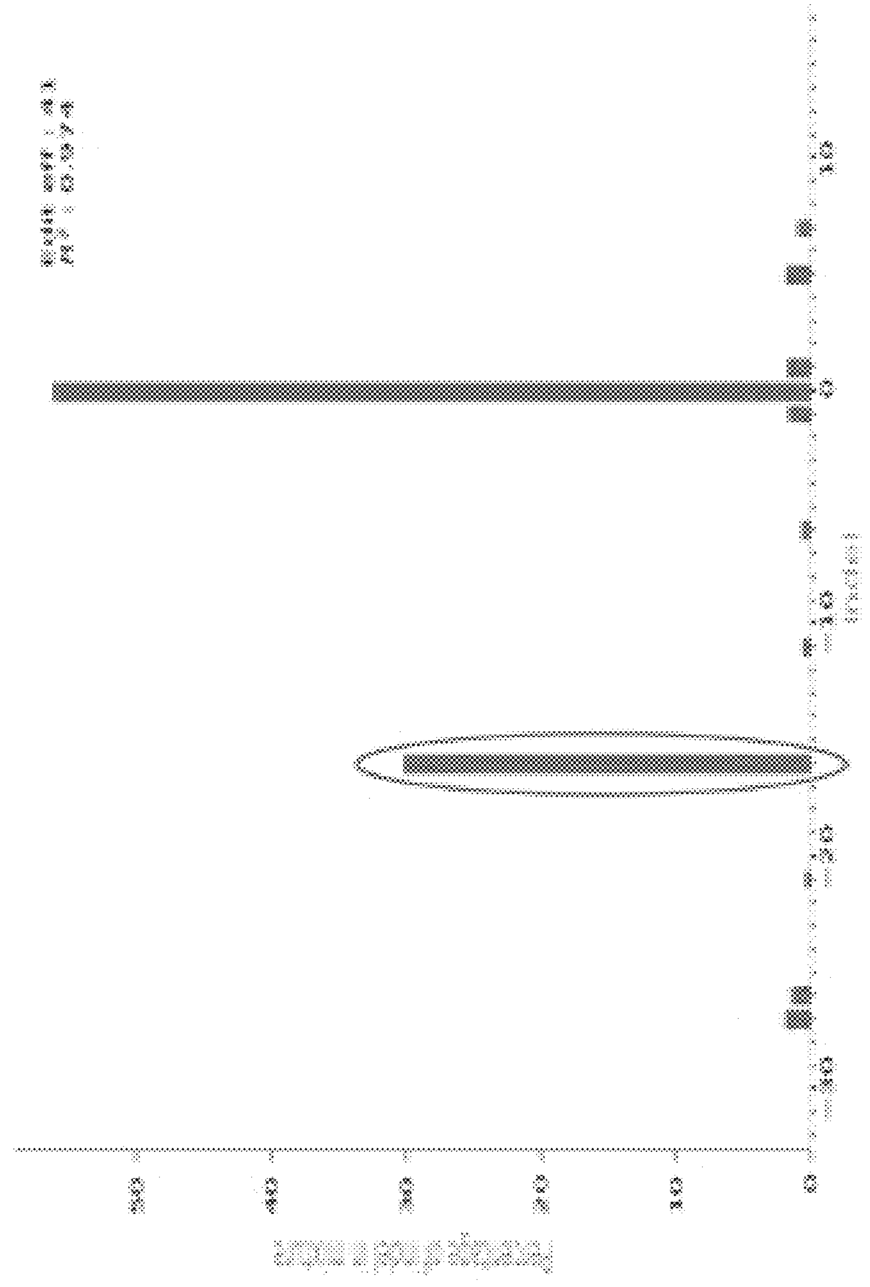
FIG. 4 presents exemplary data of an ICE analysis of sanger sequence chromatogram from SpCas9 treated HPS1 B-EBV cells. The estimated mutagenesis rate is 41% with 30% of the alleles containing a 16 bp deletion (oval), which would be consistent with a reversion to the WT sequence.

These Cas9-sgRNA complexes (e.g., Cas9 RNPs) were delivered by nucleofection to LGMD2G iPSCs, myoblast derived from LGMD2G iPSCs, or to the HPS1 B-EBV line. Following recovery and expansion of the nuclease-treated cells in culture the target genomic region was amplified by PCR from the population of treated cells and the mutagenic products were characterized by TIDE or ICE analysis of the sequence chromatograms. Brinkman et al., "Easy quantitative assessment of genome editing by sequence trace decomposition" *Nucleic Acids Research* (2014). TIDE analysis of Cas9 RNP treated LGMD2G iPSCs revealed that ~53% of the alleles were converted back to a wild-type length. See, FIG. 3. ICE (Synthego) analysis of SpCas9 treated HPS1 B-EBV cells revealed that ~30% of the alleles were converted back to a wild-type length in the context of a ~41% total editing rate. See, FIG. 4. In summary, approximately 75% of the edited HPS1 alleles were converted to wild-type length.

Figure 5:
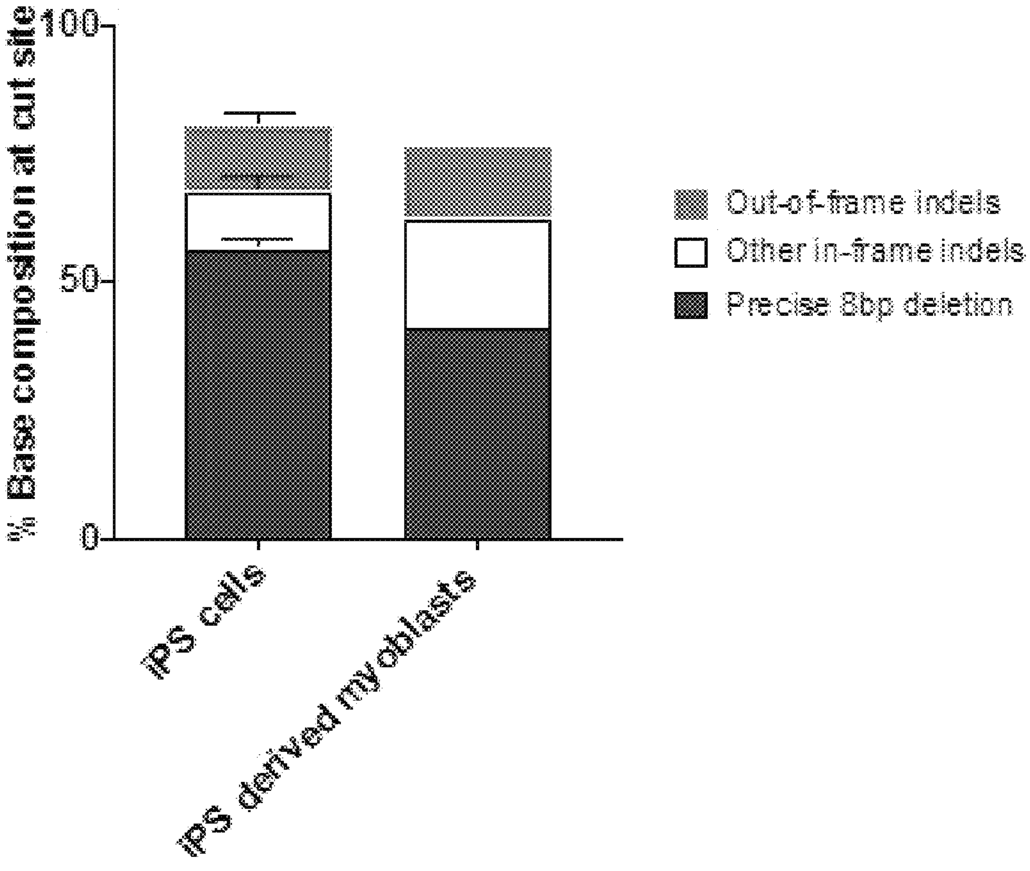
FIG. 5 presents exemplary data of a deep sequencing analysis of the editing rates and outcomes at TCAP in iPSCs or iPSC derived myoblasts that have an 8 bp duplication in both alleles. More than 50% of the alleles are either the precise 8 bp deletion or are mutations that produce an in frame sequence.

To confirm the TIDE analysis of TCAP alleles a deep sequencing analysis was performed on SpCas9 RNP treated iPSCs and iPSC derived myoblasts. See, FIG. 5. The iPSC data is from two biological replicates and the myoblast data is from a single experiment. The data confirm that the majority of the editing products are micro-homology mediated deletion of one of the duplicate sequences. There are also a large number of additional sequence that have been shifted back in frame through mutagenesis—although they are not the wild-type coding sequence. These mutant in-frame sequences may also be functional.

Figure 6:
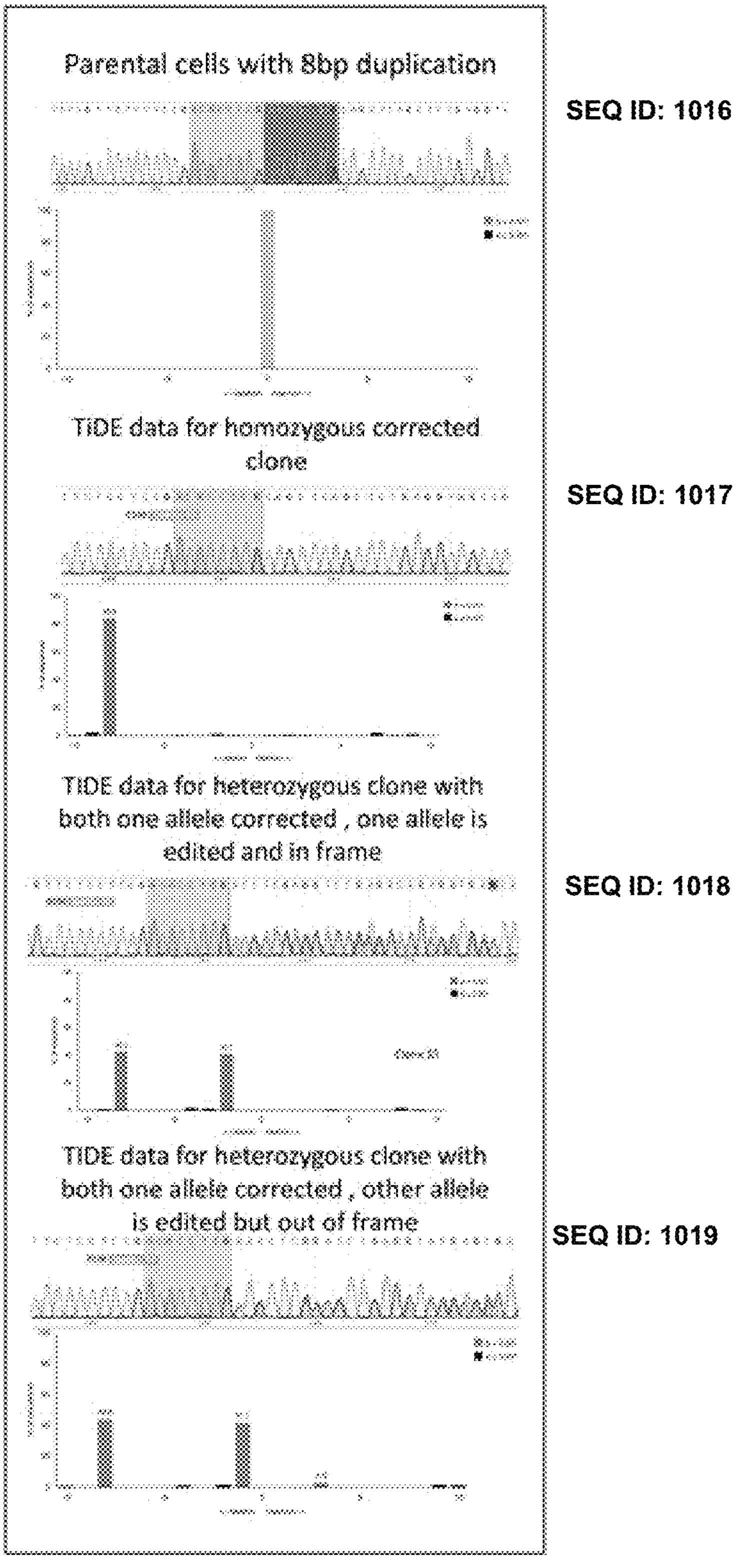
FIG. 6 presents exemplary data of TIDE analyses of sanger sequencing of individual iPSC clones from the 8 bp duplication TCAP line following treatment with a TCAP targeting SpCas9 RNP. In these four instances at least one allele was converted to the wild-type sequence.
Figure 7:
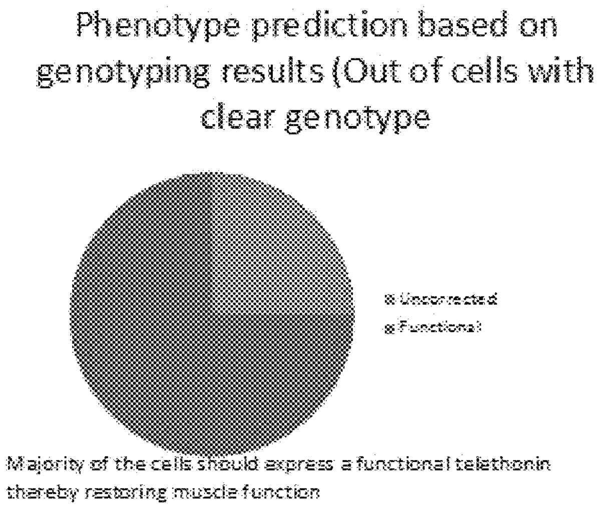
FIG. 7 presents exemplary data for a phenotype prediction iPSC clones based on the genotypes that were observed from the sequencing of the Cas9 modified alleles. 75% of the clones that could be conclusively characterized contained at least one wild-type TCAP sequence.

Individual iPSC clones were taken from a SpCas9 RNP treated TCAP microduplication cell population and expanded to determine the genotype. A variety of different genotypes were observed within the clones that were analyzed. See, FIG. 6. Two of the 24 clones that were analyzed were homozygous for the wild type (WT) allele. Six "clones" could not be defined conclusively—likely because the colonies were initiated from 2 cells generating more than 2 allele sequences. Overall the analysis of 18 clones demonstrate that the majority of iPSC clones (~75%) contain at least one corrected allele of wild type sequence. See, FIG. 7.

In one embodiment, the present invention contemplates a method of differentiating SpCas9 treated iPSC clones into myoblasts to determine the number that display expression of the TCAP encoded protein telethonin.

The methods disclosed herein show an ability to precisely revert a microduplication back to its parental (e.g., wild type) sequence that can correct genetic microduplication mutations underlying of a number of diseases. Aside from those listed in Table 1 (supra)—there may be a number of diseases that stem from microduplications given the limited depth of genomic data that is associated with rare diseases.

Figure 20A:
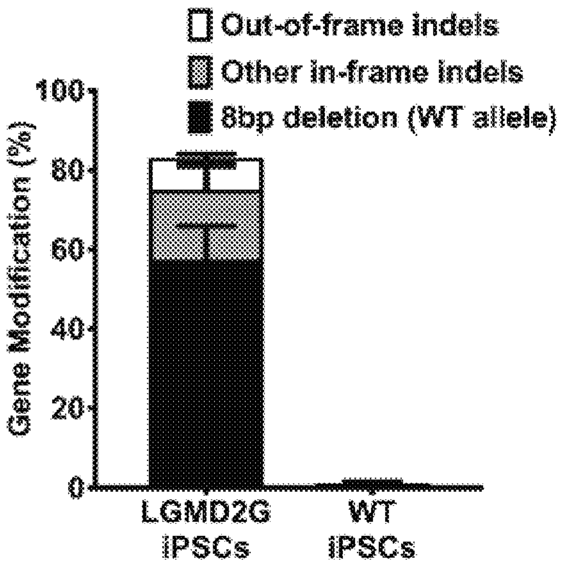

An sgRNA was designed and tested for SpyCas9 to generate a DSB one base pair away from the middle of the TCAP 8-bp microduplication. See, FIG. 10B. Purified SpyCas9 protein was complexed with a synthetic sgRNA (RNP) and electroporated into iPSCs homozygous for the TCAP microduplication that were derived from patients with LGMD2G. After four days, deep sequencing analysis was used to analyse the genomic region of interest for insertions and deletions (indels). Robust gene editing (about 80% indel rate) was observed, indicating that the SpyCas9 RNP can efficiently generate DSBs at this site. Closer examination of the sequence variants revealed that on average about 57% of the alleles contained a precise 8-bp deletion corresponding to the wild-type allele. See, FIG. 10C and FIG. 20A.

Figure 21A:
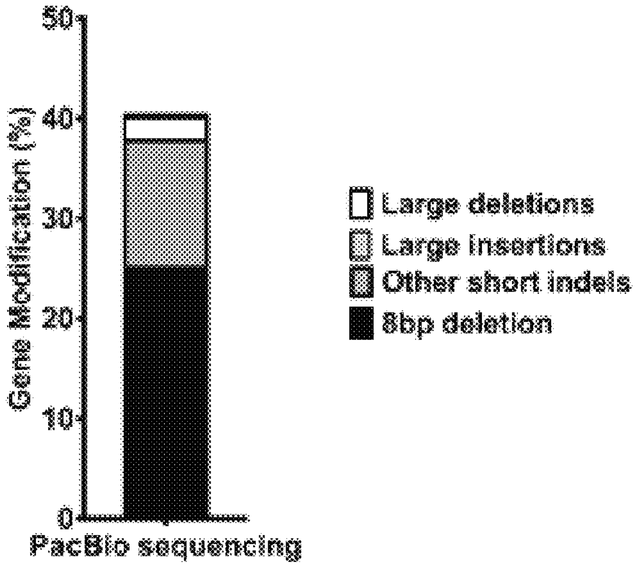
FIG. 21A-B presents exemplary data showing PacBio long-read sequencing analysis for SpyCas9-edited LGMD2G iPSCs at the TCAP locus.
Figure 21B:
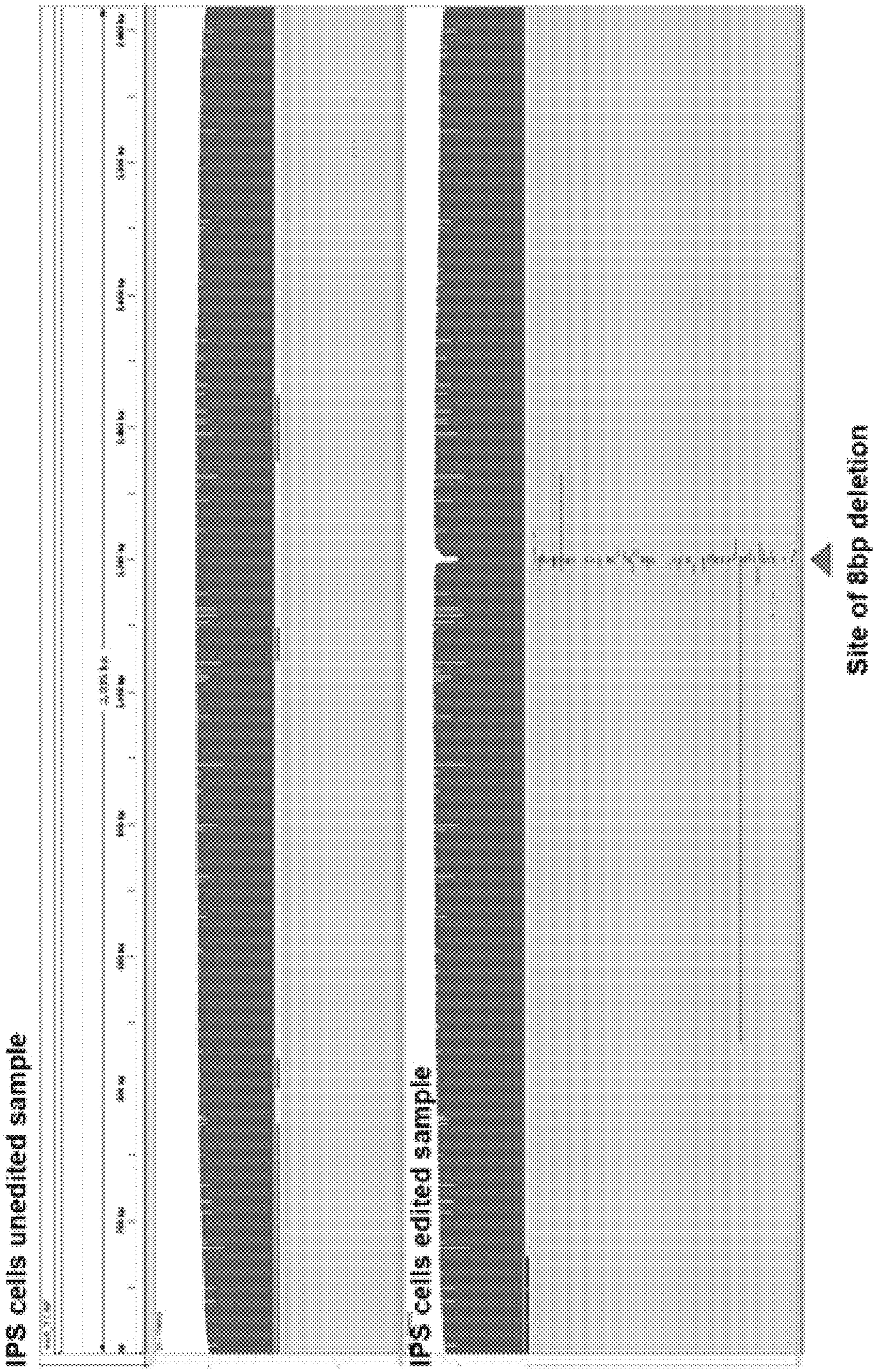
Figure 22:
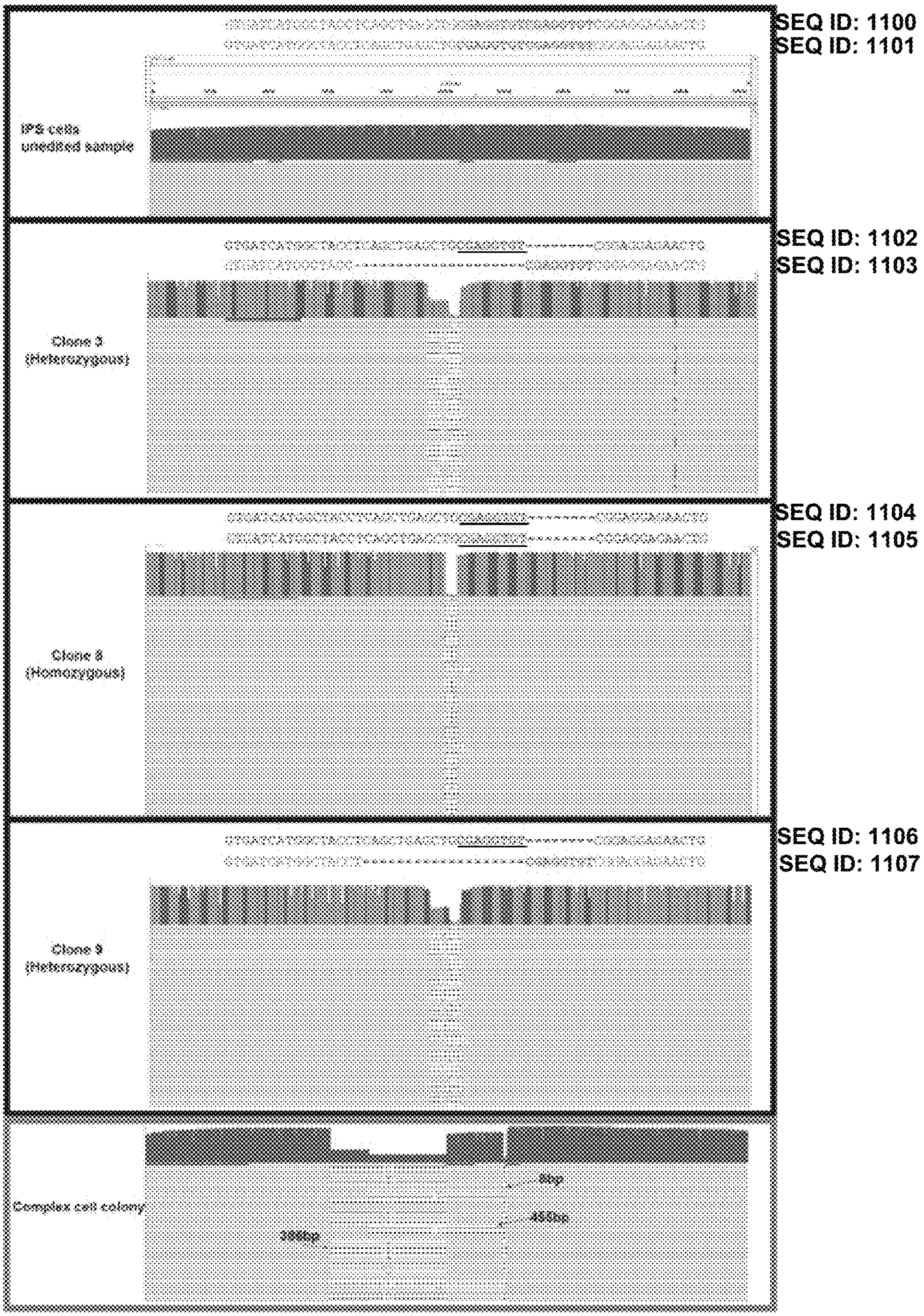
FIG. 22 presents exemplary data showing PacBio long-read sequencing analysis of SpyCas9-edited LGMD2G iPSCs clones and a complex colony at the TCAP locus. IGV graphs depicting representative reads obtained for clonal isolates of edited LGMD2G iPSCs (FIG. 10D), spanning a genomic region of about 2,035 bp surrounding the TCAP target site. The genotype of the clones (deduced by Illumina deep sequencing) is indicated beside an enlargement of the TCAP target region within the PacBio data. The sequences of the two alleles (listed above the IGV plot) obtained from sequencing are shown with repeats. Alleles that reverted to wild-type as a result of collapse of microduplication are underlined. Bottom, IGV plot for one complex iPSC colony that appears to have been nucleated by more than one cell, with large deletions present in the genome (sizes indicated).
Figures 23A, 23B:
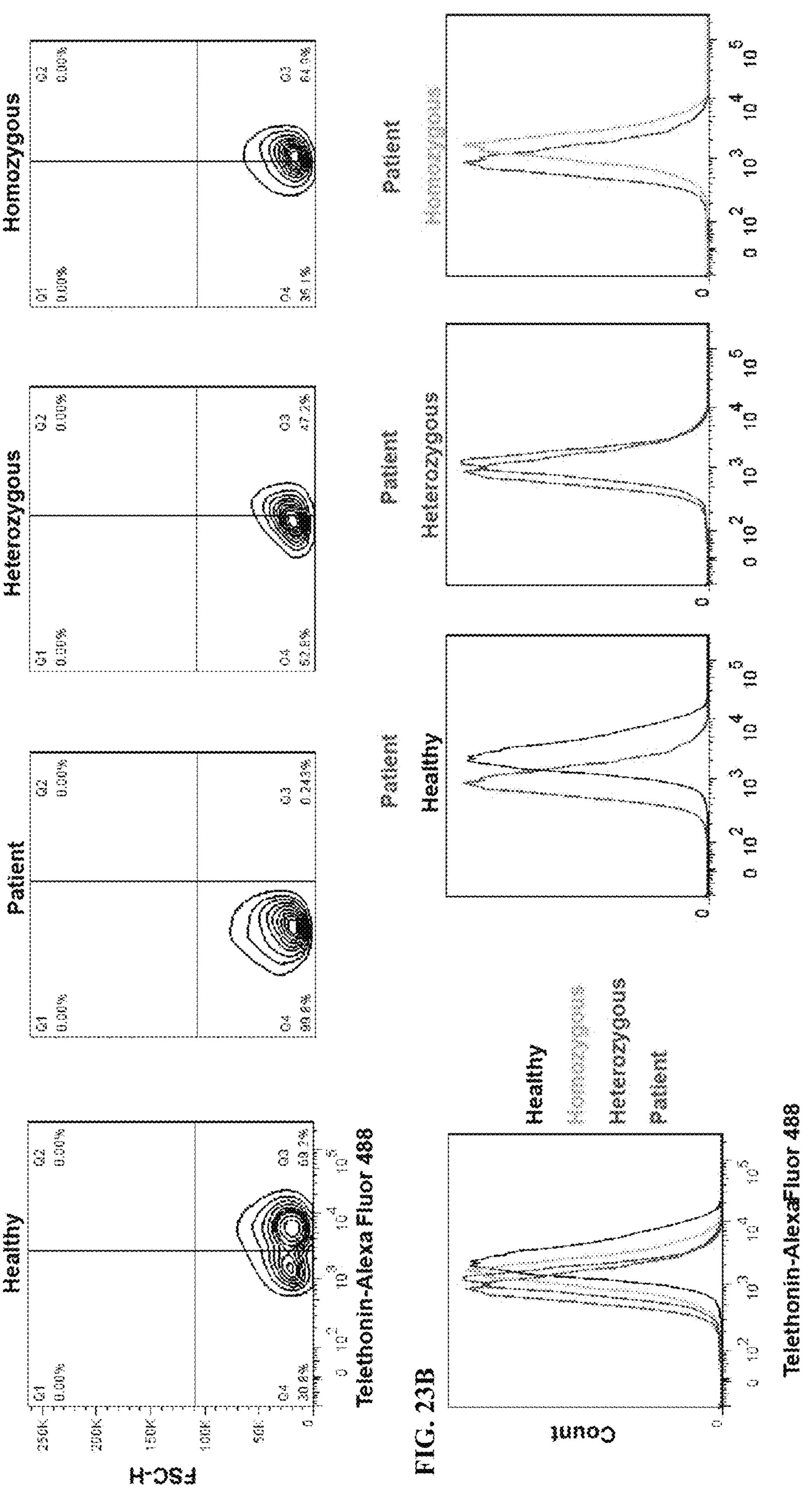
FIG. 23A-E presents exemplary data showing Detection of telethonin expression by flow cytometry in patient-derived cells treated with SpyCas9.
Figure 23C:
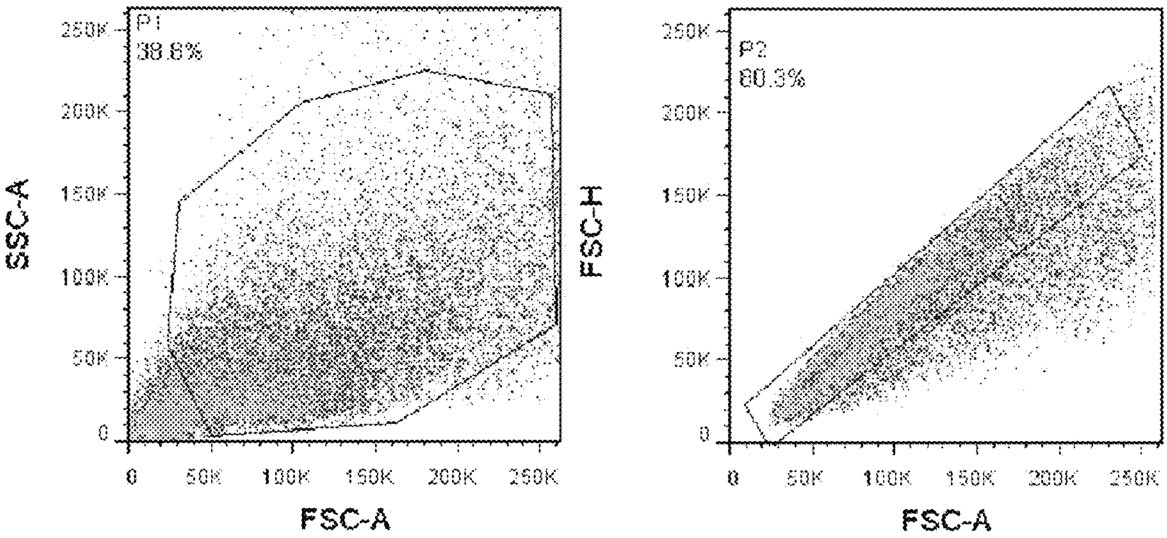
Figure 23D:
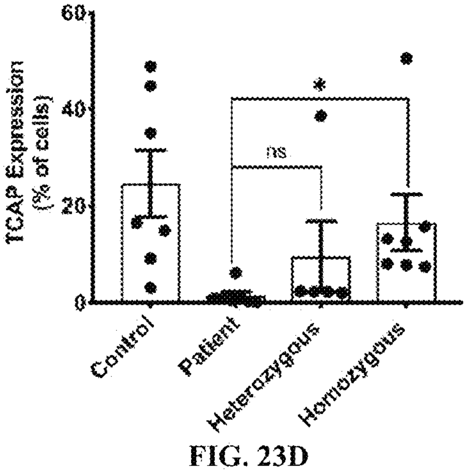
Figure 23E:
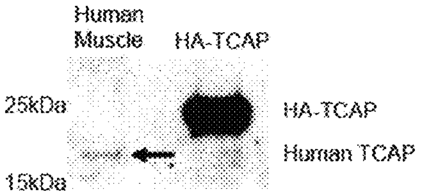

Notably, when introduced into wild-type cells containing functional TCAP, the SpyCas9 RNPs did not cause measurable editing at the TCAP allele, indicating that the corrected allele in the mutant cells is not subject to unintended damage following MMEJ-mediated reversion. See, FIG. 10C. In addition to the precise 8-bp deletion, it was also observed that an additional approximately 17% of the alleles contained in-frame mutations, and therefore may encode hypomorphic alleles with some restoration of function. See, FIG. 20A and FIG. 20C. Genotyping of 22 clones generated from a nuclease-treated LGMD2G iPSC population revealed that 77% contained at least one wild-type allele, indicating that the majority of nuclease-treated cells would be phenotypically corrected. See, FIG. 10D. To independently verify the duplication collapse rates observed in edited iPSCs by Illumina short-read sequencing, a 2-kb amplicon was sequenced spanning the TCAP locus from a population of SpyCas9-edited iPSCs using the Pacific Biosciences long-read sequencing platform (PacBio). Analysis of these reads revealed that 67% of the edited alleles with insertions or deletions below 100 bp in length corresponded to the 8-bp collapse, which is similar to the 73% rate of 8-bp collapse determined by Illumina sequencing for this sample. See FIG. 21. Treatment of cells with Cas9 nuclease can produce large deletions (>100 bp) at the target locus at a modest frequency[10]. Consistent with these findings, the PacBio analysis revealed the presence of large deletions (100-1,000 bp) that would not have been detected by Illumina sequencing at a frequency of about 2% in bulk edited iPSCs. A genotypically complex iPS cell colony was also isolated that harboured two large deletions at the TCAP locus. See, FIG. 22.

Figure 20B:
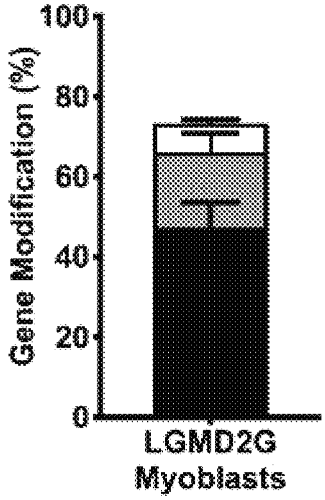

To demonstrate the translatability of the present approach to muscle cell types, LGMD2G iPSCs were differentiated into proliferative skeletal myoblasts that can be induced to terminally differentiate into myotubes[11]. iPSC-derived myoblasts can repair damaged muscle in a similar way to myogenic satellite cells (one of the primary targets of gene therapy for myopathies). Myoblasts were electroporated with SpyCas9 RNPs programmed to target the 8-bp microduplication. Following editing, about 45% of the alleles were precisely repaired back to the wild-type sequence. See, FIG. 10E, FIG. 20B, and FIG. 20D. Immunostaining of myotubes derived from corrected LGMD2G iPSC clones with an anti-telethonin antibody showed that genetic correction restored telethonin expression. See, FIG. 23. Collectively, these data show that introducing a DSB close to the centre of microduplication can efficiently achieve precise in vitro correction of the 8-bp microduplication associated with LGMD2G in iPSCs and in myoblasts that mimic cell populations that would be therapeutically targeted in vivo.

The present approach was further tested on a 16-bp pathogenic microduplication in exon 15 of HPS1, which is associated with HPS1 and leads to the production of a truncated protein responsible for this autosomal recessive disease[12]. HPS1 has a high prevalence in the Puerto Rican population, with a carrier rate of approximately 1 in 21 in the northwest region[2]. HPS proteins are involved in the biogenesis of lysosome-related organelle complexes (BLOCs), which are necessary for the proper trafficking of cargo to melanosomes, dense granules and lysosomes[13]. HPS1 patients suffer from albinism, bleeding disorders, vision loss and progressive pulmonary fibrosis, which leads to premature death[14].

Figure 24:
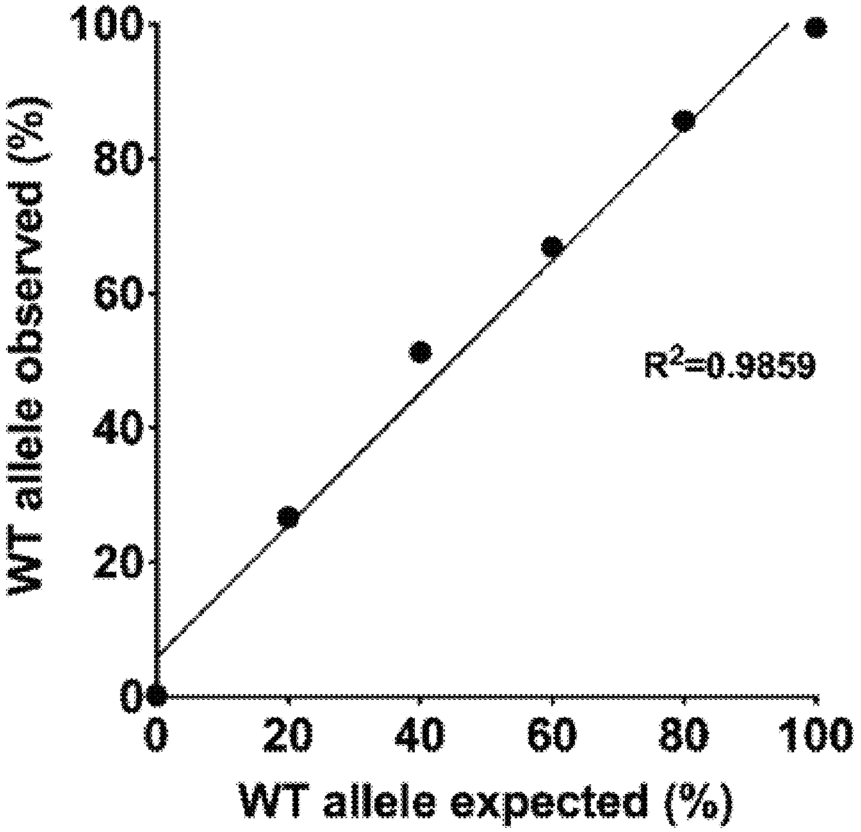
FIG. 24 presents exemplary data showing a standard curve generated with genomic DNA of wild-type and HPS1 mutant B-LCLs from UMI-based Illumina deep sequencing. Genomic DNA from wild-type cells and HPS1 cells homozygous for the 16-bp microduplication were mixed at different ratios (x-axis). These mixed DNAs were used for the construction of a UMI-based Illumina library to determine the ratio of the alleles through deep sequencing (y-axis). These data are fitted to a regression line with the R2 value reported. n=1 biological replicate.
Figure 25A:
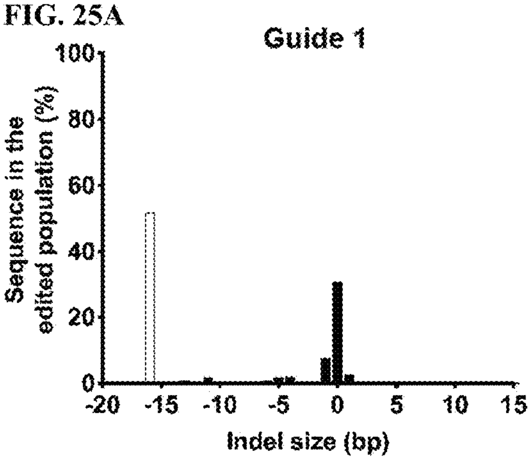
FIG. 25A-F presents exemplary data showing an Indel spectrum generated by SpyCas9 editing at the HPS1 locus in HPS1 B-LCL cells. Indel spectra of SpyCas9 nuclease cells treated with different sgRNAs determined by UMI-based Illumina deep sequencing. White bar indicates 16-bp deletion that corresponds to the deletion of one of the microduplication repeats. Data show indel spectra from one representative biological replicate out of three independent biological replicates.
Figure 25B:
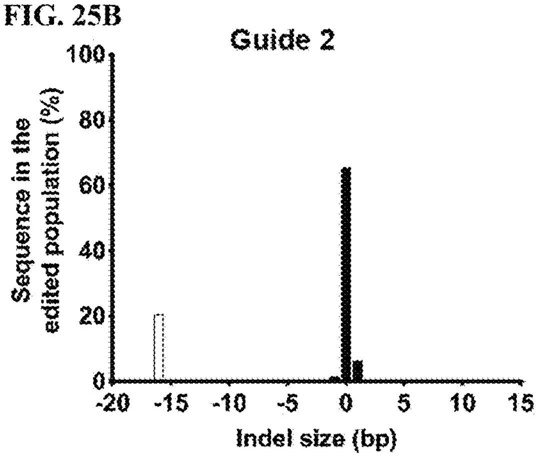
Figure 25C:
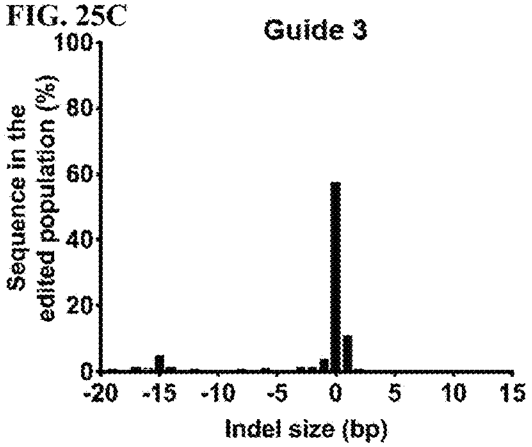
Figure 25D:
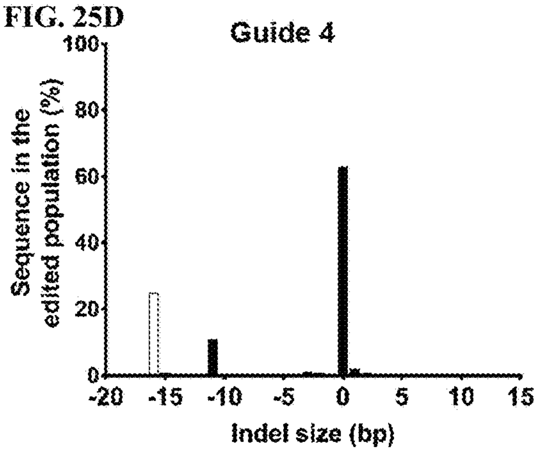
Figure 25E:
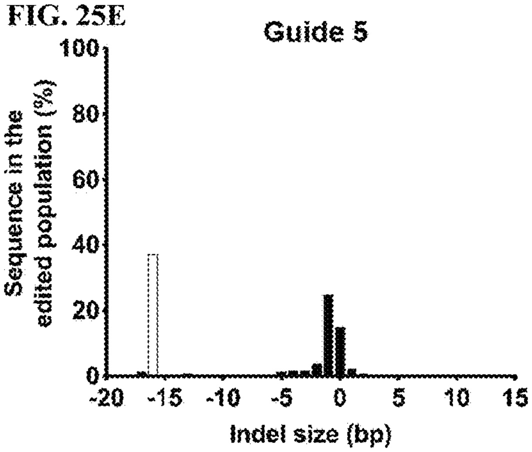
Figure 25F:
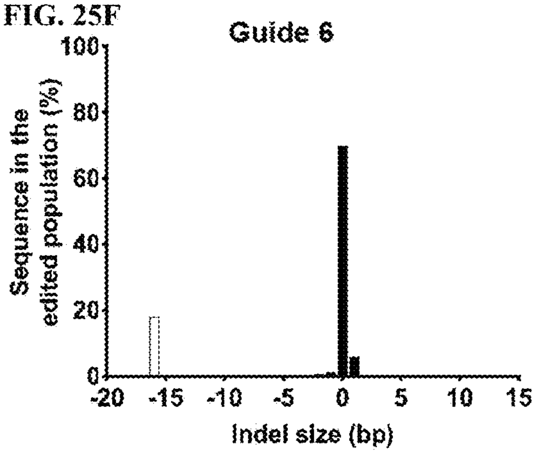

Gene correction efficacy was determined in a patient-derived B lymphocyte cell line (B-LCL) homozygous for the 16-bp microduplication by electroporating these cells with SpyCas9 RNPs programmed to cleave two base pairs away from the centre of the microduplication. See, FIG. 11A (target site 1). To accurately assess the observed editing rates, unique molecular identifiers (UMIs) were added to the PCR amplicons during Illumina library construction to allow the removal of any amplification bias[15]. It was confirmed that this approach accurately captured the relative percentage of HPS1 microduplication and wild-type alleles present in a series of test populations. See, FIG. 24. At HPS1 target site 1, editing was observed at about 46% of the alleles with around 35% restored to the wild-type sequence. See, FIG. 11B & FIG. 11C. The effect of the position of the DSB within the microduplication was further examined on the efficiency of MMEJ-mediated repair by designing five additional sgRNAs that targeted the DSB to different positions relative to the centre of the microduplication See, FIG. 11A (target sites 2-6). As the break site was shifted away from the centre, there was a decrease in the efficiency of achieving the precise 16-bp deletion. See, FIG. 11B & FIG. 11C. However, target sites 3 and 6 were notable exceptions to this trend. Target site 3 was observed to be quite efficient at generating indels to the exclusion of the 16-bp deletion, probably because the wild-type sequence, once regenerated, can also be targeted by this sgRNA for further mutagenesis. See, FIG. 25. On the other hand, target site 6 achieved efficient deletion of the 16-bp microduplication (more than 50% of the modified alleles), despite being the most distal of the cleavage sites (10 bp from the centre of the microduplication). Its efficiency may be due to the extended regions of homology that surround the cleavage site at this end of the microduplication. See, FIG. 11A (target site 6). Overall, these results demonstrate that the cleavage position within the microduplication and the presence of alternate regions of microhomology can influence the production of the desired wild-type end product. See, FIG. 11C.

Figure 12A:
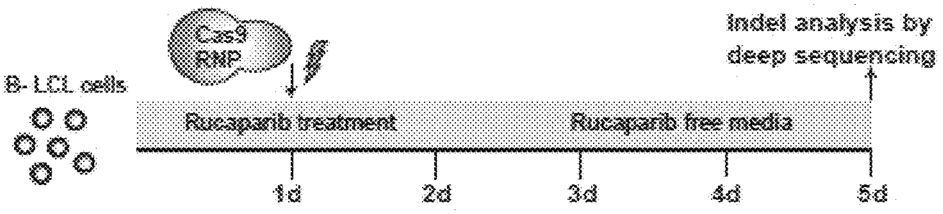
FIG. 12A-D presents exemplary data showing that PARP-1 inhibition decreases efficiency of MMEJ-based repair.
Figure 12B:
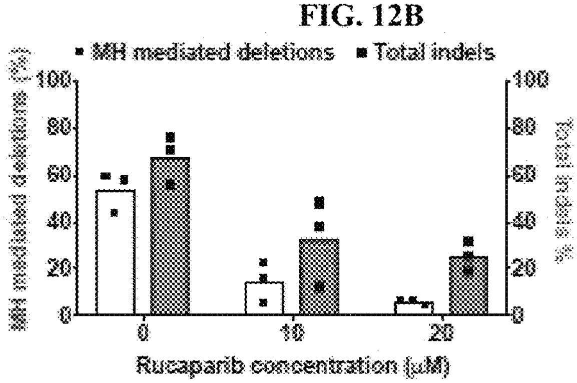
Figure 12C:
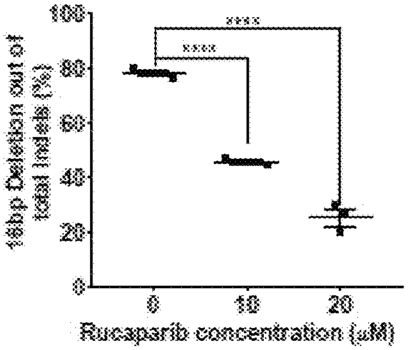
Figure 12D:
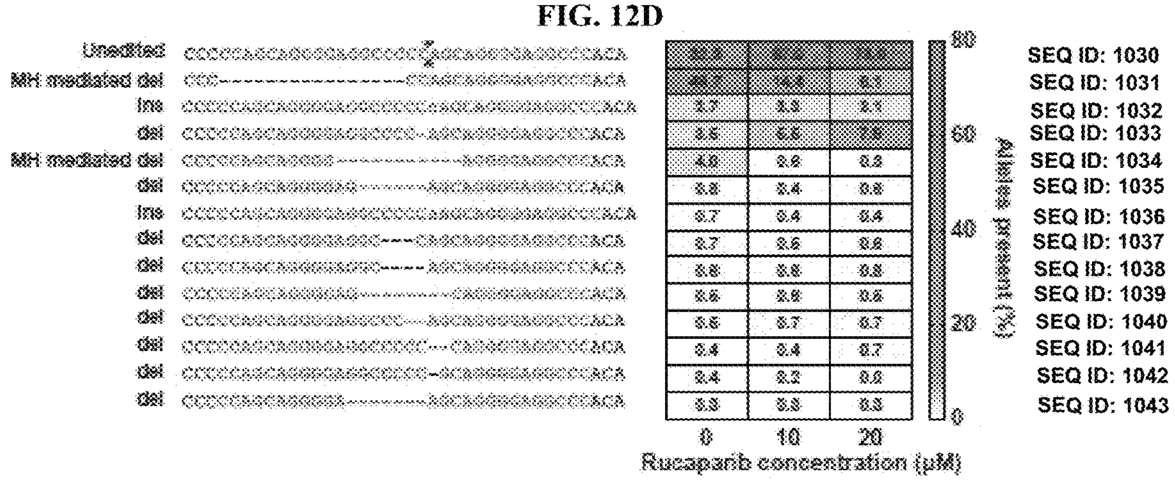

To investigate whether nuclease-mediated collapse of a microduplication occurs via the MMEJ pathway, a DNA repair factor (PARP-1) that regulates DSB flux through this pathway was inhibited. PARP-1 influences the repair of a DSB through resection-dependent DNA repair pathways, such as MMEJ[3,16], which are in competition with the non-homologous end joining pathway (NHEJ) for DSB repair[17]. See FIG. 18A. Inhibition of the catalytic activity of PARP-1 by rucaparib reduces DSB flux through the MMEJ pathway, resulting in a decrease in microhomology-based deletion products in the resulting repair events[18]. See, FIG. 18A. Patient-derived HPS1 B-LCL cells were treated with 10 UM or 20 μM rucaparib before and after treatment with SpyCas9 RNP to suppress MMEJ-mediated repair of DSBs. See, FIG. 12A. An overall reduction in editing rates was observed at the HPS1 locus upon rucaparib treatment. See, FIG. 12B. These lower editing rates were primarily the result of a reduction in the 16-bp deletion product, which decreased from about 50% in untreated cells to around 15% and 6% in cells treated with 10 μM and 20 μM rucaparib, respectively. See, FIG. 12B-12D. A similar reduction in microhomology-based deletions was observed with SpyCas9 RNP targeting the AAVS1 locus in patient-derived HPS1 B-LCL cells. See, FIG. 18. Thus, the MMEJ pathway underlies the robust correction of the microduplications for LGMD2G and HPS1 in the presence of a targeted DSB.

B. Tay-Sachs Disease (HEXA Gene)

In one embodiment, the present invention contemplates a method for HEXA editing by Cas12a to correct a mutated sequence of the Tay-Sachs locus.

Two different Cas12a (also known as Cpf1) orthologs (LbCas12a and FnCas12a) were tested for their ability to drive microhomology-mediated end joining (MMEJ) to collapse the common GATA microduplication in HEXA that is associated with Tay-Sachs disease. The GATA·GATA duplication (repeated segments) results in a frameshift within the gene that inactivates it and leads to Tay-Sachs if both HEXA alleles are disrupted). See, FIG. 14. This allele occurs with a frequency of ~1 in 100 individuals in some Jewish populations.

crRNAs were designed to target Cas12a cleavage to the region spanning the microduplication to revert it to the wild-type sequence through MMEJ repair. One crRNA was designed for FnCas12a to utilize a TTC PAM (FnCas12a Guide). See, FIG. 14. Two crRNAs were designed for LbCas12a to utilize either a CTTC PAM (LbCas12a Guide 1) or a TTCC PAM (LbCas12a Guide 2). See, FIG. 14. For LbCas12a, these PAMs are not the optimal TTTV sequence, which may result in lower activity.

crRNAs (120 pmol) were complexed with 60 pmol of purified FnCas12a-2×NLS or LbCas12a-2×NLS protein and then electroporated into a B-EBV cell line that is homozygous for the GATA microduplication in HEXA (Coriell GM11852). See, Table 3.

TABLE 3 crRNA Sequences for crRNAs targeting HEXA duplication

| SEQ ID | crRNA/Cas12a | Cas12a crRNA sequence |
|---|---|---|
| 152 | LbCas12a Hexa guide 1 | **UAAUUUCUACUAAGUGUAGAU**CAGUCAGGGCCAUAGGAUAGAUA |
| 153 | LbCas 12a Hexa guide 2 | **UAAUUUCUACUAAGUGUAGAU**AGUCAGGGCCAUAGGAUAGAUAU |
| 154 | FnCas12a Hexa guide | **UAAUUUCUACUGUUGUAGAU**CAGUCAGGGCCAUAGGAUAGAUA |

In the crRNA sequences the constant region is in bold. Double underline indicates the base pairing regions of the hairpin stem. Single underlined sequence is the guide sequence (23 nt)

After 72 hours the genomic DNA from treated cells were harvested and the genomic region of interest within HEXA was PCR amplified and submitted for Sanger sequencing. Mutation rates were determined by TIDE analysis (tide.deskgen.com) in comparison to an unedited sequence chromatogram from the same genomic region. Total indels were modest (~5 to 10%). See, FIG. 15 (grey bars). A reversion to the wild-type sequence was observed in all of the samples (brown bars), where for LbCas12a guide 2 the majority of the alleles that were edited restored the desired wild-type sequence. The experiment was performed in biological triplicate, where the error bars represent the standard error of the mean.

Representative sequence chromatograms show sequencing on the complementary strand. See, FIG. 16. The TATC duplication (complement of GATA) is boxed in and the respective guide target sequences for each nuclease are underlined.

The concentration of the delivered Cas12a: crRNA was then increased for each nuclease: guide combination from 90 pmol to 180 pmol. The editing rates after electroporation of the HEXA GATA duplication in the B-EBV line in a single experiment were improved (white bars) and the rate of wild-type sequence reversion was also increased, reaching nearly 10% for the LbCas12a guide 2 treated cells (grey bars). See, FIG. 17. These data demonstrate the feasibility of reverting the mutant allele to the wild-type DNA sequence through the introduction of a targeted double-strand break without the need of a donor DNA sequence (or homology directed repair) for this restoration.

Those in the art would appreciate that the current data showing the correction disease-causing alleles for two different diseases provides an expectation that the technology has widespread applicability. Furthermore, as more diverse programmable nuclease systems are defined (e.g., CRISPR systems) that have broader targeting range and better delivery properties, this type of approach will become easier to perform in vivo. Although it is not necessary to understand the mechanism of an invention, it is believed that this approach may also work efficiently for genetic diseases based upon repeat expansion mutations if DSBs can be targeted just inside the edges of the repeat elements to allow the induction of long-range microhomology mediated repair.

IV. Genomic Microduplication Variants

Figure 26A:
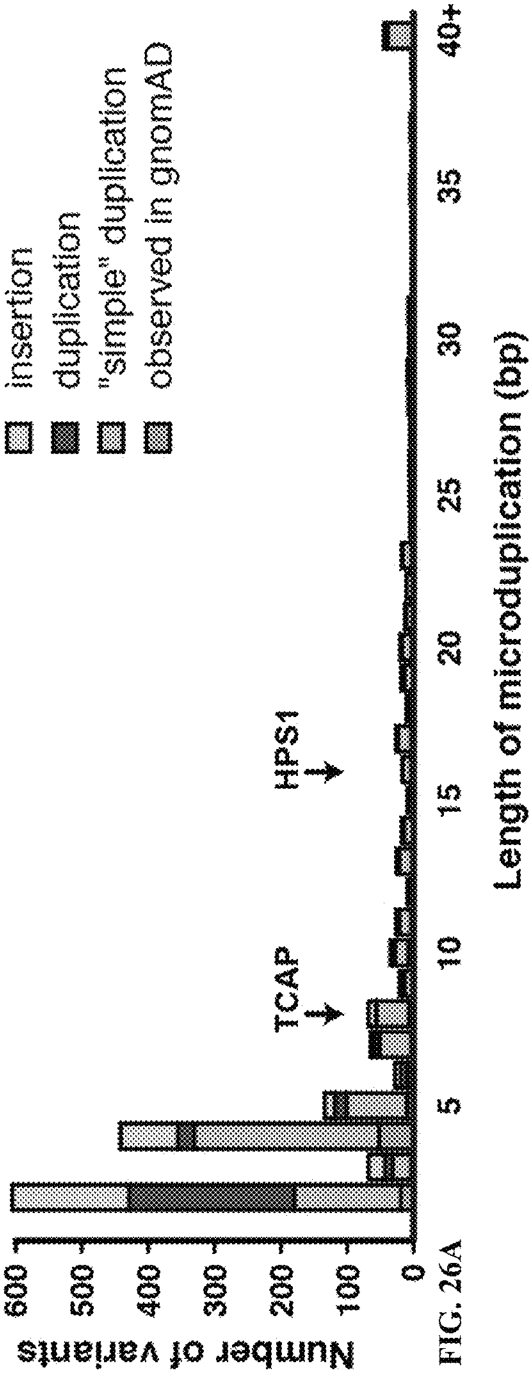
FIG. 26A-B presents exemplary data showing pathogenic microduplications and their prevalence in human populations.
Figure 26B:
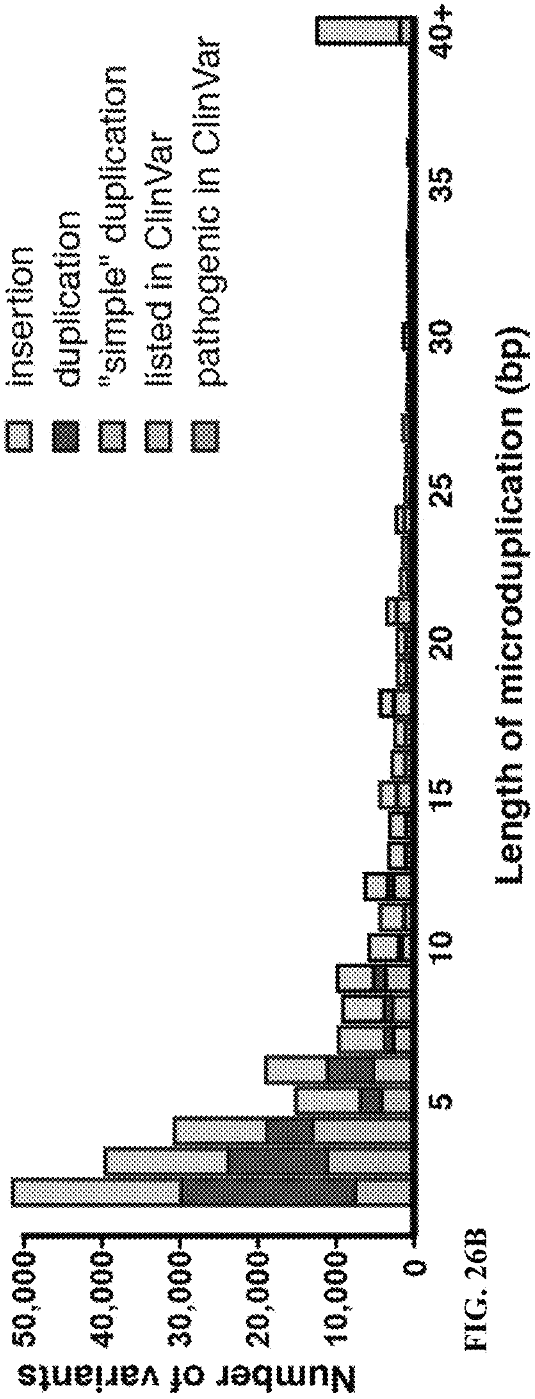
Figure 27:
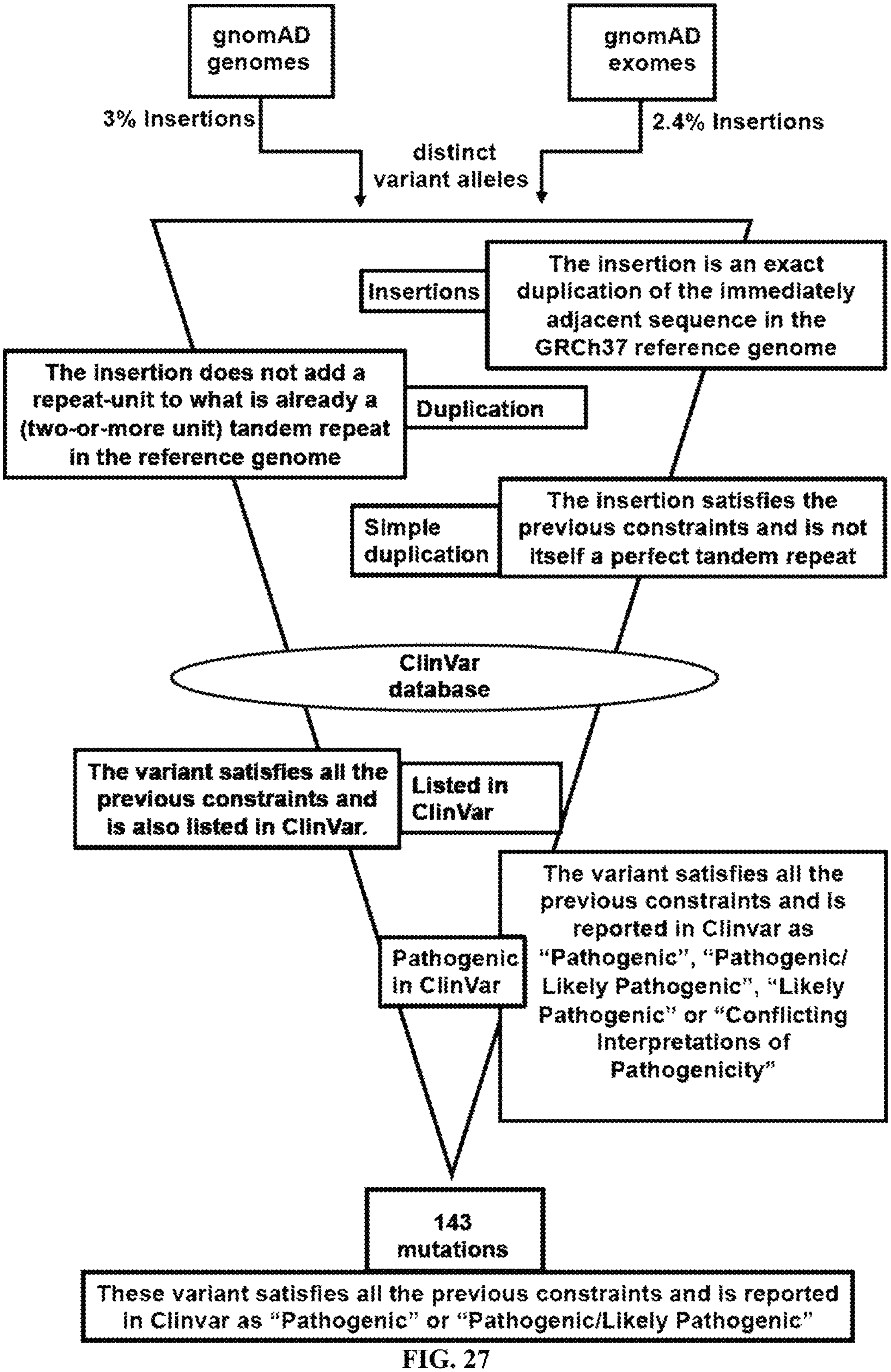
FIG. 27 presents an exemplary bioinformatics pipeline for identification of disease alleles. Schematic shows the bioinformatics pipeline used to identify all microduplications amendable to efficient MMEJ-mediated collapse from the 'coding' regions (exome_calling_regions.v1; mainly exons plus 50 flanking bases) in the gnomAD genome and exome databases (version 2.0.2). Insertion variants observed in both databases were used for analysis (variants occurring in both databases were counted once). Insertions that do not add a repeat-unit to an existing tandem repeat and are not themselves a perfect repeat were filtered to constrain only duplications that spanned 2-40 bp in length and are amendable to CRISPR-Cas9 targeting. This data set was then cross-referenced against the Clin Var database (clinvar_20180225.vcf) to apply further filters for variants reported as pathogenic, which ultimately yielded 143 likely disease-causing microduplications.

To investigate whether this MMEJ-based therapeutic strategy can be applied more broadly for correcting human genetic disorders, a bioinformatic analysis was performed to gauge the prevalence of disease-causing microduplications in human populations. The Clin Var database[20] includes about 4,700 duplications that are annotated as 'pathogenic' or 'pathogenic/likely pathogenic'. See, FIG. 26A. Duplications of lengths ranging from 2 to 40 bp were of particular interest because the data presented herein indicate that microhomologies within this range can be precisely repaired via the MMEJ pathway. See, FIG. 13. 'Simple' duplications-those for which the duplicated sequence is not part of a more complex repeat structure-were also evaluated as to whether they improve the odds that the primary homology-based collapse would result in the desired wild-type sequence. Finally, all duplications in 'coding' regions (mainly exons plus 50 flanking bases) were examined from the gnomAD exome and genome sequencing databases[21] to prioritize pathogenic duplications according to their frequencies in human populations. See, FIG. 26A and FIG. 27. The present analysis yielded 143 likely disease-causing microduplications of lengths 2-40 bp that were observed at least once in gnomAD, some of which occur in specific subpopulations at substantial frequencies (for example, Tay-Sachs disease), See, FIG. 26B.

To facilitate the utilization of a bioinformatics analysis, the present invention was accompanied by the creation of an interactive, searchable webtool (rambutan.umassmed.edu/duplications/). This bioinformatices analysis also included the identification of potential Cas9 and Cas12a cleavage sites within these microduplications[22]. As shown within the tool, 'tiling' data across HPS1 microduplications and endogenous microduplication sites, the position of the DSB break within the duplication, and the use of a guide design that avoids cleavage of the wild-type allele, facilitate an efficient, stable collapse of microduplications. Rapid advances are being made in characterizing nucleases with alternate specificities[23,24] and in engineering nucleases with alternate or expanded recognition preferences[25-27], which will make correction of disease-causing microduplications using the MMEJ-based approach even more effective.

The results below for the most part are based on the files of "coding" variants from gnomAD genomes and exomes, version 2.0.2. gnomad.broadinstitute.org/downloads. This database comprises variants in the intervals used for the ExAC database. Most of these intervals correspond to exons plus 50 flanking bases on each side, and they collectively cover 60 million bases, about 2% of the genome. Note that there are no variant calls for the Y chromosome, and these are not strictly all coding variants, as some are in introns, UTRs, miRNA, ncRNA.

The 1000 Genome Project data was taken from ftp.1000genomes.ebi.ac.uk/vol1/ftp/release/20130502/. The vcf files there include precomputed allele-frequencies for five broad super-populations and allele-frequencies for 26 more-specific populations computed from the per-individual genotypes in the vcf files aggregated using the population assignments from the file integrated_call samples_v3.20130502.ALL.panel.

The Clin Var annotations were taken from the file ftp.ncbi.nlm.nih.gov/pub/clinvar/vcf_GRCh37/clinvar_20180225.vcf.gz. Here, the variants have been normalized (trimmed and left-aligned) for the purpose of matching them up, but the HGNC notation used at Clin Var may follow the right-aligned (3'-most position) convention, in which duplications are taken to occur immediately after the repeated sequence rather than immediately before the repeated sequence.

The gnomAD genome files contain a total of 4851138 distinct variant alleles, of which 145892 (~3%) are insertions. The gnomAD exome files above contain a total of 17009588 distinct variant alleles, of which 414576 (~2.4%) are insertions. Note that many of these variants are common to both the exomes and genomes, but in the tables below variants that occur in both are counted only once.

Table 4 below focuses on the insertions, and in particular the duplications. The second column (insertions) gives the counts of all the distinct insertion variant alleles, binned by the length of the insertion (length), with all variants of length at least 40 combined into one bin. Subsequent columns give the number of variants that satisfy additional criteria, as follows:

- dup: the insertion is an exact duplication of the immediately adjacent sequence in the GRCh37 reference genome (immediately 3' with this normalization). Note that there may be polymorphism in this adjacent sequence that affect whether an insertion is indeed a perfect duplication for any given individual.
- dup2: the insertion does not add a repeat-unit to what is already a (two-or-more unit) tandem repeat in the reference genome. This eliminates e.g. the duplication of CCCGGG (SEQ ID NO: 155) in RAX2, as the reference genome already has two immediately adjacent (3') tandem copies of this: ncbi.nlm.nih.gov/projects/SNP/snp_ref.cgi?rs=rs549932754 dup2i: the insertion satisfies the previous constraints and is not itself a perfect tandem repeat (e.g., for a duplicated six-mer, it is not of the form XXXXXX, XYXYXY or XYZXYZ). Note that even if a duplicated sequence is not in itself a perfect tandem repeat it may contain internal tandem repeats—e.g. the AGGAGG (SEQ ID NO: 156) in the duplicated AAGGAGGATC (SEQ ID NO: 157) in NCF4—so depending on where the Cas9 cleavage site is this may need to be considered, to prevent a shorter internal microduplication from being collapsed instead of the full duplication.

dup2iC: the variant satisfies the previous constraints and is also listed in Clin Var.

dup2iL: the variant satisfies the previous constraints and is reported in Clinvar as "Pathogenic", "Pathogenic/Likely_pathogenic", "Likely_pathogenic" or "Conflicting_interpretations_of_pathogenicity"

dup2iP: the variant satisfies the previous constraints and is reported in Clinvar as "Pathogenic" or "Pathogenic/Likely_pathogenic"

TABLE 4

Microduplication Variant Characteristics In Clin Var And gnomAD Databases

| length | insertions | dup | dup2 | dup2i | dup2iC | dup2iL | dup2iP |
|---|---|---|---|---|---|---|---|
| 1 | 210230 | 179654 | 59169 | 59169 | 399 | 242 | 182 |
| 2 | 51418 | 29880 | 11919 | 7562 | 53 | 25 | 19 |
| 3 | 39579 | 23795 | 12892 | 11141 | 77 | 11 | 4 |
| 4 | 30704 | 18835 | 14615 | 13010 | 112 | 70 | 52 |
| 5 | 15142 | 6890 | 4754 | 4189 | 28 | 16 | 10 |
| 6 | 18971 | 11102 | 6125 | 5251 | 46 | 7 | 3 |
| 7 | 9634 | 3793 | 2976 | 2623 | 10 | 5 | 4 |
| 8 | 9123 | 3819 | 3038 | 2739 | 12 | 9 | 7 |
| 9 | 9818 | 5155 | 3979 | 3686 | 17 | 3 | 2 |
| 10 | 5756 | 1997 | 1683 | 1502 | 12 | 9 | 8 |
| 11 | 4326 | 1311 | 1236 | 1195 | 10 | 6 | 4 |
| 12 | 6249 | 3384 | 2957 | 2649 | 18 | 3 | 0 |
| 13 | 3207 | 1099 | 1068 | 1042 | 7 | 4 | 2 |
| 14 | 3068 | 1031 | 993 | 942 | 5 | 2 | 1 |
| 15 | 4307 | 2311 | 2190 | 2110 | 19 | 7 | 3 |
| 16 | 2813 | 1173 | 1128 | 1086 | 8 | 4 | 4 |
| 17 | 2438 | 1099 | 1069 | 1067 | 9 | 7 | 6 |
| 18 | 4316 | 2646 | 2552 | 2459 | 14 | 4 | 4 |
| 19 | 2065 | 1012 | 997 | 997 | 5 | 3 | 1 |
| 20 | 2148 | 1082 | 1045 | 1001 | 6 | 5 | 3 |
| 21 | 3463 | 2218 | 2141 | 2127 | 11 | 2 | 1 |
| 22 | 1687 | 818 | 806 | 799 | 1 | 0 | 0 |
| 23 | 1395 | 690 | 670 | 670 | 3 | 3 | 3 |
| 24 | 2272 | 1283 | 1244 | 1221 | 7 | 2 | 1 |
| 25 | 1149 | 485 | 477 | 471 | 1 | 1 | 1 |
| 26 | 1006 | 356 | 353 | 350 | 3 | 0 | 0 |
| 27 | 1373 | 653 | 635 | 631 | 6 | 1 | 0 |
| 28 | 878 | 314 | 308 | 304 | 3 | 1 | 1 |
| 29 | 751 | 239 | 233 | 233 | 1 | 1 | 0 |
| 30 | 1321 | 579 | 549 | 536 | 1 | 0 | 0 |
| 31 | 693 | 194 | 189 | 189 | 1 | 1 | 1 |
| 32 | 695 | 193 | 187 | 182 | 0 | 0 | 0 |
| 33 | 772 | 272 | 263 | 262 | 3 | 0 | 0 |
| 34 | 590 | 169 | 164 | 157 | 0 | 0 | 0 |
| 35 | 528 | 121 | 117 | 116 | 0 | 0 | 0 |
| 36 | 743 | 244 | 236 | 225 | 1 | 0 | 0 |
| 37 | 457 | 106 | 102 | 102 | 1 | 0 | 0 |
| 38 | 474 | 122 | 115 | 113 | 0 | 0 | 0 |
| 39 | 524 | 149 | 140 | 140 | 2 | 0 | 0 |
| 40+ | 12413 | 1818 | 1800 | 1756 | 7 | 1 | 1 |

TABLE 4

Totals:

| length | insertions | dup | dup2 | dup2i | dup2iC | dup2iL | dup2iP |
|---|---|---|---|---|---|---|---|
| 1-40+ | 468496 | 312091 | 147114 | 136004 | 919 | 455 | 328 |

Note that the filters used in columns dup2 and dup2i are included to increase the chances of MMEJ restoring the duplication to exactly its wild-type form, via removal of exactly one complete copy of the duplicated sequence, but these filters may not be strictly necessary when suitable positions in the duplication can be specifically targeted for cleavage.

A lot of duplications, do not appear annotated as "Pathogenic" in ClinVar. Certainly there are many variants listed in Clin Var that are not observed in either the gnomAD genomes or exomes, so are not accounted for in the table above, and this includes 2189 duplications that satisfy all the additional conditions for being in column dup2iP above. But 2183 of these are in these "coding" intervals, so if the variants had been observed at all in gnomAD they would have been reported in these vcfs. It also wouldn't be surprising to miss variants that are extremely rare in general, or even not-terribly-rare variants that are concentrated in populations without many samples: with only ~100 subjects per population in the TGP data one would expect to miss out on ~13% of alleles with frequency 0.01 in these populations. And a few other possibilities:

Subjects known to have severe pediatric disease were not included in the gnomAD dataset, so variants that cause these diseases may be under-represented, in particular those with dominant inheritance.

About 8% of the genome was masked during the gnomAD variant calling (e.g. some repetitive sequence), so any ClinVar variants the fall in these regions will not be reported in gnomAD. But it appears that only one of the ~13000 insertions from ClinVar falls in one of these masked region—a benign variant in SHOX1 which is masked since it's in a PAR on the Y chromosome.

gnomAD doesn't report variants on the Y chromosome at all, whether in masked regions or not. But the only "Pathogenic" duplication on the Y chromosome in ClinVar is a single-base insertion, Y: 2655380:C/CT in the gene SRY: ncbi.nlm.nih.gov/clinvar/variation/470195/·

The longest insertion reported in the gnomAD coding regions has length 621, and there are 1431 insertions of length at least 100, but it's possible that the detection sensitivity may decline for longer insertions.

The above described variants are listed below; they are mainly variants in UTRs or in intronic regions >50 bases from the nearest exons (and hence not in the "coding" intervals list). gnomAD and TGP vcfs are mainly variants in UTRs or in intronic regions >50 bases from the nearest exons. These sequences are expected to represent "Pathogenic" duplications with a length of at least 100 from Clin Var that satisfy the conditions of the column dup2iP above, none of which are observed in gnomAD. See, Table 5. The First base in the reference allele, the subsequent bases are the inserted sequence

TABLE 5

| Duplications Not Contained In "Coding " Inverval List Or Having Length At Least 100 That Are In Clin Var But Not Present In Either ClinVar Or gnomAD Databases |
|---|
| GTGAGCCACTGCGCCCAGCAGATTCAAGCTTTTTAAATGGAATTTTGAGCTGATTTAGTTG AGACTTACGTGCTTAGTTGATAAATTTTAATTTTATACTAAAATATTTTACATTAATTCAAG TTAATTTATTTCAGATTGAATTTAGTGGAAGCTTTTGTAGAAGATGCAGAATTGAGGCAGA CTTTACAAGAAGATTTACTTCGTCGATTCCCAGATCTTAACCGACTTGCCAAGAAGTTTCA AAGACAAGCAGCAAACTTACAAGATTGTTACCGACTCTATCAGGGTATAAATCAACTACC TAATGTTATACAGGCTCTGGAAAAACATGAAGGTAACAAGTGATTTTGTTTTTTTGTTTTC CTTCAACTCATACAATATATACTTGGCAATGTGCTGTCCTCATAAAGTTGGTGGTGGTGAC TCACTCTTAGGACACATTCAGATTTCTT (SEQ ID NO: 158) |
| AG |
| GT |
| GAGCTTATCAGGTTCTCCATTGGCAGGCAGGGCTCTAAGTGCAGTAACTTGATTTGCTGTT GTATTTGCTTAGGAAGAGCAGCACTTCAGAAAAGAGTGATGGCACTGCTGAGGCGCATTG AGCATCCCACTGCAGGAAACACTGAGGTATGCCCTTAGCAACAGAAACACCCCTCCCAGG CGCCCACCCTCAATTTGGAAGCCTCTTGTTACATATGTGTGATCAGGAATAGCTTTTGAAG TAAATCCAAGATACGTGCATATTACAAGTATAATATCTGAGTATTTAATATACATCAAGTT TGAAACTTGGCTGTAGCTGATTGATGTTTAGCTCT (SEQ ID NO: 159) |
| TGGGTACGAGTGTCTGCGTATATCTGTATGCTTATTTGGCTCTATGCCTGTGGGTGCACTTA CTCTGTGTGTTTAGATCAGTCAGTTTCATCTCTCTAGGGGGTCTGTCTTCTGGGCATTGATG GCAAATCATTAATGTATTTGTTCTTTCTTTAGGTTTTATTGACTGATACCAATACTCAATTT GTAGAACAAACCATAGCTATAATGAAGAACTTGCTAGATAATCATACTGAAGGCAGCTCT GAACATCTAGGGCAAGCTAGCATTGAAACAATGATGTTAAATCTGGTCAGGTAAGCATTC TACTGAAATGTAGCAGAAACATTTTAAGAGATAAGAAAAACCTCTTACACACTGATACTG GTAGTAATTGATAAAATAACTGGCCATTCTTTACTGCACACAAACTA (SEQ ID NO: 160) |
| ACCGGTTCCGGCGGCCGGGGCTG (SEQ ID NO: 161) |
| GTGAGCCACTGCGCCCAGCAGATTCAAGCTTTTTAAATGGAATTTTGAGCTGATTT AGTTGAGACTTACGTGCTTAGTTGATAAATTTTAATTTTATACTAAAATATTTTAC ATTAATTCAAGTTAATTTATTTCAGATTGAATTTAGTGGAAGCTTTTGTAGAAGAT GCAGAATTGAGGCAGACTTTACAAGAAGATTTACTTCGTCGATTCCCAGATCTTAA CCGACTTGCCAAGAAGTTTCAAAGACAAGCAGCAAACTTACAAGATTGTTACCGA CTCTATCAGGGTATAAATCAACTACCTAATGTTATACAGGCTCTGGAAAAACATG AAGGTAACAAGTGATTTTGTTTTTTTGTTTTCCTTCAACTCATACAATATATACTTG GCAATGTGCTGTCCTCATAAAGTTGGTGGTGGTGACTCACTCTTAGGACACATTCA GATTTCTT (SEQ ID NO: 162) |
| TTGGGAGCTAACGGCTTGGAGCTTCTTTCCAGGGATGGGGACCTGGAATTTGAGT ACTGGTAGACTTTTCGTTGTTCAAACCATTCCTTCACAAATTCCTGAGGAAGGCCC ACAGC (SEQ ID NO: 163) |
| TACCTTGGGCCTGGGCCGCAGAGCTGTGAGAATACCCCAGGGCCAGGAGCGCAGT CTCCACCAGCTGGCTAAAAAGCACATCTTTCCGCACCAGGACAAACTCGGCGTGT TCTTCTCTGTTGTCATATTCAAGAGAGCCGTCCAACTGCTCCACGACACAAAAGAC AGGAATCATCAA (SEQ ID NO: 164) |
| GTGCGCGGGCGGCGGCCGGAAGGGCCTCTTCATGCGGCGGCGGCGCCGGTAGTTG CCCTTCTCGAACATGTCTTCGCAGGCCGGGTCCAGCGTCCAGTAGTTGCCCTTGCG CTCGCCGCCGCCCT (SEQ ID NO: 165) |
| CCGGGCTGGAGAGGGGGATGTTGAGGAGGCTGGGGGTGGGGGCGGGGCATCGAG GGAGCTCCTGGTACTGGCGGCCCCGACTGTCCCCCCAGAAGCTGAAAATGTTGGA CACTCCTGAGAAGGCGCCTGCAGCCAGAGAGCAGAGCTGGGTGAGCGGGGTAGA CGCACCACCGCTGCCACGCCCGGTCCTCCCTCGCCCGCCCGTCGCCCGGGATACCT GACAGGGGGTTGCAAGTGTCGCTGCTCTTCTCGCAGTCCTCCATCAGGGGCTCCCC A (SEQ ID NO: 166) |
| GAGCTTATCAGGTTCTCCATTGGCAGGCAGGGCTCTAAGTGCAGTAACTTGATTTG CTGTTGTATTTGCTTAGGAAGAGCAGCACTTCAGAAAAGAGTGATGGCACTGCTG AGGCGCATTGAGCATCCCACTGCAGGAAACACTGAGGTATGCCCTTAGCAACAGA AACACCCCTCCCAGGCGCCCACCCTCAATTTGGAAGCCTCTTGTTACATATGTGTG ATCAGGAATAGCTTTTGAAGTAAATCCAAGATACGTGCATATTACAAGTATAATA TCTGAGTATTTAATATACATCAAGTTTGAAACTTGGCTGTAGCTGATTGATGTTTA GCTCT (SEQ ID NO: 167) |
| TGGGTACGAGTGTCTGCGTATATCTGTATGCTTATTTGGCTCTATGCCTGTGGGTG CACTTACTCTGTGTGTTTAGATCAGTCAGTTTCATCTCTCTAGGGGGTCTGTCTTCT GGGCATTGATGGCAAATCATTAATGTATTTGTTCTTTCTTTAGGTTTTATTGACTGA TACCAATACTCAATTTGTAGAACAAACCATAGCTATAATGAAGAACTTGCTAGAT AATCATACTGAAGGCAGCTCTGAACATCTAGGGCAAGCTAGCATTGAAACAATGA |

TABLE 5-continued

| Duplications Not Contained In "Coding " Inverval List Or Having Length At Least 100 That Are In Clin Var But Not Present In Either ClinVar Or gnomAD Databases |
|---|
| TGTTAAATCTGGTCAGGTAAGCATTCTACTGAAATGTAGCAGAAACATTTTAAGA GATAAGAAAAACCTCTTACACACTGATACTGGTAGTAATTGATAAAATAACTGGC CATTCTTTACTGCACACAAACTA (SEQ ID NO: 168) |
| CCCAATTCAATGTAGACAGACGTCTTTTGAGGTTGTATCCGCTGCTTTGTCCTCAG AGTTCTCACAGTTCCAAGGTTAGAGAGTTGGACACTGAGACTGGTTTCCTGCTAAA CAGTATGGTAAAGAACAGTCAAGCAATTGTTGGCCAGTTCTGTGCTTTTCCTCCTG AAGAGAAACTTGACACCATGGACAAAATAAATTGACCATCATCAGTCAGCTAACA TGTATGATGCCTGGAAAAAATGCCCAGGAATTTACACACTAAAATGTCTGGGGCT GGGAGCGGTAGCTCATGCCTATAATCCCAGCACTTTGGGAGGCTGGAGCAGGACT GCTTGAGGCCAGGAGTTCAAGACCAGCATAAGCAACAGAGTGAGACCCAGTCTCT ACAAAATAATAGTAGTAGTAATAATAAAATGTGTGGGATATGTGTGATTTGAATT TTTTTTTCTGTTGTCTTAAATTTTTCAAACCTGATTATGTATTATTTGTGTAATTTTT GAAGTATTAATATAGCATATTTTGAAGCTGATACTTGATATACATTCCAATCACAT CTGATAACTTTTTTTTTTGTTTTGGGGGGTGTACAGAGTCCTGCTCTGTCACCCAGG CTGGAGTGCAGTGGCGCAATCTCAGCTCACTGCAACCTCCGCCTCCTAAGTTCAAG AGATTCTCCTGCCTCAGCCTCCTGAGTAGCTGGGTCTACAAGCGTGTGCAACTATG CCTGGCTAATTTGTGTGTGTGTGTGTATATATATATACATATATATGTGTGTGTGTG TGTATATATATATATAACATATATATAACATATATATATTATATATATATAACATA TATATAACATATATATATGTTATATATATATAACATATATATAACATATATATATA TATATATATAATATATATATATATATATATATATATGTAATCCCAGCACTTTGGGATA TATGTGTATATATGTTTTTTTTTTTTGAGACAGAATCTTGCTCTGTTGCCAGGCTAG AGTGCAGTGGCGTGATCTCGGCACACTGCAACCTCCACCTCCCTGGTTCAG (SEQ ID NO: 169) |
| GGGGGCCATTGTGGAAAAGAGCCTGCAGGGAGAGCAAACAGCGCGGTCATGGCC TCGGGAGCTGTGCGCGGCGCCTCGGGCAGCGTCTCCCGCCGCTTGTCGCC (SEQ ID NO: 170) |

Duplication variants were identified as annotated as "Pathogenic" or "Pathogenic/Likely_pathogenic" in the Clin Var database (Table 4, dup2iP column), and observed in the gnomAD exome database. See, Table 6.

Table 6 has the following headings:

SEQ_DUP shows the duplicated sequence in upper-case (including the extra copy on the variant allele), and flanking sequence in lower case.

DUP_NUM labels the copies of the duplicated segment (1 for first copy, 2 for second). these positions are also color-coded yellow and cyan in the html table, but the colors are lost when exporting the table as a CSV or Excel file.

Cas9_Wa shows cleavage sites for Cas9 and xCas9 enzymes on the Watson strand, 3 bases left of PAM starts from PAM_FW_* columns.

Cas9_Cr shows cleavage sites for Cas9 enzymes and xCas9 on the Crick strand, 4 bases right of PAM starts from PAM_RC_* columns.

Cpf1_Wa shows approximate cleavage sites for Cpf1 enzymes on the Watson strand, 19 bases right of PAM ends (from the PAM starts in PAM_FW_* columns and adjusted for motif widths).

Cpf1_Cr shows approximate cleavage site for Cpf1 enzymes on the Crick strand, 18 bases left of PAM ends (from the PAM starts in PAM_FW_* and adjusted for motif widths).

TABLE 6

Selected Genes Having Microduplication Variants

| SYMBOL | MICRODUPLICATION INFORMATION | | SEQ ID NO: |
|---|---|---|---|
| PEX10 | ctgccgctgcctgaaaccgtacagcTTgcagccccatggacagcaccaggtg | SEQ_DUP; | 171 |
| | .........................12......................... | DUP_NUM; | |
| | .A..A...aB.J..A....A...A..A......aaJ..A.....aa.A..A. | Cas9_Wa; | |
| | .A.a.a..Aa.a..Aa.....Aa...A..a...A..Aaaa.....A..A.aa | Cas9_Cr; | |
| | .....L......NL..................................N... | Cpf1_Wa; | |
| | ................L................................... | Cpf1_Cr; | |
| CLCNKB | cgtggctggagggatcaccaatcccAAtcatgccaggggggtatgctctggc | SEQ_DUP; | 172 |
| | .........................12......................... | DUP_NUM; | |
| | A..aa.aaaC.................A...aaaaaA...A....aA..aaH | Cas9_Wa; | |
| | ..A.Ca...A.........Ca.aa..CaaaI.Ca..IAa...........AJ | Cas9_Cr; | |
| | ....k.M..NLL.................................L...... | Cpf1_Wa; | |
| | ....N............................................... | Cpf1_Cr; | |
| ZMPSTE24 | tgtgggagatgccggccgagaagcgTTatcttcggggccgtgctgctctttt | SEQ_DUP; | 173 |
| | .........................12......................... | DUP_NUM; | |
| | aa.aC.A..aA..a.aB.a.A........aaaA..a.A..A..........a | Cas9_Wa; | |
| | A.a.............Aa..Aa......A....Ca.Ba....Aa...A..a. | Cas9_Cr; | |
| | ......................k.........................N.M. | Cpf1_Wa; | |
| | ..................................L...............L. | Cpf1_Cr; | |
| MMACHC | tgtggcctaccatctgggccgtgttAAgagaggtgaggaaggctcagttttc | SEQ_DUP; | 174 |
| | .........................12......................... | DUP_NUM; | |
| | A..........aaA..a.A....a.a.aa.a.aaB.aA....A......... | Cas9_Wa; | |
| | a.......J.aa..Aa.Ca....Aa......J...............A.a.. | Cas9_Cr; | |
| | ..............................................N..... | Cpf1_Wa; | |
| | ....N...........LN........................k......... | Cpf1_Cr; | |
| ACADM | tccagtccccctaattagaagagccTTgggaacttggtttaatgaacacaca | SEQ_DUP; | 175 |
| | .........................12......................... | DUP_NUM; | |
| | A............aB.a.A....aaaB....aA.....Jab.J......... | Cas9_Wa; | |
| | .....Caah..aaaaa............Aa.......A.............A | Cas9_Cr; | |
| | ......N.....k..N.....M.L.....L.......N..........N... | Cpf1_Wa; | |
| | .......LLN........N..LN..................N........N. | Cpf1_Cr; | |
| ACADM | aaaactaatgagggatgccaaaatcTTatcaggtaaggttaaagatgatttt | SEQ_DUP; | 176 |
| | .........................12......................... | DUP_NUM; | |
| | .....a.aaaC.A..............aA...aA.....aC.aC.......a | Cas9_Wa; | |
| | .........A.............Aa....Ca..ICa................ | Cas9_Cr; | |
| | .k...........M..................................N.M. | Cpf1_Wa; | |
| | .............N.....k.....................N.........N | Cpf1_Cr; | |

TABLE 6-continued

Selected Genes Having Microduplication Variants

| SYMBOL | MICRODUPLICATION INFORMATION | | SEQ ID NO: |
|---|---|---|---|
| ABCA4 | ttacgatgtcccagaggaagttggtCCacccagtaggtggtggggctcactc | SEQ_DUP; | 177 |
| | .........................12......................... | DUP_NUM; | |
| | aC.A.....a.aaB.A..aA.......A..aa.aa.aaaA............ | Cas9_Wa; | |
| | ..A.a...A.....aaa............aa.aaaH..............A. | Cas9_Cr; | |
| | .......................N.......L...........N....L... | Cpf1_Wa; | |
| | ...................................M.k.....L........ | Cpf1_Cr; | |
| AGL | gaactgaccaatgagaatgcccagtAActgtcctttcagctgtgaaacacaa | SEQ_DUP; | 178 |
| | .........................12......................... | DUP_NUM; | |
| | .a......aHaB..A....A.....A........A..a.aB.......A... | Cas9_Wa; | |
| | .Baa....A...Aa..........Aaa.....A...aa..Ba..A....... | Cas9_Cr; | |
| | ...L...N..........NLL............................... | Cpf1_Wa; | |
| | ....N.................Lk.....N.........N............ | Cpf1_Cr; | |
| FLG | tgataatgataagaactagaactgtGGaggactgccacgtgactgtattcct | SEQ_DUP; | 179 |
| | .........................12......................... | DUP_NUM; | |
| | ...aC...aB....aB...a.aa.aa...A....a.a...A......Ha.a. | Cas9_Wa; | |
| | a...................A.....A.........A..Aa.a....A.... | Cas9_Cr; | |
| | .k.....kL.............N............................. | Cpf1_Wa; | |
| | ....L...............................M.......N....... | Cpf1_Cr; | |
| GBA | cccacgacactgcctgaagtagaagCCaatcctgtgaggctgccagccatga | SEQ_DUP; | 180 |
| | .........................12......................... | DUP_NUM; | |
| | .a.....A...aB.A..aB.A........a.a.aA..A...A....aC.A.. | Cas9_Wa; | |
| | .....Aaa.a..A.a..Aa...........Aa..CaaHI.....A..Aa..A | Cas9_Cr; | |
| | ....N............................................... | Cpf1_Wa; | |
| | .N....N......................................k...... | Cpf1_Cr; | |
| ASPM | ggtgcatattttgaatatcctttcgTTactttaaagcctctgtaataagact | SEQ_DUP; | 181 |
| | .........................12......................... | DUP_NUM; | |
| | .......HaB..........A..........A.....A......a..JA... | Cas9_Wa; | |
| | ..Aaa....A..J.........CaaH.Ba....A.......Aa.a....... | Cas9_Cr; | |
| | ........N........................k.....M....KL..N... | Cpf1_Wa; | |
| | ...........k..........N..N.......M...k...N.......... | Cpf1_Cr; | |
| ADCK3 | gatgagccttttgattttggcactcAAgagcaccaccgagaagatccacaac | SEQ_DUP; | 182 |
| | .........................12......................... | DUP_NUM; | |
| | .A...I..aC..J.aA......Ja.A.......a.aB.aC.......I..aC | Cas9_Wa; | |
| | aa.a.......Aa............A.a.aH....A.aa.aa.......Caa | Cas9_Cr; | |
| | ..............NL.................k.....k............ | Cpf1_Wa; | |
| | ....N..............N........N....................... | Cpf1_Cr; | |

TABLE 6-continued

Selected Genes Having Microduplication Variants

| SYMBOL | MICRODUPLICATION INFORMATION | | SEQ ID NO: |
|---|---|---|---|
| HAAO | aagggcagttcccagcggcctcaccAAgggatgggctttcctgttctgtact | SEQ_DUP; | 183 |
| | .........................12......................... | DUP_NUM; | |
| | A..A......a.aA.........aaaC.aaA.......A.J..A....A... | Cas9_Wa; | |
| | ..........A...Baaa..A..Aa.a.aa..........A..Baa...Ba. | Cas9_Cr; | |
| | ...............................NLL.................. | Cpf1_Wa; | |
| | ....N..L.................................LN..N...... | Cpf1_Cr; | |
| MSH6 | aggtaggcacaacttacgtaacagaTTaagagtgaagaagataatgaaattg | SEQ_DUP; | 184 |
| | .........................12......................... | DUP_NUM; | |
| | .aA..........A..I..aC...Ha.a.aB.aB.aC....aB....aHa.a | Cas9_Wa; | |
| | a...A.......A.a..A...A....A......................... | Cas9_Cr; | |
| | ..........kL..N.....................N...........N... | Cpf1_Wa; | |
| | ......N.....LN..N..M.N..Lk..........LN....LN........ | Cpf1_Cr; | |
| MSH6 | tgaaaaggctcgaaagactggacttAAttactcccaaagcaggctttgactc | SEQ_DUP; | 185 |
| | .........................12......................... | DUP_NUM; | |
| | ..aA...aB..a...aa.................A..aA....a..I..aC. | Cas9_Wa; | |
| | ..Aa.........A.a......A....A.......A.aaa....A...A... | Cas9_Cr; | |
| | ................k.............................N...N. | Cpf1_Wa; | |
| | ....N.........k...........................N......... | Cpf1_Cr; | |
| MSH6 | agtgtgcaggctcacaccaattgatAAgagtgtttactagacttggtgcctc | SEQ_DUP; | 186 |
| | .........................12......................... | DUP_NUM; | |
| | .A..aAJ...........aC..Ha.a.A.......a....aa.A.....a.. | Cas9_Wa; | |
| | .A.........AJ.JA.a.a.aa.................JA....A..... | Cas9_Cr; | |
| | .....N..N.....L............................N........ | Cpf1_Wa; | |
| | ..M.N................................N..N........... | Cpf1_Cr; | |
| DYSF | gcgaaaaaatgaggattcgtatcatAAgactggtgagttctgagtcttggag | SEQ_DUP; | 187 |
| | .........................12......................... | DUP_NUM; | |
| | ......aHaaC...A........a...aaHa.A...Ha.A....aa.A.... | Cas9_Wa; | |
| | a.....A..J...........BaH..Ca.J....A........Ba.....a. | Cas9_Cr; | |
| | ..NL.......kLL...L....................NL...M........ | Cpf1_Wa; | |
| | ..M.N......................L........................ | Cpf1_Cr; | |
| DYSF | ctcccagaagacccagccatccccaTTgcccccaagacagttccaccagctg | SEQ_DUP; | 188 |
| | .........................12......................... | DUP_NUM; | |
| | ..aB.a.....A...........A.......a...A........A..aA..A | Cas9_Wa; | |
| | .Caaaa.aaa......AaaH.Aa.Caaaa....Aaaaa....A...Baa.aa | Cas9_Cr; | |
| | ........NL......k.M.L....L.................L....N... | Cpf1_Wa; | |
| | ............N...........................L........... | Cpf1_Cr; | |

TABLE 6-continued

Selected Genes Having Microduplication Variants

| SYMBOL | MICRODUPLICATION INFORMATION | | SEQ ID NO: |
|---|---|---|---|
| DYSE | tggaaatgaccttggagattgtagcAAgagagtgagcatgaggagcggcctg | SEQ_DUP; | 189 |
| | .........................12......................... | DUP_NUM; | |
| | ...a.....aa.aC..A..A...aHa.a.a.A...a.aa.a.aA...A..aA | Cas9_Wa; | |
| | A...A.........Aa.............A...........A........A. | Cas9_Cr; | |
| | ........L.........................N......N.......... | Cpf1_Wa; | |
| | ....N......................................L........ | Cpf1_Cr; | |
| ALMS1 | agtaccttcaggttccttctcacatAAgagagaagcccagtattttctatca | SEQ_DUP; | 190 |
| | .........................12......................... | DUP_NUM; | |
| | ......aA...............a.a.aB.A....A...............a | Cas9_Wa; | |
| | aa..A....Aa.ba....Baa.Ba.a.a............Aaa.......ba | Cas9_Cr; | |
| | ...........L.................NL....NL..N............ | Cpf1_Wa; | |
| | ..M.N......N..................N..............M...... | Cpf1_Cr; | |
| ALMS1 | aacctctacttcttactcacaacatAAcagagaagccgagtattttctacca | SEQ_DUP; | 191 |
| | .........................12......................... | DUP_NUM; | |
| | .........................a.aB.A.Ha.A...............A | Cas9_Wa; | |
| | .A.....Aa.a..A.Ba...A.aHa..A....A.......Aa........ba | Cas9_Cr; | |
| | ................................N..N................ | Cpf1_Wa; | |
| | ..M.N......N..................N..................... | Cpf1_Cr; | |
| ERCC3 | aaaatttaaatccacaattttgtcaTTcttcgcggacgagggtcgcagtcaa | SEQ_DUP; | 192 |
| | .........................12......................... | DUP_NUM; | |
| | .................A.........a.aa..aHaaA..A..A........ | Cas9_Wa; | |
| | .Ca..I.........CaaHa........a..BaHBa.a...A......a.a. | Cas9_Cr; | |
| | L........N..................k....L........k.....N..N | Cpf1_Wa; | |
| | ............L................k...................... | Cpf1_Cr; | |
| MMADHC | acactctactctggcactttcaaagTTaagtttctgcactgttaatttcttg | SEQ_DUP; | 193 |
| | .........................12......................... | DUP_NUM; | |
| | ......J.aA..........A....A..J..A....A..........A.... | Cas9_Wa; | |
| | ....a.a.a.aH.A.aH..A.a..Ba...........Ba..A.a........ | Cas9_Cr; | |
| | ..N................N.....................kL.....N... | Cpf1_Wa; | |
| | k.....N...............N...........N................. | Cpf1_Cr; | |
| NEB | ctgcatctcaggagtgacaggggttGGcggtggctttccccacattttcttt | SEQ_DUP; | 194 |
| | .........................12......................... | DUP_NUM; | |
| | ......aa.a.a...aaaA..aa.aa.aA................J..A... | Cas9_Wa; | |
| | .A.aHa..A.Ca.a........A.........A.....A..Baaaa.a.... | Cas9_Cr; | |
| | ..k..N...N.....k..............................N..... | Cpf1_Wa; | |
| | ...................................k.........LLN.... | Cpf1_Cr; | |

TABLE 6-continued

Selected Genes Having Microduplication Variants

| SYMBOL | MICRODUPLICATION INFORMATION | | SEQ ID NO: |
|---|---|---|---|
| GALNT3 | taaaaatgtgagcgtttcagctgttGGcgactgttgctcctagcaaccgagc | SEQ_DUP; | 195 |
| | .........................12......................... | DUP_NUM; | |
| | ...a.a.a.A.....A..A..aa.a...A..A......A.....a.A..a.a | Cas9_Wa; | |
| | .A.Ca............A...Ba..A......A..A.....A.aa...A..A | Cas9_Cr; | |
| | ...M.M...N............................kL.......N.... | Cpf1_Wa; | |
| | .......................N............................ | Cpf1_Cr; | |
| TTN | ccatgacagacacggccttggtcccGGctggcatttttcactgttaaagtgt | SEQ_DUP; | 196 |
| | .........................12......................... | DUP_NUM; | |
| | a.J.a....aA....aA....aA..aA...........A.....a.A..... | Cas9_Wa; | |
| | .....Aa....A...A.a..Aa.....aaa..A...A.....Ba.a...... | Cas9_Cr; | |
| | .......N...........k....................N....L...... | Cpf1_Wa; | |
| | ........................k........................... | Cpf1_Cr; | |
| TTN | gatcagtgactgtatatcttgttttCCacacatgcctctgcattcaccttgt | SEQ_DUP; | 197 |
| | .........................12......................... | DUP_NUM; | |
| | .a.a...A........A...J........A.....A..........a.A... | Cas9_Wa; | |
| | .......Ca.....A......Ca......Baa.a.a...Aa.a..A..BaHa | Cas9_Cr; | |
| | .k....N..NL.......N.................M.M..N....kLL... | Cpf1_Wa; | |
| | ..........................................N......... | Cpf1_Cr; | |
| OBSL1 | ccacgggccagctgacctttgactgTTgacgttggccacggtgcgcacccgg | SEQ_DUP; | 198 |
| | .........................12......................... | DUP_NUM; | |
| | aaA...A..a......a...A..a..A..aA....aaJa.A.....aA.... | Cas9_Wa; | |
| | a.Baaaa.a...Aa..A...Aa.....A.......A....Aa.a....A.aJ | Cas9_Cr; | |
| | ......L............NLL...................k......N... | Cpf1_Wa; | |
| | .................................................... | Cpf1_Cr; | |
| CHRNG | tcttccgttccgcctgctctatctcAAgtcacctacttccccttcgactggc | SEQ_DUP; | 199 |
| | .........................12......................... | DUP_NUM; | |
| | ..A....A...A...........A.................a...aA..aB. | Cas9_Wa; | |
| | ..Aa.Ca.Baa..Baa.aa..A.a..Ca.a....a.aa..A.Baaaa.Ba.. | Cas9_Cr; | |
| | .M.......................NLL..NLL..........M........ | Cpf1_Wa; | |
| | ....N............................N.................. | Cpf1_Cr; | |
| GLB1 | ccccgtacccgggtcccgcagacttAAcgcgcaagccgcgcgtagggcccag | SEQ_DUP; | 200 |
| | .........................12......................... | DUP_NUM; | |
| | A....HaaA....A..a.......a.A...A..a.a.A..aaA....aB.A. | Cas9_Wa; | |
| | ..Aa.aaaa...Aaah..aaa.a...A....A.a.a...Aa.a.a....... | Cas9_Cr; | |
| | ........L.............N.L...........L........N...... | Cpf1_Wa; | |
| | ....N......N..................N........N......N..... | Cpf1_Cr; | |

TABLE 6-continued

Selected Genes Having Microduplication Variants

| SYMBOL | MICRODUPLICATION INFORMATION | | SEQ ID NO: |
|---|---|---|---|
| COL7A1 | tcccacagctccagtaggtccagtcAAggccctggaggaagagaaagttcag | SEQ_DUP; | 201 |
| | .........................12......................... | DUP_NUM; | |
| | ...A.....A..aA....A....aA....aa.aaB.a.aB..A....aaA.. | Cas9_Wa; | |
| | ......aaa.a..A.aa.......aa...a....Aaa............... | Cas9_Cr; | |
| | ...............L........L........L........L......... | Cpf1_Wa; | |
| | ....N.......L...LN....k.................N........... | Cpf1_Cr; | |
| COL7A1 | acccacagcaaatagcttgacccccTTgccccttcagcctttgggcagctgt | SEQ_DUP; | 202 |
| | .........................12......................... | DUP_NUM; | |
| | ...A......A...a........A........A.....aaA..A..a.A... | Cas9_Wa; | |
| | .aa...AaaHa..A......A....Aaaaa...Aaaa.Ba..Aa......A. | Cas9_Cr; | |
| | .....................N.................N........N... | Cpf1_Wa; | |
| | ...............................................L.... | Cpf1_Cr; | |
| DNAH1 | ggaacaccgtcaccccgcggctgatGGcgtcacttcaactacctgtctttcg | SEQ_DUP; | 203 |
| | .........................12......................... | DUP_NUM; | |
| | ....A.......a.aA..aC.aa.A...............A......A..a. | Cas9_Wa; | |
| | ...A.....A.aa..a.aaaa.a..A......A..a.a.Ba..A..Aa...a | Cas9_Cr; | |
| | .................................................... | Cpf1_Wa; | |
| | ...............N......................L............N | Cpf1_Cr; | |
| AGTR1 | gtcatgattcctactttatacagtaTTcatctttgtggtgggaatatttgga | SEQ_DUP; | 204 |
| | .........................12......................... | DUP_NUM; | |
| | .aC.......J.......A...........a.aa.aaaB......aaB.... | Cas9_Wa; | |
| | .......a.....Baa..A......A.....BahCa................ | Cas9_Cr; | |
| | .............N.......k........NL......k.M.......NL.. | Cpf1_Wa; | |
| | ...................LLN......LLk...............M..... | Cpf1_Cr; | |
| PCYT1A | ggagggggagcgctcgcgagtagggCCtgctgctggggctctgcttcgggct | SEQ_DUP; | 205 |
| | .........................12......................... | DUP_NUM; | |
| | aaaa.a.A...aHa.A..aaA...A..A..aaaA....A....aaA..aC.a | Cas9_Wa; | |
| | ...............A.a.a.a........Aa..A..A.....A.a..A.Ba | Cas9_Cr; | |
| | .................................................... | Cpf1_Wa; | |
| | .................................................... | Cpf1_Cr; | |
| WDR19 | acattttgtggtcatttctactcatAActggagagcttggtcaagagatatt | SEQ_DUP; | 206 |
| | .........................12......................... | DUP_NUM; | |
| | ...a.aA..................aa.a.A...aA....a.aC.......a | Cas9_Wa; | |
| | ......A..........a...Ba..A.aH...A.......A.....a..... | Cas9_Cr; | |
| | .......N......kL............k.........k............. | Cpf1_Wa; | |
| | ..M.N...L............N....M..............N...M.k...M | Cpf1_Cr; | |

TABLE 6-continued

Selected Genes Having Microduplication Variants

| SYMBOL | MICRODUPLICATION INFORMATION | | SEQ ID NO: |
|---|---|---|---|
| SCARB2 | ccctccatagaaagaagcaaaacttAAcacaaagtcatctaatttttgaca | SEQ_DUP; | 207 |
| | .........................12......................... | DUP_NUM; | |
| | .....aB..aB.A......J.........A..............a....... | Cas9_Wa; | |
| | A...aaaa.aa...........A....A.....A.a....a.Ca........ | Cas9_Cr; | |
| | ......................L....L..................N..... | Cpf1_Wa; | |
| | ....N....k.........N...........M.k..........LLN..... | Cpf1_Cr; | |
| FAM175A | actactaccagtatctgctttagatCCgtttgtcttgtgtatctaacaaccg | SEQ_DUP; | 208 |
| | .........................12......................... | DUP_NUM; | |
| | ......A.....A.....aC...A...A....a.A............a.aC. | Cas9_Wa; | |
| | ......A..A..Aa....Ca.JA......CaaH.....a.......Ca.J.A | Cas9_Cr; | |
| | ...k........k.M..N...N.............M......k.....L... | Cpf1_Wa; | |
| | ......................N..N..............LN.......... | Cpf1_Cr; | |
| MFSD8 | gcaataacccagcccaaaaaacttgTTatcagctgtcggatcaatctgcaga | SEQ_DUP; | 209 |
| | .........................12......................... | DUP_NUM; | |
| | .......A............A......A..A.HaaC.......A..aB..J. | Cas9_Wa; | |
| | ......A.....AaaH.Aaa......A......Ca..A...a...Ca..Ca. | Cas9_Cr; | |
| | ....k...........M.M..........................N..N.M. | Cpf1_Wa; | |
| | ................L....N........k.................N..N | Cpf1_Cr; | |
| ETFDH | tttgtgcagcatatcagtgctttcaTTgccttaaaaattaagaaaaattatc | SEQ_DUP; | 210 |
| | .........................12......................... | DUP_NUM; | |
| | .A..A.......a.A........A.............aB............. | Cas9_Wa; | |
| | ...........A..a...Ca....A..ba....Aa................. | Cas9_Cr; | |
| | ..............kL........k..........M........kL..N... | Cpf1_Wa; | |
| | ...........k......N..k.........................N.... | Cpf1_Cr; | |
| AGA | acaaactaagaagtcataccttggcAAggaagcgcatcaatatatcaccatt | SEQ_DUP; | 211 |
| | .........................12......................... | DUP_NUM; | |
| | .....aB.a.........aA...aaB.a.A...................... | Cas9_Wa; | |
| | ...BaHa...A........a...Aa....A.......A.a.Ca......Ca. | Cas9_Cr; | |
| | N...L...............NL.....................N........ | Cpf1_Wa; | |
| | ....N..LN........N..M............................... | Cpf1_Cr; | |
| DNAH5 | agttcttggtttgcacgggaatgggTTaaatttacagatgctatctccaagg | SEQ_DUP; | 212 |
| | .........................12......................... | DUP_NUM; | |
| | ...aAJ..A...aaaB.HaaA...........aC.A..........aA.... | Cas9_Wa; | |
| | ........Ba........A.a..................A.....A..Ca.a | Cas9_Cr; | |
| | ...kL........N..N.M......N..N...k..............N... | Cpf1_Wa; | |
| | ......k....................N........k.....k.......N. | Cpf1_Cr; | |

TABLE 6-continued

| Selected Genes Having Microduplication Variants | | | |
|---|---|---|---|
| SYMBOL | MICRODUPLICATION INFORMATION | | SEQ ID NO: |
| SLC25A46 | agatatccccggcagccgcaacctgCCactgggg gagaagagcccgcccta | SEQ_DUP; | 213 |
| | ........................12........................ | DUP_NUM; | |
| | ......aA..A..A......A....aaaa.a.aB.a.A..A......aa. | Cas9_Wa; | |
| | aaaaa....Caaaa..A..Aa.a..Aa..Aa.a...A........Aaa. | Cas9_Cr; | |
| | .................L........M.L..................... | Cpf1_Wa; | |
| | ................N................................. | Cpf1_Cr; | |
| SLC22A5 | ctgctgcaatatttgccccggcgctAAttccatggccactgccctcttcctg | SEQ_DUP; | 214 |
| | ........................12........................ | DUP_NUM; | |
| | .A........A...aa.A.........aA....A........Haaa.a | Cas9_Wa; | |
| | ..A..A..A..A........Aaaa..A.a...Baa...Aa.a..Aaa.a. | Cas9_Cr; | |
| | ......M....N......................k.............NL | Cpf1_Wa; | |
| | ....N............................................. | Cpf1_Cr; | |
| RAD50 | aattatcactttcttcagccccctt AAcaattttggttggacccaatggggc | SEQ_DUP; | 215 |
| | ........................12........................ | DUP_NUM; | |
| | ............A................aA..aa.......aaaa.aaaB | Cas9_Wa; | |
| | ...A.....Ca.a..Ba.Ba..Aaaaa....A.............AaaH.. | Cas9_Cr; | |
| | .......................N.M......k..NL........N..... | Cpf1_Wa; | |
| | ....N..N........L.....N.........LLk........N....... | Cpf1_Cr; | |
| RAD50 | agaaacaagagaaacagcacaagttAAgacacaggtaatacagtctgtgtcc | SEQ_DUP; | 216 |
| | ........................12........................ | DUP_NUM; | |
| | ....a.aB.J..A.....A..J.a.....aa.......A...a.A....J.. | Cas9_Wa; | |
| | Aa........A........A..A.a..........A.a.........A...a.. | Cas9_Cr; | |
| | ......L.........................................N..... | Cpf1_Wa; | |
| | ....N.........N..........................M......... | Cpf1_Cr; | |
| RAD50 | gagactcatgagacaagatattgatAAcacagaaggtaggtctgttttgctt | SEQ_DUP; | 217 |
| | ........................12........................ | DUP_NUM; | |
| | .....a.a....aC....ac........aB.aA..aA...A....A.....aC | Cas9_Wa; | |
| | .........A.aH.....A...............A.a...........a..... | Cas9_Cr; | |
| | ....................M.....................N........ | Cpf1_Wa; | |
| | ..M.N......N......................M................ | Cpf1_Cr; | |
| GRXCR2 | tgcaaatctggcaaggctgtaggccAAttctcattgcaggcagggcacctca | SEQ_DUP; | 218 |
| | ........................12........................ | DUP_NUM; | |
| | .....aA...aA..A..aA.............A..aA.JaaA.......aaA. | Cas9_Wa; | |
| | .......A...Ca..IA....A......Aa...BaHa....A...A....A. | Cas9_Cr; | |
| | ..................N...N...........................N. | Cpf1_Wa; | |
| | ....N...............................M...........k. | Cpf1_Cr; | |

TABLE 6-continued

| Selected Genes Having Microduplication Variants | | | |
|---|---|---|---|
| SYMBOL | MICRODUPLICATION INFORMATION | | SEQ ID NO: |
| DSP | agagaattgaagagaggtgcaggcgTTaagctggaggattctaccagggaga | SEQ_DUP; | 219 |
| | .........................12......................... | DUP_NUM; | |
| | B...aB.a.a.aa.A..aa.A....A..aaHaaC........aaa.a..... | Cas9_Wa; | |
| | ..Ca....................A..JA......A........BaH.Aa.. | Cas9_Cr; | |
| | .........L...................N..................N... | Cpf1_Wa; | |
| | ......N....L..............L...................k..... | Cpf1_Cr; | |
| GCM2 | cacaaattgtgttctcacctgacctAAcctgaaaaaagatcgcgttgccatc | SEQ_DUP; | 220 |
| | .........................12......................... | DUP_NUM; | |
| | ....a.A.........a.........aB.....aC..a.A..A.......A. | Cas9_Wa; | |
| | CaahCa.a.........BaJa.aa...Aa...Aa..........Ca.a.... | Cas9_Cr; | |
| | .................M.L.........N....N................. | Cpf1_Wa; | |
| | ....N....Lk....................N.......k............ | Cpf1_Cr; | |
| AARS2 | ctgacatcccagggaagatgccatcAAgagatgcagacactgagtgtgcgga | SEQ_DUP; | 221 |
| | .........................12......................... | DUP_NUM; | |
| | .......aaaB.aC.A.......a.aC.AJ.a....Ha.a.a.aHaaC.a.a | Cas9_Wa; | |
| | ....Aa...A.Caaa..........Aa.Ca........A...A.a....... | Cas9_Cr; | |
| | ....NLL.......................L..................... | Cpf1_Wa; | |
| | ....N.......................L....................... | Cpf1_Cr; | |
| MUT | catggatggttctggaggaaaaatgTTatgtatttcgaaccataaattcctt | SEQ_DUP; | 222 |
| | .........................12......................... | DUP_NUM; | |
| | aC.aA....aa.aaB.....A....A......aB................A. | Cas9_Wa; | |
| | ....Ba.........Ba......................Ba...Aa...... | Cas9_Cr; | |
| | L.....M..............kL.........N...............N.M. | Cpf1_Wa; | |
| | ...............LN...M.k............M.........L..... | Cpf1_Cr; | |
| PKHD1 | aacttcacacacctttaatgtgcagTTaagttgaggatgcttgtgttagtgt | SEQ_DUP; | 223 |
| | .........................12......................... | DUP_NUM; | |
| | .J..............a.A..A....A..aHaaC.A...a.A...a.A...A | Cas9_Wa; | |
| | a..A...A.Ba.a.a.aa..........A..J.............A...... | Cas9_Cr; | |
| | ..........N................NL.........k.........N... | Cpf1_Wa; | |
| | ......N................................N...N......... | Cpf1_Cr; | |
| PKHD1 | agtgaatgctgaccccattgatagaGGacggaaattctgtggagaccagctg | SEQ_DUP; | 224 |
| | .........................12......................... | DUP_NUM; | |
| | B..A..a........aC..a.aa..aaB......a.aa.a....A..aA..a | Cas9_Wa; | |
| | H............A...Aaaa............A.......BaH......Aa | Cas9_Cr; | |
| | ..................N.....................N........... | Cpf1_Wa; | |
| | ........LLk........L................................ | Cpf1_Cr; | |

TABLE 6-continued

Selected Genes Having Microduplication Variants

| SYMBOL | MICRODUPLICATION INFORMATION | | SEQ ID NO: |
|---|---|---|---|
| WISP3 | cttctgcttgctggcctggcacaggTTaagtcctctcccccgactctttccc | SEQ_DUP; | 225 |
| | .........................12......................... | DUP_NUM; | |
| | .A...A..aA.J.aA....aA....A...........a.............. | Cas9_Wa; | |
| | aa.a.aHBa..A...A...Aa...A.a.........aa.a.aaaaa..A.aH | Cas9_Cr; | |
| | ..............N...L.....N.....N.................N... | Cpf1_Wa; | |
| | ......N............................L................ | Cpf1_Cr; | |
| BRAT1 | ctggctccccaaagagccctggtagTTaactccccctgctgggaagcaaaaa | SEQ_DUP; | 226 |
| | .........................12......................... | DUP_NUM; | |
| | .........a.A....aA..A............A..aaaB.A........aB | Cas9_Wa; | |
| | ....aa...A.aaaa......Aaa..........A.aaaaa..A.......A | Cas9_Cr; | |
| | .....N.......................L..................N... | Cpf1_Wa; | |
| | ......N.............LLN...k.......N................. | Cpf1_Cr; | |
| ISPD | gtggtccgcgccgcgctgaccactcAAggcaaggacccggctccgccggcct | SEQ_DUP; | 227 |
| | .........................12......................... | DUP_NUM; | |
| | ...a.A..a.A..a.........aA...aa....aA....A..aA...aa.A | Cas9_Wa; | |
| | .Aa......Jaa.a.aa.a.a...Aa.a.aH...A.....AaaH.A.aa.aa | Cas9_Cr; | |
| | ............................L....................... | Cpf1_Wa; | |
| | ....N....N.......................................... | Cpf1_Cr; | |
| FAM126A | actttgtggctcctggataactttaTTagagagatgaaactaaagaactctt | SEQ_DUP; | 228 |
| | .........................12......................... | DUP_NUM; | |
| | .a.aA....HaaC...........a.a.aC.aB.......aB......A... | Cas9_Wa; | |
| | JAa.a.a.......A.aa.......A..................A....... | Cas9_Cr; | |
| | ................N.........k..................k..N... | Cpf1_Wa; | |
| | ..............Lk....k...N.............k..........M.N | Cpf1_Cr; | |
| SLC25A13 | gtagaaccatcgctgtagcaattcgTTaagtcagcaaagttacaccaaactg | SEQ_DUP; | 229 |
| | .........................12......................... | DUP_NUM; | |
| | B......A..A..A......A....A...A....a............aaaa. | Cas9_Wa; | |
| | Ca..I......Aa.Ca.a.....A...BaH......a.A........A.aa. | Cas9_Cr; | |
| | ..N.........L...............................NL..N... | Cpf1_Wa; | |
| | ......N.......k..........k................Lk........ | Cpf1_Cr; | |
| PEX2 | attcctgatttcagtggctgcagacTTgtgtacttctgtgccacacttagga | SEQ_DUP; | 230 |
| | .........................12......................... | DUP_NUM; | |
| | ..aC.....a.aA..A..a...Ja.A.......a.a........aa....A | Cas9_Wa; | |
| | Ca.a...Baa.....Ba.....A..A...A.......AJBa....Aa.a.a. | Cas9_Cr; | |
| | ......k...N..............NL.....kL..............N... | Cpf1_Wa; | |
| | ................................N...k...........k... | Cpf1_Cr; | |

TABLE 6-continued

Selected Genes Having Microduplication Variants

| SYMBOL | MICRODUPLICATION INFORMATION | | SEQ ID NO: |
|---|---|---|---|
| NBN | gaactttcacatcaatttctaactcTTggttttgtgtccttgaataactgtt | SEQ_DUP; | 231 |
| | .........................12......................... | DUP_NUM; | |
| | .......................aA....a.A....HaB......A..J... | Cas9_Wa; | |
| | ........A..Ba.a.Ca....Ba...A.aH...........aaJ....... | Cas9_Cr; | |
| | .N.......NL..........k......kL.........k........N... | Cpf1_Wa; | |
| | ....................LN..N........N.................. | Cpf1_Cr; | |
| NDUFAF6 | cctgtggccattgaactatggaaggTTaaaaaaaaaaaaataccacttttaa | SEQ_DUP; | 232 |
| | .........................12......................... | DUP_NUM; | |
| | .aA.....aB.....aaB.aA...........J..................A | Cas9_Wa; | |
| | .Ca..Aa.....Aa......A..........................Aa.a. | Cas9_Cr; | |
| | ...........L.....................N......M.......N... | Cpf1_Wa; | |
| | N.....k......................N.......LN............. | Cpf1_Cr; | |
| VPS13B | ctctagagcgccagagaagattgttAAcatttaaaatgttcatcactcagtt | SEQ_DUP; | 233 |
| | .........................12......................... | DUP_NUM; | |
| | .a.a.A...a.aB.aC..A..............A...........A....A. | Cas9_Wa; | |
| | .Ba.aa.a.....A.aa...............A...........Ba.Ca.a. | Cas9_Cr; | |
| | .......N..N...L...k........................N..N..... | Cpf1_Wa; | |
| | ....N......k...................N.................... | Cpf1_Cr; | |
| SPAG1 | aaaagaaggaaactgcagtggctgcAAttcaagattgtaacaggtaaactgc | SEQ_DUP; | 234 |
| | .........................12......................... | DUP_NUM; | |
| | aB.aaB....A..a.aA..A.....I..aC..A.....aA...J..A...A. | Cas9_Wa; | |
| | ..Aa.............A...A....A..A...BaH.........A...... | Cas9_Cr; | |
| | L................N................................NL | Cpf1_Wa; | |
| | ....N....N.......N......k.......................N... | Cpf1_Cr; | |
| SLC52A2 | cctgcaggttggagcctcccctcttAAcgtctctgtgcttgtggctctgggg | SEQ_DUP; | 235 |
| | .........................12......................... | DUP_NUM; | |
| | ..aA..aa.A..............A.....a.A...a.aA....aaaaB... | Cas9_Wa; | |
| | aa.Baaa..A.........Aa.aaaa.a....A..a.a....A..J...A.a | Cas9_Cr; | |
| | .................L..NLL........N........L.....N..... | Cpf1_Wa; | |
| | ....N........................LLN.................... | Cpf1_Cr; | |
| CDKN2A | acccacctggatcggcctccgaccgTTaactattcggtgcgttgggcagcgc | SEQ_DUP; | 236 |
| | .........................12......................... | DUP_NUM; | |
| | ...HaaC..aA.....a...A..........aa.a.A..aaA..a.A..... | Cas9_Wa; | |
| | aaHa..AaaHaa....Ca..Aa.aa..Aa.....A...BaH...A..J...A | Cas9_Cr; | |
| | ......L..................................L......N... | Cpf1_Wa; | |
| | ......N............................................. | Cpf1_Cr; | |

TABLE 6-continued

Selected Genes Having Microduplication Variants

| SYMBOL | MICRODUPLICATION INFORMATION | | SEQ ID NO: |
|---|---|---|---|
| APTX | aaaatctacaatcaccttttcccccAAcagtgtgcatatgcttaaggagttc | SEQ_DUP; | 237 |
| | .........................12......................... | DUP_NUM; | |
| | .........................a.a.A.....A.....aa.A.....aa | Cas9_Wa; | |
| | aaH.A....Ca..a..Ca.aa...Baaaaa..A......AJ.J..A...... | Cas9_Cr; | |
| | .........k...............................kLL........ | Cpf1_Wa; | |
| | ....N.........M.......N........N.................... | Cpf1_Cr; | |
| DNAI1 | ccccataaacagcctcataagcaggTTaacgtacgcacaccttccttctgat | SEQ_DUP; | 238 |
| | .........................12......................... | DUP_NUM; | |
| | .......A........A..aA..J..AJ.JA..............aC.a... | Cas9_Wa; | |
| | ...A.aaaa.....A..Aa.a.....A.......A...A.aJa.aa.Baa.B | Cas9_Cr; | |
| | ...NL.....N............L........................N... | Cpf1_Wa; | |
| | ......N............................................. | Cpf1_Cr; | |
| FANCC | tagtctgtgctctctgctgcctcccAAtcacgggggccgtagtagaaggcca | SEQ_DUP; | 239 |
| | .........................12......................... | DUP_NUM; | |
| | ..a.A......A..A............aaaaA..A..A..aB.aA....a.A | Cas9_Wa; | |
| | aHaa.....a....A.aJa..A..Aa.aaa..Ca.aI....Aa......... | Cas9_Cr; | |
| | .............................................L...... | Cpf1_Wa; | |
| | ....N...................N.....N..................... | Cpf1_Cr; | |
| MUSK | caacattccactggtacatattcttAActctggttgccttcagcggaactga | SEQ_DUP; | 240 |
| | .........................12......................... | DUP_NUM; | |
| | ......J.aA.................aA..A......a.aaB...a.aB.. | Cas9_Wa; | |
| | A.a..a..A..Baa.a.....A..J.BaH...A.aH.....Aa.Ba..A... | Cas9_Cr; | |
| | ...N........................NLL............N..N..... | Cpf1_Wa; | |
| | ....N..................LLN......k.......k........... | Cpf1_Cr; | |
| TSC1 | tgctgtgcgcgtctgctccctgctgTTatcagtctgtccagcacttccattg | SEQ_DUP; | 241 |
| | .........................12......................... | DUP_NUM; | |
| | a.a.a.A...A......A..A......A...A.J..A..........aaaa. | Cas9_Wa; | |
| | A.aa...A....A.aJ.a..A.aaa..A.....Ca...a...aa..A.a.Ba | Cas9_Cr; | |
| | ...L..N...N..NL.......N.................L.......N.M. | Cpf1_Wa; | |
| | ................................L................... | Cpf1_Cr; | |
| ADAMTS13 | ggcagcaggtgctctactgggagtcAAgagagcagccaggctgagatggagt | SEQ_DUP; | 242 |
| | .........................12......................... | DUP_NUM; | |
| | A..aa.A.......aaa.A....a.a.A..A...aA..a.aC.aa.A....a | Cas9_Wa; | |
| | aa.....A..A.....A.aJ.A.......a.......A..Aa...A...... | Cas9_Cr; | |
| | .N..............NLL................................. | Cpf1_Wa; | |
| | ....N.....................L....................LN... | Cpf1_Cr; | |
| AGPAT2 | gtacatgatgaggcccacgggccccAAggaagagcagctcccgcttggcgat | SEQ_DUP; | 243 |
| | .........................12......................... | DUP_NUM; | |
| | ..aC.a.aA.....aaA......aaB.a.A..A.....A...aa.aCJ..A. | Cas9_Wa; | |

TABLE 6-continued

Selected Genes Having Microduplication Variants

| SYMBOL | MICRODUPLICATION INFORMATION | | SEQ ID NO: |
|---|---|---|---|
| | aa......A..J......Aaa.a...Aaaa.........A..A.aaa.a... | Cas9_Cr; | |
| | N................................................... | Cpf1_Wa; | |
| | ....N..LN......................................LLN.. | Cpf1_Cr; | |
| C10orf11 | attgcaggtcactggaaggactgagCCgcattcaggagcctggaggaactca | SEQ_DUP; | 244 |
| | .........................12......................... | DUP_NUM; | |
| | ..aA.....aaB.aa...a.A..A......aa.A...aa.aaB......... | Cas9_Wa; | |
| | ....a...A...a.a..........A...Aa.a..BaH...Aa......... | Cas9_Cr; | |
| | ......kL....N.....k.....N........................... | Cpf1_Wa; | |
| | ....................L...LN.........L...N..N......... | Cpf1_Cr; | |
| PTEN | gaaagggacgaactggtgtaatgatAAtgtgcatatttattacatcggggca | SEQ_DUP; | 245 |
| | .........................12......................... | DUP_NUM; | |
| | aaa..aB...aa.A....aC....a.A...............aaaA...... | Cas9_Wa; | |
| | ..A..........A...A........J.........A..J.......A.Ca. | Cas9_Cr; | |
| | ........NL.......................................... | Cpf1_Wa; | |
| | ..M.N......M..................k.......k.......N..... | Cpf1_Cr; | |
| PTEN | tgtactttgagttccctcagccgttAAcctgtgtgtggtgatatcaaagtag | SEQ_DUP; | 246 |
| | .........................12......................... | DUP_NUM; | |
| | ...Ha.A........A..A.......a.a.a.aa.aC.......A.Ha.A.. | Cas9_Wa; | |
| | ..Ba.....A..J....Baaa.a..Aa.....Aa.......J.J....Ca.. | Cas9_Cr; | |
| | ...................NL........k....NLL.........N..... | Cpf1_Wa; | |
| | ....N..............M....k.................k.....N..N | Cpf1_Cr; | |
| PNPLA2 | ggacagctccaccaacatccacgagCCtgcgggtcaccaacaccagcatcca | SEQ_DUP; | 247 |
| | .........................12......................... | DUP_NUM; | |
| | .A................a.A...aHaaA...J........A......A... | Cas9_Wa; | |
| | aa.a....A..A.aa.aa..A.CaaHa...Aa..A....a.aa..A.aa..A | Cas9_Cr; | |
| | ..................L............L.........L.......... | Cpf1_Wa; | |
| | .................N.................N.........N...... | Cpf1_Cr; | |
| KCNQ1 | cctcgagcgtcccaccggctggaaaTTgcttcgtttaccacttcgccgtgtg | SEQ_DUP; | 248 |
| | .........................12......................... | DUP_NUM; | |
| | a.a.A.......aA..aaB....A....A...........A..a.aHa.A.. | Cas9_Wa; | |
| | ..A.Baa.a...A..aaa.aa..A.........A.Ba.....Aa.a.Ba.aa | Cas9_Cr; | |
| | ..L..................NL..........L..............N... | Cpf1_Wa; | |
| | Lk.................................................. | Cpf1_Cr; | |
| HBB | ttgtccaggtgagccaggccatcacTTaaaggcaccgagcactttcttgcca | SEQ_DUP; | 249 |
| | .........................12......................... | DUP_NUM; | |
| | ...aa.a.A...aA..........J.aA...Ja.A.........A....a.A | Cas9_Wa; | |
| | .........aa.......Aa...Aa.Ca.a.......A.aa...A.a..Ba. | Cas9_Cr; | |
| | .................N.....N...L....................N... | Cpf1_Wa; | |
| | ......k............................................. | Cpf1_Cr; | |

TABLE 6-continued

Selected Genes Having Microduplication Variants

| SYMBOL | MICRODUPLICATION INFORMATION | | SEQ ID NO: |
|---|---|---|---|
| HBB | cttcatccacgttcaccttgccccaCCagggcagtaacggcagacttctcct | SEQ_DUP; | 250 |
| | .........................12......................... | DUP_NUM; | |
| | ......A........A........aaA..A....aA..a...........aa | Cas9_Wa; | |
| | .aa..A.Ba.CaaHa..Ba.aa...Aaaa.aa....A.....A..A...A.B | Cas9_Cr; | |
| | ........................NL...L....NL....N........... | Cpf1_Wa; | |
| | ..............N..................................... | Cpf1_Cr; | |
| HBB | tgccccacagggcagtaacggcagaCCttctcctcaggagtcagatgcacca | SEQ_DUP; | 251 |
| | .........................12......................... | DUP_NUM; | |
| | .....aaA..A....aA..a............aa.A...aC.A......aa. | Cas9_Wa; | |
| | a.aa...Aaaa.a....A.....A..A...Aa.Ba.aa.a......a..... | Cas9_Cr; | |
| | ......NL...L....NL....N...........................N. | Cpf1_Wa; | |
| | .................................................... | Cpf1_Cr; | |
| ANO5 | gagaactgtagcttctaaagctcatAAgcataggtgtttggcaagacattct | SEQ_DUP; | 252 |
| | .........................12......................... | DUP_NUM; | |
| | ...A..A........A.......A....aa.A...aA...a........... | Cas9_Wa; | |
| | ..A.......A.....A.Ba.....A.a.....A..........J.A....A | Cas9_Cr; | |
| | .......N...........................N................ | Cpf1_Wa; | |
| | ..M.N...M............N.............LLN.............. | Cpf1_Cr; | |
| MYBPC3 | cctcgatcatgcgccgcgcttcatgAActcagctcctgaatcaggtcgaagt | SEQ_DUP; | 253 |
| | .........................12......................... | DUP_NUM; | |
| | aC....a.A..a.A......aB.....A....HaB....aA..aB.A....A | Cas9_Wa; | |
| | a.a.aaa.a..Ca...A.aa.a.a.Ba.....A.aH.A.aa....Ca..I.a | Cas9_Cr; | |
| | ..........................................NL........ | Cpf1_Wa; | |
| | ...LN...........LN........LN........................ | Cpf1_Cr; | |
| MYBPC3 | cgccatcgtaggcaggcggctcccaCCtgtactgtgcaggagtcctctccca | SEQ_DUP; | 254 |
| | .........................12......................... | DUP_NUM; | |
| | ...A..aA..aa.aA......J..A....a.A..aa.A...........A.. | Cas9_Wa; | |
| | A..Aaa.aa.Ca.....A...A..A.aaa.aa....A..J.A..J...aa.a | Cas9_Cr; | |
| | ............................................L....... | Cpf1_Wa; | |
| | .................................................... | Cpf1_Cr; | |
| MYBPC3 | aacacccactcatcgctgtcacctgTTgtcctctggggcatctggggctggc | SEQ_DUP; | 255 |
| | .........................12......................... | DUP_NUM; | |
| | ..........A..A......A..A......aaaA.....aaaA..aA...aA | Cas9_Wa; | |
| | ...a...A.aaaHa.aHCa.a...a.aa......aa.a.....A.Ca..... | Cas9_Cr; | |
| | ..............N..N..............................N... | Cpf1_Wa; | |
| | .................................................... | Cpf1_Cr; | |
| MYBPC3 | atggggtcatcgggggctccaggggTTaggaccattgagagctgctgagctt | SEQ_DUP; | 256 |
| | .........................12......................... | DUP_NUM; | |
| | aA.....aaaaA.....aaaA...aa......a.a.A..A..a.A...a... | Cas9_Wa; | |

TABLE 6-continued

Selected Genes Having Microduplication Variants

| SYMBOL | MICRODUPLICATION INFORMATION | | SEQ ID NO: |
|---|---|---|---|
| | ..Aa........a.Ca.....A.aa...........Aa........A..A.. | Cas9_Cr; | |
| | .........................................L......N... | Cpf1_Wa; | |
| | ...........................................k........ | Cpf1_Cr; | |
| BSCL2 | gactctggcagctcaagctctaaggTTaacacgatacggctgtccatacatc | SEQ_DUP; | 257 |
| | .........................12......................... | DUP_NUM; | |
| | ..aA..A.....A......aAJ....J.aC...aA..AJ.......J..A.. | Cas9_Wa; | |
| | a......A.aH..A..A.a...A.a.........A.a....A..A...aa.. | Cas9_Cr; | |
| | ..........N...NL................................N... | Cpf1_Wa; | |
| | N.....N.....M...........M................k.......... | Cpf1_Cr; | |
| BBS1 | cctgcgaagatggccgctgcgtcctCCatcggattccgacgcctgcggagct | SEQ_DUP; | 258 |
| | .........................12......................... | DUP_NUM; | |
| | .aB.aC.aA..A..a.A.......IHaaC....a..A...a.aa.A..a.a. | Cas9_Wa; | |
| | A..A.aa..A........Aa.a..A..aa.aa.Ca....Baa..A.aa..A. | Cas9_Cr; | |
| | .........N......................................L... | Cpf1_Wa; | |
| | .........L...............L............LN............ | Cpf1_Cr; | |
| LRP5 | tgactgtatgcacaacaacgggcagTTgtgggcagctgtgccttgccatccc | SEQ_DUP; | 259 |
| | .........................12......................... | DUP_NUM; | |
| | .AJ..A.........aaA..A..a.aaA..A..a.A....A........aa. | Cas9_Wa; | |
| | a.a.....A......AJa..A..A...A.........A..A....Aa.J.Aa | Cas9_Cr; | |
| | ....L.........................M.................N... | Cpf1_Wa; | |
| | .................................................... | Cpf1_Cr; | |
| TYR | cggcgatggtaggggccgtcctcacTTgccctgctggcagggcttgtgagct | SEQ_DUP; | 260 |
| | .........................12......................... | DUP_NUM; | |
| | aC.aA..aaaA..A.........A....A..aA..aaA...a.a.A...A.. | Cas9_Wa; | |
| | .....A..A...........Aa..aa.a.a...Aaa..A...A....A.... | Cas9_Cr; | |
| | .................N..............................N... | Cpf1_Wa; | |
| | .............................................N....k. | Cpf1_Cr; | |
| TYR | ggcagggcttgtgagcttgctgtgtCCgtcacaagagaaagcagcttcctga | SEQ_DUP; | 261 |
| | .........................12......................... | DUP_NUM; | |
| | aaA...a.a.A...A..a.A...A......a.aB..A..A......aB.aB. | Cas9_Wa; | |
| | a..A...A....A.......A...A.....aaJ.a.a.........A..A.B | Cas9_Cr; | |
| | ...............................N.......N........L... | Cpf1_Wa; | |
| | ...........N....k............LN..k.................. | Cpf1_Cr; | |
| MRE11A | tccacaaatttctggctaaagcgaaGGaacactgaaaggttcaaaacctcca | SEQ_DUP; | 262 |
| | .........................12......................... | DUP_NUM; | |
| | .........aA.....a.aB.aaB.....aB..aA................. | Cas9_Wa; | |
| | AaaH.CaaHa.....Ba...A......A.......A.a.......Ba....A | Cas9_Cr; | |
| | ......k....N............L.......k................... | Cpf1_Wa; | |
| | .LN..LN.....Lk.......k...........M..........Lk...... | Cpf1_Cr; | |

TABLE 6-continued

Selected Genes Having Microduplication Variants

| SYMBOL | MICRODUPLICATION INFORMATION | | SEQ ID NO: |
|---|---|---|---|
| ATM | acagaacaatcccagcctaaaacttAAcatacacagaatgtctgagggtttg | SEQ_DUP; | 263 |
| | .........................12......................... | DUP_NUM; | |
| | B.........A..........J.J......HaB..A...aHaaA...a.aA. | Cas9_Wa; | |
| | a.....A....A..CaaaI.Aa.....A....A...A.a.......a..... | Cas9_Cr; | |
| | ..k.......k.....k..N.M...........L............N..... | Cpf1_Wa; | |
| | ....N..M.......N...................N............k... | Cpf1_Cr; | |
| ATM | aggagtggaagaaggcactgtgctcAAgtgttggtggacaagtgaatttgct | SEQ_DUP; | 264 |
| | .........................12......................... | DUP_NUM; | |
| | a.aaB.ab.aA....a.A.....a.A..aa.aa....aHaB....AJ..... | Cas9_Wa; | |
| | A...................A.a....A.aJ.......J....A........ | Cas9_Cr; | |
| | .................................................... | Cpf1_Wa; | |
| | ...N..........L...N...LN........M...........M....... | Cpf1_Cr; | |
| DPAGT1 | tgtggtagagcaatcccaaagtggtGGaaaaaaaagggtatcatgaagtaga | SEQ_DUP; | 265 |
| | .........................12......................... | DUP_NUM; | |
| | A..a.A...........a.aa.aaB......HaaA.....aB.A..a.aaaB | Cas9_Wa; | |
| | Aa..............A..CaaaI.....................Ca.J... | Cas9_Cr; | |
| | .M.L...........N......N..............L.............. | Cpf1_Wa; | |
| | ....LLk................LN.......LLk................. | Cpf1_Cr; | |
| PKP2 | aggagaggttatgaagaatgcacacAAcaattctccgtggcctgagaaaaca | SEQ_DUP; | 266 |
| | .........................12......................... | DUP_NUM; | |
| | a.aA....aBHab.JA................a.aA...a.aB.....aa.. | Cas9_Wa; | |
| | A........................A.a.a..A...BaHaa....Aa..... | Cas9_Cr; | |
| | ..............L................N.M.................. | Cpf1_Wa; | |
| | ....N..N.................k.........N..N...........M. | Cpf1_Cr: | |
| PKP2 | ggcccgcctgctttcttggtggtgcAAgggtgtgcccagcctggcttctctg | SEQ_DUP; | 267 |
| | .........................12......................... | DUP_NUM; | |
| | .A...A.......aa.aa.A..Haaa.a.A....A...aA.......aa..A | Cas9_Wa; | |
| | ....A..Aaa.aa..A..Ba........A..J.......AaaJ.Aa...A.B | Cas9_Cr; | |
| | .M.................................k..N............. | Cpf1_Wa; | |
| | ....N.....................................N......... | Cpf1_Cr; | |
| AAAS | ggtcccagaccatggagtgagcctcTTcccccaagcctgtgggtaaggacag | SEQ_DUP; | 268 |
| | .........................12......................... | DUP_NUM; | |
| | ...a.....aa.a.a.A.............A...aHaaA...aa...aA... | Cas9_Wa; | |
| | .a......aaa...Aa..........Aa.a.Baaaaa...Aa.......... | Cas9_Cr; | |
| | ............NLL...........L.....................NLL. | Cpf1_Wa; | |
| | ...........N...........N............................ | Cpf1_Cr; | |
| MVK | ttcatggagaacatgccgtggtacaTTggcaaggtacaaagccgttagagcc | SEQ_DUP; | 269 |
| | .........................12......................... | DUP_NUM; | |
| | .aa.aB....A..a.aA......aA.J.aA......A..A...a.A.....I | Cas9_Wa; | |

TABLE 6-continued

Selected Genes Having Microduplication Variants

| SYMBOL | MICRODUPLICATION INFORMATION | | SEQ ID NO: |
|---|---|---|---|
| | a.CaaHBa........A..Aa.......A..J..A......A..J.Aa.... | Cas9_Cr; | |
| | .......L...............NL.......................N... | Cpf1_Wa; | |
| | .........N......k.................N................. | Cpf1_Cr; | |
| TCTN2 | tccggccctgcggtcagcgcgtcccTTggtcggagacaccgagggtgtgacc | SEQ_DUP; | 270 |
| | .........................12......................... | DUP_NUM; | |
| | A....a.aA...a.a.A......aA..aa.a.....aHaaa.a.a...a.A. | Cas9_Wa; | |
| | H.....aa..Aaa..A...a..A.a..aaa.....a.....A.aa....... | Cas9_Cr; | |
| | L...L.......k.M.L.......L....................L..N... | Cpf1_Wa; | |
| | ..........L......................................... | Cpf1_Cr; | |
| ATP6V0A2 | agtcgggcacggcctacgagtgcctCCagcgccctgggcgagaaaggcctgg | SEQ_DUP; | 271 |
| | .........................12......................... | DUP_NUM; | |
| | aaA...aA....Ha.a.A......a.A....aaa.a.aB..aA...aA.... | Cas9_Wa; | |
| | aa..A...a...A.a..Aa..A.....Aa.aa..A.aaa....A........ | Cas9_Cr; | |
| | ................NL..............................L... | Cpf1_Wa; | |
| | .....................k.............................. | Cpf1_Cr; | |
| GJB2 | cttcctcttcttctcatgtctccggTTaggccacgtgcatggccactaggag | SEQ_DUP; | 272 |
| | .........................12......................... | DUP_NUM; | |
| | .............A.....aA...aA....a.A...aA......aa.a.A.. | Cas9_Wa; | |
| | .....A.Baa.a.Ba.Ba.a....a.aa.......Aa.a...A..J.Aa.a. | Cas9_Cr; | |
| | ...k.M...L....N.........NL....N..N..........L...N... | Cpf1_Wa; | |
| | ........................................L.....LN.... | Cpf1_Cr; | |
| GJB2 | ccggtaggccacgtgcatggccactAAggagcgctggcgtggacacgaagat | SEQ_DUP; | 273 |
| | .........................12......................... | DUP_NUM; | |
| | ..aA....a.A...aA.......aa.a.A..aa.aJaa....aB.aC...A. | Cas9_Wa; | |
| | ...a.aa......Aa.a...A..J.Aa.a.....A.a...A.......A.a. | Cas9_Cr; | |
| | ...NL....N..N..........L............................ | Cpf1_Wa; | |
| | ....N..............L.....LN..................M.....L | Cpf1_Cr; | |
| CENPJ | ccctttttaatgcaaggaaaggctgTTatgggtttcagatttatctgactgt | SEQ_DUP; | 274 |
| | .........................12......................... | DUP_NUM; | |
| | .......A...aaB..aA..A...HaaA..I..aC.......a...a.aA.. | Cas9_Wa; | |
| | .....aaa.........A.........A...........Ba.......Ca.. | Cas9_Cr; | |
| | .......................L.....k..................N.M. | Cpf1_Wa; | |
| | ......................................N............. | Cpf1_Cr; | |
| BRCA2 | cttattttaactcctacttccaaggAAtgttctgtcaaacctagtcatgatt | SEQ_DUP; | 275 |
| | .........................12......................... | DUP_NUM; | |
| | ...................aaB..A....A.........A.I..aC...... | Cas9_Wa; | |
| | .A.a.aH........A.aa..A.Baa.........Ba...a...Aa....a. | Cas9_Cr; | |
| | M.......................N....k..........NLL......... | Cpf1_Wa; | |
| | N..LN..........k........................k...N...M... | Cpf1_Cr; | |

TABLE 6-continued

Selected Genes Having Microduplication Variants

| SYMBOL | MICRODUPLICATION INFORMATION | | SEQ ID NO: |
|---|---|---|---|
| BRCA2 | attgtaaaaatagtcatataaccccTTcagatgttattttccaagcaggatt | SEQ_DUP; | 276 |
| | .........................12......................... | DUP_NUM; | |
| | ........A................aC.A............AIHaaC..... | Cas9_Wa; | |
| | .Ba................a.......Aaaa.Ba..........Baa...A. | Cas9_Cr; | |
| | ..............N...k.....N...............M.......NL.. | Cpf1_Wa; | |
| | .....................N...........N....k....M.N....N. | Cpf1_Cr; | |
| BRCA2 | atcaccagttttagccatcaatgggCCaaagaccctaaagtacagagaggcc | SEQ_DUP; | 277 |
| | .........................12......................... | DUP_NUM; | |
| | ...A......A.......aaA.....a.....J..A....a.a.aA...A.. | Cas9_Wa; | |
| | J....Ca.aa.........Aa.Ca......Aa.....AaaH......A..J. | Cas9_Cr; | |
| | .................................k.................. | Cpf1_Wa; | |
| | .....k.........k..................k........LN....... | Cpf1_Cr; | |
| BRCA2 | caaacgaaaattatggcaggttgttAAcgaggcattggatgattcagaggat | SEQ_DUP; | 278 |
| | .........................12......................... | DUP_NUM; | |
| | .aB.......aA..aA..A.....a.aA...HaaC.aC....aHaaC..... | Cas9_Wa; | |
| | ...Aa...A............A..........A....A..........BaH. | Cas9_Cr; | |
| | ...................k.............N.M........N..N.... | Cpf1_Wa; | |
| | ...N...........L.............M........M.N.........M. | Cpf1_Cr; | |
| BRCA2 | tttctgaaatagaagatagtaccaaGGcaagtcttttccaaagtattgttta | SEQ_DUP; | 279 |
| | .........................12......................... | DUP_NUM; | |
| | .aB....aB.ac..A......aA...A...........A....A.......A | Cas9_Wa; | |
| | .......ba.................Aa.J..A....a...Baa........ | Cas9_Cr; | |
| | .N......................k........................... | Cpf1_Wa; | |
| | ..N....N..........k...........k.....N..LN........... | Cpf1_Cr; | |
| BRCA2 | gtttctttagagccgattacctgtgTTaccctttcggtaagacatgtttaaa | SEQ_DUP; | 280 |
| | .........................12......................... | DUP_NUM; | |
| | .....a.a..aC......a.A..........aA...a....A.......... | Cas9_Wa; | |
| | .Ca.....Ba.......Aa.....Aa.......aaaH.Ba.......A.... | Cas9_Cr; | |
| | ........N...k.M..........k...k.........N........N... | Cpf1_Wa; | |
| | .................N..........k.........k......N...... | Cpf1_Cr; | |
| BRCA2 | tgcccctttcgtctatttgtcagacGGaatgttacaatttactggcaataaa | SEQ_DUP; | 281 |
| | .........................12......................... | DUP_NUM; | |
| | ......A.......A...a..aaB..A............aA.......A... | Cas9_Wa; | |
| | ...A...Aaaa..Ba..a.......a...A.........A......A...A. | Cas9_Cr; | |
| | ........kLL..N........N.......kL.......k............ | Cpf1_Wa; | |
| | ....LLN.......N..........N..k.......L.M........N.... | Cpf1_Cr; | |
| BRCA2 | agatgtcttctcctaattgtgagatAAtattatcaaagtcctttatcacttt | SEQ_DUP; | 282 |
| | .........................12......................... | DUP_NUM; | |
| | .A............a.a.aC.............A..............A... | Cas9_Wa; | |

TABLE 6-continued

| SYMBOL | MICRODUPLICATION INFORMATION | | SEQ ID NO: |
|---|---|---|---|
| | Selected Genes Having Microduplication Variants | | |
| | ...Ca......a.Ba.aa...................Ca.....aa....Ca | Cas9_Cr; | |
| | .........kL.......k.M..........N.......N............ | Cpf1_Wa; | |
| | ..M.N........k.........................k....LN...... | Cpf1_Cr; | |
| ATP7B | caggagcacccgcatgaccctggggAAcgccatgggtaatggtgccagtctt | SEQ_DUP; | 283 |
| | .........................12......................... | DUP_NUM; | |
| | .A.....A...a.....aaaaB..A...HaaA....aa.A...A....A... | Cas9_Wa; | |
| | aaa..A.....A.aaaHa....AaaH......A.aa.............Aa. | Cas9_Cr; | |
| | ................L................................... | Cpf1_Wa; | |
| | ..LLN...........N.................k................. | Cpf1_Cr; | |
| ATP7B | gtccatgttggctgacctgtgtctcAAgagatttgtaggcctgaacgtagaa | SEQ_DUP; | 284 |
| | .........................12......................... | DUP_NUM; | |
| | ..A..aA..a....a.A.....Ia.aC...A..aA...aB..A..aB.A... | Cas9_Wa; | |
| | ..A.a..aa.......A...Aa.....a.a..............Aa....A. | Cas9_Cr; | |
| | .N.......................L....N..................... | Cpf1_Wa; | |
| | ....N................LN......N.....................L | Cpf1_Cr; | |
| NRL | cccagctgctgctgcagggtagccaGGccagtacagctcctccaggcctggc | SEQ_DUP; | 285 |
| | .........................12......................... | DUP_NUM; | |
| | A..A..A..A.HaaA..A...aAJ..A....A........aA...aA.Haaa | Cas9_Wa; | |
| | a..Aaaaa..A..A..A..A.......Aa...Aa....A..a.aa.aa...A | Cas9_Cr; | |
| | .................................................... | Cpf1_Wa; | |
| | .................................................... | Cpf1_Cr; | |
| RDH12 | caggagcccgagtctatattgcctgCCagagatgtactgaagggggagtctg | SEQ_DUP; | 286 |
| | .........................12......................... | DUP_NUM; | |
| | .A..Ha.A........A...A...a.aC.A....aB.aaaaa.A...A..A. | Cas9_Wa; | |
| | ...AaaH....Aaa....a.......Aa..Aa.........A..J....... | Cas9_Cr; | |
| | ...........k....N.....................M..N.......... | Cpf1_Wa; | |
| | ..................LN....L..............Lk.........L. | Cpf1_Cr; | |
| SPATA7 | atgccaaagaaaaaatagctcctttAAcctttagaagggcatgactcaacat | SEQ_DUP; | 287 |
| | .........................12......................... | DUP_NUM; | |
| | ....aB.......A...............aB.aaA...a.........aaaC | Cas9_Wa; | |
| | ........Aa.............A.aa.....Aa..........A....A.a | Cas9_Cr; | |
| | .........N..........M.........................k..... | Cpf1_Wa; | |
| | ....N........N............N.....L.........N......... | Cpf1_Cr; | |
| OCA2 | cttctcggaggaggcagatgcagacAAgaccagacacctccctgcttagcag | SEQ_DUP; | 288 |
| | .........................12......................... | DUP_NUM; | |
| | ..aa.aa.aA..aC.A..a....a..J.a..........A....A..aA... | Cas9_Wa; | |
| | .a.aaa.Ba.a........A.....A...A....Aa...A.aa.aaa..A.. | Cas9_Cr; | |
| | ..........L..........L..N........................... | Cpf1_Wa; | |
| | ....N............................................... | Cpf1_Cr; | |

TABLE 6-continued

Selected Genes Having Microduplication Variants

| SYMBOL | MICRODUPLICATION INFORMATION | | SEQ ID NO: |
|---|---|---|---|
| EIF2AK4 | ataagctcttgtgacctcctggttgTTaagtgttggccagatgtctatgtcc | SEQ_DUP; | 289 |
| | .........................12......................... | DUP_NUM; | |
| | A.....a.a.......aA..A....a.A..aA...aC.A.....A....aaA | Cas9_Wa; | |
| | ...A......A.a......Aa.aa................JAa......a.. | Cas9_Cr; | |
| | ......k......L....N............N.............N..N... | Cpf1_Wa; | |
| | ......N.................................N....N...... | Cpf1_Cr; | |
| CAPN3 | ctgagttcccaccggatgagacctcTTctcttttatagccagaagttcccca | SEQ_DUP; | 290 |
| | .........................12......................... | DUP_NUM; | |
| | A.......HaaC.a.a.................A...aB.A........... | Cas9_Wa; | |
| | ...AaaH....Baaa.aa........Aa.a.Ba.a........Aa......B | Cas9_Cr; | |
| | ........N...k.M.............NLL.................N... | Cpf1_Wa; | |
| | .............M.......N.....................LLN...... | Cpf1_Cr; | |
| TUBGCP4 | aacagctctcagcctggatgctccaTTggactcctcttggaccagcatgaag | SEQ_DUP; | 291 |
| | .........................12......................... | DUP_NUM; | |
| | A......A..HaaC.A.......aa.........aa....A...aBHaB... | Cas9_Wa; | |
| | ......JA..A.a.a..Aa......A.aa......A.aa.a.....Aa..A. | Cas9_Cr; | |
| | ...k................M........................L..N... | Cpf1_Wa; | |
| | ......L..........L.........LN..N.........k.......... | Cpf1_Cr; | |
| SPG11 | cataccttggcaagatcatacagacAAgaggacctgtcgacagtagttcttc | SEQ_DUP; | 292 |
| | .........................12......................... | DUP_NUM; | |
| | ....aA...ac.......a....a.aa....A..a...A..A.......... | Cas9_Wa; | |
| | ...A.a...Aa....A....Ca...A...A.......Aa...a..A...... | Cas9_Cr; | |
| | .................N...........N...................... | Cpf1_Wa; | |
| | ....N..............................L................ | Cpf1_Cr; | |
| SPG11 | tgggtctccaaatcccagagggtaaTTggtatagcccatcctttccacttcc | SEQ_DUP; | 293 |
| | .........................12......................... | DUP_NUM; | |
| | .............aHaaA.....aA....A.....................A | Cas9_Wa; | |
| | ..Aaa.....a.aa...CaaaI.................aaa.CaaH.Baa. | Cas9_Cr; | |
| | ..............................L.....L...........N... | Cpf1_Wa; | |
| | ..N......M......................N...k...........LN.. | Cpf1_Cr; | |
| DUOXA2 | ttcacctggcgtctgaaagagaattAAcgccgcggagtacgcgaacgcactg | SEQ_DUP; | 294 |
| | .........................12......................... | DUP_NUM; | |
| | ...aa.A...aB..aHaB......A..a.aa.A...a.ab..A....aa.aB | Cas9_Wa; | |
| | ..A...Ba.aa...A..a..............A.aa.a......A.aJ..A. | Cas9_Cr; | |
| | ......N................NL.....................N..... | Cpf1_Wa; | |
| | N...N...L...L........LN.......L...N..........L...... | Cpf1_Cr; | |
| FBN1 | aagcccaaagccttcaaagacacttAAccttggcaccttcttccactggagg | SEQ_DUP; | 295 |
| | .........................12......................... | DUP_NUM; | |
| | .....A......J.a..........J.aA..............aa.aa.... | Cas9_Wa; | |

TABLE 6-continued

Selected Genes Having Microduplication Variants

| SYMBOL | MICRODUPLICATION INFORMATION | | SEQ ID NO: |
|---|---|---|---|
| | ........Aaa....Aa.Ba.....A.a....Aa....A.aa.Ba.Baa.a. | Cas9_Cr; | |
| | ...................N...............NL..........N.... | Cpf1_Wa; | |
| | ....N....................L.......N..Lk..........L... | Cpf1_Cr; | |
| KIF7 | gtgccgcgccgcgttgcccatctccAAggaggctcagcacctcatccaggcc | SEQ_DUP; | 296 |
| | .........................12......................... | DUP_NUM; | |
| | .a.A..a.A..A...........aa.aA.J..A...........aA...... | Cas9_Wa; | |
| | aaa.....Aa.a.aa.a....Aaa.Ca.aa.......A.a..A.aa.a.Caa | Cas9_Cr; | |
| | ...N..............L.................N.........L..... | Cpf1_Wa; | |
| | ....N............................................... | Cpf1_Cr; | |
| BLM | aagcagtattttttttccaactagTTggggacatgattttcgtcaagatta | SEQ_DUP; | 297 |
| | .........................12......................... | DUP_NUM; | |
| | .A..................A..aaaa.I..aC.....A.I..aC....... | Cas9_Wa; | |
| | a.......A.......J....Baa..A..........A.......Ba..a.. | Cas9_Cr; | |
| | .........L............................kLL.......N... | Cpf1_Wa; | |
| | ........L...............N.......k....N..LN.......... | Cpf1_Cr; | |
| BLM | tccttctgttccggtgatggctcttAAcggccacagctaatcccagggtaca | SEQ_DUP; | 298 |
| | .........................12......................... | DUP_NUM; | |
| | ...A....aa.aC.aA........aA....A.........haaA....aB.a | Cas9_Wa; | |
| | .....Baa.Ba...Baa........A.a....A..Aa.a..A...CaaaI.. | Cas9_Cr; | |
| | ......M...NL..........kL..N....NLL............N..... | Cpf1_Wa; | |
| | ....N............N..............N................... | Cpf1_Cr; | |
| BLM | tgtccattacttcaatatttttaatAAccgtcactctcaagaagcttgcagg | SEQ_DUP; | 299 |
| | .........................12......................... | DUP_NUM; | |
| | .........................A..........aB.A...A..aahaaA | Cas9_Wa; | |
| | ........aaJ...A.Ba..............Aa..a.a.aHa......A.. | Cas9_Cr; | |
| | ...................k......L..N...NL........k........ | Cpf1_Wa; | |
| | .N..N............N..N............................... | Cpf1_Cr; | |
| ERCC4 | gtactacatgaagtggagccaagatAAcgtggttctttatgacgcagagcta | SEQ_DUP; | 300 |
| | .........................12......................... | DUP_NUM; | |
| | .....aB.a.aa.A....aC....a.aA........a..A..a.A....... | Cas9_Wa; | |
| | A.......A..a...........Aa.......A.....Ba.......A.a.. | Cas9_Cr; | |
| | .........M.......................................... | Cpf1_Wa; | |
| | ..M.N.........................N..................Lk. | Cpf1_Cr; | |
| PALB2 | cagaaagggtcccactgctactaacTTagcctcctctttgtcaggccaagca | SEQ_DUP; | 301 |
| | .........................12......................... | DUP_NUM; | |
| | .HaaA.......A...........A..........A...aA.J..A....A. | Cas9_Wa; | |
| | ....Ca.........aaa.a..A..A...A....Aa.aa.a.....a...Aa | Cas9_Cr; | |
| | .........N.....N..N..............L..............N... | Cpf1_Wa; | |
| | .N........................N............M............ | Cpf1_Cr; | |

TABLE 6-continued

Selected Genes Having Microduplication Variants

| SYMBOL | MICRODUPLICATION INFORMATION | | SEQ ID NO: |
|---|---|---|---|
| PALB2 | gtgctgactactaccgctatctgatAAgagtctgtaaaggaactgtagtcgc | SEQ_DUP; | 302 |
| | .........................12......................... | DUP_NUM; | |
| | .a.........A......aC..Ha.A...A....aaB...A..A..A....a | Cas9_Wa; | |
| | BaJ.....A..JA..A..Aa.a..Ca..........a..........A.... | Cas9_Cr; | |
| | ...k.............NL......................M.......... | Cpf1_Wa; | |
| | ..M.N.........k...LN.................Lk............. | Cpf1_Cr; | |
| CLN3 | ctcttaccagcggtattgctgagcgTTgactcagggaagtgttccagaaaaa | SEQ_DUP; | 303 |
| | .........................12......................... | DUP_NUM; | |
| | .....a.aA....A..a.a.A..a.....aaaB.a.A.....aB....a.aa | Cas9_Wa; | |
| | a.a.aa.a...Aa..A.......a....A.....A.aH.........Baa.. | Cas9_Cr; | |
| | ..L.......................N...........N.........N... | Cpf1_Wa; | |
| | .............LLN..........k.............k......N..k. | Cpf1_Cr; | |
| CLN3 | atggacagcagggtctgctgaggggAAgaggccggcctgggtgaggcccagg | SEQ_DUP; | 304 |
| | .........................12......................... | DUP_NUM; | |
| | ...A.HaaA...A..a.aaaaB.a.aA..aA..Haaa.a.aA....aA..aa | Cas9_Wa; | |
| | aaH.A.....A..A.....a..A.............Aa..Aa.........A | Cas9_Cr; | |
| | .................................................... | Cpf1_Wa; | |
| | ..LLN............................................... | Cpf1_Cr; | |
| TK2 | ggcggcccagccccgcagcggccacAAgcagcatagccgggcgagcggatcc | SEQ_DUP; | 305 |
| | .........................12......................... | DUP_NUM; | |
| | A....A....A..a.aA......A..A....A..aaa.a.aHaaC....a.a | Cas9_Wa; | |
| | .aaa...A..Aaa..Aaaa.a..A..Aa.a...A..A....Aa...A...A. | Cas9_Cr; | |
| | .................................................... | Cpf1_Wa; | |
| | ....N......M.............L.......................... | Cpf1_Cr; | |
| APRT | agcagttggctgcggggagacccttAAccaccagtggccagcagatcatcca | SEQ_DUP; | 306 |
| | .........................12......................... | DUP_NUM; | |
| | A..aA..a.aaaa.a..............a.aA...A..aC........a.. | Cas9_Wa; | |
| | .Aa.a..A......A..A.......AaaH...Aa.aa.....Aa..A...Ca | Cas9_Cr; | |
| | .L...........N..............N.................N..... | Cpf1_Wa; | |
| | ....N............................................... | Cpf1_Cr; | |
| SPG7 | ttcagccaaggcctgcagcagatgaTTggaccatgtgagtcggctctggcca | SEQ_DUP; | 307 |
| | .........................12......................... | DUP_NUM; | |
| | A....aA...A..A..aC.aC..aa.....aHa.A..aA....aa....... | Cas9_Wa; | |
| | .aaaa.Ba..Aa....Aa..A..A...........Aa........a..A.a. | Cas9_Cr; | |
| | ....................NL..........................N... | Cpf1_Wa; | |
| | .................................................... | Cpf1_Cr; | |

TABLE 6-continued

Selected Genes Having Microduplication Variants

| SYMBOL | MICRODUPLICATION INFORMATION | | SEQ ID NO: |
|---|---|---|---|
| CTNS | cttcagcctgcacgcggttgtcctcAAcgctgatcatcatcgtgcagtgctg | SEQ_DUP; | 308 |
| | .........................12......................... | DUP_NUM; | |
| | .AJ..A...a.aA..A........A..aC........a.A..a.A..A...A | Cas9_Wa; | |
| | ..a.Ba.Ba..Aa..A.a.a......aa.a..A.a...Ca.Ca.Ca...A.. | Cas9_Cr; | |
| | .....................N..NL..............N........... | Cpf1_Wa; | |
| | ....N............................................... | Cpf1_Cr; | |
| CTNS | ctcgcccccagcgcggtggccagcgCCgtgtcctggcctgccatcggcttcc | SEQ_DUP; | 309 |
| | .........................12......................... | DUP_NUM; | |
| | ......a.a.aa.aA...a.A..a.A....aA...A.....aA......aa. | Cas9_Wa; | |
| | a.aa.a.a.aaaaa..A.a.....Aa..A.aa....aaJ..Aa..Aa.Ca.. | Cas9_Cr; | |
| | .....L.............................................. | Cpf1_Wa; | |
| | .................................................... | Cpf1_Cr; | |
| FLCN | cgtactggctgctgtatgggatgatGGcggacgcagcccacgggaagcatgg | SEQ_DUP; | 310 |
| | .........................12......................... | DUP_NUM; | |
| | ..aA..A..A...aaaC.aC.aa.aa..A..A.....aaaB.A...aA...a | Cas9_Wa; | |
| | a.aa.a...A..JA..A.......J.......A...A.a..Aaa.a...... | Cas9_Cr; | |
| | ....N.................................M............. | Cpf1_Wa; | |
| | .....................LLN............................ | Cpf1_Cr; | |
| FLCN | ggcctggcggacaatgctgaagagcTTgggggtggctggggtgctggtggct | SEQ_DUP; | 311 |
| | .........................12......................... | DUP_NUM; | |
| | .aa.aa.....A..aB.a.A...aaaaa.aA..aaaa.A..aa.aA..a..A | Cas9_Wa; | |
| | .A.a...Aa...A...A....A.......A..........A.......A..J | Cas9_Cr; | |
| | ..............L.................................N... | Cpf1_Wa; | |
| | ........................................N..L........ | Cpf1_Cr; | |
| RAD51D | gcacagtccgaccctgagcacgcccAAtgttccccgcaggccggaacagccc | SEQ_DUP; | 312 |
| | .........................12......................... | DUP_NUM; | |
| | .A...a....Ja.A...A......A......A..aA..aaB...A.....aa | 8 Cas9_Wa; | |
| | Aa....A.a...aa..AaaH...A.a.aaa.....Baaaa.a...Aa....A | 8 Cas9_Cr; | |
| | ..............................L..................... | Cpf1_Wa; | |
| | ....N................LLN............L............... | Cpf1_Cr; | |
| BRCA1 | cactctcgggtcaccacaggtgcctCCacacatctgcccaattgctggagac | SEQ_DUP; | 313 |
| | .........................12......................... | DUP_NUM; | |
| | ..HaaA..........aa.A..J........A.......A..aa.a...aJa | Cas9_Wa; | |
| | .A.aaaHa.aHa....a.aa.a.....Aa.aa.a.a.Ca..Aaa.....A.. | Cas9_Cr; | |
| | ...............L................................L... | Cpf1_Wa; | |
| | ..................N......L.........N....N........... | Cpf1_Cr; | |
| BRCA1 | agggaagctcttcatcctcactagaTTaagttctcttctgaggactctaatt | SEQ_DUP; | 314 |
| | .........................12......................... | DUP_NUM; | |
| | B.A.............I..aC....A.........a.aa............. | Cas9_Wa; | |

TABLE 6-continued

Selected Genes Having Microduplication Variants

| SYMBOL | MICRODUPLICATION INFORMATION | | SEQ ID NO: |
|---|---|---|---|
| | J...A.......A.a.Ba.CaaHa.a..........Ba.a.Ba......A.a | Cas9_Cr; | |
| | ...............N.................NL.............N... | Cpf1_Wa; | |
| | ......N....................N.....................N.. | Cpf1_Cr; | |
| BRCA1 | tagataagttctcttctgaggactcTTaatttcttggcccctcttcggtaac | SEQ_DUP; | 315 |
| | .........................12......................... | DUP_NUM; | |
| | ...A.........a.aa..............aA.........aA.......a | Cas9_Wa; | |
| | aHa.a.........Ba.a.Ba......A.aH.....Ba....Aaaa.a.Ba. | Cas9_Cr; | |
| | ............NL.................N....N...........N... | Cpf1_Wa; | |
| | ......N.....................N..........k............ | Cpf1_Cr; | |
| BRCA1 | cttttgttttattctcatgaccactAAttagtaatattcatcacttgaccat | SEQ_DUP; | 316 |
| | .........................12......................... | DUP_NUM; | |
| | .A............a...........A...............a........A | Cas9_Wa; | |
| | .Ca.aa...........BaHa....Aa.a.............BaHCa.a... | Cas9_Cr; | |
| | .k.....N..................k....k..N...............N. | Cpf1_Wa; | |
| | ....N......N........................................ | Cpf1_Cr; | |
| RAD51C | gaatgtctcacaaataaaccaagatAAtgctggtacatctgagtcacacaag | SEQ_DUP; | 317 |
| | .........................12......................... | DUP_NUM; | |
| | A.................aC....AJ.aA......Ha.a........aBJa. | Cas9_Wa; | |
| | ...........a.a.a.......Aa.........A.....A.Ca.....a.a | Cas9_Cr; | |
| | ............N.M..................................... | Cpf1_Wa; | |
| | ..M.N.......................N..N.............LLN.... | Cpf1_Cr; | |
| BRIP1 | tgaggtactgtactttaaagaggtcAActtcaagtgtagactcattgtcctg | SEQ_DUP; | 318 |
| | .........................12......................... | DUP_NUM; | |
| | A.J..A.........a.aA..........a.A..a.......A....A.... | Cas9_Wa; | |
| | ............A..J.A..J........a..A.Ba........JA.aH... | Cas9_Cr; | |
| | .N......NLL..........................k.............N | Cpf1_Wa; | |
| | ....N.....N.....................M................... | Cpf1_Cr; | |
| BRIP1 | actcactttaccacgacaaactgctAAccaggagagctccatcttaaacaac | SEQ_DUP; | 319 |
| | .........................12......................... | DUP_NUM; | |
| | ..........a.......A.......aa.a.A.................aB. | Cas9_Wa; | |
| | AaaHa.a.aHa....Aa.a..A...A..A...Aa.......A.aa.Ca.... | Cas9_Cr; | |
| | .............L................k..................... | Cpf1_Wa; | |
| | ....N...................k...N....k.......M.....k.... | Cpf1_Cr; | |
| BRIP1 | ttagcctccagctggatagtaaatgTTaacaccaagttctgacgaaaaggat | SEQ_DUP; | 320 |
| | .........................12......................... | DUP_NUM; | |
| | ......A.HaaC..A.....AJ.........A....a..aB.IHaaC..... | Cas9_Wa; | |
| | .........Aa.aa..A..................A.aa....Ba...A... | Cas9_Cr; | |
| | ...........k.......M...N......L.................N... | Cpf1_Wa; | |
| | ......N.....N.........Lk.................M.N........ | Cpf1_Cr; | |

TABLE 6-continued

Selected Genes Having Microduplication Variants

| SYMBOL | MICRODUPLICATION INFORMATION | | SEQ ID NO: |
|---|---|---|---|
| CANT1 | tggcgggcgcctggccgagcctccaGGttgtgtgcattgtgggtggggggcc | SEQ_DUP; | 321 |
| | ........................12.......................... | DUP_NUM; | |
| | aaa.A...aA..a.A......aA..a.a.A....aHaaa.aaaaaA...A.. | Cas9_Wa; | |
| | Aa.J....A...A.aa...Aa...Aa.aa..........AJ.J......... | Cas9_Cr; | |
| | .............N........N......................L....N. | Cpf1_Wa; | |
| | ..................................................L. | Cpf1_Cr; | |
| PYCR1 | cccacctgggggcctacctgctgctGGtgaagcccttggccagggcaaaagc | SEQ_DUP; | 322 |
| | ........................12.......................... | DUP_NUM; | |
| | ...aaaaA.......A..A..aa.aB.A.....aA...aaA.....A...A. | Cas9_Wa; | |
| | a..aaaaa.aa......Aa..Aa..A..A........Aaa....Aa....A. | Cas9_Cr; | |
| | ...L.................L.............................. | Cpf1_Wa; | |
| | .......LN................k.......................LN. | Cpf1_Cr; | |
| NPC1 | aaaaggatgacaggaacatactgggAAgccacttctcctaggaccctgccca | SEQ_DUP; | 323 |
| | ........................12.......................... | DUP_NUM; | |
| | aaC.a...aab.......aaaB.A............aa.....A....A..A | Cas9_Wa; | |
| | a.a............A.....A...A.......Aa.a.Ba.aa.....AaaH | Cas9_Cr; | |
| | .................................................... | Cpf1_Wa; | |
| | ..LLN............................................... | Cpf1_Cr; | |
| LAMA3 | tcaaagtcaactgcaagcgagttatGGtggagtttagacccagccaggtaac | SEQ_DUP; | 324 |
| | ........................12.......................... | DUP_NUM; | |
| | .A......A...aHa.A....aa.aa.A....a.....A...aA....A... | Cas9_Wa; | |
| | aaa...a.....a..A..A...A....................AaaH.Aa.. | Cas9_Cr; | |
| | .......k..NL......L.........................N.M..... | Cpf1_Wa; | |
| | .......L....................N..........N............ | Cpf1_Cr; | |
| SERPINB7 | ctgctgtaatggtgctggtgaatgcTTgtgtacttcaaaggcaagtggcaat | SEQ_DUP; | 325 |
| | ........................12.......................... | DUP_NUM; | |
| | .A....aa.A..aaHaB..A..Ja.A.........aA...a.aA......A. | Cas9_Wa; | |
| | A.a.Ca..A..........A..J......A.......AJBa.....A..... | Cas9_Cr; | |
| | ................................................N... | Cpf1_Wa; | |
| | ...............k.....N......N.............N.....Lk.. | Cpf1_Cr; | |
| LDLR | acggctcagacgagcaaggctgtcgTTaagtgtggccctgcctttgctattg | SEQ_DUP; | 326 |
| | ........................12.......................... | DUP_NUM; | |
| | ....a..a.A...aA..A..A....a.a.aA....A.....A.....a.A.. | Cas9_Wa; | |
| | A..A..A..A.a...A...A....A...a...........aaa..Aa....A | Cas9_Cr; | |
| | ................................................N... | Cpf1_Wa; | |
| | ......N..........................................L.. | Cpf1_Cr; | |
| LDLR | agcccccaagacgtgctcccaggacGGagtttcgctgccacgatgggaagtg | SEQ_DUP; | 327 |
| | ........................12.......................... | DUP_NUM; | |
| | .....a..a.A......aa..aa.A....A..A....aC.aaaB.a.A.... | Cas9_Wa; | |

TABLE 6-continued

Selected Genes Having Microduplication Variants

| SYMBOL | MICRODUPLICATION INFORMATION | | SEQ ID NO: |
|---|---|---|---|
| | aa..A..Aaaaa....A...A.aaa....A......Ba.a..Aa.a...... | Cas9_Cr; | |
| | .............L...L.................................. | Cpf1_Wa; | |
| | ....L..................LLN.......................... | Cpf1_Cr; | |
| LDLR | gagtgcctgtgccccgacggcttccAAgctggtggcccagcgaagatgcgaa | SEQ_DUP; | 328 |
| | .........................12......................... | DUP_NUM; | |
| | A...a.A....a..aA.......A..aa.aA....a.aB.aC.a.aB.aa.a | Cas9_Wa; | |
| | .A..A.....Aa.J..Aaaa..A..A.Baa...A......Aaa..A...... | Cas9_Cr; | |
| | .........N.................................NLL...... | Cpf1_Wa; | |
| | ....N...............LN......LN................L..... | Cpf1_Cr; | |
| LDLR | atctgtgcctccctgccccgcagatCCaacccccactcgcccaagtttacct | SEQ_DUP; | 329 |
| | .........................12......................... | DUP_NUM; | |
| | a.A.......A....A..aC..............A....A........a.A. | Cas9_Wa; | |
| | Aa....Ca.J..Aa.aaa..Aaaa.a...CaaH.Aaaaa.a.aHaaa..... | Cas9_Cr; | |
| | .......................M.........L..............L... | Cpf1_Wa; | |
| | ......N..............N.................L............ | Cpf1_Cr; | |
| LDLR | aggctaaaggtcagctccacagccgTTaaggacacagcacacaaccacccga | SEQ_DUP; | 330 |
| | .........................12......................... | DUP_NUM; | |
| | ....aA...A.......A..A...Jaa..J.JA.............a....A | Cas9_Wa; | |
| | aa..a...A.......a..A.aa.a..Aa........A.a..A.a.a..Aa. | Cas9_Cr; | |
| | ...............L.......................L........N... | Cpf1_Wa; | |
| | ......N..............N.............................. | Cpf1_Cr; | |
| ACP5 | agcgcagatagccgttggggaccttGGcgctggtgccgctttgaggggtcca | SEQ_DUP; | 331 |
| | .........................12......................... | DUP_NUM; | |
| | ..aC..A..A..aaaa.....aa.A..aa.A..A....a.aaaA.....aB. | Cas9_Wa; | |
| | .......A.a......Aa........Aa....A.a.....Aa.a........ | Cas9_Cr; | |
| | ......NL....L........................N........N..... | Cpf1_Wa; | |
| | ................................Lk.................. | Cpf1_Cr; | |
| CYP4F22 | ctggggctggagaagacggcgttccGGcatatacgcggtgtccacccttctc | SEQ_DUP; | 332 |
| | .........................12......................... | DUP_NUM; | |
| | aA..aa.aB.a..aa.A....aAJ......a.aa.A................ | Cas9_Wa; | |
| | .aa.aa....A.........A..A..Baa..A.....A.a......aaJaaa | Cas9_Cr; | |
| | ...........................................NLL...... | Cpf1_Wa; | |
| | .......M.M.......................................... | Cpf1_Cr; | |
| JAK3 | ggaggaaggggctcacctttgggtcTTggggatacagcaggaagtgagggtc | SEQ_DUP; | 333 |
| | .........................12......................... | DUP_NUM; | |
| | aB.aaaA........HaaA....aaaaC....A..aaB.a.aHaaA.....A | Cas9_Wa; | |
| | aa.............A.a.aa........a.........A..A......... | Cas9_Cr; | |
| | ................NLL......................k......N... | Cpf1_Wa; | |
| | ........L.M........LN............................... | Cpf1_Cr; | |

TABLE 6-continued

| Selected Genes Having Microduplication Variants | | | |
|---|---|---|---|
| SYMBOL | MICRODUPLICATION INFORMATION | | SEQ ID NO: |
| ADCK4 | ctggggagactcacctcgatgtaaTTggtctgtgaactctgtcccaaactc | SEQ_DUP; | 334 |
| | ........................12........................ | DUP_NUM; | |
| | aaa.a........aC.A.....aA...a.aB....A............aA | Cas9_Wa; | |
| | .....a........A.aHaa.a...........a......A.aH..aaa. | Cas9_Cr; | |
| | ......kL......................................N... | Cpf1_Wa; | |
| | ..N.........LN..........k................k........ | Cpf1_Cr; | |
| ZNF575 | agtttggtccccggactgaccagcaTTagagcagccgcagccccagctcctt | SEQ_DUP; | 335 |
| | ........................12........................ | DUP_NUM; | |
| | .aA....aa...a....A.....a.A..A..A..A....A......aC.. | Cas9_Wa; | |
| | aaH.........aaaa...A...Aa..A......A..Aa.a..Aaaa..A | 8 Cas9_Cr; | |
| | .................L.......k...L................N... | 8 Cpf1_Wa; | |
| | .................................................. | Cpf1_Cr; | |
| PNKP | cctcggcttccagctctcggagcttAAcggggaatctctgggtacaagatcc | SEQ_DUP; | 336 |
| | ........................12........................ | DUP_NUM; | |
| | aA.....A.....aa.A.....aaaaB.....haaA.....aC......a | Cas9_Wa; | |
| | ....Aaa.a..A.Baa..A.a.a....A...A.....Ca.aI.....A.. | Cas9_Cr; | |
| | ...............N............NLL.............N..... | Cpf1_Wa; | |
| | ....N...LLN............N.................LN....... | Cpf1_Cr; | |
| NLRP12 | cccaggggataccccagggatacttAAcagctgcaccaacagcgtgtgcgct | SEQ_DUP; | 337 |
| | ........................12........................ | DUP_NUM; | |
| | aaaaC......aaaC.........a..A.......a.a.a.a.A.....a | Cas9_Wa; | |
| | .A..Aaaa.......Aaaa.......A...A..A..A.aa..A..A.... | Cas9_Cr; | |
| | ............................................N..... | Cpf1_Wa; | |
| | ....N..........N..................L............... | Cpf1_Cr; | |
| DNAAF3 | tcatgcgcaggtcccagtcgctgacAAccgcgccgggcgtcgtagcgggagc | SEQ_DUP; | 338 |
| | ........................12........................ | DUP_NUM; | |
| | a.A..aA....A..A..a.....a.A..aaa.A..A..a.aaa.A....a | Cas9_Wa; | |
| | A..A.Ba..A.a....aaa...a.a...A..Aa.a.aa...A..a....A. | Cas9_Cr; | |
| | .....................NL...........L............... | Cpf1_Wa; | |
| | ....N....................L........................ | Cpf1_Cr; | |
| DNAAF3 | caggtgccgtccatccacagagcccAAgaagcagcacatctagctcggggtt | SEQ_DUP; | 339 |
| | ........................12........................ | DUP_NUM; | |
| | .A..A.........a.A.....aB.a..A.......A...aaaA..A.Ja | Cas9_Wa; | |
| | a.a..A....Aa.Jaa.CaaHa....Aaa......A..A.a.Ca..A.a. | Cas9_Cr; | |
| | NL..............L...............L..L.............. | Cpf1_Wa; | |
| | ....N..N.......................................... | Cpf1_Cr; | |
| KCNE1 | gaaagggcgtcaccgctgtggtgttAAgacaggatcatcctgggcattaagg | SEQ_DUP; | 340 |
| | ........................12........................ | DUP_NUM; | |
| | aaa.A.....A..a.aa.A...a..HaaC......aaA......aA.... | Cas9_Wa; | |

TABLE 6-continued

Selected Genes Having Microduplication Variants

| SYMBOL | MICRODUPLICATION INFORMATION | | SEQ ID NO: |
|---|---|---|---|
| | ...a........A..a.aa.a..........J..A....Ca.CaaH...A.. | Cas9_Cr; | |
| | ................N.............................N..... | Cpf1_Wa; | |
| | ....N......................N....................k... | Cpf1_Cr; | |
| HLCS | tcgggaatggactccctggtagcaaTTgaccaacagcagacagttgtccgtc | SEQ_DUP; | 341 |
| | .........................12......................... | DUP_NUM; | |
| | aB..aa.......aA..A.....a.......A..a...A..A...A....Ha | Cas9_Wa; | |
| | .J.a.Ba.........A.aaa......A......Aa..A..A...A...... | Cas9_Cr; | |
| | ........N.............NL............L...........N... | Cpf1_Wa; | |
| | ..N.......N......................................... | Cpf1_Cr; | |
| TMPRSS3 | aggtaaccacgtggccagaggcacaTTccctccctaaagcggagaaaaagta | SEQ_DUP; | 342 |
| | .........................12......................... | DUP_NUM; | |
| | ......a.aA...a.aA.................a.aa.aB....A..aA.. | Cas9_Wa; | |
| | aJ.A.......Aa.a....Aa.....A.a..Baaa.aaa.....A....... | Cas9_Cr; | |
| | .......N........................................NLL. | Cpf1_Wa; | |
| | ..............k....L...k...............Lk........... | Cpf1_Cr; | |
| PCNT | ctggcagccgcctccacctaggttcTTgcccgcagggctgccggctcggatg | SEQ_DUP; | 343 |
| | .........................12......................... | DUP_NUM; | |
| | ..A..A..........aA.....A...A..aaA..A..aA..HaaC.a.aa. | Cas9_Wa; | |
| | ....Aa.J.A..Aa.aa.aa.aa.....Ba...Aaa.a....A..Aa..A.a | Cas9_Cr; | |
| | ....................................L........N..N... | Cpf1_Wa; | |
| | ..........................L.....L...........LLN..... | Cpf1_Cr; | |
| PEX26 | agctcattggaggtgaagtgctcccTTgtgtgttgtggggatccaggccctg | SEQ_DUP; | 344 |
| | .........................12......................... | DUP_NUM; | |
| | ....aa.aa.aB.a.A.......a.a.A..a.aaaaC....aA....aA..a | Cas9_Wa; | |
| | A...A..A.a...............A.aaa........J.J.....CaaH.. | Cas9_Cr; | |
| | ......N......k...............N...............L..N... | Cpf1_Wa; | |
| | .................L.................k...L..........N. | Cpf1_Cr; | |
| SNAP29 | agaacaggaagcaaagtaccaggccAAgccacccaaaccttagaaagctgga | SEQ_DUP; | 345 |
| | .........................12......................... | DUP_NUM; | |
| | ..aaB.A.J..A.....aA....A..............aB..A.Haac.aC. | Cas9_Wa; | |
| | .J.......A......A......Aa.J.Aa...Aa.aaaH..Aa........ | Cas9_Cr; | |
| | .........M.......................................... | Cpf1_Wa; | |
| | ....N........k........k.....L....M.......N...L.M.... | Cpf1_Cr; | |
| CHEK2 | accctttcatattcatacctttctcTTgagacttctgcccagacttcaggaa | SEQ_DUP; | 346 |
| | .........................12......................... | DUP_NUM; | |
| | .......J...............a.a......A....a......aaB..aB. | Cas9_Wa; | |
| | BaH...AaaH.Ba....BaH..Aa..Ba.a......A.Ba..Aaa...A.Ba | Cas9_Cr; | |
| | ..k..............N..N.......kL....NL.......k....N... | Cpf1_Wa; | |
| | ............................LN..LN.................. | Cpf1_Cr; | |

TABLE 6-continued

Selected Genes Having Microduplication Variants

| SYMBOL | MICRODUPLICATION INFORMATION | | SEQ ID NO: |
|---|---|---|---|
| CHEK2 | gaacaggcactgctgccatgagactGGctgagcctcaacatccgactcccga | SEQ_DUP; | 347 |
| | .........................12......................... | DUP_NUM; | |
| | .aA....A..A....a.a...aA..a.A...........a......a.a... | Cas9_Wa; | |
| | .A......A...A.a..A..Aa......A...A....Aa.a..A.CaaH.A. | Cas9_Cr; | |
| | .................................................... | Cpf1_Wa; | |
| | ...............N.............................k.....k | Cpf1_Cr; | |
| CYBB | tgagtaaacaaagcatctccaactcTTgagtctggccctcggggagtgcatt | SEQ_DUP; | 348 |
| | .........................12......................... | DUP_NUM; | |
| | ........A.............Ha.A...aA.....aaaa.a.A........ | Cas9_Wa; | |
| | ..AaaH.......A....A.Ca.aa..A.aH.....a...Aaa.a....... | Cas9_Cr; | |
| | ..........N..............................L......N... | Cpf1_Wa; | |
| | .....................L.................N..N..Lk..... | Cpf1_Cr; | |
| CHM | tcatgagttatcaattatttttcttAAcctatctccatttcagtatatggaa | SEQ_DUP; | 349 |
| | .........................12......................... | DUP_NUM; | |
| | a.A...................................A.....aaB..... | Cas9_Wa; | |
| | .Baa.Ca........Ca.........Ba....Aa..Ca.aa...Ba...... | Cas9_Cr; | |
| | M......N....N.....kLL.........N.M....N.....k..N..... | Cpf1_Wa; | |
| | ....N..................M...LLN..k...N..........N.... | Cpf1_Cr; | |
| CHM | gaacagcaaaagttcctggttcctcTTgctggcactgtcaaaatggaaatct | SEQ_DUP; | 350 |
| | .........................12......................... | DUP_NUM; | |
| | .A.....A.....aA........AJ.aA....A.......aaB......... | Cas9_Wa; | |
| | ..AaaH..A..A......Baa....Baa.a...A...A.a...a........ | Cas9_Cr; | |
| | ...................................NL.....NL....N... | Cpf1_Wa; | |
| | ..................k....LLk.....k......k....k........ | Cpf1_Cr; | |
| ABCA4 | tctcccacaaaggcaatggcaaccgACACagctttctctgcatgccacctggag | SEQ_DUP; | 351 |
| | .........................1122......................... | DUP_NUM; | |
| | .......aA....aA...J.a.....A........A...A......aa.aA... | Cas9_Wa; | |
| | ...A.Ca.aaa.a.....A.....A..Aa..A.a..A..Ba.a..A...Aa.aa | Cas9_Cr; | |
| | ...L.............N........L........................... | Cpf1_Wa; | |
| | .............................L.......N..N......L...... | Cpf1_Cr; | |
| FLAD1 | cactcatgatgatgtgacctttgagGCGCagtggcacaggcctttggagatgag | SEQ_DUP; | 352 |
| | .........................1122......................... | DUP_NUM; | |
| | ...aC.aC.a.a......a.aa.A..a.aA....aA.....aa.aC.a.A..aB | Cas9_Wa; | |
| | ..Aaaa.a.aH...........Aa.......A.a.....A.a...Aa....... | Cas9_Cr; | |
| | ...........................................k.......... | Cpf1_Wa; | |
| | ........................L..........LN...........N....L | Cpf1_Cr; | |
| MSH6 | atttggccgttattcagattccctgGTGTgcagaagggctataaagtagcacga | SEQ_DUP; | 353 |
| | .........................1122......................... | DUP_NUM; | |
| | aA..A....I..aC......aa.a.A..aB.aaA.......a..A..Ha.a.aa | Cas9_Wa; | |

TABLE 6-continued

Selected Genes Having Microduplication Variants

| SYMBOL | MICRODUPLICATION INFORMATION | | SEQ ID NO: |
|---|---|---|---|
| | ....A......Aa.....BaH...Baaa.......AJ.J....A.......... | Cas9_Cr; | |
| | ..N.......kL.......N.....k......N..NL....NLL.......... | Cpf1_Wa; | |
| | ............N......M.k.............LLN................ | Cpf1_Cr; | |
| SLC19A3 | ataaggaatggttctgagggtctcaTCTCatggagaaaaaaccaaataagcaga | SEQ_DUP; | 354 |
| | ........................1122.......................... | DUP_NUM; | |
| | aaB..aA....aHaaA...........aa.aB.............A..aHaaC. | Cas9_Wa; | |
| | .................Ba.......a.a.Ca.a............Aa...... | Cas9_Cr; | |
| | .M.......L........M...............N................... | Cpf1_Wa; | |
| | ...........L...k......k...N.....................k..... | Cpf1_Cr; | |
| AGXT | tccaacctgcctcctcgcatcatggCACAgccggggggctgcagatgatcgggt | SEQ_DUP; | 355 |
| | ........................1122.......................... | DUP_NUM; | |
| | ....A.......A....J.aA....A..aaaaaA..A..aC.aC.HaaA..... | Cas9_Wa; | |
| | ..aa.Baa..Aa..Aa.aa.a.a.Ca....A.a..Aa......A..A......C | Cas9_Cr; | |
| | ......................NLL............................. | Cpf1_Wa; | |
| | .........................................N...M........ | Cpf1_Cr; | |
| DNAH5 | catttgttccatcagctgtcgcacTATAtctcattcgtaacctacaaaagaca | SEQ_DUP; | 356 |
| | ........................1122.......................... | DUP_NUM; | |
| | ..A........A..a..A...............A............a....... | Cas9_Wa; | |
| | ...CaaHI.....Baa.Ca..A...a.a.a....Ca.a..BaH..Aa..A... | Cas9_Cr; | |
| | ....N........N.M......L....k..NLL................M.M.. | Cpf1_Wa; | |
| | .....M............N......k......N........N...k........ | Cpf1_Cr; | |
| DNAH8 | acaatattagaacaaatttttgatAGAGacaccattgcaaaacaacataaagt | SEQ_DUP; | 357 |
| | ........................1122.......................... | DUP_NUM; | |
| | .....aB...........aC..a.a........A..............A...A. | Cas9_Wa; | |
| | ......A..........A.................A.aa....A....A..A.. | Cas9_Cr; | |
| | .......k...NLL......N........N.............k.......... | Cpf1_Wa; | |
| | ..M...............k....N..M.k....N.....N....M......... | Cpf1_Cr; | |
| WISP3 | atttgtcttttctggatgctcaagtACACtcagagttacaaacccactttttgt | SEQ_DUP; | 358 |
| | ........................1122.......................... | DUP_NUM; | |
| | A.......HaaC.A..J.JA.......Ha.A.................a.aaB. | Cas9_Wa; | |
| | ...........a...Ba......A.a.....A.aJaH......A...AaaHa.. | Cas9_Cr; | |
| | kLL.......L..............k......k..................... | 8 Cpf1_Wa; | |
| | N.................k..............LLN........L.M.N..... | 8 Cpf1_Cr; | |
| AHI1 | agctggatggaatttagccgtgtaaACACaaaagaaggatgaggtaaaactctg | SEQ_DUP; | 359 |
| | ........................1122.......................... | DUP_NUM; | |
| | aaC.aaB.....A..a.AJ..........aBHaaC.a.aA.........aB..A | Cas9_Wa; | |
| | a...A..A..............Aa......JA.a.................... | Cas9_Cr; | |
| | ...................N................k................. | Cpf1_Wa; | |
| | ..k.....k....N..........k.......Lk.................... | Cpf1_Cr; | |

TABLE 6-continued

Selected Genes Having Microduplication Variants

| SYMBOL | MICRODUPLICATION INFORMATION | | SEQ ID NO: |
|---|---|---|---|
| CFTR | tattatgtgttttacatttacgtggGAGAgtagccgacactttgcttgctatgg | SEQ_DUP; | 360 |
| | .........................1122......................... | DUP_NUM; | |
| | ..a.A............a.aaaHa.A..AJ.a.......A...A...IaaaC.. | Cas9_Wa; | |
| | ..Ba......J......J.A.....A............Aa..A.a....A...A | Cas9_Cr; | |
| | ...N.M.............NL....N.M......k.....k............. | Cpf1_Wa; | |
| | ...L............................L..................... | Cpf1_Cr; | |
| TMEM70 | gtccccgggcctctgtctcccgggcGTGTcctccagcagcgggccttcggggcc | SEQ_DUP; | 361 |
| | .........................1122......................... | DUP_NUM; | |
| | ..aaA.....A......aaa.a.A.......A..a.aaA.....aaaA..aA.. | Cas9_Wa; | |
| | aa.....aaaa..Aa.a...a.aaa...A....aaJaa..A..A...Aa.Ba. | Cas9_Cr; | |
| | ..................L......L...............L............ | Cpf1_Wa; | |
| | ............................................L......... | Cpf1_Cr; | |
| BRCA2 | actctgaagaacttttctcagacaaTGTGagaataattttgtcttccaagtagc | SEQ_DUP; | 362 |
| | .........................1122......................... | DUP_NUM; | |
| | .aB.aB..........a.....a.aHaB........A........A..A..... | Cas9_Wa; | |
| | CaaHI.A.aH......A...Ba.a...A...................a.Baa.. | Cas9_Cr; | |
| | kL.................L.................k................ | Cpf1_Wa; | |
| | ..N.......N..N............N.......N..Lk...LN..N....... | Cpf1_Cr; | |
| POMT2 | gttgttgtagtccttgtgcaaatagGTGTggtgacctgggtggggggtgggggc | SEQ_DUP; | 363 |
| | .........................1122......................... | DUP_NUM; | |
| | ..A..A.....a.A......aa.a.aa.a...Haaa.aaaaaa.aaaaa.aa.a | Cas9_Wa; | |
| | aHa.............aa.....A..J.........J..Aa............. | Cas9_Cr; | |
| | N.M...k..N.......L......N..N........N................. | Cpf1_Wa; | |
| | .................................L...LLN....LN........ | Cpf1_Cr; | |
| PALB2 | atagagtctgtaaaggaactgtagtCGCGccctggtgaaattaggtcttcttag | SEQ_DUP; | 364 |
| | .........................1122......................... | DUP_NUM; | |
| | .A...A....aaB...A..A..a.A....aa.aB.....aA........aaB.. | Cas9_Wa; | |
| | .Ca.........a..........A......a.a.aaa..............a.B | Cas9_Cr; | |
| | ..................M................................... | Cpf1_Wa; | |
| | ................Lk...............LN.......N........... | Cpf1_Cr; | |
| RAD51D | gtatagagaccagcatcaagcagttTATAtcaagactgatggcagaagagaaga | SEQ_DUP; | 365 |
| | .........................1122......................... | DUP_NUM; | |
| | .a.a....A......A..A..........a...aC.aA..aB.a.aB.aB...J | Cas9_Wa; | |
| | a.aa.......J..Aa..A.Ca...A........Ca....A......A...... | Cas9_Cr; | |
| | .......kL.......N...L....M.....................k.M.M.. | Cpf1_Wa; | |
| | .....M....N.............N....N..k.....N....N.......... | Cpf1_Cr; | |
| BRCA1 | gcacacacacacacgctttttacctGAGAgtggttaaaatgtcactctgagagg | SEQ_DUP; | 366 |
| | .........................1122......................... | DUP_NUM; | |
| | .J.J......A..........aHa.a.aA.......A.......a.aHaaC..A | Cas9_Wa; | |

TABLE 6-continued

Selected Genes Having Microduplication Variants

| SYMBOL | MICRODUPLICATION INFORMATION | | SEQ ID NO: |
|---|---|---|---|
| | a.....A.aJa.a.a.a.a.a.....Aa...................a.a.aH. | 8 Cas9_Cr; | |
| | ..........................................k........... | 8 Cpf1_Wa; | |
| | ..............k..................M.................... | Cpf1_Cr; | |
| BRCA1 | ccttgattttcttccttttgttcacATATtcaaaagtgacttttggactttgtt | SEQ_DUP; | 367 |
| | .........................1122......................... | DUP_NUM; | |
| | aC.............A...............a.a......aa.....A...... | Cas9_Wa; | |
| | BaH.Baa.......Ba.Baa......Ba.a....BaH.......A.......A. | Cas9_Cr; | |
| | ..N.....N........N...kL..N.....k..NL....k..NL......NL. | Cpf1_Wa; | |
| | ....M.....k............L..............N............... | Cpf1_Cr; | |
| BRCA1 | agcgcatgaatatgcctggtagaagACACttcctcctcagcctattctttttag | SEQ_DUP; | 368 |
| | .........................1122......................... | DUP_NUM; | |
| | ..HaB....A...aA..ab.a..............A.............aa.A. | Cas9_Wa; | |
| | ..Ba...A.a.........Aa..........A.a.Baa.aa.a..Aa...BaH. | Cas9_Cr; | |
| | ...k...............NL.............M.................NL | Cpf1_Wa; | |
| | .N.......................................LN.....L.M... | Cpf1_Cr; | |
| KPTN | ggcctctttcggggcctctcctaccTATActggtcaggttcgtcagctctggga | SEQ_DUP; | 369 |
| | .........................1122......................... | DUP_NUM; | |
| | ......aaaA.........J.......aA...aA...A...A....aaaB.a.a | Cas9_Wa; | |
| | aa.....Aa.a..Ba....Aa.a.aa..Aa....A....a....Ba..a..A.a | Cas9_Cr; | |
| | ................L.............kL.................M.... | Cpf1_Wa; | |
| | .....M........................LLN..................... | Cpf1_Cr; | |
| SPTA1 | actgctggaacttcagggcccgcagCAACAActggtcacccttctccagggtcagc | SEQ_DUP; | 370 |
| | .........................111222......................... | DUP_NUM; | |
| | ..aaB......aaA...A..A........aA............HaaA...A..... | Cas9_Wa; | |
| | ..A..JA..A.....A.Ba....Aaa.a..A..A..A....a.aaaHBa.aa.... | Cas9_Cr; | |
| | ..................................NL.................... | Cpf1_Wa; | |
| | .....N..N.............................N................. | Cpf1_Cr; | |
| TREX1 | ctccagactcgcacacggctgagggTGATGAtgtcctggccctgctcagcatctgt | SEQ_DUP; | 371 |
| | .........................111222......................... | DUP_NUM; | |
| | .a.J.JA.....aA..aHaaa.aC.aC.A....aA....A....A.....A...a. | Cas9_Wa; | |
| | ..aaaa.aa...A.aHa.a.a..A...............aa...Aaa..A.a..A. | Cas9_Cr; | |
| | ...........M........L....L.............................. | Cpf1_Wa; | |
| | ........................................................ | Cpf1_Cr; | |
| SLC26A3 | acgatatacacatctaccttgatccTGATGAtaaattcttgcaaaatctgttaaaa | SEQ_DUP; | 372 |
| | .........................111222......................... | DUP_NUM; | |
| | J...............aC....aC.aC.........A........A.......aB. | Cas9_Wa; | |
| | .Baa..A......A.a.Ca..Aa....CaaH..........BaH..A....Ca..I | Cas9_Cr; | |
| | ........N.........NLL.......M............N.............. | Cpf1_Wa; | |
| | .........M.k.........k.........k.....k.....M............ | Cpf1_Cr; | |

TABLE 6-continued

Selected Genes Having Microduplication Variants

| SYMBOL | MICRODUPLICATION INFORMATION | | SEQ ID NO: |
|---|---|---|---|
| CDKN2A | agctcctcagccaggtccacgggcaGACGACggccccaggcatcgcgcacgtccag | SEQ_DUP; | 373 |
| | .........................111222......................... | DUP_NUM; | |
| | .....A...aA.....aaA..a..a..aA.....aA...Ja.A...A....A..a. | Cas9_Wa; | |
| | ..Aaa..A.aa.a..Aa....aa.a...A...A..A..Aaaa...A.Ca.a.a.a. | Cas9_Cr; | |
| | ......................................L................. | Cpf1_Wa; | |
| | ........................................................ | Cpf1_Cr; | |
| USH2A | ctgtgccaaagggtggacccgcgggTGGCTGGCtgccagggcaacggcaatgtgattg | SEQ_DUP; | 374 |
| | .........................11112222......................... | DUP_NUM; | |
| | A....Haaa.aa....aHaaa.aA..aA..A...aaA....aA...Ia.aC..aaA.. | Cas9_Wa; | |
| | ..Aa.a....Aa.J........AaaHa......A...A..Aa....A..A..A..... | Cas9_Cr; | |
| | ......N................................................... | Cpf1_Wa; | |
| | .....................N.....N................N.......N..... | Cpf1_Cr; | |
| TPO | gcgggccctgcttcctggccggagaCGGCCGGCcgcgccagcgaggtcccctccctga | SEQ_DUP; | 375 |
| | .........................11112222......................... | DUP_NUM; | |
| | A....A......aA..aa.a..aA..aA..a.A...a.a.aA..........aJ.aA. | Cas9_Wa; | |
| | ..AaaHa...Aaa..A.Baa...Aa.....A..Aa..Aa.a.aa..A.....aaaa.a | Cas9_Cr; | |
| | .........L........................NL...................... | Cpf1_Wa; | |
| | .......................................................... | Cpf1_Cr; | |
| HADHA | caaatccttcctcttcacaccctccTGATTGATagatgtaaaagcccttcccagattt | SEQ_DUP; | 376 |
| | .........................11112222......................... | DUP_NUM; | |
| | .........J.........I..aC..aC..aC.A.....A......I..aC.....a. | Cas9_Wa; | |
| | ....BaH..CaaHbaa.a.Ba.a.aaaHaa...................Aaa.Baaa. | Cas9_Cr; | |
| | ........M.L..........NL.......NL....NL.............N...... | Cpf1_Wa; | |
| | ..........M.......k.........................k........N..k. | Cpf1_Cr; | |
| HADHB | tgggccactctgcagaccgactggcCGCTCGCTgcctttgctgtttctcggctggaac | SEQ_DUP; | 377 |
| | .........................11112222......................... | DUP_NUM; | |
| | .......A..a...a...aA..A...A..A.....A..A......aA..aaB..HaaC | Cas9_Wa; | |
| | ..Aa.....Aa.a.aH.A...Aa..A...Aa.a.a.a..Aa....A....Ba.a..A. | Cas9_Cr; | |
| | ....N...L................................................. | Cpf1_Wa; | |
| | ................................LLN.......LN.............. | Cpf1_Cr; | |
| MSH6 | tttttttggagatgattttattcctAATGAATGacattctaataggctgtgaggaaga | SEQ_DUP; | 378 |
| | .........................11112222......................... | DUP_NUM; | |
| | ...aa.aC.aC............HaB..a...........aA..a.a.aaB.a.aa.A | Cas9_Wa; | |
| | ....A.....................Baa..........A..BaH......A...... | Cas9_Cr; | |
| | ........N....N..............k...........k..NL............. | Cpf1_Wa; | |
| | ....N..LN..........N.............LN.........Lk.......k.... | Cpf1_Cr; | |
| MSH6 | tttaaggtgaaagtacattttttgtTGAATGAAttaagtgaaactgccagcatactca | SEQ_DUP; | 379 |
| | .........................11112222......................... | DUP_NUM; | |
| | .aa.ab..A..........A.HaB.HaB.....a.aB....A..JA.........A.. | Cas9_Wa; | |

TABLE 6-continued

Selected Genes Having Microduplication Variants

| SYMBOL | MICRODUPLICATION INFORMATION | | SEQ ID NO: |
|---|---|---|---|
| | ....................A..J.......................A..Aa..A.. | Cas9_Cr; | |
| | ..NL...k................k...................k..N........N. | Cpf1_Wa; | |
| | .....LN..LN...N...Lk.........M............N............ | Cpf1_Cr; | |
| MSH6 | ttactttaacaggaagaggtactgcAACAAACAtttgatgggacggcaatagcaaatg | SEQ_DUP; | 380 |
| | .........................11112222......................... | DUP_NUM; | |
| | .......aaB.a.aA....A...........aC.aaa..aA.....A.....A..A. | Cas9_Wa; | |
| | ........A.....A...........A..a..A...A...........A..A.....A | Cas9_Cr; | |
| | ....N...NL..N.M........k....k...........................k | Cpf1_Wa; | |
| | ....N..k..........L......N.....k...........k...N........ | Cpf1_Cr; | |
| MSH6 | cattattttcaactcactaccattcATTAATTAgtagaagattattctcaaaatgttg | SEQ_DUP; | 381 |
| | .........................11112222......................... | DUP_NUM; | |
| | ..............................A..aB.aC............A..A..a. | Cas9_Wa; | |
| | .a...A..J....Ba..A.aHa..Aa..BaH..................BaHa.... | Cas9_Cr; | |
| | ..........M.............N....kL............NL..N...N.... | Cpf1_Wa; | |
| | .......N........N..........k.....................M..... | Cpf1_Cr; | |
| MSH6 | aaaagcaagagaatttgagaagatgAATCAATCagtcactacgattatttcggtaact | SEQ_DUP; | 382 |
| | .........................11112222......................... | DUP_NUM; | |
| | A...aHaB....a.aB.aCHaB........A....I..aC.......aA......... | Cas9_Wa; | |
| | A.........A....................Ca..ca..Ia.a..A.......Ba.. | Cas9_Cr; | |
| | ....N..NL..........................k.................... | Cpf1_Wa; | |
| | ...LN...N.......................N...N...N...M.N..LLN...M. | Cpf1_Cr; | |
| MSH6 | aagcaagagaatttgagaagatgaaTCAGTCAGtcactacgattatttcggtaactaa | SEQ_DUP; | 383 |
| | .........................11112222......................... | DUP_NUM; | |
| | ..aHaB....a.aB.aCHaB....A...A....I..aC.......aA........... | Cas9_Wa; | |
| | ........A....................Ca..Ia...a.a..A......Ba..... | Cas9_Cr; | |
| | ..N..NL...........................k...................... | Cpf1_Wa; | |
| | .LN..........................N...N...N...M.N..LLN...M.N. | Cpf1_Cr; | |
| ALMS1 | tgacctgtcatgtatggcaacagatAGTAAGTAtatcaaggcaatagtagaacacaaa | SEQ_DUP; | 384 |
| | .........................11112222......................... | DUP_NUM; | |
| | ..A....A...aA.....aC..A...A........aA.....A.JaB..........J | Cas9_Wa; | |
| | Baa.....Aa...a........a..A..............Ca....A..........A | Cas9_Cr; | |
| | ..k.....kL....N..NLL..N.............M..................M.M | Cpf1_Wa; | |
| | ..M....N...M....N....N.......N...k.........M....N......... | Cpf1_Cr; | |
| DGUOK | cagtgctggtgttggatgtcaatgaTGATTGATttttctgaggaagtaaccaaacaag | SEQ_DUP; | 385 |
| | .........................11112222......................... | DUP_NUM; | |
| | A..aa.A.HaaC.A.....aC.ac..aC.......a.aaB.A...........aB.a. | Cas9_Wa; | |
| | A..Baa....A..J.....J....a................Ba...........Aa.. | Cas9_Cr; | |
| | ..k.................NLL...........N................N...... | Cpf1_Wa; | |
| | .....................LN...N...k...N..N..................L | Cpf1_Cr; | |

TABLE 6-continued

Selected Genes Having Microduplication Variants

| SYMBOL | MICRODUPLICATION INFORMATION | | SEQ ID NO: |
|---|---|---|---|
| ORC4 | cggcagtcataaatgggtgcgatgcTGTTTGTTactcgatttaaagcaagcatctagg | SEQ_DUP; | 386 |
| | .........................11112222......................... | DUP_NUM; | |
| | .A.......Haaa.a.aC.A..A...A...I..aC......A...A......aaaB.. | Cas9_Wa; | |
| | .Ca..A..A...a...........A..J.A.........A.aH........A...A.C | Cas9_Cr; | |
| | N....N...NLL..N....................................k..N... | Cpf1_Wa; | |
| | .....................k....N.........LLK............k.....N | Cpf1_Cr; | |
| NEB | tcccttgcccatgttttctttgtatAACAAACAcctgtgcgataagaaagcatccaga | SEQ_DUP; | 387 |
| | .........................11112222......................... | DUP_NUM; | |
| | ..A.....A........A.....J........a.a.aC...aB..A......aB.... | Cas9_Wa; | |
| | .....Baaa...Aaa......Ba.........a...A.aa....A..J.......A.C | Cas9_Cr; | |
| | ......................NLL..N..........k...k...M........... | Cpf1_Wa; | |
| | ..M.N..k............M.N..k..........k.....N.........N..... | Cpf1_Cr; | |
| NEB | actctctgtatctctggggtgtccaAAACAAACagtctcataatacgacatggacttc | SEQ_DUP; | 388 |
| | .........................11112222......................... | DUP_NUM; | |
| | ...A.......aaaa.A.............A....J......a....aa........A | Cas9_Wa; | |
| | aaa...A.aHa....Ca.a........aaJ...A...A...a.a.......A..A... | Cas9_Cr; | |
| | .....N....k...N...L.............M............L............ | Cpf1_Wa; | |
| | ...k....k.........M.N.........L........................... | Cpf1_Cr; | |
| TTN | aatgctaatggcattcaaaacaatgGTATGTATcccctgctttaattgttagcccatc | SEQ_DUP; | 389 |
| | .........................11112222......................... | DUP_NUM; | |
| | .....aA.............aA...A........A........A...A.......... | Cas9_Wa; | |
| | Aa.......A......A..BaH...A..........JCaaaa..A............A | Cas9_Cr; | |
| | ....k..........k....................NL............M...M.L. | 8 Cpf1_Wa; | |
| | N.....................N........................L....N..... | 8 Cpf1_Cr; | |
| BARD1 | gaagctttactcacaacatatctgaCTTTCTTTcttacttcgagggctaaaccacatt | SEQ_DUP; | 390 |
| | .........................11112222......................... | DUP_NUM; | |
| | ...................a.................a.aaA................ | Cas9_Wa; | |
| | .A.a.....A....A.aHa..A...Ca...A..Ba..Ba...A.Ba.....A....Aa | Cas9_Cr; | |
| | k..N............k............k............M.......k...k..N | Cpf1_Wa; | |
| | ...........................k...........N...LN............. | Cpf1_Cr; | |
| UGT1A8 | tcattcagatcacatgaccttcctgCAGCCAGCgggtgaagaacatgctcattgcctt | SEQ_DUP; | 391 |
| | .........................11112222......................... | DUP_NUM; | |
| | ...aC......a........A..A...aHaaa.aB.aB....A......A........ | Cas9_Wa; | |
| | .aa.a.a..BaH..Ca.a....Aa.Baa..A..Aa..A..........A...A.a... | Cas9_Cr; | |
| | ..........................NL..............NL.............. | Cpf1_Wa; | |
| | ................LN..N.......................N............. | Cpf1_Cr; | |
| TREX1 | gatgtcctggccctgctcagcatctGTCAGTCAgtggagaccacaggccctgctgcgg | SEQ_DUP; | 392 |
| | .........................11112222......................... | DUP_NUM; | |
| | ....aA....A....A.....A...A...a.aa.a......aA....A..a.aaHaaa | Cas9_Wa; | |

TABLE 6-continued

Selected Genes Having Microduplication Variants

| SYMBOL | MICRODUPLICATION INFORMATION | | SEQ ID NO: |
|---|---|---|---|
| | ..........aa...Aaa..A.a..A.Ca...a...a........Aa.a...Aaa..A | Cas9_Cr; | |
| | .......................................................... | Cpf1_Wa; | |
| | ..............L...........................L.............. | Cpf1_Cr; | |
| COL7A1 | cagcctcgacacacgacccacaggcTCAGTCAGgggctggggacagaggcaaggtaag | SEQ_DUP; | 393 |
| | .........................11112222......................... | DUP_NUM; | |
| | .J.a......a.......aA....A...aaaA..aaaa...a.aA...aA...aaaA. | Cas9_Wa; | |
| | .Ca..A..Aa.a..A.a.a..AaaHa...A.a...a.....A......A.....A... | Cas9_Cr; | |
| | ............N............................................. | Cpf1_Wa; | |
| | ...................L.........N....N...........N........... | Cpf1_Cr; | |
| IQCB1 | gaaaacccttccaataggcttgaatCAAGCAAGcatgctgcttgatgtagtttctgaa | SEQ_DUP; | 394 |
| | .........................11112222......................... | DUP_NUM; | |
| | ............aA..HaB.....A...A...A..A...aC.A..A.....aB...A. | Cas9_Wa; | |
| | ...a......AaaHBaa......A.....Ca..IA...A...A..A...........B | Cas9_Cr; | |
| | .N...k........k..N.............NLL........N............... | Cpf1_Wa; | |
| | LN...N...N.......................Lk......Lk....N........M | Cpf1_Cr; | |
| DOK7 | acagatgaactgggctcactgctcaGCCTGCCTgccagcagcgggggcccccgagccc | SEQ_DUP; | 395 |
| | .........................11112222......................... | DUP_NUM; | |
| | C.aB...aaA......A....A...A...A...A..a.aaaaA.....a.A....A.. | Cas9_Wa; | |
| | ...Aa.a.......A....A.a.a..A.a..Aa..Aa..Aa..A..A.....Aaaaa. | Cas9_Cr; | |
| | .......................................................... | Cpf1_Wa; | |
| | .......................................................... | Cpf1_Cr; | |
| WES1 | gccatcatggagatcaaggagtaccTGATTGATtgacatggcctccagggcaggcatg | SEQ_DUP; | 396 |
| | .........................11112222......................... | DUP_NUM; | |
| | ....aa.aC....aa.A..I..ac..aC..a....aA......aaA..aAJ..A.... | Cas9_Wa; | |
| | ..A.a.aa.Ca.......Ca........Aa.J.........A....Aa.aa....A.. | Cas9_Cr; | |
| | ...................................................N...N.. | Cpf1_Wa; | |
| | .......................................................... | Cpf1_Cr; | |
| CC2D2A | ctctttattaccattgagccccagcTGGTTGGTtcctggagagtccattcgagaaaag | SEQ_DUP; | 397 |
| | .........................11112222......................... | DUP_NUM; | |
| | ...........a.A.....A..aA..aA.....aaHa.A.......a.aB...aA... | Cas9_Wa; | |
| | ...AaaHa.......Aa......Aaaa..A.......Baa.........aa..BaH.. | 8 Cas9_Cr; | |
| | ..................N........k..N.....N..............N...NL. | 8 Cpf1_Wa; | |
| | ................L..............k......N.......M......LLk. | Cpf1_Cr; | |
| SPINK5 | gatgggaaaacatatgacaacagatGTGCGTGCactgtgtgctgagaatgcgtgagta | SEQ_DUP; | 398 |
| | .........................11112222......................... | DUP_NUM; | |
| | aaB........a......aC.a.aJa.A....a.a.A..aHaB..a.aHa.A...... | Cas9_Wa; | |
| | .A.a...........A......A..A.......A..JA.aJ.....AJ.J.....A.. | Cas9_Cr; | |
| | .N.M.........k.....................M..................... | Cpf1_Wa; | |
| | .........................N.................LN............ | Cpf1_Cr; | |

TABLE 6-continued

| SYMBOL | MICRODUPLICATION INFORMATION | | SEQ ID NO: |
|---|---|---|---|
| | Selected Genes Having Microduplication Variants | | |
| SH3TC2 | cactagactcacggtcaggcaggcaGGCCGGCCagcagggcacctgccttttccaaca | SEQ_DUP; | 399 |
| | .........................11112222......................... | DUP_NUM; | |
| | .a......aA...aA..aA..aA..aA...A.JaaA.....A............aaa. | Cas9_Wa; | |
| | A....A.a....A.aHa...a...A...A...Aa..Aa..A....A.aa..Aa...Ba | Cas9_Cr; | |
| | ............NL.....N...................................... | Cpf1_Wa; | |
| | ..................................N.......L................ | Cpf1_Cr; | |
| DDX41 | cagacatacctggttttgatggggtCATCCATCatacgtaatgcccttagccatctcc | SEQ_DUP; | 400 |
| | .........................11112222......................... | DUP_NUM; | |
| | .......aA....aC.aaaA......J......A....A......A............ | Cas9_Wa; | |
| | A....A..JA...Aa...............a.CaaHCa...A......Aaa....Aa. | Cas9_Cr; | |
| | ......................................k............L...... | Cpf1_Wa; | |
| | ............M.....N............................N.....LN. | Cpf1_Cr; | |
| CDSN | accgctggagtcacccttcccagtgAGGCAGGCaggggtcgttaggggaggtgatacg | SEQ_DUP; | 401 |
| | .........................11112222......................... | DUP_NUM; | |
| | ..aa.A............a.a.aA..aA..aaaA..A...aaaa.aa.aC...a.a.a | Cas9_Wa; | |
| | A.....Aa.a......a.aaaHBaaa.......A...A......a............. | Cas9_Cr; | |
| | .......................................NLL................ | Cpf1_Wa; | |
| | .........................L......M......................... | Cpf1_Cr; | |
| LAMA2 | ggcataaagtcactgccaacaagatCAAACAAAcaccgcattgagctcacagtcgatg | SEQ_DUP; | 402 |
| | .........................11112222......................... | DUP_NUM; | |
| | ...A.....A........aC.....J.......A.....a.A......A..aC.aaaB. | Cas9_Wa; | |
| | .A....A........a.a..Aa..A....Ca...A...A.aa.a......A.a.a... | Cas9_Cr; | |
| | ......k................................................... | Cpf1_Wa; | |
| | ....k...k..........................LLN.......LLN.....k.. | Cpf1_Cr; | |
| SERAC1 | tttgacttccaacgaggggaagagaAGATAGATagcgaatattaacagagtattcagc | SEQ_DUP; | 403 |
| | .........................11112222......................... | DUP_NUM; | |
| | .........a.aaaaB.a.aB.aC..aC..aHaB........Ha.A......A..... | Cas9_Wa; | |
| | ...Ba.....A.Baa..A.....................A.........A....... | Cas9_Cr; | |
| | ......N.....N.......N...k....NLL.......................... | Cpf1_Wa; | |
| | ...N..M...M....LN.....N..............k..................L | Cpf1_Cr; | |
| SERAC1 | cgctgaggctggtgtcatactccacAGATAGATataattcggagagcaggacagtctt | SEQ_DUP; | 404 |
| | .........................11112222......................... | DUP_NUM; | |
| | a.aA..aa.a............aC..aC........aa.a.A..aa...A......A. | Cas9_Wa; | |
| | aa...a.a.....A......a.J.A.aa.a.............BaH.....A....A. | Cas9_Cr; | |
| | ...........N......L........................L...........M. | Cpf1_Wa; | |
| | ......M...M.M.N....L.....................N.........N...k. | Cpf1_Cr; | |
| SLC26A4 | acacagccttctctgtctctcttggCAGTCAGTcggtcttggcagctgttgtaattgc | SEQ_DUP; | 405 |
| | .........................11112222......................... | DUP_NUM; | |
| | .A........A........aA..A...A..aA....aA..A..A..A.....A..... | 8 Cas9_Wa; | |
| | ......A.a..Aa.Ba.a...a.a.a....A...a...a...a....A..A....... | 8 Cas9_Cr; | |

TABLE 6-continued

| Selected Genes Having Microduplication Variants | | | |
|---|---|---|---|
| SYMBOL | MICRODUPLICATION INFORMATION | | SEQ ID NO: |
| | ............NLL................N............N............. | Cpf1_Wa; | |
| | ...............................N......N....Lk...L......... | Cpf1_Cr; | |
| CFTR | cacttcttggtactcctgtcctgaaAGATAGATattaatttcaagatagaaagaggac | SEQ_DUP; | 406 |
| | .........................11112222......................... | DUP_NUM; | |
| | ..J.aA.......A....aB..aC..aC............aC..aB..a.aa...A.. | Cas9_Wa; | |
| | ..Ba.a.a.Ba......A.aa...aa...................Ba........... | Cas9_Cr; | |
| | .......N..NL.......k......N..N...........................N | Cpf1_Wa; | |
| | .Lk...M...M....N.....N..M...k.........................L... | Cpf1_Cr; | |
| RP1 | aaatgattggacagttttcatatagTGAATGAAgaaagggaaagtggggaaaacaagt | SEQ_DUP; | 407 |
| | .........................11112222......................... | DUP_NUM; | |
| | aC..aa...A..........aHaB..aB.aB..aaaB..a.aaaaB......A..Ha. | Cas9_Wa; | |
| | ................A.....Ba.................................. | Cas9_Cr; | |
| | M.............NL.............N.........kL...M............. | Cpf1_Wa; | |
| | M....LN..LN..k...LLk......LLk....N........................ | Cpf1_Cr; | |
| GLDC | ataagcccaggaaatgggcaagatgGAACGAACtggagccccatggggccgcactgac | SEQ_DUP; | 408 |
| | .........................11112222......................... | DUP_NUM; | |
| | A....aaB...aaA...aC.aaB..aB...aa.A......aaaa..A....a..aA.. | Cas9_Wa; | |
| | ..........Aaa..........A.........A...A.....Aaaa......Aa.a. | Cas9_Cr; | |
| | .....L............N....M.................................. | Cpf1_Wa; | |
| | ...LLN..LN...L............................................ | Cpf1_Cr; | |
| GNE | ctgagatacgtacctagccacatgcGAATGAATgatgctcatgtagtctttgttcttg | SEQ_DUP; | 409 |
| | .........................11112222......................... | DUP_NUM; | |
| | aCJ..A......A......aHaB.HaB..aC.A.....A..A.....A.....aA..a | Cas9_Wa; | |
| | .....a.......A...Aa.J.Aa.a...A............A.a.......a..... | Cas9_Cr; | |
| | .......N.................................................. | Cpf1_Wa; | |
| | ...LN..LN....................................N........M... | Cpf1_Cr; | |
| CYP17A1 | gagtcgatcagaaagaccaccttggGGATGGATgccttccagggagggcagctgccca | SEQ_DUP; | 410 |
| | .........................11112222......................... | DUP_NUM; | |
| | .aC...aB..a........aaaaCHaaC.A.......aaa.aaA..A..A........ | Cas9_Wa; | |
| | .........a..Ca.......Aa.aa.............Aa.Baa........A..A. | Cas9_Cr; | |
| | .....N.....NL...k...........................N............. | Cpf1_Wa; | |
| | ....L...L............L...................................L | Cpf1_Cr; | |
| ATM | actacacaaagagaatctagtgattACAGACAGtgtcccttgcaaaaggaagaaaata | SEQ_DUP; | 411 |
| | .........................11112222......................... | DUP_NUM; | |
| | ......aHaB....Ia.aC.....a...a.A......A.....aaB.aB.....aB.. | Cas9_Wa; | |
| | IA.a..A..A.a........Ca..I......A...A.....aaa...A.......... | Cas9_Cr; | |
| | .......k........N.............................N........... | Cpf1_Wa; | |
| | ......................k....LN..k......N.........LLN...N..k | Cpf1_Cr; | |

TABLE 6-continued

Selected Genes Having Microduplication Variants

| SYMBOL | MICRODUPLICATION INFORMATION | | SEQ ID NO: |
|---|---|---|---|
| FOXRED1 | aagtttccctggataaacacagaggGAGTGAGTggctttggcgtcttatggtgaggct | SEQ_DUP; | 412 |
| | .........................11112222......................... | DUP_NUM; | |
| | .....HaaCJ.......a.aaa.aHa.a.aA....aa.A......aa.a.aA...A.. | Cas9_Wa; | |
| | ....A.....Baaa........A.a...............A.....A..a........ | Cas9_Cr; | |
| | ...............NL..........kLL............................ | Cpf1_Wa; | |
| | ..L..............................................L........ | Cpf1_Cr; | |
| C12orf65 | ggctttgggagaagctgacgttgttATCCATCCccaggaatagctgtcactccggtcc | SEQ_DUP; | 413 |
| | .........................11112222......................... | DUP_NUM; | |
| | ..aaa.aB.A..a..A..A.............aaB...A..A.......aA....aC. | Cas9_Wa; | |
| | .A.aa..A...........A...A.......CaaHCaaaa........A...a.a.aa | Cas9_Cr; | |
| | M....................L.....k...............N..N.M.L...L... | Cpf1_Wa; | |
| | ................LN..............................N..N...... | Cpf1_Cr; | |
| GJB2 | tccacagtgttgggacaaggccaggCGTTCGTTgcacttcaccagccgctgcatggag | SEQ_DUP; | 414 |
| | .........................11112222......................... | DUP_NUM; | |
| | ..a.A..aaa....aA...aa.A...a..A..........A..A..A...aa.aB.A. | Cas9_Wa; | |
| | ..A...aa.a........J..A....Aa...A..Ba...A.a.Ba.aa..Aa.a..A. | Cas9_Cr; | |
| | L........................L.......N................NL..N... | Cpf1_Wa; | |
| | ..................................L...N...............M... | Cpf1_Cr; | |
| BRCA2 | ctgaaaatgaagataacaaatatacTGCTTGCTgccagtagaaattctcataacttag | SEQ_DUP; | 415 |
| | .........................11112222......................... | DUP_NUM; | |
| | ....aB.aC.....J.......A...A..A...A..aB..............HaB... | Cas9_Wa; | |
| | .....A...............A.......A..A...A..Aa.........BaHa.... | Cas9_Cr; | |
| | .........N..................................M......N...... | Cpf1_Wa; | |
| | M...................k.......M.N......N..................N. | Cpf1_Cr; | |
| BRCA2 | ttgtttctccggctgcacagaaggcATTTATTTcagccaccaaggagttgtggcacca | SEQ_DUP; | 416 |
| | .........................11112222......................... | DUP_NUM; | |
| | ......aa..A....aB.aA...........A.......aa.A..a.aA...J..... | Cas9_Wa; | |
| | ..A..J....Ba.aa..A..A.a......A.......Ba..Aa.aa............ | Cas9_Cr; | |
| | .....N....L....k.......k...k...L..................k...kL.. | Cpf1_Wa; | |
| | ....................N...............k.....Lk.......M.k...k | Cpf1_Cr; | |
| EIF2AK4 | tcctcagcagctcggtggagtggagCACTCACTtcgggcgagcgctcggccagtgccc | SEQ_DUP; | 417 |
| | .........................11112222......................... | DUP_NUM; | |
| | ..A..A...aa.aa.a.aa.A..........aaa.a.a.A...aA...a.A...A... | Cas9_Wa; | |
| | .aaaHCaaHa..A..A.a............A.a.aHa.Ba...A...A.a.a..Aa.. | Cas9_Cr; | |
| | .......................................................NL. | Cpf1_Wa; | |
| | L......................................................... | Cpf1_Cr; | |
| HEXA | gaaatccttccagtcagggccatagGATAGATAtacggttcaggtaccagggggcaga | SEQ_DUP; | 418 |
| | .........................11112222......................... | DUP_NUM; | |
| | ........A...aaA....HaaC..aC.....aA..J.aA.....aaaaA..a.a.aB | Cas9_Wa; | |

TABLE 6-continued

Selected Genes Having Microduplication Variants

| SYMBOL | MICRODUPLICATION INFORMATION | | SEQ ID NO: |
|---|---|---|---|
| | .........CaaHbaa...a....Aa..............A...Ba.....Aa.J... | Cas9_Cr; | |
| | ...........NLL....M...........NLL......................M.. | Cpf1_Wa; | |
| | M....M...M.M............................N.......LLN....... | Cpf1_Cr; | |
| PEX12 | acagaaaggccagtagacagggataAGGCAGGCaacacccccaacagctttcttcaga | SEQ_DUP; | 419 |
| | .........................11112222......................... | DUP_NUM; | |
| | B..aA...A..a...aaaC...aA..aa..............A.........a.A.Ha | Cas9_Wa; | |
| | A.aaaHa.......Aa......A..........A...A..A.aaaaa..A..A..Ba. | Cas9_Cr; | |
| | .......................................................... | Cpf1_Wa; | |
| | .M.N........N........N...................................N | Cpf1_Cr; | |
| MKS1 | agacagtgcaagcggaaggtgacagTGCCTGCCtgtggtctctgtgcggagtccaaag | SEQ_DUP; | 420 |
| | .........................11112222......................... | DUP_NUM; | |
| | .a.A...a.aaB.aa.a...a.A...A...a.aA.....a.a.aa.A......a.aA. | Cas9_Wa; | |
| | .A..A...A....A..JA.........A....Aa.JAa......a.a....A..J..a | Cas9_Cr; | |
| | .......................................................... | Cpf1_Wa; | |
| | ..........................L......k........................ | Cpf1_Cr; | |
| NPC1 | tactcacggagctgcccatgtgggcAAGTAAGTgcctcttccgcgcgctccacgcggc | SEQ_DUP; | 421 |
| | .........................11112222......................... | DUP_NUM; | |
| | ...aa.A..A.....a.aaA...A...a.A........a.a.A......a.aA..A.. | Cas9_Wa; | |
| | a......A.aha....A..Aaa.......A.........Aa.a.Baa.a.a.a.aa.a | Cas9_Cr; | |
| | .......................................................... | Cpf1_Wa; | |
| | ....N...N...............................................LN | Cpf1_Cr; | |
| PNPLA6 | agcgttgtacgcggaggagcgcagcGCCAGCCAgccgcacgaagcagcgggcccggga | SEQ_DUP; | 422 |
| | .........................11112222......................... | DUP_NUM; | |
| | ..A...a.aa.aa.a.A..a.A...A...a..A...aB.A..a.aaA...aaa.a.aa | Cas9_Wa; | |
| | .Ca....A......A.aJ......A.a..A.aa..Aa..Aa.a.a....A..A...Aa | Cas9_Cr; | |
| | ....L..N.......kL..........N.............................. | Cpf1_Wa; | |
| | ...................LN.............L.........N............. | Cpf1_Cr; | |
| LDLR | gcagccagctctgcgtgaacctggaGGGTGGGTggctacaagtgccagtgtgaggaag | SEQ_DUP; | 423 |
| | .........................11112222......................... | DUP_NUM; | |
| | ...A....a.a.aB....aaHaaaHaaa.aA......a.A...a.a.a.aaB.aA... | Cas9_Wa; | |
| | A.aa..A..Aa..A.a..A.....Aa..............A..A.....Aa.J..... | Cas9_Cr; | |
| | .............L............................................ | Cpf1_Wa; | |
| | .L................N..............LN............L.......... | Cpf1_Cr; | |
| FKRP | ggcccccgtgtcaccgtcctggtgcGGGAGGGAgttcgaggcatttgacaacgcggtg | SEQ_DUP; | 424 |
| | .........................11112222......................... | DUP_NUM; | |
| | ...a.A.....A....aa.a.aaa.aaa.A...a.aA.....a.....a.aa.A...a | Cas9_Wa; | |
| | A..Aa..Aaaaa....a.aa..aa.....A..J.......Ba....A......A..A. | Cas9_Cr; | |
| | .........................................................N | Cpf1_Wa; | |
| | .....L...L..................N............................. | Cpf1_Cr; | |

TABLE 6-continued

Selected Genes Having Microduplication Variants

| SYMBOL | MICRODUPLICATION INFORMATION | | SEQ ID NO: |
|---|---|---|---|
| CHEK2 | atttaccttccaagagtttttgacaTGATTGATgtattcatctcttaatgccttagga | SEQ_DUP; | 425 |
| | .........................11112222......................... | DUP_NUM; | |
| | ........Ha.A.....a.I..aC..aC.A...............A....HaaC.... | Cas9_Wa; | |
| | ..........Aa.Baa............A.............BahCa.a......Aa. | Cas9_Cr; | |
| | ........k.M.M............k....NLL.........k........N...... | Cpf1_Wa; | |
| | .........................N..........M.k................... | Cpf1_Cr; | |
| NPHP4 | aactcggcgacccccagcgtggcgtGGAGCGGAGCgtgtgctccgtggtgatggccaggc | SEQ_DUP; | 426 |
| | .........................1111122222......................... | DUP_NUM; | |
| | .aa.a.......a.a.aa.a.aa.a.aa.a.a.a.A....a.aa.aC.aA...aA....A | Cas9_Wa; | |
| | aH.....A.aH.A..Aaaaa..A....A......A....A.....AJaa..........A | Cas9_Cr; | |
| | ..N..N...................................................... | Cpf1_Wa; | |
| | ....L....L.................................................. | Cpf1_Cr; | |
| IDUA | caggcttcctgaactactacgatgcCTGCTCTGCTcggagggtctgcgcgccgccagccc | SEQ_DUP; | 427 |
| | .........................1111122222......................... | DUP_NUM; | |
| | ......aB........aC.A...A....A...aaHaaA...a.a.A..A...A....A.. | Cas9_Wa; | |
| | a..Aaa...A.Baa....A..A..A....Aa..A.a..A.a.......a..A.a.aa.aa | Cas9_Cr; | |
| | ..............L.....................................L....... | Cpf1_Wa; | |
| | ...............L............................................ | Cpf1_Cr; | |
| CCNO | aggtctgtagatctagctgcgccacGGGCTGGGCTgggccgggccgggcagggggctacc | SEQ_DUP; | 428 |
| | .........................1111122222......................... | DUP_NUM; | |
| | ..A..aC....A..a.A....aaA..aaA..aaA..aaA..aaA..aaaaA......... | Cas9_Wa; | |
| | .a.......a......Ca...A..A.aa.a...A....A....Aa...Aa...A...... | Cas9_Cr; | |
| | ............................................................ | Cpf1_Wa; | |
| | ............................................................ | Cpf1_Cr; | |
| CCNO | gctgcgccacgggctgggccgggccGGGCAGGGCAgggggctaccaccccgcgccgcaga | SEQ_DUP; | 429 |
| | .........................1111122222......................... | DUP_NUM; | |
| | .A....aaA..aaA..aaA..aaA..aaA..aaaaA..........a.A..A..a.aaaA | Cas9_Wa; | |
| | .Ca...A..A.aa.a...A....Aa...Aa....A.......A..A..Aa.aaaa.a.aa | Cas9_Cr; | |
| | ............................................................ | Cpf1_Wa; | |
| | ............................................................ | Cpf1_Cr; | |
| MYBPC3 | ctcatgcccttgagcctctttagcaTGCCGTGCCGcgcaggtcagtgacgccgtactgga | SEQ_DUP; | 430 |
| | .........................1111122222......................... | DUP_NUM; | |
| | .A.....a.A.A..........A..a.A..a.A..aA...a.a..a..A....aaB.aa. | Cas9_Wa; | |
| | a.a.aa.a...Aaa.....Aa.a.....A...Aa...Aa.a.a....a.....A.aa... | Cas9_Cr; | |
| | ........N..N....................N.........k................. | Cpf1_Wa; | |
| | ....................................LLN..................... | Cpf1_Cr; | |

TABLE 6-continued

Selected Genes Having Microduplication Variants

| SYMBOL | MICRODUPLICATION INFORMATION | | SEQ ID NO: |
|---|---|---|---|
| CHRNE | agatgagggtgggggtagcttaccaGTGAGGTGAGatgagattcgtcagggtgaccttga | SEQ_DUP; | 431 |
| | .........................1111122222......................... | DUP_NUM; | |
| | aHaaa.aaaaA..A.......a.a.aa.a.aCIa.aC...A..Haaa.a.....a.aA.. | Cas9_Wa; | |
| | .A.....................A...Aa..................BaH.a.......A | Cas9_Cr; | |
| | ...............k....N.....................N................. | Cpf1_Wa; | |
| | ............................................................ | Cpf1_Cr; | |
| BRCA1 | attgtgctcactgtacttggaatgtTCTCATCTCAtttcccatttctctttcaggtgaca | SEQ_DUP; | 432 |
| | .........................1111122222......................... | DUP_NUM; | |
| | .A...J..A.....aaB..A.............................aa.a....HaB | Cas9_Wa; | |
| | ..A.........A.aJa....A..J.....Ba.a.Ca.a...Baaa...Ba.a..Ba... | Cas9_Cr; | |
| | .k..........N..N.........N.............N.......N...........k | Cpf1_Wa; | |
| | .........................................LN.........k....... | Cpf1_Cr; | |
| SGCA | tacaatcgggacagctttgataccaCTCGGCTCGGcagaggctggtgctggagattgggg | SEQ_DUP; | 433 |
| | .........................1111122222......................... | DUP_NUM; | |
| | ...aaa...A..J.aC........aA...aA..a.aA..aa.A..aa.aC..aaaa.... | Cas9_Wa; | |
| | a..Aa..A..Ca..I.A..A.......Aa.a.aH.A.a..A.....A.....A..J.... | Cas9_Cr; | |
| | kLL....L...............................k.................... | Cpf1_Wa; | |
| | ............................L........L.......N.............. | Cpf1_Cr; | |
| PNKP | aggaagcagcggcaggggacgcccgCGGCTCGGCTcgggcacactggacgtacctgtggg | SEQ_DUP; | 434 |
| | .........................1111122222......................... | DUP_NUM; | |
| | .A..a.aA..aaaa..A...a.aA...aA..JaaA......aa..A.....a.aaaaaB. | Cas9_Wa; | |
| | ...........A..A..A......A.aaa.a..A.a..A.a...A.a.a....A...Aa. | Cas9_Cr; | |
| | ......L..................................................... | Cpf1_Wa; | |
| | ........................L..............LLN.......L.......... | Cpf1_Cr; | |
| DNAAF3 | gtcccagtcgctgacaccgcgccggGCGTCGCGTCgtagcgggagcccaggtagtggcgc | SEQ_DUP; | 435 |
| | .........................1111122222......................... | DUP_NUM; | |
| | ..A..AJ.a.....a.A..aaa.A..a.A..A..a.aaa.A....aA..a.aa.A..aa. | Cas9_Wa; | |
| | A.a....aaa...a.a...A.aa.a.aa...A..a.a..a....A....Aaa........ | Cas9_Cr; | |
| | ............NL...........L.................................. | Cpf1_Wa; | |
| | ....................L....................................... | Cpf1_Cr; | |
| MUTYH | cccttcctcccctggagtcacctgcATCCATATCCATccggtatagtagttgatcacagtgg | SEQ_DUP; | 436 |
| | .........................111111222222......................... | DUP_NUM; | |
| | .........aa.A......A...............aA....A..A..aC.....a.aA.... | 8 Cas9_Wa; | |
| | AaaHBaaa.Baa.aaaa......a.aa..A.CaaH..CaaHCaaH......J......Ca.a | 8 Cas9_Cr; | |
| | .....................NLL..NL...L..................L...M.L...L. | Cpf1_Wa; | |
| | ........M............M....................N................... | Cpf1_Cr; | |
| SLC22A5 | aggatgaccatatcagtgggctattTTGGGCTTGGGCtttcgcttgatactcctaacttgca | SEQ_DUP; | 437 |
| | .........................111111222222......................... | DUP_NUM; | |
| | .a.........a.aaA.......aaA...aaA.....A.J.aC............A...aaa | Cas9_Wa; | |

TABLE 6-continued

Selected Genes Having Microduplication Variants

| SYMBOL | MICRODUPLICATION INFORMATION | | SEQ ID NO: |
|---|---|---|---|
| | ...Ba.......Aa...Ca......A.........A.....A..Ba.a......A.aa...A | Cas9_Cr; | |
| | ....k..N............kL............M.............k.....N......k | Cpf1_Wa; | |
| | .........................M.......N..........L...........LN.... | Cpf1_Cr; | |
| FOXC1 | agcagcagctcgtcgtccctgagtcACGGCGACGGCGgcggcggcggcggcggcgggggagg | SEQ_DUP; | 438 |
| | .........................111111222222......................... | DUP_NUM; | |
| | A..A...A..A....Ha.A....aa.a..aa.aa.aa.aa.aa.aa.aa.aaaaa.aA...a | Cas9_Wa; | |
| | .a.aa..A..A..A.a..a..aaa.....a.a..A..A..A..A..A..A..A..A..A... | Cas9_Cr; | |
| | ..............L........................L...................... | Cpf1_Wa; | |
| | ....................................L......................... | Cpf1_Cr; | |
| RMRP | ttcagcacgaaccacgtcctcagctTCACAGATCACAGAgtagtattttatagccctaaagaaa | SEQ_DUP; | 439 |
| | .........................11111112222222......................... | DUP_NUM; | |
| | A...aB.....A......A.......aC....Ha.A..A.........A.......aB....a. | Cas9_Wa; | |
| | ...Aa.Ba..A.a...Aa.a..aa.a..A.Ba.a...Ca.a............J....Aaa... | Cas9_Cr; | |
| | .......................NL......................NL............... | Cpf1_Wa; | |
| | ............................M.......k...k....................... | Cpf1_Cr; | |
| CHRNE | ggtcccctgccggtgcctctgccccTCAAACATCAAACAcgagctcgctccgtggctttttcag | SEQ_DUP; | 440 |
| | .........................11111112222222......................... | DUP_NUM; | |
| | ....A..aa.A.....A............J......a.A...A....a.aA........A.... | Cas9_Wa; | |
| | H.aa....aaaa..Aa....Aa.a..Aaaa.a...A.Ca...A.a...A.a.a.aa....A... | Cas9_Cr; | |
| | ....................L.....L..................................... | Cpf1_Wa; | |
| | ......k......k.................................................. | Cpf1_Cr; | |
| RBCK1 | ccaggtccccgcctcataccagcccGACGAGGGACGAGGaggagcgagcgcgcctggcgggcga | SEQ_DUP; | 441 |
| | .........................11111112222222......................... | DUP_NUM; | |
| | A.....A.J........A...a..a.aaa..a.aa.aa.a.a.a.a.A...aa.aaa.a.aa.a | Cas9_Wa; | |
| | .Aa..Aa....aaaa.aa.a...Aa..Aaa..A......A.........A...A.a.aa...A. | Cas9_Cr; | |
| | ................................................................ | Cpf1_Wa; | |
| | ..........L..................................................... | Cpf1_Cr; | |
| ABHD12 | ctgtacttgccactgaaaatggatgGCTCTTAGCTCTTAgcttcttcgcggatattagtgaatg | SEQ_DUP; | 442 |
| | .........................11111112222222......................... | DUP_NUM; | |
| | ....A.....aB...HaaC.aA......A......A.......aHaaC.....aHaB..aa.aC | Cas9_Wa; | |
| | ....Ca..I.A..JAa.a.............A.a....A.a....A.Ba.Ba.a.......... | Cas9_Cr; | |
| | ......N......k...............N...................N.........N.... | Cpf1_Wa; | |
| | ............................L.M.......LN..L.....N..M.N.......... | Cpf1_Cr; | |
| MSH6 | tggctttaatgcagcaaggcttgctAATCTCCCAATCTCCCagaggaagttattcaaaagggacat | SEQ_DUP; | 443 |
| | .........................1111111122222222......................... | DUP_NUM; | |
| | ......A..A...aA...A...................a.aaB.A..........aaa.....aB. | Cas9_Wa; | |
| | ..A.....A.......A..A....A...A...Ca.aaa..Ca.aaa............BaH..... | Cas9_Cr; | |
| | ........N.............M.....k..............N.........L.....L...... | Cpf1_Wa; | |
| | ....N.......N...........LN........k....L...M...k.....N....N....... | Cpf1_Cr; | |

TABLE 6-continued

Selected Genes Having Microduplication Variants

| SYMBOL | MICRODUPLICATION INFORMATION | | SEQ ID NO: |
|---|---|---|---|
| LAMA2 | ttgaagaagaggaagaagatacagaACGTGTTCACGTGTTCtccagcttatgattatcttagaggt | SEQ_DUP; | 444 |
| | .........................1111111122222222......................... | DUP_NUM; | |
| | .aB.a.aaB.ab.aC....aB..a.A.....a.A.......A..I..aC........a.aA.ha.A | Cas9_Wa; | |
| | ...Aa.....................A....A....BaJa....BaJaa..A.........Ca... | Cas9_Cr; | |
| | .....k......M....M.....N.............................NL......N...L | Cpf1_Wa; | |
| | .................................................................. | Cpf1_Cr; | |
| TCTN2 | agacgtcaatcctccttttgatcagCTCTGCTCCTCTGCTCtgctgggacgacgacacgtggtgtc | SEQ_DUP; | 445 |
| | .........................1111111122222222......................... | DUP_NUM; | |
| | A..............aC...A....A.......A....A..aaa..aJ.a....a.aa.A..I..a | Cas9_Wa; | |
| | J.......A..a..CaaHaa......Ca..A.a..A.aa.a..A.a..A.....A..A..A.a... | Cas9_Cr; | |
| | ...NL...........k.......................k......................... | Cpf1_Wa; | |
| | .........................L........................................ | Cpf1_Cr; | |
| BRCA2 | gaatttgacaggataatagaaaatcAAGAAAAAAAGAAAAAtccttaaaggcttcaaaaagcactc | SEQ_DUP; | 446 |
| | .........................1111111122222222......................... | DUP_NUM; | |
| | ..a..HaaC.....aB.......aB......aB............aA.....J..A........aC | Cas9_Wa; | |
| | .............A..............Ca..I.............CaaHI....A.Ba....... | Cas9_Cr; | |
| | ..............N..N.........k...................................... | Cpf1_Wa; | |
| | ....N..k.......k.........k........k.................k............. | Cpf1_Cr; | |
| TCAP | tcatggctacctcagagctgagctgCGAGGTGTCGAGGTGTcggaggagaactgtgagcgccggga | SEQ_DUP; | 447 |
| | .........................1111111122222222......................... | DUP_NUM; | |
| | aA........a.A..a.A..a.a.aa.A..a.aa.A..aa.aa.aB...a.a.a.A..aaa.aA.. | Cas9_Wa; | |
| | .....Ca....A..Aa.a....A....A..A.......a.J.....a.J.......A......A.a | Cas9_Cr; | |
| | .................................................................. | Cpf1_Wa; | |
| | .....................L......N.............L................N..LLN. | Cpf1_Cr; | |
| LDLR | gatggtggccccgactgcaaggacaAATCTGACAATCTGACgaggaaaactgcggtatgggcgggg | SEQ_DUP; | 448 |
| | .........................1111111122222222......................... | DUP_NUM; | |
| | a.aA....a...A...aa........a.......a..a.aaB.....a.aA...aaa.aaaA..Ha | Cas9_Wa; | |
| | .a...........Aaaa..A..A.....A...Ca..IA..Ca..IA........A..A.......J | Cas9_Cr; | |
| | ....L....L........................................................ | Cpf1_Wa; | |
| | ...k........N..........Lk......................................... | Cpf1_Cr; | |
| ITPA | agcctatgcgctctgcacgtttgcaCTCAGCACCTCAGCACcggggacccaagccagcccgtgcgc | SEQ_DUP; | 449 |
| | .........................1111111122222222......................... | DUP_NUM; | |
| | ...a.A.J..A...AJ..A...J..A....J..A....aaaa......A...A...a.a.A...A. | Cas9_Wa; | |
| | ....a..Aa....A.a.a..A.a.....A.a.aH.A.aa.a..A.aa.....AaaH..Aa..Aaa. | Cas9_Cr; | |
| | .........NL.................M..............k...................... | Cpf1_Wa; | |
| | .......................L.....N............................L....... | Cpf1_Cr; | |
| PEX1 | tccagcaggacaacagatggctgcaTCCACACTGTCCACACTGcctctgagaaagccacctctagggt | SEQ_DUP; | 450 |
| | .........................111111111222222222......................... | DUP_NUM; | |
| | A..aa......aC.aA..A..J.......AJ.......A.....a.aB..A........HaaA..... | Cas9_Wa; | |

TABLE 6-continued

Selected Genes Having Microduplication Variants

| SYMBOL | MICRODUPLICATION INFORMATION | | SEQ ID NO: |
|---|---|---|---|
| | ...a.CaaH.A....A..A......A..A.CaaHa.a...aa.a.a..Aa.a........Aa.aa.a. | Cas9_Cr; | |
| | ..L....................L...............................L......... | Cpf1_Wa; | |
| | ............................k.............................N..... | Cpf1_Cr; | |
| IGFALS | gcctgttgcccgc agcaccagctcGCGCAGGCTGCGCAGGCTgcccaggccgcggaacgccgcatcg | SEQ_DUP; | 451 |
| | ........................11111111122222222......................... | DUP_NUM; | |
| | A..A...AJ..A.....A...a.A..aA..a.A..aA..A....aA..a.aaB..A..A...aaaa. | Cas9_Wa; | |
| | ..Aa..Aa.....Aaa.aa..A.aa..A.a.a.a...A..A.a...A..Aaa...Aa.a....A.aa. | Cas9_Cr; | |
| | ............................N.................................... | Cpf1_Wa; | |
| | ................................LLN............L............... | Cpf1_Cr; | |
| SEPN1 | gcagccgccgccagccgcagccatgGGCCGGGCCCGGCCGGGCCCggccgggccaacgcgggccgcccag | SEQ_DUP; | 452 |
| | ........................11111111112222222222......................... | DUP_NUM; | |
| | ..A..A...A..A..A....aaA..aaA...aA..aaA...aA..aaA.....a.aaA..A....A.... | Cas9_Wa; | |
| | a.aa..A..Aa.aa.aa..Aa.a..Aa.....Aa...Aaa..Aa...Aaa..Aa...Aa..A.a...Aa. | Cas9_Cr; | |
| | ....kL...NLL......................................................... | Cpf1_Wa; | |
| | ..............................N.................................. | Cpf1_Cr; | |
| CYP1B1 | agcccaagacagaggtgttggcagtGGTGGCATGAGGTGGCATGAggaatagtgacaggcacaaagctgg | SEQ_DUP; | 453 |
| | ........................11111111112222222222......................... | DUP_NUM; | |
| | ...a...a.aa.A..aA..a.aa.aA...a.aa.aA...a.aaB...a.a.J.aA......A..aa.aB. | Cas9_Wa; | |
| | .......Aaa....A.........JA.......A.........A.............A...A.a... | Cas9_Cr; | |
| | ..........N...........................N............................ | Cpf1_Wa; | |
| | ........................LN.............k....L...N.............M.k.. | Cpf1_Cr; | |
| CYP27A1 | gtgcaggcgcgcgagcacaacccatGGCTGCGCTGGGCTGCGCTGggctgcgcgaggctgaggtgggcgc | SEQ_DUP; | 454 |
| | ........................11111111112222222222......................... | DUP_NUM; | |
| | .aa.a.aJa.A..........aA..a.A..aaA..a.A..aaA..a.a.a.aA..a.aa.aaa.A..a.a | Cas9_Wa; | |
| | aH......A..JA.a.a...A.a..AaaH...A..A.a....A..A.a....A..A.a....A....... | Cas9_Cr; | |
| | ...................................................................... | Cpf1_Wa; | |
| | ...................................................................... | Cpf1_Cr; | |
| RMRP | ttcagcacgaaccacgtcctcagctTCACAGAGTATCACAGAGTAgtattttatagccctaaagaaattg | SEQ_DUP; | 455 |
| | ........................11111111112222222222......................... | DUP_NUM; | |
| | A...aB.....A......A......Ha.A......Ha.A..A.........A.......aB....a.A.. | Cas9_Wa; | |
| | ...Aa.Ba..A.a...Aa.a..aa.a..A.Ba.a......Ca.a...........J....Aaa...... | Cas9_Cr; | |
| | ......................NL.....................NL.........M............ | Cpf1_Wa; | |
| | ..............................M.......k...k........................k | Cpf1_Cr; | |
| SPG11 | catggaggcatttgcttgtcagcacTTCCAGGTTATTCCAGGTTAgttaccacttcattactggagggca | SEQ_DUP; | 456 |
| | ........................11111111112222222222......................... | DUP_NUM; | |
| | a.aA.....A...AJ..A........aA........aA...A...............aaJaaA....A. | Cas9_Wa; | |
| | a.Baaa.......A.....A....a..A.a.Baa.......Baa..........Aa.a.Ba....A.... | Cas9_Cr; | |
| | ............N..NLL................k...N.........NLL....N..NLL....N...N | Cpf1_Wa; | |
| | ......................................L.............k............ | Cpf1_Cr; | |

TABLE 6-continued

Selected Genes Having Microduplication Variants

| SYMBOL | MICRODUPLICATION INFORMATION | | SEQ ID NO: |
|---|---|---|---|
| SPG11 | gtaggagagcatggatctctgggtgCAGATCCTCCCAGATCCTCCatactagcttcccctgaggccagtg | SEQ_DUP; | 457 |
| | .........................11111111112222222222......................... | DUP_NUM; | |
| | a.a.A..HaaC....Haaa.A..aC........aC...J........A........a.aA...a.A.... | Cas9_Wa; | |
| | .a............A.....Ca.a......A..JCaaHaaa...CaaHaa...A...A.Baaaa.....A | Cas9_Cr; | |
| | NL...................k..................................L.........L... | Cpf1_Wa; | |
| | .......................M....................................N.....N... | Cpf1_Cr; | |
| BRCA1 | taatgagctggcatgagtatttgtgCCACATGGCTCCACATGGCTccacatgcaagtttgaaacagaact | SEQ_DUP; | 458 |
| | .........................11111111112222222222......................... | DUP_NUM; | |
| | a.A..aA..Ha.A.....a.A......aA........aA........A...A...aB....aB......J | Cas9_Wa; | |
| | ..A.........A...A..........J..Aa.a....A.aa.a....A.aa.a...A..........A. | Cas9_Cr; | |
| | ............N..............................k..............L.........L. | Cpf1_Wa; | |
| | ................................N.....Lk....N..........M.........L.... | Cpf1_Cr; | |
| NCF4 | gttttcgtcatcgaggtgaagacaaAAGGAGGATCAAGGAGGATCcaagtacctcatctaccgccgctac | SEQ_DUP; | 459 |
| | .........................11111111112222222222......................... | DUP_NUM; | |
| | ..A.....a.aa.aB.a......aaHaaC....aaHaaC..J..A.............A..A.....A.. | Cas9_Wa; | |
| | a........Ba..a.Ca..........A..........Ca........CaaH....Aa.a.Ca..Aa.aa | Cas9_Cr; | |
| | ...................N.......kL......................................... | Cpf1_Wa; | |
| | ..............N..........N............................................ | Cpf1_Cr; | |
| SLC22A5 | gaggtgccccacagctgccgccgctACCGGCTCGCCACCGGCTCGCCaccatcgccaacttctcggcgcttg | SEQ_DUP; | 460 |
| | .........................1111111111122222222222......................... | DUP_NUM; | |
| | .A........A..A..A..A.....aA...A....aA...A........A..........aa.A...aaA.. | Cas9_Wa; | |
| | .Aa.a......Aaaa.a..A..Aa.aa.a..Aa..A.a.aa.aa..A.a.aa.aa.Ca.aa..A.Ba.a..A | Cas9_Cr; | |
| | ........................................................................ | Cpf1_Wa; | |
| | ...................................N...................L................ | Cpf1_Cr; | |
| KCNQ1 | gtggtgttcttcgggacggagtacgTGGTCCGCCTCTGGTCCGCCTCtggtccgccggctgccgcagcaagt | SEQ_DUP; | 461 |
| | .........................1111111111122222222222......................... | DUP_NUM; | |
| | .A......aaa..aa.A...a.aA...A.....aA...A.....aA...A..aA..A..A..AJ..A...a. | Cas9_Wa; | |
| | ..A..J......BaJBa....A......A..J..aa.aa.a....aa.aa.a....aa.aa..A..Aa.a.. | Cas9_Cr; | |
| | ...L.........................N..NL..................L..........L........ | Cpf1_Wa; | |
| | ...............................................N........................ | Cpf1_Cr; | |
| MYO7A | gctgtgaacccctaccagctgctctCCATCTACTCGCCATCTACTCGccagagcacatccgccagtatacca | SEQ_DUP; | 462 |
| | .........................1111111111122222222222......................... | DUP_NUM; | |
| | .aB..........A..A..............A..........A..Ja.A.......A..JA........... | Cas9_Wa; | |
| | H.....A......Aaaa..Aa..A..A.a.aa.Ca..A.aHaa.Ca..A.aHaa....A.a.CaaHaa.... | Cas9_Cr; | |
| | ...M........L...................................L....................... | Cpf1_Wa; | |
| | .............................................M....N..N..N.......L....... | Cpf1_Cr; | |
| CEP57 | ccacaagccctagccatgccgtggtAGCCAATGTTCAGCCAATGTTCagcttgtcttgcatctaatgaagca | SEQ_DUP; | 463 |
| | .........................1111111111122222222222......................... | DUP_NUM; | |
| | ..A.....A....A..a.aA..A.....A....A.....A....A..A....A........aB.a....... | Cas9_Wa; | |
| | .....aa.a...Aaa...Aa...Aa.......Aa.....Ba..Aa.....Ba..A....a...A.Ca..... | Cas9_Cr; | |

TABLE 6-continued

Selected Genes Having Microduplication Variants

| SYMBOL | MICRODUPLICATION INFORMATION | | SEQ ID NO: |
|---|---|---|---|
| | kL........k..NL...k....L................................NL.........NL... | Cpf1_Wa; | |
| | ........N..........N......................N..LN...N.......k...........N. | Cpf1_Cr; | |
| ACADM | gaaatggcaatgaaagttgaactagCTAGAATGAGTTACTAGAATGAGTTAccagagagcagcttgggaggttgat | SEQ_DUP; | 464 |
| | .........................11111111111112222222222222......................... | DUP_NUM; | |
| | .aA....aB..A..aB....A..HaB.Ha.A....HaB.Ha.A.......a.a.A..A...aaa.aa..aC....a | Cas9_Wa; | |
| | ...A........A.............A...A...........A.............Aa......A..A........ | Cas9_Cr; | |
| | .......M....k.M.......................N...................N............N.... | Cpf1_Wa; | |
| | ........N............N.....................L....................Lk.......... | Cpf1_Cr; | |
| GAMT | gaggggcaccttgtgtgtctgccgtGGGGCCCAGTCCCGGGGCCCAGTCCCggagccgctggaagacgccgtcatt | SEQ_DUP; | 465 |
| | .........................11111111111112222222222222......................... | DUP_NUM; | |
| | aA......a.a.A...A..a.aaaA....A....aaaA....A....aa.A..A..aaB.a..A..A..J..A... | Cas9_Wa; | |
| | ...A.......A.aa......a.JAa........Aaa...aaa....Aaa...aaa....Aa.a.......A.aa. | Cas9_Cr; | |
| | .................................N........................L............L.... | Cpf1_Wa; | |
| | ..............................L........LLN...........................N...... | Cpf1_Cr; | |
| CHRNE | ccacctcttcggcattgtacgtctgAGAGCTGCGGAGCCAGAGCTGCGGAGCCagggccgggagcccaccccagaagc | SEQ_DUP; | 466 |
| | .........................1111111111111122222222222222......................... | DUP_NUM; | |
| | ......aA.J..A...A...a.a.A..a.aa.A...a.A..a.aa.A...aaA..aaa.A.........aB.A..... | Cas9_Wa; | |
| | ...A.aa.aa.a.Ba..A......A..a......A..A....Aa....A..A....Aa....Aa.....Aaa.aaaa. | Cas9_Cr; | |
| | .N.....................L......NL.....N........................................ | Cpf1_Wa; | |
| | ............L.............L............L.............N........................ | Cpf1_Cr; | |
| RMRP | gccttcagcacgaaccacgtcctcaGCTTCACAGAGTAGTGCTTCACAGAGTAGTattttatagccctaaagaaattgtg | SEQ_DUP; | 467 |
| | .........................111111111111111222222222222222......................... | DUP_NUM; | |
| | J..A...aB.....A......A......Ha.A..a.A......Ha.A..A.........A.......aB....a.A...I | Cas9_Wa; | |
| | ..A...Aa.Ba..A.a...Aa.a..aa.a..A.Ba.a.........A.Ba.a..........J....Aaa.......... | Cas9_Cr; | |
| | ..........................NL......................NL............................ | Cpf1_Wa; | |
| | .......................................M.......k...k............................ | Cpf1_Cr; | |
| ABCC8 | acagcggtgtgaccaagatatggaaGAGGGAGAGGGAGGCGAGGGAGAGGGAGGCaaaggccacggagggcgagaagtcg | SEQ_DUP; | 468 |
| | .........................111111111111111222222222222222......................... | DUP_NUM; | |
| | .aa.a.a.....aC...aaB.a.aaa.a.aaa.aa.a.aaa.a.aaa.aA....aA....aa.aaa.a.aB.A..aA... | Cas9_Wa; | |
| | A.....A..A.......aa.........................A..............A.....Aa.a......A.... | Cas9_Cr; | |
| | ..........................................M..................................... | Cpf1_Wa; | |
| | LLN....L.....L........L.....L....k.........:.........N.............LN..N........ | Cpf1_Cr; | |
| MMAB | tctctccagccctcttaccgtctctCGGCCCGGCGGCACACGGCCCGGCGGCACAcggcccggcagaaatgcagcgccga | SEQ_DUP; | 469 |
| | .........................111111111111111222222222222222......................... | DUP_NUM; | |
| | ....A..........A......aA...aa.aA.....aA...aa.aA.....aA...aA..aB...A..a.A..a.A..a | Cas9_Wa; | |
| | a.aaa.a.a.aa..Aaa.a...Aa..a.a.a..Aaa..A..A.a.a..Aaa..A..A.a.a..Aaa..A.......A..A | Cas9_Cr; | |
| | L.....L..N..........L.......L........N.......................................... | Cpf1_Wa; | |
| | .............................................k.................................L | Cpf1_Cr; | |
| WES1 | actggctggtcctcgccgcgaagcaGGGCCGTCGCGAGGCTGGGCCGTCGCGAGGCTgtgaagctgcttcgccggtgcttgg | SEQ_DUP; | 470 |
| | .........................11111111111111112222222222222222......................... | DUP_NUM; | |

TABLE 6-continued

Selected Genes Having Microduplication Variants

| SYMBOL | MICRODUPLICATION INFORMATION | | SEQ ID NO: |
|---|---|---|---|
| | A..aA.....A..a.aB.A..aaA..A..a.a.aA..aaA..A..a.a.aA..a.aB.A..A....A..aa.A...aa.aa. | Cas9_Wa; | |
| | ......A...A....aa.a.aa.a....A....Aa..a.a....A....Aa..a.a....A.......A..A.Ba.aa.... | Cas9_Cr; | |
| | .................................................................................. | Cpf1_Wa; | |
| | ...................................LN.....................L......N............. | Cpf1_Cr; | |
| CRB2 | cgctgggcggcctgcccctgcccttGGCGCGGCCCCGGCCCGGCGCGGCCCCGGCCCggcgcggcccctggcgcccgagagc | SEQ_DUP; | 471 |
| | .........................11111111111111112222222222222222......................... | DUP_NUM; | |
| | aaa.aA...A.....A.....aa.a.aA....aA...aa.a.aA....aA...aa.a.aA.....aa.A...aJa.A..... | Cas9_Wa; | |
| | a....A.a....A..Aa..Aaaa..Aaa....A.a..Aaaa..Aaa..A.a..Aaaa..Aaa..A.a..Aaaa...A.aaa. | Cas9_Cr; | |
| | ..........N....................................N.................................. | Cpf1_Wa; | |
| | ...............................................................................L.. | Cpf1_Cr; | |
| HPS1 | gtcctgcaggtgctggggcaggtgtGGGCCTCCCCTGCTGGGGGCCTCCCCTGCTGGgggctgtggtcagaaagttcagccg | SEQ_DUP; | 472 |
| | .........................11111111111111112222222222222222......................... | DUP_NUM; | |
| | .A..aa.A..aaaA..aa.a.aaA.......A..aaaaA........A..aaaaA..a.aA...aB..A....A..aA..a | Cas9_Wa; | |
| | .a.....aa..A.....A..J..A........JAa.aaaa..A......Aa.aaaa..A......A......a.......Ba | Cas9_Cr; | |
| | ....................N..................................L...............L.......... | Cpf1_Wa; | |
| | ................................................k................................. | Cpf1_Cr; | |
| DNAAF2 | ggtgaccccggagcccgcagccccaGCCACGCAGGTATCGTGCCACGCAGGTATCGTggcctccgtcctccgcgcgactcct | SEQ_DUP; | 473 |
| | .........................11111111111111112222222222222222......................... | DUP_NUM; | |
| | .....aa.A...A..A.....A....A..aA....a.A....A..aA....a.aA.....A......a.a.a.......aHa | Cas9_Wa; | |
| | ..........Aaaa....Aaa.a..Aaaa..Aa.a.a.....Ca.J.Aa.a.a.....Ca.J..Aa.aa..aa.aa.a.a.. | Cas9_Cr; | |
| | .......L................................................M...............M...... | Cpf1_Wa; | |
| | .................................................................................. | Cpf1_Cr; | |
| RMRP | cctaggatacaggccttcagcacgaACCACGTCCTCAGCTTCACCACGTCCTCAGCTTCacagagtagtattttatagccctaa | SEQ_DUP; | 474 |
| | .........................1111111111111111122222222222222222......................... | DUP_NUM; | |
| | aaC....aA...J..A...aB.....A......A.........A......A......Ha.A..A..........A......aB. | Cas9_Wa; | |
| | ...J.aa.......A...Aa.Ba..A.a...Aa.a..aa.a..A.Ba.aa.a..aa.a..A.Ba.a............J....A | Cas9_Cr; | |
| | .....................................NL.......................NL...............NL... | Cpf1_Wa; | |
| | ..LN................................................M.......k...k.................. | Cpf1_Cr; | |
| RMRP | gatacaggccttcagcacgaaccacGTCCTCAGCTTCACAGAGTCCTCAGCTTCACAGAgtagtattttatagccctaaagaaa | SEQ_DUP; | 475 |
| | .........................1111111111111111122222222222222222......................... | DUP_NUM; | |
| | ..aA...J..A...aB.....A......A......Ha.A......A......Ha.A..A.........A........aB....a. | Cas9_Wa; | |
| | aa.......A...Aa.Ba..A.a...Aa.a..aa.a..A.Ba.a.....aa.a..A.Ba.a.............J....Aaa... | Cas9_Cr; | |
| | ................................NL........................NL................NL........ | Cpf1_Wa; | |
| | ...............................................M.......k...k....................... | Cpf1_Cr; | |
| PALB2 | caagacagactgagtctttcaaatgAGCAAGTTGGGGTGTGCAGCAAGTTGGGGTGTGCagcaagttcgtccagcaacttctgt | SEQ_DUP; | 476 |
| | .........................1111111111111111122222222222222222......................... | DUP_NUM; | |
| | ...a..Ha.A..........a.A...A..aaaa.a.A..A...A..aaaa.a.A..A...A...A....A........A..aC. | Cas9_Wa; | |
| | .a...A....A...A.....a..Ba.......A..............AJ.a..............AJ.a....Ba..aa..A..A. | Cas9_Cr; | |
| | ......N...k....M.......................kL...............N.............N.......... | Cpf1_Wa; | |
| | .......N................N................N...............N.................M....... | Cpf1_Cr; | |

TABLE 6-continued

Selected Genes Having Microduplication Variants

| SYMBOL | MICRODUPLICATION INFORMATION | | SEQ ID NO: |
|---|---|---|---|
| PNKP | cgcggctcgcggcgtctgggtttgtGTTGTCGATGGCGACCCGTTGTCGATGGCGACCCgtttcccttgcttcagggctgtctc | SEQ_DUP; | 477 |
| | .........................1111111111111111122222222222222222......................... | DUP_NUM; | |
| | A...a.aa.A..HaaA...a.A..A..aC.aa.a....A..A..aC.aa.a....A........A.....aaA..A.J...... | Cas9_Wa; | |
| | Aa...A.a..A.a.a..A..a............Ja.....A..AaaH....a.....A..AaaH..Baaa...A.Ba....A. | Cas9_Cr; | |
| | ............................................k...N.................N................. | Cpf1_Wa; | |
| | .................................................................................... | Cpf1_Cr; | |
| F12 | atgaagcctaggggacaccggggtcGGAGGCGCCGCCTGGGTTGGAGGCGCCGCCTGGGTTggggtctggcactgtgccaggtcgc | SEQ_DUP; | 478 |
| | .........................111111111111111111222222222222222222......................... | DUP_NUM; | |
| | .A....aaaa.....aaaA..aa.aa.A..A..HaaA..aa.aa.A..A..HaaA..aaaA.J.aA....a.A...aA..a..A.. | Cas9_Wa; | |
| | ....A......Aa.......A.aa.....a.....A.aa.aa..........A.aa.aa..........a...A.a....Aa.J | Cas9_Cr; | |
| | ......................................................................N.................N... | Cpf1_Wa; | |
| | ....L................L................................................................ | Cpf1_Cr; | |
| YARS2 | gagcttctttaaacaactcttttaaCTCCTGATCAGACATGACCTCCTGATCAGACATGACctccagtgcatctatgctactgtga | SEQ_DUP; | 479 |
| | .........................111111111111111111222222222222222222......................... | DUP_NUM; | |
| | ..........................aC...a....a.......aC...a....a.......a.A.......A.....a.aC.... | Cas9_Wa; | |
| | ........A.Ba......A..A.aH.....A.aa...Ca...A....Aa.aa...Ca...A....Aa.aa....A.Ca....A..A | Cas9_Cr; | |
| | ............NL.............N...k...........k.......................................... | Cpf1_Wa; | |
| | ..N...............................................................M.k.................L | Cpf1_Cr; | |
| LDLR | cagctggcgctgtgatggtggccccGACTGCAAGGACAAATCTGACTGCAAGGACAAATCTgacgaggaaaactgcggtatgggcg | SEQ_DUP; | 480 |
| | .........................111111111111111111222222222222222222......................... | DUP_NUM; | |
| | .aa.A..a.aC.aa.aA....a...A...aa........a...A...aa........a..a.aaB.....a.aA...aaa.aaaA. | Cas9_Wa; | |
| | aHa.aa..A...A.a..........Aaaa..A..A.....A...Ca..IA..A.....A...Ca..IA........A..A..... | Cas9_Cr; | |
| | .................L....L................................................................ | Cpf1_Wa; | |
| | ..........N.....k...........N.....k..........Lk....................................... | Cpf1_Cr; | |
| KPTN | tcgggagatgggaccgtcctgcaggACCGACCACATCTGCAGAACCGACCACATCTGCAGAacctctgcgtggagagcgaggattc | SEQ_DUP; | 481 |
| | .........................111111111111111111222222222222222222......................... | DUP_NUM; | |
| | a.aC.aaa...A....A..aa...a.........A..aB...a.........A..aB......a.a.aa.a.a.aHaaC....a.A | Cas9_Wa; | |
| | .Ca.aIaH..........Aa..aa..A....Aa....Aa.a.Ca..A....Aa..Aa.a.Ca..A....Aa.a..A......A... | Cas9_Cr; | |
| | ...................................................................................... | Cpf1_Wa; | |
| | ....................N...................N..............L..................N.......... | Cpf1_Cr; | |
| MSH6 | ttgctaatctcccagaggaagttatTCAAAAGGGACATAGAAAATCAAAAGGGACATAGAAAAgcaagagaatttgagaagatgaatc | SEQ_DUP; | 482 |
| | .........................11111111111111111112222222222222222222......................... | DUP_NUM; | |
| | ..........a.aaB.A..........aaa.....aB.........aaa.....aB...A...aHaB....a.aB.aCHaB....A.. | Cas9_Wa; | |
| | ....A...A...Ca.aaa.............BaH.......A........Ca..I.....A.........A.................. | Cas9_Cr; | |
| | ..M.....k...............N.........L..........N..NL...................................... | Cpf1_Wa; | |
| | ......k...L...M...k......k...L...M...k.....N....N.......N...LN......................... | Cpf1_Cr; | |
| BARD1 | cttctgcgtggaccttcaggaatttCATACTTTTCTTCCTGTTCACATACTTTTCTTCCTGTTCAcatacttttcttcgtagacatgctt | SEQ_DUP; | 483 |
| | .........................1111111111111111111122222222222222222222......................... | DUP_NUM; | |
| | .a.a.aa.......aaB..J...............A..J...............A..J...............A..a....A....... | Cas9_Wa; | |
| | .Aa..A.Ba..A.....Aa.Ba.......Ba...A...Ba.Baa...Ba.a...A...Ba.Baa...Ba.a...A...Ba.Ba.....A. | Cas9_Cr; | |

TABLE 6-continued

Selected Genes Having Microduplication Variants

| SYMBOL | MICRODUPLICATION INFORMATION | | SEQ ID NO: |
|---|---|---|---|
| | .......N......N..........N...........NL.......kL.......k..NL....NL.........K..NL....NL.... | Cpf1_Wa; | |
| | .....M...................M.................M................................k.......N. | Cpf1_Cr; | |
| MRE11A | ctgcacctacctttgatctgtctttGAAGTGGTAGGAAAAATGTCGAAGTGGTAGGAAAAATGTCttcttccacatctgattcatctacc | SEQ_DUP; | 484 |
| | .........................1111111111111111111122222222222222222222......................... | DUP_NUM; | |
| | ..........aC...A.....aB.a.aA..aaB.....A..aB.a.aA..aaB.....A............I..aC.............. | Cas9_Wa; | |
| | ..Ca.aI.A.aa..Aa.....Ca...a.....................a...................a.Ba.Baa.a.Ca....BaHC | Cas9_Cr; | |
| | .....k....k.......................k.........k.......................................N. | Cpf1_Wa; | |
| | ....LN........Lk.......LN.........Lk................................N.........N..Lk... | Cpf1_Cr; | |
| PYGL | ctccacgcccacgatgccgcggatgCTGATCTGCCGCCGCTTCTCCTGATCTGCCGCCGCTTCTCctggtccgtcaggggcttcgccatg | SEQ_DUP; | 485 |
| | .........................1111111111111111111122222222222222222222......................... | DUP_NUM; | |
| | ..A.....aC.A..aHaaC.A..aC...A..A..A........aC...A..A..A........aA...A...aaaA....A....aA..a | Cas9_Wa; | |
| | .a..Ba.aa.a.aaa.a....Aa.a.....A...Ca..Aa.aa.a.Ba.aa...Ca..Aa.aa.a.Ba.aa....aa..a.....A.Ba. | Cas9_Cr; | |
| | ...N..NL............N...L.................................N..................N...... | Cpf1_Wa; | |
| | .......................................................................................... | Cpf1_Cr; | |
| SLC34A1 | acccggtggccgggctggtggtgggGATCCTGGTGACCGTGCTGGTGATCCTGGTGACCGTGCTGGTgcagagctccagcacctccacatcc | SEQ_DUP; | 486 |
| | .........................111111111111111111111222222222222222222222......................... | DUP_NUM; | |
| | aa.aA..aaA..aa.aa.aaaaC....aa.a...a.A..aa.aC....aa.a...a.A..aa.A..a.A..J..A................ | Cas9_Wa; | |
| | ..aa..AaaH....Aa...A............CaaH.....Aa...A..J...CaaH.....Aa...A..J..A..J.A.aa..A.aa.aa. | Cas9_Cr; | |
| | ...................L........................................................................ | Cpf1_Wa; | |
| | ...L........................................................................................ | Cpf1_Cr; | |
| SLC25A13 | actccgctgtaagtggtttggccagCCCGGGCAGCCACCTGTAATCTCCCCGGGCAGCCACCTGTAATCTCgtcttgataacatcagcaggggtca | SEQ_DUP; | 487 |
| | .........................11111111111111111111111222222222222222222222222......................... | DUP_NUM; | |
| | .A..A...a.aA...aA...A...aaA..A......A..........aaA..A.....A.....A.......aC........A..aaaA....... | Cas9_Wa; | |
| | a..Ca.a.aa.a.............Aa..Aaa...A..Aa.aa......Ca.aaaa...A..Aa.aa.....Ca.aI.a.......A.Ca..A... | Cas9_Cr; | |
| | ..M...k.............M.....L...........k..............................L........................ | Cpf1_Wa; | |
| | ...................N...................N...........M.N.................k.............M... | Cpf1_Cr; | |
| PKP2 | cggccgcctggccgacagtcaagtgCGCTCTCCTCCCGCTGGAATCCACGCTCTCCTCCCGCTGGAATCCAcggcgacactgggcccagcttccct | SEQ_DUP; | 488 |
| | .........................11111111111111111111111222222222222222222222222......................... | DUP_NUM; | |
| | .A...aA..a...A....a.a.A..........A..aaB......A..........A..aaB......aa.a.....aaA....A.........a. | Cas9_Wa; | |
| | aaa..A..Aa.aa...Aa..A...a.....A.aJa.aa.aaa.a.....CaaHa.a.a.aa.aaa.a.....CaaHa..A..A.a....Aaa..A. | Cas9_Cr; | |
| | .......NLL....NLL...............................L..........L..........L.........L.... | Cpf1_Wa; | |
| AMH | gccgacgggccgtgcgcgctgcgcgAGCTCAGCGTAGACCTCCGCGCCAGCTCAGCGTAGACCTCCGCGCCgagcgctccgtactcatccccgaga | Cpf1_Cr; | 489 |
| | .........................11111111111111111111111222222222222222222222222......................... | SEQ_DUP; | |
| | ..aaA..a.a.a.A..a.a.a.A....a.A..a......a.A...A....a.A..a......a.A..a.a.A.J..A...........a.a..... | DUP_NUM; | |
| | aa.aa.aa..A...Aa...A.aJa..A.a...A.a..A.....Aa.aa.a.aa..A.a..A.....Aa.aa.a.aa...A.a.aa...A.ahCaaa | Cas9_Wa; | |
| | .................................................................L..................L........ | Cas9_Cr; | |
| | ..................................................................................N..N....... | Cpf1_Wa; | |
| HPS4 | gatcatggccagacaagcatccgttCTCCTTCCTGCCATCTGGACAAGCCTCCTTCCTGCCATCTGGACAAGCttcgtcaggggatgtgggatctggg | Cpf1_Cr; | 490 |
| | .........................1111111111111111111111111222222222222222222222222......................... | SEQ_DUP; | |
| | ..aA...a....A.....A..........A......aa....A..........A......aa....A....A...aaaaC.a.aaaC...aaaa.aA | DUP_NUM; | |

TABLE 6-continued

Selected Genes Having Microduplication Variants

| SYMBOL | MICRODUPLICATION INFORMATION | | SEQ ID NO: |
|---|---|---|---|
| | a.aa...Ca....Aa...A...A.CaaH.Ba.aa.Baa..Aa.Ca....A...Aa.aa.Baa..Aa.Ca....A...A.Ba..a.............C | Cas9_Wa; | |
| | ....................L......................L..N....NL.......................NL..................NL | Cas9_Cr; | |
| | ....................L..N....................L..N.............L.....L.......................L...... | Cpf1_Wa; | |
| | .L. | Cpf1_Cr; | |
| ASL | tgcccctggcttcccacagccacgcCGTGGCACTGACCCGAGACTCTGAGCGTGGCACTGACCCGAGACTCTGAGcggctgctggaggtgcggaagcgga | SEQ_DUP; | 491 |
| | .........................11111111111111111111111112222222222222222222222222......................... | DUP_NUM; | |
| | ...aA........A....A..a.aA....a....a.a.....a.a.a.aA....a.....a.a.....a.a.aA..A..aa.aa.a.aaB.aHaaC.... | Cas9_Wa; | |
| | aaHaa..Aaaa...A.Baaa.a..Aa.a.aa....A.a...AaaH...A.aH...A....A.a...AaaH...A.aH...A..A..A........A..J. | Cas9_Cr; | |
| | .................................NLL................................................................ | Cpf1_Wa; | |
| | ..............................................................L.......LLN..L...N.................L.. | Cpf1_Cr; | |
| EPG5 | tcagagcttggtcaggggtgaaagcAGAGTTTATCACCAATTCCCCTTCAATAAGAGTTTATCACCAATTCCCCTTCAATAactctccggagctgggagtcctctt | SEQ_DUP; | 492 |
| | .........................11111111111111111111111111112222222222222222222222222222......................... | DUP_NUM; | |
| | .A...aA...aaaa.aB..A.Ha.A........................Ha.A...............................aa.A..aaa.A........... | Cas9_Wa; | |
| | ..Aa.ba....A.....a...........A...........Ca.aa...Baaaa.Ba............Ca.aa...Baaaa.Ba.....A.aHaa.A.......a | Cas9_Cr; | |
| | ..............k.......NL......N........................k.M.......NLL...NL.......k.M.......NLL...NL....... | Cpf1_Wa; | |
| | ...............N...........N..N...............N.........N..N......L.......L........k.....L............ | Cpf1_Cr; | |
| ABCC8 | ttgggcacaagaagaaaaaccacatGAGCTGATTGGTGTCGATGGCAACCAGATTAGAGCTGATTGGTGTCGATGGC<br>AACCAGATTAcagatctgtccagcagtcatttctc | SEQ_DUP; | 493 |
| | .........................1111111111111111111111111111111222222222222222222222<br>2222222222......................... | DUP_NUM; | |
| | A.....aB.aB..........a.a..aC..aa.A..aC.aA...I..aC...a.a..aC..aa.A..aC.aA...I.<br>.aC.....aC...A....A..A............ | Cas9_Wa; | |
| | ..........A.a..........Aa.a.....A..........a.J...A..Aa.........A..........a.<br>J...A..Aa......A...Ca...aa..A...a.. | Cas9_Cr; | |
| | ......................k..............................N....................N<br>.........N....................N.... | Cpf1_Wa; | |
| | ........................N..............................N....................<br>..................L........L.....L. | Cpf1_Cr; | |

TABLE 6-continued

| Selected Genes Having Microduplication Variants | | | |
|---|---|---|---|
| SYMBOL | MICRODUPLICATION INFORMATION | | SEQ ID NO: |
| LAMB3 | cttgccttcggtgtggtcccggcaaTTGTCACACACACCTCCATATGCCCCCTGGCTGGCGGCAAACACAGCGGGGT<br>CAAAGTGACATGTCTCTGAGTGCCCTTGTCACACACACCTCCATATGCCCCCTGGCTGGCGGCAAACACAGCGGGGT<br>CAAAGTGACATGTCTCTGAGTGCCCattgcagtcgcaccctggaaaaaga | SEQ_DUP; | 494 |
| | .........................1111111111111111111111111111111111111111111111111111<br>1111111111111111111111111222222222222222222222222222222222222222222222222222222<br>2222222222222222222222222......................... | DUP_NUM; | |
| | .....aa.a.aA....aA....a.J.J...............A......aA..aa.aAJ.......a.aaaA.....<br>a.a....A....Ha.a.A....a.J.J...............A......aA..aa.aAJ.......a.aaaA.....<br>a.a....A....Ha.a.A......A..a..A......aaB....aHa.A. | Cas9_Wa; | |
| | a...Ba...Aa.Ba.......Jaaa..A......a.a.a.a.aa.aa.....Aaaaa...A...A..A...A.a..A<br>.....a.......A....a.a......AaaJ...a.a.a.a.aa.aa.....Aaaaa...A...A..A...A.a..A<br>.....a.......A....a.a......AaaJ...A...a.a.aaaH.... | Cas9_Cr; | |
| | .....................N..N....NL.........L.......N..............L...M.........<br>................................................N..............L...M.........<br>.................................................N | Cpf1_Wa; | |
| | ..N..................M....................k..............k...................<br>.....................M....................k..............k...................<br>....................LLk........................... | Cpf1_Cr; | |

The +/−1 base differences in shifts between Watson and Crick tracks is so that cleavage positions are to the immediate left of the indicated base in both cases (which wouldn't be an issue if we were labelling the spaces between bases rather than the bases themselves).

The Cpf1 cleavage sites are staggered on the two strands, leaving an overhang in the double-stranded break, not indicated in these schematics The cleavage sites are labeled according to the Legend column in the table of PAM sequences below, Table 9 with an upper-case letter is it's the only matching PAM sequence, and a lower-case letter if it's the first of more-then-one matching PAM sequence.

Motifs are scanned for in flanking regions of size 50 and the table includes flanking regions of size 25, so cleavage sites should be shown even if the PAM site itself does not fall within the displayed sequence (as the distance between the cleavage site and the furthest position in the PAM site is no more than 25 bases). The above tracks, from top to bottom are shown for specific genes: See, Table 6

The variants identified in Table 6 with insertion lengths between 2 and 40 were then prioritized for therapeutic applications where the following microduplications were identified. See, Table 7. The headings of Table 7 are as follows:

Sequence ID: Arbitrary number assigned to each sequence.

VARIANT: of the form CHR-POS-REF-ALT, where CHR is the chromosome and POS is the start position of the reference (REF) allele in GRCh37, and ALT is the alternate allele; variants have been left-normalized with vt. genome.sph.umich.edu/wiki/Vt.

INSERT_LENGTH: length in nucleotides of the inserted sequence in the variant. (This is one less than the number of characters in ALT, as the first character of ALT is the REF base within the genome.)

ALLELE_ID: allele ID from the ClinVar VCF (version clinvar_20180225.vcf.gz)

GENE INFO: of the form SYMBOL:ENTREZID, from the ClinVar VCF. Note: some variants have more than one gene listed in GENEINFO, and this column just shows the first of them, in the interest of space.

CLNDN: the associated disease name from the Clin Var vcf; if there is more than one disease listed in the vcf just the first is shown here in the interest of space.

MAX_AF: allele frequency for the variant from the gnomAD genomes or exomes (version 2.0.2), whichever one is larger.

Microduplication Sequences: The information on potential CRISPR cut-sites that shows the duplicated sequence, the two copies are enclosed by square brackets and separated by a vertical bar, with 5 flanking bases on either side. A base is shown in lower case if there is a predicted CRISPR cleavage site immediately to the left of the base.

TABLE 7

Preferred Microduplication Sequences For Clinical Application

<table>
<tr><th>Seq ID</th><th>VARIANT (CHR-POS-REF-ALT)</th><th>INSERT_LENGTH</th><th>ALLELE_ID</th><th>GENE_INFO</th><th>CLNDN</th><th>MAX_AF</th><th>NNNNN[Duplication 1|Duplication 2]NNNNN lowercase = Cas9/Cpf1 cut site</th></tr>
<tr><td>Seq .ID. 1</td><td>4-3494833-A-AGCCT</td><td>4</td><td>16312</td><td>DOK7: 285489</td><td>Congenital myasthenic syndrome</td><td>0.0011653</td><td>GcTcA[gcCt|gCct]gCcaG (SEQ ID: 495)</td></tr>
<tr><td>Seq .ID. 2</td><td>9-126135887-T-TGGCGCGGCCCCGGCCC</td><td>16</td><td>178866</td><td>CRB2: 286204</td><td>Focal segmental glomeru-losclerosis 9</td><td>0.0009596</td><td>cccTt[ggcGCGGcccCGgccc|GgcgcgGcccCGgccc]Ggcgc (SEQ ID: 496)</td></tr>
<tr><td>Seq .ID. 3</td><td>15-72638920-G-GGATA</td><td>4</td><td>18928</td><td>HEXA: 3073</td><td>Tay-Sachs disease</td><td>0.0008041</td><td>catAg[gaTA|Gata]tACgG (SEQ ID: 497)</td></tr>
<tr><td>Seq ID. 4</td><td>2-1481219-A-ACGGC</td><td>4</td><td>421275</td><td>TPO: 7173</td><td>not provided</td><td>0.0006493</td><td>GGaga[CggC|CgGc]cgcgc (SEQ ID: 498)</td></tr>
<tr><td>Seq .ID. 5</td><td>19-47983175-G-GACCGACCACATCTGCAGA</td><td>18</td><td>106552</td><td>KPTN: 11133</td><td>Mental retardation, autosomal recessive 41</td><td>0.0005026</td><td>gcagg[AcCGACcaCatctgcaga|AcCGACcaCatctgCagA]AccTc (SEQ ID: 499)</td></tr>
<tr><td>Seq ID. 6</td><td>19-50365057-T-TGTTGTCGATGGCGACCC</td><td>17</td><td>19886</td><td>PNKP: 11284</td><td>Early infantile epileptic encephal-opathy 10</td><td>0.0002277</td><td>ttTGt[GTtgTcgAtggCGaCCc|GTtgtcgatGgCGaCCc]GTttc (SEQ ID: 500)</td></tr>
<tr><td>Seq .ID. 7</td><td>11-126144895-G-GGAGT</td><td>4</td><td>101651</td><td>FOXRED1: 55572</td><td>Mitochon-drial complex I deficiency</td><td>0.0002261</td><td>agagg[gAgt|gaGT]GGctT (SEQ ID: 501)</td></tr>
<tr><td>Seq .ID. 8</td><td>2-38298287-T-TGGTGGCATGA</td><td>10</td><td>79358</td><td>CYP1B1: 1545</td><td>Glaucoma, congenital</td><td>0.0002156</td><td>GcaGt[ggTGgCatGa|gGTGgcatgA]gGaAt (SEQ ID: 502)</td></tr>
<tr><td>Seq .ID. 9</td><td>1-158651385-G-GCAA</td><td>3</td><td>27886</td><td>SPTA1: 6708</td><td>Ellipto-cytosis 2</td><td>0.0001939</td><td>cGCag[cAa|Caa]CTggt (SEQ ID: 503)</td></tr>
</table>

TABLE 7-continued

Preferred Microduplication Sequences For Clinical Application

| Seq ID | VARIANT (CHR-POS-REF-ALT) | INSERT_LENGTH | ALLELE_ID | GENE_INFO | CLNDN | MAX_AF | NNNNN[Duplication 1\|Duplication 2]NNNNN lowercase = Cas9/Cpf1 cut site |
|---|---|---|---|---|---|---|---|
| Seq .ID. 10 | 6-158535858-A-AAGAT | 4 | 423256 | SERAC1: 84947 | 3-methyl-glutaconic aciduria with deafness, encephalopathy, and Leigh-like syndrome | 0.0001666 | aGaga[AgaT\|agat]aGCGA (SEQ ID: 504) |
| Seq .ID. 11 | 9-35658024-A-AGCTTCACAGAGTAGT | 15 | 29250 | RMRP: 6023 | Metaphyseal chondro-dysplasia, McKusick type | 0.0001567 | cctCA[gcttcAcAgaGtAGt\|GCTtcAcagagtAGT]ATTTt (SEQ ID: 505) |
| Seq .ID. 12 | 19-7620610-C-CGCCA | 4 | 21646 | PNPLA6: 10908 | Laurence-Moon syndrome | 0.0001307 | gcAGc[gccA\|gCca]Gccgc (SEQ ID: 506) |
| Seq .ID. 13 | 1-26126724-G-GGGCCGGGCCC | 10 | 190596 | SELENON: 57190 | Eichsfeld type congenital muscular dystrophy | 0.0001207 | ccaTG[ggcCGGgccC\|ggccgGgccC]ggccg (SEQ ID: 507) |
| Seq .ID. 14 | 19-47984017-C-CTA | 2 | 264742 | KPTN: 11133 | not provided | 0.0001056 | cTaCc[tA\|ta]ctggt (SEQ ID: 508) |
| Seq .ID. 15 | 6-1612016-C-CACGGCG | 6 | 136584 | FOXC1: 2296 | not provided | 0.0001046 | Gagtc[AcGGcg\|acggcg]gcggc (SEQ ID: 509) |
| Seq .ID. 16 | 7-107412534-C-CTGA | 3 | 70627 | SLC26A3: 1811 | Congenital secretory diarrhea, chloride type | 0.0000969 | gatcC[tga\|tga]tAAAT (SEQ ID: 510) |
| Seq .ID. 17 | 5-176942945-T-TCATC | 4 | 207209 | DDX41: 51428 | Acute myeloid leukemia | 0.0000853 | GGGGT[CaTC\|CaTc]atacg (SEQ ID: 511) |
| Seq .ID. 18 | 7-95751240-G-GCCCGGGCAGCCACCTGTAATCTC | 23 | 21042 | SLC25A13: 10165 | Citrullinemia type II | 0.0000853 | gcCAg[cccGggcaGCCaCCtgTaatCTc\|cccGggcagCcaCCtgTaatCTc]GtcTt (SEQ ID: 512) |
| Seq .ID. 19 | 17-37821635-G-GCGAGGTGT | 8 | 441954 | TCAP: 8557 | not provided | 0.0000813 | agcTg[cGagGtGt\|cGaGGtgt]cgGag (SEQ ID: 513) |
| Seq ID. 20 | 9-35658027-T-TTCACAGAGTA | 10 | 29249 | RMRP: 6023 | Meta-physeal chondro-dysplasia, McKusick type | 0.0000752 | CAgct[tcAcAgaGtA\|tcAcagaGtA]GTatT (SEQ ID: 514) |
| Seq .ID. 21 | 17-56283862-G-GTGCC | 4 | 71256 | MKS1: 54903 | Joubert syndrome | 0.0000732 | gAcAG[TgcC\|TgCc]tGtgg (SEQ ID: 515) |
| Seq .ID. 22 | 17-48245341-A-ACTCGG | 5 | 467925 | SGCA: 6442 | Limb-girdle muscular dystrophy, type 2D | 0.000069 | TACCa[cTcgg\|cTcgG]cagAg (SEQ ID: 516) |
| Seq .ID. 23 | 14-50100653-A-AGCCACGCAGGTATCGT | 16 | 205407 | DNAAF2: 55172 | Kartagener syndrome | 0.000065 | cccCA[gccacgcaGgtatCGT\|GccAcgcaGgtatcGT]Ggcct (SEQ ID: 517) |
| Seq .ID. 24 | 3-121514389-T-TCAAG | 4 | 393234 | IQCB1: 9657 | Nephron-ophthisis | 0.0000648 | TGAat[CAAg\|caag]catGC (SEQ ID: 518) |
| Seq .ID. 25 | 20-3199224-A-ACTCAGCAC | 8 | 214745 | ITPA: 3704 | Epileptic encephal-opathy, early infantile, 35 | 0.0000647 | tTgcA[cTCagcAc\|cTcAgcac]cGgGg (SEQ ID: 519) |

TABLE 7-continued

Preferred Microduplication Sequences For Clinical Application

| Seq ID | VARIANT (CHR-POS-REF-ALT) | INSERT_LENGTH | ALLELE_ID | GENE_INFO | CLNDN | MAX_AF | NNNNN[Duplication 1\|Duplication 2]NNNNN lowercase = Cas9/Cpf1 cut site |
|---|---|---|---|---|---|---|---|
| Seq .ID. 26 | 10-100183554-T-TGGGCCTCCCCTGCTGG | 16 | 20316 | HPS1: 3257 | Hermansky-Pudlak syndrome 1 | 0.0000647 | ggtgT[GGGCCTCccctgctgG\|GgGCCTCccctgctgG]GgGct (SEQ ID: 520) |
| Seq .ID. 27 | 6-135754331-A-AAC | 2 | 214240 | AHI1: 54806 | Joubert syndrome 3 | 0.0000646 | TGtaa[AC\|AC]aaaag (SEQ ID: 521) |
| Seq .ID. 28 | 1-216498866-G-GTGGC | 4 | 57777 | USH2A: 7399 | Retinitis pigmentosa | 0.0000646 | gcggg[tggC\|TgGC]tgcca (SEQ ID: 522) |
| Seq .ID. 29 | 18-21114427-C-CAAGT | 4 | 410327 | NPC1: 4864 | Niemann-Pick disease type C1 | 0.0000646 | tgGgC[AAgT\|aAGT]GCCTC (SEQ ID: 523) |
| Seq .ID. 30 | 9-35658027-T-TTCACAGA | 7 | 264540 | RMRP: 6023 | not provided | 0.0000646 | CAgct[tcacAga\|tcAcaga]GtAGT (SEQ ID: 524) |
| Seq .ID. 31 | 6-129571327-A-AACGTGTTC | 8 | 46903 | LAMA2: 3908 | Merosin deficient congenital muscular dystrophy | 0.0000646 | aCAgA[acGTGTtC\|aCGtgttC]tCCag (SEQ ID: 525) |
| Seq .ID. 32 | 11-94169012-T-TGAAGTGGTAGGAAAAATGTC | 20 | 150739 | MRE11: 4361 | Hereditary cancer-predisposing syndrome | 0.0000646 | TctTt[gaaGTggtAggAAaAAtgTc\|GaaGtggtAGGAAaAATGTC]TTCTt (SEQ ID: 526) |
| Seq .ID. 33 | 2-215595181-T-TCATACTTTTCTTCCTGTTCA | 20 | 133182 | BARD1: 580 | Hereditary cancer-predisposing syndrome | 0.0000609 | aaTTt[cATActTTTcTtcctGttcA\|cataCtTTTcttCctGttca]cAtaC (SEQ ID: 527) |
| Seq .ID. 34 | 17-33434458-T-TTA | 2 | 242729 | RAD51D: 5892 | Hereditary cancer-predisposing syndrome | 0.0000569 | caGTt[tA\|TA]tCAag (SEQ ID: 528) |
| Seq .ID. 35 | 19-1399807-T-TGGGGCCCAGTCCC | 13 | 23341 | GAMT: 2593 | Deficiency of guanidinoacetate methyl-transferase | 0.0000557 | Gccgt[gggGccCAgtccc\|GgggcCCAGtccc]GGagc (SEQ ID: 529) |
| Seq .ID. 36 | 11-95560975-T-TAGCCAATGTTC | 11 | 39648 | CEP57: 9702 | Mosaic variegated aneuploidy syndrome 2 | 0.0000528 | GTggt[AGCcAATgtTC\|AGCcaAtgttc]AgCtt (SEQ ID: 530) |
| Seq .ID. 37 | 6-112390619-T-TAC | 2 | 21424 | WISP3: 8838 | Progressive pseudo-rheumatoid dysplasia | 0.0000488 | CAAgT[aC\|ac]Tcaga (SEQ ID: 531) |
| Seq .ID. 38 | 2-241808397-G-GCA | 2 | 200432 | AGXT: 189 | Primary hyper-oxaluria, type I | 0.0000411 | cAtgg[cA\|Ca]gccgg (SEQ ID: 532) |
| Seq .ID. 39 | 7-107335062-G-GCAGT | 4 | 52676 | SLC26A4: 5172 | Pendred's syndrome | 0.0000407 | ctTgG[cAgT\|CagT]CgGtc (SEQ ID: 533) |
| Seq .ID. 40 | 5-131705914-T-TACCGGCTCGCC | 11 | 47395 | SLC22A5: 6584 | Renal carnitine transport defect | 0.0000385 | CCgct[acCggCtcGCc\|acCggCtcGCc]Accat (SEQ ID: 534) |
| Seq .ID. 41 | 22-26860623-T-TCTCCTTCCTGCCATCTGGACAAGC | 24 | 19168 | HPS4: 89781 | Hermansky-Pudlak syndrome 4 | 0.0000366 | cCgTt[ctcCttCctGccatCtgGacAaGc\|cTCcttCctGccatCtgGacAAGc]tTCgt (SEQ ID: 535) |
| Seq .ID. 42 | 5-54529099-C-CGGGCA | 5 | 143224 | CCNO: 10309 | Primary ciliary dyskinesia | 0.0000351 | Gggcc[Gggca\|Gggca]gGGgG (SEQ ID: 536) |
| Seq .ID. 43 | 4-6290805-A-AGGGCCGTCGCGAGGCT | 16 | 19558 | WFS1: 7466 | Diabetes mellitus AND insipidus with optic atrophy AND deafness | 0.000035 | aagcA[GgGccGtCgcGAggcT\|GgGccGtCgcGAgGct]GtGaa (SEQ ID: 537) |

TABLE 7-continued

Preferred Microduplication Sequences For Clinical Application

| Seq ID | VARIANT (CHR-POS-REF-ALT) | INSERT_LENGTH | ALLELE_ID | GENE_INFO | CLNDN | MAX_AF | NNNNN[Duplication 1\|Duplication 2]NNNNN lowercase = Cas9/Cpf1 cut site |
|---|---|---|---|---|---|---|---|
| Seq .ID. 44 | 9-35658017-C-CGTCCTCAGCTTCACAGA | 17 | 29253 | RMRP: 6023 | Metaphyseal chondro-dysplasia, McKusick type | 0.0000327 | accAC[GtcctCAgcttcAcAga\|GtCcTCagcTtcAcaga]GtAGT (SEQ ID: 538) |
| Seq .ID. 45 | 1-76226858-G-GCTAGAATGAGTTA | 13 | 18626 | ACADM: 34 | Medium-chain acyl-coenzyme A dehydro-genase deficiency | 0.0000325 | acTag[ctagAaTGAGTta\|ctagAaTgAGTTa]CcAgA (SEQ ID: 539) |
| Seq .ID. 46 | 5-147466073-T-TGTGC | 4 | 406655 | SPINK5: 11005 | not provided | 0.0000324 | Cagat[gTgC\|GTGc]acTgt (SEQ ID: 540) |
| Seq .ID. 47 | 6-31085224-G-GAGGC | 4 | 167426 | CDSN: 1041 | Peeling skin syndrome | 0.0000324 | cagtg[aggC\|Aggc]aGGgg (SEQ ID: 541) |
| Seq .ID. 48 | 5-54529084-C-CGGGCT | 5 | 143228 | CCNO: 10309 | Primary ciliary dyskinesia | 0.0000324 | Gccac[Gggct\|GggcT]GggcC (SEQ ID: 542) |
| Seq .ID. 49 | 2-219646907-T-TGGCTGCGCTG | 10 | 264076 | CYP27A1: 1593 | not provided | 0.0000324 | cccAT[ggctGcgcTG\|gGcTGcgcTG]gGcTg (SEQ ID: 543) |
| Seq .ID. 50 | 22-37260985-A-AAAGGAGGATC | 10 | 224721 | NCF4: 4689 | Chronic granulo-matous disease | 0.0000324 | GACaa[aaggAGGAtc\|aaggaGgATc]CAAgt (SEQ ID: 544) |
| Seq ID. 51 | 1-154960775-G-GGC | 2 | 226515 | FLAD1: 80308 | Glutaric aciduria, type 2 | 0.0000323 | ttgag[Gc\|Gc]aGtGg (SEQ ID: 545) |
| Seq .ID. 52 | 2-228566952-A-ATC | 2 | 353889 | SLC19A3: 80704 | Basal ganglia disease, biotin-responsive | 0.0000323 | TCtCA[Tc\|tc]AtgGa (SEQ ID: 546) |
| Seq .ID. 53 | 8-74888632-C-CGT | 2 | 200167 | TMEM70: 54968 | not provided | 0.0000323 | CgGgc[gT\|GT]cCtCC (SEQ ID: 547) |
| Seq .ID. 54 | 2-152364571-A-AAAAC | 4 | 29086 | NEB: 4703 | Nemaline myopathy 2 | 0.0000323 | gTCCA[AAac\|aaAc]aGtCt (SEQ ID: 548) |
| Seq .ID. 55 | 4-15575920-C-CTGGT | 4 | 214183 | CC2D2A: 57545 | Joubert syndrome 9 | 0.0000323 | CCagc[tggT\|tgGt]tcctG (SEQ ID: 549) |
| Seq .ID. 56 | 6-129835627-T-TCAAA | 4 | 98901 | LAMA2: 3908 | Merosin deficient congenital muscular dystrophy | 0.0000323 | aaGAt[cAAA\|caAA]caCCg (SEQ ID: 550) |
| Seq .ID. 57 | 6-158538811-C-CAGAT | 4 | 211210 | SERAC1: 84947 | not provided | 0.0000323 | tCcac[AgaT\|aGAT]ATAat (SEQ ID: 551) |
| Seq .ID. 58 | 12-123738316-T-TATCC | 4 | 211578 | C12orf65: 91574 | not provided | 0.0000323 | TtGtT[ATcC\|ATcc]ccagg (SEQ ID: 552) |
| Seq .ID. 59 | 13-20763209-G-GCGTT | 4 | 186855 | GJB2: 2706 | Deafness, autosomal recessive 1A | 0.0000323 | cCaGg[cgTT\|cgTt]gcACt (SEQ ID: 553) |
| Seq .ID. 60 | 13-32972540-C-CATTT | 4 | 180697 | BRCA2: 675 | Hereditary cancer-predisposing syndrome | 0.0000323 | aAggC[ATtT\|aTtT]CAGcc (SEQ ID: 554) |
| Seq .ID. 61 | 2-48033707-T-TAATCTCCC | 8 | 94955 | MSH6: 2956 | Lynch syndrome | 0.0000323 | TTgCt[aATcTCCc\|aatctccc]agagg (SEQ ID: 555) |
| Seq .ID. 62 | 12-124171469-G-GCTCTGCTC | 8 | 462224 | TCTN2: 79867 | Meckel-Gruber syndrome | 0.0000323 | aTCAG[ctcTGcTc\|cTcTgcTc]tgcTg (SEQ ID: 556) |

TABLE 7-continued

Preferred Microduplication Sequences For Clinical Application

| Seq ID | VARIANT (CHR-POS-REF-ALT) | INSERT_LENGTH | ALLELE_ID | GENE_INFO | CLNDN | MAX_AF | NNNNN[Duplication 1\|Duplication 2]NNNNN lowercase = Cas9/Cpf1 cut site |
|---|---|---|---|---|---|---|---|
| Seq .ID. 63 | 15-44867171-C-CTTCCAGGTTA | 10 | 465073 | SPG11: 80208 | Spastic paraplegia 11, autosomal recessive | 0.0000323 | agCAc[TtcCaGgtta\|TtccAGgttA]GTTac (SEQ ID: 557) |
| Seq .ID. 64 | 17-41246723-G-GCCACATGGCT | 10 | 70390 | BRCA1: 672 | Hereditary cancer-predisposing syndrome | 0.0000323 | [TGTG[CCacAtggcT\|CCacatgGcT]cCacA (SEQ ID: 558) |
| Seq .ID. 65 | 11-76867001-T-TCCATCTACTCG | 11 | 408477 | MYO7A: 4647 | not provided | 0.0000323 | gCTCT[CcAtCtaCtcG\|CcAtctaCtcg]CcAga (SEQ ID: 559) |
| Seq .ID. 66 | 17-4804916-G-GAGAGCTGCGGAGCC | 14 | 468369 | CHRNE: 1145 | Myasthenic syndrome, congenital, 4a, slow-channel | 0.0000323 | gTctg[AgaGctgcGgAgcc\|aGagctGcGgAgcc]aGggc (SEQ ID: 560) |
| Seq .ID. 67 | 7-117188810-A-AAGAT | 4 | 186745 | CFTR: 1080 | Cystic fibrosis | 0.0000294 | ctgaa[agat\|aGAT]ATTAA (SEQ ID: 561) |
| Seq .ID. 68 | 5-148407494-A-AGGCC | 4 | 244469 | SH3TC2: 79628 | not provided | 0.0000244 | aggCa[ggCc\|GgCc]agcag (SEQ ID: 562) |
| Seq .ID. 69 | 10-104590547-G-GGGAT | 4 | 16816 | CYP17A1: 1586 | Congenital adrenal hyperplasia | 0.0000214 | cttgg[ggaT\|gGAT]GCCTt (SEQ ID: 563) |
| Seq .ID. 70 | 20-400315-C-CGACGAGG | 7 | 150333 | RBCK1: 10616 | Polyglucosan body myopathy 1 with or without immuno-deficiency | 0.0000213 | AgCcc[GacgaGg\|gacGagG]aGgAg (SEQ ID: 564) |
| Seq .ID. 71 | 1-94508433-G-GAC | 2 | 359278 | ABCA4: 24 | Stargardt disease 1 | 0.0000203 | aACCg[Ac\|ac]aGcTt (SEQ ID: 565) |
| Seq .ID. 72 | 2-73635784-T-TAGTA | 4 | 393242 | ALMS1: 7840 | Alstrom syndrome | 0.0000203 | CagAT[agTA\|aGTA]TatcA (SEQ ID: 566) |
| Seq .ID. 73 | 2-74185326-A-ATGAT | 4 | 23194 | DGUOK: 1716 | Mitochon-drial DNA-depletion syndrome 3, hepa-tocerebral | 0.0000203 | aatga[TgaT\|TgAT]TttTc (SEQ ID: 567) |
| Seq .ID. 74 | 17-4805917-A-AGTGAG | 5 | 422179 | CHRNE: 1145 | not provided | 0.0000203 | taCcA[gtgaG\|gtgaG]atGAG (SEQ ID: 568) |
| Seq .ID. 75 | 5-176813493-G-GGATCCTGGTGACCGTGCTGGT | 21 | 27972 | SLC34A1: 6569 | Fanconi renotubular syndrome 2 | 0.0000203 | gtgGG[GAtcCtGgtgacCGtgctgGT\|gAtcCtGgtgacCGtgctGGt]gcAga (SEQ ID: 569) |
| Seq .ID. 76 | 22-29115401-A-ATGAT | 4 | 185622 | CHEK2: 11200 | Hereditary cancer-predisposing syndrome | 0.000018 | TGacA[tgat\|tgat]GTAtT (SEQ ID: 570) |
| Seq .ID. 77 | 2-48033769-A-ATCAG | 4 | 94970 | MSH6: 2956 | Hereditary nonpoly-posis colon cancer | 0.0000166 | ATGAa[TCAg\|TcaG]tcact (SEQ ID: 571) |
| Seq .ID. 78 | 17-33903147-A-AAGGC | 4 | 358425 | PEX12: 5193 | Infantile Refsum's disease | 0.0000163 | GgatA[AggC\|AGGC]aACAc (SEQ ID: 572) |
| Seq .ID. 79 | 17-41244495-T-TTCTCA | 5 | 69430 | BRCA1: 672 | Hereditary cancer-predisposing syndrome | 0.0000163 | aATgt[TCTCA\|tcTcA]ttTcc (SEQ ID: 573) |

TABLE 7-continued

Preferred Microduplication Sequences For Clinical Application

| Seq ID | VARIANT (CHR-POS-REF-ALT) | INSERT_LENGTH | ALLELE_ID | GENE_INFO | CLNDN | MAX_AF | NNNNN[Duplication 1\|Duplication 2]NNNNN lowercase = Cas9/Cpf1 cut site |
|---|---|---|---|---|---|---|---|
| Seq .ID. 80 | 9-35658012-A-AACCACGTCCTCAGCTTC | 17 | 29260 | RMRP: 6023 | Metaphyseal chondro-dysplasia, McKusick type | 0.0000162 | cacGA[accACGtcctCAgcttC\|AcCacGtcctCagcTtc]Acaga (SEQ ID: 574) |
| Seq .ID. 81 | 12-32902980-A-ACTCCTGATCAGACATGAC | 18 | 414707 | YARS2: 51067 | Mitochon-drial diseases | 0.0000162 | TtTaa[CtcCTgatcAGacaTGAc\|CtcCtgatcAGacaTGAc]CtCca (SEQ ID: 575) |
| Seq .ID. 82 | 11-17470110-T-TGAGCTGATTGGTGTCGATGGCAACCAGATTA | 31 | 429214 | ABCC8: 6833 | Persistent hyperin-sulinemic hypo-glycemia of infancy | 0.0000162 | CaCat[gagCTgaTtGGtgTcgATGgCaacCaGatta\|gagCTgaTtGGtgTcgATGgcaacCaGAtta]CAGaT (SEQ ID: 576) |
| Seq .ID. 83 | 16-1841827-C-CGCGCAGGCT | 0 9 | 23168 | IGFALS: 3483 | Acid-labile subunit deficiency | 0.0000142 | AgCtc[Gcgcaggct\|gcgcAggCt]GcccA (SEQ ID: 577) |
| Seq ID. 84 | 15-40268931-G-GCACT | 4 | 414416 | EIF2AK4: 440275 | Familial pulmonary capillary hemangi-omatosis | 0.0000134 | tGGAG[CACT\|Cact]tcggg (SEQ ID: 578) |
| Seq .ID. 85 | 6-38850803-T-TAG | 2 | 456184 | DNAH8: 1769 | Primary ciliary dyskinesia | 0.0000128 | [Tgat[Ag\|Ag]aCACc (SEQ ID: 579) |
| Seq .ID. 86 | 9-21971020-A-AGAC | 3 | 182930 | CDKN2A: 1029 | Hereditary cancer-predisposing syndrome | 0.0000128 | GggCa[GAc\|gAC]GgCcc (SEQ ID: 580) |
| Seq .ID. 87 | 2-234669554-G-GCAGC | 4 | 428001 | UGT1A: 7361 | Crigler-Najjar syndrome | 0.0000122 | tCctG[cagc\|cagC]ggGtg (SEQ ID: 581) |
| Seq .ID. 88 | 1-5935033-T-TGGAGC | 5 | 101577 | NPHP4: 261734 | not provided | 0.0000122 | GgcGt[GgaGc\|GgAgc]gTGTg (SEQ ID: 582) |
| Seq .ID. 89 | 7-92134156-A-ATCCACACTG | 9 | 99009 | PEX1: 5189 | not provided | 0.0000122 | CtGCa[tCCacactg\|tCcAcActG]cctct (SEQ ID: 583) |
| Seq .ID. 90 | 11-17452431-A-AGAGGGAGAGGGAGGC | 15 | 214503 | ABCC8: 6833 | not provided | 0.0000122 | Tggaa[gAgggagAggGaGgc\|gAgggagAggGAGgc]aAAGg (SEQ ID: 584) |
| Seq ID. 91 | 2-152354227-T-TAACA | 4 | 448783 | NEB: 4703 | Nemaline myopathy 2 | 0.0000106 | tgtat[aAcA\|AACa]CcTgt (SEQ ID: 585) |
| Seq .ID. 92 | 19-47258867-C-CGGGA | 4 | 267103 | FKRP: 79147 | Congenital muscular dystrophy-dystro-glycanopathy (with or without mental retardation) type B5 | 0.0000088 | GgtgC[ggga\|gGGa]gTtcG (SEQ ID: 586) |
| Seq ID. 93 | 4-995488-C-CCTGCT | 5 | 26960 | IDUA: 3425 | Mucopoly-saccha-ridosis type I | 0.0000088 | GaTgc[CTGct\|cTgct]cggaG (SEQ ID: 587) |
| Seq .ID. 94 | 5-176831303-C-CGGAGGCGCCGCCTGGGTT | 18 | 390679 | F12: 2161 | Hereditary angione-urotic edema with normal C1 esterase inhibitor activity | 0.0000087 | gggtc[gGaGgcGCcgcctgggtt\|gGaGGcGCcgcctgggtt]GgGgt (SEQ ID: 588) |

TABLE 7-continued

Preferred Microduplication Sequences For Clinical Application

| Seq ID | VARIANT (CHR-POS-REF-ALT) | INSERT_LENGTH | ALLELE_ID | GENE_INFO | CLNDN | MAX_AF | NNNNN[Duplication 1\|Duplication 2]NNNNN lowercase = Cas9/Cpf1 cut site |
|---|---|---|---|---|---|---|---|
| Seq .ID. 95 | 2-179442173-G-GGTAT | 4 | 391746 | TTN: 7273 | Limb-girdle muscular dystrophy, type 2J | 0.0000082 | caaTG[gTAT\|GTAT]CcCct (SEQ ID: 589) |
| Seq .ID. 96 | 12-109998851-T-TCGGCCCGGCGGCACA | 15 | 200227 | MMAB: 326625 | not provided | 0.0000082 | tCtcT[CggcCcgGcggCacA\|CggcCcgGcggCacA]CggcC (SEQ ID: 590) |
| Seq .ID. 97 | 17-41244840-C-CAT | 2 | 46039 | BRCA1: 672 | Hereditary cancer-predisposing syndrome | 0.0000081 | TtcaC[at\|aT]tCaAa (SEQ ID: 591) |
| Seq .ID. 98 | 3-48508650-G-GTGA | 3 | 19220 | TREX1: 11277 | Aicardi Goutieres syndrome 1 | 0.0000081 | gAggG[tgA\|tGA]TGtcC (SEQ ID: 592) |
| Seq .ID. 99 | 2-26415259-C-CTGAT | 4 | 199995 | HADHA: 3030 | not provided | 0.0000081 | cctcc[tgat\|tgaT]aGAtg (SEQ ID: 593) |
| Seq .ID. 100 | 2-148696793-C-CTGTT | 4 | 39252 | ORC4: 5000 | Meier-Gorlin syndrome 2 | 0.0000081 | GatGc[TgtT\|tgTT]acTcg (SEQ ID: 594) |
| Seq .ID. 101 | 3-48508676-T-TGTCA | 4 | 131925 | TREX1: 11277 | Aicardi Goutieres syndrome 1 | 0.0000081 | catCT[gTca\|gTca]GtGgA (SEQ ID: 595) |
| Seq .ID. 102 | 8-55537899-G-GTGAA | 4 | 21010 | RP1: 6101 | Retinitis pigmentosa 1 | 0.0000081 | tataG[Tgaa\|tgAA]gaaaG (SEQ ID: 596) |
| Seq .ID. 103 | 11-108119732-T-TACAG | 4 | 264571 | ATM: 472 | Ataxia-telangiec-tasia syndrome | 0.0000081 | tgaTt[ACag\|AcaG]TGtCc (SEQ ID: 597) |
| Seq .ID. 104 | 15-44876096-G-GCAGATCCTCC | 10 | 409235 | SPG11: 80208 | Spastic paraplegia 11, autosomal recessive | 0.0000081 | ggGtg[CAGATcCTcc\|cagatcCTCc]atact (SEQ ID: 598) |
| Seq .ID. 105 | 19-55673062-G-GGCGTC | 5 | 404089 | DNAAF3: 352909 | Primary ciliary dyskinesia | 0.0000076 | gccgg[gcgtC\|GcGTc]Gtagc (SEQ ID: 599) |
| Seq .ID. 106 | 19-50364929-G-GCGGCT | 5 | 203579 | PNKP: 11284 | Early infantile epileptic encephal-opathy 10 | 0.0000071 | gCccg[CggcT\|cggct]cGGgc (SEQ ID: 600) |
| Seq .ID. 107 | 13-32911149-A-ATG | 2 | 248942 | BRCA2: 675 | Breast-ovarian cancer, familial 2 | 0.0000044 | gacaa[tg\|tG]AGAAT (SEQ ID: 601) |
| Seq .ID. 108 | 13-32912466-C-CTGCT | 4 | 66246 | BRCA2: 675 | Hereditary cancer-predisposing syndrome | 0.0000044 | tatAC[TgCt\|tgCt]gCCag (SEQ ID: 602) |
| Seq .ID. 109 | 7-65551736-C-CCGTGGCACTGACCCGAGACTCTGAG | 25 | 200151 | ASL: 435 | not provided | 0.0000044 | CacGc[cGtGgcACtgaCcCGAgactcTgag\|cgTGGcACTGaCcCGAgactctgaG]cgGCt (SEQ ID: 603) |
| Seq .ID. 110 | 17-4802524-C-CTCAAACA | 7 | 467870 | CHRNE: 1145 | Myasthenic syndrome, congenital, 4a, slow-channel | 0.0000043 | gcCcC[TcaaaCa\|TCAaaca]CGAgC (SEQ ID: 604) |
| Seq .ID. 111 | 19-2251669-G-GAGCTCAGCGTAGACCTCCGCGCC | 23 | 23664 | AMH: 268 | Persistent mullerian duct syndrome, type I | 0.0000043 | gcgcG[AgctcAGcGtAGaCcTcCgcgcc\|AgctcAGcGtAGaCcTcCgcGcc]gagcg (SEQ ID: 605) |
| Seq .ID. 112 | 14-77757715-G-GGT | 2 | 266684 | POMT2: 29954 | Congenital muscular dystrophy-dystro- | 0.0000042 | aaTag[gt\|gt]GGTga (SEQ ID: 606) |

TABLE 7-continued

<table>
<tr><th colspan="8">Preferred Microduplication Sequences For Clinical Application</th></tr>
<tr><th>Seq ID</th><th>VARIANT (CHR-POS-REF-ALT)</th><th>INSERT_LENGTH</th><th>ALLELE_ID</th><th>GENE_INFO</th><th>CLNDN</th><th>MAX_AF</th><th>NNNNN[Duplication 1|Duplication 2]NNNNN lowercase = Cas9/Cpf1 cut site</th></tr>
<tr><td></td><td></td><td></td><td></td><td></td><td>glycanopathy with brain and eye anomalies, type A2</td><td></td><td></td></tr>
<tr><td>Seq .ID. 113</td><td>17-41242962-T-TGA</td><td>2</td><td>69791</td><td>BRCA1: 672</td><td>Hereditary cancer-predisposing syndrome</td><td>0.0000042</td><td>taccT[gA|ga]GTGGt (SEQ ID: 607)</td></tr>
<tr><td>Seq .ID. 114</td><td>2-48026541-G-GGT</td><td>2</td><td>94667</td><td>MSH6: 2956</td><td>Hereditary nonpoly-posis colon cancer</td><td>0.0000041</td><td>ccCtg[gt|gt]gCaga (SEQ ID: 608)</td></tr>
<tr><td>Seq .ID. 115</td><td>5-13793822-C-CTA</td><td>2</td><td>395008</td><td>DNAH5: 1767</td><td>Primary ciliary dyskinesia</td><td>0.0000041</td><td>CgcAC[tA|tA]tctca (SEQ ID: 609)</td></tr>
<tr><td>Seq .ID. 116</td><td>7-117243689-G-GGA</td><td>2</td><td>68231</td><td>CFTR: 1080</td><td>Cystic fibrosis</td><td>0.0000041</td><td>cgtgG[gA|ga]gTagC (SEQ ID: 610)</td></tr>
<tr><td>Seq .ID. 117</td><td>16-23647131-T-TCG</td><td>2</td><td>478268</td><td>PALB2: 79728</td><td>Hereditary cancer-predisposing syndrome</td><td>0.0000041</td><td>GTagt[CG|CG]ccCtg (SEQ ID: 611)</td></tr>
<tr><td>Seq .ID. 118</td><td>17-41245704-G-GAC</td><td>2</td><td>249143</td><td>BRCA1: 672</td><td>Breast-ovarian cancer, familial 1</td><td>0.0000041</td><td>aGAAG[AC|AC]TTcCt (SEQ ID: 612)</td></tr>
<tr><td>Seq .ID. 119</td><td>2-26502064-C-CCGCT</td><td>4</td><td>425487</td><td>HADHB: 3032</td><td>not provided</td><td>0.0000041</td><td>CtgGC[cgCT|cgCt]gcctT (SEQ ID: 613)</td></tr>
<tr><td>Seq .ID. 120</td><td>2-48030716-T-TAATG</td><td>4</td><td>214607</td><td>MSH6: 2956</td><td>Hereditary nonpoly-posis colon cancer</td><td>0.0000041</td><td>TTCct[aatg|AATg]aCATT (SEQ ID: 614)</td></tr>
<tr><td>Seq .ID. 121</td><td>2-48032775-T-TTGAA</td><td>4</td><td>451638</td><td>MSH6: 2956</td><td>Hereditary nonpoly-posis colon cancer</td><td>0.0000041</td><td>tttgt[tgaA|TgAA]tTaaG (SEQ ID: 615)</td></tr>
<tr><td>Seq .ID. 122</td><td>2-48033355-C-CAACA</td><td>4</td><td>419562</td><td>MSH6: 2956</td><td>Hereditary cancer-predisposing syndrome</td><td>0.0000041</td><td>ACTgC[AaCa|aACa]tTtga (SEQ ID: 616)</td></tr>
<tr><td>Seq .ID. 123</td><td>2-48033448-C-CATTA</td><td>4</td><td>231582</td><td>MSH6: 2956</td><td>Hereditary cancer-predisposing syndrome</td><td>0.0000041</td><td>caTTc[aTTa|atta]gTagA (SEQ ID: 617)</td></tr>
<tr><td>Seq .ID. 124</td><td>2-48033767-G-GAATC</td><td>4</td><td>182191</td><td>MSH6: 2956</td><td>Hereditary nonpoly-posis colon cancer</td><td>0.0000041</td><td>agATG[AATC|AaTc]aGtca (SEQ ID: 618)</td></tr>
<tr><td>Seq .ID. 125</td><td>2-215646137-A-ACTTT</td><td>4</td><td>232427</td><td>BARD1: 580</td><td>Hereditary cancer-predisposing syndrome</td><td>0.0000041</td><td>TcTGA[cttT|ctTT]ctTAc (SEQ ID: 619)</td></tr>
<tr><td>Seq .ID. 126</td><td>3-48626421-C-CTCAG</td><td>4</td><td>411522</td><td>COL7A1: 1294</td><td>Recessive dystrophic epiderm-olysis bullosa</td><td>0.0000041</td><td>Caggc[tCAg|tcaG]Gggct (SEQ ID: 620)</td></tr>
<tr><td>Seq .ID. 127</td><td>4-6302429-C-CTGAT</td><td>4</td><td>211040</td><td>WFS1: 7466</td><td>not provided</td><td>0.0000041</td><td>GTacC[Tgat|tgaT]TGacA (SEQ ID: 621)</td></tr>
<tr><td>Seq .ID. 128</td><td>9-6553398-G-GGAAC</td><td>4</td><td>266395</td><td>GLDC: 2731</td><td>Non-ketotic hyper-glycinemia</td><td>0.0000041</td><td>agatG[gaAC|GaaC]tGGAg (SEQ ID: 622)</td></tr>
</table>

TABLE 7-continued

<table>
<tr><th colspan="8">Preferred Microduplication Sequences For Clinical Application</th></tr>
<tr><th>Seq ID</th><th>VARIANT (CHR-POS-REF-ALT)</th><th>INSERT_LENGTH</th><th>ALLELE_ID</th><th>GENE_INFO</th><th>CLNDN</th><th>MAX_AF</th><th>NNNNN[Duplication 1|Duplication 2]NNNNN lowercase = Cas9/Cpf1 cut site</th></tr>
<tr><td>Seq .ID. 129</td><td>9-36246039-C-CGAAT</td><td>4</td><td>265527</td><td>GNE: 10020</td><td>Inclusion body myopathy 2</td><td>0.0000041</td><td>catgc[gaAT|gaAt]GATGC (SEQ ID: 623)</td></tr>
<tr><td>Seq ID. 130</td><td>19-11222244-A-AGGGT</td><td>4</td><td>228160</td><td>LDLR: 3949</td><td>Familial hyper-cholesterol-emia</td><td>0.0000041</td><td>ctgga[gggT|ggGT]ggCTa (SEQ ID: 624)</td></tr>
<tr><td>Seq .ID. 131</td><td>11-47367805-A-ATGCCG</td><td>5</td><td>178182</td><td>MYBPC3: 4607</td><td>Cardio-myopathy</td><td>0.0000041</td><td>tAgCA[tGccG|tGccG]cgcaG (SEQ ID: 625)</td></tr>
<tr><td>Seq .ID. 132</td><td>1-45798772-C-CATCCAT</td><td>6</td><td>232268</td><td>MUTYH: 4595</td><td>Hereditary cancer-predisposing syndrome</td><td>0.0000041</td><td>CctgC[atcCaT|atccat]ccggt (SEQ ID: 626)</td></tr>
<tr><td>Seq .ID. 133</td><td>5-131726404-T-TTTGGGC</td><td>6</td><td>359651</td><td>SLC22A5: 6584</td><td>not provided</td><td>0.0000041</td><td>ctAtt[tTGGgc|tTgggC][TtCg (SEQ ID: 627)</td></tr>
<tr><td>Seq .ID. 134</td><td>20-25288616-G-GGCTCTTA</td><td>7</td><td>15065</td><td>ABHD12: 26090</td><td>Polyneuro-pathy, hearing loss, ataxia, retinitis pigmentosa, and cataract</td><td>0.0000041</td><td>ggATG[GCTctta|GcTcTTa]gcTtc (SEQ ID: 628)</td></tr>
<tr><td>Seq .ID. 135</td><td>13-32918751-C-CAAGAAAAA</td><td>8</td><td>262824</td><td>BRCA2: 675</td><td>Breast-ovarian cancer, familial 2</td><td>0.0000041</td><td>AAAtc[aAgaaAaa|AaGAAAAA]TCCTt (SEQ ID: 629)</td></tr>
<tr><td>Seq .ID. 136</td><td>19-11216255-A-AAATCTGAC</td><td>8</td><td>245718</td><td>LDLR: 3949</td><td>Familial hyper-cholesterol-emia</td><td>0.0000041</td><td>GGaca[AaTcTGAc|aaTctGac]gAGga (SEQ ID: 630)</td></tr>
<tr><td>Seq .ID. 137</td><td>11-2591894-G-GTGGTCCGCCTC</td><td>11</td><td>247639</td><td>KCNQ1: 3784</td><td>Long QT syndrome 1</td><td>0.0000041</td><td>gtacG[TGgtcCgcctc|TggTcCGCctc]tggTc (SEQ ID: 631)</td></tr>
<tr><td>Seq .ID. 138</td><td>16-23641191-G-GAGCAAGTTGGGGTGTGC</td><td>17</td><td>244957</td><td>PALB2: 79728</td><td>Hereditary cancer-predisposing syndrome</td><td>0.0000041</td><td>aAatg[AgCAagttGgGgTGtgc|AgCAagttGgGgtGtGC]AgCAa (SEQ ID: 632)</td></tr>
<tr><td>Seq .ID. 139</td><td>19-11216242-C-CGACTGCAAGGACAAATCT</td><td>18</td><td>18772</td><td>LDLR: 3949</td><td>Familial hyper-cholesterol-emia</td><td>0.0000041</td><td>GccCC[gactgcAaGgaCAAaTcT|gActgcaaGGaCAAaTct]GacgA (SEQ ID: 633)</td></tr>
<tr><td>Seq .ID. 140</td><td>2-48033727-T-TTCAAAAGGGACATAGAAAA</td><td>19</td><td>94960</td><td>MSH6: 2956</td><td>Hereditary nonpoly-posis colon cancer</td><td>0.0000041</td><td>GTTaT[tCaaaagggacaTaGaAAA|tCaaaagGGacaTaGaAAa]gcaaG (SEQ ID: 634)</td></tr>
<tr><td>Seq .ID. 141</td><td>14-51411077-G-GCTGATCTGCCGCCGCTTCTC</td><td>20</td><td>187131</td><td>PYGL: 5836</td><td>Glycogen storage disease, type VI</td><td>0.0000041</td><td>ggatg[cTGaTctGCcgCCgcTtctc|CtgatctGCcgCCgcTtctc]Ctggt (SEQ ID: 635)</td></tr>
<tr><td>Seq .ID. 142</td><td>12-33030862-G-GCGCTCTCCTCCCGCTGGAATCCA</td><td>23</td><td>398966</td><td>PKP2: 5318</td><td>Arrhythmo-genic right ventricular cardio-myopathy, type 9</td><td>0.0000041</td><td>aagTg[CGCTCtCctcCcgctggaatcCA|CgctctCctcCcgctggAaTccA]cggcg (SEQ ID: 636)</td></tr>
<tr><td>Seq .ID. 143</td><td>18-43493697-C-CAGAGTTTATCACCAATTCCCCTTCAATA</td><td>28</td><td>469361</td><td>EPG5: 57724</td><td>Absent corpus callosum cataract immuno-deficiency</td><td>0.0000041</td><td>Aaagc[AGAgtttATCACCaaTtcCCcttcaaTa|aGagTTtATCaccaaTtcCCCttcaaTa]aCtct (SEQ ID: 637)</td></tr>
</table>

As noted earlier there are over 2000 duplications annotated as pathogenic in ClinVar that do not appear in gnomAD at all, and hence are not listed in table 6 above, but may nonetheless be promising candidates for MMEJ. In particular the developers of gnomAD have "made every effort to exclude individuals with severe pediatric diseases from the gnomAD data set" (gnomad.broadinstitute.org/faq), and because of this, allele frequencies for dominant diseases in particular may be underestimated in gnomAD, or the variants may be entirely absent. To illustrate some of the potential MMEJ candidates of this sort, in Table 8 below we list those duplications of length 4-20 that satisfy all of the conditions from column dup2iP from Table 4 except they are absent from gnomAD, and for which the OMIM ID associated with the Clin Var entry in listed as having an autosomal dominant mode of inheritance. The columns are the same as for Table 7, although the MAX_AF column is excluded, as these variants do not appear in gnomAD.

TABLE 8

Additonal Microduplication Sequences Associated with Autosomal Dominant Diseases

| Sequence ID | VARIANT | INS_LEN | ALLELEID | GENE INFO | CLNDN | NNNNN[Duplication 1\|Duplication 2]NNNNN lowercase = Cas9/Cpf1 cut site |
|---|---|---|---|---|---|---|
| B1-638 | 1-149898309-T-TTGGG | 4 | 205400 | SF3B4: 10262 | Nager syndrome | Aggat[Tggg\|TgGGJagcag (SEQ ID: 810) |
| B2-639 | 2-16082251-A-ACTCG | 4 | 426707 | MYCN: 4613 | Feingold syndrome 1 | TtTGa[CTCg\|CtCg]ctAca (SEQ ID: 811) |
| B3-640 | 2-48033635-T-TATTA | 4 | 94949 | MSH6: 2956 | Hereditary nonpolyposis colon cancer | agAcT[ATTa\|AtTa]CGtTC (SEQ ID: 812) |
| B4-641 | 2-145156539-T-TGGAG | 4 | 442547 | ZEB2: 9839 | Mowat-Wilson syndrome | GttAt[ggAg\|GGaG]TCcaT (SEQ ID: 813) |
| B5-642 | 2-145156576-A-AGAGT | 4 | 101526 | ZEB2: 9839 | Mowat-Wilson syndrome | atAaa[gAgT\|GAGT]Ctttt (SEQ ID: 814) |
| B6-643 | 2-166848432-T-TGACC | 4 | 187710 | SCN1A: 6323 | Severe myoclonic epilepsy in infancy | agGat[gACC\|gAcc]gcGat (SEQ ID: 815) |
| B7-644 | 2-166848788-G-GACAT | 4 | 187727 | SCN1A: 6323 | Severe myoclonic epilepsy in infancy | aaGGG[ACAT\|aCaT]CAtca (SEQ ID: 816) |
| B8-645 | 2-166897853-G-GGGTC | 4 | 187812 | SCN1A: 6323 | Severe myoclonic epilepsy in infancy | aaaTg[ggTC\|GgTC]cATCa (SEQ ID: 817) |
| B9-646 | 3-128200679-A-AGAGG | 4 | 213545 | GATA2: 2624 | Lymphedema, primary, with myelodysplasia | TaGta[gAgg\|GAgG]CcaCa (SEQ ID: 818) |
| B10-647 | 3-128200780-G-GCGGC | 4 | 227183 | GATA2: 2624 | Dendritic cell, monocyte, B lymphocyte, and natural killer lymphocyte deficiency | tctgG[cggC\|CgGC]cgact (SEQ ID: 819) |
| B11-648 | 5-36985675-C-CTGAA | 4 | 207223 | NIPBL: 25836 | Cornelia de Lange syndrome 1 | cgagC[tgaA\|tGaA]GCCTt (SEQ ID: 820) |
| B12-649 | 5-37019478-C-CACTG | 4 | 207238 | NIPBL: 25836 | Cornelia de Lange syndrome 1 | AAAAc[ACTg\|actg]AgacT (SEQ ID: 821) |
| B13-650 | 5-37045600-T-TCTAA | 4 | 428429 | NIPBL: 25836 | Cornelia de Lange syndrome 1 | cAcTt[cTaA\|ctAA]CaAAc (SEQ ID: 822) |
| B14-651 | 5-112173974-T-TCAGC | 4 | 453932 | APC: 324 | Familial adenomatous polyposis 1 | AGTgt[CAgc\|cagc]caTtc (SEQ ID: 823) |
| B15-652 | 5-176696704-A-ATGAC | 4 | 207196 | NSD1: 64324 | Sotos syndrome 1 | TCtaa[tgAC\|TGAC]taTtt (SEQ ID: 824) |
| B16-653 | 6-7578754-A-AGGTT | 4 | 456063 | DSP: 1832 | Arrhythmogenic right ventricular cardiomyopathy, type 8 | TtaCa[ggtt\|GGTT]CtTaa (SEQ ID: 825) |
| B17-654 | 6-42689651-T-TAGTA | 4 | 28213 | PRPH2: 5961 | Patterned dystrophy of retinal pigment epithelium | cCggt[agTA\|AGTA]CTtCA (SEQ ID: 826) |
| B18-655 | 7-155604807-G-GCAGC | 4 | 76761 | SHH: 6469 | Holoprosencephaly 3 | gccag[Cagc\|CaGC]agCAt (SEQ ID: 827) |
| B19-656 | 9-135779065-T-TGCTG | 4 | 459513 | TSC1: 7248 | Tuberous sclerosis 1 | gagct[gCtg\|Gctg]ctttG (SEQ ID: 828) |
| B20-657 | 10-76789950-G-GCCAA | 4 | 39483 | KAT6B: 23522 | Young Simpson syndrome | caACG[cCAa\|ccaA]catTG (SEQ ID: 829) |
| B21-658 | 10-88678975-C-CTATT | 4 | 397998 | BMPRIA: 657 | Juvenile polyposis syndrome | AGcTc[tAtT\|tatt]tgaTt (SEQ ID: 830) |

TABLE 8-continued

Additonal Microduplication Sequences Associated with Autosomal Dominant Diseases

| Sequence ID | VARIANT | INS_LEN | ALLELEID | GENE INFO | CLNDN | NNNNN[Duplication 1\|Duplication 2]NNNNN lowercase = Cas9/Cpf1 cut site |
|---|---|---|---|---|---|---|
| B22-659 | 11-31823171-C-CAAAG | 4 | 424532 | PAX6: 5080 | Aniridia 1 | CAagc[aAAg\|aAag]Atgg a (SEQ ID: 831) |
| B23-660 | 11-31823224-G-GGAGT | 4 | 485944 | PAX6: 5080 | Aniridia 1 | ttCtg[gagT\|GaGt]CGCtA (SEQ ID: 832) |
| B24-661 | 11-44129659-C-CTGCT | 4 | 264541 | EXT2: 2132 | Multiple exostoses type 2 | TGaAC[tgCT\|tgCt]cATg G (SEQ ID: 833) |
| B25-662 | 11-47372123-C-CTCAG | 4 | 248635 | MYBPC3: 4607 | Familial hypertrophic cardiomyopathy 4 | TggCc[TcAg\|tcag]cagGg (SEQ ID: 834) |
| B26-663 | 12-32977056-T-TCATC | 4 | 399705 | PKP2: 5318 | Arrhythmogenic right ventricular cardiomyopathy, type 9 | cTtCt[cAtc\|caTc]gcttt (SEQ ID: 835) |
| B27-664 | 12-114832576-A-AAACG | 4 | 462429 | TBX5: 6910 | Aortic valve disease 2 | ctaTa[aACg\|AAcg]CAGt c (SEQ ID: 836) |
| B28-665 | 13-32900728-C-CCTTA | 4 | 66682 | BRCA2: 675 | Breast-ovarian cancer, familial 2 | CcaCc[ctta\|ctta]GttCt (SEQ ID: 837) |
| B29-666 | 13-32903617-T-TGATA | 4 | 180558 | BRCA2: 675 | Familial cancer of breast | Ctcat[gatA\|GATA]CtACt (SEQ ID: 838) |
| B30-667 | 13-32906470-G-GTCAA | 4 | 234629 | BRCA2: 675 | Hereditary cancer-predisposing syndrome | gAAAG[TCaA\|Tcaa]tgcC a (SEQ ID: 839) |
| B31-668 | 13-32906777-G-GTACC | 4 | 183659 | BRCA2: 675 | Hereditary cancer-predisposing syndrome | aGTTG[taCC\|tACc]gTctt (SEQ ID: 840) |
| B32-669 | 13-32907062-G-GCAGT | 4 | 261077 | BRCA2: 675 | Hereditary breast and ovarian cancer syndrome | tcttG[cagt\|caGt] AaagC (SEQ ID: 841) |
| B33-670 | 13-32910470-A-ACTAG | 4 | 261113 | BRCA2: 675 | Breast-ovarian cancer, familial 2 | cTtAa[cTAg\|CtAG]ctCtt (SEQ ID: 842) |
| B34-671 | 13-32913932-G-GTGAC | 4 | 261296 | BRCA2: 675 | Breast-ovarian cancer, familial 2 | aCtTG[TgAc\|TGaC]taGct (SEQ ID: 843) |
| B35-672 | 13-32914339-T-TGTTA | 4 | 66619 | BRCA2: 675 | Hereditary cancer-predisposing syndrome | GtgAT[gttA\|gTTA]gttTG (SEQ ID: 844) |
| B36-673 | 13-32914758-A-AGCAT | 4 | 180628 | BRCA2: 675 | Familial cancer of breast | acTGa[gcAT\|gcaT]AgtC T (SEQ ID: 845) |
| B37-674 | 13-32914858-G-GGAAA | 4 | 183912 | BRCA2: 675 | Hereditary cancer-predisposing syndrome | aaatG[gaaA\|GAAa]AAaC C (SEQ ID: 846) |
| B38-675 | 13-32929209-G-GTTCC | 4 | 261402 | BRCA2: 675 | Breast-ovarian cancer, familial 2 | CTTTG[[TCC\|TTcc]aCctt (SEQ ID: 847) |
| B39-676 | 13-32936669-T-TGACA | 4 | 131698 | BRCA2: 675 | Hereditary breast and ovarian cancer syndrome | Tgtgt[gaCa\|GaCa]ctcca (SEQ ID: 848) |
| B40-677 | 13-32936731-G-GGATC | 4 | 261438 | BRCA2: 675 | Breast-ovarian cancer, familial 2 | agaTg[gaTC\|GaTc]atatg (SEQ ID: 849) |
| B41-678 | 13-32937507-A-ATGGG | 4 | 67186 | BRCA2: 675 | Breast-ovarian cancer, familial 2 | acaga[tggg\|Tggg]TGgTA (SEQ ID: 850) |
| B42-679 | 13-32944599-C-CCTAG | 4 | 261474 | BRCA2: 675 | Breast-ovarian cancer, familial 2 | tgacc[CTAg\|ctaG]AccTT (SEQ ID: 851) |
| B43-680 | 13-32950917-G-GCTTA | 4 | 131727 | BRCA2: 675 | Hereditary cancer-predisposing syndrome | ccCAG[ctta\|ctTA]ccttg (SEQ ID: 852) |
| B44-681 | 14-95577661-G-GGGTA | 4 | 463789 | DICER1: 23405 | DICER 1-related pleuropulmonary blastoma cancer predisposition syndrome | ttttg[ggTA\|ggta]GcACT (SEQ ID: 853) |
| B45-682 | 16-2121893-C-CTACT | 4 | 27434 | TSC2: 7249 | Tuberous sclerosis syndrome | TGccC[TAct\|taCt]cCCtG (SEQ ID: 854) |

TABLE 8-continued

<table>
<tr><th colspan="7">Additonal Microduplication Sequences Associated with Autosomal Dominant Diseases</th></tr>
<tr><th>Sequence<br>ID</th><th>VARIANT</th><th>INS_LEN</th><th>ALLELEID</th><th>GENE<br>INFO</th><th>CLNDN</th><th>NNNNN[Duplication<br>1|Duplication 2]NNNNN<br>lowercase = Cas9/Cpf1<br>cut site</th></tr>
<tr><td>B46-<br>683</td><td>16-23637659-A-<br>ACAAC</td><td>4</td><td>180720</td><td>PALB2:<br>79728</td><td>Hereditary cancer-predisposing<br>syndrome</td><td>CTTta[cAAc|CaaC]cgGC<br>t (SEQ ID: 855)</td></tr>
<tr><td>B47-<br>684</td><td>17-29559831-A-<br>ACTGT</td><td>4</td><td>425126</td><td>NF1:<br>4763</td><td>Neurofibromatosis, type 1</td><td>aGgca[CTgt|ctgt]AcGGT<br>(SEQ ID: 856)</td></tr>
<tr><td>B48-<br>685</td><td>17-29657434-T-<br>TATTA</td><td>4</td><td>401825</td><td>NF1:<br>4763</td><td>Neurofibromatosis, type 1</td><td>TCTCT[AtTalaTtA]gTA<br>Ag (SEQ ID: 857)</td></tr>
<tr><td>B49-<br>686</td><td>17-42426621-G-<br>GCTGC</td><td>4</td><td>31049</td><td>GRN:<br>2896</td><td>Frontotemporal dementia,<br>ubiquitin-positive</td><td>gcCtG[CtgC|Ctgc]ctGGa<br>(SEQ ID: 858)</td></tr>
<tr><td>B50-<br>687</td><td>17-59763312-T-<br>TGATA</td><td>4</td><td>402202</td><td>BRIP1:<br>83990</td><td>Familial cancer of breast</td><td>Ctggt[gaTA|gata]GATga<br>(SEQ ID: 859)</td></tr>
<tr><td>B51-<br>688</td><td>18-48586254-T-<br>TTGCA</td><td>4</td><td>36159</td><td>SMAD4:<br>4089</td><td>Juvenile polyposis syndrome</td><td>GagCT[tgCa|TgCa]TtccA<br>(SEQ ID: 860)</td></tr>
<tr><td>B52-<br>689</td><td>19-11200255-A-<br>ACCGT</td><td>4</td><td>245343</td><td>LDLR:<br>3949</td><td>Familial hypercholesterolemia</td><td>CTGgA[cCgT|CcgT]Cgc<br>CT (SEQ ID: 861)</td></tr>
<tr><td>B53-<br>690</td><td>19-11216012-C-<br>CCGGT</td><td>4</td><td>245559</td><td>LDLR:<br>3949</td><td>Familial hypercholesterolemia</td><td>ctgcc[cggt|cgGT]GcTCa<br>(SEQ ID: 862)</td></tr>
<tr><td>B54-<br>691</td><td>19-11218164-G-<br>GGTCA</td><td>4</td><td>245855</td><td>LDLR:<br>3949</td><td>Familial hypercholesterolemia</td><td>gacTg[gTcA|gtCa]gATg<br>A (SEQ ID: 863)</td></tr>
<tr><td>B55-<br>692</td><td>19-11222196-A-<br>ATGAG</td><td>4</td><td>245974</td><td>LDLR:<br>3949</td><td>Familial hypercholesterolemia</td><td>atcGa[tgag|TgAG]tgtca<br>(SEQ ID: 864)</td></tr>
<tr><td>B56-<br>693</td><td>19-11222247-G-<br>GTGGC</td><td>4</td><td>245999</td><td>LDLR:<br>3949</td><td>Familial hypercholesterolemia</td><td>gaggG[TggC|TggC]taCaa<br>(SEQ ID: 865)</td></tr>
<tr><td>B57-<br>694</td><td>19-11224220-T-<br>TGACA</td><td>4</td><td>228168</td><td>LDLR:<br>3949</td><td>Familial hypercholesterolemia</td><td>agctt[gAcA|gAca]GAGcc<br>(SEQ ID: 866)</td></tr>
<tr><td>B58-<br>695</td><td>19-11224266-G-<br>GACAT</td><td>4</td><td>246144</td><td>LDLR:<br>3949</td><td>Familial hypercholesterolemia</td><td>cagaG[aCaT|ACat]cCagg<br>(SEQ ID: 867)</td></tr>
<tr><td>B59-<br>696</td><td>19-11226884-C-<br>CCTAG</td><td>4</td><td>246281</td><td>LDLR:<br>3949</td><td>Familial hypercholesterolemia</td><td>TCAcc[ctAg|ctaG]gtATg<br>(SEQ ID: 868)</td></tr>
<tr><td>B60-<br>697</td><td>19-11231165-C-<br>CTGCT</td><td>4</td><td>246517</td><td>LDLR:<br>3949</td><td>Familial hypercholesterolemia</td><td>CatGC[tgCT|tgCt]GgccA<br>(SEQ ID: 869)</td></tr>
<tr><td>B61-<br>698</td><td>19-11233960-C-<br>CGGCT</td><td>4</td><td>390629</td><td>LDLR:<br>3949</td><td>Familial hypercholesterolemia</td><td>CtcCc[ggct|gGCt]gcctG<br>(SEQ ID: 870)</td></tr>
<tr><td>B62-<br>699</td><td>19-11240244-T-<br>TAAGA</td><td>4</td><td>18744</td><td>LDLR:<br>3949</td><td>Familial hypercholesterolemia</td><td>ggctt[aagalaAGA]ACaTC<br>(SEQ ID: 871)</td></tr>
<tr><td>B63-<br>700</td><td>22-24133984-G-<br>GAGAT</td><td>4</td><td>469954</td><td>SMARCB1:<br>6598</td><td>Rhabdoid tumor predisposition<br>syndrome 1</td><td>acaag[Agat|aGAT]ACcC<br>C (SEQ ID: 872)</td></tr>
<tr><td>B64-<br>701</td><td>22-29121073-C-<br>CTTCT</td><td>4</td><td>222871</td><td>CHEK2:<br>11200</td><td>Familial cancer of breast</td><td>tGaTC[[TCt|ttct]AtgtA<br>(SEQ ID: 873)</td></tr>
<tr><td>B65-<br>702</td><td>22-29130554-G-<br>GGACT</td><td>4</td><td>471012</td><td>CHEK2:<br>11200</td><td>Familial cancer of breast</td><td>gaGAG[gACT|gaCt]ggCt<br>G (SEQ ID: 874)</td></tr>
<tr><td>B66-<br>703</td><td>22-29886645-A-<br>AAGCC</td><td>4</td><td>227465</td><td>NEFH:<br>4744</td><td>Charcot-Marie-Tooth disease,<br>axonal, type 2CC</td><td>CAgCa[agCc|aGCc]tccag<br>(SEQ ID: 875)</td></tr>
<tr><td>B67-<br>704</td><td>22-41572424-C-<br>CATGT</td><td>4</td><td>247756</td><td>EP300:<br>2033</td><td>Rubinstein-Taybi syndrome 2</td><td>ccacC[atgt|aTGT]gCAtg<br>(SEQ ID: 876)</td></tr>
<tr><td>B68-<br>705</td><td>1-153800743-G-<br>GACATC</td><td>5</td><td>423707</td><td>GATAD2B:<br>57459</td><td>Mental retardation, autosomal<br>dominant 18</td><td>cCAGG[acATC|acAtc]At<br>Ctc (SEQ ID: 877)</td></tr>
<tr><td>B69-<br>706</td><td>1-155317481-T-<br>TCCTTG</td><td>5</td><td>440033</td><td>ASH1L:<br>55870</td><td>MENTAL RETARDATION,<br>AUTOSOMAL DOMINANT 52</td><td>tTCat[cctTg|ccttg]tagAG<br>(SEQ ID: 878)</td></tr>
</table>

TABLE 8-continued

| Sequence ID | VARIANT | INS_LEN | ALLELEID | GENE INFO | CLNDN | NNNNN[Duplication 1\|Duplication 2]NNNNN lowercase = Cas9/Cpf1 cut site |
|---|---|---|---|---|---|---|
| Additonal Microduplication Sequences Associated with Autosomal Dominant Diseases | | | | | | |
| B70-707 | 2-166848901-A-ATACTT | 5 | 187732 | SCN1A: 6323 | Severe myoclonic epilepsy in infancy | CGAaA[tACTt\|TAcTT]T tcTa (SEQ ID: 879) |
| B71-708 | 3-39453229-G-GGTCAT | 5 | 75607 | RPSA: 3921 | Asplenia, isolated congenital | gggaG[GtcaT\|GtcAT]gcc TG (SEQ ID: 880) |
| B72-709 | 3-136162210-A-ATAAAC | 5 | 431522 | STAG1: 10274 | STAG1-related disorder | TCcca[TaaaC\|tAaac]TGT Cc (SEQ ID: 881) |
| B73-710 | 3-181430665-A-ATGATG | 5 | 272798 | SOX2: 6657 | Microphthalmia syndromic 3 | CAgcA[tGatG\|tGAtg]CA GGa (SEQ ID: 882) |
| B74-711 | 5-86682703-T-TTTTTA | 5 | 239865 | RASA1: 5921 | Capillary malformation-arteriovenous malformation | CATGt[[TTTA\|TttTa]gA TgA (SEQ ID: 883) |
| B75-712 | 8-116617181-A-AATCTG | 5 | 432085 | TRPS1: 7227 | Trichorhinophalangeal dysplasia type I | tggcA[atctG\|atctG]gtgtt (SEQ ID: 884) |
| B76-713 | 11-2797207-C-CGATGT | 5 | 442554 | KCNQ1: 3784 | Long QT syndrome 1 | Cttac[gatGt\|GaTgt]gCGg G (SEQ ID: 885) |
| B77-714 | 11-31811508-A-ACATAT | 5 | 191325 | PAX6: 5080 | Aniridia 1 | TgAGA[CAtat\|cAtat]caG Gt (SEQ ID: 886) |
| B78-715 | 11-31812376-G-GGAGTA | 5 | 461519 | PAX6: 5080 | Aniridia 1 | tgCaG[gagtA\|GagTa]tGa gG (SEQ ID: 887) |
| B79-716 | 11-64577297-G-GGCGGT | 5 | 398421 | MEN1: 4221 | Multiple endocrine neoplasia, type 1 | tcTgg[gcGgt\|GcgGt]Gaag c (SEQ ID: 888) |
| B80-717 | 13-32900712-T-TAGCTA | 5 | 261019 | BRCA2: 675 | Breast-ovarian cancer, familial 2 | tCtTT[agctA\|AGctA]CAc CA (SEQ ID: 889) |
| B81-718 | 13-32932021-T-TCATAC | 5 | 261432 | BRCA2: 675 | Breast-ovarian cancer, familial 2 | TGGCt[cataC\|cATAc]cc TCc (SEQ ID: 890) |
| B82-719 | 15-48718033-A-ATCGTG | 5 | 400146 | FBN1: 2200 | Marfan syndrome | aaAca[tCGtg\|tcGtG]Aata A (SEQ ID: 891) |
| B83-720 | 17-29653013-T-TACGAC | 5 | 467484 | NF1: 4763 | Neurofibromatosis, type 1 | Tgctt[ACgaC\|acGac]AaC gt (SEQ ID: 892) |
| B84-721 | 17-48264062-G-GCTGCC | 5 | 413977 | COL1A1: 1277 | Osteogenesis imperfecta type I | tGcgG[cTgcC\|cTGcc]ctct g (SEQ ID: 893) |
| B85-722 | 19-11216237-G-GGCCCC | 5 | 245693 | LDLR: 3949 | Familial hypercholesterolemia | tggTG[GccCC\|Gcccc]gac tg (SEQ ID: 894) |
| B86-723 | 19-11224008-T-TGGACC | 5 | 246065 | LDLR: 3949 | Familial hypercholesterolemia | AcgCT[GgacC\|Ggacc]gg agc (SEQ ID: 895) |
| B87-724 | 19-11230868-C-CAGAGG | 5 | 246422 | LDLR: 3949 | Familial hypercholesterolemia | TCcCc[agagg\|agAGG]at ATG (SEQ ID: 896) |
| B88-725 | 19-11230879-G-GTTCTC | 5 | 246429 | LDLR: 3949 | Familial hypercholesterolemia | tATGG[TTCTC\|Ttctc]Ttc Ca (SEQ ID: 897) |
| B89-726 | 19-11233887-C-CGTCAG | 5 | 390628 | LDLR: 3949 | Familial hypercholesterolemia | CcaCc[gtcag\|gtcAG]GCta A (SEQ ID: 898) |
| B90-727 | 19-13136144-A-AAGATC | 5 | 205791 | NFIX: 4784 | Sotos syndrome 2 | gGgcA[AGatC\|AGatc]cg gcg (SEQ ID: 899) |
| B91-728 | 20-62044881-T-TAGGGC | 5 | 361908 | KCNQ2: 3785 | Benign familial neonatal seizures 1 | Gtcgt[AGggc\|AGgGc]cg CAg (SEQ ID: 900) |
| B92-729 | 2-239757079-G-GAGCGCC | 6 | 204358 | TWIST2: 117581 | Barber-Say syndrome | gCgCg[AgCgcc\|Agcgcc] AgCgc (SEQ ID: 901) |
| B93-730 | 9-140056954-C-CCGGCAT | 6 | 384406 | GRIN1: 2902 | Mental retardation, autosomal dominant 8 | aactc[Cggcat\|CGgcat]cgg gg (SEQ ID: 902) |

TABLE 8-continued

Additonal Microduplication Sequences Associated with Autosomal Dominant Diseases

| Sequence ID | VARIANT | INS_LEN | ALLELEID | GENE INFO | CLNDN | NNNNN[Duplication 1\|Duplication 2]NNNNN lowercase = Cas9/Cpf1 cut site |
|---|---|---|---|---|---|---|
| B94-731 | 10-102510456-A-ACGAGAC | 6 | 28839 | PAX2: 5076 | Renal coloboma syndrome | TacTa[CgagAc\|cgAgac]C gGCa (SEQ ID: 903) |
| B95-732 | 3-123383092-T-TCGCTTTC | 7 | 259621 | MYLK: 4638 | Visceral myopathy | gtgCT[CGCtttc\|cgCtttc]c TGga (SEQ ID: 904) |
| B96-733 | 6-7580155-G-GGAAAATC | 7 | 197069 | DSP: 1832 | Arrhythmogenic right ventricular cardiomyopathy, type 8 | caaGg[gaAaaTc\|gaAaatc] gAgat (SEQ ID: 905) |
| B97-734 | 13-32937340-C-CAGAAGAT | 7 | 67137 | BRCA2: 675 | Breast-ovarian cancer, familial 2 | GAagC[agAAgaT\|agaAg at]cGGCt (SEQ ID: 906) |
| B98-735 | 13-32968822-C-CTAGGACT | 7 | 262861 | BRCA2: 675 | Breast-ovarian cancer, familial 2 | CATtc[taGgact\|TAGgaC T]Tgccc (SEQ ID: 907) |
| B99-736 | 16-2142114-T-TCGTAATC | 7 | 442559 | PKD1: 5310 | Polycystic kidney disease, adult type | aAcgt[CGtaatC\|CGTaatc] gCtgg (SEQ ID: 908) |
| B100-737 | 17-7578448-G-GCCATGGC | 7 | 27419 | TP53: 7157 | Osteosarcoma | gATGG[ccATGgc\|ccAtg gc]GCgga (SEQ ID: 909) |
| B101-738 | 17-48273539-C-CACCATCA | 7 | 414018 | COL1A1: 1277 | Osteogenesis imperfecta type I | gTagC[ACCAtCa\|aCcaT Ca]tTtcC (SEQ ID: 910) |
| B102-739 | 18-48575180-G-GTGTCTGT | 7 | 36142 | SMAD4: 4089 | Juvenile polyposis syndrome | gataG[TgTCtGT\|Tgtctgt] GtGAA (SEQ ID: 911) |
| B103-740 | 19-11213391-G-GCTGCATT | 7 | 362671 | LDLR: 3949 | Familial hypercholesterolemia | aAccg[CtgcAtT\|CtGCatt] CcTCa (SEQ ID: 912) |
| B104-741 | 19-11216256-A-AATCTGAC | 7 | 245719 | LDLR: 3949 | Familial hypercholesterolemia | GacAA[aTcTGAc\|aTCtga c]gAGGa (SEQ ID: 913) |
| B105-742 | 19-11231163-T-TGCTGCTG | 7 | 246518 | LDLR: 3949 | Familial hypercholesterolemia | ggCat[GCtgCTg\|GCtgCT g]gccAG (SEQ ID: 914) |
| B106-743 | 22-32200157-T-TGGATTTG | 7 | 259349 | DEPDC5: 9681 | Epilepsy, familial focal, with variable foci 1 | ggtgT[GgatttG\|gGatTtG]g TgTg (SEQ ID: 915) |
| B107-744 | 2-166848493-G-GAAAATTCC | 8 | 187713 | SCN1 A: 6323 | Severe myoclonic epilepsy in infancy | aaaAg[AAAATTCC\|AAa atTCCJaacag (SEQ ID: 916) |
| B108-745 | 6-33405537-C-CCTGGATGA | 8 | 456125 | SYNGAP1: 8831 | Mental retardation, autosomal dominant 5 | TCtgc[ctgGatga\|cTgGAt Ga]CAtgc (SEQ ID: 917) |
| B109-746 | 8-61728946-C-CTCTTATCT | 8 | 207553 | CHD7: 55636 | CHARGE association | tcaGC[tcTTatcT\|TCttAtc T]TcatT (SEQ ID: 918) |
| B110-747 | 8-116427276-C-CGTTGTTTT | 8 | 432065 | TRPS1: 7227 | Trichorhinophalangeal dysplasia type I | tcAcc[GtTgtTTt\|GtTGtT TT]GTtta (SEQ ID: 919) |
| B111-748 | 11-64572225-C-CCCACGGCT | 8 | 419786 | MEN1: 4221 | Multiple endocrine neoplasia, type 1 | tCgcc[ccAcggct\|ccAcGgc t]ccTcG (SEQ ID: 920) |
| B112-749 | 13-32914325-A-ATATCACCT | 8 | 261315 | BRCA2: 675 | Breast-ovarian cancer, familial 2 | tAAaa[TATCaCCt\|tatcAc Ct]tGtga (SEQ ID: 921) |
| B113-750 | 13-32915019-A-ACATTCATG | 8 | 261369 | BRCA2: 675 | Hereditary breast and ovarian cancer syndrome | GAGAA[cattCaTg\|cattCa TG]ttttG (SEQ ID: 922) |
| B114-751 | 16-23619228-C-CGCTGAGAG | 8 | 465434 | PALB2: 79728 | Familial cancer of breast | ccCac[gctgaGag\|gcTgAG aG]TCGtc (SEQ ID: 923) |
| B115-752 | 16-23634319-T-TACTTGTTG | 8 | 465443 | PALB2: 79728 | Familial cancer of breast | ctTCT[acttGTtG\|aCTtgTt GJatCag (SEQ ID: 924) |
| B116-753 | 17-17118378-C-CAATCTTAT | 8 | 467434 | FLCN: 201163 | Multiple fibrofolliculomas | GCTtc[aaTctTat\|aATcTT at]tcAgg (SEQ ID: 925) |

TABLE 8-continued

| Additonal Microduplication Sequences Associated with Autosomal Dominant Diseases | | | | | | |
|---|---|---|---|---|---|---|
| Sequence ID | VARIANT | INS_LEN | ALLELEID | GENE INFO | CLNDN | NNNNN[Duplication 1\|Duplication 2]NNNNN lowercase = Cas9/Cpf1 cut site |
| B117-754 | 19-1220430-A-AAGGACATC | 8 | 469353 | STK11: 6794 | Peutz-Jeghers syndrome | gCacA[AggacatC\|AgGacAtCJAagcc (SEQ ID: 926) |
| B118-755 | 19-11216107-T-TGGCTCGGA | 8 | 245617 | LDLR: 3949 | Familial hypercholesterolemia | aagaT[GgcTcgGa\|ggctcgGa]TgaGT (SEQ ID: 927) |
| B119-756 | 19-11221433-A-AGCGAAGAT | 8 | 245939 | LDLR: 3949 | Familial hypercholesterolemia | Gccca[GcgaaGat\|gcgAaGat]GcgAa (SEQ ID: 928) |
| B120-757 | 19-11226844-C-CGCTGGTGA | 8 | 246266 | LDLR: 3949 | Familial hypercholesterolemia | tactc[gCtGgtga\|gCtGGTga]CTGAA (SEQ ID: 929) |
| B121-758 | 19-42794719-G-GCAAGAGAC | 8 | 424692 | CIC: 23152 | MENTAL RETARDATION, AUTOSOMAL DOMINANT 45 | cggcg[caAgAgAc\|CaAGagac]ccgAa (SEQ ID: 930) |
| B122-759 | 7-142458427-A-ATGACAAGAT | 9 | 46926 | PRSS1: 5644 | Hereditary pancreatitis | gAtGa[TgacAAgAt\|TgacaAgAt]cgttg (SEQ ID: 931) |
| B123-760 | 10-43607601-T-TGGAGTGTGA | 9 | 28980 | RET: 5979 | Familial medullary thyroid carcinoma | CggCt[ggAgTgtGa\|GgAgTgtGa]GgAgt (SEQ ID: 932) |
| B124-761 | 10-43609946-T-TGTGCCGCAC | 9 | 36267 | RET: 5979 | Multiple endocrine neoplasia, type 2a | GaGct[GtGcCgcac\|gtgCcgcAc]gGtga (SEQ ID: 933) |
| B125-762 | 17-42992481-A-AGCCGCAGCT | 9 | 188181 | GFAP: 2670 | Alexander's disease | ccGca[gccgCagct\|gCcgCAgct]cTcgC (SEQ ID: 934) |
| B126-763 | 5-176673777-A-AAAGAGATTCC | 10 | 207192 | NSD1: 64324 | Sotos syndrome 1 | GTcaa[aagAGATtcC\|aagagATtcCJAGgct (SEQ ID: 935) |
| B127-764 | 10-76789773-A-AGCTGCAGCAT | 10 | 47605 | KAT6B: 23522 | Young Simpson syndrome | CggGa[gCtGCAgcat\|GCtGCAgCAt]GCtGC (SEQ ID: 936) |
| B128-765 | 13-48835344-C-CTTTAATTTGT | 10 | 21019 | ITM2B: 9445 | Dementia, familial Danish | gaAaC[TTTaaTTTGT\|ttTAaTTTGT]tcTTg (SEQ ID: 937) |
| B129-766 | 17-42328803-A-ACATCTGGGTG | 10 | 32797 | SLC4A1: 6521 | Spherocytosis type 4 | GgGCa[catcTgGgtG\|catctgggtG]atact (SEQ ID: 938) |
| B130-767 | 19-11218087-C-CAACAAGTTCA | 10 | 434258 | LDLR: 3949 | Familial hypercholesterolemia | gACcC[AacaagTtCA\|AacaaGTtCa]AGtgT (SEQ ID: 939) |
| B131-768 | 3-138664603-T-TGGCCCGGCGGC | 11 | 354105 | FOXL2: 668 | Blepharophimosis, ptosis, and epicanthus inversus | GagcT[GgcccgGcggC\|GgcCcgGcggc]GgcGc (SEQ ID: 940) |
| B132-769 | 8-61742962-G-GAAGAAACTATT | 11 | 481218 | CHD7: 55636 | CHARGE association | caaag[aAGAaaCTAtt\|aAGAaACtATtJaTtGA (SEQ ID: 941) |
| B133-770 | 8-61777949-T-TAACCCTCTGTC | 11 | 194201 | CHD7: 55636 | CHARGE association | TgAAT[aACCctCtgtc\|aacCcTctgtc]aGCTg (SEQ ID: 942) |
| B134-771 | 19-11216021-A-ACCTGTGGTCCC | 11 | 434823 | LDLR: 3949 | Familial hypercholesterolemia | gcTCa[CctgtggTCCc\|CctgtggtCCC]gCcag (SEQ ID: 943) |

TABLE 8-continued

Additonal Microduplication Sequences Associated with Autosomal Dominant Diseases

| Sequence ID | VARIANT | INS_LEN | ALLELEID | GENE INFO | CLNDN | NNNNN[Duplication 1\|Duplication 2]NNNNN lowercase = Cas9/Cpf1 cut site |
|---|---|---|---|---|---|---|
| B135-772 | 19-11216250-A-AGGACAAATCTG | 11 | 245708 | LDLR: 3949 | Familial hypercholesterolemia | tgcAa[GGaCAAatcTG\|GgaCAaaTctGJacgAG (SEQ ID: 944) |
| B136-773 | 10-43609939-G-GACGAGCTGTGCC | 12 | 36265 | RET: 79 | Multiple endocrine neoplasia, type 2a | gtgcG[aCGaGctGTGcC\|acGagctGtGcC]gcAcg (SEQ ID: 945) |
| B137-774 | 19-11227654-T-TTCTCCTTGGCCG | 12 | 424332 | LDLR: 3949 | Familial hypercholesterolemia | CcccT[tctccttggcCG\|TCtccTtggccG]Tcttt (SEQ ID: 946) |
| B138-775 | 15-73617341-T-TGGTGAGCACGCTG | 13 | 361763 | HCN4: 10021 | Sick sinus syndrome 2, autosomal dominant | Ccctt[ggtgAgCacgctg\|ggtGAgCAcgctGJaccAC (SEQ ID: 947) |
| B139-776 | 19-11216242-C-CGACTGCAAGGACA | 13 | 245695 | LDLR: 3949 | Familial hypercholesterolemia | GcccC[gactgcAaGgaCA\|gACtgcAaGGaCA]AaTct (SEQ ID: 948) |
| B140-777 | 19-11233897-A-AAGGTCAGCTCCAC | 13 | 246545 | LDLR: 3949 | Familial hypercholesterolemia | GCtaA[AggTCAGCtccac\|AggTcAGCTccAcJagccg (SEQ ID: 949) |
| B141-778 | 5-176637714-G-GCAGCAAATCAAGCT | 14 | 394847 | NSD1: 64324 | Beckwith-Wiedemann syndrome | tGggG[CAgCAaAtcAAGct\|CAgcaaAtcAAgct]CTa[T (SEQ ID: 950) |
| B142-779 | 6-117996952-G-GCTGCCGCGCCGCCT | 14 | 480769 | NUS1: 116150 | MENTAL RETARDATION, AUTOSOMAL DOMINANT 55, WITH SEIZURES | cGctG[ctgcCgcGccGcct\|ctgcCgcGccGcct]ctgcc (SEQ ID: 951) |
| B143-780 | 13-32971081-T-TACTGCATGCAAATG | 14 | 261554 | BRCA2: 675 | Breast-ovarian cancer, familial 2 | CATAt[aCtgCAtGCaAAtg\|AcTgCAtgCaaAtg]ATccC (SEQ ID: 952) |
| B144-781 | 19-11216249-A-AAGGACAAATCTGAC | 14 | 245706 | LDLR: 3949 | Familial hypercholesterolemia | ctgcA[aGGaCAAaTctgac\|aGGacAAaTctGac]gAGga (SEQ ID: 953) |
| B145-782 | 2-189853347-A-AACCTGGGCAAGCTGG | 15 | 107099 | COL3A1: 1281 | Ehlers-Danlos syndrome, type 4 | ggtgA[accTGGgcAagCtGG\|acctGGgcAagCtGg]TcCtT (SEQ ID: 954) |
| B146-783 | 18-59992633-G-GCTCTGCGCGCTGCTC | 15 | 204405 | TNFR SF11A: 8792 | Paget disease of bone 2, early-onset | tgCTg[cTcTgcGcgctGcTc\|cTcTgcGcgCtgcTc]gccCg (SEQ ID: 955) |
| B147-784 | 3-41280628-C-CTAGCTATCGTTCTTTT | 16 | 227080 | CTNNB1: 1499 | Exudative vitreoretinopathy 1 | gatcC[TAgctaTCgTTctttt\|tAGCtAtCgTTctTTt]cActc (SEQ ID: 956) |
| B148-785 | 3-71019923-G-GCTGCTCTGCATGTTTT | 16 | 102121 | FOXP1: 27086 | Mental retardation with language impairment and with or without autistic features | cgTgg[cTGcTcTgcAtGtttt\|CTgctcTgcAtGTtTT]TAata (SEQ ID: 957) |
| B149-786 | 11-31815221-T-TTGGTTGGTAGACACTG | 16 | 190738 | PAX6: 5080 | Aniridia 1 | GGaaT[TggtTgGTAGAcActG\|tggtTggTAGacactGIgtgCT (SEQ ID: 958) |
| B150-787 | 16-23647409-C-CTCTTCTGCTGCTTCTT | 16 | 466297 | PALB2: 79728 | Hereditary cancer-predisposing syndrome | TGTCC[TCttctgCtgCTtCTt\|TctTCtgCtgCTtCTt]Tc(TC (SEQ ID: 959) |
| B151-788 | 19-49469932-T-TGGCCCGGAGGCTGGGC | 16 | 31527 | FTL: 2512 | Neuroferritinopathy | tggGt[ggcCcgGaggcTggGc\|GgcCcgGaggcTgggc]tgGgc (SEQ ID: 960) |
| B152-789 | 3-138664693-T-TGGGGGTGCGGCGGAGGC | 17 | 19905 | FOXL2: 668 | Blepharophimosis, ptosis, and epicanthus inversus | Cgggt[gGgGgtGcgGcggaggc\|gGgGgtGcgGcggaggc]gGgGg (SEQ ID: 961) |

TABLE 8-continued

Additonal Microduplication Sequences Associated with Autosomal Dominant Diseases

| Sequence ID | VARIANT | INS_LEN | ALLELEID | GENE INFO | CLNDN | NNNNN[Duplication 1\|Duplication 2]NNNNN lowercase = Cas9/Cpf1 cut site |
|---|---|---|---|---|---|---|
| B153-790 | 3-138664705-G-GGAGGCGGGGGTGCGGCC | 17 | 171758 | FOXL2: 668 | Blepharophimosis, ptosis, and epicanthus inversus | cgGcg[gaggcgGgGgtGCgGcc\|gaggcgGgGgtGCggCc]ggCgg (SEQ ID: 962) |
| B154-791 | 3-138664707-A-AGGCGGGGGTGCGGCCGG | 17 | 178773 | FOXL2: 668 | Blepharophimosis, ptosis, and epicanthus inversus | Gcgga[ggcgGgGgtGCggccgg\|ggcgGgGgtGCggCcgg]CggGC (SEQ ID: 963) |
| B155-792 | 9-140674107-A-ACCCAAAGCAGCTGTACT | 17 | 431918 | EHMT1: 79813 | Chromosome 9q deletion syndrome | ttcCa[CccaAagcaGCTgtacT\|CccaAagcaGCTgTAcT]TcTcC (SEQ ID: 964) |
| B156-793 | 10-103990523-G-GCCCAGGCCCTGCAGGGC | 17 | 459553 | PITX3: 5309 | Cataract, posterior polar, 4 | CCCCg[cccaGgccCtgcagGGc\|ccCAggccCtgcagGGc]ccCAg (SEQ ID: 965) |
| B157-794 | 16-2134369-G-GAGCAAGTCCAGCTCCTC | 17 | 75949 | TSC2: 7249 | Tuberous sclerosis syndrome | cccTg[agcaaGtcCAGCtccTc\|AgcAaGtcCAGCtcCTc]tccCg (SEQ ID: 966) |
| B158-795 | 17-17118596-T-TGCGGCTGCGTGGACCTC | 17 | 247655 | FLCN: 201163 | Hereditary cancer-predisposing syndrome | AaCgt[GCgGcTgcGtGGacCtc\|GcgGcTgcgtGGaCCTc]cacga (SEQ ID: 967) |
| B159-796 | 19-11216246-T-TGCAAGGACAAATCTGAC | 17 | 362682 | LDLR: 3949 | Familial hypercholesterolemia | Cgact[gcAagGaCAAaTctGAc\|gcAagGaCAAaTctGac]gAGga (SEQ ID: 968) |
| B160-797 | 11-47353677-T-TGCAGACATAGATGCCCCC | 18 | 23642 | MYBPC3: 4607 | Hypertrophic cardiomyopathy | GcCCt[GcagAcaTaGaTgCcCCc\|gcagacaTaGaTGCcCCC]gtcaa (SEQ ID: 969) |
| B161-798 | 18-59992620-T-TCGCGCTGCTGCTGCTCTG | 18 | 204404 | TNFRSF11A: 8792 | Familial expansile osteolysis | Ctgtt[cGcGctGctgCTgcTcTg\|cGcgctGctgCTgcTcTglcGcgC (SEQ ID: 970) |
| B162-799 | 18-59992630-G-GCTGCTCTGCGCGCTGCTC | 18 | 21338 | TNFRSF11A: 8792 | Familial expansile osteolysis | tGctg[CTgcTcTgcGcgctGctc\|CTgctcTgcGcgCtgcTcIgccCg (SEQ ID: 971) |
| B163-800 | 3-138664581-G-GGCTGGGCTGGCAGGGCTGA | 19 | 171757 | FOXL2: 668 | Blepharophimosis, ptosis, and epicanthus inversus | cggTg[gcTGggcTggcaGgGcTGalgcTGggcTggcaGgGcTGa]gcTGg (SEQ ID: 972) |
| B164-801 | 12-12870830-G-GCAGGCGGAGCACCCCAAGC | 19 | 181495 | CDKNIB: 1027 | Multiple endocrine neoplasia, type 4 | cCAgg[caggcgGAGcACCccAagc\|cagGcgGAGcAccccAagc]ccTCg (SEQ ID: 973) |
| B165-802 | 19-11216046-G-GCAACAGCTCCACCTGCATC | 19 | 245580 | LDLR: 3949 | Familial hypercholesterolemia | caGtg[caACAgcTcCacCtgcatC\|CaAcagcTcCacctgCatC]ccCca (SEQ ID: 974) |
| B166-803 | 19-11218155-G-GCCGGGACTGGTCAGATGAA | 19 | 228148 | LDLR: 3949 | Familial hypercholesterolemia | gaCtg[ccgGgacTGgtcagatgaa\|cCGGgacTGgtcagATgAAJCCCAt (SEQ ID: 975) |
| B167-804 | 19-11224421-G-GGTGGATCCTGTTCATGGGT | 19 | 434302 | LDLR: 3949 | Familial hypercholesterolemia | tcgtg[gtGgAtCCTGttcaTgggt\|gTGGAtCCTgttcatgggTIGCGTA (SEQ ID: 976) |
| B168-805 | 2-131355422-C-CGCGCACCCCTGTGCCCACCT | 20 | 20229 | CFC1: 55997 | Heterotaxy, visceral, 2, autosomal | acccc[GcgcaCcCcTgtgcccaCct\|gcgcACcCcTgtgcCCaCct]gcgcc (SEQ ID: 977) |

TABLE 8-continued

Additonal Microduplication Sequences Associated with Autosomal Dominant Diseases

| Sequence ID | VARIANT | INS_LEN | ALLELEID | GENE INFO | CLNDN | NNNNN[Duplication 1\|Duplication 2]NNNNN lowercase = Cas9/Cpf1 cut site |
|---|---|---|---|---|---|---|
| B169-806 | 3-138664638-T-TGGGGCAGGCGGCGGTGCGGC | 20 | 354106 | FOXL2: 668 | Blepharophimosis, ptosis, and epicanthus inversus | Gcggt[GgggcagGcgGcGgtGcggc\|GgggcagGcgGcGgtGcgGC]ggcCg (SEQ ID: 978) |
| B170-807 | 9-135778022-C-CTCTCGGTCATGCTGCAGCTG | 20 | 397173 | TSC1: 7248 | Tuberous sclerosis 1 | ATTcc[tctcgGtCatGctGCagCTg\|tctCGGtCatGCtgCagCTg]tCtGa (SEQ ID: 979) |
| B171-808 | 19-11216243-G-GACTGCAAGGACAAATCTGAC | 20 | 434241 | LDLR: 3949 | Familial hypercholesterolemia | ccCCg[actgcAaGGacaAaTcTGAclaCtgcAaGGaCAAaTctGac]gAGga (SEQ ID: 980) |
| B172-809 | 20-10632292-C-CCTTACAGCTGCCTCTGTTGT | 20 | 270939 | JAG1: 182 | Alagille syndrome 1 | GTCTC[CTtAcaGCTgCctCtgtTgT\|CTtAcaGCTgCctCtgtTgt]gacag (SEQ ID: 981) |

IV. Protospacer Adjacent Motif (PAM) Sequences

Below are exemplary PAM sequences. addgene.org/crispr/guide/#pam-table. blog.addgene.org/xcas9-engineering-a-crispr-variant-with-pam-flexibility Table 9.

TABLE 9

Exemplary PAM Sequences

| Legend | Species_and_Variant_of_Cas9 | Side | Pattern | Expanded | CleavageSite | Width | SEQ ID NOS: |
|---|---|---|---|---|---|---|---|
| A/a | xCas9_NG | 3' | NG | [ACGT]G | -3 from start | 2 | 982, 983 |
| B/b | xCas9_GAA | 3' | GAA | GAA | -3 from start | 3 | 984, 985 |
| C/c | xCas9_GAT | 3' | GAT | GAT | -3 from start | 3 | 986, 987 |
| D/d | SpCas9 | 3' | NGG | [ACGT]GG | -3 from start | 3 | 988, 989 |
| E/e | SpCas9 VRER variant | 3' | NGCG | [ACGT]GCG | -3 from start | 4 | 990, 991 |
| F/f | SpCas9 EQR variant | 3' | NGAG | [ACGT]GAG | -3 from start | 4 | 992, 993 |
| G/g | SpCas9 VQR variant | 3' | NGAN\|NGNG | [ACGT]GA[ACGT]\|[ACGT]G[ACGT]G | -3 from start | 4 | 994, 995 |
| H/h | SaCas9 | 3' | NNGRRT | [ACGT][ACGT]G[AG][AG]T | -3 from start | 6 | 996, 997 |
| I/i | NMe1 | 3' | NNNNGATT | [ACGT][ACGT][ACGT][ACGT]GATT | -3 from start | 8 | 998, 999 |
| J/j | CjeCas9 | 3' | NNNNRYAC | [ACGT][ACGT][ACGT][ACGT][AG][CT]AC | -3 from start | 8 | 1000, 1001 |
| K/k | AsCpf1 and LbCpf1 | 5' | TTTV | TTT[ACG] | approx +18 from end | 4 | 1002, 1003 |
| M/m | AsCpf1 and LbCpf1 RR variant | 5' | TYCV | T[CT]C[ACG] | approx +18 from end | 4 | 1004, 1005 |
| N/n | AsCpf1 RVR variant | 5' | TATV | TAT[ACG] | approx +18 from end | 4 | 1006, 1007 |
| O/o | FnCpf1 | 5' | TTV | TT[ACG] | approx +18 from end | 3 | 1008, 1009 |

V. Adeno-Associated Virus Nucleic Acid Delivery Platforms

Adeno-associated virus (AAV) is a small virus which infects humans and some other primate species. AAV is not currently known to cause disease. In many cases, AAV vectors integrate into the host cell genome, making it useful as gene therapy delivery platform. Gene therapy vectors using AAV can infect both dividing and quiescent cells and persist in an extrachromosomal state without integrating into the genome of the host cell, although in the native virus some integration of virally carried genes into the host genome does occur. Deyle et al., (August 2009). "Adeno-associated virus vector integration". *Current Opinion in Molecular Therapeutics* 11 (4): 442-447. These features make AAV a very attractive candidate for creating viral vectors for gene therapy. Grieger et al., (2005). "Adeno-associated virus as a gene therapy vector: vector development, production and clinical applications" *Advances in Biochemical Engineering/Biotechnology. Advances in Biochemical Engineering/Biotechnology* 99:119-145 Recent human clinical trials using AAV for gene therapy in the retina have shown promise. Maguire et al., (May 2008) "Safety and efficacy of gene transfer for Leber's congenital amaurosis" *The New England Journal of Medicine* 358 (21): 2240-2248. AAV belongs to the genus Dependoparvovirus, which in turn belongs to the family Parvoviridae. The virus is a small (20 nm) replication-defective, nonenveloped virus.

Wild-type AAV has attracted considerable interest from gene therapy researchers due to a number of features. Chief amongst these is the virus's apparent lack of pathogenicity. It can also infect non-dividing cells and has the ability to stably integrate into the host cell genome at a specific site (designated AAVS1) in the human chromosome 19. Kotin et al., (March 1990). "Site-specific integration by adeno-associated virus". *PNAS* USA 87 (6): 2211-2215; and Surosky et al., (October 1997) "Adeno-associated virus Rep proteins target DNA sequences to a unique locus in the human genome" *Journal of Virology* 71 (10): 7951-7959. This feature makes it somewhat more predictable than retroviruses, which present the threat of a random insertion and of mutagenesis, which is sometimes followed by development of a cancer.

The AAV genome integrates most frequently into the site mentioned, while random incorporations into the genome take place with a negligible frequency. Development of AAVs as gene therapy vectors, however, has eliminated this integrative capacity by removal of the rep and cap from the DNA of the vector. The desired gene together with a promoter to drive transcription of the gene is inserted between the inverted terminal repeats (ITR) that aid in concatemer formation in the nucleus after the single-stranded vector DNA is converted by host cell DNA polymerase complexes into double-stranded DNA. AAV-based gene therapy vectors form episomal concatemers in the host cell nucleus. In non-dividing cells, these concatemers remain intact for the life of the host cell. In dividing cells, AAV DNA is lost through cell division, since the episomal DNA is not replicated along with the host cell DNA. Random integration of AAV DNA into the host genome is detectable but occurs at very low frequency. AAVs also present very low immunogenicity, seemingly restricted to generation of neutralizing antibodies, while they induce no clearly defined cytotoxic response. This feature, along with the ability to infect quiescent cells present their dominance over adenoviruses as vectors for human gene therapy. Daya et al., (October 2008). "Gene therapy using adeno-associated virus vectors" *Clinical Microbiology Reviews* 21 (4): 583-593; Chirmule et al., (September 1999) "Immune responses to adenovirus and adeno-associated virus in humans" *Gene Therapy* 6 (9): 1574-1583; Hernandez et al., (October 1999) "Latent adeno-associated virus infection elicits humoral but not cell-mediated immune responses in a nonhuman primate model". *Journal of Virology* 73 (10): 8549-8558; and Ponnazhagan et al., (April 1997) "Adeno-associated virus 2-mediated gene transfer in vivo: organ-tropism and expression of transduced sequences in mice" *Gene* 190 (1): 203-210.

VI. Pharmaceutical Formulations And Compositions

The present invention further provides pharmaceutical compositions (e.g., comprising the nucleases described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 μg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the compound is administered in maintenance doses, ranging from 0.01 μg to 100 g per kg of body weight, once or more daily, to once every 20 years.

EXPERIMENTAL

Example I

Human Subjects

Cells for reprogramming TCAP iPSC lines were recovered, with consent, from a skin biopsy from a patient with LGMD2G under a UMMS-IRB-approved protocol and assigned a de-identified ID number unlinked to the patient's medical record. The consent process included conditions for sharing de-identified samples and information with other investigators. No PHI will be shared at any time per HIPAA guidelines.

Example II

Cell Culture

LGMD2G primary dermal fibroblasts were isolated from a skin biopsy from a patient with LGMD2G as described31. Fibroblasts were reprogrammed using the CytoTune 2.0 iPS Sendai Virus Reprogramming Kit (Thermo-Fisher) according to the manufacturer's directions. Clonal lines were expanded for 6-10 passages before banking. Immunostaining was performed to confirm the absence of Sendai virus and expression of OCT4. Human iPSCs were cultured in iPS-Brew XF medium (Miltenyi Biotec) and passaged every 3-5 days with Passaging Solution (Miltenyi Biotec) according to the manufacturer's directions.

Myoblasts were induced from iPSCs using a modification of the Genea Biocells protocol[11]. Following the generation of differentiated myotubes as described, cells were reseeded and cultured in human primary myoblast medium[32]. CD56+ cells were purified by FACS using an anti-CD56-APC antibody (BD Biosciences) or MACS (Miltenyi Biotec) according to the manufacturer's directions. Myogenicity was confirmed by immunostaining myoblast and myotube cultures using the mouse monoclonal antibodies MyoD clone 5.8 (Dako) and MF20 (DSHB) (data not shown).

A lymphoblastoid cell line from B lymphocytes (B-LCL) derived from a patient with HPS1 who was homozygous for the 16-bp microduplication was purchased from Coriell (Catalog GM14606). A lymphoblastoid cell line from B lymphocytes (B-LCL) derived from a patient with Tay-sachs who was homozygous for the GATA microduplication in HEXA was purchased from Coriell (Catalog GM11852) These cell lines was cultured following the recommended procedure using RPM1 1640 with 2 mM L-glutamine, 15% FBS and 1% penicillin/streptomycin.

HEK293T cells were cultured following the recommended procedure using Dulbecco's modified Eagle's medium (DMEM), 10% FBS and 1% penicillin/streptomycin. All cultures were maintained in a humidified incubator with 5% $CO_2$ at 37° C.

Example III

Purification Of SpyCas9 And LbaCas12a

Protein purification for 3×NLS-SpCas9 and LbaCas12a-2×NLS followed a common protocol. The generation and characterization of the 3×NLS-SpCas9 (Addgene #114365) and LbaCas12a-2×NLS (Addgene #114366) constructs have been described (Wu et al. Nature Medicine (in press) & Liu et al. *Nucleic Acids Research* (PMID 30892626). The pET21a plasmid backbone (Novagen) is used to drive the expression of a hexa-His-tagged version of each protein. The plasmid expressing 3×NLS-SpCas9 (or LbaCas12a-2×NLS) was transformed into *Escherichia coli* Rosetta (DE3) pLysS cells (EMD Millipore) for protein production. Cells were grown at 37° C. to an OD600 of ~0.2, then shifted to 18° C. and induced at an OD600 of ~0.4 for 16 h with isopropyl β-D-1-thiogalactopyranoside (IPTG, 1 mM final concentration).

Following induction, cells were pelleted by centrifugation and then resuspended with Ni-NTA buffer (20 mM TRIS pH 7.5, 1 M NaCl, 20 mM imidazole, 1 mM TCEP) supplemented with HALT Protease Inhibitor Cocktail, EDTA-Free (100×) (ThermoFisher) and lysed with M-110s Microfluidizer (Microfluidics) following the manufacturer's instructions. The protein was purified from the cell lysate using Ni-NTA resin, washed with five volumes of Ni-NTA buffer and then eluted with elution buffer (20 mM TRIS, 500 mM NaCl, 500 mM imidazole, 10% glycerol, pH 7.5). The 3×NLS-SpCas9 (or LbaCas12a protein) was dialysed overnight at 4° C. in 20 mM HEPES, 500 mM NaCl, 1 mM EDTA, 10% glycerol, pH 7.5.

Subsequently, the protein was step dialysed from 500 mM NaCl to 200 mM NaCl (final dialysis buffer: 20 mM HEPES, 200 mM NaCl, 1 mM EDTA, 10% glycerol, pH 7.5). Next, the protein was purified by cation exchange chromatography (5 ml HiTrap-S column, buffer A: 20 mM HEPES pH 7.5, 1 mM TCEP; buffer B: 20 mM HEPES pH 7.5, 1 M NaCl, 1 mM TCEP; flow rate 5 ml/min, column volume (CV) 5 ml) followed by size-exclusion chromatography (SEC) on a Superdex-200 (16/60) column (isocratic size-exclusion running buffer: 20 mM HEPES pH 7.5, 150 mM NaCl, 1 mM TCEP for 3×NLS-SpCas9 or 20 mM HEPES pH 7.5, 300 mM NaCl, 1 mM TCEP for LbCpf1-2×NLS).

The primary protein peak from the SEC was concentrated in an Ultra-15 Centrifugal Filters Ultracel-30K (Amicon) to a concentration around 100 μM based on absorbance at 280 nm. The purified protein quality was assessed by SDS-PAGE/Coomassie staining to be >95% pure and protein concentration was quantified with a Pierce BCA Protein Assay Kit (ThermoFisher Scientific). Protein was stored at −80° C. until further use.

Example IV

In Vitro Transcription Of Guide RNAs

The DNA cassette containing the U6 promoter and the sgRNA framework for SpyCas9 was cloned from pLKO1-puro vector[33] into pBluescript SK II+ backbone (Liu et al., Nucleic Acids Research, submitted). Plasmids expressing each guide RNA from the U6 promoter were constructed by annealing oligonuleotides encoding guide RNA and cloning it into BfuAI cleavage sites in this vector. Templates for in vitro transcription of SpyCas9 guides were amplified from the cognate plasmids using NEB Q5 High-Fidelity DNA Polymerase for 30 cycles (98° C., 15 s; 65° C. 25 s; 72° C. 20 s) using primer sets designed to include the T7 scaffold.

To generate CRISPR RNA (crRNA) for LbaCas12a, templates for in vitro transcription were generated by PCR amplification of oligonucleotides designed to include the T7 scaffold along with the guide RNA and a 15-mer overlap sequence to allow annealing between the oligos. The oligonucleotides encoded the full-length direct repeat crRNA sequence (Liu et al. Nucleic Acids Research, (PMID 30892626). Thirty cycles of amplification were conducted using NEB Q5 High-Fidelity DNA polymerase (98° C., 15 s; 60° C. 25 s; 72° C. 20 s). The PCR products were purified using Zymo DNA Clean & Concentrator Kit (Zymo Cat. #D4005).

In vitro transcription reactions were performed using the HiScribe T7 High Yield RNA Synthesis Kit using 300 ng of PCR product as template (NEB Cat. #E2040S). After incubation for 16 h at 37° C., samples were treated with DNase I for 40 min at 37° C. to remove any DNA contamination. Each guide RNA was purified using the Zymo RNA Clean and Concentrator Kit. Final RNA concentration was measured using Nanodrop and RNA was stored at −80° C. until further use.

Example V

Electroporation Of Cell Lines

3×NLS-SpyCas9 protein was precomplexed with sgRNAs either purchased from Synthego or made in-house by T7 transcription and electroporated into cells using the Neon transfection system (Thermo Fisher).

Electroporation of IPSCs

After washing with PBS, iPSCs were dissociated into single cells with 3:1 TrypLE: 0.5 mM EDTA and neutralized with Ham's F10+20% FBS. To form RNP complexes, 20 pmol 3×NLS-SpyCas9 protein and 25 pmol gRNA were combined in 10 μl Neon Buffer R and incubated for 10 min at room temperature. iPSCs ($1\times10^5$) were resuspended in 10 μl RNP-Buffer R mix and then nucleofected as follows: pulse voltage 1,500 V, pulse width 20 ms, pulse number 1.

After transfection, the cells were plated onto Matrigel-coated 24-well plates with iPS Brew XF supplemented with 10 μM Y27632 for expansion and grown in a humidified incubator at 37° C., 5% $CO_2$, for 4 days before harvesting them for analysis. iPSC-derived myoblasts were electroporated using two pulses of 1,400 V and 20 ms width and plated onto a 24-well dish containing pre-warmed antibiotic-free human primary myoblast growth medium and cultured for four to six days before analysis.

Electroporation of HPS1 Patient-Derived B-LCL Cells

Forty (40) pmol of 3×NLS-SpyCas9 protein was precomplexed with 50 pmol of sgRNA in buffer R for 10-20 min at room temperature in a final volume of 12 μl. Three hundred thousand cells per reaction were resuspended in 10 μl of RNP-buffer R mix and electroporated with 2 pulses at 1,700V for 20 ms using the 10-μl tip. Cells were then plated in 24-well plates with 500 μl of pre-equilibrated antibiotic-free culture medium and grown in a humidified incubator at 37° C. and 5% $CO_2$ for 7 days before indel analysis.

For the PARP-1 inhibition experiments, 300,000 HPS1 patient-derived B-LCL cells were treated with 10 μM or 20 μM rucaparib camsylate (Sigma-Aldrich PZ0036) in standard growth medium for 24 h. Treated cells were electroporated with SpyCas9 RNPs following previously described protocol. Following another 24 h incubation in rucaparib-containing medium, cells were resuspended in PARP-1 inhibitor-free medium and harvested for analysis after 7 days.

Electroporation of HEK293T Cells

Twenty (20) pmol of 3×NLS-SpyCas9 protein and 25 pmol of in vitro transcribed sgRNA were pre-complexed in Neon Buffer R for 10-20 min at room temperature. One hundred thousand cells per reaction were resuspended in 10 μl of RNP-buffer R mix and nucleofected with SpyCas9 guide RNA complex using two pulses at 1,150 V for 20 ms using the 10-μl tip. Cells were then plated in 24-well plates with 500 μl of pre-equilibrated antibiotic-free culture medium and grown for 3 days before analysis. F or Cas12a editing experiments at endogenous microduplications, 80 pmol of LbaCas12a protein was pre-complexed with 100 pmol of in vitro transcribed crRNA and 100,000 cells per reaction were nucleofected as described above.

Example VI

Indel Analysis By TIDE

Genomic DNA was extracted from HEK293T cells using GenElute Mammalian Genomic DNA Miniprep Kit (Sigma Aldrich) according to the manufacturer's instructions. The DNA region containing the 24-bp microduplication was amplified using genomic DNA as template and primers using NEB Q5 High-Fidelity DNA Polymerase (98° C., 15 s; 67° C. 25 s; 72° C. 20 s)×30 cycles. See, Table 10.

Table 10: List of Primers Used to Amplify Genomic Regions for TIDE Analysis

| Primer Name | Primer Sequence |
|---|---|
| Endo_24 bp_F | GAAGCGCTACCTGATTCCAATTC (SEQ ID NO: 1010) |
| Endo_24 bp_R | TGGCAGTTAGGAAGGTTGTATCG (SEQ ID NO: 1011) |

Subsequently, the PCR product was purified using the DNA Clean & Concentrator-5 kit (Zymo research) and sequenced. Sanger sequencing trace data were analysed using the TIDE webtool at tide.nki.nl/to infer the compositions of indels created at the sites of DSBs34.

Example VII

Library Construction For Illumina Deep Sequencing

Library construction for deep sequencing was performed using a modified version of a previously described protocol[26]. In brief, iPSCs and myoblasts were harvested following nuclease treatment and genomic DNA was extracted using the GenElute Mammalian Genomic DNA Miniprep Kit (Sigma GIN350). Genomic loci spanning the target sites were PCR amplified with locus-specific primers carrying tails complementary to the TruSeq adapters (Deepseq_TCAP_primer_fwd and Deepseq_TCAP_primer_rev). Fifty (50) nanograms of input genomic DNA was PCR amplified with Q5 High-Fidelity DNA Polymerase (New England Biolabs): (98° C., 15 s; 67° C., 25 s; 72° C., 20 s)×30 cycles. Next, 0.1 μl of each PCR reaction was amplified with barcoded primers to reconstitute the TruSeq adaptors using Q5 High-Fidelity DNA Polymerase (New England Biolabs): (98° C., 15 s; 67° C., 25 s; 72° C., 20 s)×10 cycles. Products were qualitatively analysed by gel electrophoresis. Equal amounts of the products were pooled and gel-purified using QIAquick Gel Extraction Kit (Qiagen Cat. #28704). The purified library was deep sequenced using a paired-end 150-bp Illumina MiSeq run.

Example VIII

Illumina Deep Sequencing Analysis

MiSeq data analysis was performed using Unix-based software tools. First, d FastQC (version 0.11.3; bioinformatics.babraham.ac.uk/projects/fastqc/) was used to determine the quality of paired-end sequencing reads (R1 and R2 fastq files). Next, a paired-end read merger (PEAR; version 0.9.8) 35 was used to pool raw paired-end reads and generate single merged high-quality full-length reads.

Reads were then filtered according to quality via FASTQ36 for a mean PHRED quality score above 30 and a minimum per base score above 24. After that, BWA (version 0.7.5) and SAMtools (version 0.1.19) were used to align each group of filtered reads to a corresponding reference sequence.

To determine lesion type, frequency, size and distribution, all edited reads from each experimental replicate were combined and aligned, as described above. Lesion types and frequencies were then catalogued in a text output format at each base using bam-readcount. For each treatment group, the average background lesion frequencies (based on lesion type, position and frequency) of the triplicate negative control group were subtracted to obtain the nuclease-dependent lesion frequencies.

Example IX

Library Construction For UMI-Based Illumina Deep Sequencing

The construction of the UMI-based library used a linear amplification step to incorporate UMIs within the amplicons from the target locus[15]. HPS1 B-LCL cells and HEK293 Ts were harvested following nuclease treatment for genomic DNA extraction using the GenElute Mammalian Genomic DNA Miniprep Kit (Sigma GIN350).

Randomized unique molecular identifiers (UMIs) were incorporated within the 5' locus-specific primers carrying tails complementary to TruSeq adaptors. In brief, 50 ng of input genomic DNA was linear amplified with NEB Q5 High-Fidelity DNA Polymerase (98° C., 15 s; 67° C., 25 s; 72° C., 20 s) for 10 cycles using the 5' locus-specific primer with TruSeq adaptor conjugated with a UMI sequence.

Next a 5' constant primer along with the 3' locus-specific primer with TruSeq adaptor were added and further amplified for 30 cycles. Indexes were then incorporated using barcoded primers to diluted PCR products using NEB Q5 High-Fidelity DNA Polymerase (98° C., 15 s; 67° C., 25 s; 72° C., 20 s) for 10 cycles. Products were qualitatively analysed by gel electrophoresis. Equal amounts of the products were pooled and gel-purified using QIAquick Gel Extraction Kit (Qiagen Cat. #28704) for DNA recovery. The purified library was deep sequenced using a paired-end 150-bp Illumina MiSeq run.

Example X

UMI-Based Deep Sequencing Analysis

The analysis of the UMI-tagged deep sequencing reads was adapted from a previous protocol[15]. Initially, BWA (version 0.7.5) and SAMtools (version 0.1.19) were used to align each group of filtered merged-read pairs to a corresponding reference sequence, ignoring the unique molecular barcodes. Next, a custom Python and PySAM script was used to process mapped reads into counts of UMI-labelled reads for each target. The mapped reads were filtered by requiring a mapping value (MAPQ) larger than 30. Alignments were categorized into different categories of indels using VarScan 237.

Next, UMI duplicates were identified to create a minimal set of amplicons that can account for the full set of reads with unique UMIs. For each unique UMI, a minimum of five observations of the same sequence was required to consider the sequence to have a low likelihood of being an artefact (sequencing error in the UMI element). For sequences that met this threshold, all common sequences associated with the UMI were consolidated to one read for analysis of the distribution of sequence modifications that were present at a locus. The resulting UMI number tables, which describe the type of each sequence modification and its length, were concatenated and loaded into GraphPad Prism 7 for data visualization. Microsoft Excel version 16.21.1 was used for statistical analysis.

Example XI

PacBio Library Preparation

Single molecule, real-time (SMRT) sequencing is modified from Pacific Biosciences (PacBio). Nuclease-treated patient-derived iPSCs were harvested for genomic DNA extraction with GenElute Mammalian Genomic DNA Miniprep Kit (Sigma GIN350). In brief, regions that flanked the TCAP target site were PCR amplified using locus-specific primers. See, Table 10. The forward primer was designed to have the barcode sequence followed by the UMI and locus-specific primer sequence. The reverse primer contains the barcode followed by the locus-specific primer sequence. Input DNA (25-50 ng) was PCR amplified with Phusion High Fidelity DNA Polymerase (New England Biolabs): (98° C., 15 s; 65° C., 25 s; 72° C., 18 s)x30 cycles. The products were qualitatively analysed by gel electrophoresis and subsequently gel purified with QIAquick Gel Extraction Kit (Qiagen Cat. #28704). The purified products sequenced at the UMASS Medical School Deep Sequencing Core for SMRTbell Library Preparation using a Pacific Biosciences Sequel Instrument.

Example XII

PacBio Sequencing Data Analysis

For PacBio sequencing data analysis, Minimap2 (version 2.1438,) was used to align the raw Consensus_ROI (reads_of_insert.fastq) data to the 2-kb reference sequence. Alignment quality control and filtering were performed using custom Perl script to remove errors and filter out alignments with poor quality. For variation calling, a custom Python script was used to extract deletions or insertions larger than 5 bp for each read from the SAM files. Subsequently, deletions or insertions were classified into different groups on the basis of their length. IGV (version 2.4.16) was used for alignment visualization of the aligned reads using Quick consensus mode39.

Example XIII

Clonal Analysis Of iPSCs

Following confirmation of MMEJ-mediated correction in the population of LGMD2G iPSCs, clonal analysis was performed. Cells from the corrected population were seeded into 96-well plates in the presence of Y27632 at a frequency of 0.8 cells per well. iPSC clones were cultured for several weeks in iPS Brew XF (Miltenyi Biotec) before being collected for sequence analysis by deep-sequencing.

Example IVX

Myoblast Differentiation And Detection Of Telethonin Expression iPSC-derived myoblasts were plated into 0.1% gelatin-coated 6-well plates at a density of 100,000 cells per well in myoblast expansion medium containing Ham's F-10 (Cellgro) supplemented with 20% fetal bovine serum (Hyclone, SH30071.03), 1.2 mM $CaCl_2$) (EMD OmniPur 3000) and 1% chick embryo extract isolated from day 12 SPF Premium Fertilized White Leghorn Chicken Eggs (Charles River, North Franklin, CT). After 4 days of expansion, the cells were incubated with myotube differentiation medium including DMEM/F12 (Thermo-Fisher) supplemented with 1% $N_2$ (Thermo-Fisher, 17502-048) and 1% insulin-transferrin-selenium (Thermo-Fisher, 41400045).

After 10 days of differentiation, the cells were dissociated into single cells using TrypLE. Subsequently the cells were fixed with 2% PFA for 15 min and blocked with PBS including 2% BSA, 2% horse serum, 2% goat serum and 2% Triton X-100 for 20 min. The cells were then incubated with anti-telethonin antibody (Santa Cruz, sc-25327, 1:50) at 4° C. for 2 days and IgG goat anti-mouse secondary antibody labelled with Alexa 488 fluorophore (Invitrogen, A11017, 1:800) at room temperature for 1 h. The cells were suspended in flow buffer (PBS including 0.2% FBS) and flow cytometry was performed using a BD FACSAria Ilu (UMMS Flow Cytometry Core Laboratory). Roughly 20,000 cells were included for analysis. FlowJo software (version 7.6) was used for data analysis.

Example XV

Survey Of Microduplications In Clin Var And In Human Reference Populations

Annotations of pathogenicity from ClinVar (ftp.ncbi.nlm.nih.gov/pub/clinvar/vcf_GRCh37/clinvar_20180225.vcf.gz) 20 were combined with annotations of allele-frequencies from gnomAD console.cloud.google.com/storage/browser/gnomad-public/release/2.0.2/vcf) 21 and from the 1000 Genome Project ftp.1000genomes.ebi.ac.uk/vol1/ftp/release/20130502/) 40 using the annotate function in bcf tools[41] (1.9), after decomposition of multi-allelic sites and normalization of variants with vt42 (v0.5772) against a reference genome (broadinstitute.org/ftp/pub/seq/references/Homo_sapiens_assemblyl9.fasta). Most analyses were restricted to the intervals in ftp.broadinstitute.org/pub/ExAC_release/release1/resources/exome_calling_regions.v1.interval list.

Insertions were extracted using vt (view -h -f "VTYPE==INDEL&&DLEN>0"); then duplications were identified, repeat units counted, internal shift-symmetries determined, and flanking genomic regions extracted using a modified version of the vt function annotate indels. Additional processing (filtering, finding maximal allele frequencies among different populations, scanning for PAM sites and so on) was performed using R (3.4.3), including the VariantAnnotation (1.24.5) package[43].

Exact tandem repeats in the reference genome were identified using the Tandem Repeats Finder program (4.09) 44 and checked for exact matches elsewhere in the genome with bwa fastmap (0.7.17) 45. Examples of different lengths were manually selected to use for the tests of collapse of endogenous microduplications.

Example XVI

Code Availability Statement

Data analysis used a combination of publicly available software and custom code, as detailed in the Methods. Custom python (CRESA-lpp.py) and R (indel_background_filtering.R) scripts used in the Illumina data analysis and the shell script (Tcap_pacbio_analysis.sh) used for the analysis of the PacBio data are hosted on GitHub (github.com/locusliu/PCR_Amplicon_target_deep_seq). Scripts for the bioinformatic analysis of pathogenic microduplications are hosted at rambutan.umassmed.edu/duplications/.

REFERENCES

1. Moreira, E. S. et al. Limb-girdle muscular dystrophy type 2G is caused by mutations in the gene encoding the sarcomeric protein telethonin. Nat. Genet. 24, 163-166 (2000).
2. El-Chemaly, S. & Young, L. R. Hermansky-Pudlak syndrome. Clin. Chest Med. 37, 505-511 (2016).
3. Sfeir, A. & Symington, L. S. Microhomology-mediated end joining: a back-up survival mechanism or dedicated pathway? Trends Biochem. Sci. 40, 701-714 (2015).
4. Bae, S., Kweon, J., Kim, H. S. & Kim, J.-S. Microhomology-based choice of Cas9 nuclease target sites. Nat. Methods 11, 705-706 (2014).
5. Kim, S.-I. et al. Microhomology-assisted scarless genome editing in human iPSCs. Nat. Commun. 9, 939 (2018).
6. Hisano, Y. et al. Precise in-frame integration of exogenous DNA mediated by CRISPR/Cas9 system in zebrafish. Sci. Rep. 5, 8841 (2015).
7. Sakuma, T., Nakade, S., Sakane, Y., Suzuki, K. T. & Yamamoto, T. MMEJ-assisted gene knock-in using TALENs and CRISPR-Cas9 with the PITCh systems. Nat. Protocols 11, 118-133 (2016).
8. Bertz, M., Wilmanns, M. & Rief, M. The titin-telethonin complex is a directed, superstable molecular bond in the muscle Z-disk. Proc. Natl Acad. Sci. USA 106, 13307-13310 (2009).
9. Nigro, V. & Savarese, M. Genetic basis of limb-girdle muscular dystrophies: the 2014 update. Acta Myol. 33, 1-12 (2014).
10. Kosicki, M., Tomberg, K. & Bradley, A. Repair of double-strand breaks induced by CRISPR-Cas9 leads to large deletions and complex rearrangements. Nat. Biotechnol. 36, 765-771 (2018). 10.1038/nbt.4192
11. Caron, L. et al. A human pluripotent stem cell model of facioscapulohumeral muscular dystrophy-affected skeletal muscles. Stem Cells Transl. Med. 5, 1145-1161 (2016).
12. Oh, J. et al. Positional cloning of a gene for Hermansky-Pudlak syndrome, a disorder of cytoplasmic organelles. Nat. Genet. 14, 300-306 (1996).
13. Richmond, B. et al. Melanocytes derived from patients with Hermansky-Pudlak syndrome types 1, 2, and 3 have distinct defects in cargo trafficking. J. Invest. Dermatol. 124, 420-427 (2005).
14. Brantly, M. et al. Pulmonary function and high-resolution CT findings in patients with an inherited form of pulmonary fibrosis, Hermansky-Pudlak syndrome, due to mutations in HPS-1. Chest 117, 129-136 (2000).
15. Bolukbasi, M. F. et al. Orthogonal Cas9-Cas9 chimeras provide a versatile platform for genome editing. Nat. Commun. 9, 4856 (2018).
16. Sharma, S. et al. Homology and enzymatic requirements of microhomology-dependent alternative end joining. Cell Death Dis. 6, e1697 (2015).
17. Wang, M. et al. PARP-1 and Ku compete for repair of DNA double strand breaks by distinct NHEJ pathways. Nucleic Acids Res. 34, 6170-6182 (2006).
18. Dutta, A. et al. Microhomology-mediated end joining is activated in irradiated human cells due to phosphorylation-dependent formation of the XRCC1 repair complex. Nucleic Acids Res. 45, 2585-2599 (2017).
19. Zetsche, B. et al. Cpf1 is a single RNA-guided endonuclease of a class 2 CRISPR-Cas system. Cell 163, 759-771 (2015).

20 Landrum, M. J. et al. ClinVar: improving access to variant interpretations and supporting evidence. Nucleic Acids Res. 46, D1062-D1067 (2018).

21. Lek, M. et al. Analysis of protein-coding genetic variation in 60,706 humans. Nature 536, 285-291 (2016).
22. Komor, A. C., Badran, A. H. & Liu, D. R. CRISPR-based technologies for the manipulation of eukaryotic genomes. Cell 168, 20-36 (2017).
23. Kim, E. et al. In vivo genome editing with a small Cas9 orthologue derived from Campylobacter jejuni. Nat. Commun. 8, 14500 (2017).

24 Edraki, A. et al. A compact, high-accuracy Cas9 with a dinucleotide PAM for in vivo genome editing. Mol. Cell 73, 714-726.e4 (2019).

25. Kleinstiver, B. P. et al. Engineered CRISPR-Cas9 nucleases with altered PAM specificities. Nature 523, 481-485 (2015).
26. Bolukbasi, M. F. et al. DNA-binding-domain fusions enhance the targeting range and precision of Cas9. Nat. Methods 12, 1150-1156 (2015).
27. Hu, J. H. et al. Evolved Cas9 variants with broad PAM compatibility and high DNA specificity. Nature 556, 57-63 (2018).
28. van Overbeek, M. et al. DNA repair profiling reveals nonrandom outcomes at Cas9-mediated breaks. Mol. Cell 63, 633-646 (2016).
29. Suzuki, K. et al. In vivo genome editing via CRISPR/Cas9 mediated homology-independent targeted integration. Nature 540, 144-149 (2016).
30. Shen, M. W. et al. Predictable and precise template-free CRISPR editing of pathogenic variants. Nature 563, 646-651 (2018).
31. Rittié, L. & Fisher, G. J. Isolation and culture of skin fibroblasts. Methods Mol. Med. 117, 83-98 (2005).
32. Stadler, G. et al. Establishment of clonal myogenic cell lines from severely affected dystrophic muscles-CDK4 maintains the myogenic population. Skelet. Muscle 1, 12 (2011).
33. Kearns, N. A. et al. Cas9 effector-mediated regulation of transcription and differentiation in human pluripotent stem cells. Development 141, 219-223 (2014).

34 Brinkman, E. K., Chen, T., Amendola, M. & van Steensel, B. Easy quantitative assessment of genome editing by sequence trace decomposition. Nucleic Acids Res. 42, e168 (2014).

35. Zhang, J., Kobert, K., Flouri, T. & Stamatakis, A. PEAR: a fast and accurate Illumina Paired-End reAd mergeR. Bioinformatics 30, 614-620 (2014).
36. Blankenberg, D. et al. Manipulation of FASTQ data with Galaxy. Bioinformatics 26, 1783-1785 (2010).
37. Koboldt, D. C. et al. VarScan 2: somatic mutation and copy number alteration discovery in cancer by exome sequencing. Genome Res. 22, 568-576 (2012).
38. Li, H. Minimap2: pairwise alignment for nucleotide sequences. Bioinformatics 34, 3094-3100 (2018).
39. Robinson, J. T. et al. Integrative genomics viewer. Nat. Biotechnol. 29, 24-26 (2011).

40. 1000 Genomes Project Consortium A global reference for human genetic variation. Nature 526, 68-74 (2015).

41. Li, H. et al. The Sequence Alignment/Map format and SAMtools. Bioinformatics 25, 2078-2079 (2009).

42. Tan, A., Abecasis, G. R. & Kang, H. M. Unified representation of genetic variants. Bioinformatics 31, 2202-2204 (2015).

43. Obenchain, V. et al. VariantAnnotation: a Bioconductor package for exploration and annotation of genetic variants. Bioinformatics 30, 2076-2078 (2014).

44. Benson, G. Tandem repeats finder: a program to analyze DNA sequences. Nucleic Acids Res. 27, 573-580 (1999).

45. Li, H. Exploring single-sample SNP and INDEL calling with whole-genome de novo assembly. Bioinformatics 28, 1838-1844 (2012).

We claim:

1. A composition comprising a Class II CRISPR single effector programmable nuclease bound to an intervening region joining first and second microhomologous sequences within a microduplication sequence and a single guide ribonucleic acid complementary to said microduplication sequence.

2. The composition of claim 1, wherein said microduplication sequence further comprises, or is adjacent to, a protospacer adjacent motif sequence.

3. The composition of claim 1, wherein said Class II CRISPR single effector nuclease is selected from the group consisting of a Cas9 nuclease and a Cas12 nuclease.

4. The composition of claim 1, wherein said microduplication sequence has a length of between 1-40 nucleotides.

5. The composition of claim 1, wherein said microduplication sequence has a length of greater than 40 nucleotides.

6. The composition of claim 1, wherein said microduplication sequence is in the form of a direct repeat.

* * * * *

SEQUENCE LISTING

<160> NUMBER OF SEQ ID NOS: 1107

<210> SEQ ID NO 1
<211> LENGTH: 5
<212> TYPE: DNA
<213> ORGANISM: Artificial Sequence
<220> FEATURE:
<223> OTHER INFORMATION: Synthetic

<400> SEQUENCE: 1 agcct 5

<210> SEQ ID NO 2
<211> LENGTH: 17
<212> TYPE: DNA
<213> ORGANISM: Artificial Sequence
<220> FEATURE:
<223> OTHER INFORMATION: Synthetic

<400> SEQUENCE: 2
tggcgcggcc ccggccc 17

<210> SEQ ID NO 3
<211> LENGTH: 5
<212> TYPE: DNA
<213> ORGANISM: Artificial Sequence
<220> FEATURE:
<223> OTHER INFORMATION: Synthetic

<400> SEQUENCE: 3 ggata 5

<210> SEQ ID NO 4
<211> LENGTH: 5
<212> TYPE: DNA
<213> ORGANISM: Artificial Sequence
<220> FEATURE:
<223> OTHER INFORMATION: Synthetic

<400> SEQUENCE: 4 acggc 5

<210> SEQ ID NO 5
<211> LENGTH: 19
<212> TYPE: DNA
<213> ORGANISM: Artificial Sequence
<220> FEATURE:
<223> OTHER INFORMATION: Synthetic

<400> SEQUENCE: 5
gaccgaccac atctgcaga 19

<210> SEQ ID NO 6
<211> LENGTH: 18
<212> TYPE: DNA
<213> ORGANISM: Artificial Sequence
<220> FEATURE:

<223> OTHER INFORMATION: Synthetic

<400> SEQUENCE: 6
tgttgtcgat ggcgaccc 18

<210> SEQ ID NO 7
<211> LENGTH: 5
<212> TYPE: DNA
<213> ORGANISM: Artificial Sequence
<220> FEATURE:
<223> OTHER INFORMATION: Synthetic

<400> SEQUENCE: 7 ggagt 5

<210> SEQ ID NO 8
<211> LENGTH: 11
<212> TYPE: DNA
<213> ORGANISM: Artificial Sequence
<220> FEATURE:
<223> OTHER INFORMATION: Synthetic

<400> SEQUENCE: 8
tggtggcatg a 11

<210> SEQ ID NO 9
<211> LENGTH: 4
<212> TYPE: DNA
<213> ORGANISM: Artificial Sequence
<220> FEATURE:
<223> OTHER INFORMATION: Synthetic

<400> SEQUENCE: 9 gcaa 4

<210> SEQ ID NO 10
<211> LENGTH: 5
<212> TYPE: DNA
<213> ORGANISM: Artificial Sequence
<220> FEATURE:
<223> OTHER INFORMATION: Synthetic

<400> SEQUENCE: 10 aagat 5

<210> SEQ ID NO 11
<211> LENGTH: 16
<212> TYPE: DNA
<213> ORGANISM: Artificial Sequence
<220> FEATURE:
<223> OTHER INFORMATION: Synthetic

<400> SEQUENCE: 11
agcttcacag agtagt 16

<210> SEQ ID NO 12
<211> LENGTH: 5
<212> TYPE: DNA
<213> ORGANISM: Artificial Sequence
<220> FEATURE:
<223> OTHER INFORMATION: Synthetic

<400> SEQUENCE: 12 cgcca 5

<210> SEQ ID NO 13
<211> LENGTH: 11
<212> TYPE: DNA
<213> ORGANISM: Artificial Sequence
<220> FEATURE:
<223> OTHER INFORMATION: Synthetic

<400> SEQUENCE: 13
gggccgggcc c 11

<210> SEQ ID NO 14
<211> LENGTH: 3
<212> TYPE: DNA
<213> ORGANISM: Artificial Sequence
<220> FEATURE:
<223> OTHER INFORMATION: Synthetic

<400> SEQUENCE: 14 cta 3

<210> SEQ ID NO 15
<211> LENGTH: 7
<212> TYPE: DNA
<213> ORGANISM: Artificial Sequence
<220> FEATURE:
<223> OTHER INFORMATION: Synthetic

<400> SEQUENCE: 15 cacggcg 7

<210> SEQ ID NO 16
<211> LENGTH: 4
<212> TYPE: DNA
<213> ORGANISM: Artificial Sequence
<220> FEATURE:
<223> OTHER INFORMATION: Synthetic

<400> SEQUENCE: 16 ctga 4

<210> SEQ ID NO 17
<211> LENGTH: 5
<212> TYPE: DNA
<213> ORGANISM: Artificial Sequence
<220> FEATURE:
<223> OTHER INFORMATION: Synthetic

<400> SEQUENCE: 17 tcatc 5

<210> SEQ ID NO 18
<211> LENGTH: 24
<212> TYPE: DNA
<213> ORGANISM: Artificial Sequence
<220> FEATURE:
<223> OTHER INFORMATION: Synthetic

<400> SEQUENCE: 18
gcccgggcag ccacctgtaa tctc 24

<210> SEQ ID NO 19
<211> LENGTH: 9
<212> TYPE: DNA
<213> ORGANISM: Artificial Sequence
<220> FEATURE:
<223> OTHER INFORMATION: Synthetic

<400> SEQUENCE: 19 gcgaggtgt 9

<210> SEQ ID NO 20
<211> LENGTH: 11
<212> TYPE: DNA
<213> ORGANISM: Artificial Sequence
<220> FEATURE:
<223> OTHER INFORMATION: Synthetic

<400> SEQUENCE: 20
ttcacagagt a 11

<210> SEQ ID NO 21
<211> LENGTH: 5
<212> TYPE: DNA
<213> ORGANISM: Artificial Sequence
<220> FEATURE:
<223> OTHER INFORMATION: Synthetic

<400> SEQUENCE: 21 gtgcc 5

<210> SEQ ID NO 22
<211> LENGTH: 6
<212> TYPE: DNA
<213> ORGANISM: Artificial Sequence
<220> FEATURE:
<223> OTHER INFORMATION: Synthetic

<400> SEQUENCE: 22 actcgg 6

<210> SEQ ID NO 23
<211> LENGTH: 17
<212> TYPE: DNA
<213> ORGANISM: Artificial Sequence
<220> FEATURE:
<223> OTHER INFORMATION: Synthetic

<400> SEQUENCE: 23
agccacgcag gtatcgt 17

<210> SEQ ID NO 24
<211> LENGTH: 5
<212> TYPE: DNA
<213> ORGANISM: Artificial Sequence
<220> FEATURE:
<223> OTHER INFORMATION: Synthetic

<400> SEQUENCE: 24 tcaag 5

<210> SEQ ID NO 25
<211> LENGTH: 9
<212> TYPE: DNA
<213> ORGANISM: Artificial Sequence
<220> FEATURE:
<223> OTHER INFORMATION: Synthetic

<400> SEQUENCE: 25 actcagcac 9

<210> SEQ ID NO 26
<211> LENGTH: 17

<212> TYPE: DNA
<213> ORGANISM: Artificial Sequence
<220> FEATURE:
<223> OTHER INFORMATION: Synthetic

<400> SEQUENCE: 26
tgggcctccc ctgctgg 17

<210> SEQ ID NO 27
<211> LENGTH: 3
<212> TYPE: DNA
<213> ORGANISM: Artificial Sequence
<220> FEATURE:
<223> OTHER INFORMATION: Synthetic

<400> SEQUENCE: 27 aac 3

<210> SEQ ID NO 28
<211> LENGTH: 5
<212> TYPE: DNA
<213> ORGANISM: Artificial Sequence
<220> FEATURE:
<223> OTHER INFORMATION: Synthetic

<400> SEQUENCE: 28 gtggc 5

<210> SEQ ID NO 29
<211> LENGTH: 5
<212> TYPE: DNA
<213> ORGANISM: Artificial Sequence
<220> FEATURE:
<223> OTHER INFORMATION: Synthetic

<400> SEQUENCE: 29 caagt 5

<210> SEQ ID NO 30
<211> LENGTH: 8
<212> TYPE: DNA
<213> ORGANISM: Artificial Sequence
<220> FEATURE:
<223> OTHER INFORMATION: Synthetic

<400> SEQUENCE: 30 ttcacaga 8

<210> SEQ ID NO 31
<211> LENGTH: 9
<212> TYPE: DNA
<213> ORGANISM: Artificial Sequence
<220> FEATURE:
<223> OTHER INFORMATION: Synthetic

<400> SEQUENCE: 31 aacgtgttc 9

<210> SEQ ID NO 32
<211> LENGTH: 21
<212> TYPE: DNA
<213> ORGANISM: Artificial Sequence
<220> FEATURE:
<223> OTHER INFORMATION: Synthetic

<400> SEQUENCE: 32

-continued tgaagtggta ggaaaaatgt c 21

<210> SEQ ID NO 33
<211> LENGTH: 21
<212> TYPE: DNA
<213> ORGANISM: Artificial Sequence
<220> FEATURE:
<223> OTHER INFORMATION: Synthetic

<400> SEQUENCE: 33
tcatactttt cttcctgttc a 21

<210> SEQ ID NO 34
<211> LENGTH: 3
<212> TYPE: DNA
<213> ORGANISM: Artificial Sequence
<220> FEATURE:
<223> OTHER INFORMATION: Synthetic

<400> SEQUENCE: 34 tta 3

<210> SEQ ID NO 35
<211> LENGTH: 14
<212> TYPE: DNA
<213> ORGANISM: Artificial Sequence
<220> FEATURE:
<223> OTHER INFORMATION: Synthetic

<400> SEQUENCE: 35
tggggcccag tccc 14

<210> SEQ ID NO 36
<211> LENGTH: 12
<212> TYPE: DNA
<213> ORGANISM: Artificial Sequence
<220> FEATURE:
<223> OTHER INFORMATION: Synthetic

<400> SEQUENCE: 36
tagccaatgt tc 12

<210> SEQ ID NO 37
<211> LENGTH: 3
<212> TYPE: DNA
<213> ORGANISM: Artificial Sequence
<220> FEATURE:
<223> OTHER INFORMATION: Synthetic

<400> SEQUENCE: 37 tac 3

<210> SEQ ID NO 38
<211> LENGTH: 3
<212> TYPE: DNA
<213> ORGANISM: Artificial Sequence
<220> FEATURE:
<223> OTHER INFORMATION: Synthetic

<400> SEQUENCE: 38 gca 3

<210> SEQ ID NO 39
<211> LENGTH: 5
<212> TYPE: DNA
<213> ORGANISM: Artificial Sequence
<220> FEATURE:
<223> OTHER INFORMATION: Synthetic

<400> SEQUENCE: 39 gcagt 5

<210> SEQ ID NO 40
<211> LENGTH: 12
<212> TYPE: DNA
<213> ORGANISM: Artificial Sequence
<220> FEATURE:
<223> OTHER INFORMATION: Synthetic

<400> SEQUENCE: 40
taccggctcg cc 12

<210> SEQ ID NO 41
<211> LENGTH: 25
<212> TYPE: DNA
<213> ORGANISM: Artificial Sequence
<220> FEATURE:
<223> OTHER INFORMATION: Synthetic

<400> SEQUENCE: 41
tctccttcct gccatctgga caagc 25

<210> SEQ ID NO 42
<211> LENGTH: 6
<212> TYPE: DNA
<213> ORGANISM: Artificial Sequence
<220> FEATURE:
<223> OTHER INFORMATION: Synthetic

<400> SEQUENCE: 42 cgggca 6

<210> SEQ ID NO 43
<211> LENGTH: 17
<212> TYPE: DNA
<213> ORGANISM: Artificial Sequence
<220> FEATURE:
<223> OTHER INFORMATION: Synthetic

<400> SEQUENCE: 43
agggccgtcg cgaggct 17

<210> SEQ ID NO 44
<211> LENGTH: 18
<212> TYPE: DNA
<213> ORGANISM: Artificial Sequence
<220> FEATURE:
<223> OTHER INFORMATION: Synthetic

<400> SEQUENCE: 44
cgtcctcagc ttcacaga 18

<210> SEQ ID NO 45
<211> LENGTH: 14
<212> TYPE: DNA
<213> ORGANISM: Artificial Sequence
<220> FEATURE:
<223> OTHER INFORMATION: Synthetic

<400> SEQUENCE: 45
gctagaatga gtta 14

-continued

<210> SEQ ID NO 46
<211> LENGTH: 5
<212> TYPE: DNA
<213> ORGANISM: Artificial Sequence
<220> FEATURE:
<223> OTHER INFORMATION: Synthetic

<400> SEQUENCE: 46 tgtgc 5

<210> SEQ ID NO 47
<211> LENGTH: 5
<212> TYPE: DNA
<213> ORGANISM: Artificial Sequence
<220> FEATURE:
<223> OTHER INFORMATION: Synthetic

<400> SEQUENCE: 47 gaggc 5

<210> SEQ ID NO 48
<211> LENGTH: 6
<212> TYPE: DNA
<213> ORGANISM: Artificial Sequence
<220> FEATURE:
<223> OTHER INFORMATION: Synthetic

<400> SEQUENCE: 48 cgggct 6

<210> SEQ ID NO 49
<211> LENGTH: 11
<212> TYPE: DNA
<213> ORGANISM: Artificial Sequence
<220> FEATURE:
<223> OTHER INFORMATION: Synthetic

<400> SEQUENCE: 49
tggctgcgct g 11

<210> SEQ ID NO 50
<211> LENGTH: 11
<212> TYPE: DNA
<213> ORGANISM: Artificial Sequence
<220> FEATURE:
<223> OTHER INFORMATION: Synthetic

<400> SEQUENCE: 50
aaaggaggat c 11

<210> SEQ ID NO 51
<211> LENGTH: 3
<212> TYPE: DNA
<213> ORGANISM: Artificial Sequence
<220> FEATURE:
<223> OTHER INFORMATION: Synthetic

<400> SEQUENCE: 51 ggc 3

<210> SEQ ID NO 52
<211> LENGTH: 3
<212> TYPE: DNA
<213> ORGANISM: Artificial Sequence
<220> FEATURE:
<223> OTHER INFORMATION: Synthetic

<400> SEQUENCE: 52 atc 3

<210> SEQ ID NO 53
<211> LENGTH: 3
<212> TYPE: DNA
<213> ORGANISM: Artificial Sequence
<220> FEATURE:
<223> OTHER INFORMATION: Synthetic

<400> SEQUENCE: 53 cgt 3

<210> SEQ ID NO 54
<211> LENGTH: 5
<212> TYPE: DNA
<213> ORGANISM: Artificial Sequence
<220> FEATURE:
<223> OTHER INFORMATION: Synthetic

<400> SEQUENCE: 54 aaaac 5

<210> SEQ ID NO 55
<211> LENGTH: 5
<212> TYPE: DNA
<213> ORGANISM: Artificial Sequence
<220> FEATURE:
<223> OTHER INFORMATION: Synthetic

<400> SEQUENCE: 55 ctggt 5

<210> SEQ ID NO 56
<211> LENGTH: 5
<212> TYPE: DNA
<213> ORGANISM: Artificial Sequence
<220> FEATURE:
<223> OTHER INFORMATION: Synthetic

<400> SEQUENCE: 56 tcaaa 5

<210> SEQ ID NO 57
<211> LENGTH: 5
<212> TYPE: DNA
<213> ORGANISM: Artificial Sequence
<220> FEATURE:
<223> OTHER INFORMATION: Synthetic

<400> SEQUENCE: 57 cagat 5

<210> SEQ ID NO 58
<211> LENGTH: 5
<212> TYPE: DNA
<213> ORGANISM: Artificial Sequence
<220> FEATURE:
<223> OTHER INFORMATION: Synthetic

<400> SEQUENCE: 58 tatcc 5

<210> SEQ ID NO 59

<211> LENGTH: 5
<212> TYPE: DNA
<213> ORGANISM: Artificial Sequence
<220> FEATURE:
<223> OTHER INFORMATION: Synthetic

<400> SEQUENCE: 59 gcgtt 5

<210> SEQ ID NO 60
<211> LENGTH: 5
<212> TYPE: DNA
<213> ORGANISM: Artificial Sequence
<220> FEATURE:
<223> OTHER INFORMATION: Synthetic

<400> SEQUENCE: 60 cattt 5

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 taatctccc 9

<210> SEQ ID NO 62
<211> LENGTH: 9
<212> TYPE: DNA
<213> ORGANISM: Artificial Sequence
<220> FEATURE:
<223> OTHER INFORMATION: Synthetic

<400> SEQUENCE: 62 gctctgctc 9

<210> SEQ ID NO 63
<211> LENGTH: 11
<212> TYPE: DNA
<213> ORGANISM: Artificial Sequence
<220> FEATURE:
<223> OTHER INFORMATION: Synthetic

<400> SEQUENCE: 63
cttccaggtt a 11

<210> SEQ ID NO 64
<211> LENGTH: 11
<212> TYPE: DNA
<213> ORGANISM: Artificial Sequence
<220> FEATURE:
<223> OTHER INFORMATION: Synthetic

<400> SEQUENCE: 64
gccacatggc t 11

<210> SEQ ID NO 65
<211> LENGTH: 12
<212> TYPE: DNA
<213> ORGANISM: Artificial Sequence
<220> FEATURE:
<223> OTHER INFORMATION: Synthetic

<400> SEQUENCE: 65
tccatctact cg 12

<210> SEQ ID NO 66
<211> LENGTH: 15
<212> TYPE: DNA
<213> ORGANISM: Artificial Sequence
<220> FEATURE:
<223> OTHER INFORMATION: Synthetic

<400> SEQUENCE: 66
gagagctgcg gagcc 15

<210> SEQ ID NO 67
<211> LENGTH: 5
<212> TYPE: DNA
<213> ORGANISM: Artificial Sequence
<220> FEATURE:
<223> OTHER INFORMATION: Synthetic

<400> SEQUENCE: 67 aagat 5

<210> SEQ ID NO 68
<211> LENGTH: 5
<212> TYPE: DNA
<213> ORGANISM: Artificial Sequence
<220> FEATURE:
<223> OTHER INFORMATION: Synthetic

<400> SEQUENCE: 68 aggcc 5

<210> SEQ ID NO 69
<211> LENGTH: 5
<212> TYPE: DNA
<213> ORGANISM: Artificial Sequence
<220> FEATURE:
<223> OTHER INFORMATION: Synthetic

<400> SEQUENCE: 69 gggat 5

<210> SEQ ID NO 70
<211> LENGTH: 8
<212> TYPE: DNA
<213> ORGANISM: Artificial Sequence
<220> FEATURE:
<223> OTHER INFORMATION: Synthetic

<400> SEQUENCE: 70 cgacgagg 8

<210> SEQ ID NO 71
<211> LENGTH: 3
<212> TYPE: DNA
<213> ORGANISM: Artificial Sequence
<220> FEATURE:
<223> OTHER INFORMATION: Synthetic

<400> SEQUENCE: 71 gac 3

<210> SEQ ID NO 72
<211> LENGTH: 5
<212> TYPE: DNA

<213> ORGANISM: Artificial Sequence
<220> FEATURE:
<223> OTHER INFORMATION: Synthetic

<400> SEQUENCE: 72 tagta 5

<210> SEQ ID NO 73
<211> LENGTH: 5
<212> TYPE: DNA
<213> ORGANISM: Artificial Sequence
<220> FEATURE:
<223> OTHER INFORMATION: Synthetic

<400> SEQUENCE: 73 atgat 5

<210> SEQ ID NO 74
<211> LENGTH: 6
<212> TYPE: DNA
<213> ORGANISM: Artificial Sequence
<220> FEATURE:
<223> OTHER INFORMATION: Synthetic

<400> SEQUENCE: 74 agtgag 6

<210> SEQ ID NO 75
<211> LENGTH: 22
<212> TYPE: DNA
<213> ORGANISM: Artificial Sequence
<220> FEATURE:
<223> OTHER INFORMATION: Synthetic

<400> SEQUENCE: 75
ggatcctggt gaccgtgctg gt 22

<210> SEQ ID NO 76
<211> LENGTH: 5
<212> TYPE: DNA
<213> ORGANISM: Artificial Sequence
<220> FEATURE:
<223> OTHER INFORMATION: Synthetic

<400> SEQUENCE: 76 atgat 5

<210> SEQ ID NO 77
<211> LENGTH: 5
<212> TYPE: DNA
<213> ORGANISM: Artificial Sequence
<220> FEATURE:
<223> OTHER INFORMATION: Synthetic

<400> SEQUENCE: 77 atcag 5

<210> SEQ ID NO 78
<211> LENGTH: 5
<212> TYPE: DNA
<213> ORGANISM: Artificial Sequence
<220> FEATURE:
<223> OTHER INFORMATION: Synthetic

<400> SEQUENCE: 78 aaggc 5

<210> SEQ ID NO 79
<211> LENGTH: 6
<212> TYPE: DNA
<213> ORGANISM: Artificial Sequence
<220> FEATURE:
<223> OTHER INFORMATION: Synthetic

<400> SEQUENCE: 79 ttctca 6

<210> SEQ ID NO 80
<211> LENGTH: 18
<212> TYPE: DNA
<213> ORGANISM: Artificial Sequence
<220> FEATURE:
<223> OTHER INFORMATION: Synthetic

<400> SEQUENCE: 80
aaccacgtcc tcagcttc 18

<210> SEQ ID NO 81
<211> LENGTH: 19
<212> TYPE: DNA
<213> ORGANISM: Artificial Sequence
<220> FEATURE:
<223> OTHER INFORMATION: Synthetic

<400> SEQUENCE: 81
actcctgatc agacatgac 19

<210> SEQ ID NO 82
<211> LENGTH: 32
<212> TYPE: DNA
<213> ORGANISM: Artificial Sequence
<220> FEATURE:
<223> OTHER INFORMATION: Synthetic

<400> SEQUENCE: 82
tgagctgatt ggtgtcgatg gcaaccagat ta 32

<210> SEQ ID NO 83
<211> LENGTH: 10
<212> TYPE: DNA
<213> ORGANISM: Artificial Sequence
<220> FEATURE:
<223> OTHER INFORMATION: Synthetic

<400> SEQUENCE: 83
cgcgcaggct 10

<210> SEQ ID NO 84
<211> LENGTH: 5
<212> TYPE: DNA
<213> ORGANISM: Artificial Sequence
<220> FEATURE:
<223> OTHER INFORMATION: Synthetic

<400> SEQUENCE: 84 gcact 5

<210> SEQ ID NO 85
<211> LENGTH: 3
<212> TYPE: DNA
<213> ORGANISM: Artificial Sequence
<220> FEATURE:

<223> OTHER INFORMATION: Synthetic

<400> SEQUENCE: 85 tag 3

<210> SEQ ID NO 86
<211> LENGTH: 4
<212> TYPE: DNA
<213> ORGANISM: Artificial Sequence
<220> FEATURE:
<223> OTHER INFORMATION: Synthetic

<400> SEQUENCE: 86 agac 4

<210> SEQ ID NO 87
<211> LENGTH: 5
<212> TYPE: DNA
<213> ORGANISM: Artificial Sequence
<220> FEATURE:
<223> OTHER INFORMATION: Synthetic

<400> SEQUENCE: 87 gcagc 5

<210> SEQ ID NO 88
<211> LENGTH: 6
<212> TYPE: DNA
<213> ORGANISM: Artificial Sequence
<220> FEATURE:
<223> OTHER INFORMATION: Synthetic

<400> SEQUENCE: 88 tggagc 6

<210> SEQ ID NO 89
<211> LENGTH: 10
<212> TYPE: DNA
<213> ORGANISM: Artificial Sequence
<220> FEATURE:
<223> OTHER INFORMATION: Synthetic

<400> SEQUENCE: 89
atccacactg 10

<210> SEQ ID NO 90
<211> LENGTH: 16
<212> TYPE: DNA
<213> ORGANISM: Artificial Sequence
<220> FEATURE:
<223> OTHER INFORMATION: Synthetic

<400> SEQUENCE: 90
agagggagag ggaggc 16

<210> SEQ ID NO 91
<211> LENGTH: 5
<212> TYPE: DNA
<213> ORGANISM: Artificial Sequence
<220> FEATURE:
<223> OTHER INFORMATION: Synthetic

<400> SEQUENCE: 91 taaca 5

<210> SEQ ID NO 92
<211> LENGTH: 5
<212> TYPE: DNA
<213> ORGANISM: Artificial Sequence
<220> FEATURE:
<223> OTHER INFORMATION: Synthetic

<400> SEQUENCE: 92 cggga 5

<210> SEQ ID NO 93
<211> LENGTH: 6
<212> TYPE: DNA
<213> ORGANISM: Artificial Sequence
<220> FEATURE:
<223> OTHER INFORMATION: Synthetic

<400> SEQUENCE: 93 cctgct 6

<210> SEQ ID NO 94
<211> LENGTH: 19
<212> TYPE: DNA
<213> ORGANISM: Artificial Sequence
<220> FEATURE:
<223> OTHER INFORMATION: Synthetic

<400> SEQUENCE: 94
cggaggcgcc gcctgggtt 19

<210> SEQ ID NO 95
<211> LENGTH: 5
<212> TYPE: DNA
<213> ORGANISM: Artificial Sequence
<220> FEATURE:
<223> OTHER INFORMATION: Synthetic

<400> SEQUENCE: 95 ggtat 5

<210> SEQ ID NO 96
<211> LENGTH: 16
<212> TYPE: DNA
<213> ORGANISM: Artificial Sequence
<220> FEATURE:
<223> OTHER INFORMATION: Synthetic

<400> SEQUENCE: 96
tcggcccggc ggcaca 16

<210> SEQ ID NO 97
<211> LENGTH: 3
<212> TYPE: DNA
<213> ORGANISM: Artificial Sequence
<220> FEATURE:
<223> OTHER INFORMATION: Synthetic

<400> SEQUENCE: 97 cat 3

<210> SEQ ID NO 98
<211> LENGTH: 4
<212> TYPE: DNA
<213> ORGANISM: Artificial Sequence
<220> FEATURE:
<223> OTHER INFORMATION: Synthetic

<400> SEQUENCE: 98 gtga 4

<210> SEQ ID NO 99
<211> LENGTH: 5
<212> TYPE: DNA
<213> ORGANISM: Artificial Sequence
<220> FEATURE:
<223> OTHER INFORMATION: Synthetic

<400> SEQUENCE: 99 ctgat 5

<210> SEQ ID NO 100
<211> LENGTH: 5
<212> TYPE: DNA
<213> ORGANISM: Artificial Sequence
<220> FEATURE:
<223> OTHER INFORMATION: Synthetic

<400> SEQUENCE: 100 ctgtt 5

<210> SEQ ID NO 101
<211> LENGTH: 5
<212> TYPE: DNA
<213> ORGANISM: Artificial Sequence
<220> FEATURE:
<223> OTHER INFORMATION: Synthetic

<400> SEQUENCE: 101 tgtca 5

<210> SEQ ID NO 102
<211> LENGTH: 5
<212> TYPE: DNA
<213> ORGANISM: Artificial Sequence
<220> FEATURE:
<223> OTHER INFORMATION: Synthetic

<400> SEQUENCE: 102 gtgaa 5

<210> SEQ ID NO 103
<211> LENGTH: 5
<212> TYPE: DNA
<213> ORGANISM: Artificial Sequence
<220> FEATURE:
<223> OTHER INFORMATION: Synthetic

<400> SEQUENCE: 103 tacag 5

<210> SEQ ID NO 104
<211> LENGTH: 11
<212> TYPE: DNA
<213> ORGANISM: Artificial Sequence
<220> FEATURE:
<223> OTHER INFORMATION: Synthetic

<400> SEQUENCE: 104
gcagatcctc c 11

<210> SEQ ID NO 105
<211> LENGTH: 6

```
<212> TYPE: DNA
<213> ORGANISM: Artificial Sequence
<220> FEATURE:
<223> OTHER INFORMATION: Synthetic

<400> SEQUENCE: 105

ggcgtc                                                                6


<210> SEQ ID NO 106
<211> LENGTH: 6
<212> TYPE: DNA
<213> ORGANISM: Artificial Sequence
<220> FEATURE:
<223> OTHER INFORMATION: Synthetic

<400> SEQUENCE: 106

gcggct                                                                6


<210> SEQ ID NO 107
<211> LENGTH: 3
<212> TYPE: DNA
<213> ORGANISM: Artificial Sequence
<220> FEATURE:
<223> OTHER INFORMATION: Synthetic

<400> SEQUENCE: 107

atg                                                                   3


<210> SEQ ID NO 108
<211> LENGTH: 5
<212> TYPE: DNA
<213> ORGANISM: Artificial Sequence
<220> FEATURE:
<223> OTHER INFORMATION: Synthetic

<400> SEQUENCE: 108

ctgct                                                                 5


<210> SEQ ID NO 109
<211> LENGTH: 26
<212> TYPE: DNA
<213> ORGANISM: Artificial Sequence
<220> FEATURE:
<223> OTHER INFORMATION: Synthetic

<400> SEQUENCE: 109

ccgtggcact gacccgagac tctgag                                         26


<210> SEQ ID NO 110
<211> LENGTH: 8
<212> TYPE: DNA
<213> ORGANISM: Artificial Sequence
<220> FEATURE:
<223> OTHER INFORMATION: Synthetic

<400> SEQUENCE: 110

ctcaaaca                                                              8


<210> SEQ ID NO 111
<211> LENGTH: 24
<212> TYPE: DNA
<213> ORGANISM: Artificial Sequence
<220> FEATURE:
<223> OTHER INFORMATION: Synthetic

<400> SEQUENCE: 111
```

gagctcagcg tagacctccg cgcc 24

<210> SEQ ID NO 112
<211> LENGTH: 3
<212> TYPE: DNA
<213> ORGANISM: Artificial Sequence
<220> FEATURE:
<223> OTHER INFORMATION: Synthetic

<400> SEQUENCE: 112 ggt 3

<210> SEQ ID NO 113
<211> LENGTH: 3
<212> TYPE: DNA
<213> ORGANISM: Artificial Sequence
<220> FEATURE:
<223> OTHER INFORMATION: Synthetic

<400> SEQUENCE: 113 tga 3

<210> SEQ ID NO 114
<211> LENGTH: 3
<212> TYPE: DNA
<213> ORGANISM: Artificial Sequence
<220> FEATURE:
<223> OTHER INFORMATION: Synthetic

<400> SEQUENCE: 114 ggt 3

<210> SEQ ID NO 115
<211> LENGTH: 3
<212> TYPE: DNA
<213> ORGANISM: Artificial Sequence
<220> FEATURE:
<223> OTHER INFORMATION: Synthetic

<400> SEQUENCE: 115 cta 3

<210> SEQ ID NO 116
<211> LENGTH: 3
<212> TYPE: DNA
<213> ORGANISM: Artificial Sequence
<220> FEATURE:
<223> OTHER INFORMATION: Synthetic

<400> SEQUENCE: 116 gga 3

<210> SEQ ID NO 117
<211> LENGTH: 3
<212> TYPE: DNA
<213> ORGANISM: Artificial Sequence
<220> FEATURE:
<223> OTHER INFORMATION: Synthetic

<400> SEQUENCE: 117 tcg 3

<210> SEQ ID NO 118
<211> LENGTH: 3
<212> TYPE: DNA
<213> ORGANISM: Artificial Sequence
<220> FEATURE:
<223> OTHER INFORMATION: Synthetic

<400> SEQUENCE: 118 gac 3

<210> SEQ ID NO 119
<211> LENGTH: 5
<212> TYPE: DNA
<213> ORGANISM: Artificial Sequence
<220> FEATURE:
<223> OTHER INFORMATION: Synthetic

<400> SEQUENCE: 119 ccgct 5

<210> SEQ ID NO 120
<211> LENGTH: 5
<212> TYPE: DNA
<213> ORGANISM: Artificial Sequence
<220> FEATURE:
<223> OTHER INFORMATION: Synthetic

<400> SEQUENCE: 120 taatg 5

<210> SEQ ID NO 121
<211> LENGTH: 5
<212> TYPE: DNA
<213> ORGANISM: Artificial Sequence
<220> FEATURE:
<223> OTHER INFORMATION: Synthetic

<400> SEQUENCE: 121 ttgaa 5

<210> SEQ ID NO 122
<211> LENGTH: 5
<212> TYPE: DNA
<213> ORGANISM: Artificial Sequence
<220> FEATURE:
<223> OTHER INFORMATION: Synthetic

<400> SEQUENCE: 122 caaca 5

<210> SEQ ID NO 123
<211> LENGTH: 5
<212> TYPE: DNA
<213> ORGANISM: Artificial Sequence
<220> FEATURE:
<223> OTHER INFORMATION: Synthetic

<400> SEQUENCE: 123 catta 5

<210> SEQ ID NO 124
<211> LENGTH: 5
<212> TYPE: DNA
<213> ORGANISM: Artificial Sequence
<220> FEATURE:
<223> OTHER INFORMATION: Synthetic

<400> SEQUENCE: 124 gaatc 5

<210> SEQ ID NO 125
<211> LENGTH: 5
<212> TYPE: DNA
<213> ORGANISM: Artificial Sequence
<220> FEATURE:
<223> OTHER INFORMATION: Synthetic

<400> SEQUENCE: 125 acttt 5

<210> SEQ ID NO 126
<211> LENGTH: 5
<212> TYPE: DNA
<213> ORGANISM: Artificial Sequence
<220> FEATURE:
<223> OTHER INFORMATION: Synthetic

<400> SEQUENCE: 126 ctcag 5

<210> SEQ ID NO 127
<211> LENGTH: 5
<212> TYPE: DNA
<213> ORGANISM: Artificial Sequence
<220> FEATURE:
<223> OTHER INFORMATION: Synthetic

<400> SEQUENCE: 127 ctgat 5

<210> SEQ ID NO 128
<211> LENGTH: 5
<212> TYPE: DNA
<213> ORGANISM: Artificial Sequence
<220> FEATURE:
<223> OTHER INFORMATION: Synthetic

<400> SEQUENCE: 128 ggaac 5

<210> SEQ ID NO 129
<211> LENGTH: 5
<212> TYPE: DNA
<213> ORGANISM: Artificial Sequence
<220> FEATURE:
<223> OTHER INFORMATION: Synthetic

<400> SEQUENCE: 129 cgaat 5

<210> SEQ ID NO 130
<211> LENGTH: 5
<212> TYPE: DNA
<213> ORGANISM: Artificial Sequence
<220> FEATURE:
<223> OTHER INFORMATION: Synthetic

<400> SEQUENCE: 130 agggt 5

<210> SEQ ID NO 131
<211> LENGTH: 6
<212> TYPE: DNA
<213> ORGANISM: Artificial Sequence
<220> FEATURE:
<223> OTHER INFORMATION: Synthetic

<400> SEQUENCE: 131 atgccg 6

<210> SEQ ID NO 132
<211> LENGTH: 7
<212> TYPE: DNA
<213> ORGANISM: Artificial Sequence
<220> FEATURE:
<223> OTHER INFORMATION: Synthetic

<400> SEQUENCE: 132 catccat 7

<210> SEQ ID NO 133
<211> LENGTH: 7
<212> TYPE: DNA
<213> ORGANISM: Artificial Sequence
<220> FEATURE:
<223> OTHER INFORMATION: Synthetic

<400> SEQUENCE: 133 tttgggc 7

<210> SEQ ID NO 134
<211> LENGTH: 8
<212> TYPE: DNA
<213> ORGANISM: Artificial Sequence
<220> FEATURE:
<223> OTHER INFORMATION: Synthetic

<400> SEQUENCE: 134 ggctctta 8

<210> SEQ ID NO 135
<211> LENGTH: 9
<212> TYPE: DNA
<213> ORGANISM: Artificial Sequence
<220> FEATURE:
<223> OTHER INFORMATION: Synthetic

<400> SEQUENCE: 135 caagaaaaa 9

<210> SEQ ID NO 136
<211> LENGTH: 9
<212> TYPE: DNA
<213> ORGANISM: Artificial Sequence
<220> FEATURE:
<223> OTHER INFORMATION: Synthetic

<400> SEQUENCE: 136 aaatctgac 9

<210> SEQ ID NO 137
<211> LENGTH: 12
<212> TYPE: DNA
<213> ORGANISM: Artificial Sequence
<220> FEATURE:
<223> OTHER INFORMATION: Synthetic

<400> SEQUENCE: 137
gtggtccgcc tc 12

<210> SEQ ID NO 138

<211> LENGTH: 18
<212> TYPE: DNA
<213> ORGANISM: Artificial Sequence
<220> FEATURE:
<223> OTHER INFORMATION: Synthetic

<400> SEQUENCE: 138
gagcaagttg gggtgtgc 18

<210> SEQ ID NO 139
<211> LENGTH: 19
<212> TYPE: DNA
<213> ORGANISM: Artificial Sequence
<220> FEATURE:
<223> OTHER INFORMATION: Synthetic

<400> SEQUENCE: 139
cgactgcaag gacaaatct 19

<210> SEQ ID NO 140
<211> LENGTH: 20
<212> TYPE: DNA
<213> ORGANISM: Artificial Sequence
<220> FEATURE:
<223> OTHER INFORMATION: Synthetic

<400> SEQUENCE: 140
ttcaaaaggg acatagaaaa 20

<210> SEQ ID NO 141
<211> LENGTH: 21
<212> TYPE: DNA
<213> ORGANISM: Artificial Sequence
<220> FEATURE:
<223> OTHER INFORMATION: Synthetic

<400> SEQUENCE: 141
gctgatctgc cgccgcttct c 21

<210> SEQ ID NO 142
<211> LENGTH: 24
<212> TYPE: DNA
<213> ORGANISM: Artificial Sequence
<220> FEATURE:
<223> OTHER INFORMATION: Synthetic

<400> SEQUENCE: 142
gcgctctcct cccgctggaa tcca 24

<210> SEQ ID NO 143
<211> LENGTH: 29
<212> TYPE: DNA
<213> ORGANISM: Artificial Sequence
<220> FEATURE:
<223> OTHER INFORMATION: Synthetic

<400> SEQUENCE: 143
cagagtttat caccaattcc ccttcaata 29

<210> SEQ ID NO 144
<211> LENGTH: 8
<212> TYPE: DNA
<213> ORGANISM: Artificial Sequence
<220> FEATURE:
<223> OTHER INFORMATION: Synthetic

<400> SEQUENCE: 144 cgaggtgt 8

<210> SEQ ID NO 145
<211> LENGTH: 16
<212> TYPE: DNA
<213> ORGANISM: Artificial Sequence
<220> FEATURE:
<223> OTHER INFORMATION: Synthetic

<400> SEQUENCE: 145
ccagcagggg aggccc 16

<210> SEQ ID NO 146
<211> LENGTH: 4
<212> TYPE: DNA
<213> ORGANISM: Artificial Sequence
<220> FEATURE:
<223> OTHER INFORMATION: Synthetic

<400> SEQUENCE: 146 gata 4

<210> SEQ ID NO 147
<211> LENGTH: 4
<212> TYPE: DNA
<213> ORGANISM: Artificial Sequence
<220> FEATURE:
<223> OTHER INFORMATION: Synthetic

<400> SEQUENCE: 147 gcct 4

<210> SEQ ID NO 148
<211> LENGTH: 6
<212> TYPE: DNA
<213> ORGANISM: Artificial Sequence
<220> FEATURE:
<223> OTHER INFORMATION: Synthetic

<400> SEQUENCE: 148 cccggg 6

<210> SEQ ID NO 149
<211> LENGTH: 17
<212> TYPE: DNA
<213> ORGANISM: Artificial Sequence
<220> FEATURE:
<223> OTHER INFORMATION: Synthetic

<400> SEQUENCE: 149
tgggcctccc ctgctgg 17

<210> SEQ ID NO 150
<211> LENGTH: 20
<212> TYPE: DNA
<213> ORGANISM: Artificial Sequence
<220> FEATURE:
<223> OTHER INFORMATION: Synthetic

<400> SEQUENCE: 150
agctgagctg cgaggtgtcg 20

<210> SEQ ID NO 151
<211> LENGTH: 20
<212> TYPE: DNA

<213> ORGANISM: Artificial Sequence
<220> FEATURE:
<223> OTHER INFORMATION: Synthetic

<400> SEQUENCE: 151
cagcagggga ggcccccagc 20

<210> SEQ ID NO 152
<211> LENGTH: 44
<212> TYPE: DNA
<213> ORGANISM: Artificial Sequence
<220> FEATURE:
<223> OTHER INFORMATION: Synthetic

<400> SEQUENCE: 152
uaauuucuac uaaguguaga ucagucaggg ccauaggaua gaua 44

<210> SEQ ID NO 153
<211> LENGTH: 44
<212> TYPE: DNA
<213> ORGANISM: Artificial Sequence
<220> FEATURE:
<223> OTHER INFORMATION: Synthetic

<400> SEQUENCE: 153
uaauuucuac uaaguguaga uagucagggc cauaggauag auau 44

<210> SEQ ID NO 154
<211> LENGTH: 43
<212> TYPE: DNA
<213> ORGANISM: Artificial Sequence
<220> FEATURE:
<223> OTHER INFORMATION: Synthetic

<400> SEQUENCE: 154
uaauuucuac uguuguagau cagucagggc cauaggauag aua 43

<210> SEQ ID NO 155
<211> LENGTH: 6
<212> TYPE: DNA
<213> ORGANISM: Artificial Sequence
<220> FEATURE:
<223> OTHER INFORMATION: Synthetic

<400> SEQUENCE: 155 cccggg 6

<210> SEQ ID NO 156
<211> LENGTH: 6
<212> TYPE: DNA
<213> ORGANISM: Artificial Sequence
<220> FEATURE:
<223> OTHER INFORMATION: Synthetic

<400> SEQUENCE: 156 aggagg 6

<210> SEQ ID NO 157
<211> LENGTH: 10
<212> TYPE: DNA
<213> ORGANISM: Artificial Sequence
<220> FEATURE:
<223> OTHER INFORMATION: Synthetic

<400> SEQUENCE: 157
aaggaggatc 10

<210> SEQ ID NO 158
<211> LENGTH: 455
<212> TYPE: DNA
<213> ORGANISM: Artificial Sequence
<220> FEATURE:
<223> OTHER INFORMATION: Synthetic

<400> SEQUENCE: 158
gtgagccact gcgcccagca gattcaagct ttttaaatgg aattttgagc tgatttagtt 60
gagacttacg tgcttagttg ataaatttta attttatact aaaatatttt acattaattc 120
aagttaattt atttcagatt gaatttagtg gaagcttttg tagaagatgc agaattgagg 180
cagactttac aagaagattt acttcgtcga ttcccagatc ttaaccgact tgccaagaag 240
tttcaaagac aagcagcaaa cttacaagat tgttaccgac tctatcaggg tataaatcaa 300
ctacctaatg ttatacaggc tctggaaaaa catgaaggta acaagtgatt ttgttttttt 360
gttttccttc aactcataca atatatactt ggcaatgtgc tgtcctcata aagttggtgg 420
tggtgactca ctcttaggac acattcagat ttctt 455

<210> SEQ ID NO 159
<211> LENGTH: 338
<212> TYPE: DNA
<213> ORGANISM: Artificial Sequence
<220> FEATURE:
<223> OTHER INFORMATION: Synthetic

<400> SEQUENCE: 159
gagcttatca ggttctccat tggcaggcag ggctctaagt gcagtaactt gatttgctgt 60
tgtatttgct taggaagagc agcacttcag aaaagagtga tggcactgct gaggcgcatt 120
gagcatccca ctgcaggaaa cactgaggta tgcccttagc aacagaaaca cccctcccag 180
gcgcccaccc tcaatttgga agcctcttgt tacatatgtg tgatcaggaa tagcttttga 240
agtaaatcca agatacgtgc atattacaag tataatatct gagtatttaa tatacatcaa 300
gtttgaaact tggctgtagc tgattgatgt ttagctct 338

<210> SEQ ID NO 160
<211> LENGTH: 413
<212> TYPE: DNA
<213> ORGANISM: Artificial Sequence
<220> FEATURE:
<223> OTHER INFORMATION: Synthetic

<400> SEQUENCE: 160
tgggtacgag tgtctgcgta tatctgtatg cttatttggc tctatgcctg tgggtgcact 60
tactctgtgt gtttagatca gtcagtttca tctctctagg gggtctgtct tctgggcatt 120
gatggcaaat cattaatgta tttgttcttt ctttaggttt tattgactga taccaatact 180
caatttgtag aacaaaccat agctataatg aagaacttgc tagataatca tactgaaggc 240
agctctgaac atctagggca agctagcatt gaaacaatga tgttaaatct ggtcaggtaa 300
gcattctact gaaatgtagc agaaacattt taagagataa gaaaaacctc ttacacactg 360
atactggtag taattgataa aataactggc cattctttac tgcacacaaa cta 413

<210> SEQ ID NO 161
<211> LENGTH: 23
<212> TYPE: DNA
<213> ORGANISM: Artificial Sequence
<220> FEATURE:

<223> OTHER INFORMATION: Synthetic

<400> SEQUENCE: 161
accggttccg gcggccgggg ctg 23

<210> SEQ ID NO 162
<211> LENGTH: 455
<212> TYPE: DNA
<213> ORGANISM: Artificial Sequence
<220> FEATURE:
<223> OTHER INFORMATION: Synthetic

<400> SEQUENCE: 162
gtgagccact gcgcccagca gattcaagct ttttaaatgg aattttgagc tgatttagtt 60
gagacttacg tgcttagttg ataaatttta attttatact aaaatatttt acattaattc 120
aagttaattt atttcagatt gaatttagtg gaagcttttg tagaagatgc agaattgagg 180
cagactttac aagaagattt acttcgtcga ttcccagatc ttaaccgact tgccaagaag 240
tttcaaagac aagcagcaaa cttacaagat tgttaccgac tctatcaggg tataaatcaa 300
ctacctaatg ttatacaggc tctggaaaaa catgaaggta acaagtgatt ttgttttttt 360
gttttccttc aactcataca atatatactt ggcaatgtgc tgtcctcata aagttggtgg 420
tggtgactca ctcttaggac acattcagat ttctt 455

<210> SEQ ID NO 163
<211> LENGTH: 116
<212> TYPE: DNA
<213> ORGANISM: Artificial Sequence
<220> FEATURE:
<223> OTHER INFORMATION: Synthetic

<400> SEQUENCE: 163
ttgggagcta acggcttgga gcttctttcc agggatgggg acctggaatt tgagtactgg 60
tagacttttc gttgttcaaa ccattccttc acaaattcct gaggaaggcc cacagc 116

<210> SEQ ID NO 164
<211> LENGTH: 178
<212> TYPE: DNA
<213> ORGANISM: Artificial Sequence
<220> FEATURE:
<223> OTHER INFORMATION: Synthetic

<400> SEQUENCE: 164
taccttgggc ctgggccgca gagctgtgag aataccccag ggccaggagc gcagtctcca 60
ccagctggct aaaaagcaca tctttccgca ccaggacaaa ctcggcgtgt tcttctctgt 120
tgtcatattc aagagagccg tccaactgct ccacgacaca aaagacagga atcatcaa 178

<210> SEQ ID NO 165
<211> LENGTH: 125
<212> TYPE: DNA
<213> ORGANISM: Artificial Sequence
<220> FEATURE:
<223> OTHER INFORMATION: Synthetic

<400> SEQUENCE: 165
gtgcgcgggc ggcggccgga agggcctctt catgcggcgg cggcgccggt agttgccctt 60
ctcgaacatg tcttcgcagg ccgggtccag cgtccagtag ttgcccttgc gctcgccgcc 120
gccct 125

-continued

<210> SEQ ID NO 166
<211> LENGTH: 276
<212> TYPE: DNA
<213> ORGANISM: Artificial Sequence
<220> FEATURE:
<223> OTHER INFORMATION: Synthetic

<400> SEQUENCE: 166
ccgggctgga gagggggatg ttgaggaggc tgggggtggg ggcggggcat cgagggagct 60
cctggtactg gcggccccga ctgtccccccc agaagctgaa aatgttggac actcctgaga 120
aggcgcctgc agccagagag cagagctggg tgagcggggt agacgcacca ccgctgccac 180
gcccggtcct ccctcgcccg cccgtcgccc gggatacctg acagggggtt gcaagtgtcg 240
ctgctcttct cgcagtcctc catcaggggc tcccca 276

<210> SEQ ID NO 167
<211> LENGTH: 338
<212> TYPE: DNA
<213> ORGANISM: Artificial Sequence
<220> FEATURE:
<223> OTHER INFORMATION: Synthetic

<400> SEQUENCE: 167
gagcttatca ggttctccat tggcaggcag ggctctaagt gcagtaactt gatttgctgt 60
tgtatttgct taggaagagc agcacttcag aaaagagtga tggcactgct gaggcgcatt 120
gagcatccca ctgcaggaaa cactgaggta tgcccttagc aacagaaaca cccctcccag 180
gcgcccaccc tcaatttgga agcctcttgt tacatatgtg tgatcaggaa tagcttttga 240
agtaaatcca agatacgtgc atattacaag tataatatct gagtatttaa tatacatcaa 300
gtttgaaact tggctgtagc tgattgatgt ttagctct 338

<210> SEQ ID NO 168
<211> LENGTH: 413
<212> TYPE: DNA
<213> ORGANISM: Artificial Sequence
<220> FEATURE:
<223> OTHER INFORMATION: Synthetic

<400> SEQUENCE: 168
tgggtacgag tgtctgcgta tatctgtatg cttatttggc tctatgcctg tgggtgcact 60
tactctgtgt gtttagatca gtcagtttca tctctctagg gggtctgtct tctgggcatt 120
gatggcaaat cattaatgta tttgttcttt ctttaggttt tattgactga taccaatact 180
caatttgtag aacaaaccat agctataatg aagaacttgc tagataatca tactgaaggc 240
agctctgaac atctagggca agctagcatt gaaacaatga tgttaaatct ggtcaggtaa 300
gcattctact gaaatgtagc agaaacattt taagagataa gaaaaacctc ttacacactg 360
atactggtag taattgataa aataactggc cattctttac tgcacacaaa cta 413

<210> SEQ ID NO 169
<211> LENGTH: 1059
<212> TYPE: DNA
<213> ORGANISM: Artificial Sequence
<220> FEATURE:
<223> OTHER INFORMATION: Synthetic

<400> SEQUENCE: 169
cccaattcaa tgtagacaga cgtcttttga ggttgtatcc gctgctttgt cctcagagtt 60
ctcacagttc caaggttaga gagttggaca ctgagactgg tttcctgcta aacagtatgg 120

```
taaagaacag tcaagcaatt gttggccagt tctgtgcttt tcctcctgaa gagaaacttg    180

acaccatgga caaaataaat tgaccatcat cagtcagcta acatgtatga tgcctggaaa    240

aaatgcccag gaatttacac actaaaatgt ctggggctgg gagcggtagc tcatgcctat    300

aatcccagca ctttgggagg ctggagcagg actgcttgag gccaggagtt caagaccagc    360

ataagcaaca gagtgagacc cagtctctac aaaataatag tagtagtaat aataaaatgt    420

gtgggatatg tgtgatttga attttttttt ctgttgtctt aaatttttca aacctgatta    480

tgtattattt gtgtaatttt tgaagtatta atatagcata ttttgaagct gatacttgat    540

atacattcca atcacatctg ataacttttt tttttgtttt ggggggtgta cagagtcctg    600

ctctgtcacc caggctggag tgcagtggcg caatctcagc tcactgcaac ctccgcctcc    660

taagttcaag agattctcct gcctcagcct cctgagtagc tgggtctaca agcgtgtgca    720

actatgcctg gctaatttgt gtgtgtgtgt gtatatatat atacatatat atgtgtgtgt    780

gtgtgtatat atatatataa catatatata acatatatat attatatata tataacatat    840

atataacata tatatatgtt atatatatat aacatatata taacatatat atatatatat    900

atataatata tatatatata tatatatatg taatcccagc actttgggat atatgtgtat    960

atatgttttt tttttttgag acagaatctt gctctgttgc caggctagag tgcagtggcg   1020

tgatctcggc acactgcaac ctccacctcc ctggttcag                          1059
```

<210> SEQ ID NO 170
<211> LENGTH: 104
<212> TYPE: DNA
<213> ORGANISM: Artificial Sequence
<220> FEATURE:
<223> OTHER INFORMATION: Synthetic

<400> SEQUENCE: 170

```
gggggccatt gtggaaaaga gcctgcaggg agagcaaaca gcgcggtcat ggcctcggga     60

gctgtgcgcg gcgcctcggg cagcgtctcc cgccgcttgt cgcc                     104
```

<210> SEQ ID NO 171
<211> LENGTH: 52
<212> TYPE: DNA
<213> ORGANISM: Artificial Sequence
<220> FEATURE:
<223> OTHER INFORMATION: Synthetic

<400> SEQUENCE: 171

```
ctgccgctgc ctgaaaccgt acagcttgca gccccatgga cagcaccagg tg             52
```

<210> SEQ ID NO 172
<211> LENGTH: 52
<212> TYPE: DNA
<213> ORGANISM: Artificial Sequence
<220> FEATURE:
<223> OTHER INFORMATION: Synthetic

<400> SEQUENCE: 172

```
cgtggctgga gggatcacca atcccaatca tgccaggggg gtatgctctg gc             52
```

<210> SEQ ID NO 173
<211> LENGTH: 52
<212> TYPE: DNA
<213> ORGANISM: Artificial Sequence
<220> FEATURE:
<223> OTHER INFORMATION: Synthetic

<400> SEQUENCE: 173
tgtgggagat gccggccgag aagcgttatc ttcggggccg tgctgctctt tt 52

<210> SEQ ID NO 174
<211> LENGTH: 52
<212> TYPE: DNA
<213> ORGANISM: Artificial Sequence
<220> FEATURE:
<223> OTHER INFORMATION: Synthetic

<400> SEQUENCE: 174
tgtggcctac catctgggcc gtgttaagag aggtgaggaa ggctcagttt tc 52

<210> SEQ ID NO 175
<211> LENGTH: 52
<212> TYPE: DNA
<213> ORGANISM: Artificial Sequence
<220> FEATURE:
<223> OTHER INFORMATION: Synthetic

<400> SEQUENCE: 175
tccagtcccc ctaattagaa gagccttggg aacttggttt aatgaacaca ca 52

<210> SEQ ID NO 176
<211> LENGTH: 52
<212> TYPE: DNA
<213> ORGANISM: Artificial Sequence
<220> FEATURE:
<223> OTHER INFORMATION: Synthetic

<400> SEQUENCE: 176
aaaactaatg agggatgcca aaatcttatc aggtaaggtt aaagatgatt tt 52

<210> SEQ ID NO 177
<211> LENGTH: 52
<212> TYPE: DNA
<213> ORGANISM: Artificial Sequence
<220> FEATURE:
<223> OTHER INFORMATION: Synthetic

<400> SEQUENCE: 177
ttacgatgtc ccagaggaag ttggtccacc cagtaggtgg tggggctcac tc 52

<210> SEQ ID NO 178
<211> LENGTH: 52
<212> TYPE: DNA
<213> ORGANISM: Artificial Sequence
<220> FEATURE:
<223> OTHER INFORMATION: Synthetic

<400> SEQUENCE: 178
gaactgacca atgagaatgc ccagtaactg tcctttcagc tgtgaaacac aa 52

<210> SEQ ID NO 179
<211> LENGTH: 52
<212> TYPE: DNA
<213> ORGANISM: Artificial Sequence
<220> FEATURE:
<223> OTHER INFORMATION: Synthetic

<400> SEQUENCE: 179
tgataatgat aagaactaga actgtggagg actgccacgt gactgtattc ct 52

<210> SEQ ID NO 180
<211> LENGTH: 52
<212> TYPE: DNA

<213> ORGANISM: Artificial Sequence
<220> FEATURE:
<223> OTHER INFORMATION: Synthetic

<400> SEQUENCE: 180
cccacgacac tgcctgaagt agaagccaat cctgtgaggc tgccagccat ga 52

<210> SEQ ID NO 181
<211> LENGTH: 52
<212> TYPE: DNA
<213> ORGANISM: Artificial Sequence
<220> FEATURE:
<223> OTHER INFORMATION: Synthetic

<400> SEQUENCE: 181
ggtgcatatt ttgaatatcc tttcgttact ttaaagcctc tgtaataaga ct 52

<210> SEQ ID NO 182
<211> LENGTH: 52
<212> TYPE: DNA
<213> ORGANISM: Artificial Sequence
<220> FEATURE:
<223> OTHER INFORMATION: Synthetic

<400> SEQUENCE: 182
gatgagcctt ttgattttgg cactcaagag caccaccgag aagatccaca ac 52

<210> SEQ ID NO 183
<211> LENGTH: 52
<212> TYPE: DNA
<213> ORGANISM: Artificial Sequence
<220> FEATURE:
<223> OTHER INFORMATION: Synthetic

<400> SEQUENCE: 183
aagggcagtt cccagcggcc tcaccaaggg atgggctttc ctgttctgta ct 52

<210> SEQ ID NO 184
<211> LENGTH: 52
<212> TYPE: DNA
<213> ORGANISM: Artificial Sequence
<220> FEATURE:
<223> OTHER INFORMATION: Synthetic

<400> SEQUENCE: 184
aggtaggcac aacttacgta acagattaag agtgaagaag ataatgaaat tg 52

<210> SEQ ID NO 185
<211> LENGTH: 52
<212> TYPE: DNA
<213> ORGANISM: Artificial Sequence
<220> FEATURE:
<223> OTHER INFORMATION: Synthetic

<400> SEQUENCE: 185
tgaaaaggct cgaaagactg gacttaatta ctcccaaagc aggctttgac tc 52

<210> SEQ ID NO 186
<211> LENGTH: 52
<212> TYPE: DNA
<213> ORGANISM: Artificial Sequence
<220> FEATURE:
<223> OTHER INFORMATION: Synthetic

<400> SEQUENCE: 186
agtgtgcagg ctcacaccaa ttgataagag tgtttactag acttggtgcc tc 52

<210> SEQ ID NO 187
<211> LENGTH: 52
<212> TYPE: DNA
<213> ORGANISM: Artificial Sequence
<220> FEATURE:
<223> OTHER INFORMATION: Synthetic

<400> SEQUENCE: 187
gcgaaaaaat gaggattcgt atcataagac tggtgagttc tgagtcttgg ag 52

<210> SEQ ID NO 188
<211> LENGTH: 52
<212> TYPE: DNA
<213> ORGANISM: Artificial Sequence
<220> FEATURE:
<223> OTHER INFORMATION: Synthetic

<400> SEQUENCE: 188
ctcccagaag acccagccat ccccattgcc cccaagacag ttccaccagc tg 52

<210> SEQ ID NO 189
<211> LENGTH: 52
<212> TYPE: DNA
<213> ORGANISM: Artificial Sequence
<220> FEATURE:
<223> OTHER INFORMATION: Synthetic

<400> SEQUENCE: 189
tggaaatgac cttggagatt gtagcaagag agtgagcatg aggagcggcc tg 52

<210> SEQ ID NO 190
<211> LENGTH: 52
<212> TYPE: DNA
<213> ORGANISM: Artificial Sequence
<220> FEATURE:
<223> OTHER INFORMATION: Synthetic

<400> SEQUENCE: 190
agtaccttca ggttccttct cacataagag agaagcccag tattttctat ca 52

<210> SEQ ID NO 191
<211> LENGTH: 52
<212> TYPE: DNA
<213> ORGANISM: Artificial Sequence
<220> FEATURE:
<223> OTHER INFORMATION: Synthetic

<400> SEQUENCE: 191
aacctctact tcttactcac aacataacag agaagccgag tattttctac ca 52

<210> SEQ ID NO 192
<211> LENGTH: 52
<212> TYPE: DNA
<213> ORGANISM: Artificial Sequence
<220> FEATURE:
<223> OTHER INFORMATION: Synthetic

<400> SEQUENCE: 192
aaaatttaaa tccacaattt tgtcattctt cgcggacgag ggtcgcagtc aa 52

<210> SEQ ID NO 193
<211> LENGTH: 52
<212> TYPE: DNA
<213> ORGANISM: Artificial Sequence
<220> FEATURE:

<223> OTHER INFORMATION: Synthetic

<400> SEQUENCE: 193
acactctact ctggcacttt caaagttaag tttctgcact gttaatttct tg 52

<210> SEQ ID NO 194
<211> LENGTH: 52
<212> TYPE: DNA
<213> ORGANISM: Artificial Sequence
<220> FEATURE:
<223> OTHER INFORMATION: Synthetic

<400> SEQUENCE: 194
ctgcatctca ggagtgacag gggttggcgg tggctttccc cacattttct tt 52

<210> SEQ ID NO 195
<211> LENGTH: 52
<212> TYPE: DNA
<213> ORGANISM: Artificial Sequence
<220> FEATURE:
<223> OTHER INFORMATION: Synthetic

<400> SEQUENCE: 195
taaaaatgtg agcgtttcag ctgttggcga ctgttgctcc tagcaaccga gc 52

<210> SEQ ID NO 196
<211> LENGTH: 52
<212> TYPE: DNA
<213> ORGANISM: Artificial Sequence
<220> FEATURE:
<223> OTHER INFORMATION: Synthetic

<400> SEQUENCE: 196
ccatgacaga cacggccttg gtcccggctg gcatttttca ctgttaaagt gt 52

<210> SEQ ID NO 197
<211> LENGTH: 52
<212> TYPE: DNA
<213> ORGANISM: Artificial Sequence
<220> FEATURE:
<223> OTHER INFORMATION: Synthetic

<400> SEQUENCE: 197
gatcagtgac tgtatatctt gttttccaca catgcctctg cattcacctt gt 52

<210> SEQ ID NO 198
<211> LENGTH: 52
<212> TYPE: DNA
<213> ORGANISM: Artificial Sequence
<220> FEATURE:
<223> OTHER INFORMATION: Synthetic

<400> SEQUENCE: 198
ccacgggcca gctgaccttt gactgttgac gttggccacg gtgcgcaccc gg 52

<210> SEQ ID NO 199
<211> LENGTH: 52
<212> TYPE: DNA
<213> ORGANISM: Artificial Sequence
<220> FEATURE:
<223> OTHER INFORMATION: Synthetic

<400> SEQUENCE: 199
tcttccgttc cgcctgctct atctcaagtc acctacttcc ccttcgactg gc 52

<210> SEQ ID NO 200
<211> LENGTH: 52
<212> TYPE: DNA
<213> ORGANISM: Artificial Sequence
<220> FEATURE:
<223> OTHER INFORMATION: Synthetic

<400> SEQUENCE: 200
ccccgtaccc gggtcccgca gacttaacgc gcaagccgcg cgtagggccc ag 52

<210> SEQ ID NO 201
<211> LENGTH: 52
<212> TYPE: DNA
<213> ORGANISM: Artificial Sequence
<220> FEATURE:
<223> OTHER INFORMATION: Synthetic

<400> SEQUENCE: 201
tcccacagct ccagtaggtc cagtcaaggc cctggaggaa gagaaagttc ag 52

<210> SEQ ID NO 202
<211> LENGTH: 52
<212> TYPE: DNA
<213> ORGANISM: Artificial Sequence
<220> FEATURE:
<223> OTHER INFORMATION: Synthetic

<400> SEQUENCE: 202
acccacagca aatagcttga ccccttgcc ccttcagcct ttgggcagct gt 52

<210> SEQ ID NO 203
<211> LENGTH: 52
<212> TYPE: DNA
<213> ORGANISM: Artificial Sequence
<220> FEATURE:
<223> OTHER INFORMATION: Synthetic

<400> SEQUENCE: 203
ggaacaccgt caccccgcgg ctgatggcgt cacttcaact acctgtcttt cg 52

<210> SEQ ID NO 204
<211> LENGTH: 52
<212> TYPE: DNA
<213> ORGANISM: Artificial Sequence
<220> FEATURE:
<223> OTHER INFORMATION: Synthetic

<400> SEQUENCE: 204
gtcatgattc ctactttata cagtattcat ctttgtggtg ggaatatttg ga 52

<210> SEQ ID NO 205
<211> LENGTH: 52
<212> TYPE: DNA
<213> ORGANISM: Artificial Sequence
<220> FEATURE:
<223> OTHER INFORMATION: Synthetic

<400> SEQUENCE: 205
ggagggggag cgctcgcgag tagggcctgc tgctggggct ctgcttcggg ct 52

<210> SEQ ID NO 206
<211> LENGTH: 52
<212> TYPE: DNA
<213> ORGANISM: Artificial Sequence
<220> FEATURE:
<223> OTHER INFORMATION: Synthetic

<400> SEQUENCE: 206
acattttgtg gtcatttcta ctcataactg gagagcttgg tcaagagata tt 52

<210> SEQ ID NO 207
<211> LENGTH: 52
<212> TYPE: DNA
<213> ORGANISM: Artificial Sequence
<220> FEATURE:
<223> OTHER INFORMATION: Synthetic

<400> SEQUENCE: 207
ccctccatag aaagaagcaa aacttaacac aaagtcatct aattttttga ca 52

<210> SEQ ID NO 208
<211> LENGTH: 52
<212> TYPE: DNA
<213> ORGANISM: Artificial Sequence
<220> FEATURE:
<223> OTHER INFORMATION: Synthetic

<400> SEQUENCE: 208
actactacca gtatctgctt tagatccgtt tgtcttgtgt atctaacaac cg 52

<210> SEQ ID NO 209
<211> LENGTH: 52
<212> TYPE: DNA
<213> ORGANISM: Artificial Sequence
<220> FEATURE:
<223> OTHER INFORMATION: Synthetic

<400> SEQUENCE: 209
gcaataaccc agcccaaaaa acttgttatc agctgtcgga tcaatctgca ga 52

<210> SEQ ID NO 210
<211> LENGTH: 52
<212> TYPE: DNA
<213> ORGANISM: Artificial Sequence
<220> FEATURE:
<223> OTHER INFORMATION: Synthetic

<400> SEQUENCE: 210
tttgtgcagc atatcagtgc tttcattgcc ttaaaaatta agaaaaatta tc 52

<210> SEQ ID NO 211
<211> LENGTH: 52
<212> TYPE: DNA
<213> ORGANISM: Artificial Sequence
<220> FEATURE:
<223> OTHER INFORMATION: Synthetic

<400> SEQUENCE: 211
acaaactaag aagtcatacc ttggcaagga agcgcatcaa tatatcacca tt 52

<210> SEQ ID NO 212
<211> LENGTH: 52
<212> TYPE: DNA
<213> ORGANISM: Artificial Sequence
<220> FEATURE:
<223> OTHER INFORMATION: Synthetic

<400> SEQUENCE: 212
agttcttggt ttgcacggga atgggttaaa tttacagatg ctatctccaa gg 52

<210> SEQ ID NO 213
<211> LENGTH: 52

<212> TYPE: DNA
<213> ORGANISM: Artificial Sequence
<220> FEATURE:
<223> OTHER INFORMATION: Synthetic

<400> SEQUENCE: 213
agatatcccc ggcagccgca acctgccact ggggcgagaa gagcccgccc ta 52

<210> SEQ ID NO 214
<211> LENGTH: 52
<212> TYPE: DNA
<213> ORGANISM: Artificial Sequence
<220> FEATURE:
<223> OTHER INFORMATION: Synthetic

<400> SEQUENCE: 214
ctgctgcaat atttgccccg gcgctaattc catggccact gccctcttcc tg 52

<210> SEQ ID NO 215
<211> LENGTH: 52
<212> TYPE: DNA
<213> ORGANISM: Artificial Sequence
<220> FEATURE:
<223> OTHER INFORMATION: Synthetic

<400> SEQUENCE: 215
aattatcact ttcttcagcc cccttaacaa ttttggttgg acccaatggg gc 52

<210> SEQ ID NO 216
<211> LENGTH: 52
<212> TYPE: DNA
<213> ORGANISM: Artificial Sequence
<220> FEATURE:
<223> OTHER INFORMATION: Synthetic

<400> SEQUENCE: 216
agaaacaaga gaaacagcac aagttaagac acaggtaata cagtctgtgt cc 52

<210> SEQ ID NO 217
<211> LENGTH: 52
<212> TYPE: DNA
<213> ORGANISM: Artificial Sequence
<220> FEATURE:
<223> OTHER INFORMATION: Synthetic

<400> SEQUENCE: 217
gagactcatg agacaagata ttgataacac agaaggtagg tctgttttgc tt 52

<210> SEQ ID NO 218
<211> LENGTH: 52
<212> TYPE: DNA
<213> ORGANISM: Artificial Sequence
<220> FEATURE:
<223> OTHER INFORMATION: Synthetic

<400> SEQUENCE: 218
tgcaaatctg gcaaggctgt aggccaattc tcattgcagg cagggcacct ca 52

<210> SEQ ID NO 219
<211> LENGTH: 52
<212> TYPE: DNA
<213> ORGANISM: Artificial Sequence
<220> FEATURE:
<223> OTHER INFORMATION: Synthetic

<400> SEQUENCE: 219
agagaattga agagaggtgc aggcgttaag ctggaggatt ctaccaggga ga 52

<210> SEQ ID NO 220
<211> LENGTH: 52
<212> TYPE: DNA
<213> ORGANISM: Artificial Sequence
<220> FEATURE:
<223> OTHER INFORMATION: Synthetic

<400> SEQUENCE: 220
cacaaattgt gttctcacct gacctaacct gaaaaaagat cgcgttgcca tc 52

<210> SEQ ID NO 221
<211> LENGTH: 52
<212> TYPE: DNA
<213> ORGANISM: Artificial Sequence
<220> FEATURE:
<223> OTHER INFORMATION: Synthetic

<400> SEQUENCE: 221
ctgacatccc agggaagatg ccatcaagag atgcagacac tgagtgtgcg ga 52

<210> SEQ ID NO 222
<211> LENGTH: 52
<212> TYPE: DNA
<213> ORGANISM: Artificial Sequence
<220> FEATURE:
<223> OTHER INFORMATION: Synthetic

<400> SEQUENCE: 222
catggatggt tctggaggaa aaatgttatg tatttcgaac cataaattcc tt 52

<210> SEQ ID NO 223
<211> LENGTH: 52
<212> TYPE: DNA
<213> ORGANISM: Artificial Sequence
<220> FEATURE:
<223> OTHER INFORMATION: Synthetic

<400> SEQUENCE: 223
aacttcacac acctttaatg tgcagttaag ttgaggatgc ttgtgttagt gt 52

<210> SEQ ID NO 224
<211> LENGTH: 52
<212> TYPE: DNA
<213> ORGANISM: Artificial Sequence
<220> FEATURE:
<223> OTHER INFORMATION: Synthetic

<400> SEQUENCE: 224
agtgaatgct gaccccattg atagaggacg gaaattctgt ggagaccagc tg 52

<210> SEQ ID NO 225
<211> LENGTH: 52
<212> TYPE: DNA
<213> ORGANISM: Artificial Sequence
<220> FEATURE:
<223> OTHER INFORMATION: Synthetic

<400> SEQUENCE: 225
cttctgcttg ctggcctggc acaggttaag tcctctcccc cgactctttc cc 52

<210> SEQ ID NO 226
<211> LENGTH: 52
<212> TYPE: DNA
<213> ORGANISM: Artificial Sequence
<220> FEATURE:
<223> OTHER INFORMATION: Synthetic

<400> SEQUENCE: 226
ctggctcccc aaagagccct ggtagttaac tccccctgct gggaagcaaa aa 52

<210> SEQ ID NO 227
<211> LENGTH: 52
<212> TYPE: DNA
<213> ORGANISM: Artificial Sequence
<220> FEATURE:
<223> OTHER INFORMATION: Synthetic

<400> SEQUENCE: 227
gtggtccgcg ccgcgctgac cactcaaggc aaggacccgg ctccgccggc ct 52

<210> SEQ ID NO 228
<211> LENGTH: 52
<212> TYPE: DNA
<213> ORGANISM: Artificial Sequence
<220> FEATURE:
<223> OTHER INFORMATION: Synthetic

<400> SEQUENCE: 228
actttgtggc tcctggataa ctttattaga gagatgaaac taaagaactc tt 52

<210> SEQ ID NO 229
<211> LENGTH: 52
<212> TYPE: DNA
<213> ORGANISM: Artificial Sequence
<220> FEATURE:
<223> OTHER INFORMATION: Synthetic

<400> SEQUENCE: 229
gtagaaccat cgctgtagca attcgttaag tcagcaaagt tacaccaaac tg 52

<210> SEQ ID NO 230
<211> LENGTH: 52
<212> TYPE: DNA
<213> ORGANISM: Artificial Sequence
<220> FEATURE:
<223> OTHER INFORMATION: Synthetic

<400> SEQUENCE: 230
attcctgatt tcagtggctg cagacttgtg tacttctgtg ccacacttag ga 52

<210> SEQ ID NO 231
<211> LENGTH: 52
<212> TYPE: DNA
<213> ORGANISM: Artificial Sequence
<220> FEATURE:
<223> OTHER INFORMATION: Synthetic

<400> SEQUENCE: 231
gaactttcac atcaatttct aactcttggt tttgtgtcct tgaataactg tt 52

<210> SEQ ID NO 232
<211> LENGTH: 52
<212> TYPE: DNA
<213> ORGANISM: Artificial Sequence
<220> FEATURE:
<223> OTHER INFORMATION: Synthetic

<400> SEQUENCE: 232
cctgtggcca ttgaactatg gaaggttaaa aaaaaaaaaa taccactttt aa 52

<210> SEQ ID NO 233
<211> LENGTH: 52
<212> TYPE: DNA
<213> ORGANISM: Artificial Sequence
<220> FEATURE:
<223> OTHER INFORMATION: Synthetic

<400> SEQUENCE: 233
ctctagagcg ccagagaaga ttgttaacat ttaaaatgtt catcactcag tt 52

<210> SEQ ID NO 234
<211> LENGTH: 52
<212> TYPE: DNA
<213> ORGANISM: Artificial Sequence
<220> FEATURE:
<223> OTHER INFORMATION: Synthetic

<400> SEQUENCE: 234
aaaagaagga aactgcagtg gctgcaattc aagattgtaa caggtaaact gc 52

<210> SEQ ID NO 235
<211> LENGTH: 52
<212> TYPE: DNA
<213> ORGANISM: Artificial Sequence
<220> FEATURE:
<223> OTHER INFORMATION: Synthetic

<400> SEQUENCE: 235
cctgcaggtt ggagcctccc ctcttaacgt ctctgtgctt gtggctctgg gg 52

<210> SEQ ID NO 236
<211> LENGTH: 52
<212> TYPE: DNA
<213> ORGANISM: Artificial Sequence
<220> FEATURE:
<223> OTHER INFORMATION: Synthetic

<400> SEQUENCE: 236
acccacctgg atcggcctcc gaccgttaac tattcggtgc gttgggcagc gc 52

<210> SEQ ID NO 237
<211> LENGTH: 52
<212> TYPE: DNA
<213> ORGANISM: Artificial Sequence
<220> FEATURE:
<223> OTHER INFORMATION: Synthetic

<400> SEQUENCE: 237
aaaatctaca atcacctttt cccccaacag tgtgcatatg cttaaggagt tc 52

<210> SEQ ID NO 238
<211> LENGTH: 52
<212> TYPE: DNA
<213> ORGANISM: Artificial Sequence
<220> FEATURE:
<223> OTHER INFORMATION: Synthetic

<400> SEQUENCE: 238
ccccataaac agcctcataa gcaggttaac gtacgcacac cttccttctg at 52

<210> SEQ ID NO 239
<211> LENGTH: 52
<212> TYPE: DNA
<213> ORGANISM: Artificial Sequence
<220> FEATURE:
<223> OTHER INFORMATION: Synthetic

<400> SEQUENCE: 239
tagtctgtgc tctctgctgc ctcccaatca cgggggccgt agtagaaggc ca 52

<210> SEQ ID NO 240
<211> LENGTH: 52
<212> TYPE: DNA
<213> ORGANISM: Artificial Sequence
<220> FEATURE:
<223> OTHER INFORMATION: Synthetic

<400> SEQUENCE: 240
caacattcca ctggtacata ttcttaactc tggttgcctt cagcggaact ga 52

<210> SEQ ID NO 241
<211> LENGTH: 52
<212> TYPE: DNA
<213> ORGANISM: Artificial Sequence
<220> FEATURE:
<223> OTHER INFORMATION: Synthetic

<400> SEQUENCE: 241
tgctgtgcgc gtctgctccc tgctgttatc agtctgtcca gcacttccat tg 52

<210> SEQ ID NO 242
<211> LENGTH: 52
<212> TYPE: DNA
<213> ORGANISM: Artificial Sequence
<220> FEATURE:
<223> OTHER INFORMATION: Synthetic

<400> SEQUENCE: 242
ggcagcaggt gctctactgg gagtcaagag agcagccagg ctgagatgga gt 52

<210> SEQ ID NO 243
<211> LENGTH: 52
<212> TYPE: DNA
<213> ORGANISM: Artificial Sequence
<220> FEATURE:
<223> OTHER INFORMATION: Synthetic

<400> SEQUENCE: 243
gtacatgatg aggcccacgg gccccaagga agagcagctc ccgcttggcg at 52

<210> SEQ ID NO 244
<211> LENGTH: 52
<212> TYPE: DNA
<213> ORGANISM: Artificial Sequence
<220> FEATURE:
<223> OTHER INFORMATION: Synthetic

<400> SEQUENCE: 244
attgcaggtc actggaagga ctgagccgca ttcaggagcc tggaggaact ca 52

<210> SEQ ID NO 245
<211> LENGTH: 52
<212> TYPE: DNA
<213> ORGANISM: Artificial Sequence
<220> FEATURE:
<223> OTHER INFORMATION: Synthetic

<400> SEQUENCE: 245
gaaagggacg aactggtgta atgataatgt gcatatttat tacatcgggg ca 52

<210> SEQ ID NO 246

<211> LENGTH: 52
<212> TYPE: DNA
<213> ORGANISM: Artificial Sequence
<220> FEATURE:
<223> OTHER INFORMATION: Synthetic

<400> SEQUENCE: 246
tgtactttga gttccctcag ccgttaacct gtgtgtggtg atatcaaagt ag 52

<210> SEQ ID NO 247
<211> LENGTH: 52
<212> TYPE: DNA
<213> ORGANISM: Artificial Sequence
<220> FEATURE:
<223> OTHER INFORMATION: Synthetic

<400> SEQUENCE: 247
ggacagctcc accaacatcc acgagcctgc gggtcaccaa caccagcatc ca 52

<210> SEQ ID NO 248
<211> LENGTH: 52
<212> TYPE: DNA
<213> ORGANISM: Artificial Sequence
<220> FEATURE:
<223> OTHER INFORMATION: Synthetic

<400> SEQUENCE: 248
cctcgagcgt cccaccggct ggaaattgct tcgtttacca cttcgccgtg tg 52

<210> SEQ ID NO 249
<211> LENGTH: 52
<212> TYPE: DNA
<213> ORGANISM: Artificial Sequence
<220> FEATURE:
<223> OTHER INFORMATION: Synthetic

<400> SEQUENCE: 249
ttgtccaggt gagccaggcc atcacttaaa ggcaccgagc actttcttgc ca 52

<210> SEQ ID NO 250
<211> LENGTH: 52
<212> TYPE: DNA
<213> ORGANISM: Artificial Sequence
<220> FEATURE:
<223> OTHER INFORMATION: Synthetic

<400> SEQUENCE: 250
cttcatccac gttcaccttg ccccaccagg gcagtaacgg cagacttctc ct 52

<210> SEQ ID NO 251
<211> LENGTH: 52
<212> TYPE: DNA
<213> ORGANISM: Artificial Sequence
<220> FEATURE:
<223> OTHER INFORMATION: Synthetic

<400> SEQUENCE: 251
tgccccacag ggcagtaacg gcagaccttc tcctcaggag tcagatgcac ca 52

<210> SEQ ID NO 252
<211> LENGTH: 52
<212> TYPE: DNA
<213> ORGANISM: Artificial Sequence
<220> FEATURE:
<223> OTHER INFORMATION: Synthetic

<400> SEQUENCE: 252
gagaactgta gcttctaaag ctcataagca taggtgtttg gcaagacatt ct 52

<210> SEQ ID NO 253
<211> LENGTH: 52
<212> TYPE: DNA
<213> ORGANISM: Artificial Sequence
<220> FEATURE:
<223> OTHER INFORMATION: Synthetic

<400> SEQUENCE: 253
cctcgatcat gcgccgcgct tcatgaactc agctcctgaa tcaggtcgaa gt 52

<210> SEQ ID NO 254
<211> LENGTH: 52
<212> TYPE: DNA
<213> ORGANISM: Artificial Sequence
<220> FEATURE:
<223> OTHER INFORMATION: Synthetic

<400> SEQUENCE: 254
cgccatcgta ggcaggcggc tcccacctgt actgtgcagg agtcctctcc ca 52

<210> SEQ ID NO 255
<211> LENGTH: 52
<212> TYPE: DNA
<213> ORGANISM: Artificial Sequence
<220> FEATURE:
<223> OTHER INFORMATION: Synthetic

<400> SEQUENCE: 255
aacacccact catcgctgtc acctgttgtc ctctggggca tctggggctg gc 52

<210> SEQ ID NO 256
<211> LENGTH: 52
<212> TYPE: DNA
<213> ORGANISM: Artificial Sequence
<220> FEATURE:
<223> OTHER INFORMATION: Synthetic

<400> SEQUENCE: 256
atggggtcat cgggggctcc aggggttagg accattgaga gctgctgagc tt 52

<210> SEQ ID NO 257
<211> LENGTH: 52
<212> TYPE: DNA
<213> ORGANISM: Artificial Sequence
<220> FEATURE:
<223> OTHER INFORMATION: Synthetic

<400> SEQUENCE: 257
gactctggca gctcaagctc taaggttaac acgatacggc tgtccataca tc 52

<210> SEQ ID NO 258
<211> LENGTH: 52
<212> TYPE: DNA
<213> ORGANISM: Artificial Sequence
<220> FEATURE:
<223> OTHER INFORMATION: Synthetic

<400> SEQUENCE: 258
cctgcgaaga tggccgctgc gtcctccatc ggattccgac gcctgcggag ct 52

<210> SEQ ID NO 259
<211> LENGTH: 51
<212> TYPE: DNA

<213> ORGANISM: Artificial Sequence
<220> FEATURE:
<223> OTHER INFORMATION: Synthetic

<400> SEQUENCE: 259
tgactgtatg cacaacaacg ggcagttgtg ggcagctgtg ccttgccatc c 51

<210> SEQ ID NO 260
<211> LENGTH: 52
<212> TYPE: DNA
<213> ORGANISM: Artificial Sequence
<220> FEATURE:
<223> OTHER INFORMATION: Synthetic

<400> SEQUENCE: 260
cggcgatggt aggggccgtc ctcacttgcc ctgctggcag ggcttgtgag ct 52

<210> SEQ ID NO 261
<211> LENGTH: 52
<212> TYPE: DNA
<213> ORGANISM: Artificial Sequence
<220> FEATURE:
<223> OTHER INFORMATION: Synthetic

<400> SEQUENCE: 261
ggcagggctt gtgagcttgc tgtgtccgtc acaagagaaa gcagcttcct ga 52

<210> SEQ ID NO 262
<211> LENGTH: 52
<212> TYPE: DNA
<213> ORGANISM: Artificial Sequence
<220> FEATURE:
<223> OTHER INFORMATION: Synthetic

<400> SEQUENCE: 262
tccacaaatt tctggctaaa gcgaaggaac actgaaaggt tcaaaacctc ca 52

<210> SEQ ID NO 263
<211> LENGTH: 52
<212> TYPE: DNA
<213> ORGANISM: Artificial Sequence
<220> FEATURE:
<223> OTHER INFORMATION: Synthetic

<400> SEQUENCE: 263
acagaacaat cccagcctaa aacttaacat acacagaatg tctgagggtt tg 52

<210> SEQ ID NO 264
<211> LENGTH: 52
<212> TYPE: DNA
<213> ORGANISM: Artificial Sequence
<220> FEATURE:
<223> OTHER INFORMATION: Synthetic

<400> SEQUENCE: 264
aggagtggaa gaaggcactg tgctcaagtg ttggtggaca agtgaatttg ct 52

<210> SEQ ID NO 265
<211> LENGTH: 52
<212> TYPE: DNA
<213> ORGANISM: Artificial Sequence
<220> FEATURE:
<223> OTHER INFORMATION: Synthetic

<400> SEQUENCE: 265
tgtggtagag caatcccaaa gtggtggaaa aaaaagggta tcatgaagta ga 52

<210> SEQ ID NO 266
<211> LENGTH: 52
<212> TYPE: DNA
<213> ORGANISM: Artificial Sequence
<220> FEATURE:
<223> OTHER INFORMATION: Synthetic

<400> SEQUENCE: 266
aggagaggtt atgaagaatg cacacaacaa ttctccgtgg cctgagaaaa ca 52

<210> SEQ ID NO 267
<211> LENGTH: 52
<212> TYPE: DNA
<213> ORGANISM: Artificial Sequence
<220> FEATURE:
<223> OTHER INFORMATION: Synthetic

<400> SEQUENCE: 267
ggcccgcctg ctttcttggt ggtgcaaggg tgtgcccagc ctggcttctc tg 52

<210> SEQ ID NO 268
<211> LENGTH: 52
<212> TYPE: DNA
<213> ORGANISM: Artificial Sequence
<220> FEATURE:
<223> OTHER INFORMATION: Synthetic

<400> SEQUENCE: 268
ggtcccagac catggagtga gcctcttccc ccaagcctgt gggtaaggac ag 52

<210> SEQ ID NO 269
<211> LENGTH: 52
<212> TYPE: DNA
<213> ORGANISM: Artificial Sequence
<220> FEATURE:
<223> OTHER INFORMATION: Synthetic

<400> SEQUENCE: 269
ttcatggaga acatgccgtg gtacattggc aaggtacaaa gccgttagag cc 52

<210> SEQ ID NO 270
<211> LENGTH: 52
<212> TYPE: DNA
<213> ORGANISM: Artificial Sequence
<220> FEATURE:
<223> OTHER INFORMATION: Synthetic

<400> SEQUENCE: 270
tccggccctg cggtcagcgc gtcccttggt cggagacacc gagggtgtga cc 52

<210> SEQ ID NO 271
<211> LENGTH: 52
<212> TYPE: DNA
<213> ORGANISM: Artificial Sequence
<220> FEATURE:
<223> OTHER INFORMATION: Synthetic

<400> SEQUENCE: 271
agtcgggcac ggcctacgag tgcctccagc gccctgggcg agaaaggcct gg 52

<210> SEQ ID NO 272
<211> LENGTH: 52
<212> TYPE: DNA
<213> ORGANISM: Artificial Sequence
<220> FEATURE:

<223> OTHER INFORMATION: Synthetic

<400> SEQUENCE: 272
cttcctcttc ttctcatgtc tccggttagg ccacgtgcat ggccactagg ag 52

<210> SEQ ID NO 273
<211> LENGTH: 52
<212> TYPE: DNA
<213> ORGANISM: Artificial Sequence
<220> FEATURE:
<223> OTHER INFORMATION: Synthetic

<400> SEQUENCE: 273
ccggtaggcc acgtgcatgg ccactaagga gcgctggcgt ggacacgaag at 52

<210> SEQ ID NO 274
<211> LENGTH: 52
<212> TYPE: DNA
<213> ORGANISM: Artificial Sequence
<220> FEATURE:
<223> OTHER INFORMATION: Synthetic

<400> SEQUENCE: 274 cccttttaa tgcaaggaaa ggctgttatg ggtttcagat ttatctgact gt 52

<210> SEQ ID NO 275
<211> LENGTH: 52
<212> TYPE: DNA
<213> ORGANISM: Artificial Sequence
<220> FEATURE:
<223> OTHER INFORMATION: Synthetic

<400> SEQUENCE: 275
cttattttaa ctcctacttc caaggaatgt tctgtcaaac ctagtcatga tt 52

<210> SEQ ID NO 276
<211> LENGTH: 52
<212> TYPE: DNA
<213> ORGANISM: Artificial Sequence
<220> FEATURE:
<223> OTHER INFORMATION: Synthetic

<400> SEQUENCE: 276
attgtaaaaa tagtcatata accccttcag atgttatttt ccaagcagga tt 52

<210> SEQ ID NO 277
<211> LENGTH: 52
<212> TYPE: DNA
<213> ORGANISM: Artificial Sequence
<220> FEATURE:
<223> OTHER INFORMATION: Synthetic

<400> SEQUENCE: 277
atcaccagtt ttagccatca atgggccaaa gaccctaaag tacagagagg cc 52

<210> SEQ ID NO 278
<211> LENGTH: 52
<212> TYPE: DNA
<213> ORGANISM: Artificial Sequence
<220> FEATURE:
<223> OTHER INFORMATION: Synthetic

<400> SEQUENCE: 278
caaacgaaaa ttatggcagg ttgttaacga ggcattggat gattcagagg at 52

<210> SEQ ID NO 279
<211> LENGTH: 52
<212> TYPE: DNA
<213> ORGANISM: Artificial Sequence
<220> FEATURE:
<223> OTHER INFORMATION: Synthetic

<400> SEQUENCE: 279
tttctgaaat agaagatagt accaaggcaa gtcttttcca aagtattgtt ta 52

<210> SEQ ID NO 280
<211> LENGTH: 52
<212> TYPE: DNA
<213> ORGANISM: Artificial Sequence
<220> FEATURE:
<223> OTHER INFORMATION: Synthetic

<400> SEQUENCE: 280
gtttctttag agccgattac ctgtgttacc ctttcggtaa gacatgttta aa 52

<210> SEQ ID NO 281
<211> LENGTH: 52
<212> TYPE: DNA
<213> ORGANISM: Artificial Sequence
<220> FEATURE:
<223> OTHER INFORMATION: Synthetic

<400> SEQUENCE: 281
tgcccctttc gtctatttgt cagacggaat gttacaattt actggcaata aa 52

<210> SEQ ID NO 282
<211> LENGTH: 52
<212> TYPE: DNA
<213> ORGANISM: Artificial Sequence
<220> FEATURE:
<223> OTHER INFORMATION: Synthetic

<400> SEQUENCE: 282
agatgtcttc tcctaattgt gagataatat tatcaaagtc ctttatcact tt 52

<210> SEQ ID NO 283
<211> LENGTH: 52
<212> TYPE: DNA
<213> ORGANISM: Artificial Sequence
<220> FEATURE:
<223> OTHER INFORMATION: Synthetic

<400> SEQUENCE: 283
caggagcacc cgcatgaccc tggggaacgc catgggtaat ggtgccagtc tt 52

<210> SEQ ID NO 284
<211> LENGTH: 52
<212> TYPE: DNA
<213> ORGANISM: Artificial Sequence
<220> FEATURE:
<223> OTHER INFORMATION: Synthetic

<400> SEQUENCE: 284
gtccatgttg gctgacctgt gtctcaagag atttgtaggc ctgaacgtag aa 52

<210> SEQ ID NO 285
<211> LENGTH: 52
<212> TYPE: DNA
<213> ORGANISM: Artificial Sequence
<220> FEATURE:
<223> OTHER INFORMATION: Synthetic

<400> SEQUENCE: 285
cccagctgct gctgcagggt agccaggcca gtacagctcc tccaggcctg gc 52

<210> SEQ ID NO 286
<211> LENGTH: 52
<212> TYPE: DNA
<213> ORGANISM: Artificial Sequence
<220> FEATURE:
<223> OTHER INFORMATION: Synthetic

<400> SEQUENCE: 286
caggagcccg agtctatatt gcctgccaga gatgtactga agggggagtc tg 52

<210> SEQ ID NO 287
<211> LENGTH: 52
<212> TYPE: DNA
<213> ORGANISM: Artificial Sequence
<220> FEATURE:
<223> OTHER INFORMATION: Synthetic

<400> SEQUENCE: 287
atgccaaaga aaaaatagct cctttaacct ttagaagggc atgactcaac at 52

<210> SEQ ID NO 288
<211> LENGTH: 52
<212> TYPE: DNA
<213> ORGANISM: Artificial Sequence
<220> FEATURE:
<223> OTHER INFORMATION: Synthetic

<400> SEQUENCE: 288
cttctcggag gaggcagatg cagacaagac cagacacctc cctgcttagc ag 52

<210> SEQ ID NO 289
<211> LENGTH: 52
<212> TYPE: DNA
<213> ORGANISM: Artificial Sequence
<220> FEATURE:
<223> OTHER INFORMATION: Synthetic

<400> SEQUENCE: 289
ataagctctt gtgacctcct ggttgttaag tgttggccag atgtctatgt cc 52

<210> SEQ ID NO 290
<211> LENGTH: 52
<212> TYPE: DNA
<213> ORGANISM: Artificial Sequence
<220> FEATURE:
<223> OTHER INFORMATION: Synthetic

<400> SEQUENCE: 290
ctgagttccc accggatgag acctcttctc ttttatagcc agaagttccc ca 52

<210> SEQ ID NO 291
<211> LENGTH: 52
<212> TYPE: DNA
<213> ORGANISM: Artificial Sequence
<220> FEATURE:
<223> OTHER INFORMATION: Synthetic

<400> SEQUENCE: 291
aacagctctc agcctggatg ctccattgga ctcctcttgg accagcatga ag 52

<210> SEQ ID NO 292
<211> LENGTH: 52

<212> TYPE: DNA
<213> ORGANISM: Artificial Sequence
<220> FEATURE:
<223> OTHER INFORMATION: Synthetic

<400> SEQUENCE: 292
cataccttgg caagatcata cagacaagag gacctgtcga cagtagttct tc 52

<210> SEQ ID NO 293
<211> LENGTH: 52
<212> TYPE: DNA
<213> ORGANISM: Artificial Sequence
<220> FEATURE:
<223> OTHER INFORMATION: Synthetic

<400> SEQUENCE: 293
tgggtctcca aatcccagag ggtaattggt atagcccatc ctttccactt cc 52

<210> SEQ ID NO 294
<211> LENGTH: 52
<212> TYPE: DNA
<213> ORGANISM: Artificial Sequence
<220> FEATURE:
<223> OTHER INFORMATION: Synthetic

<400> SEQUENCE: 294
ttcacctggc gtctgaaaga gaattaacgc cgcggagtac gcgaacgcac tg 52

<210> SEQ ID NO 295
<211> LENGTH: 52
<212> TYPE: DNA
<213> ORGANISM: Artificial Sequence
<220> FEATURE:
<223> OTHER INFORMATION: Synthetic

<400> SEQUENCE: 295
aagcccaaag ccttcaaaga cacttaacct tggcaccttc ttccactgga gg 52

<210> SEQ ID NO 296
<211> LENGTH: 52
<212> TYPE: DNA
<213> ORGANISM: Artificial Sequence
<220> FEATURE:
<223> OTHER INFORMATION: Synthetic

<400> SEQUENCE: 296
gtgccgcgcc gcgttgccca tctccaagga ggctcagcac ctcatccagg cc 52

<210> SEQ ID NO 297
<211> LENGTH: 52
<212> TYPE: DNA
<213> ORGANISM: Artificial Sequence
<220> FEATURE:
<223> OTHER INFORMATION: Synthetic

<400> SEQUENCE: 297
aagcagtatt tttttttcca actagttggg gacatgattt tcgtcaagat ta 52

<210> SEQ ID NO 298
<211> LENGTH: 52
<212> TYPE: DNA
<213> ORGANISM: Artificial Sequence
<220> FEATURE:
<223> OTHER INFORMATION: Synthetic

<400> SEQUENCE: 298

-continued tccttctgtt ccggtgatgg ctcttaacgg ccacagctaa tcccagggta ca 52

<210> SEQ ID NO 299
<211> LENGTH: 52
<212> TYPE: DNA
<213> ORGANISM: Artificial Sequence
<220> FEATURE:
<223> OTHER INFORMATION: Synthetic

<400> SEQUENCE: 299
tgtccattac ttcaatattt ttaataaccg tcactctcaa gaagcttgca gg 52

<210> SEQ ID NO 300
<211> LENGTH: 52
<212> TYPE: DNA
<213> ORGANISM: Artificial Sequence
<220> FEATURE:
<223> OTHER INFORMATION: Synthetic

<400> SEQUENCE: 300
gtactacatg aagtggagcc aagataacgt ggttctttat gacgcagagc ta 52

<210> SEQ ID NO 301
<211> LENGTH: 52
<212> TYPE: DNA
<213> ORGANISM: Artificial Sequence
<220> FEATURE:
<223> OTHER INFORMATION: Synthetic

<400> SEQUENCE: 301
cagaaagggt cccactgcta ctaacttagc ctcctctttg tcaggccaag ca 52

<210> SEQ ID NO 302
<211> LENGTH: 52
<212> TYPE: DNA
<213> ORGANISM: Artificial Sequence
<220> FEATURE:
<223> OTHER INFORMATION: Synthetic

<400> SEQUENCE: 302
gtgctgacta ctaccgctat ctgataagag tctgtaaagg aactgtagtc gc 52

<210> SEQ ID NO 303
<211> LENGTH: 52
<212> TYPE: DNA
<213> ORGANISM: Artificial Sequence
<220> FEATURE:
<223> OTHER INFORMATION: Synthetic

<400> SEQUENCE: 303
ctcttaccag cggtattgct gagcgttgac tcagggaagt gttccagaaa aa 52

<210> SEQ ID NO 304
<211> LENGTH: 52
<212> TYPE: DNA
<213> ORGANISM: Artificial Sequence
<220> FEATURE:
<223> OTHER INFORMATION: Synthetic

<400> SEQUENCE: 304
atggacagca gggtctgctg aggggaagag gccggcctgg gtgaggccca gg 52

<210> SEQ ID NO 305
<211> LENGTH: 52
<212> TYPE: DNA
<213> ORGANISM: Artificial Sequence
<220> FEATURE:
<223> OTHER INFORMATION: Synthetic

<400> SEQUENCE: 305
ggcggcccag ccccgcagcg gccacaagca gcatagccgg gcgagcggat cc 52

<210> SEQ ID NO 306
<211> LENGTH: 52
<212> TYPE: DNA
<213> ORGANISM: Artificial Sequence
<220> FEATURE:
<223> OTHER INFORMATION: Synthetic

<400> SEQUENCE: 306
agcagttggc tgcggggaga cccttaacca ccagtggcca gcagatcatc ca 52

<210> SEQ ID NO 307
<211> LENGTH: 52
<212> TYPE: DNA
<213> ORGANISM: Artificial Sequence
<220> FEATURE:
<223> OTHER INFORMATION: Synthetic

<400> SEQUENCE: 307
ttcagccaag gcctgcagca gatgattgga ccatgtgagt cggctctggc ca 52

<210> SEQ ID NO 308
<211> LENGTH: 52
<212> TYPE: DNA
<213> ORGANISM: Artificial Sequence
<220> FEATURE:
<223> OTHER INFORMATION: Synthetic

<400> SEQUENCE: 308
cttcagcctg cacgcggttg tcctcaacgc tgatcatcat cgtgcagtgc tg 52

<210> SEQ ID NO 309
<211> LENGTH: 52
<212> TYPE: DNA
<213> ORGANISM: Artificial Sequence
<220> FEATURE:
<223> OTHER INFORMATION: Synthetic

<400> SEQUENCE: 309
ctcgccccca gcgcggtggc cagcgccgtg tcctggcctg ccatcggctt cc 52

<210> SEQ ID NO 310
<211> LENGTH: 52
<212> TYPE: DNA
<213> ORGANISM: Artificial Sequence
<220> FEATURE:
<223> OTHER INFORMATION: Synthetic

<400> SEQUENCE: 310
cgtactggct gctgtatggg atgatggcgg acgcagccca cgggaagcat gg 52

<210> SEQ ID NO 311
<211> LENGTH: 52
<212> TYPE: DNA
<213> ORGANISM: Artificial Sequence
<220> FEATURE:
<223> OTHER INFORMATION: Synthetic

<400> SEQUENCE: 311
ggcctggcgg acaatgctga agagcttggg ggtggctggg gtgctggtgg ct 52

<210> SEQ ID NO 312
<211> LENGTH: 52
<212> TYPE: DNA
<213> ORGANISM: Artificial Sequence
<220> FEATURE:
<223> OTHER INFORMATION: Synthetic

<400> SEQUENCE: 312
gcacagtccg accctgagca cgcccaatgt tccccgcagg ccggaacagc cc 52

<210> SEQ ID NO 313
<211> LENGTH: 52
<212> TYPE: DNA
<213> ORGANISM: Artificial Sequence
<220> FEATURE:
<223> OTHER INFORMATION: Synthetic

<400> SEQUENCE: 313
cactctcggg tcaccacagg tgcctccaca catctgccca attgctggag ac 52

<210> SEQ ID NO 314
<211> LENGTH: 52
<212> TYPE: DNA
<213> ORGANISM: Artificial Sequence
<220> FEATURE:
<223> OTHER INFORMATION: Synthetic

<400> SEQUENCE: 314
agggaagctc ttcatcctca ctagattaag ttctcttctg aggactctaa tt 52

<210> SEQ ID NO 315
<211> LENGTH: 52
<212> TYPE: DNA
<213> ORGANISM: Artificial Sequence
<220> FEATURE:
<223> OTHER INFORMATION: Synthetic

<400> SEQUENCE: 315
tagataagtt ctcttctgag gactcttaat ttcttggccc ctcttcggta ac 52

<210> SEQ ID NO 316
<211> LENGTH: 52
<212> TYPE: DNA
<213> ORGANISM: Artificial Sequence
<220> FEATURE:
<223> OTHER INFORMATION: Synthetic

<400> SEQUENCE: 316
cttttgtttt attctcatga ccactaatta gtaatattca tcacttgacc at 52

<210> SEQ ID NO 317
<211> LENGTH: 52
<212> TYPE: DNA
<213> ORGANISM: Artificial Sequence
<220> FEATURE:
<223> OTHER INFORMATION: Synthetic

<400> SEQUENCE: 317
gaatgtctca caaataaacc aagataatgc tggtacatct gagtcacaca ag 52

<210> SEQ ID NO 318
<211> LENGTH: 52
<212> TYPE: DNA
<213> ORGANISM: Artificial Sequence
<220> FEATURE:
<223> OTHER INFORMATION: Synthetic

<400> SEQUENCE: 318
tgaggtactg tactttaaag aggtcaactt caagtgtaga ctcattgtcc tg 52

<210> SEQ ID NO 319
<211> LENGTH: 52
<212> TYPE: DNA
<213> ORGANISM: Artificial Sequence
<220> FEATURE:
<223> OTHER INFORMATION: Synthetic

<400> SEQUENCE: 319
actcacttta ccacgacaaa ctgctaacca ggagagctcc atcttaaaca ac 52

<210> SEQ ID NO 320
<211> LENGTH: 52
<212> TYPE: DNA
<213> ORGANISM: Artificial Sequence
<220> FEATURE:
<223> OTHER INFORMATION: Synthetic

<400> SEQUENCE: 320
ttagcctcca gctggatagt aaatgttaac accaagttct gacgaaaagg at 52

<210> SEQ ID NO 321
<211> LENGTH: 52
<212> TYPE: DNA
<213> ORGANISM: Artificial Sequence
<220> FEATURE:
<223> OTHER INFORMATION: Synthetic

<400> SEQUENCE: 321
tggcgggcgc ctggccgagc ctccaggttg tgtgcattgt gggtgggggg cc 52

<210> SEQ ID NO 322
<211> LENGTH: 52
<212> TYPE: DNA
<213> ORGANISM: Artificial Sequence
<220> FEATURE:
<223> OTHER INFORMATION: Synthetic

<400> SEQUENCE: 322
cccacctggg ggcctacctg ctgctggtga agcccttggc cagggcaaaa gc 52

<210> SEQ ID NO 323
<211> LENGTH: 52
<212> TYPE: DNA
<213> ORGANISM: Artificial Sequence
<220> FEATURE:
<223> OTHER INFORMATION: Synthetic

<400> SEQUENCE: 323
aaaaggatga caggaacata ctgggaagcc acttctccta ggaccctgcc ca 52

<210> SEQ ID NO 324
<211> LENGTH: 52
<212> TYPE: DNA
<213> ORGANISM: Artificial Sequence
<220> FEATURE:
<223> OTHER INFORMATION: Synthetic

<400> SEQUENCE: 324
tcaaagtcaa ctgcaagcga gttatggtgg agtttagacc cagccaggta ac 52

<210> SEQ ID NO 325

<211> LENGTH: 52
<212> TYPE: DNA
<213> ORGANISM: Artificial Sequence
<220> FEATURE:
<223> OTHER INFORMATION: Synthetic

<400> SEQUENCE: 325
ctgctgtaat ggtgctggtg aatgcttgtg tacttcaaag gcaagtggca at 52

<210> SEQ ID NO 326
<211> LENGTH: 52
<212> TYPE: DNA
<213> ORGANISM: Artificial Sequence
<220> FEATURE:
<223> OTHER INFORMATION: Synthetic

<400> SEQUENCE: 326
acggctcaga cgagcaaggc tgtcgttaag tgtggccctg cctttgctat tg 52

<210> SEQ ID NO 327
<211> LENGTH: 52
<212> TYPE: DNA
<213> ORGANISM: Artificial Sequence
<220> FEATURE:
<223> OTHER INFORMATION: Synthetic

<400> SEQUENCE: 327
agcccccaag acgtgctccc aggacggagt ttcgctgcca cgatgggaag tg 52

<210> SEQ ID NO 328
<211> LENGTH: 52
<212> TYPE: DNA
<213> ORGANISM: Artificial Sequence
<220> FEATURE:
<223> OTHER INFORMATION: Synthetic

<400> SEQUENCE: 328
gagtgcctgt gccccgacgg cttccaagct ggtggcccag cgaagatgcg aa 52

<210> SEQ ID NO 329
<211> LENGTH: 52
<212> TYPE: DNA
<213> ORGANISM: Artificial Sequence
<220> FEATURE:
<223> OTHER INFORMATION: Synthetic

<400> SEQUENCE: 329
atctgtgcct ccctgccccg cagatccaac ccccactcgc ccaagtttac ct 52

<210> SEQ ID NO 330
<211> LENGTH: 52
<212> TYPE: DNA
<213> ORGANISM: Artificial Sequence
<220> FEATURE:
<223> OTHER INFORMATION: Synthetic

<400> SEQUENCE: 330
aggctaaagg tcagctccac agccgttaag gacacagcac acaaccaccc ga 52

<210> SEQ ID NO 331
<211> LENGTH: 52
<212> TYPE: DNA
<213> ORGANISM: Artificial Sequence
<220> FEATURE:
<223> OTHER INFORMATION: Synthetic

<400> SEQUENCE: 331
agcgcagata gccgttgggg accttggcgc tggtgccgct ttgaggggtc ca 52

<210> SEQ ID NO 332
<211> LENGTH: 52
<212> TYPE: DNA
<213> ORGANISM: Artificial Sequence
<220> FEATURE:
<223> OTHER INFORMATION: Synthetic

<400> SEQUENCE: 332
ctggggctgg agaagacggc gttccggcat atacgcggtg tccacccttc tc 52

<210> SEQ ID NO 333
<211> LENGTH: 52
<212> TYPE: DNA
<213> ORGANISM: Artificial Sequence
<220> FEATURE:
<223> OTHER INFORMATION: Synthetic

<400> SEQUENCE: 333
ggaggaaggg gctcaccttt gggtcttggg gatacagcag gaagtgaggg tc 52

<210> SEQ ID NO 334
<211> LENGTH: 52
<212> TYPE: DNA
<213> ORGANISM: Artificial Sequence
<220> FEATURE:
<223> OTHER INFORMATION: Synthetic

<400> SEQUENCE: 334
ctgggggaga ctcacctcga tgtaattggt ctgtgaactc tgtcccaaac tc 52

<210> SEQ ID NO 335
<211> LENGTH: 52
<212> TYPE: DNA
<213> ORGANISM: Artificial Sequence
<220> FEATURE:
<223> OTHER INFORMATION: Synthetic

<400> SEQUENCE: 335
agtttggtcc ccggactgac cagcattaga gcagccgcag ccccagctcc tt 52

<210> SEQ ID NO 336
<211> LENGTH: 52
<212> TYPE: DNA
<213> ORGANISM: Artificial Sequence
<220> FEATURE:
<223> OTHER INFORMATION: Synthetic

<400> SEQUENCE: 336
cctcggcttc cagctctcgg agcttaacgg ggaatctctg ggtacaagat cc 52

<210> SEQ ID NO 337
<211> LENGTH: 52
<212> TYPE: DNA
<213> ORGANISM: Artificial Sequence
<220> FEATURE:
<223> OTHER INFORMATION: Synthetic

<400> SEQUENCE: 337
cccaggggat accccaggga tacttaacag ctgcaccaac agcgtgtgcg ct 52

<210> SEQ ID NO 338
<211> LENGTH: 52
<212> TYPE: DNA

<213> ORGANISM: Artificial Sequence
<220> FEATURE:
<223> OTHER INFORMATION: Synthetic

<400> SEQUENCE: 338
tcatgcgcag gtcccagtcg ctgacaaccg cgccgggcgt cgtagcggga gc 52

<210> SEQ ID NO 339
<211> LENGTH: 52
<212> TYPE: DNA
<213> ORGANISM: Artificial Sequence
<220> FEATURE:
<223> OTHER INFORMATION: Synthetic

<400> SEQUENCE: 339
caggtgccgt ccatccacag agcccaagaa gcagcacatc tagctcgggg tt 52

<210> SEQ ID NO 340
<211> LENGTH: 52
<212> TYPE: DNA
<213> ORGANISM: Artificial Sequence
<220> FEATURE:
<223> OTHER INFORMATION: Synthetic

<400> SEQUENCE: 340
gaaagggcgt caccgctgtg gtgttaagac aggatcatcc tgggcattaa gg 52

<210> SEQ ID NO 341
<211> LENGTH: 52
<212> TYPE: DNA
<213> ORGANISM: Artificial Sequence
<220> FEATURE:
<223> OTHER INFORMATION: Synthetic

<400> SEQUENCE: 341
tcgggaatgg actccctggt agcaattgac caacagcaga cagttgtccg tc 52

<210> SEQ ID NO 342
<211> LENGTH: 52
<212> TYPE: DNA
<213> ORGANISM: Artificial Sequence
<220> FEATURE:
<223> OTHER INFORMATION: Synthetic

<400> SEQUENCE: 342
aggtaaccac gtggccagag gcacattccc tccctaaagc ggagaaaaag ta 52

<210> SEQ ID NO 343
<211> LENGTH: 52
<212> TYPE: DNA
<213> ORGANISM: Artificial Sequence
<220> FEATURE:
<223> OTHER INFORMATION: Synthetic

<400> SEQUENCE: 343
ctggcagccg cctccaccta ggttcttgcc cgcagggctg ccggctcgga tg 52

<210> SEQ ID NO 344
<211> LENGTH: 52
<212> TYPE: DNA
<213> ORGANISM: Artificial Sequence
<220> FEATURE:
<223> OTHER INFORMATION: Synthetic

<400> SEQUENCE: 344
agctcattgg aggtgaagtg ctcccttgtg tgttgtgggg atccaggccc tg 52

<210> SEQ ID NO 345
<211> LENGTH: 52
<212> TYPE: DNA
<213> ORGANISM: Artificial Sequence
<220> FEATURE:
<223> OTHER INFORMATION: Synthetic

<400> SEQUENCE: 345
agaacaggaa gcaaagtacc aggccaagcc acccaaacct tagaaagctg ga 52

<210> SEQ ID NO 346
<211> LENGTH: 52
<212> TYPE: DNA
<213> ORGANISM: Artificial Sequence
<220> FEATURE:
<223> OTHER INFORMATION: Synthetic

<400> SEQUENCE: 346
accctttcat attcatacct ttctcttgag acttctgccc agacttcagg aa 52

<210> SEQ ID NO 347
<211> LENGTH: 52
<212> TYPE: DNA
<213> ORGANISM: Artificial Sequence
<220> FEATURE:
<223> OTHER INFORMATION: Synthetic

<400> SEQUENCE: 347
gaacaggcac tgctgccatg agactggctg agcctcaaca tccgactccc ga 52

<210> SEQ ID NO 348
<211> LENGTH: 52
<212> TYPE: DNA
<213> ORGANISM: Artificial Sequence
<220> FEATURE:
<223> OTHER INFORMATION: Synthetic

<400> SEQUENCE: 348
tgagtaaaca aagcatctcc aactcttgag tctggccctc ggggagtgca tt 52

<210> SEQ ID NO 349
<211> LENGTH: 52
<212> TYPE: DNA
<213> ORGANISM: Artificial Sequence
<220> FEATURE:
<223> OTHER INFORMATION: Synthetic

<400> SEQUENCE: 349
tcatgagtta tcaattattt ttcttaacct atctccattt cagtatatgg aa 52

<210> SEQ ID NO 350
<211> LENGTH: 52
<212> TYPE: DNA
<213> ORGANISM: Artificial Sequence
<220> FEATURE:
<223> OTHER INFORMATION: Synthetic

<400> SEQUENCE: 350
gaacagcaaa agttcctggt tcctcttgct ggcactgtca aaatggaaat ct 52

<210> SEQ ID NO 351
<211> LENGTH: 54
<212> TYPE: DNA
<213> ORGANISM: Artificial Sequence
<220> FEATURE:

<223> OTHER INFORMATION: Synthetic

<400> SEQUENCE: 351
tctcccacaa aggcaatggc aaccgacaca gctttctctg catgccacct ggag 54

<210> SEQ ID NO 352
<211> LENGTH: 54
<212> TYPE: DNA
<213> ORGANISM: Artificial Sequence
<220> FEATURE:
<223> OTHER INFORMATION: Synthetic

<400> SEQUENCE: 352
cactcatgat gatgtgacct ttgaggcgca gtggcacagg cctttggaga tgag 54

<210> SEQ ID NO 353
<211> LENGTH: 54
<212> TYPE: DNA
<213> ORGANISM: Artificial Sequence
<220> FEATURE:
<223> OTHER INFORMATION: Synthetic

<400> SEQUENCE: 353
atttggccgt tattcagatt ccctggtgtg cagaagggct ataaagtagc acga 54

<210> SEQ ID NO 354
<211> LENGTH: 54
<212> TYPE: DNA
<213> ORGANISM: Artificial Sequence
<220> FEATURE:
<223> OTHER INFORMATION: Synthetic

<400> SEQUENCE: 354
ataaggaatg gttctgaggg tctcatctca tggagaaaaa accaaataag caga 54

<210> SEQ ID NO 355
<211> LENGTH: 54
<212> TYPE: DNA
<213> ORGANISM: Artificial Sequence
<220> FEATURE:
<223> OTHER INFORMATION: Synthetic

<400> SEQUENCE: 355
tccaacctgc ctcctcgcat catggcacag ccggggggct gcagatgatc gggt 54

<210> SEQ ID NO 356
<211> LENGTH: 54
<212> TYPE: DNA
<213> ORGANISM: Artificial Sequence
<220> FEATURE:
<223> OTHER INFORMATION: Synthetic

<400> SEQUENCE: 356
cattttgttc catcagctgt cgcactatat ctcattcgta acctacaaaa gaca 54

<210> SEQ ID NO 357
<211> LENGTH: 54
<212> TYPE: DNA
<213> ORGANISM: Artificial Sequence
<220> FEATURE:
<223> OTHER INFORMATION: Synthetic

<400> SEQUENCE: 357
acaatattag aacaaatttt ttgatagaga caccattgca aaacaacata aagt 54

<210> SEQ ID NO 358
<211> LENGTH: 54
<212> TYPE: DNA
<213> ORGANISM: Artificial Sequence
<220> FEATURE:
<223> OTHER INFORMATION: Synthetic

<400> SEQUENCE: 358
atttgtcttt tctggatgct caagtacact cagagttaca aacccacttt ttgt 54

<210> SEQ ID NO 359
<211> LENGTH: 54
<212> TYPE: DNA
<213> ORGANISM: Artificial Sequence
<220> FEATURE:
<223> OTHER INFORMATION: Synthetic

<400> SEQUENCE: 359
agctggatgg aatttagccg tgtaaacaca aaagaaggat gaggtaaaac tctg 54

<210> SEQ ID NO 360
<211> LENGTH: 54
<212> TYPE: DNA
<213> ORGANISM: Artificial Sequence
<220> FEATURE:
<223> OTHER INFORMATION: Synthetic

<400> SEQUENCE: 360
tattatgtgt tttacattta cgtgggagag tagccgacac tttgcttgct atgg 54

<210> SEQ ID NO 361
<211> LENGTH: 54
<212> TYPE: DNA
<213> ORGANISM: Artificial Sequence
<220> FEATURE:
<223> OTHER INFORMATION: Synthetic

<400> SEQUENCE: 361
gtccccgggc ctctgtctcc cgggcgtgtc ctccagcagc gggccttcgg ggcc 54

<210> SEQ ID NO 362
<211> LENGTH: 54
<212> TYPE: DNA
<213> ORGANISM: Artificial Sequence
<220> FEATURE:
<223> OTHER INFORMATION: Synthetic

<400> SEQUENCE: 362
actctgaaga acttttctca gacaatgtga gaataatttt gtcttccaag tagc 54

<210> SEQ ID NO 363
<211> LENGTH: 54
<212> TYPE: DNA
<213> ORGANISM: Artificial Sequence
<220> FEATURE:
<223> OTHER INFORMATION: Synthetic

<400> SEQUENCE: 363
gttgttgtag tccttgtgca aataggtgtg gtgacctggg tggggggtgg gggc 54

<210> SEQ ID NO 364
<211> LENGTH: 54
<212> TYPE: DNA
<213> ORGANISM: Artificial Sequence
<220> FEATURE:
<223> OTHER INFORMATION: Synthetic

<400> SEQUENCE: 364
atagagtctg taaaggaact gtagtcgcgc cctggtgaaa ttaggtcttc ttag 54

<210> SEQ ID NO 365
<211> LENGTH: 54
<212> TYPE: DNA
<213> ORGANISM: Artificial Sequence
<220> FEATURE:
<223> OTHER INFORMATION: Synthetic

<400> SEQUENCE: 365
gtatagagac cagcatcaag cagtttatat caagactgat ggcagaagag aaga 54

<210> SEQ ID NO 366
<211> LENGTH: 54
<212> TYPE: DNA
<213> ORGANISM: Artificial Sequence
<220> FEATURE:
<223> OTHER INFORMATION: Synthetic

<400> SEQUENCE: 366
gcacacacac acacgctttt tacctgagag tggttaaaat gtcactctga gagg 54

<210> SEQ ID NO 367
<211> LENGTH: 54
<212> TYPE: DNA
<213> ORGANISM: Artificial Sequence
<220> FEATURE:
<223> OTHER INFORMATION: Synthetic

<400> SEQUENCE: 367
ccttgatttt cttccttttg ttcacatatt caaaagtgac ttttggactt tgtt 54

<210> SEQ ID NO 368
<211> LENGTH: 54
<212> TYPE: DNA
<213> ORGANISM: Artificial Sequence
<220> FEATURE:
<223> OTHER INFORMATION: Synthetic

<400> SEQUENCE: 368
agcgcatgaa tatgcctggt agaagacact tcctcctcag cctattcttt ttag 54

<210> SEQ ID NO 369
<211> LENGTH: 54
<212> TYPE: DNA
<213> ORGANISM: Artificial Sequence
<220> FEATURE:
<223> OTHER INFORMATION: Synthetic

<400> SEQUENCE: 369
ggcctctttc ggggcctctc ctacctatac tggtcaggtt cgtcagctct ggga 54

<210> SEQ ID NO 370
<211> LENGTH: 56
<212> TYPE: DNA
<213> ORGANISM: Artificial Sequence
<220> FEATURE:
<223> OTHER INFORMATION: Synthetic

<400> SEQUENCE: 370
actgctggaa cttcagggcc cgcagcaaca actggtcacc cttctccagg gtcagc 56

<210> SEQ ID NO 371
<211> LENGTH: 56

<212> TYPE: DNA
<213> ORGANISM: Artificial Sequence
<220> FEATURE:
<223> OTHER INFORMATION: Synthetic

<400> SEQUENCE: 371
ctccagactc gcacacggct gagggtgatg atgtcctggc cctgctcagc atctgt 56

<210> SEQ ID NO 372
<211> LENGTH: 56
<212> TYPE: DNA
<213> ORGANISM: Artificial Sequence
<220> FEATURE:
<223> OTHER INFORMATION: Synthetic

<400> SEQUENCE: 372
acgatataca catctacctt gatcctgatg ataaattctt gcaaaatctg ttaaaa 56

<210> SEQ ID NO 373
<211> LENGTH: 56
<212> TYPE: DNA
<213> ORGANISM: Artificial Sequence
<220> FEATURE:
<223> OTHER INFORMATION: Synthetic

<400> SEQUENCE: 373
agctcctcag ccaggtccac gggcagacga cggccccagg catcgcgcac gtccag 56

<210> SEQ ID NO 374
<211> LENGTH: 58
<212> TYPE: DNA
<213> ORGANISM: Artificial Sequence
<220> FEATURE:
<223> OTHER INFORMATION: Synthetic

<400> SEQUENCE: 374
ctgtgccaaa gggtggaccc gcgggtggct ggctgccagg gcaacggcaa tgtgattg 58

<210> SEQ ID NO 375
<211> LENGTH: 58
<212> TYPE: DNA
<213> ORGANISM: Artificial Sequence
<220> FEATURE:
<223> OTHER INFORMATION: Synthetic

<400> SEQUENCE: 375
gcgggccctg cttcctggcc ggagacggcc ggccgcgcca gcgaggtccc ctccctga 58

<210> SEQ ID NO 376
<211> LENGTH: 58
<212> TYPE: DNA
<213> ORGANISM: Artificial Sequence
<220> FEATURE:
<223> OTHER INFORMATION: Synthetic

<400> SEQUENCE: 376
caaatccttc ctcttcacac cctcctgatt gatagatgta aaagcccttc ccagattt 58

<210> SEQ ID NO 377
<211> LENGTH: 58
<212> TYPE: DNA
<213> ORGANISM: Artificial Sequence
<220> FEATURE:
<223> OTHER INFORMATION: Synthetic

<400> SEQUENCE: 377
tgggccactc tgcagaccga ctggccgctc gctgcctttg ctgtttctcg gctggaac        58

<210> SEQ ID NO 378
<211> LENGTH: 58
<212> TYPE: DNA
<213> ORGANISM: Artificial Sequence
<220> FEATURE:
<223> OTHER INFORMATION: Synthetic

<400> SEQUENCE: 378
tttttttgga gatgatttta ttcctaatga atgacattct aataggctgt gaggaaga        58

<210> SEQ ID NO 379
<211> LENGTH: 58
<212> TYPE: DNA
<213> ORGANISM: Artificial Sequence
<220> FEATURE:
<223> OTHER INFORMATION: Synthetic

<400> SEQUENCE: 379
tttaaggtga aagtacattt tttgttgaat gaattaagtg aaactgccag catactca        58

<210> SEQ ID NO 380
<211> LENGTH: 58
<212> TYPE: DNA
<213> ORGANISM: Artificial Sequence
<220> FEATURE:
<223> OTHER INFORMATION: Synthetic

<400> SEQUENCE: 380
ttactttaac aggaagaggt actgcaacaa acatttgatg ggacggcaat agcaaatg        58

<210> SEQ ID NO 381
<211> LENGTH: 58
<212> TYPE: DNA
<213> ORGANISM: Artificial Sequence
<220> FEATURE:
<223> OTHER INFORMATION: Synthetic

<400> SEQUENCE: 381
cattattttc aactcactac cattcattaa ttagtagaag attattctca aaatgttg        58

<210> SEQ ID NO 382
<211> LENGTH: 58
<212> TYPE: DNA
<213> ORGANISM: Artificial Sequence
<220> FEATURE:
<223> OTHER INFORMATION: Synthetic

<400> SEQUENCE: 382
aaaagcaaga gaatttgaga agatgaatca atcagtcact acgattattt cggtaact        58

<210> SEQ ID NO 383
<211> LENGTH: 58
<212> TYPE: DNA
<213> ORGANISM: Artificial Sequence
<220> FEATURE:
<223> OTHER INFORMATION: Synthetic

<400> SEQUENCE: 383
aagcaagaga atttgagaag atgaatcagt cagtcactac gattatttcg gtaactaa        58

<210> SEQ ID NO 384
<211> LENGTH: 58
<212> TYPE: DNA
<213> ORGANISM: Artificial Sequence
<220> FEATURE:
<223> OTHER INFORMATION: Synthetic

<400> SEQUENCE: 384
tgacctgtca tgtatggcaa cagatagtaa gtatatcaag gcaatagtag aacacaaa 58

<210> SEQ ID NO 385
<211> LENGTH: 58
<212> TYPE: DNA
<213> ORGANISM: Artificial Sequence
<220> FEATURE:
<223> OTHER INFORMATION: Synthetic

<400> SEQUENCE: 385
cagtgctggt gttggatgtc aatgatgatt gatttttctg aggaagtaac caaacaag 58

<210> SEQ ID NO 386
<211> LENGTH: 58
<212> TYPE: DNA
<213> ORGANISM: Artificial Sequence
<220> FEATURE:
<223> OTHER INFORMATION: Synthetic

<400> SEQUENCE: 386
cggcagtcat aaatgggtgc gatgctgttt gttactcgat ttaaagcaag catctagg 58

<210> SEQ ID NO 387
<211> LENGTH: 58
<212> TYPE: DNA
<213> ORGANISM: Artificial Sequence
<220> FEATURE:
<223> OTHER INFORMATION: Synthetic

<400> SEQUENCE: 387
tcccttgccc atgttttctt tgtataacaa acacctgtgc gataagaaag catccaga 58

<210> SEQ ID NO 388
<211> LENGTH: 58
<212> TYPE: DNA
<213> ORGANISM: Artificial Sequence
<220> FEATURE:
<223> OTHER INFORMATION: Synthetic

<400> SEQUENCE: 388
actctctgta tctctggggt gtccaaaaca aacagtctca taatacgaca tggacttc 58

<210> SEQ ID NO 389
<211> LENGTH: 58
<212> TYPE: DNA
<213> ORGANISM: Artificial Sequence
<220> FEATURE:
<223> OTHER INFORMATION: Synthetic

<400> SEQUENCE: 389
aatgctaatg gcattcaaaa caatggtatg tatcccctgc tttaattgtt agcccatc 58

<210> SEQ ID NO 390
<211> LENGTH: 58
<212> TYPE: DNA
<213> ORGANISM: Artificial Sequence
<220> FEATURE:
<223> OTHER INFORMATION: Synthetic

<400> SEQUENCE: 390
gaagctttac tcacaacata tctgactttc tttcttactt cgagggctaa accacatt 58

<210> SEQ ID NO 391
<211> LENGTH: 58
<212> TYPE: DNA
<213> ORGANISM: Artificial Sequence
<220> FEATURE:
<223> OTHER INFORMATION: Synthetic

<400> SEQUENCE: 391
tcattcagat cacatgacct tcctgcagcc agcgggtgaa gaacatgctc attgcctt 58

<210> SEQ ID NO 392
<211> LENGTH: 58
<212> TYPE: DNA
<213> ORGANISM: Artificial Sequence
<220> FEATURE:
<223> OTHER INFORMATION: Synthetic

<400> SEQUENCE: 392
gatgtcctgg ccctgctcag catctgtcag tcagtggaga ccacaggccc tgctgcgg 58

<210> SEQ ID NO 393
<211> LENGTH: 58
<212> TYPE: DNA
<213> ORGANISM: Artificial Sequence
<220> FEATURE:
<223> OTHER INFORMATION: Synthetic

<400> SEQUENCE: 393
cagcctcgac acacgaccca caggctcagt caggggctgg ggacagaggc aaggtaag 58

<210> SEQ ID NO 394
<211> LENGTH: 58
<212> TYPE: DNA
<213> ORGANISM: Artificial Sequence
<220> FEATURE:
<223> OTHER INFORMATION: Synthetic

<400> SEQUENCE: 394
gaaaaccctt ccaataggct tgaatcaagc aagcatgctg cttgatgtag tttctgaa 58

<210> SEQ ID NO 395
<211> LENGTH: 58
<212> TYPE: DNA
<213> ORGANISM: Artificial Sequence
<220> FEATURE:
<223> OTHER INFORMATION: Synthetic

<400> SEQUENCE: 395
acagatgaac tgggctcact gctcagcctg cctgccagca gcgggggccc ccgagccc 58

<210> SEQ ID NO 396
<211> LENGTH: 58
<212> TYPE: DNA
<213> ORGANISM: Artificial Sequence
<220> FEATURE:
<223> OTHER INFORMATION: Synthetic

<400> SEQUENCE: 396
gccatcatgg agatcaagga gtacctgatt gattgacatg gcctccaggg caggcatg 58

<210> SEQ ID NO 397
<211> LENGTH: 58
<212> TYPE: DNA
<213> ORGANISM: Artificial Sequence
<220> FEATURE:
<223> OTHER INFORMATION: Synthetic

<400> SEQUENCE: 397
ctctttatta ccattgagcc ccagctggtt ggttcctgga gagtccattc gagaaaag 58

<210> SEQ ID NO 398
<211> LENGTH: 58
<212> TYPE: DNA
<213> ORGANISM: Artificial Sequence
<220> FEATURE:
<223> OTHER INFORMATION: Synthetic

<400> SEQUENCE: 398
gatgggaaaa catatgacaa cagatgtgcg tgcactgtgt gctgagaatg cgtgagta 58

<210> SEQ ID NO 399
<211> LENGTH: 58
<212> TYPE: DNA
<213> ORGANISM: Artificial Sequence
<220> FEATURE:
<223> OTHER INFORMATION: Synthetic

<400> SEQUENCE: 399
cactagactc acggtcaggc aggcaggccg gccagcaggg cacctgcctt ttccaaca 58

<210> SEQ ID NO 400
<211> LENGTH: 58
<212> TYPE: DNA
<213> ORGANISM: Artificial Sequence
<220> FEATURE:
<223> OTHER INFORMATION: Synthetic

<400> SEQUENCE: 400
cagacatacc tggttttgat ggggtcatcc atcatacgta atgcccttag ccatctcc 58

<210> SEQ ID NO 401
<211> LENGTH: 58
<212> TYPE: DNA
<213> ORGANISM: Artificial Sequence
<220> FEATURE:
<223> OTHER INFORMATION: Synthetic

<400> SEQUENCE: 401
accgctggag tcacccttcc cagtgaggca ggcaggggtc gttaggggag gtgatacg 58

<210> SEQ ID NO 402
<211> LENGTH: 58
<212> TYPE: DNA
<213> ORGANISM: Artificial Sequence
<220> FEATURE:
<223> OTHER INFORMATION: Synthetic

<400> SEQUENCE: 402
ggcataaagt cactgccaac aagatcaaac aaacaccgca ttgagctcac agtcgatg 58

<210> SEQ ID NO 403
<211> LENGTH: 58
<212> TYPE: DNA
<213> ORGANISM: Artificial Sequence
<220> FEATURE:
<223> OTHER INFORMATION: Synthetic

<400> SEQUENCE: 403
tttgacttcc aacgagggga agagaagata gatagcgaat attaacagag tattcagc 58

<210> SEQ ID NO 404

<211> LENGTH: 58
<212> TYPE: DNA
<213> ORGANISM: Artificial Sequence
<220> FEATURE:
<223> OTHER INFORMATION: Synthetic

<400> SEQUENCE: 404
cgctgaggct ggtgtcatac tccacagata gatataattc ggagagcagg acagtctt 58

<210> SEQ ID NO 405
<211> LENGTH: 58
<212> TYPE: DNA
<213> ORGANISM: Artificial Sequence
<220> FEATURE:
<223> OTHER INFORMATION: Synthetic

<400> SEQUENCE: 405
acacagcctt ctctgtctct cttggcagtc agtcggtctt ggcagctgtt gtaattgc 58

<210> SEQ ID NO 406
<211> LENGTH: 58
<212> TYPE: DNA
<213> ORGANISM: Artificial Sequence
<220> FEATURE:
<223> OTHER INFORMATION: Synthetic

<400> SEQUENCE: 406
cacttcttgg tactcctgtc ctgaaagata gatattaatt tcaagataga aagaggac 58

<210> SEQ ID NO 407
<211> LENGTH: 58
<212> TYPE: DNA
<213> ORGANISM: Artificial Sequence
<220> FEATURE:
<223> OTHER INFORMATION: Synthetic

<400> SEQUENCE: 407
aaatgattgg acagttttca tatagtgaat gaagaaaggg aaagtgggga aaacaagt 58

<210> SEQ ID NO 408
<211> LENGTH: 58
<212> TYPE: DNA
<213> ORGANISM: Artificial Sequence
<220> FEATURE:
<223> OTHER INFORMATION: Synthetic

<400> SEQUENCE: 408
ataagcccag gaaatgggca agatggaacg aactggagcc ccatggggcc gcactgac 58

<210> SEQ ID NO 409
<211> LENGTH: 58
<212> TYPE: DNA
<213> ORGANISM: Artificial Sequence
<220> FEATURE:
<223> OTHER INFORMATION: Synthetic

<400> SEQUENCE: 409
ctgagatacg tacctagcca catgcgaatg aatgatgctc atgtagtctt tgttcttg 58

<210> SEQ ID NO 410
<211> LENGTH: 58
<212> TYPE: DNA
<213> ORGANISM: Artificial Sequence
<220> FEATURE:
<223> OTHER INFORMATION: Synthetic

<400> SEQUENCE: 410
gagtcgatca gaaagaccac cttggggatg gatgccttcc agggagggca gctgccca 58

<210> SEQ ID NO 411
<211> LENGTH: 58
<212> TYPE: DNA
<213> ORGANISM: Artificial Sequence
<220> FEATURE:
<223> OTHER INFORMATION: Synthetic

<400> SEQUENCE: 411
actacacaaa gagaatctag tgattacaga cagtgtccct tgcaaaagga agaaaata 58

<210> SEQ ID NO 412
<211> LENGTH: 58
<212> TYPE: DNA
<213> ORGANISM: Artificial Sequence
<220> FEATURE:
<223> OTHER INFORMATION: Synthetic

<400> SEQUENCE: 412
aagtttccct ggataaacac agagggagtg agtggctttg gcgtcttatg gtgaggct 58

<210> SEQ ID NO 413
<211> LENGTH: 58
<212> TYPE: DNA
<213> ORGANISM: Artificial Sequence
<220> FEATURE:
<223> OTHER INFORMATION: Synthetic

<400> SEQUENCE: 413
ggctttggga gaagctgacg ttgttatcca tccccaggaa tagctgtcac tccggtcc 58

<210> SEQ ID NO 414
<211> LENGTH: 58
<212> TYPE: DNA
<213> ORGANISM: Artificial Sequence
<220> FEATURE:
<223> OTHER INFORMATION: Synthetic

<400> SEQUENCE: 414
tccacagtgt tgggacaagg ccaggcgttc gttgcacttc accagccgct gcatggag 58

<210> SEQ ID NO 415
<211> LENGTH: 58
<212> TYPE: DNA
<213> ORGANISM: Artificial Sequence
<220> FEATURE:
<223> OTHER INFORMATION: Synthetic

<400> SEQUENCE: 415
ctgaaaatga agataacaaa tatactgctt gctgccagta gaaattctca taacttag 58

<210> SEQ ID NO 416
<211> LENGTH: 58
<212> TYPE: DNA
<213> ORGANISM: Artificial Sequence
<220> FEATURE:
<223> OTHER INFORMATION: Synthetic

<400> SEQUENCE: 416
ttgtttctcc ggctgcacag aaggcattta tttcagccac caaggagttg tggcacca 58

<210> SEQ ID NO 417
<211> LENGTH: 58
<212> TYPE: DNA

```
<213> ORGANISM: Artificial Sequence
<220> FEATURE:
<223> OTHER INFORMATION: Synthetic

<400> SEQUENCE: 417

tcctcagcag ctcggtggag tggagcactc acttcgggcg agcgctcggc cagtgccc         58

<210> SEQ ID NO 418
<211> LENGTH: 58
<212> TYPE: DNA
<213> ORGANISM: Artificial Sequence
<220> FEATURE:
<223> OTHER INFORMATION: Synthetic

<400> SEQUENCE: 418

gaaatccttc cagtcagggc cataggatag atatacggtt caggtaccag ggggcaga         58

<210> SEQ ID NO 419
<211> LENGTH: 58
<212> TYPE: DNA
<213> ORGANISM: Artificial Sequence
<220> FEATURE:
<223> OTHER INFORMATION: Synthetic

<400> SEQUENCE: 419

acagaaaggc cagtagacag ggataaggca ggcaacaccc ccaacagctt tcttcaga         58

<210> SEQ ID NO 420
<211> LENGTH: 58
<212> TYPE: DNA
<213> ORGANISM: Artificial Sequence
<220> FEATURE:
<223> OTHER INFORMATION: Synthetic

<400> SEQUENCE: 420

agacagtgca agcggaaggt gacagtgcct gcctgtggtc tctgtgcgga gtccaaag         58

<210> SEQ ID NO 421
<211> LENGTH: 58
<212> TYPE: DNA
<213> ORGANISM: Artificial Sequence
<220> FEATURE:
<223> OTHER INFORMATION: Synthetic

<400> SEQUENCE: 421

tactcacgga gctgcccatg tgggcaagta agtgcctctt ccgcgcgctc cacgcggc         58

<210> SEQ ID NO 422
<211> LENGTH: 58
<212> TYPE: DNA
<213> ORGANISM: Artificial Sequence
<220> FEATURE:
<223> OTHER INFORMATION: Synthetic

<400> SEQUENCE: 422

agcgttgtac gcggaggagc gcagcgccag ccagccgcac gaagcagcgg gcccggga         58

<210> SEQ ID NO 423
<211> LENGTH: 58
<212> TYPE: DNA
<213> ORGANISM: Artificial Sequence
<220> FEATURE:
<223> OTHER INFORMATION: Synthetic

<400> SEQUENCE: 423

gcagccagct ctgcgtgaac ctggagggtg ggtggctaca agtgccagtg tgaggaag         58
```

<210> SEQ ID NO 424
<211> LENGTH: 58
<212> TYPE: DNA
<213> ORGANISM: Artificial Sequence
<220> FEATURE:
<223> OTHER INFORMATION: Synthetic

<400> SEQUENCE: 424
ggcccccgtg tcaccgtcct ggtgcgggag ggagttcgag gcatttgaca acgcggtg 58

<210> SEQ ID NO 425
<211> LENGTH: 58
<212> TYPE: DNA
<213> ORGANISM: Artificial Sequence
<220> FEATURE:
<223> OTHER INFORMATION: Synthetic

<400> SEQUENCE: 425
atttaccttc caagagtttt tgacatgatt gatgtattca tctcttaatg ccttagga 58

<210> SEQ ID NO 426
<211> LENGTH: 60
<212> TYPE: DNA
<213> ORGANISM: Artificial Sequence
<220> FEATURE:
<223> OTHER INFORMATION: Synthetic

<400> SEQUENCE: 426
aactcggcga cccccagcgt ggcgtggagc ggagcgtgtg ctccgtggtg atggccaggc 60

<210> SEQ ID NO 427
<211> LENGTH: 60
<212> TYPE: DNA
<213> ORGANISM: Artificial Sequence
<220> FEATURE:
<223> OTHER INFORMATION: Synthetic

<400> SEQUENCE: 427
caggcttcct gaactactac gatgcctgct ctgctcggag ggtctgcgcg ccgccagccc 60

<210> SEQ ID NO 428
<211> LENGTH: 60
<212> TYPE: DNA
<213> ORGANISM: Artificial Sequence
<220> FEATURE:
<223> OTHER INFORMATION: Synthetic

<400> SEQUENCE: 428
aggtctgtag atctagctgc gccacgggct gggctgggcc gggccgggca gggggctacc 60

<210> SEQ ID NO 429
<211> LENGTH: 60
<212> TYPE: DNA
<213> ORGANISM: Artificial Sequence
<220> FEATURE:
<223> OTHER INFORMATION: Synthetic

<400> SEQUENCE: 429
gctgcgccac gggctgggcc gggccgggca gggcaggggg ctaccacccc gcgccgcaga 60

<210> SEQ ID NO 430
<211> LENGTH: 60
<212> TYPE: DNA
<213> ORGANISM: Artificial Sequence
<220> FEATURE:

<223> OTHER INFORMATION: Synthetic

<400> SEQUENCE: 430
ctcatgccct tgagcctctt tagcatgccg tgccgcgcag gtcagtgacg ccgtactgga 60

<210> SEQ ID NO 431
<211> LENGTH: 60
<212> TYPE: DNA
<213> ORGANISM: Artificial Sequence
<220> FEATURE:
<223> OTHER INFORMATION: Synthetic

<400> SEQUENCE: 431
agatgagggt gggggtagct taccagtgag gtgagatgag attcgtcagg gtgaccttga 60

<210> SEQ ID NO 432
<211> LENGTH: 60
<212> TYPE: DNA
<213> ORGANISM: Artificial Sequence
<220> FEATURE:
<223> OTHER INFORMATION: Synthetic

<400> SEQUENCE: 432
attgtgctca ctgtacttgg aatgttctca tctcatttcc catttctctt tcaggtgaca 60

<210> SEQ ID NO 433
<211> LENGTH: 60
<212> TYPE: DNA
<213> ORGANISM: Artificial Sequence
<220> FEATURE:
<223> OTHER INFORMATION: Synthetic

<400> SEQUENCE: 433
tacaatcggg acagctttga taccactcgg ctcggcagag gctggtgctg gagattgggg 60

<210> SEQ ID NO 434
<211> LENGTH: 60
<212> TYPE: DNA
<213> ORGANISM: Artificial Sequence
<220> FEATURE:
<223> OTHER INFORMATION: Synthetic

<400> SEQUENCE: 434
aggaagcagc ggcaggggac gcccgcggct cggctcgggc acactggacg tacctgtggg 60

<210> SEQ ID NO 435
<211> LENGTH: 60
<212> TYPE: DNA
<213> ORGANISM: Artificial Sequence
<220> FEATURE:
<223> OTHER INFORMATION: Synthetic

<400> SEQUENCE: 435
gtcccagtcg ctgacaccgc gccgggcgtc gcgtcgtagc gggagcccag gtagtggcgc 60

<210> SEQ ID NO 436
<211> LENGTH: 62
<212> TYPE: DNA
<213> ORGANISM: Artificial Sequence
<220> FEATURE:
<223> OTHER INFORMATION: Synthetic

<400> SEQUENCE: 436
cccttcctcc cctggagtca cctgcatcca tatccatccg gtatagtagt tgatcacagt 60
gg 62

<210> SEQ ID NO 437
<211> LENGTH: 62
<212> TYPE: DNA
<213> ORGANISM: Artificial Sequence
<220> FEATURE:
<223> OTHER INFORMATION: Synthetic

<400> SEQUENCE: 437
aggatgacca tatcagtggg ctattttggg cttgggcttt cgcttgatac tcctaacttg 60
ca 62

<210> SEQ ID NO 438
<211> LENGTH: 62
<212> TYPE: DNA
<213> ORGANISM: Artificial Sequence
<220> FEATURE:
<223> OTHER INFORMATION: Synthetic

<400> SEQUENCE: 438
agcagcagct cgtcgtccct gagtcacggc gacggcggcg gcggcggcgg cggcggggga 60
gg 62

<210> SEQ ID NO 439
<211> LENGTH: 64
<212> TYPE: DNA
<213> ORGANISM: Artificial Sequence
<220> FEATURE:
<223> OTHER INFORMATION: Synthetic

<400> SEQUENCE: 439
ttcagcacga accacgtcct cagcttcaca gatcacagag tagtatttta tagccctaaa 60
gaaa 64

<210> SEQ ID NO 440
<211> LENGTH: 64
<212> TYPE: DNA
<213> ORGANISM: Artificial Sequence
<220> FEATURE:
<223> OTHER INFORMATION: Synthetic

<400> SEQUENCE: 440
ggtcccctgc cggtgcctct gcccctcaaa catcaaacac gagctcgctc cgtggctttt 60
tcag 64

<210> SEQ ID NO 441
<211> LENGTH: 64
<212> TYPE: DNA
<213> ORGANISM: Artificial Sequence
<220> FEATURE:
<223> OTHER INFORMATION: Synthetic

<400> SEQUENCE: 441
ccaggtcccc gcctcatacc agcccgacga gggacgagga ggagcgagcg cgcctggcgg 60
gcga 64

<210> SEQ ID NO 442
<211> LENGTH: 64
<212> TYPE: DNA
<213> ORGANISM: Artificial Sequence
<220> FEATURE:
<223> OTHER INFORMATION: Synthetic

<400> SEQUENCE: 442
ctgtacttgc cactgaaaat ggatggctct tagctcttag cttcttcgcg gatattagtg 60
aatg 64

<210> SEQ ID NO 443
<211> LENGTH: 66
<212> TYPE: DNA
<213> ORGANISM: Artificial Sequence
<220> FEATURE:
<223> OTHER INFORMATION: Synthetic

<400> SEQUENCE: 443
tggctttaat gcagcaaggc ttgctaatct cccaatctcc cagaggaagt tattcaaaag 60
ggacat 66

<210> SEQ ID NO 444
<211> LENGTH: 66
<212> TYPE: DNA
<213> ORGANISM: Artificial Sequence
<220> FEATURE:
<223> OTHER INFORMATION: Synthetic

<400> SEQUENCE: 444
ttgaagaaga ggaagaagat acagaacgtg ttcacgtgtt ctccagctta tgattatctt 60
agaggt 66

<210> SEQ ID NO 445
<211> LENGTH: 66
<212> TYPE: DNA
<213> ORGANISM: Artificial Sequence
<220> FEATURE:
<223> OTHER INFORMATION: Synthetic

<400> SEQUENCE: 445
agacgtcaat cctccttttg atcagctctg ctcctctgct ctgctgggac gacgacacgt 60
ggtgtc 66

<210> SEQ ID NO 446
<211> LENGTH: 66
<212> TYPE: DNA
<213> ORGANISM: Artificial Sequence
<220> FEATURE:
<223> OTHER INFORMATION: Synthetic

<400> SEQUENCE: 446
gaatttgaca ggataataga aaatcaagaa aaaaagaaaa atccttaaag gcttcaaaaa 60
gcactc 66

<210> SEQ ID NO 447
<211> LENGTH: 66
<212> TYPE: DNA
<213> ORGANISM: Artificial Sequence
<220> FEATURE:
<223> OTHER INFORMATION: Synthetic

<400> SEQUENCE: 447
tcatggctac ctcagagctg agctgcgagg tgtcgaggtg tcggaggaga actgtgagcg 60
ccggga 66

<210> SEQ ID NO 448
<211> LENGTH: 66

<212> TYPE: DNA
<213> ORGANISM: Artificial Sequence
<220> FEATURE:
<223> OTHER INFORMATION: Synthetic

<400> SEQUENCE: 448
gatggtggcc ccgactgcaa ggacaaatct gacaatctga cgaggaaaac tgcggtatgg 60
gcgggg 66

<210> SEQ ID NO 449
<211> LENGTH: 66
<212> TYPE: DNA
<213> ORGANISM: Artificial Sequence
<220> FEATURE:
<223> OTHER INFORMATION: Synthetic

<400> SEQUENCE: 449
agcctatgcg ctctgcacgt ttgcactcag cacctcagca ccggggaccc aagccagccc 60
gtgcgc 66

<210> SEQ ID NO 450
<211> LENGTH: 68
<212> TYPE: DNA
<213> ORGANISM: Artificial Sequence
<220> FEATURE:
<223> OTHER INFORMATION: Synthetic

<400> SEQUENCE: 450
tccagcagga caacagatgg ctgcatccac actgtccaca ctgcctctga gaaagccacc 60
tctagggt 68

<210> SEQ ID NO 451
<211> LENGTH: 68
<212> TYPE: DNA
<213> ORGANISM: Artificial Sequence
<220> FEATURE:
<223> OTHER INFORMATION: Synthetic

<400> SEQUENCE: 451
gcctgttgcc cgccagcacc agctcgcgca ggctgcgcag gctgcccagg ccgcggaacg 60
ccgcatcg 68

<210> SEQ ID NO 452
<211> LENGTH: 70
<212> TYPE: DNA
<213> ORGANISM: Artificial Sequence
<220> FEATURE:
<223> OTHER INFORMATION: Synthetic

<400> SEQUENCE: 452
gcagccgccg ccagccgcag ccatgggccg ggcccggccg ggcccggccg ggccaacgcg 60
ggccgcccag 70

<210> SEQ ID NO 453
<211> LENGTH: 70
<212> TYPE: DNA
<213> ORGANISM: Artificial Sequence
<220> FEATURE:
<223> OTHER INFORMATION: Synthetic

<400> SEQUENCE: 453
agcccaagac agaggtgttg gcagtggtgg catgaggtgg catgaggaat agtgacaggc 60
acaaagctgg 70

<210> SEQ ID NO 454
<211> LENGTH: 70
<212> TYPE: DNA
<213> ORGANISM: Artificial Sequence
<220> FEATURE:
<223> OTHER INFORMATION: Synthetic

<400> SEQUENCE: 454
gtgcaggcgc gcgagcacaa cccatggctg cgctgggctg cgctgggctg cgcgaggctg 60
aggtgggcgc 70

<210> SEQ ID NO 455
<211> LENGTH: 70
<212> TYPE: DNA
<213> ORGANISM: Artificial Sequence
<220> FEATURE:
<223> OTHER INFORMATION: Synthetic

<400> SEQUENCE: 455
ttcagcacga accacgtcct cagcttcaca gagtatcaca gagtagtatt ttatagccct 60
aaagaaattg 70

<210> SEQ ID NO 456
<211> LENGTH: 70
<212> TYPE: DNA
<213> ORGANISM: Artificial Sequence
<220> FEATURE:
<223> OTHER INFORMATION: Synthetic

<400> SEQUENCE: 456
catggaggca tttgcttgtc agcacttcca ggttattcca ggttagttac cacttcatta 60
ctggagggca 70

<210> SEQ ID NO 457
<211> LENGTH: 70
<212> TYPE: DNA
<213> ORGANISM: Artificial Sequence
<220> FEATURE:
<223> OTHER INFORMATION: Synthetic

<400> SEQUENCE: 457
gtaggagagc atggatctct gggtgcagat cctcccagat cctccatact agcttcccct 60
gaggccagtg 70

<210> SEQ ID NO 458
<211> LENGTH: 70
<212> TYPE: DNA
<213> ORGANISM: Artificial Sequence
<220> FEATURE:
<223> OTHER INFORMATION: Synthetic

<400> SEQUENCE: 458
taatgagctg gcatgagtat ttgtgccaca tggctccaca tggctccaca tgcaagtttg 60
aaacagaact 70

<210> SEQ ID NO 459
<211> LENGTH: 70
<212> TYPE: DNA
<213> ORGANISM: Artificial Sequence
<220> FEATURE:
<223> OTHER INFORMATION: Synthetic

<400> SEQUENCE: 459
gttttcgtca tcgaggtgaa gacaaaagga ggatcaagga ggatccaagt acctcatcta 60
ccgccgctac 70

<210> SEQ ID NO 460
<211> LENGTH: 72
<212> TYPE: DNA
<213> ORGANISM: Artificial Sequence
<220> FEATURE:
<223> OTHER INFORMATION: Synthetic

<400> SEQUENCE: 460
gaggtgcccc acagctgccg ccgctaccgg ctcgccaccg gctcgccacc atcgccaact 60
tctcggcgct tg 72

<210> SEQ ID NO 461
<211> LENGTH: 72
<212> TYPE: DNA
<213> ORGANISM: Artificial Sequence
<220> FEATURE:
<223> OTHER INFORMATION: Synthetic

<400> SEQUENCE: 461
gtggtgttct tcgggacgga gtacgtggtc cgcctctggt ccgcctctgg tccgccggct 60
gccgcagcaa gt 72

<210> SEQ ID NO 462
<211> LENGTH: 72
<212> TYPE: DNA
<213> ORGANISM: Artificial Sequence
<220> FEATURE:
<223> OTHER INFORMATION: Synthetic

<400> SEQUENCE: 462
gctgtgaacc cctaccagct gctctccatc tactcgccat ctactcgcca gagcacatcc 60
gccagtatac ca 72

<210> SEQ ID NO 463
<211> LENGTH: 72
<212> TYPE: DNA
<213> ORGANISM: Artificial Sequence
<220> FEATURE:
<223> OTHER INFORMATION: Synthetic

<400> SEQUENCE: 463
ccacaagccc tagccatgcc gtggtagcca atgttcagcc aatgttcagc ttgtcttgca 60
tctaatgaag ca 72

<210> SEQ ID NO 464
<211> LENGTH: 76
<212> TYPE: DNA
<213> ORGANISM: Artificial Sequence
<220> FEATURE:
<223> OTHER INFORMATION: Synthetic

<400> SEQUENCE: 464
gaaatggcaa tgaaagttga actagctaga atgagttact agaatgagtt accagagagc 60
agcttgggag gttgat 76

<210> SEQ ID NO 465

<211> LENGTH: 76
<212> TYPE: DNA
<213> ORGANISM: Artificial Sequence
<220> FEATURE:
<223> OTHER INFORMATION: Synthetic

<400> SEQUENCE: 465
gaaatggcaa tgaaagttga actagctaga atgagttact agaatgagtt accagagagc 60
agcttgggag gttgat 76

<210> SEQ ID NO 466
<211> LENGTH: 78
<212> TYPE: DNA
<213> ORGANISM: Artificial Sequence
<220> FEATURE:
<223> OTHER INFORMATION: Synthetic

<400> SEQUENCE: 466
ccacctcttc ggcattgtac gtctgagagc tgcggagcca gagctgcgga gccagggccg 60
ggagcccacc ccagaagc 78

<210> SEQ ID NO 467
<211> LENGTH: 80
<212> TYPE: DNA
<213> ORGANISM: Artificial Sequence
<220> FEATURE:
<223> OTHER INFORMATION: Synthetic

<400> SEQUENCE: 467
gccttcagca cgaaccacgt cctcagcttc acagagtagt gcttcacaga gtagtatttt 60
atagccctaa agaaattgtg 80

<210> SEQ ID NO 468
<211> LENGTH: 80
<212> TYPE: DNA
<213> ORGANISM: Artificial Sequence
<220> FEATURE:
<223> OTHER INFORMATION: Synthetic

<400> SEQUENCE: 468
acagcggtgt gaccaagata tggaagaggg agagggaggc gagggagagg gaggcaaagg 60
ccacggaggg cgagaagtcg 80

<210> SEQ ID NO 469
<211> LENGTH: 80
<212> TYPE: DNA
<213> ORGANISM: Artificial Sequence
<220> FEATURE:
<223> OTHER INFORMATION: Synthetic

<400> SEQUENCE: 469
tctctccagc cctcttaccg tctctcggcc cggcggcaca cggcccggcg gcacacggcc 60
cggcagaaat gcagcgccga 80

<210> SEQ ID NO 470
<211> LENGTH: 82
<212> TYPE: DNA
<213> ORGANISM: Artificial Sequence
<220> FEATURE:
<223> OTHER INFORMATION: Synthetic

<400> SEQUENCE: 470
actggctggt cctcgccgcg aagcagggcc gtcgcgaggc tgggccgtcg cgaggctgtg 60
aagctgcttc gccggtgctt gg 82

<210> SEQ ID NO 471
<211> LENGTH: 82
<212> TYPE: DNA
<213> ORGANISM: Artificial Sequence
<220> FEATURE:
<223> OTHER INFORMATION: Synthetic

<400> SEQUENCE: 471
cgctgggcgg cctgcccctg cccttggcgc ggccccggcc cggcgcggcc ccggcccggc 60
gcggcccctg gcgcccgaga gc 82

<210> SEQ ID NO 472
<211> LENGTH: 82
<212> TYPE: DNA
<213> ORGANISM: Artificial Sequence
<220> FEATURE:
<223> OTHER INFORMATION: Synthetic

<400> SEQUENCE: 472
gtcctgcagg tgctggggca ggtgtgggcc tcccctgctg gggcctccc ctgctggggg 60 ctgtggtcag aaagttcagc cg 82

<210> SEQ ID NO 473
<211> LENGTH: 82
<212> TYPE: DNA
<213> ORGANISM: Artificial Sequence
<220> FEATURE:
<223> OTHER INFORMATION: Synthetic

<400> SEQUENCE: 473
ggtgaccccg gagcccgcag ccccagccac gcaggtatcg tgccacgcag gtatcgtggc 60
ctccgtcctc cgcgcgactc ct 82

<210> SEQ ID NO 474
<211> LENGTH: 84
<212> TYPE: DNA
<213> ORGANISM: Artificial Sequence
<220> FEATURE:
<223> OTHER INFORMATION: Synthetic

<400> SEQUENCE: 474
cctaggatac aggccttcag cacgaaccac gtcctcagct tcaccacgtc ctcagcttca 60
cagagtagta ttttatagcc ctaa 84

<210> SEQ ID NO 475
<211> LENGTH: 84
<212> TYPE: DNA
<213> ORGANISM: Artificial Sequence
<220> FEATURE:
<223> OTHER INFORMATION: Synthetic

<400> SEQUENCE: 475
gatacaggcc ttcagcacga accacgtcct cagcttcaca gagtcctcag cttcacagag 60
tagtatttta tagccctaaa gaaa 84

<210> SEQ ID NO 476
<211> LENGTH: 84
<212> TYPE: DNA
<213> ORGANISM: Artificial Sequence
<220> FEATURE:

<223> OTHER INFORMATION: Synthetic

<400> SEQUENCE: 476
caagacagac tgagtctttc aaatgagcaa gttggggtgt gcagcaagtt ggggtgtgca 60
gcaagttcgt ccagcaactt ctgt 84

<210> SEQ ID NO 477
<211> LENGTH: 84
<212> TYPE: DNA
<213> ORGANISM: Artificial Sequence
<220> FEATURE:
<223> OTHER INFORMATION: Synthetic

<400> SEQUENCE: 477
cgcggctcgc ggcgtctggg tttgtgttgt cgatggcgac ccgttgtcga tggcgacccg 60
tttcccttgc ttcagggctg tctc 84

<210> SEQ ID NO 478
<211> LENGTH: 86
<212> TYPE: DNA
<213> ORGANISM: Artificial Sequence
<220> FEATURE:
<223> OTHER INFORMATION: Synthetic

<400> SEQUENCE: 478
atgaagccta ggggacaccg gggtcggagg cgccgcctgg gttggaggcg ccgcctgggt 60
tggggtctgg cactgtgcca ggtcgc 86

<210> SEQ ID NO 479
<211> LENGTH: 86
<212> TYPE: DNA
<213> ORGANISM: Artificial Sequence
<220> FEATURE:
<223> OTHER INFORMATION: Synthetic

<400> SEQUENCE: 479
gagcttcttt aaacaactct tttaactcct gatcagacat gacctcctga tcagacatga 60
cctccagtgc atctatgcta ctgtga 86

<210> SEQ ID NO 480
<211> LENGTH: 86
<212> TYPE: DNA
<213> ORGANISM: Artificial Sequence
<220> FEATURE:
<223> OTHER INFORMATION: Synthetic

<400> SEQUENCE: 480
cagctggcgc tgtgatggtg gccccgactg caaggacaaa tctgactgca aggacaaatc 60
tgacgaggaa aactgcggta tgggcg 86

<210> SEQ ID NO 481
<211> LENGTH: 86
<212> TYPE: DNA
<213> ORGANISM: Artificial Sequence
<220> FEATURE:
<223> OTHER INFORMATION: Synthetic

<400> SEQUENCE: 481
tcgggagatg ggaccgtcct gcaggaccga ccacatctgc agaaccgacc acatctgcag 60
aacctctgcg tggagagcga ggattc 86

<210> SEQ ID NO 482
<211> LENGTH: 88
<212> TYPE: DNA
<213> ORGANISM: Artificial Sequence
<220> FEATURE:
<223> OTHER INFORMATION: Synthetic

<400> SEQUENCE: 482
ttgctaatct cccagaggaa gttattcaaa agggacatag aaaatcaaaa gggacataga 60
aaagcaagag aatttgagaa gatgaatc 88

<210> SEQ ID NO 483
<211> LENGTH: 90
<212> TYPE: DNA
<213> ORGANISM: Artificial Sequence
<220> FEATURE:
<223> OTHER INFORMATION: Synthetic

<400> SEQUENCE: 483
cttctgcgtg gaccttcagg aatttcatac ttttcttcct gttcacatac ttttcttcct 60
gttcacatac ttttcttcgt agacatgctt 90

<210> SEQ ID NO 484
<211> LENGTH: 90
<212> TYPE: DNA
<213> ORGANISM: Artificial Sequence
<220> FEATURE:
<223> OTHER INFORMATION: Synthetic

<400> SEQUENCE: 484
ctgcacctac ctttgatctg tctttgaagt ggtaggaaaa atgtcgaagt ggtaggaaaa 60
atgtcttctt ccacatctga ttcatctacc 90

<210> SEQ ID NO 485
<211> LENGTH: 90
<212> TYPE: DNA
<213> ORGANISM: Artificial Sequence
<220> FEATURE:
<223> OTHER INFORMATION: Synthetic

<400> SEQUENCE: 485
ctccacgccc acgatgccgc ggatgctgat ctgccgccgc ttctcctgat ctgccgccgc 60
ttctcctggt ccgtcagggg cttcgccatg 90

<210> SEQ ID NO 486
<211> LENGTH: 92
<212> TYPE: DNA
<213> ORGANISM: Artificial Sequence
<220> FEATURE:
<223> OTHER INFORMATION: Synthetic

<400> SEQUENCE: 486
acccggtggc cgggctggtg gtggggatcc tggtgaccgt gctggtgatc ctggtgaccg 60
tgctggtgca gagctccagc acctccacat cc 92

<210> SEQ ID NO 487
<211> LENGTH: 96
<212> TYPE: DNA
<213> ORGANISM: Artificial Sequence
<220> FEATURE:
<223> OTHER INFORMATION: Synthetic

<400> SEQUENCE: 487

```
actccgctgt aagtggtttg gccagcccgg gcagccacct gtaatctccc cgggcagcca    60

cctgtaatct cgtcttgata acatcagcag gggtca                             96
```

<210> SEQ ID NO 488
<211> LENGTH: 96
<212> TYPE: DNA
<213> ORGANISM: Artificial Sequence
<220> FEATURE:
<223> OTHER INFORMATION: Synthetic

<400> SEQUENCE: 488

```
cggccgcctg gccgacagtc aagtgcgctc tcctcccgct ggaatccacg ctctcctccc    60

gctggaatcc acggcgacac tgggcccagc ttccct                             96
```

<210> SEQ ID NO 489
<211> LENGTH: 96
<212> TYPE: DNA
<213> ORGANISM: Artificial Sequence
<220> FEATURE:
<223> OTHER INFORMATION: Synthetic

<400> SEQUENCE: 489

```
gccgacgggc cgtgcgcgct gcgcgagctc agcgtagacc tccgcgccag ctcagcgtag    60

acctccgcgc cgagcgctcc gtactcatcc ccgaga                             96
```

<210> SEQ ID NO 490
<211> LENGTH: 98
<212> TYPE: DNA
<213> ORGANISM: Artificial Sequence
<220> FEATURE:
<223> OTHER INFORMATION: Synthetic

<400> SEQUENCE: 490

```
gatcatggcc agacaagcat ccgttctcct tcctgccatc tggacaagcc tccttcctgc    60

catctggaca agcttcgtca ggggatgtgg gatctggg                           98
```

<210> SEQ ID NO 491
<211> LENGTH: 100
<212> TYPE: DNA
<213> ORGANISM: Artificial Sequence
<220> FEATURE:
<223> OTHER INFORMATION: Synthetic

<400> SEQUENCE: 491

```
tgcccctggc ttcccacagc cacgccgtgg cactgacccg agactctgag cgtggcactg    60

acccgagact ctgagcggct gctggaggtg cggaagcgga                         100
```

<210> SEQ ID NO 492
<211> LENGTH: 106
<212> TYPE: DNA
<213> ORGANISM: Artificial Sequence
<220> FEATURE:
<223> OTHER INFORMATION: Synthetic

<400> SEQUENCE: 492

```
tcagagcttg gtcaggggtg aaagcagagt ttatcaccaa ttccccttca ataagagttt    60

atcaccaatt ccccttcaat aactctccgg agctgggagt cctctt                  106
```

<210> SEQ ID NO 493
<211> LENGTH: 112
<212> TYPE: DNA
<213> ORGANISM: Artificial Sequence
<220> FEATURE:
<223> OTHER INFORMATION: Synthetic

<400> SEQUENCE: 493
ttgggcacaa gaagaaaaac cacatgagct gattggtgtc gatggcaacc agattagagc 60
tgattggtgt cgatggcaac cagattacag atctgtccag cagtcatttc tc 112

<210> SEQ ID NO 494
<211> LENGTH: 204
<212> TYPE: DNA
<213> ORGANISM: Artificial Sequence
<220> FEATURE:
<223> OTHER INFORMATION: Synthetic

<400> SEQUENCE: 494
cttgccttcg gtgtggtccc ggcaattgtc acacacacct ccatatgccc cctggctggc 60
ggcaaacaca gcggggtcaa agtgacatgt ctctgagtgc ccttgtcaca cacacctcca 120
tatgccccct ggctggcggc aaacacagcg gggtcaaagt gacatgtctc tgagtgccca 180
ttgcagtcgc accctggaaa aaga 204

<210> SEQ ID NO 495
<211> LENGTH: 18
<212> TYPE: DNA
<213> ORGANISM: Artificial Sequence
<220> FEATURE:
<223> OTHER INFORMATION: Synthetic

<400> SEQUENCE: 495
gctcagcctg cctgccag 18

<210> SEQ ID NO 496
<211> LENGTH: 42
<212> TYPE: DNA
<213> ORGANISM: Artificial Sequence
<220> FEATURE:
<223> OTHER INFORMATION: Synthetic

<400> SEQUENCE: 496
cccttggcgc ggccccggcc cggcgcggcc ccggcccggc gc 42

<210> SEQ ID NO 497
<211> LENGTH: 18
<212> TYPE: DNA
<213> ORGANISM: Artificial Sequence
<220> FEATURE:
<223> OTHER INFORMATION: Synthetic

<400> SEQUENCE: 497
cataggatag atatacgg 18

<210> SEQ ID NO 498
<211> LENGTH: 18
<212> TYPE: DNA
<213> ORGANISM: Artificial Sequence
<220> FEATURE:
<223> OTHER INFORMATION: Synthetic

<400> SEQUENCE: 498
cataggatag atatacgg 18

<210> SEQ ID NO 499
<211> LENGTH: 46
<212> TYPE: DNA

<213> ORGANISM: Artificial Sequence
<220> FEATURE:
<223> OTHER INFORMATION: Synthetic

<400> SEQUENCE: 499
gcaggaccga ccacatctgc agaaccgacc acatctgcag aacctc 46

<210> SEQ ID NO 500
<211> LENGTH: 44
<212> TYPE: DNA
<213> ORGANISM: Artificial Sequence
<220> FEATURE:
<223> OTHER INFORMATION: Synthetic

<400> SEQUENCE: 500
tttgtgttgt cgatggcgac ccgttgtcga tggcgacccg tttc 44

<210> SEQ ID NO 501
<211> LENGTH: 18
<212> TYPE: DNA
<213> ORGANISM: Artificial Sequence
<220> FEATURE:
<223> OTHER INFORMATION: Synthetic

<400> SEQUENCE: 501
agagggagtg agtggctt 18

<210> SEQ ID NO 502
<211> LENGTH: 30
<212> TYPE: DNA
<213> ORGANISM: Artificial Sequence
<220> FEATURE:
<223> OTHER INFORMATION: Synthetic

<400> SEQUENCE: 502
gcagtggtgg catgaggtgg catgaggaat 30

<210> SEQ ID NO 503
<211> LENGTH: 16
<212> TYPE: DNA
<213> ORGANISM: Artificial Sequence
<220> FEATURE:
<223> OTHER INFORMATION: Synthetic

<400> SEQUENCE: 503
cgcagcaaca actggt 16

<210> SEQ ID NO 504
<211> LENGTH: 18
<212> TYPE: DNA
<213> ORGANISM: Artificial Sequence
<220> FEATURE:
<223> OTHER INFORMATION: Synthetic

<400> SEQUENCE: 504
agagaagata gatagcga 18

<210> SEQ ID NO 505
<211> LENGTH: 40
<212> TYPE: DNA
<213> ORGANISM: Artificial Sequence
<220> FEATURE:
<223> OTHER INFORMATION: Synthetic

<400> SEQUENCE: 505
cctcagcttc acagagtagt gcttcacaga gtagtatttt 40

<210> SEQ ID NO 506
<211> LENGTH: 18
<212> TYPE: DNA
<213> ORGANISM: Artificial Sequence
<220> FEATURE:
<223> OTHER INFORMATION: Synthetic

<400> SEQUENCE: 506
gcagcgccag ccagccgc 18

<210> SEQ ID NO 507
<211> LENGTH: 30
<212> TYPE: DNA
<213> ORGANISM: Artificial Sequence
<220> FEATURE:
<223> OTHER INFORMATION: Synthetic

<400> SEQUENCE: 507
ccatgggccg ggcccggccg ggcccggccg 30

<210> SEQ ID NO 508
<211> LENGTH: 14
<212> TYPE: DNA
<213> ORGANISM: Artificial Sequence
<220> FEATURE:
<223> OTHER INFORMATION: Synthetic

<400> SEQUENCE: 508
ctacctatac tggt 14

<210> SEQ ID NO 509
<211> LENGTH: 22
<212> TYPE: DNA
<213> ORGANISM: Artificial Sequence
<220> FEATURE:
<223> OTHER INFORMATION: Synthetic

<400> SEQUENCE: 509
gagtcacggc gacggcggcg gc 22

<210> SEQ ID NO 510
<211> LENGTH: 16
<212> TYPE: DNA
<213> ORGANISM: Artificial Sequence
<220> FEATURE:
<223> OTHER INFORMATION: Synthetic

<400> SEQUENCE: 510
gatcctgatg ataaat 16

<210> SEQ ID NO 511
<211> LENGTH: 18
<212> TYPE: DNA
<213> ORGANISM: Artificial Sequence
<220> FEATURE:
<223> OTHER INFORMATION: Synthetic

<400> SEQUENCE: 511
ggggtcatcc atcatacg 18

<210> SEQ ID NO 512
<211> LENGTH: 56
<212> TYPE: DNA
<213> ORGANISM: Artificial Sequence
<220> FEATURE:

<223> OTHER INFORMATION: Synthetic

<400> SEQUENCE: 512
gccagcccgg gcagccacct gtaatctccc cgggcagcca cctgtaatct cgtctt 56

<210> SEQ ID NO 513
<211> LENGTH: 26
<212> TYPE: DNA
<213> ORGANISM: Artificial Sequence
<220> FEATURE:
<223> OTHER INFORMATION: Synthetic

<400> SEQUENCE: 513
agctgcgagg tgtcgaggtg tcggag 26

<210> SEQ ID NO 514
<211> LENGTH: 30
<212> TYPE: DNA
<213> ORGANISM: Artificial Sequence
<220> FEATURE:
<223> OTHER INFORMATION: Synthetic

<400> SEQUENCE: 514
cagcttcaca gagtatcaca gagtagtatt 30

<210> SEQ ID NO 515
<211> LENGTH: 18
<212> TYPE: DNA
<213> ORGANISM: Artificial Sequence
<220> FEATURE:
<223> OTHER INFORMATION: Synthetic

<400> SEQUENCE: 515
gacagtgcct gcctgtgg 18

<210> SEQ ID NO 516
<211> LENGTH: 20
<212> TYPE: DNA
<213> ORGANISM: Artificial Sequence
<220> FEATURE:
<223> OTHER INFORMATION: Synthetic

<400> SEQUENCE: 516
taccactcgg ctcggcagag 20

<210> SEQ ID NO 517
<211> LENGTH: 42
<212> TYPE: DNA
<213> ORGANISM: Artificial Sequence
<220> FEATURE:
<223> OTHER INFORMATION: Synthetic

<400> SEQUENCE: 517
ccccagccac gcaggtatcg tgccacgcag gtatcgtggc ct 42

<210> SEQ ID NO 518
<211> LENGTH: 18
<212> TYPE: DNA
<213> ORGANISM: Artificial Sequence
<220> FEATURE:
<223> OTHER INFORMATION: Synthetic

<400> SEQUENCE: 518
tgaatcaagc aagcatgc 18

<210> SEQ ID NO 519
<211> LENGTH: 26
<212> TYPE: DNA
<213> ORGANISM: Artificial Sequence
<220> FEATURE:
<223> OTHER INFORMATION: Synthetic

<400> SEQUENCE: 519
ttgcactcag cacctcagca ccgggg 26

<210> SEQ ID NO 520
<211> LENGTH: 42
<212> TYPE: DNA
<213> ORGANISM: Artificial Sequence
<220> FEATURE:
<223> OTHER INFORMATION: Synthetic

<400> SEQUENCE: 520
ggtgtgggcc tcccctgctg ggggcctccc ctgctggggg ct 42

<210> SEQ ID NO 521
<211> LENGTH: 14
<212> TYPE: DNA
<213> ORGANISM: Artificial Sequence
<220> FEATURE:
<223> OTHER INFORMATION: Synthetic

<400> SEQUENCE: 521
tgtaaacaca aaag 14

<210> SEQ ID NO 522
<211> LENGTH: 18
<212> TYPE: DNA
<213> ORGANISM: Artificial Sequence
<220> FEATURE:
<223> OTHER INFORMATION: Synthetic

<400> SEQUENCE: 522
gcgggtggct ggctgcca 18

<210> SEQ ID NO 523
<211> LENGTH: 18
<212> TYPE: DNA
<213> ORGANISM: Artificial Sequence
<220> FEATURE:
<223> OTHER INFORMATION: Synthetic

<400> SEQUENCE: 523
tgggcaagta agtgcctc 18

<210> SEQ ID NO 524
<211> LENGTH: 24
<212> TYPE: DNA
<213> ORGANISM: Artificial Sequence
<220> FEATURE:
<223> OTHER INFORMATION: Synthetic

<400> SEQUENCE: 524
cagcttcaca gatcacagag tagt 24

<210> SEQ ID NO 525
<211> LENGTH: 26
<212> TYPE: DNA
<213> ORGANISM: Artificial Sequence
<220> FEATURE:
<223> OTHER INFORMATION: Synthetic

<400> SEQUENCE: 525
acagaacgtg ttcacgtgtt ctccag 26

<210> SEQ ID NO 526
<211> LENGTH: 50
<212> TYPE: DNA
<213> ORGANISM: Artificial Sequence
<220> FEATURE:
<223> OTHER INFORMATION: Synthetic

<400> SEQUENCE: 526
tctttgaagt ggtaggaaaa atgtcgaagt ggtaggaaaa atgtcttctt 50

<210> SEQ ID NO 527
<211> LENGTH: 50
<212> TYPE: DNA
<213> ORGANISM: Artificial Sequence
<220> FEATURE:
<223> OTHER INFORMATION: Synthetic

<400> SEQUENCE: 527
aatttcatac ttttcttcct gttcacatac ttttcttcct gttcacatac 50

<210> SEQ ID NO 528
<211> LENGTH: 14
<212> TYPE: DNA
<213> ORGANISM: Artificial Sequence
<220> FEATURE:
<223> OTHER INFORMATION: Synthetic

<400> SEQUENCE: 528
cagtttatat caag 14

<210> SEQ ID NO 529
<211> LENGTH: 36
<212> TYPE: DNA
<213> ORGANISM: Artificial Sequence
<220> FEATURE:
<223> OTHER INFORMATION: Synthetic

<400> SEQUENCE: 529
gccgtggggc ccagtcccgg ggcccagtcc cggagc 36

<210> SEQ ID NO 530
<211> LENGTH: 32
<212> TYPE: DNA
<213> ORGANISM: Artificial Sequence
<220> FEATURE:
<223> OTHER INFORMATION: Synthetic

<400> SEQUENCE: 530
gtggtagcca atgttcagcc aatgttcagc tt 32

<210> SEQ ID NO 531
<211> LENGTH: 14
<212> TYPE: DNA
<213> ORGANISM: Artificial Sequence
<220> FEATURE:
<223> OTHER INFORMATION: Synthetic

<400> SEQUENCE: 531
caagtacact caga 14

<210> SEQ ID NO 532
<211> LENGTH: 14

<212> TYPE: DNA
<213> ORGANISM: Artificial Sequence
<220> FEATURE:
<223> OTHER INFORMATION: Synthetic

<400> SEQUENCE: 532
catggcacag ccgg 14

<210> SEQ ID NO 533
<211> LENGTH: 18
<212> TYPE: DNA
<213> ORGANISM: Artificial Sequence
<220> FEATURE:
<223> OTHER INFORMATION: Synthetic

<400> SEQUENCE: 533
cttggcagtc agtcggtc 18

<210> SEQ ID NO 534
<211> LENGTH: 32
<212> TYPE: DNA
<213> ORGANISM: Artificial Sequence
<220> FEATURE:
<223> OTHER INFORMATION: Synthetic

<400> SEQUENCE: 534
ccgctaccgg ctcgccaccg gctcgccacc at 32

<210> SEQ ID NO 535
<211> LENGTH: 58
<212> TYPE: DNA
<213> ORGANISM: Artificial Sequence
<220> FEATURE:
<223> OTHER INFORMATION: Synthetic

<400> SEQUENCE: 535
ccgttctcct tcctgccatc tggacaagcc tccttcctgc catctggaca agcttcgt 58

<210> SEQ ID NO 536
<211> LENGTH: 20
<212> TYPE: DNA
<213> ORGANISM: Artificial Sequence
<220> FEATURE:
<223> OTHER INFORMATION: Synthetic

<400> SEQUENCE: 536
gggccgggca gggcaggggg 20

<210> SEQ ID NO 537
<211> LENGTH: 42
<212> TYPE: DNA
<213> ORGANISM: Artificial Sequence
<220> FEATURE:
<223> OTHER INFORMATION: Synthetic

<400> SEQUENCE: 537
aagcagggcc gtcgcgaggc tgggccgtcg cgaggctgtg aa 42

<210> SEQ ID NO 538
<211> LENGTH: 44
<212> TYPE: DNA
<213> ORGANISM: Artificial Sequence
<220> FEATURE:
<223> OTHER INFORMATION: Synthetic

<400> SEQUENCE: 538

-continued accacgtcct cagcttcaca gagtcctcag cttcacagag tagt 44

<210> SEQ ID NO 539
<211> LENGTH: 36
<212> TYPE: DNA
<213> ORGANISM: Artificial Sequence
<220> FEATURE:
<223> OTHER INFORMATION: Synthetic

<400> SEQUENCE: 539
actagctaga atgagttact agaatgagtt accaga 36

<210> SEQ ID NO 540
<211> LENGTH: 18
<212> TYPE: DNA
<213> ORGANISM: Artificial Sequence
<220> FEATURE:
<223> OTHER INFORMATION: Synthetic

<400> SEQUENCE: 540
cagatgtgcg tgcactgt 18

<210> SEQ ID NO 541
<211> LENGTH: 18
<212> TYPE: DNA
<213> ORGANISM: Artificial Sequence
<220> FEATURE:
<223> OTHER INFORMATION: Synthetic

<400> SEQUENCE: 541
cagtgaggca ggcagggg 18

<210> SEQ ID NO 542
<211> LENGTH: 20
<212> TYPE: DNA
<213> ORGANISM: Artificial Sequence
<220> FEATURE:
<223> OTHER INFORMATION: Synthetic

<400> SEQUENCE: 542
gccacgggct gggctgggcc 20

<210> SEQ ID NO 543
<211> LENGTH: 30
<212> TYPE: DNA
<213> ORGANISM: Artificial Sequence
<220> FEATURE:
<223> OTHER INFORMATION: Synthetic

<400> SEQUENCE: 543
cccatggctg cgctgggctg cgctgggctg 30

<210> SEQ ID NO 544
<211> LENGTH: 30
<212> TYPE: DNA
<213> ORGANISM: Artificial Sequence
<220> FEATURE:
<223> OTHER INFORMATION: Synthetic

<400> SEQUENCE: 544
gacaaaagga ggatcaagga ggatccaagt 30

<210> SEQ ID NO 545
<211> LENGTH: 14
<212> TYPE: DNA
<213> ORGANISM: Artificial Sequence
<220> FEATURE:
<223> OTHER INFORMATION: Synthetic

<400> SEQUENCE: 545
ttgaggcgca gtgg 14

<210> SEQ ID NO 546
<211> LENGTH: 14
<212> TYPE: DNA
<213> ORGANISM: Artificial Sequence
<220> FEATURE:
<223> OTHER INFORMATION: Synthetic

<400> SEQUENCE: 546
tctcatctca tgga 14

<210> SEQ ID NO 547
<211> LENGTH: 14
<212> TYPE: DNA
<213> ORGANISM: Artificial Sequence
<220> FEATURE:
<223> OTHER INFORMATION: Synthetic

<400> SEQUENCE: 547
cgggcgtgtc ctcc 14

<210> SEQ ID NO 548
<211> LENGTH: 18
<212> TYPE: DNA
<213> ORGANISM: Artificial Sequence
<220> FEATURE:
<223> OTHER INFORMATION: Synthetic

<400> SEQUENCE: 548
gtccaaaaca aacagtct 18

<210> SEQ ID NO 549
<211> LENGTH: 18
<212> TYPE: DNA
<213> ORGANISM: Artificial Sequence
<220> FEATURE:
<223> OTHER INFORMATION: Synthetic

<400> SEQUENCE: 549
ccagctggtt ggttcctg 18

<210> SEQ ID NO 550
<211> LENGTH: 18
<212> TYPE: DNA
<213> ORGANISM: Artificial Sequence
<220> FEATURE:
<223> OTHER INFORMATION: Synthetic

<400> SEQUENCE: 550
aagatcaaac aaacaccg 18

<210> SEQ ID NO 551
<211> LENGTH: 18
<212> TYPE: DNA
<213> ORGANISM: Artificial Sequence
<220> FEATURE:
<223> OTHER INFORMATION: Synthetic

<400> SEQUENCE: 551
tccacagata gatataat 18

<210> SEQ ID NO 552
<211> LENGTH: 18
<212> TYPE: DNA
<213> ORGANISM: Artificial Sequence
<220> FEATURE:
<223> OTHER INFORMATION: Synthetic

<400> SEQUENCE: 552
ttgttatcca tccccagg 18

<210> SEQ ID NO 553
<211> LENGTH: 18
<212> TYPE: DNA
<213> ORGANISM: Artificial Sequence
<220> FEATURE:
<223> OTHER INFORMATION: Synthetic

<400> SEQUENCE: 553
ccaggcgttc gttgcact 18

<210> SEQ ID NO 554
<211> LENGTH: 18
<212> TYPE: DNA
<213> ORGANISM: Artificial Sequence
<220> FEATURE:
<223> OTHER INFORMATION: Synthetic

<400> SEQUENCE: 554
aaggcattta tttcagcc 18

<210> SEQ ID NO 555
<211> LENGTH: 26
<212> TYPE: DNA
<213> ORGANISM: Artificial Sequence
<220> FEATURE:
<223> OTHER INFORMATION: Synthetic

<400> SEQUENCE: 555
ttgctaatct cccaatctcc cagagg 26

<210> SEQ ID NO 556
<211> LENGTH: 26
<212> TYPE: DNA
<213> ORGANISM: Artificial Sequence
<220> FEATURE:
<223> OTHER INFORMATION: Synthetic

<400> SEQUENCE: 556
atcagctctg ctcctctgct ctgctg 26

<210> SEQ ID NO 557
<211> LENGTH: 30
<212> TYPE: DNA
<213> ORGANISM: Artificial Sequence
<220> FEATURE:
<223> OTHER INFORMATION: Synthetic

<400> SEQUENCE: 557
agcacttcca ggttattcca ggttagttac 30

<210> SEQ ID NO 558
<211> LENGTH: 30
<212> TYPE: DNA
<213> ORGANISM: Artificial Sequence
<220> FEATURE:
<223> OTHER INFORMATION: Synthetic

<400> SEQUENCE: 558
ttgtgccaca tggctccaca tggctccaca 30

<210> SEQ ID NO 559
<211> LENGTH: 32
<212> TYPE: DNA
<213> ORGANISM: Artificial Sequence
<220> FEATURE:
<223> OTHER INFORMATION: Synthetic

<400> SEQUENCE: 559
gctctccatc tactcgccat ctactcgcca ga 32

<210> SEQ ID NO 560
<211> LENGTH: 38
<212> TYPE: DNA
<213> ORGANISM: Artificial Sequence
<220> FEATURE:
<223> OTHER INFORMATION: Synthetic

<400> SEQUENCE: 560
gtctgagagc tgcggagcca gagctgcgga gccagggc 38

<210> SEQ ID NO 561
<211> LENGTH: 18
<212> TYPE: DNA
<213> ORGANISM: Artificial Sequence
<220> FEATURE:
<223> OTHER INFORMATION: Synthetic

<400> SEQUENCE: 561
ctgaaagata gatattaa 18

<210> SEQ ID NO 562
<211> LENGTH: 18
<212> TYPE: DNA
<213> ORGANISM: Artificial Sequence
<220> FEATURE:
<223> OTHER INFORMATION: Synthetic

<400> SEQUENCE: 562
aggcaggccg gccagcag 18

<210> SEQ ID NO 563
<211> LENGTH: 18
<212> TYPE: DNA
<213> ORGANISM: Artificial Sequence
<220> FEATURE:
<223> OTHER INFORMATION: Synthetic

<400> SEQUENCE: 563
cttggggatg gatgcctt 18

<210> SEQ ID NO 564
<211> LENGTH: 24
<212> TYPE: DNA
<213> ORGANISM: Artificial Sequence
<220> FEATURE:
<223> OTHER INFORMATION: Synthetic

<400> SEQUENCE: 564
agcccgacga gggacgagga ggag 24

<210> SEQ ID NO 565

<211> LENGTH: 14
<212> TYPE: DNA
<213> ORGANISM: Artificial Sequence
<220> FEATURE:
<223> OTHER INFORMATION: Synthetic

<400> SEQUENCE: 565
aaccgacaca gctt 14

<210> SEQ ID NO 566
<211> LENGTH: 18
<212> TYPE: DNA
<213> ORGANISM: Artificial Sequence
<220> FEATURE:
<223> OTHER INFORMATION: Synthetic

<400> SEQUENCE: 566
cagatagtaa gtatatca 18

<210> SEQ ID NO 567
<211> LENGTH: 18
<212> TYPE: DNA
<213> ORGANISM: Artificial Sequence
<220> FEATURE:
<223> OTHER INFORMATION: Synthetic

<400> SEQUENCE: 567
aatgatgatt gatttttc 18

<210> SEQ ID NO 568
<211> LENGTH: 20
<212> TYPE: DNA
<213> ORGANISM: Artificial Sequence
<220> FEATURE:
<223> OTHER INFORMATION: Synthetic

<400> SEQUENCE: 568
taccagtgag gtgagatgag 20

<210> SEQ ID NO 569
<211> LENGTH: 52
<212> TYPE: DNA
<213> ORGANISM: Artificial Sequence
<220> FEATURE:
<223> OTHER INFORMATION: Synthetic

<400> SEQUENCE: 569
gtggggatcc tggtgaccgt gctggtgatc ctggtgaccg tgctggtgca ga 52

<210> SEQ ID NO 570
<211> LENGTH: 18
<212> TYPE: DNA
<213> ORGANISM: Artificial Sequence
<220> FEATURE:
<223> OTHER INFORMATION: Synthetic

<400> SEQUENCE: 570
tgacatgatt gatgtatt 18

<210> SEQ ID NO 571
<211> LENGTH: 18
<212> TYPE: DNA
<213> ORGANISM: Artificial Sequence
<220> FEATURE:
<223> OTHER INFORMATION: Synthetic

<400> SEQUENCE: 571

-continued atgaatcagt cagtcact 18

<210> SEQ ID NO 572
<211> LENGTH: 18
<212> TYPE: DNA
<213> ORGANISM: Artificial Sequence
<220> FEATURE:
<223> OTHER INFORMATION: Synthetic

<400> SEQUENCE: 572
ggataaggca ggcaacac 18

<210> SEQ ID NO 573
<211> LENGTH: 20
<212> TYPE: DNA
<213> ORGANISM: Artificial Sequence
<220> FEATURE:
<223> OTHER INFORMATION: Synthetic

<400> SEQUENCE: 573
aatgttctca tctcatttcc 20

<210> SEQ ID NO 574
<211> LENGTH: 44
<212> TYPE: DNA
<213> ORGANISM: Artificial Sequence
<220> FEATURE:
<223> OTHER INFORMATION: Synthetic

<400> SEQUENCE: 574
cacgaaccac gtcctcagct tcaccacgtc ctcagcttca caga 44

<210> SEQ ID NO 575
<211> LENGTH: 46
<212> TYPE: DNA
<213> ORGANISM: Artificial Sequence
<220> FEATURE:
<223> OTHER INFORMATION: Synthetic

<400> SEQUENCE: 575
tttaactcct gatcagacat gacctcctga tcagacatga cctcca 46

<210> SEQ ID NO 576
<211> LENGTH: 72
<212> TYPE: DNA
<213> ORGANISM: Artificial Sequence
<220> FEATURE:
<223> OTHER INFORMATION: Synthetic

<400> SEQUENCE: 576
cacatgagct gattggtgtc gatggcaacc agattagagc tgattggtgt cgatggcaac 60
cagattacag at 72

<210> SEQ ID NO 577
<211> LENGTH: 28
<212> TYPE: DNA
<213> ORGANISM: Artificial Sequence
<220> FEATURE:
<223> OTHER INFORMATION: Synthetic

<400> SEQUENCE: 577
agctcgcgca ggctgcgcag gctgccca 28

<210> SEQ ID NO 578

<211> LENGTH: 18
<212> TYPE: DNA
<213> ORGANISM: Artificial Sequence
<220> FEATURE:
<223> OTHER INFORMATION: Synthetic

<400> SEQUENCE: 578
tggagcactc acttcggg 18

<210> SEQ ID NO 579
<211> LENGTH: 14
<212> TYPE: DNA
<213> ORGANISM: Artificial Sequence
<220> FEATURE:
<223> OTHER INFORMATION: Synthetic

<400> SEQUENCE: 579
ttgatagaga cacc 14

<210> SEQ ID NO 580
<211> LENGTH: 16
<212> TYPE: DNA
<213> ORGANISM: Artificial Sequence
<220> FEATURE:
<223> OTHER INFORMATION: Synthetic

<400> SEQUENCE: 580
gggcagacga cggccc 16

<210> SEQ ID NO 581
<211> LENGTH: 18
<212> TYPE: DNA
<213> ORGANISM: Artificial Sequence
<220> FEATURE:
<223> OTHER INFORMATION: Synthetic

<400> SEQUENCE: 581
tcctgcagcc agcgggtg 18

<210> SEQ ID NO 582
<211> LENGTH: 20
<212> TYPE: DNA
<213> ORGANISM: Artificial Sequence
<220> FEATURE:
<223> OTHER INFORMATION: Synthetic

<400> SEQUENCE: 582
ggcgtggagc ggagcgtgtg 20

<210> SEQ ID NO 583
<211> LENGTH: 28
<212> TYPE: DNA
<213> ORGANISM: Artificial Sequence
<220> FEATURE:
<223> OTHER INFORMATION: Synthetic

<400> SEQUENCE: 583
ctgcatccac actgtccaca ctgcctct 28

<210> SEQ ID NO 584
<211> LENGTH: 40
<212> TYPE: DNA
<213> ORGANISM: Artificial Sequence
<220> FEATURE:
<223> OTHER INFORMATION: Synthetic

<400> SEQUENCE: 584
tggaagaggg agagggaggc gagggagagg gaggcaaagg 40

<210> SEQ ID NO 585
<211> LENGTH: 18
<212> TYPE: DNA
<213> ORGANISM: Artificial Sequence
<220> FEATURE:
<223> OTHER INFORMATION: Synthetic

<400> SEQUENCE: 585
tgtataacaa acacctgt 18

<210> SEQ ID NO 586
<211> LENGTH: 18
<212> TYPE: DNA
<213> ORGANISM: Artificial Sequence
<220> FEATURE:
<223> OTHER INFORMATION: Synthetic

<400> SEQUENCE: 586
ggtgcgggag ggagttcg 18

<210> SEQ ID NO 587
<211> LENGTH: 20
<212> TYPE: DNA
<213> ORGANISM: Artificial Sequence
<220> FEATURE:
<223> OTHER INFORMATION: Synthetic

<400> SEQUENCE: 587
gatgcctgct ctgctcggag 20

<210> SEQ ID NO 588
<211> LENGTH: 46
<212> TYPE: DNA
<213> ORGANISM: Artificial Sequence
<220> FEATURE:
<223> OTHER INFORMATION: Synthetic

<400> SEQUENCE: 588
gggtcggagg cgccgcctgg gttggaggcg ccgcctgggt tggggt 46

<210> SEQ ID NO 589
<211> LENGTH: 18
<212> TYPE: DNA
<213> ORGANISM: Artificial Sequence
<220> FEATURE:
<223> OTHER INFORMATION: Synthetic

<400> SEQUENCE: 589
caatggtatg tatcccct 18

<210> SEQ ID NO 590
<211> LENGTH: 40
<212> TYPE: DNA
<213> ORGANISM: Artificial Sequence
<220> FEATURE:
<223> OTHER INFORMATION: Synthetic

<400> SEQUENCE: 590
tctctcggcc cggcggcaca cggcccggcg gcacacggcc 40

<210> SEQ ID NO 591
<211> LENGTH: 14
<212> TYPE: DNA

<213> ORGANISM: Artificial Sequence
<220> FEATURE:
<223> OTHER INFORMATION: Synthetic

<400> SEQUENCE: 591
ttcacatatt caaa 14

<210> SEQ ID NO 592
<211> LENGTH: 16
<212> TYPE: DNA
<213> ORGANISM: Artificial Sequence
<220> FEATURE:
<223> OTHER INFORMATION: Synthetic

<400> SEQUENCE: 592
gagggtgatg atgtcc 16

<210> SEQ ID NO 593
<211> LENGTH: 18
<212> TYPE: DNA
<213> ORGANISM: Artificial Sequence
<220> FEATURE:
<223> OTHER INFORMATION: Synthetic

<400> SEQUENCE: 593
cctcctgatt gatagatg 18

<210> SEQ ID NO 594
<211> LENGTH: 18
<212> TYPE: DNA
<213> ORGANISM: Artificial Sequence
<220> FEATURE:
<223> OTHER INFORMATION: Synthetic

<400> SEQUENCE: 594
gatgctgttt gttactcg 18

<210> SEQ ID NO 595
<211> LENGTH: 18
<212> TYPE: DNA
<213> ORGANISM: Artificial Sequence
<220> FEATURE:
<223> OTHER INFORMATION: Synthetic

<400> SEQUENCE: 595
catctgtcag tcagtgga 18

<210> SEQ ID NO 596
<211> LENGTH: 18
<212> TYPE: DNA
<213> ORGANISM: Artificial Sequence
<220> FEATURE:
<223> OTHER INFORMATION: Synthetic

<400> SEQUENCE: 596
tatagtgaat gaagaaag 18

<210> SEQ ID NO 597
<211> LENGTH: 18
<212> TYPE: DNA
<213> ORGANISM: Artificial Sequence
<220> FEATURE:
<223> OTHER INFORMATION: Synthetic

<400> SEQUENCE: 597
tgattacaga cagtgtcc 18

<210> SEQ ID NO 598
<211> LENGTH: 30
<212> TYPE: DNA
<213> ORGANISM: Artificial Sequence
<220> FEATURE:
<223> OTHER INFORMATION: Synthetic

<400> SEQUENCE: 598
gggtgcagat cctcccagat cctccatact 30

<210> SEQ ID NO 599
<211> LENGTH: 20
<212> TYPE: DNA
<213> ORGANISM: Artificial Sequence
<220> FEATURE:
<223> OTHER INFORMATION: Synthetic

<400> SEQUENCE: 599
gccgggcgtc gcgtcgtagc 20

<210> SEQ ID NO 600
<211> LENGTH: 20
<212> TYPE: DNA
<213> ORGANISM: Artificial Sequence
<220> FEATURE:
<223> OTHER INFORMATION: Synthetic

<400> SEQUENCE: 600
gcccgcggct cggctcgggc 20

<210> SEQ ID NO 601
<211> LENGTH: 14
<212> TYPE: DNA
<213> ORGANISM: Artificial Sequence
<220> FEATURE:
<223> OTHER INFORMATION: Synthetic

<400> SEQUENCE: 601
gacaatgtga gaat 14

<210> SEQ ID NO 602
<211> LENGTH: 18
<212> TYPE: DNA
<213> ORGANISM: Artificial Sequence
<220> FEATURE:
<223> OTHER INFORMATION: Synthetic

<400> SEQUENCE: 602
tatactgctt gctgccag 18

<210> SEQ ID NO 603
<211> LENGTH: 60
<212> TYPE: DNA
<213> ORGANISM: Artificial Sequence
<220> FEATURE:
<223> OTHER INFORMATION: Synthetic

<400> SEQUENCE: 603
cacgccgtgg cactgacccg agactctgag cgtggcactg acccgagact ctgagcggct 60

<210> SEQ ID NO 604
<211> LENGTH: 24
<212> TYPE: DNA
<213> ORGANISM: Artificial Sequence
<220> FEATURE:

<223> OTHER INFORMATION: Synthetic

<400> SEQUENCE: 604
gcccctcaaa catcaaacac gagc 24

<210> SEQ ID NO 605
<211> LENGTH: 56
<212> TYPE: DNA
<213> ORGANISM: Artificial Sequence
<220> FEATURE:
<223> OTHER INFORMATION: Synthetic

<400> SEQUENCE: 605
gcgcgagctc agcgtagacc tccgcgccag ctcagcgtag acctccgcgc cgagcg 56

<210> SEQ ID NO 606
<211> LENGTH: 14
<212> TYPE: DNA
<213> ORGANISM: Artificial Sequence
<220> FEATURE:
<223> OTHER INFORMATION: Synthetic

<400> SEQUENCE: 606
aataggtgtg gtga 14

<210> SEQ ID NO 607
<211> LENGTH: 14
<212> TYPE: DNA
<213> ORGANISM: Artificial Sequence
<220> FEATURE:
<223> OTHER INFORMATION: Synthetic

<400> SEQUENCE: 607
tacctgagag tggt 14

<210> SEQ ID NO 608
<211> LENGTH: 14
<212> TYPE: DNA
<213> ORGANISM: Artificial Sequence
<220> FEATURE:
<223> OTHER INFORMATION: Synthetic

<400> SEQUENCE: 608
ccctggtgtg caga 14

<210> SEQ ID NO 609
<211> LENGTH: 14
<212> TYPE: DNA
<213> ORGANISM: Artificial Sequence
<220> FEATURE:
<223> OTHER INFORMATION: Synthetic

<400> SEQUENCE: 609
cgcactatat ctca 14

<210> SEQ ID NO 610
<211> LENGTH: 14
<212> TYPE: DNA
<213> ORGANISM: Artificial Sequence
<220> FEATURE:
<223> OTHER INFORMATION: Synthetic

<400> SEQUENCE: 610
cgtgggagag tagc 14

-continued

<210> SEQ ID NO 611
<211> LENGTH: 14
<212> TYPE: DNA
<213> ORGANISM: Artificial Sequence
<220> FEATURE:
<223> OTHER INFORMATION: Synthetic

<400> SEQUENCE: 611
gtagtcgcgc cctg 14

<210> SEQ ID NO 612
<211> LENGTH: 14
<212> TYPE: DNA
<213> ORGANISM: Artificial Sequence
<220> FEATURE:
<223> OTHER INFORMATION: Synthetic

<400> SEQUENCE: 612
agaagacact tcct 14

<210> SEQ ID NO 613
<211> LENGTH: 18
<212> TYPE: DNA
<213> ORGANISM: Artificial Sequence
<220> FEATURE:
<223> OTHER INFORMATION: Synthetic

<400> SEQUENCE: 613
ctggccgctc gctgcctt 18

<210> SEQ ID NO 614
<211> LENGTH: 18
<212> TYPE: DNA
<213> ORGANISM: Artificial Sequence
<220> FEATURE:
<223> OTHER INFORMATION: Synthetic

<400> SEQUENCE: 614
ttcctaatga atgacatt 18

<210> SEQ ID NO 615
<211> LENGTH: 18
<212> TYPE: DNA
<213> ORGANISM: Artificial Sequence
<220> FEATURE:
<223> OTHER INFORMATION: Synthetic

<400> SEQUENCE: 615
tttgttgaat gaattaag 18

<210> SEQ ID NO 616
<211> LENGTH: 18
<212> TYPE: DNA
<213> ORGANISM: Artificial Sequence
<220> FEATURE:
<223> OTHER INFORMATION: Synthetic

<400> SEQUENCE: 616
actgcaacaa acatttga 18

<210> SEQ ID NO 617
<211> LENGTH: 18
<212> TYPE: DNA
<213> ORGANISM: Artificial Sequence
<220> FEATURE:
<223> OTHER INFORMATION: Synthetic

<400> SEQUENCE: 617
cattcattaa ttagtaga 18

<210> SEQ ID NO 618
<211> LENGTH: 18
<212> TYPE: DNA
<213> ORGANISM: Artificial Sequence
<220> FEATURE:
<223> OTHER INFORMATION: Synthetic

<400> SEQUENCE: 618
agatgaatca atcagtca 18

<210> SEQ ID NO 619
<211> LENGTH: 18
<212> TYPE: DNA
<213> ORGANISM: Artificial Sequence
<220> FEATURE:
<223> OTHER INFORMATION: Synthetic

<400> SEQUENCE: 619
tctgactttc tttcttac 18

<210> SEQ ID NO 620
<211> LENGTH: 18
<212> TYPE: DNA
<213> ORGANISM: Artificial Sequence
<220> FEATURE:
<223> OTHER INFORMATION: Synthetic

<400> SEQUENCE: 620
caggctcagt caggggct 18

<210> SEQ ID NO 621
<211> LENGTH: 18
<212> TYPE: DNA
<213> ORGANISM: Artificial Sequence
<220> FEATURE:
<223> OTHER INFORMATION: Synthetic

<400> SEQUENCE: 621
gtacctgatt gattgaca 18

<210> SEQ ID NO 622
<211> LENGTH: 18
<212> TYPE: DNA
<213> ORGANISM: Artificial Sequence
<220> FEATURE:
<223> OTHER INFORMATION: Synthetic

<400> SEQUENCE: 622
agatggaacg aactggag 18

<210> SEQ ID NO 623
<211> LENGTH: 18
<212> TYPE: DNA
<213> ORGANISM: Artificial Sequence
<220> FEATURE:
<223> OTHER INFORMATION: Synthetic

<400> SEQUENCE: 623
catgcgaatg aatgatgc 18

<210> SEQ ID NO 624
<211> LENGTH: 18

<212> TYPE: DNA
<213> ORGANISM: Artificial Sequence
<220> FEATURE:
<223> OTHER INFORMATION: Synthetic

<400> SEQUENCE: 624
ctggagggtg ggtggcta 18

<210> SEQ ID NO 625
<211> LENGTH: 20
<212> TYPE: DNA
<213> ORGANISM: Artificial Sequence
<220> FEATURE:
<223> OTHER INFORMATION: Synthetic

<400> SEQUENCE: 625
tagcatgccg tgccgcgcag 20

<210> SEQ ID NO 626
<211> LENGTH: 22
<212> TYPE: DNA
<213> ORGANISM: Artificial Sequence
<220> FEATURE:
<223> OTHER INFORMATION: Synthetic

<400> SEQUENCE: 626
cctgcatcca tatccatccg gt 22

<210> SEQ ID NO 627
<211> LENGTH: 22
<212> TYPE: DNA
<213> ORGANISM: Artificial Sequence
<220> FEATURE:
<223> OTHER INFORMATION: Synthetic

<400> SEQUENCE: 627
ctattttggg cttgggcttt cg 22

<210> SEQ ID NO 628
<211> LENGTH: 24
<212> TYPE: DNA
<213> ORGANISM: Artificial Sequence
<220> FEATURE:
<223> OTHER INFORMATION: Synthetic

<400> SEQUENCE: 628
ggatggctct tagctcttag cttc 24

<210> SEQ ID NO 629
<211> LENGTH: 26
<212> TYPE: DNA
<213> ORGANISM: Artificial Sequence
<220> FEATURE:
<223> OTHER INFORMATION: Synthetic

<400> SEQUENCE: 629
aaatcaagaa aaaaagaaaa atcctt 26

<210> SEQ ID NO 630
<211> LENGTH: 26
<212> TYPE: DNA
<213> ORGANISM: Artificial Sequence
<220> FEATURE:
<223> OTHER INFORMATION: Synthetic

<400> SEQUENCE: 630
ggacaaatct gacaatctga cgagga 26

<210> SEQ ID NO 631
<211> LENGTH: 32
<212> TYPE: DNA
<213> ORGANISM: Artificial Sequence
<220> FEATURE:
<223> OTHER INFORMATION: Synthetic

<400> SEQUENCE: 631
gtacgtggtc cgcctctggt ccgcctctgg tc 32

<210> SEQ ID NO 632
<211> LENGTH: 44
<212> TYPE: DNA
<213> ORGANISM: Artificial Sequence
<220> FEATURE:
<223> OTHER INFORMATION: Synthetic

<400> SEQUENCE: 632
aaatgagcaa gttggggtgt gcagcaagtt ggggtgtgca gcaa 44

<210> SEQ ID NO 633
<211> LENGTH: 46
<212> TYPE: DNA
<213> ORGANISM: Artificial Sequence
<220> FEATURE:
<223> OTHER INFORMATION: Synthetic

<400> SEQUENCE: 633
gccccgactg caaggacaaa tctgactgca aggacaaatc tgacga 46

<210> SEQ ID NO 634
<211> LENGTH: 48
<212> TYPE: DNA
<213> ORGANISM: Artificial Sequence
<220> FEATURE:
<223> OTHER INFORMATION: Synthetic

<400> SEQUENCE: 634
gttattcaaa agggacatag aaaatcaaaa gggacataga aaagcaag 48

<210> SEQ ID NO 635
<211> LENGTH: 50
<212> TYPE: DNA
<213> ORGANISM: Artificial Sequence
<220> FEATURE:
<223> OTHER INFORMATION: Synthetic

<400> SEQUENCE: 635
ggatgctgat ctgccgccgc ttctcctgat ctgccgccgc ttctcctggt 50

<210> SEQ ID NO 636
<211> LENGTH: 56
<212> TYPE: DNA
<213> ORGANISM: Artificial Sequence
<220> FEATURE:
<223> OTHER INFORMATION: Synthetic

<400> SEQUENCE: 636
aagtgcgctc tcctcccgct ggaatccacg ctctcctccc gctggaatcc acggcg 56

<210> SEQ ID NO 637
<211> LENGTH: 66
<212> TYPE: DNA
<213> ORGANISM: Artificial Sequence
<220> FEATURE:
<223> OTHER INFORMATION: Synthetic

<400> SEQUENCE: 637
aaagcagagt ttatcaccaa ttccccttca ataagagttt atcaccaatt ccccttcaat 60
aactct 66

<210> SEQ ID NO 638
<211> LENGTH: 5
<212> TYPE: DNA
<213> ORGANISM: Artificial Sequence
<220> FEATURE:
<223> OTHER INFORMATION: Synthetic

<400> SEQUENCE: 638 ttggg 5

<210> SEQ ID NO 639
<211> LENGTH: 5
<212> TYPE: DNA
<213> ORGANISM: Artificial Sequence
<220> FEATURE:
<223> OTHER INFORMATION: Synthetic

<400> SEQUENCE: 639 actcg 5

<210> SEQ ID NO 640
<211> LENGTH: 5
<212> TYPE: DNA
<213> ORGANISM: Artificial Sequence
<220> FEATURE:
<223> OTHER INFORMATION: Synthetic

<400> SEQUENCE: 640 tatta 5

<210> SEQ ID NO 641
<211> LENGTH: 5
<212> TYPE: DNA
<213> ORGANISM: Artificial Sequence
<220> FEATURE:
<223> OTHER INFORMATION: Synthetic

<400> SEQUENCE: 641 tatta 5

<210> SEQ ID NO 642
<211> LENGTH: 5
<212> TYPE: DNA
<213> ORGANISM: Artificial Sequence
<220> FEATURE:
<223> OTHER INFORMATION: Synthetic

<400> SEQUENCE: 642 agagt 5

<210> SEQ ID NO 643
<211> LENGTH: 5
<212> TYPE: DNA
<213> ORGANISM: Artificial Sequence
<220> FEATURE:
<223> OTHER INFORMATION: Synthetic

<400> SEQUENCE: 643 tgacc 5

<210> SEQ ID NO 644
<211> LENGTH: 5
<212> TYPE: DNA
<213> ORGANISM: Artificial Sequence
<220> FEATURE:
<223> OTHER INFORMATION: Synthetic

<400> SEQUENCE: 644 gacat 5

<210> SEQ ID NO 645
<211> LENGTH: 5
<212> TYPE: DNA
<213> ORGANISM: Artificial Sequence
<220> FEATURE:
<223> OTHER INFORMATION: Synthetic

<400> SEQUENCE: 645 gggtc 5

<210> SEQ ID NO 646
<211> LENGTH: 5
<212> TYPE: DNA
<213> ORGANISM: Artificial Sequence
<220> FEATURE:
<223> OTHER INFORMATION: Synthetic

<400> SEQUENCE: 646 agagg 5

<210> SEQ ID NO 647
<211> LENGTH: 5
<212> TYPE: DNA
<213> ORGANISM: Artificial Sequence
<220> FEATURE:
<223> OTHER INFORMATION: Synthetic

<400> SEQUENCE: 647 gcggc 5

<210> SEQ ID NO 648
<211> LENGTH: 5
<212> TYPE: DNA
<213> ORGANISM: Artificial Sequence
<220> FEATURE:
<223> OTHER INFORMATION: Synthetic

<400> SEQUENCE: 648 ctgaa 5

<210> SEQ ID NO 649
<211> LENGTH: 5
<212> TYPE: DNA
<213> ORGANISM: Artificial Sequence
<220> FEATURE:
<223> OTHER INFORMATION: Synthetic

<400> SEQUENCE: 649 cactg 5

<210> SEQ ID NO 650
<211> LENGTH: 5
<212> TYPE: DNA
<213> ORGANISM: Artificial Sequence
<220> FEATURE:
<223> OTHER INFORMATION: Synthetic

<400> SEQUENCE: 650 tctaa 5

<210> SEQ ID NO 651
<211> LENGTH: 5
<212> TYPE: DNA
<213> ORGANISM: Artificial Sequence
<220> FEATURE:
<223> OTHER INFORMATION: Synthetic

<400> SEQUENCE: 651 tcagc 5

<210> SEQ ID NO 652
<211> LENGTH: 5
<212> TYPE: DNA
<213> ORGANISM: Artificial Sequence
<220> FEATURE:
<223> OTHER INFORMATION: Synthetic

<400> SEQUENCE: 652 atgac 5

<210> SEQ ID NO 653
<211> LENGTH: 5
<212> TYPE: DNA
<213> ORGANISM: Artificial Sequence
<220> FEATURE:
<223> OTHER INFORMATION: Synthetic

<400> SEQUENCE: 653 aggtt 5

<210> SEQ ID NO 654
<211> LENGTH: 5
<212> TYPE: DNA
<213> ORGANISM: Artificial Sequence
<220> FEATURE:
<223> OTHER INFORMATION: Synthetic

<400> SEQUENCE: 654 tagta 5

<210> SEQ ID NO 655
<211> LENGTH: 5
<212> TYPE: DNA
<213> ORGANISM: Artificial Sequence
<220> FEATURE:
<223> OTHER INFORMATION: Synthetic

<400> SEQUENCE: 655 gcagc 5

<210> SEQ ID NO 656
<211> LENGTH: 5
<212> TYPE: DNA
<213> ORGANISM: Artificial Sequence
<220> FEATURE:
<223> OTHER INFORMATION: Synthetic

<400> SEQUENCE: 656 tgctg 5

<210> SEQ ID NO 657
<211> LENGTH: 5
<212> TYPE: DNA
<213> ORGANISM: Artificial Sequence
<220> FEATURE:
<223> OTHER INFORMATION: Synthetic

<400> SEQUENCE: 657 gccaa 5

<210> SEQ ID NO 658
<211> LENGTH: 5
<212> TYPE: DNA
<213> ORGANISM: Artificial Sequence
<220> FEATURE:
<223> OTHER INFORMATION: Synthetic

<400> SEQUENCE: 658 ctatt 5

<210> SEQ ID NO 659
<211> LENGTH: 5
<212> TYPE: DNA
<213> ORGANISM: Artificial Sequence
<220> FEATURE:
<223> OTHER INFORMATION: Synthetic

<400> SEQUENCE: 659 caaag 5

<210> SEQ ID NO 660
<211> LENGTH: 5
<212> TYPE: DNA
<213> ORGANISM: Artificial Sequence
<220> FEATURE:
<223> OTHER INFORMATION: Synthetic

<400> SEQUENCE: 660 ggagt 5

<210> SEQ ID NO 661
<211> LENGTH: 5
<212> TYPE: DNA
<213> ORGANISM: Artificial Sequence
<220> FEATURE:
<223> OTHER INFORMATION: Synthetic

<400> SEQUENCE: 661 ctgct 5

<210> SEQ ID NO 662
<211> LENGTH: 5
<212> TYPE: DNA
<213> ORGANISM: Artificial Sequence
<220> FEATURE:
<223> OTHER INFORMATION: Synthetic

<400> SEQUENCE: 662 ctcag 5

<210> SEQ ID NO 663
<211> LENGTH: 5
<212> TYPE: DNA
<213> ORGANISM: Artificial Sequence
<220> FEATURE:
<223> OTHER INFORMATION: Synthetic

<400> SEQUENCE: 663 tcatc 5

<210> SEQ ID NO 664
<211> LENGTH: 5
<212> TYPE: DNA
<213> ORGANISM: Artificial Sequence
<220> FEATURE:
<223> OTHER INFORMATION: Synthetic

<400> SEQUENCE: 664 aaacg 5

<210> SEQ ID NO 665
<211> LENGTH: 5
<212> TYPE: DNA
<213> ORGANISM: Artificial Sequence
<220> FEATURE:
<223> OTHER INFORMATION: Synthetic

<400> SEQUENCE: 665 cctta 5

<210> SEQ ID NO 666
<211> LENGTH: 5
<212> TYPE: DNA
<213> ORGANISM: Artificial Sequence
<220> FEATURE:
<223> OTHER INFORMATION: Synthetic

<400> SEQUENCE: 666 tgata 5

<210> SEQ ID NO 667
<211> LENGTH: 5
<212> TYPE: DNA
<213> ORGANISM: Artificial Sequence
<220> FEATURE:
<223> OTHER INFORMATION: Synthetic

<400> SEQUENCE: 667 gtcaa 5

<210> SEQ ID NO 668
<211> LENGTH: 5
<212> TYPE: DNA
<213> ORGANISM: Artificial Sequence
<220> FEATURE:
<223> OTHER INFORMATION: Synthetic

<400> SEQUENCE: 668 gtacc 5

<210> SEQ ID NO 669
<211> LENGTH: 5
<212> TYPE: DNA
<213> ORGANISM: Artificial Sequence
<220> FEATURE:
<223> OTHER INFORMATION: Synthetic

<400> SEQUENCE: 669 gcagt 5

<210> SEQ ID NO 670

<211> LENGTH: 5
<212> TYPE: DNA
<213> ORGANISM: Artificial Sequence
<220> FEATURE:
<223> OTHER INFORMATION: Synthetic

<400> SEQUENCE: 670 actag 5

<210> SEQ ID NO 671
<211> LENGTH: 5
<212> TYPE: DNA
<213> ORGANISM: Artificial Sequence
<220> FEATURE:
<223> OTHER INFORMATION: Synthetic

<400> SEQUENCE: 671 gtgac 5

<210> SEQ ID NO 672
<211> LENGTH: 5
<212> TYPE: DNA
<213> ORGANISM: Artificial Sequence
<220> FEATURE:
<223> OTHER INFORMATION: Synthetic

<400> SEQUENCE: 672 tgtta 5

<210> SEQ ID NO 673
<211> LENGTH: 5
<212> TYPE: DNA
<213> ORGANISM: Artificial Sequence
<220> FEATURE:
<223> OTHER INFORMATION: Synthetic

<400> SEQUENCE: 673 agcat 5

<210> SEQ ID NO 674
<211> LENGTH: 5
<212> TYPE: DNA
<213> ORGANISM: Artificial Sequence
<220> FEATURE:
<223> OTHER INFORMATION: Synthetic

<400> SEQUENCE: 674 ggaaa 5

<210> SEQ ID NO 675
<211> LENGTH: 5
<212> TYPE: DNA
<213> ORGANISM: Artificial Sequence
<220> FEATURE:
<223> OTHER INFORMATION: Synthetic

<400> SEQUENCE: 675 gttcc 5

<210> SEQ ID NO 676
<211> LENGTH: 5
<212> TYPE: DNA
<213> ORGANISM: Artificial Sequence
<220> FEATURE:
<223> OTHER INFORMATION: Synthetic

<400> SEQUENCE: 676 tgaca 5

<210> SEQ ID NO 677
<211> LENGTH: 5
<212> TYPE: DNA
<213> ORGANISM: Artificial Sequence
<220> FEATURE:
<223> OTHER INFORMATION: Synthetic

<400> SEQUENCE: 677 ggatc 5

<210> SEQ ID NO 678
<211> LENGTH: 5
<212> TYPE: DNA
<213> ORGANISM: Artificial Sequence
<220> FEATURE:
<223> OTHER INFORMATION: Synthetic

<400> SEQUENCE: 678 atggg 5

<210> SEQ ID NO 679
<211> LENGTH: 5
<212> TYPE: DNA
<213> ORGANISM: Artificial Sequence
<220> FEATURE:
<223> OTHER INFORMATION: Synthetic

<400> SEQUENCE: 679 cctag 5

<210> SEQ ID NO 680
<211> LENGTH: 5
<212> TYPE: DNA
<213> ORGANISM: Artificial Sequence
<220> FEATURE:
<223> OTHER INFORMATION: Synthetic

<400> SEQUENCE: 680 gctta 5

<210> SEQ ID NO 681
<211> LENGTH: 5
<212> TYPE: DNA
<213> ORGANISM: Artificial Sequence
<220> FEATURE:
<223> OTHER INFORMATION: Synthetic

<400> SEQUENCE: 681 gggta 5

<210> SEQ ID NO 682
<211> LENGTH: 5
<212> TYPE: DNA
<213> ORGANISM: Artificial Sequence
<220> FEATURE:
<223> OTHER INFORMATION: Synthetic

<400> SEQUENCE: 682 ctact 5

<210> SEQ ID NO 683
<211> LENGTH: 5
<212> TYPE: DNA

<213> ORGANISM: Artificial Sequence
<220> FEATURE:
<223> OTHER INFORMATION: Synthetic

<400> SEQUENCE: 683 acaac 5

<210> SEQ ID NO 684
<211> LENGTH: 5
<212> TYPE: DNA
<213> ORGANISM: Artificial Sequence
<220> FEATURE:
<223> OTHER INFORMATION: Synthetic

<400> SEQUENCE: 684 actgt 5

<210> SEQ ID NO 685
<211> LENGTH: 5
<212> TYPE: DNA
<213> ORGANISM: Artificial Sequence
<220> FEATURE:
<223> OTHER INFORMATION: Synthetic

<400> SEQUENCE: 685 tatta 5

<210> SEQ ID NO 686
<211> LENGTH: 5
<212> TYPE: DNA
<213> ORGANISM: Artificial Sequence
<220> FEATURE:
<223> OTHER INFORMATION: Synthetic

<400> SEQUENCE: 686 gctgc 5

<210> SEQ ID NO 687
<211> LENGTH: 5
<212> TYPE: DNA
<213> ORGANISM: Artificial Sequence
<220> FEATURE:
<223> OTHER INFORMATION: Synthetic

<400> SEQUENCE: 687 tgata 5

<210> SEQ ID NO 688
<211> LENGTH: 5
<212> TYPE: DNA
<213> ORGANISM: Artificial Sequence
<220> FEATURE:
<223> OTHER INFORMATION: Synthetic

<400> SEQUENCE: 688 ttgca 5

<210> SEQ ID NO 689
<211> LENGTH: 5
<212> TYPE: DNA
<213> ORGANISM: Artificial Sequence
<220> FEATURE:
<223> OTHER INFORMATION: Synthetic

<400> SEQUENCE: 689 accgt 5

<210> SEQ ID NO 690
<211> LENGTH: 5
<212> TYPE: DNA
<213> ORGANISM: Artificial Sequence
<220> FEATURE:
<223> OTHER INFORMATION: Synthetic

<400> SEQUENCE: 690 ccggt 5

<210> SEQ ID NO 691
<211> LENGTH: 5
<212> TYPE: DNA
<213> ORGANISM: Artificial Sequence
<220> FEATURE:
<223> OTHER INFORMATION: Synthetic

<400> SEQUENCE: 691 ggtca 5

<210> SEQ ID NO 692
<211> LENGTH: 5
<212> TYPE: DNA
<213> ORGANISM: Artificial Sequence
<220> FEATURE:
<223> OTHER INFORMATION: Synthetic

<400> SEQUENCE: 692 atgag 5

<210> SEQ ID NO 693
<211> LENGTH: 5
<212> TYPE: DNA
<213> ORGANISM: Artificial Sequence
<220> FEATURE:
<223> OTHER INFORMATION: Synthetic

<400> SEQUENCE: 693 gtggc 5

<210> SEQ ID NO 694
<211> LENGTH: 5
<212> TYPE: DNA
<213> ORGANISM: Artificial Sequence
<220> FEATURE:
<223> OTHER INFORMATION: Synthetic

<400> SEQUENCE: 694 tgaca 5

<210> SEQ ID NO 695
<211> LENGTH: 5
<212> TYPE: DNA
<213> ORGANISM: Artificial Sequence
<220> FEATURE:
<223> OTHER INFORMATION: Synthetic

<400> SEQUENCE: 695 gacat 5

<210> SEQ ID NO 696
<211> LENGTH: 5
<212> TYPE: DNA
<213> ORGANISM: Artificial Sequence
<220> FEATURE:

<223> OTHER INFORMATION: Synthetic

<400> SEQUENCE: 696 cctag 5

<210> SEQ ID NO 697
<211> LENGTH: 5
<212> TYPE: DNA
<213> ORGANISM: Artificial Sequence
<220> FEATURE:
<223> OTHER INFORMATION: Synthetic

<400> SEQUENCE: 697 ctgct 5

<210> SEQ ID NO 698
<211> LENGTH: 5
<212> TYPE: DNA
<213> ORGANISM: Artificial Sequence
<220> FEATURE:
<223> OTHER INFORMATION: Synthetic

<400> SEQUENCE: 698 cggct 5

<210> SEQ ID NO 699
<211> LENGTH: 5
<212> TYPE: DNA
<213> ORGANISM: Artificial Sequence
<220> FEATURE:
<223> OTHER INFORMATION: Synthetic

<400> SEQUENCE: 699 taaga 5

<210> SEQ ID NO 700
<211> LENGTH: 5
<212> TYPE: DNA
<213> ORGANISM: Artificial Sequence
<220> FEATURE:
<223> OTHER INFORMATION: Synthetic

<400> SEQUENCE: 700 gagat 5

<210> SEQ ID NO 701
<211> LENGTH: 5
<212> TYPE: DNA
<213> ORGANISM: Artificial Sequence
<220> FEATURE:
<223> OTHER INFORMATION: Synthetic

<400> SEQUENCE: 701 cttct 5

<210> SEQ ID NO 702
<211> LENGTH: 5
<212> TYPE: DNA
<213> ORGANISM: Artificial Sequence
<220> FEATURE:
<223> OTHER INFORMATION: Synthetic

<400> SEQUENCE: 702 cttct 5

<210> SEQ ID NO 703
<211> LENGTH: 5
<212> TYPE: DNA
<213> ORGANISM: Artificial Sequence
<220> FEATURE:
<223> OTHER INFORMATION: Synthetic

<400> SEQUENCE: 703 aagcc 5

<210> SEQ ID NO 704
<211> LENGTH: 5
<212> TYPE: DNA
<213> ORGANISM: Artificial Sequence
<220> FEATURE:
<223> OTHER INFORMATION: Synthetic

<400> SEQUENCE: 704 catgt 5

<210> SEQ ID NO 705
<211> LENGTH: 6
<212> TYPE: DNA
<213> ORGANISM: Artificial Sequence
<220> FEATURE:
<223> OTHER INFORMATION: Synthetic

<400> SEQUENCE: 705 gacatc 6

<210> SEQ ID NO 706
<211> LENGTH: 6
<212> TYPE: DNA
<213> ORGANISM: Artificial Sequence
<220> FEATURE:
<223> OTHER INFORMATION: Synthetic

<400> SEQUENCE: 706 tccttg 6

<210> SEQ ID NO 707
<211> LENGTH: 6
<212> TYPE: DNA
<213> ORGANISM: Artificial Sequence
<220> FEATURE:
<223> OTHER INFORMATION: Synthetic

<400> SEQUENCE: 707 atactt 6

<210> SEQ ID NO 708
<211> LENGTH: 6
<212> TYPE: DNA
<213> ORGANISM: Artificial Sequence
<220> FEATURE:
<223> OTHER INFORMATION: Synthetic

<400> SEQUENCE: 708 ggtcat 6

<210> SEQ ID NO 709
<211> LENGTH: 6
<212> TYPE: DNA
<213> ORGANISM: Artificial Sequence
<220> FEATURE:
<223> OTHER INFORMATION: Synthetic

<400> SEQUENCE: 709 ataaac 6

<210> SEQ ID NO 710
<211> LENGTH: 6
<212> TYPE: DNA
<213> ORGANISM: Artificial Sequence
<220> FEATURE:
<223> OTHER INFORMATION: Synthetic

<400> SEQUENCE: 710 atgatg 6

<210> SEQ ID NO 711
<211> LENGTH: 6
<212> TYPE: DNA
<213> ORGANISM: Artificial Sequence
<220> FEATURE:
<223> OTHER INFORMATION: Synthetic

<400> SEQUENCE: 711 ttttta 6

<210> SEQ ID NO 712
<211> LENGTH: 6
<212> TYPE: DNA
<213> ORGANISM: Artificial Sequence
<220> FEATURE:
<223> OTHER INFORMATION: Synthetic

<400> SEQUENCE: 712 aatctg 6

<210> SEQ ID NO 713
<211> LENGTH: 6
<212> TYPE: DNA
<213> ORGANISM: Artificial Sequence
<220> FEATURE:
<223> OTHER INFORMATION: Synthetic

<400> SEQUENCE: 713 cgatgt 6

<210> SEQ ID NO 714
<211> LENGTH: 6
<212> TYPE: DNA
<213> ORGANISM: Artificial Sequence
<220> FEATURE:
<223> OTHER INFORMATION: Synthetic

<400> SEQUENCE: 714 acatat 6

<210> SEQ ID NO 715
<211> LENGTH: 6
<212> TYPE: DNA
<213> ORGANISM: Artificial Sequence
<220> FEATURE:
<223> OTHER INFORMATION: Synthetic

<400> SEQUENCE: 715 ggagta 6

<210> SEQ ID NO 716
<211> LENGTH: 6

<212> TYPE: DNA
<213> ORGANISM: Artificial Sequence
<220> FEATURE:
<223> OTHER INFORMATION: Synthetic

<400> SEQUENCE: 716 ggcggt 6

<210> SEQ ID NO 717
<211> LENGTH: 6
<212> TYPE: DNA
<213> ORGANISM: Artificial Sequence
<220> FEATURE:
<223> OTHER INFORMATION: Synthetic

<400> SEQUENCE: 717 tagcta 6

<210> SEQ ID NO 718
<211> LENGTH: 6
<212> TYPE: DNA
<213> ORGANISM: Artificial Sequence
<220> FEATURE:
<223> OTHER INFORMATION: Synthetic

<400> SEQUENCE: 718 tcatac 6

<210> SEQ ID NO 719
<211> LENGTH: 6
<212> TYPE: DNA
<213> ORGANISM: Artificial Sequence
<220> FEATURE:
<223> OTHER INFORMATION: Synthetic

<400> SEQUENCE: 719 atcgtg 6

<210> SEQ ID NO 720
<211> LENGTH: 6
<212> TYPE: DNA
<213> ORGANISM: Artificial Sequence
<220> FEATURE:
<223> OTHER INFORMATION: Synthetic

<400> SEQUENCE: 720 tacgac 6

<210> SEQ ID NO 721
<211> LENGTH: 6
<212> TYPE: DNA
<213> ORGANISM: Artificial Sequence
<220> FEATURE:
<223> OTHER INFORMATION: Synthetic

<400> SEQUENCE: 721 gctgcc 6

<210> SEQ ID NO 722
<211> LENGTH: 6
<212> TYPE: DNA
<213> ORGANISM: Artificial Sequence
<220> FEATURE:
<223> OTHER INFORMATION: Synthetic

<400> SEQUENCE: 722 ggcccc 6

<210> SEQ ID NO 723
<211> LENGTH: 6
<212> TYPE: DNA
<213> ORGANISM: Artificial Sequence
<220> FEATURE:
<223> OTHER INFORMATION: Synthetic

<400> SEQUENCE: 723 tggacc 6

<210> SEQ ID NO 724
<211> LENGTH: 6
<212> TYPE: DNA
<213> ORGANISM: Artificial Sequence
<220> FEATURE:
<223> OTHER INFORMATION: Synthetic

<400> SEQUENCE: 724 cagagg 6

<210> SEQ ID NO 725
<211> LENGTH: 6
<212> TYPE: DNA
<213> ORGANISM: Artificial Sequence
<220> FEATURE:
<223> OTHER INFORMATION: Synthetic

<400> SEQUENCE: 725 gttctc 6

<210> SEQ ID NO 726
<211> LENGTH: 6
<212> TYPE: DNA
<213> ORGANISM: Artificial Sequence
<220> FEATURE:
<223> OTHER INFORMATION: Synthetic

<400> SEQUENCE: 726 cgtcag 6

<210> SEQ ID NO 727
<211> LENGTH: 6
<212> TYPE: DNA
<213> ORGANISM: Artificial Sequence
<220> FEATURE:
<223> OTHER INFORMATION: Synthetic

<400> SEQUENCE: 727 aagatc 6

<210> SEQ ID NO 728
<211> LENGTH: 6
<212> TYPE: DNA
<213> ORGANISM: Artificial Sequence
<220> FEATURE:
<223> OTHER INFORMATION: Synthetic

<400> SEQUENCE: 728 tagggc 6

<210> SEQ ID NO 729
<211> LENGTH: 7
<212> TYPE: DNA
<213> ORGANISM: Artificial Sequence
<220> FEATURE:
<223> OTHER INFORMATION: Synthetic

<400> SEQUENCE: 729 gagcgcc 7

<210> SEQ ID NO 730
<211> LENGTH: 7
<212> TYPE: DNA
<213> ORGANISM: Artificial Sequence
<220> FEATURE:
<223> OTHER INFORMATION: Synthetic

<400> SEQUENCE: 730 ccggcat 7

<210> SEQ ID NO 731
<211> LENGTH: 7
<212> TYPE: DNA
<213> ORGANISM: Artificial Sequence
<220> FEATURE:
<223> OTHER INFORMATION: Synthetic

<400> SEQUENCE: 731 acgagac 7

<210> SEQ ID NO 732
<211> LENGTH: 8
<212> TYPE: DNA
<213> ORGANISM: Artificial Sequence
<220> FEATURE:
<223> OTHER INFORMATION: Synthetic

<400> SEQUENCE: 732 tcgctttc 8

<210> SEQ ID NO 733
<211> LENGTH: 8
<212> TYPE: DNA
<213> ORGANISM: Artificial Sequence
<220> FEATURE:
<223> OTHER INFORMATION: Synthetic

<400> SEQUENCE: 733 ggaaaatc 8

<210> SEQ ID NO 734
<211> LENGTH: 8
<212> TYPE: DNA
<213> ORGANISM: Artificial Sequence
<220> FEATURE:
<223> OTHER INFORMATION: Synthetic

<400> SEQUENCE: 734 cagaagat 8

<210> SEQ ID NO 735
<211> LENGTH: 8
<212> TYPE: DNA
<213> ORGANISM: Artificial Sequence
<220> FEATURE:
<223> OTHER INFORMATION: Synthetic

<400> SEQUENCE: 735 ctaggact 8

<210> SEQ ID NO 736
<211> LENGTH: 8
<212> TYPE: DNA
<213> ORGANISM: Artificial Sequence
<220> FEATURE:
<223> OTHER INFORMATION: Synthetic

<400> SEQUENCE: 736 tcgtaatc 8

<210> SEQ ID NO 737
<211> LENGTH: 8
<212> TYPE: DNA
<213> ORGANISM: Artificial Sequence
<220> FEATURE:
<223> OTHER INFORMATION: Synthetic

<400> SEQUENCE: 737 gccatggc 8

<210> SEQ ID NO 738
<211> LENGTH: 8
<212> TYPE: DNA
<213> ORGANISM: Artificial Sequence
<220> FEATURE:
<223> OTHER INFORMATION: Synthetic

<400> SEQUENCE: 738 caccatca 8

<210> SEQ ID NO 739
<211> LENGTH: 8
<212> TYPE: DNA
<213> ORGANISM: Artificial Sequence
<220> FEATURE:
<223> OTHER INFORMATION: Synthetic

<400> SEQUENCE: 739 gtgtctgt 8

<210> SEQ ID NO 740
<211> LENGTH: 8
<212> TYPE: DNA
<213> ORGANISM: Artificial Sequence
<220> FEATURE:
<223> OTHER INFORMATION: Synthetic

<400> SEQUENCE: 740 gctgcatt 8

<210> SEQ ID NO 741
<211> LENGTH: 8
<212> TYPE: DNA
<213> ORGANISM: Artificial Sequence
<220> FEATURE:
<223> OTHER INFORMATION: Synthetic

<400> SEQUENCE: 741 aatctgac 8

<210> SEQ ID NO 742
<211> LENGTH: 8
<212> TYPE: DNA
<213> ORGANISM: Artificial Sequence
<220> FEATURE:
<223> OTHER INFORMATION: Synthetic

<400> SEQUENCE: 742 tgctgctg 8

<210> SEQ ID NO 743
<211> LENGTH: 8
<212> TYPE: DNA
<213> ORGANISM: Artificial Sequence
<220> FEATURE:
<223> OTHER INFORMATION: Synthetic

<400> SEQUENCE: 743 tggatttg 8

<210> SEQ ID NO 744
<211> LENGTH: 9
<212> TYPE: DNA
<213> ORGANISM: Artificial Sequence
<220> FEATURE:
<223> OTHER INFORMATION: Synthetic

<400> SEQUENCE: 744 gaaaattcc 9

<210> SEQ ID NO 745
<211> LENGTH: 9
<212> TYPE: DNA
<213> ORGANISM: Artificial Sequence
<220> FEATURE:
<223> OTHER INFORMATION: Synthetic

<400> SEQUENCE: 745 cctggatga 9

<210> SEQ ID NO 746
<211> LENGTH: 9
<212> TYPE: DNA
<213> ORGANISM: Artificial Sequence
<220> FEATURE:
<223> OTHER INFORMATION: Synthetic

<400> SEQUENCE: 746 ctcttatct 9

<210> SEQ ID NO 747
<211> LENGTH: 9
<212> TYPE: DNA
<213> ORGANISM: Artificial Sequence
<220> FEATURE:
<223> OTHER INFORMATION: Synthetic

<400> SEQUENCE: 747 cgttgtttt 9

<210> SEQ ID NO 748
<211> LENGTH: 9
<212> TYPE: DNA
<213> ORGANISM: Artificial Sequence
<220> FEATURE:
<223> OTHER INFORMATION: Synthetic

<400> SEQUENCE: 748 cccacggct 9

<210> SEQ ID NO 749

-continued

<211> LENGTH: 9
<212> TYPE: DNA
<213> ORGANISM: Artificial Sequence
<220> FEATURE:
<223> OTHER INFORMATION: Synthetic

<400> SEQUENCE: 749 atatcacct 9

<210> SEQ ID NO 750
<211> LENGTH: 9
<212> TYPE: DNA
<213> ORGANISM: Artificial Sequence
<220> FEATURE:
<223> OTHER INFORMATION: Synthetic

<400> SEQUENCE: 750 acattcatg 9

<210> SEQ ID NO 751
<211> LENGTH: 9
<212> TYPE: DNA
<213> ORGANISM: Artificial Sequence
<220> FEATURE:
<223> OTHER INFORMATION: Synthetic

<400> SEQUENCE: 751 cgctgagag 9

<210> SEQ ID NO 752
<211> LENGTH: 9
<212> TYPE: DNA
<213> ORGANISM: Artificial Sequence
<220> FEATURE:
<223> OTHER INFORMATION: Synthetic

<400> SEQUENCE: 752 tacttgttg 9

<210> SEQ ID NO 753
<211> LENGTH: 9
<212> TYPE: DNA
<213> ORGANISM: Artificial Sequence
<220> FEATURE:
<223> OTHER INFORMATION: Synthetic

<400> SEQUENCE: 753 caatcttat 9

<210> SEQ ID NO 754
<211> LENGTH: 9
<212> TYPE: DNA
<213> ORGANISM: Artificial Sequence
<220> FEATURE:
<223> OTHER INFORMATION: Synthetic

<400> SEQUENCE: 754 aaggacatc 9

<210> SEQ ID NO 755
<211> LENGTH: 9
<212> TYPE: DNA
<213> ORGANISM: Artificial Sequence
<220> FEATURE:
<223> OTHER INFORMATION: Synthetic

<400> SEQUENCE: 755 tggctcgga 9

<210> SEQ ID NO 756
<211> LENGTH: 9
<212> TYPE: DNA
<213> ORGANISM: Artificial Sequence
<220> FEATURE:
<223> OTHER INFORMATION: Synthetic

<400> SEQUENCE: 756 agcgaagat 9

<210> SEQ ID NO 757
<211> LENGTH: 9
<212> TYPE: DNA
<213> ORGANISM: Artificial Sequence
<220> FEATURE:
<223> OTHER INFORMATION: Synthetic

<400> SEQUENCE: 757 cgctggtga 9

<210> SEQ ID NO 758
<211> LENGTH: 9
<212> TYPE: DNA
<213> ORGANISM: Artificial Sequence
<220> FEATURE:
<223> OTHER INFORMATION: Synthetic

<400> SEQUENCE: 758 gcaagagac 9

<210> SEQ ID NO 759
<211> LENGTH: 10
<212> TYPE: DNA
<213> ORGANISM: Artificial Sequence
<220> FEATURE:
<223> OTHER INFORMATION: Synthetic

<400> SEQUENCE: 759
atgacaagat 10

<210> SEQ ID NO 760
<211> LENGTH: 10
<212> TYPE: DNA
<213> ORGANISM: Artificial Sequence
<220> FEATURE:
<223> OTHER INFORMATION: Synthetic

<400> SEQUENCE: 760
tggagtgtga 10

<210> SEQ ID NO 761
<211> LENGTH: 10
<212> TYPE: DNA
<213> ORGANISM: Artificial Sequence
<220> FEATURE:
<223> OTHER INFORMATION: Synthetic

<400> SEQUENCE: 761
tgtgccgcac 10

<210> SEQ ID NO 762
<211> LENGTH: 10
<212> TYPE: DNA

<213> ORGANISM: Artificial Sequence
<220> FEATURE:
<223> OTHER INFORMATION: Synthetic

<400> SEQUENCE: 762
agccgcagct 10

<210> SEQ ID NO 763
<211> LENGTH: 11
<212> TYPE: DNA
<213> ORGANISM: Artificial Sequence
<220> FEATURE:
<223> OTHER INFORMATION: Synthetic

<400> SEQUENCE: 763
aaagagattc c 11

<210> SEQ ID NO 764
<211> LENGTH: 11
<212> TYPE: DNA
<213> ORGANISM: Artificial Sequence
<220> FEATURE:
<223> OTHER INFORMATION: Synthetic

<400> SEQUENCE: 764
agctgcagca t 11

<210> SEQ ID NO 765
<211> LENGTH: 11
<212> TYPE: DNA
<213> ORGANISM: Artificial Sequence
<220> FEATURE:
<223> OTHER INFORMATION: Synthetic

<400> SEQUENCE: 765
ctttaatttg t 11

<210> SEQ ID NO 766
<211> LENGTH: 11
<212> TYPE: DNA
<213> ORGANISM: Artificial Sequence
<220> FEATURE:
<223> OTHER INFORMATION: Synthetic

<400> SEQUENCE: 766
acatctgggt g 11

<210> SEQ ID NO 767
<211> LENGTH: 11
<212> TYPE: DNA
<213> ORGANISM: Artificial Sequence
<220> FEATURE:
<223> OTHER INFORMATION: Synthetic

<400> SEQUENCE: 767
caacaagttc a 11

<210> SEQ ID NO 768
<211> LENGTH: 12
<212> TYPE: DNA
<213> ORGANISM: Artificial Sequence
<220> FEATURE:
<223> OTHER INFORMATION: Synthetic

<400> SEQUENCE: 768
tggcccggcg gc 12

-continued

<210> SEQ ID NO 769
<211> LENGTH: 12
<212> TYPE: DNA
<213> ORGANISM: Artificial Sequence
<220> FEATURE:
<223> OTHER INFORMATION: Synthetic

<400> SEQUENCE: 769
gaagaaacta tt 12

<210> SEQ ID NO 770
<211> LENGTH: 12
<212> TYPE: DNA
<213> ORGANISM: Artificial Sequence
<220> FEATURE:
<223> OTHER INFORMATION: Synthetic

<400> SEQUENCE: 770
taaccctctg tc 12

<210> SEQ ID NO 771
<211> LENGTH: 12
<212> TYPE: DNA
<213> ORGANISM: Artificial Sequence
<220> FEATURE:
<223> OTHER INFORMATION: Synthetic

<400> SEQUENCE: 771
acctgtggtc cc 12

<210> SEQ ID NO 772
<211> LENGTH: 12
<212> TYPE: DNA
<213> ORGANISM: Artificial Sequence
<220> FEATURE:
<223> OTHER INFORMATION: Synthetic

<400> SEQUENCE: 772
aggacaaatc tg 12

<210> SEQ ID NO 773
<211> LENGTH: 13
<212> TYPE: DNA
<213> ORGANISM: Artificial Sequence
<220> FEATURE:
<223> OTHER INFORMATION: Synthetic

<400> SEQUENCE: 773
gacgagctgt gcc 13

<210> SEQ ID NO 774
<211> LENGTH: 13
<212> TYPE: DNA
<213> ORGANISM: Artificial Sequence
<220> FEATURE:
<223> OTHER INFORMATION: Synthetic

<400> SEQUENCE: 774
ttctccttgg ccg 13

<210> SEQ ID NO 775
<211> LENGTH: 14
<212> TYPE: DNA
<213> ORGANISM: Artificial Sequence
<220> FEATURE:

<223> OTHER INFORMATION: Synthetic

<400> SEQUENCE: 775
tggtgagcac gctg 14

<210> SEQ ID NO 776
<211> LENGTH: 14
<212> TYPE: DNA
<213> ORGANISM: Artificial Sequence
<220> FEATURE:
<223> OTHER INFORMATION: Synthetic

<400> SEQUENCE: 776
cgactgcaag gaca 14

<210> SEQ ID NO 777
<211> LENGTH: 14
<212> TYPE: DNA
<213> ORGANISM: Artificial Sequence
<220> FEATURE:
<223> OTHER INFORMATION: Synthetic

<400> SEQUENCE: 777
aaggtcagct ccac 14

<210> SEQ ID NO 778
<211> LENGTH: 15
<212> TYPE: DNA
<213> ORGANISM: Artificial Sequence
<220> FEATURE:
<223> OTHER INFORMATION: Synthetic

<400> SEQUENCE: 778
gcagcaaatc aagct 15

<210> SEQ ID NO 779
<211> LENGTH: 15
<212> TYPE: DNA
<213> ORGANISM: Artificial Sequence
<220> FEATURE:
<223> OTHER INFORMATION: Synthetic

<400> SEQUENCE: 779
gctgccgcgc cgcct 15

<210> SEQ ID NO 780
<211> LENGTH: 15
<212> TYPE: DNA
<213> ORGANISM: Artificial Sequence
<220> FEATURE:
<223> OTHER INFORMATION: Synthetic

<400> SEQUENCE: 780
tactgcatgc aaatg 15

<210> SEQ ID NO 781
<211> LENGTH: 15
<212> TYPE: DNA
<213> ORGANISM: Artificial Sequence
<220> FEATURE:
<223> OTHER INFORMATION: Synthetic

<400> SEQUENCE: 781
aaggacaaat ctgac 15

-continued

<210> SEQ ID NO 782
<211> LENGTH: 16
<212> TYPE: DNA
<213> ORGANISM: Artificial Sequence
<220> FEATURE:
<223> OTHER INFORMATION: Synthetic

<400> SEQUENCE: 782
aacctgggca agctgg 16

<210> SEQ ID NO 783
<211> LENGTH: 16
<212> TYPE: DNA
<213> ORGANISM: Artificial Sequence
<220> FEATURE:
<223> OTHER INFORMATION: Synthetic

<400> SEQUENCE: 783
gctctgcgcg ctgctc 16

<210> SEQ ID NO 784
<211> LENGTH: 17
<212> TYPE: DNA
<213> ORGANISM: Artificial Sequence
<220> FEATURE:
<223> OTHER INFORMATION: Synthetic

<400> SEQUENCE: 784
ctagctatcg ttctttt 17

<210> SEQ ID NO 785
<211> LENGTH: 17
<212> TYPE: DNA
<213> ORGANISM: Artificial Sequence
<220> FEATURE:
<223> OTHER INFORMATION: Synthetic

<400> SEQUENCE: 785
gctgctctgc atgtttt 17

<210> SEQ ID NO 786
<211> LENGTH: 17
<212> TYPE: DNA
<213> ORGANISM: Artificial Sequence
<220> FEATURE:
<223> OTHER INFORMATION: Synthetic

<400> SEQUENCE: 786
ttggttggta gacactg 17

<210> SEQ ID NO 787
<211> LENGTH: 17
<212> TYPE: DNA
<213> ORGANISM: Artificial Sequence
<220> FEATURE:
<223> OTHER INFORMATION: Synthetic

<400> SEQUENCE: 787
ctcttctgct gcttctt 17

<210> SEQ ID NO 788
<211> LENGTH: 17
<212> TYPE: DNA
<213> ORGANISM: Artificial Sequence
<220> FEATURE:
<223> OTHER INFORMATION: Synthetic

<400> SEQUENCE: 788
tggcccggag gctgggc 17

<210> SEQ ID NO 789
<211> LENGTH: 18
<212> TYPE: DNA
<213> ORGANISM: Artificial Sequence
<220> FEATURE:
<223> OTHER INFORMATION: Synthetic

<400> SEQUENCE: 789
tgggggtgcg gcggaggc 18

<210> SEQ ID NO 790
<211> LENGTH: 18
<212> TYPE: DNA
<213> ORGANISM: Artificial Sequence
<220> FEATURE:
<223> OTHER INFORMATION: Synthetic

<400> SEQUENCE: 790
ggaggcgggg gtgcggcc 18

<210> SEQ ID NO 791
<211> LENGTH: 18
<212> TYPE: DNA
<213> ORGANISM: Artificial Sequence
<220> FEATURE:
<223> OTHER INFORMATION: Synthetic

<400> SEQUENCE: 791
aggcgggggt gcggccgg 18

<210> SEQ ID NO 792
<211> LENGTH: 18
<212> TYPE: DNA
<213> ORGANISM: Artificial Sequence
<220> FEATURE:
<223> OTHER INFORMATION: Synthetic

<400> SEQUENCE: 792
acccaaagca gctgtact 18

<210> SEQ ID NO 793
<211> LENGTH: 18
<212> TYPE: DNA
<213> ORGANISM: Artificial Sequence
<220> FEATURE:
<223> OTHER INFORMATION: Synthetic

<400> SEQUENCE: 793
gcccaggccc tgcagggc 18

<210> SEQ ID NO 794
<211> LENGTH: 18
<212> TYPE: DNA
<213> ORGANISM: Artificial Sequence
<220> FEATURE:
<223> OTHER INFORMATION: Synthetic

<400> SEQUENCE: 794
gagcaagtcc agctcctc 18

<210> SEQ ID NO 795
<211> LENGTH: 18

<212> TYPE: DNA
<213> ORGANISM: Artificial Sequence
<220> FEATURE:
<223> OTHER INFORMATION: Synthetic

<400> SEQUENCE: 795
tgcggctgcg tggacctc 18

<210> SEQ ID NO 796
<211> LENGTH: 18
<212> TYPE: DNA
<213> ORGANISM: Artificial Sequence
<220> FEATURE:
<223> OTHER INFORMATION: Synthetic

<400> SEQUENCE: 796
tgcaaggaca aatctgac 18

<210> SEQ ID NO 797
<211> LENGTH: 19
<212> TYPE: DNA
<213> ORGANISM: Artificial Sequence
<220> FEATURE:
<223> OTHER INFORMATION: Synthetic

<400> SEQUENCE: 797
tgcagacata gatgccccc 19

<210> SEQ ID NO 798
<211> LENGTH: 19
<212> TYPE: DNA
<213> ORGANISM: Artificial Sequence
<220> FEATURE:
<223> OTHER INFORMATION: Synthetic

<400> SEQUENCE: 798
tcgcgctgct gctgctctg 19

<210> SEQ ID NO 799
<211> LENGTH: 19
<212> TYPE: DNA
<213> ORGANISM: Artificial Sequence
<220> FEATURE:
<223> OTHER INFORMATION: Synthetic

<400> SEQUENCE: 799
gctgctctgc gcgctgctc 19

<210> SEQ ID NO 800
<211> LENGTH: 20
<212> TYPE: DNA
<213> ORGANISM: Artificial Sequence
<220> FEATURE:
<223> OTHER INFORMATION: Synthetic

<400> SEQUENCE: 800
ggctgggctg gcagggctga 20

<210> SEQ ID NO 801
<211> LENGTH: 20
<212> TYPE: DNA
<213> ORGANISM: Artificial Sequence
<220> FEATURE:
<223> OTHER INFORMATION: Synthetic

<400> SEQUENCE: 801

-continued gcaggcggag caccccaagc 20

<210> SEQ ID NO 802
<211> LENGTH: 20
<212> TYPE: DNA
<213> ORGANISM: Artificial Sequence
<220> FEATURE:
<223> OTHER INFORMATION: Synthetic

<400> SEQUENCE: 802
gcaacagctc cacctgcatc 20

<210> SEQ ID NO 803
<211> LENGTH: 20
<212> TYPE: DNA
<213> ORGANISM: Artificial Sequence
<220> FEATURE:
<223> OTHER INFORMATION: Synthetic

<400> SEQUENCE: 803
gccgggactg gtcagatgaa 20

<210> SEQ ID NO 804
<211> LENGTH: 20
<212> TYPE: DNA
<213> ORGANISM: Artificial Sequence
<220> FEATURE:
<223> OTHER INFORMATION: Synthetic

<400> SEQUENCE: 804
ggtggatcct gttcatgggt 20

<210> SEQ ID NO 805
<211> LENGTH: 21
<212> TYPE: DNA
<213> ORGANISM: Artificial Sequence
<220> FEATURE:
<223> OTHER INFORMATION: Synthetic

<400> SEQUENCE: 805
cgcgcacccc tgtgcccacc t 21

<210> SEQ ID NO 806
<211> LENGTH: 21
<212> TYPE: DNA
<213> ORGANISM: Artificial Sequence
<220> FEATURE:
<223> OTHER INFORMATION: Synthetic

<400> SEQUENCE: 806
tggggcaggc ggcggtgcgg c 21

<210> SEQ ID NO 807
<211> LENGTH: 21
<212> TYPE: DNA
<213> ORGANISM: Artificial Sequence
<220> FEATURE:
<223> OTHER INFORMATION: Synthetic

<400> SEQUENCE: 807
ctctcggtca tgctgcagct g 21

<210> SEQ ID NO 808
<211> LENGTH: 21
<212> TYPE: DNA
<213> ORGANISM: Artificial Sequence
<220> FEATURE:
<223> OTHER INFORMATION: Synthetic

<400> SEQUENCE: 808
gactgcaagg acaaatctga c 21

<210> SEQ ID NO 809
<211> LENGTH: 21
<212> TYPE: DNA
<213> ORGANISM: Artificial Sequence
<220> FEATURE:
<223> OTHER INFORMATION: Synthetic

<400> SEQUENCE: 809
ccttacagct gcctctgttg t 21

<210> SEQ ID NO 810
<211> LENGTH: 18
<212> TYPE: DNA
<213> ORGANISM: Artificial Sequence
<220> FEATURE:
<223> OTHER INFORMATION: Synthetic

<400> SEQUENCE: 810
aggattgggt gggagcag 18

<210> SEQ ID NO 811
<211> LENGTH: 18
<212> TYPE: DNA
<213> ORGANISM: Artificial Sequence
<220> FEATURE:
<223> OTHER INFORMATION: Synthetic

<400> SEQUENCE: 811
tttgactcgc tcgctaca 18

<210> SEQ ID NO 812
<211> LENGTH: 18
<212> TYPE: DNA
<213> ORGANISM: Artificial Sequence
<220> FEATURE:
<223> OTHER INFORMATION: Synthetic

<400> SEQUENCE: 812
agactattaa ttacgttc 18

<210> SEQ ID NO 813
<211> LENGTH: 18
<212> TYPE: DNA
<213> ORGANISM: Artificial Sequence
<220> FEATURE:
<223> OTHER INFORMATION: Synthetic

<400> SEQUENCE: 813
gttatggagg gagtccat 18

<210> SEQ ID NO 814
<211> LENGTH: 18
<212> TYPE: DNA
<213> ORGANISM: Artificial Sequence
<220> FEATURE:
<223> OTHER INFORMATION: Synthetic

<400> SEQUENCE: 814
ataaagagtg agtctttt 18

<210> SEQ ID NO 815
<211> LENGTH: 18
<212> TYPE: DNA
<213> ORGANISM: Artificial Sequence
<220> FEATURE:
<223> OTHER INFORMATION: Synthetic

<400> SEQUENCE: 815
aggatgaccg accgcgat 18

<210> SEQ ID NO 816
<211> LENGTH: 18
<212> TYPE: DNA
<213> ORGANISM: Artificial Sequence
<220> FEATURE:
<223> OTHER INFORMATION: Synthetic

<400> SEQUENCE: 816
aagggacata catcatca 18

<210> SEQ ID NO 817
<211> LENGTH: 18
<212> TYPE: DNA
<213> ORGANISM: Artificial Sequence
<220> FEATURE:
<223> OTHER INFORMATION: Synthetic

<400> SEQUENCE: 817
aaatgggtcg gtccatca 18

<210> SEQ ID NO 818
<211> LENGTH: 18
<212> TYPE: DNA
<213> ORGANISM: Artificial Sequence
<220> FEATURE:
<223> OTHER INFORMATION: Synthetic

<400> SEQUENCE: 818
tagtagaggg aggccaca 18

<210> SEQ ID NO 819
<211> LENGTH: 18
<212> TYPE: DNA
<213> ORGANISM: Artificial Sequence
<220> FEATURE:
<223> OTHER INFORMATION: Synthetic

<400> SEQUENCE: 819
tctggcggcc ggccgact 18

<210> SEQ ID NO 820
<211> LENGTH: 18
<212> TYPE: DNA
<213> ORGANISM: Artificial Sequence
<220> FEATURE:
<223> OTHER INFORMATION: Synthetic

<400> SEQUENCE: 820
cgagctgaat gaagcctt 18

<210> SEQ ID NO 821
<211> LENGTH: 18
<212> TYPE: DNA
<213> ORGANISM: Artificial Sequence
<220> FEATURE:
<223> OTHER INFORMATION: Synthetic

<400> SEQUENCE: 821
aaaacactga ctgagact 18

<210> SEQ ID NO 822
<211> LENGTH: 18
<212> TYPE: DNA
<213> ORGANISM: Artificial Sequence
<220> FEATURE:
<223> OTHER INFORMATION: Synthetic

<400> SEQUENCE: 822
cacttctaac taacaaac 18

<210> SEQ ID NO 823
<211> LENGTH: 18
<212> TYPE: DNA
<213> ORGANISM: Artificial Sequence
<220> FEATURE:
<223> OTHER INFORMATION: Synthetic

<400> SEQUENCE: 823
agtgtcagcc agccattc 18

<210> SEQ ID NO 824
<211> LENGTH: 18
<212> TYPE: DNA
<213> ORGANISM: Artificial Sequence
<220> FEATURE:
<223> OTHER INFORMATION: Synthetic

<400> SEQUENCE: 824
tctaatgact gactattt 18

<210> SEQ ID NO 825
<211> LENGTH: 18
<212> TYPE: DNA
<213> ORGANISM: Artificial Sequence
<220> FEATURE:
<223> OTHER INFORMATION: Synthetic

<400> SEQUENCE: 825
ttacaggttg gttcttaa 18

<210> SEQ ID NO 826
<211> LENGTH: 18
<212> TYPE: DNA
<213> ORGANISM: Artificial Sequence
<220> FEATURE:
<223> OTHER INFORMATION: Synthetic

<400> SEQUENCE: 826
ccggtagtaa gtacttca 18

<210> SEQ ID NO 827
<211> LENGTH: 18
<212> TYPE: DNA
<213> ORGANISM: Artificial Sequence
<220> FEATURE:
<223> OTHER INFORMATION: Synthetic

<400> SEQUENCE: 827
gccagcagcc agcagcat 18

<210> SEQ ID NO 828

<211> LENGTH: 18
<212> TYPE: DNA
<213> ORGANISM: Artificial Sequence
<220> FEATURE:
<223> OTHER INFORMATION: Synthetic

<400> SEQUENCE: 828
gagctgctgg ctgctttg 18

<210> SEQ ID NO 829
<211> LENGTH: 18
<212> TYPE: DNA
<213> ORGANISM: Artificial Sequence
<220> FEATURE:
<223> OTHER INFORMATION: Synthetic

<400> SEQUENCE: 829
caacgccaac caacattg 18

<210> SEQ ID NO 830
<211> LENGTH: 18
<212> TYPE: DNA
<213> ORGANISM: Artificial Sequence
<220> FEATURE:
<223> OTHER INFORMATION: Synthetic

<400> SEQUENCE: 830
agctctattt atttgatt 18

<210> SEQ ID NO 831
<211> LENGTH: 18
<212> TYPE: DNA
<213> ORGANISM: Artificial Sequence
<220> FEATURE:
<223> OTHER INFORMATION: Synthetic

<400> SEQUENCE: 831
caagcaaaga aagatgga 18

<210> SEQ ID NO 832
<211> LENGTH: 18
<212> TYPE: DNA
<213> ORGANISM: Artificial Sequence
<220> FEATURE:
<223> OTHER INFORMATION: Synthetic

<400> SEQUENCE: 832
ttctggagtg agtcgcta 18

<210> SEQ ID NO 833
<211> LENGTH: 18
<212> TYPE: DNA
<213> ORGANISM: Artificial Sequence
<220> FEATURE:
<223> OTHER INFORMATION: Synthetic

<400> SEQUENCE: 833
tgaactgctt gctcatgg 18

<210> SEQ ID NO 834
<211> LENGTH: 18
<212> TYPE: DNA
<213> ORGANISM: Artificial Sequence
<220> FEATURE:
<223> OTHER INFORMATION: Synthetic

<400> SEQUENCE: 834

-continued tggcctcagt cagcaggg 18

<210> SEQ ID NO 835
<211> LENGTH: 18
<212> TYPE: DNA
<213> ORGANISM: Artificial Sequence
<220> FEATURE:
<223> OTHER INFORMATION: Synthetic

<400> SEQUENCE: 835
cttctcatcc atcgcttt 18

<210> SEQ ID NO 836
<211> LENGTH: 18
<212> TYPE: DNA
<213> ORGANISM: Artificial Sequence
<220> FEATURE:
<223> OTHER INFORMATION: Synthetic

<400> SEQUENCE: 836
ctataaacga acgcagtc 18

<210> SEQ ID NO 837
<211> LENGTH: 18
<212> TYPE: DNA
<213> ORGANISM: Artificial Sequence
<220> FEATURE:
<223> OTHER INFORMATION: Synthetic

<400> SEQUENCE: 837
ccacccttac ttagttct 18

<210> SEQ ID NO 838
<211> LENGTH: 18
<212> TYPE: DNA
<213> ORGANISM: Artificial Sequence
<220> FEATURE:
<223> OTHER INFORMATION: Synthetic

<400> SEQUENCE: 838
ctcatgatag atactact 18

<210> SEQ ID NO 839
<211> LENGTH: 18
<212> TYPE: DNA
<213> ORGANISM: Artificial Sequence
<220> FEATURE:
<223> OTHER INFORMATION: Synthetic

<400> SEQUENCE: 839
gaaagtcaat caatgcca 18

<210> SEQ ID NO 840
<211> LENGTH: 18
<212> TYPE: DNA
<213> ORGANISM: Artificial Sequence
<220> FEATURE:
<223> OTHER INFORMATION: Synthetic

<400> SEQUENCE: 840
agttgtacct accgtctt 18

<210> SEQ ID NO 841
<211> LENGTH: 18
<212> TYPE: DNA

<213> ORGANISM: Artificial Sequence
<220> FEATURE:
<223> OTHER INFORMATION: Synthetic

<400> SEQUENCE: 841
tcttgcagtc agtaaagc 18

<210> SEQ ID NO 842
<211> LENGTH: 18
<212> TYPE: DNA
<213> ORGANISM: Artificial Sequence
<220> FEATURE:
<223> OTHER INFORMATION: Synthetic

<400> SEQUENCE: 842
cttaactagc tagctctt 18

<210> SEQ ID NO 843
<211> LENGTH: 18
<212> TYPE: DNA
<213> ORGANISM: Artificial Sequence
<220> FEATURE:
<223> OTHER INFORMATION: Synthetic

<400> SEQUENCE: 843
acttgtgact gactagct 18

<210> SEQ ID NO 844
<211> LENGTH: 18
<212> TYPE: DNA
<213> ORGANISM: Artificial Sequence
<220> FEATURE:
<223> OTHER INFORMATION: Synthetic

<400> SEQUENCE: 844
gtgatgttag ttagtttg 18

<210> SEQ ID NO 845
<211> LENGTH: 18
<212> TYPE: DNA
<213> ORGANISM: Artificial Sequence
<220> FEATURE:
<223> OTHER INFORMATION: Synthetic

<400> SEQUENCE: 845
actgagcatg catagtct 18

<210> SEQ ID NO 846
<211> LENGTH: 18
<212> TYPE: DNA
<213> ORGANISM: Artificial Sequence
<220> FEATURE:
<223> OTHER INFORMATION: Synthetic

<400> SEQUENCE: 846
aaatggaaag aaaaaacc 18

<210> SEQ ID NO 847
<211> LENGTH: 18
<212> TYPE: DNA
<213> ORGANISM: Artificial Sequence
<220> FEATURE:
<223> OTHER INFORMATION: Synthetic

<400> SEQUENCE: 847
ctttgttcct tccacctt 18

<210> SEQ ID NO 848
<211> LENGTH: 18
<212> TYPE: DNA
<213> ORGANISM: Artificial Sequence
<220> FEATURE:
<223> OTHER INFORMATION: Synthetic

<400> SEQUENCE: 848
tgtgtgacag acactcca 18

<210> SEQ ID NO 849
<211> LENGTH: 18
<212> TYPE: DNA
<213> ORGANISM: Artificial Sequence
<220> FEATURE:
<223> OTHER INFORMATION: Synthetic

<400> SEQUENCE: 849
agatggatcg atcatatg 18

<210> SEQ ID NO 850
<211> LENGTH: 18
<212> TYPE: DNA
<213> ORGANISM: Artificial Sequence
<220> FEATURE:
<223> OTHER INFORMATION: Synthetic

<400> SEQUENCE: 850
acagatgggt gggtggta 18

<210> SEQ ID NO 851
<211> LENGTH: 18
<212> TYPE: DNA
<213> ORGANISM: Artificial Sequence
<220> FEATURE:
<223> OTHER INFORMATION: Synthetic

<400> SEQUENCE: 851
tgaccctagc tagacctt 18

<210> SEQ ID NO 852
<211> LENGTH: 18
<212> TYPE: DNA
<213> ORGANISM: Artificial Sequence
<220> FEATURE:
<223> OTHER INFORMATION: Synthetic

<400> SEQUENCE: 852
cccagcttac ttaccttg 18

<210> SEQ ID NO 853
<211> LENGTH: 18
<212> TYPE: DNA
<213> ORGANISM: Artificial Sequence
<220> FEATURE:
<223> OTHER INFORMATION: Synthetic

<400> SEQUENCE: 853
ttttgggtag gtagcact 18

<210> SEQ ID NO 854
<211> LENGTH: 18
<212> TYPE: DNA
<213> ORGANISM: Artificial Sequence
<220> FEATURE:

<223> OTHER INFORMATION: Synthetic

<400> SEQUENCE: 854
tgccctactt actccctg 18

<210> SEQ ID NO 855
<211> LENGTH: 18
<212> TYPE: DNA
<213> ORGANISM: Artificial Sequence
<220> FEATURE:
<223> OTHER INFORMATION: Synthetic

<400> SEQUENCE: 855
ctttacaacc aaccggct 18

<210> SEQ ID NO 856
<211> LENGTH: 18
<212> TYPE: DNA
<213> ORGANISM: Artificial Sequence
<220> FEATURE:
<223> OTHER INFORMATION: Synthetic

<400> SEQUENCE: 856
aggcactgtc tgtacggt 18

<210> SEQ ID NO 857
<211> LENGTH: 18
<212> TYPE: DNA
<213> ORGANISM: Artificial Sequence
<220> FEATURE:
<223> OTHER INFORMATION: Synthetic

<400> SEQUENCE: 857
tctctattaa ttagtaag 18

<210> SEQ ID NO 858
<211> LENGTH: 18
<212> TYPE: DNA
<213> ORGANISM: Artificial Sequence
<220> FEATURE:
<223> OTHER INFORMATION: Synthetic

<400> SEQUENCE: 858
gcctgctgcc tgcctgga 18

<210> SEQ ID NO 859
<211> LENGTH: 18
<212> TYPE: DNA
<213> ORGANISM: Artificial Sequence
<220> FEATURE:
<223> OTHER INFORMATION: Synthetic

<400> SEQUENCE: 859
ctggtgatag atagatga 18

<210> SEQ ID NO 860
<211> LENGTH: 18
<212> TYPE: DNA
<213> ORGANISM: Artificial Sequence
<220> FEATURE:
<223> OTHER INFORMATION: Synthetic

<400> SEQUENCE: 860
gagcttgcat gcattcca 18

<210> SEQ ID NO 861
<211> LENGTH: 18
<212> TYPE: DNA
<213> ORGANISM: Artificial Sequence
<220> FEATURE:
<223> OTHER INFORMATION: Synthetic

<400> SEQUENCE: 861
ctggaccgtc cgtcgcct 18

<210> SEQ ID NO 862
<211> LENGTH: 18
<212> TYPE: DNA
<213> ORGANISM: Artificial Sequence
<220> FEATURE:
<223> OTHER INFORMATION: Synthetic

<400> SEQUENCE: 862
ctgcccggtc ggtgctca 18

<210> SEQ ID NO 863
<211> LENGTH: 18
<212> TYPE: DNA
<213> ORGANISM: Artificial Sequence
<220> FEATURE:
<223> OTHER INFORMATION: Synthetic

<400> SEQUENCE: 863
gactggtcag tcagatga 18

<210> SEQ ID NO 864
<211> LENGTH: 18
<212> TYPE: DNA
<213> ORGANISM: Artificial Sequence
<220> FEATURE:
<223> OTHER INFORMATION: Synthetic

<400> SEQUENCE: 864
atcgatgagt gagtgtca 18

<210> SEQ ID NO 865
<211> LENGTH: 18
<212> TYPE: DNA
<213> ORGANISM: Artificial Sequence
<220> FEATURE:
<223> OTHER INFORMATION: Synthetic

<400> SEQUENCE: 865
gagggtggct ggctacaa 18

<210> SEQ ID NO 866
<211> LENGTH: 18
<212> TYPE: DNA
<213> ORGANISM: Artificial Sequence
<220> FEATURE:
<223> OTHER INFORMATION: Synthetic

<400> SEQUENCE: 866
agcttgacag acagagcc 18

<210> SEQ ID NO 867
<211> LENGTH: 18
<212> TYPE: DNA
<213> ORGANISM: Artificial Sequence
<220> FEATURE:
<223> OTHER INFORMATION: Synthetic

```
<400> SEQUENCE: 867

cagagacata catccagg                                                  18

<210> SEQ ID NO 868
<211> LENGTH: 18
<212> TYPE: DNA
<213> ORGANISM: Artificial Sequence
<220> FEATURE:
<223> OTHER INFORMATION: Synthetic

<400> SEQUENCE: 868

tcaccctagc taggtatg                                                  18

<210> SEQ ID NO 869
<211> LENGTH: 18
<212> TYPE: DNA
<213> ORGANISM: Artificial Sequence
<220> FEATURE:
<223> OTHER INFORMATION: Synthetic

<400> SEQUENCE: 869

catgctgctt gctggcca                                                  18

<210> SEQ ID NO 870
<211> LENGTH: 18
<212> TYPE: DNA
<213> ORGANISM: Artificial Sequence
<220> FEATURE:
<223> OTHER INFORMATION: Synthetic

<400> SEQUENCE: 870

ctcccggctg gctgcctg                                                  18

<210> SEQ ID NO 871
<211> LENGTH: 18
<212> TYPE: DNA
<213> ORGANISM: Artificial Sequence
<220> FEATURE:
<223> OTHER INFORMATION: Synthetic

<400> SEQUENCE: 871

ggcttaagaa agaacatc                                                  18

<210> SEQ ID NO 872
<211> LENGTH: 18
<212> TYPE: DNA
<213> ORGANISM: Artificial Sequence
<220> FEATURE:
<223> OTHER INFORMATION: Synthetic

<400> SEQUENCE: 872

acaagagata gatacccc                                                  18

<210> SEQ ID NO 873
<211> LENGTH: 18
<212> TYPE: DNA
<213> ORGANISM: Artificial Sequence
<220> FEATURE:
<223> OTHER INFORMATION: Synthetic

<400> SEQUENCE: 873

tgatcttctt tctatgta                                                  18

<210> SEQ ID NO 874
<211> LENGTH: 18
```

<212> TYPE: DNA
<213> ORGANISM: Artificial Sequence
<220> FEATURE:
<223> OTHER INFORMATION: Synthetic

<400> SEQUENCE: 874
gagaggactg actggctg 18

<210> SEQ ID NO 875
<211> LENGTH: 18
<212> TYPE: DNA
<213> ORGANISM: Artificial Sequence
<220> FEATURE:
<223> OTHER INFORMATION: Synthetic

<400> SEQUENCE: 875
cagcaagcca gcctccag 18

<210> SEQ ID NO 876
<211> LENGTH: 18
<212> TYPE: DNA
<213> ORGANISM: Artificial Sequence
<220> FEATURE:
<223> OTHER INFORMATION: Synthetic

<400> SEQUENCE: 876
ccaccatgta tgtgcatg 18

<210> SEQ ID NO 877
<211> LENGTH: 20
<212> TYPE: DNA
<213> ORGANISM: Artificial Sequence
<220> FEATURE:
<223> OTHER INFORMATION: Synthetic

<400> SEQUENCE: 877
ccaggacatc acatcatctc 20

<210> SEQ ID NO 878
<211> LENGTH: 20
<212> TYPE: DNA
<213> ORGANISM: Artificial Sequence
<220> FEATURE:
<223> OTHER INFORMATION: Synthetic

<400> SEQUENCE: 878
ttcatccttg ccttgtagag 20

<210> SEQ ID NO 879
<211> LENGTH: 20
<212> TYPE: DNA
<213> ORGANISM: Artificial Sequence
<220> FEATURE:
<223> OTHER INFORMATION: Synthetic

<400> SEQUENCE: 879
cgaaatactt tacttttcta 20

<210> SEQ ID NO 880
<211> LENGTH: 20
<212> TYPE: DNA
<213> ORGANISM: Artificial Sequence
<220> FEATURE:
<223> OTHER INFORMATION: Synthetic

<400> SEQUENCE: 880
gggaggtcat gtcatgcctg 20

<210> SEQ ID NO 881
<211> LENGTH: 20
<212> TYPE: DNA
<213> ORGANISM: Artificial Sequence
<220> FEATURE:
<223> OTHER INFORMATION: Synthetic

<400> SEQUENCE: 881
tcccataaac taaactgtcc 20

<210> SEQ ID NO 882
<211> LENGTH: 20
<212> TYPE: DNA
<213> ORGANISM: Artificial Sequence
<220> FEATURE:
<223> OTHER INFORMATION: Synthetic

<400> SEQUENCE: 882
cagcatgatg tgatgcagga 20

<210> SEQ ID NO 883
<211> LENGTH: 20
<212> TYPE: DNA
<213> ORGANISM: Artificial Sequence
<220> FEATURE:
<223> OTHER INFORMATION: Synthetic

<400> SEQUENCE: 883
catgttttta ttttagatga 20

<210> SEQ ID NO 884
<211> LENGTH: 20
<212> TYPE: DNA
<213> ORGANISM: Artificial Sequence
<220> FEATURE:
<223> OTHER INFORMATION: Synthetic

<400> SEQUENCE: 884
tggcaatctg atctggtgtt 20

<210> SEQ ID NO 885
<211> LENGTH: 20
<212> TYPE: DNA
<213> ORGANISM: Artificial Sequence
<220> FEATURE:
<223> OTHER INFORMATION: Synthetic

<400> SEQUENCE: 885
cttacgatgt gatgtgcggg 20

<210> SEQ ID NO 886
<211> LENGTH: 20
<212> TYPE: DNA
<213> ORGANISM: Artificial Sequence
<220> FEATURE:
<223> OTHER INFORMATION: Synthetic

<400> SEQUENCE: 886
tgagacatat catatcaggt 20

<210> SEQ ID NO 887
<211> LENGTH: 20
<212> TYPE: DNA
<213> ORGANISM: Artificial Sequence
<220> FEATURE:
<223> OTHER INFORMATION: Synthetic

<400> SEQUENCE: 887
tgcaggagta gagtatgagg 20

<210> SEQ ID NO 888
<211> LENGTH: 20
<212> TYPE: DNA
<213> ORGANISM: Artificial Sequence
<220> FEATURE:
<223> OTHER INFORMATION: Synthetic

<400> SEQUENCE: 888
tctgggcggt gcggtgaagc 20

<210> SEQ ID NO 889
<211> LENGTH: 20
<212> TYPE: DNA
<213> ORGANISM: Artificial Sequence
<220> FEATURE:
<223> OTHER INFORMATION: Synthetic

<400> SEQUENCE: 889
tctttagcta agctacacca 20

<210> SEQ ID NO 890
<211> LENGTH: 20
<212> TYPE: DNA
<213> ORGANISM: Artificial Sequence
<220> FEATURE:
<223> OTHER INFORMATION: Synthetic

<400> SEQUENCE: 890
tggctcatac cataccctcc 20

<210> SEQ ID NO 891
<211> LENGTH: 20
<212> TYPE: DNA
<213> ORGANISM: Artificial Sequence
<220> FEATURE:
<223> OTHER INFORMATION: Synthetic

<400> SEQUENCE: 891
aaacatcgtg tcgtgaataa 20

<210> SEQ ID NO 892
<211> LENGTH: 20
<212> TYPE: DNA
<213> ORGANISM: Artificial Sequence
<220> FEATURE:
<223> OTHER INFORMATION: Synthetic

<400> SEQUENCE: 892
tgcttacgac acgacaacgt 20

<210> SEQ ID NO 893
<211> LENGTH: 20
<212> TYPE: DNA
<213> ORGANISM: Artificial Sequence
<220> FEATURE:
<223> OTHER INFORMATION: Synthetic

<400> SEQUENCE: 893
tgcggctgcc ctgccctctg 20

-continued

<210> SEQ ID NO 894
<211> LENGTH: 20
<212> TYPE: DNA
<213> ORGANISM: Artificial Sequence
<220> FEATURE:
<223> OTHER INFORMATION: Synthetic

<400> SEQUENCE: 894
tggtggcccc gccccgactg 20

<210> SEQ ID NO 895
<211> LENGTH: 20
<212> TYPE: DNA
<213> ORGANISM: Artificial Sequence
<220> FEATURE:
<223> OTHER INFORMATION: Synthetic

<400> SEQUENCE: 895
acgctggacc ggaccggagc 20

<210> SEQ ID NO 896
<211> LENGTH: 20
<212> TYPE: DNA
<213> ORGANISM: Artificial Sequence
<220> FEATURE:
<223> OTHER INFORMATION: Synthetic

<400> SEQUENCE: 896
tccccagagg agaggatatg 20

<210> SEQ ID NO 897
<211> LENGTH: 20
<212> TYPE: DNA
<213> ORGANISM: Artificial Sequence
<220> FEATURE:
<223> OTHER INFORMATION: Synthetic

<400> SEQUENCE: 897
tatggttctc ttctcttcca 20

<210> SEQ ID NO 898
<211> LENGTH: 20
<212> TYPE: DNA
<213> ORGANISM: Artificial Sequence
<220> FEATURE:
<223> OTHER INFORMATION: Synthetic

<400> SEQUENCE: 898
ccaccgtcag gtcaggctaa 20

<210> SEQ ID NO 899
<211> LENGTH: 20
<212> TYPE: DNA
<213> ORGANISM: Artificial Sequence
<220> FEATURE:
<223> OTHER INFORMATION: Synthetic

<400> SEQUENCE: 899
gggcaagatc agatccggcg 20

<210> SEQ ID NO 900
<211> LENGTH: 20
<212> TYPE: DNA
<213> ORGANISM: Artificial Sequence
<220> FEATURE:
<223> OTHER INFORMATION: Synthetic

<400> SEQUENCE: 900
gtcgtagggc agggccgcag 20

<210> SEQ ID NO 901
<211> LENGTH: 22
<212> TYPE: DNA
<213> ORGANISM: Artificial Sequence
<220> FEATURE:
<223> OTHER INFORMATION: Synthetic

<400> SEQUENCE: 901
gcgcgagcgc cagcgccagc gc 22

<210> SEQ ID NO 902
<211> LENGTH: 22
<212> TYPE: DNA
<213> ORGANISM: Artificial Sequence
<220> FEATURE:
<223> OTHER INFORMATION: Synthetic

<400> SEQUENCE: 902
aactccggca tcggcatcgg gg 22

<210> SEQ ID NO 903
<211> LENGTH: 22
<212> TYPE: DNA
<213> ORGANISM: Artificial Sequence
<220> FEATURE:
<223> OTHER INFORMATION: Synthetic

<400> SEQUENCE: 903
tactacgaga ccgagaccgg ca 22

<210> SEQ ID NO 904
<211> LENGTH: 24
<212> TYPE: DNA
<213> ORGANISM: Artificial Sequence
<220> FEATURE:
<223> OTHER INFORMATION: Synthetic

<400> SEQUENCE: 904
gtgctcgctt tccgctttcc tgga 24

<210> SEQ ID NO 905
<211> LENGTH: 24
<212> TYPE: DNA
<213> ORGANISM: Artificial Sequence
<220> FEATURE:
<223> OTHER INFORMATION: Synthetic

<400> SEQUENCE: 905
caagggaaaa tcgaaaatcg agat 24

<210> SEQ ID NO 906
<211> LENGTH: 24
<212> TYPE: DNA
<213> ORGANISM: Artificial Sequence
<220> FEATURE:
<223> OTHER INFORMATION: Synthetic

<400> SEQUENCE: 906
gaagcagaag atagaagatc ggct 24

<210> SEQ ID NO 907

<211> LENGTH: 24
<212> TYPE: DNA
<213> ORGANISM: Artificial Sequence
<220> FEATURE:
<223> OTHER INFORMATION: Synthetic

<400> SEQUENCE: 907
cattctagga cttaggactt gccc 24

<210> SEQ ID NO 908
<211> LENGTH: 24
<212> TYPE: DNA
<213> ORGANISM: Artificial Sequence
<220> FEATURE:
<223> OTHER INFORMATION: Synthetic

<400> SEQUENCE: 908
aacgtcgtaa tccgtaatcg ctgg 24

<210> SEQ ID NO 909
<211> LENGTH: 24
<212> TYPE: DNA
<213> ORGANISM: Artificial Sequence
<220> FEATURE:
<223> OTHER INFORMATION: Synthetic

<400> SEQUENCE: 909
gatggccatg gcccatggcg cgga 24

<210> SEQ ID NO 910
<211> LENGTH: 24
<212> TYPE: DNA
<213> ORGANISM: Artificial Sequence
<220> FEATURE:
<223> OTHER INFORMATION: Synthetic

<400> SEQUENCE: 910
gtagcaccat caaccatcat ttcc 24

<210> SEQ ID NO 911
<211> LENGTH: 24
<212> TYPE: DNA
<213> ORGANISM: Artificial Sequence
<220> FEATURE:
<223> OTHER INFORMATION: Synthetic

<400> SEQUENCE: 911
gatagtgtct gttgtctgtg tgaa 24

<210> SEQ ID NO 912
<211> LENGTH: 24
<212> TYPE: DNA
<213> ORGANISM: Artificial Sequence
<220> FEATURE:
<223> OTHER INFORMATION: Synthetic

<400> SEQUENCE: 912
aaccgctgca ttctgcattc ctca 24

<210> SEQ ID NO 913
<211> LENGTH: 24
<212> TYPE: DNA
<213> ORGANISM: Artificial Sequence
<220> FEATURE:
<223> OTHER INFORMATION: Synthetic

<400> SEQUENCE: 913
gacaaatctg acatctgacg agga 24

<210> SEQ ID NO 914
<211> LENGTH: 24
<212> TYPE: DNA
<213> ORGANISM: Artificial Sequence
<220> FEATURE:
<223> OTHER INFORMATION: Synthetic

<400> SEQUENCE: 914
ggcatgctgc tggctgctgg ccag 24

<210> SEQ ID NO 915
<211> LENGTH: 24
<212> TYPE: DNA
<213> ORGANISM: Artificial Sequence
<220> FEATURE:
<223> OTHER INFORMATION: Synthetic

<400> SEQUENCE: 915
ggtgtggatt tgggatttgg tgtg 24

<210> SEQ ID NO 916
<211> LENGTH: 26
<212> TYPE: DNA
<213> ORGANISM: Artificial Sequence
<220> FEATURE:
<223> OTHER INFORMATION: Synthetic

<400> SEQUENCE: 916
aaaagaaaat tccaaaattc caacag 26

<210> SEQ ID NO 917
<211> LENGTH: 26
<212> TYPE: DNA
<213> ORGANISM: Artificial Sequence
<220> FEATURE:
<223> OTHER INFORMATION: Synthetic

<400> SEQUENCE: 917
tctgcctgga tgactggatg acatgc 26

<210> SEQ ID NO 918
<211> LENGTH: 26
<212> TYPE: DNA
<213> ORGANISM: Artificial Sequence
<220> FEATURE:
<223> OTHER INFORMATION: Synthetic

<400> SEQUENCE: 918
tcagctctta tcttcttatc ttcatt 26

<210> SEQ ID NO 919
<211> LENGTH: 26
<212> TYPE: DNA
<213> ORGANISM: Artificial Sequence
<220> FEATURE:
<223> OTHER INFORMATION: Synthetic

<400> SEQUENCE: 919
tcaccgttgt tttgttgttt tgttta 26

<210> SEQ ID NO 920
<211> LENGTH: 26
<212> TYPE: DNA

<213> ORGANISM: Artificial Sequence
<220> FEATURE:
<223> OTHER INFORMATION: Synthetic

<400> SEQUENCE: 920
tcgccccacg gctccacggc tcctcg 26

<210> SEQ ID NO 921
<211> LENGTH: 26
<212> TYPE: DNA
<213> ORGANISM: Artificial Sequence
<220> FEATURE:
<223> OTHER INFORMATION: Synthetic

<400> SEQUENCE: 921
taaaatatca ccttatcacc ttgtga 26

<210> SEQ ID NO 922
<211> LENGTH: 26
<212> TYPE: DNA
<213> ORGANISM: Artificial Sequence
<220> FEATURE:
<223> OTHER INFORMATION: Synthetic

<400> SEQUENCE: 922
gagaacattc atgcattcat gttttg 26

<210> SEQ ID NO 923
<211> LENGTH: 26
<212> TYPE: DNA
<213> ORGANISM: Artificial Sequence
<220> FEATURE:
<223> OTHER INFORMATION: Synthetic

<400> SEQUENCE: 923
cccacgctga gaggctgaga gtcgtc 26

<210> SEQ ID NO 924
<211> LENGTH: 26
<212> TYPE: DNA
<213> ORGANISM: Artificial Sequence
<220> FEATURE:
<223> OTHER INFORMATION: Synthetic

<400> SEQUENCE: 924
cttctacttg ttgacttgtt gatcag 26

<210> SEQ ID NO 925
<211> LENGTH: 26
<212> TYPE: DNA
<213> ORGANISM: Artificial Sequence
<220> FEATURE:
<223> OTHER INFORMATION: Synthetic

<400> SEQUENCE: 925
gcttcaatct tataatctta ttcagg 26

<210> SEQ ID NO 926
<211> LENGTH: 26
<212> TYPE: DNA
<213> ORGANISM: Artificial Sequence
<220> FEATURE:
<223> OTHER INFORMATION: Synthetic

<400> SEQUENCE: 926
gcacaaggac atcaggacat caagcc 26

<210> SEQ ID NO 927
<211> LENGTH: 26
<212> TYPE: DNA
<213> ORGANISM: Artificial Sequence
<220> FEATURE:
<223> OTHER INFORMATION: Synthetic

<400> SEQUENCE: 927
aagatggctc ggaggctcgg atgagt 26

<210> SEQ ID NO 928
<211> LENGTH: 26
<212> TYPE: DNA
<213> ORGANISM: Artificial Sequence
<220> FEATURE:
<223> OTHER INFORMATION: Synthetic

<400> SEQUENCE: 928
gcccagcgaa gatgcgaaga tgcgaa 26

<210> SEQ ID NO 929
<211> LENGTH: 26
<212> TYPE: DNA
<213> ORGANISM: Artificial Sequence
<220> FEATURE:
<223> OTHER INFORMATION: Synthetic

<400> SEQUENCE: 929
tactcgctgg tgagctggtg actgaa 26

<210> SEQ ID NO 930
<211> LENGTH: 26
<212> TYPE: DNA
<213> ORGANISM: Artificial Sequence
<220> FEATURE:
<223> OTHER INFORMATION: Synthetic

<400> SEQUENCE: 930
cggcgcaaga gaccaagaga cccgaa 26

<210> SEQ ID NO 931
<211> LENGTH: 28
<212> TYPE: DNA
<213> ORGANISM: Artificial Sequence
<220> FEATURE:
<223> OTHER INFORMATION: Synthetic

<400> SEQUENCE: 931
gatgatgaca agattgacaa gatcgttg 28

<210> SEQ ID NO 932
<211> LENGTH: 28
<212> TYPE: DNA
<213> ORGANISM: Artificial Sequence
<220> FEATURE:
<223> OTHER INFORMATION: Synthetic

<400> SEQUENCE: 932
cggctggagt gtgaggagtg tgaggagt 28

<210> SEQ ID NO 933
<211> LENGTH: 28
<212> TYPE: DNA
<213> ORGANISM: Artificial Sequence
<220> FEATURE:

<223> OTHER INFORMATION: Synthetic

<400> SEQUENCE: 933
gagctgtgcc gcacgtgccg cacggtga 28

<210> SEQ ID NO 934
<211> LENGTH: 28
<212> TYPE: DNA
<213> ORGANISM: Artificial Sequence
<220> FEATURE:
<223> OTHER INFORMATION: Synthetic

<400> SEQUENCE: 934
ccgcagccgc agctgccgca gctctcgc 28

<210> SEQ ID NO 935
<211> LENGTH: 30
<212> TYPE: DNA
<213> ORGANISM: Artificial Sequence
<220> FEATURE:
<223> OTHER INFORMATION: Synthetic

<400> SEQUENCE: 935
gtcaaaagag attccaagag attccaggct 30

<210> SEQ ID NO 936
<211> LENGTH: 30
<212> TYPE: DNA
<213> ORGANISM: Artificial Sequence
<220> FEATURE:
<223> OTHER INFORMATION: Synthetic

<400> SEQUENCE: 936
cgggagctgc agcatgctgc agcatgctgc 30

<210> SEQ ID NO 937
<211> LENGTH: 30
<212> TYPE: DNA
<213> ORGANISM: Artificial Sequence
<220> FEATURE:
<223> OTHER INFORMATION: Synthetic

<400> SEQUENCE: 937
gaaactttaa tttgttttaa tttgttcttg 30

<210> SEQ ID NO 938
<211> LENGTH: 30
<212> TYPE: DNA
<213> ORGANISM: Artificial Sequence
<220> FEATURE:
<223> OTHER INFORMATION: Synthetic

<400> SEQUENCE: 938
gggcacatct gggtgcatct gggtgatact 30

<210> SEQ ID NO 939
<211> LENGTH: 30
<212> TYPE: DNA
<213> ORGANISM: Artificial Sequence
<220> FEATURE:
<223> OTHER INFORMATION: Synthetic

<400> SEQUENCE: 939
gacccaacaa gttcaaacaa gttcaagtgt 30

<210> SEQ ID NO 940
<211> LENGTH: 32
<212> TYPE: DNA
<213> ORGANISM: Artificial Sequence
<220> FEATURE:
<223> OTHER INFORMATION: Synthetic

<400> SEQUENCE: 940
gagctggccc ggcggcggcc cggcggcggc gc 32

<210> SEQ ID NO 941
<211> LENGTH: 32
<212> TYPE: DNA
<213> ORGANISM: Artificial Sequence
<220> FEATURE:
<223> OTHER INFORMATION: Synthetic

<400> SEQUENCE: 941
caaagaagaa actattaaga aactattatt ga 32

<210> SEQ ID NO 942
<211> LENGTH: 32
<212> TYPE: DNA
<213> ORGANISM: Artificial Sequence
<220> FEATURE:
<223> OTHER INFORMATION: Synthetic

<400> SEQUENCE: 942
tgaataaccc tctgtcaacc ctctgtcagc tg 32

<210> SEQ ID NO 943
<211> LENGTH: 32
<212> TYPE: DNA
<213> ORGANISM: Artificial Sequence
<220> FEATURE:
<223> OTHER INFORMATION: Synthetic

<400> SEQUENCE: 943
gctcacctgt ggtccccctg tggtcccgcc ag 32

<210> SEQ ID NO 944
<211> LENGTH: 32
<212> TYPE: DNA
<213> ORGANISM: Artificial Sequence
<220> FEATURE:
<223> OTHER INFORMATION: Synthetic

<400> SEQUENCE: 944
tgcaaggaca aatctgggac aaatctgacg ag 32

<210> SEQ ID NO 945
<211> LENGTH: 34
<212> TYPE: DNA
<213> ORGANISM: Artificial Sequence
<220> FEATURE:
<223> OTHER INFORMATION: Synthetic

<400> SEQUENCE: 945
gtgcgacgag ctgtgccacg agctgtgccg cacg 34

<210> SEQ ID NO 946
<211> LENGTH: 34
<212> TYPE: DNA
<213> ORGANISM: Artificial Sequence
<220> FEATURE:
<223> OTHER INFORMATION: Synthetic

<400> SEQUENCE: 946 cccc ttctcc ttggccgtct ccttggccgt cttt 34

<210> SEQ ID NO 947
<211> LENGTH: 36
<212> TYPE: DNA
<213> ORGANISM: Artificial Sequence
<220> FEATURE:
<223> OTHER INFORMATION: Synthetic

<400> SEQUENCE: 947
cccttggtga gcacgctggg tgagcacgct gaccac 36

<210> SEQ ID NO 948
<211> LENGTH: 36
<212> TYPE: DNA
<213> ORGANISM: Artificial Sequence
<220> FEATURE:
<223> OTHER INFORMATION: Synthetic

<400> SEQUENCE: 948
gccccgactg caaggacaga ctgcaaggac aaatct 36

<210> SEQ ID NO 949
<211> LENGTH: 36
<212> TYPE: DNA
<213> ORGANISM: Artificial Sequence
<220> FEATURE:
<223> OTHER INFORMATION: Synthetic

<400> SEQUENCE: 949
gctaaaggtc agctccacag gtcagctcca cagccg 36

<210> SEQ ID NO 950
<211> LENGTH: 38
<212> TYPE: DNA
<213> ORGANISM: Artificial Sequence
<220> FEATURE:
<223> OTHER INFORMATION: Synthetic

<400> SEQUENCE: 950
tggggcagca aatcaagctc agcaaatcaa gctctatt 38

<210> SEQ ID NO 951
<211> LENGTH: 38
<212> TYPE: DNA
<213> ORGANISM: Artificial Sequence
<220> FEATURE:
<223> OTHER INFORMATION: Synthetic

<400> SEQUENCE: 951
cgctgctgcc gcgccgcctc tgccgcgccg cctctgcc 38

<210> SEQ ID NO 952
<211> LENGTH: 38
<212> TYPE: DNA
<213> ORGANISM: Artificial Sequence
<220> FEATURE:
<223> OTHER INFORMATION: Synthetic

<400> SEQUENCE: 952
catatactgc atgcaaatga ctgcatgcaa atgatccc 38

<210> SEQ ID NO 953
<211> LENGTH: 38

<212> TYPE: DNA
<213> ORGANISM: Artificial Sequence
<220> FEATURE:
<223> OTHER INFORMATION: Synthetic

<400> SEQUENCE: 953
ctgcaaggac aaatctgaca ggacaaatct gacgagga 38

<210> SEQ ID NO 954
<211> LENGTH: 40
<212> TYPE: DNA
<213> ORGANISM: Artificial Sequence
<220> FEATURE:
<223> OTHER INFORMATION: Synthetic

<400> SEQUENCE: 954
ggtgaacctg ggcaagctgg acctgggcaa gctggtcctt 40

<210> SEQ ID NO 955
<211> LENGTH: 40
<212> TYPE: DNA
<213> ORGANISM: Artificial Sequence
<220> FEATURE:
<223> OTHER INFORMATION: Synthetic

<400> SEQUENCE: 955
tgctgctctg cgcgctgctc ctctgcgcgc tgctcgcccg 40

<210> SEQ ID NO 956
<211> LENGTH: 42
<212> TYPE: DNA
<213> ORGANISM: Artificial Sequence
<220> FEATURE:
<223> OTHER INFORMATION: Synthetic

<400> SEQUENCE: 956
gatcctagct atcgttcttt ttagctatcg ttcttttcac tc 42

<210> SEQ ID NO 957
<211> LENGTH: 42
<212> TYPE: DNA
<213> ORGANISM: Artificial Sequence
<220> FEATURE:
<223> OTHER INFORMATION: Synthetic

<400> SEQUENCE: 957
cgtggctgct ctgcatgttt tctgctctgc atgtttttaa ta 42

<210> SEQ ID NO 958
<211> LENGTH: 42
<212> TYPE: DNA
<213> ORGANISM: Artificial Sequence
<220> FEATURE:
<223> OTHER INFORMATION: Synthetic

<400> SEQUENCE: 958
ggaattggtt ggtagacact gtggttggta gacactggtg ct 42

<210> SEQ ID NO 959
<211> LENGTH: 42
<212> TYPE: DNA
<213> ORGANISM: Artificial Sequence
<220> FEATURE:
<223> OTHER INFORMATION: Synthetic

<400> SEQUENCE: 959
tgtcctcttc tgctgcttct ttcttctgct gcttctttct tc 42

<210> SEQ ID NO 960
<211> LENGTH: 42
<212> TYPE: DNA
<213> ORGANISM: Artificial Sequence
<220> FEATURE:
<223> OTHER INFORMATION: Synthetic

<400> SEQUENCE: 960
tgggtggccc ggaggctggg cggcccggag gctgggctgg gc 42

<210> SEQ ID NO 961
<211> LENGTH: 44
<212> TYPE: DNA
<213> ORGANISM: Artificial Sequence
<220> FEATURE:
<223> OTHER INFORMATION: Synthetic

<400> SEQUENCE: 961
cgggtggggg tgcggcggag gcgggggtgc ggcggaggcg gggg 44

<210> SEQ ID NO 962
<211> LENGTH: 44
<212> TYPE: DNA
<213> ORGANISM: Artificial Sequence
<220> FEATURE:
<223> OTHER INFORMATION: Synthetic

<400> SEQUENCE: 962
cggcggaggc gggggtgcgg ccgaggcggg ggtgcggccg gcgg 44

<210> SEQ ID NO 963
<211> LENGTH: 44
<212> TYPE: DNA
<213> ORGANISM: Artificial Sequence
<220> FEATURE:
<223> OTHER INFORMATION: Synthetic

<400> SEQUENCE: 963
gcggaggcgg gggtgcggcc ggggcggggg tgcggccggc gggc 44

<210> SEQ ID NO 964
<211> LENGTH: 44
<212> TYPE: DNA
<213> ORGANISM: Artificial Sequence
<220> FEATURE:
<223> OTHER INFORMATION: Synthetic

<400> SEQUENCE: 964
ttccacccaa agcagctgta ctcccaaagc agctgtactt ctcc 44

<210> SEQ ID NO 965
<211> LENGTH: 44
<212> TYPE: DNA
<213> ORGANISM: Artificial Sequence
<220> FEATURE:
<223> OTHER INFORMATION: Synthetic

<400> SEQUENCE: 965
ccccgcccag gccctgcagg gccccaggcc ctgcagggcc ccag 44

<210> SEQ ID NO 966
<211> LENGTH: 44
<212> TYPE: DNA
<213> ORGANISM: Artificial Sequence
<220> FEATURE:
<223> OTHER INFORMATION: Synthetic

<400> SEQUENCE: 966
ccctgagcaa gtccagctcc tcagcaagtc cagctcctct cccg 44

<210> SEQ ID NO 967
<211> LENGTH: 44
<212> TYPE: DNA
<213> ORGANISM: Artificial Sequence
<220> FEATURE:
<223> OTHER INFORMATION: Synthetic

<400> SEQUENCE: 967
aacgtgcggc tgcgtggacc tcgcggctgc gtggacctcc acga 44

<210> SEQ ID NO 968
<211> LENGTH: 44
<212> TYPE: DNA
<213> ORGANISM: Artificial Sequence
<220> FEATURE:
<223> OTHER INFORMATION: Synthetic

<400> SEQUENCE: 968
cgactgcaag gacaaatctg acgcaaggac aaatctgacg agga 44

<210> SEQ ID NO 969
<211> LENGTH: 46
<212> TYPE: DNA
<213> ORGANISM: Artificial Sequence
<220> FEATURE:
<223> OTHER INFORMATION: Synthetic

<400> SEQUENCE: 969
gccctgcaga catagatgcc cccgcagaca tagatgcccc cgtcaa 46

<210> SEQ ID NO 970
<211> LENGTH: 46
<212> TYPE: DNA
<213> ORGANISM: Artificial Sequence
<220> FEATURE:
<223> OTHER INFORMATION: Synthetic

<400> SEQUENCE: 970
ctgttcgcgc tgctgctgct ctgcgcgctg ctgctgctct gcgcgc 46

<210> SEQ ID NO 971
<211> LENGTH: 46
<212> TYPE: DNA
<213> ORGANISM: Artificial Sequence
<220> FEATURE:
<223> OTHER INFORMATION: Synthetic

<400> SEQUENCE: 971
tgctgctgct ctgcgcgctg ctcctgctct gcgcgctgct cgcccg 46

<210> SEQ ID NO 972
<211> LENGTH: 48
<212> TYPE: DNA
<213> ORGANISM: Artificial Sequence
<220> FEATURE:
<223> OTHER INFORMATION: Synthetic

<400> SEQUENCE: 972
cggtggctgg gctggcaggg ctgagctggg ctggcagggc tgagctgg 48

<210> SEQ ID NO 973
<211> LENGTH: 48
<212> TYPE: DNA
<213> ORGANISM: Artificial Sequence
<220> FEATURE:
<223> OTHER INFORMATION: Synthetic

<400> SEQUENCE: 973
ccaggcaggc ggagcacccc aagccaggcg gagcacccca agccctcg 48

<210> SEQ ID NO 974
<211> LENGTH: 48
<212> TYPE: DNA
<213> ORGANISM: Artificial Sequence
<220> FEATURE:
<223> OTHER INFORMATION: Synthetic

<400> SEQUENCE: 974
cagtgcaaca gctccacctg catccaacag ctccacctgc atccccca 48

<210> SEQ ID NO 975
<211> LENGTH: 48
<212> TYPE: DNA
<213> ORGANISM: Artificial Sequence
<220> FEATURE:
<223> OTHER INFORMATION: Synthetic

<400> SEQUENCE: 975
gactgccggg actggtcaga tgaaccggga ctggtcagat gaacccat 48

<210> SEQ ID NO 976
<211> LENGTH: 48
<212> TYPE: DNA
<213> ORGANISM: Artificial Sequence
<220> FEATURE:
<223> OTHER INFORMATION: Synthetic

<400> SEQUENCE: 976
tcgtggtgga tcctgttcat gggtgtggat cctgttcatg ggtgcgta 48

<210> SEQ ID NO 977
<211> LENGTH: 50
<212> TYPE: DNA
<213> ORGANISM: Artificial Sequence
<220> FEATURE:
<223> OTHER INFORMATION: Synthetic

<400> SEQUENCE: 977
accccgcgca cccctgtgcc cacctgcgca cccctgtgcc cacctgcgcc 50

<210> SEQ ID NO 978
<211> LENGTH: 50
<212> TYPE: DNA
<213> ORGANISM: Artificial Sequence
<220> FEATURE:
<223> OTHER INFORMATION: Synthetic

<400> SEQUENCE: 978
gcggtggggc aggcggcggt gcggcggggc aggcggcggt gcggcggccg 50

<210> SEQ ID NO 979
<211> LENGTH: 50
<212> TYPE: DNA
<213> ORGANISM: Artificial Sequence
<220> FEATURE:
<223> OTHER INFORMATION: Synthetic

<400> SEQUENCE: 979
attcctctcg gtcatgctgc agctgtctcg gtcatgctgc agctgtctga 50

<210> SEQ ID NO 980
<211> LENGTH: 50
<212> TYPE: DNA
<213> ORGANISM: Artificial Sequence
<220> FEATURE:
<223> OTHER INFORMATION: Synthetic

<400> SEQUENCE: 980
ccccgactgc aaggacaaat ctgacactgc aaggacaaat ctgacgagga 50

<210> SEQ ID NO 981
<211> LENGTH: 50
<212> TYPE: DNA
<213> ORGANISM: Artificial Sequence
<220> FEATURE:
<223> OTHER INFORMATION: Synthetic

<400> SEQUENCE: 981
gtctccttac agctgcctct gttgtcttac agctgcctct gttgtgacag 50

<210> SEQ ID NO 982
<211> LENGTH: 2
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, t or u

<400> SEQUENCE: 982 ng 2

<210> SEQ ID NO 983
<211> LENGTH: 5
<212> TYPE: DNA
<213> ORGANISM: Artificial Sequence
<220> FEATURE:
<223> OTHER INFORMATION: Synthetic

<400> SEQUENCE: 983 acgtg 5

<210> SEQ ID NO 984
<211> LENGTH: 3
<212> TYPE: DNA
<213> ORGANISM: Artificial Sequence
<220> FEATURE:
<223> OTHER INFORMATION: Synthetic

<400> SEQUENCE: 984 gaa 3

<210> SEQ ID NO 985
<211> LENGTH: 3
<212> TYPE: DNA
<213> ORGANISM: Artificial Sequence
<220> FEATURE:
<223> OTHER INFORMATION: Synthetic

<400> SEQUENCE: 985 gaa 3

<210> SEQ ID NO 986
<211> LENGTH: 3
<212> TYPE: DNA
<213> ORGANISM: Artificial Sequence
<220> FEATURE:
<223> OTHER INFORMATION: Synthetic

<400> SEQUENCE: 986 gat 3

<210> SEQ ID NO 987
<211> LENGTH: 3
<212> TYPE: DNA
<213> ORGANISM: Artificial Sequence
<220> FEATURE:
<223> OTHER INFORMATION: Synthetic

<400> SEQUENCE: 987 gat 3

<210> SEQ ID NO 988
<211> LENGTH: 3
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, t or u

<400> SEQUENCE: 988 ngg 3

<210> SEQ ID NO 989
<211> LENGTH: 6
<212> TYPE: DNA
<213> ORGANISM: Artificial Sequence
<220> FEATURE:
<223> OTHER INFORMATION: Synthetic

<400> SEQUENCE: 989 acgtgg 6

<210> SEQ ID NO 990
<211> LENGTH: 4
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, t or u

<400> SEQUENCE: 990 ngcg 4

<210> SEQ ID NO 991
<211> LENGTH: 7
<212> TYPE: DNA
<213> ORGANISM: Artificial Sequence
<220> FEATURE:
<223> OTHER INFORMATION: Synthetic

<400> SEQUENCE: 991 acgtgcg 7

<210> SEQ ID NO 992
<211> LENGTH: 4
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, t or u

<400> SEQUENCE: 992 ngag 4

<210> SEQ ID NO 993
<211> LENGTH: 7
<212> TYPE: DNA
<213> ORGANISM: Artificial Sequence
<220> FEATURE:
<223> OTHER INFORMATION: Synthetic

<400> SEQUENCE: 993 acgtgag 7

<210> SEQ ID NO 994
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (4)..(5)
<223> OTHER INFORMATION: n is a, c, g, t or u
<220> FEATURE:
<221> NAME/KEY: misc_feature
<222> LOCATION: (7)..(7)
<223> OTHER INFORMATION: n is a, c, g, t or u

<400> SEQUENCE: 994 nganngng 8

<210> SEQ ID NO 995
<211> LENGTH: 20
<212> TYPE: DNA
<213> ORGANISM: Artificial Sequence
<220> FEATURE:
<223> OTHER INFORMATION: Synthetic

<400> SEQUENCE: 995
acgtgaacgt acgtgacgtg 20

<210> SEQ ID NO 996
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, t or u

<400> SEQUENCE: 996 nngrrt 6

<210> SEQ ID NO 997
<211> LENGTH: 14
<212> TYPE: DNA
<213> ORGANISM: Artificial Sequence
<220> FEATURE:
<223> OTHER INFORMATION: Synthetic

<400> SEQUENCE: 997
acgtacgtga gagt 14

<210> SEQ ID NO 998
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, t or u

<400> SEQUENCE: 998 nnnngatt 8

<210> SEQ ID NO 999
<211> LENGTH: 20
<212> TYPE: DNA
<213> ORGANISM: Artificial Sequence
<220> FEATURE:
<223> OTHER INFORMATION: Synthetic

<400> SEQUENCE: 999
acgtacgtac gtacgtgatt 20

<210> SEQ ID NO 1000
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, t or u

<400> SEQUENCE: 1000 nnnnryac 8

<210> SEQ ID NO 1001
<211> LENGTH: 22
<212> TYPE: DNA
<213> ORGANISM: Artificial Sequence
<220> FEATURE:
<223> OTHER INFORMATION: Synthetic

<400> SEQUENCE: 1001
acgtacgtac gtacgtagct ac 22

<210> SEQ ID NO 1002
<211> LENGTH: 4
<212> TYPE: DNA
<213> ORGANISM: Artificial Sequence
<220> FEATURE:
<223> OTHER INFORMATION: Synthetic

<400> SEQUENCE: 1002 tttv 4

<210> SEQ ID NO 1003
<211> LENGTH: 6
<212> TYPE: DNA
<213> ORGANISM: Artificial Sequence
<220> FEATURE:
<223> OTHER INFORMATION: Synthetic

<400> SEQUENCE: 1003 tttacg 6

<210> SEQ ID NO 1004
<211> LENGTH: 4
<212> TYPE: DNA
<213> ORGANISM: Artificial Sequence
<220> FEATURE:
<223> OTHER INFORMATION: Synthetic

<400> SEQUENCE: 1004 tycv 4

<210> SEQ ID NO 1005
<211> LENGTH: 7
<212> TYPE: DNA
<213> ORGANISM: Artificial Sequence
<220> FEATURE:
<223> OTHER INFORMATION: Synthetic

<400> SEQUENCE: 1005 tctcacg 7

<210> SEQ ID NO 1006
<211> LENGTH: 4
<212> TYPE: DNA
<213> ORGANISM: Artificial Sequence
<220> FEATURE:
<223> OTHER INFORMATION: Synthetic

<400> SEQUENCE: 1006 tatv 4

<210> SEQ ID NO 1007
<211> LENGTH: 6
<212> TYPE: DNA
<213> ORGANISM: Artificial Sequence
<220> FEATURE:
<223> OTHER INFORMATION: Synthetic

<400> SEQUENCE: 1007 tatacg 6

<210> SEQ ID NO 1008
<211> LENGTH: 3
<212> TYPE: DNA
<213> ORGANISM: Artificial Sequence
<220> FEATURE:
<223> OTHER INFORMATION: Synthetic

<400> SEQUENCE: 1008 ttv 3

<210> SEQ ID NO 1009

<211> LENGTH: 5
<212> TYPE: DNA
<213> ORGANISM: Artificial Sequence
<220> FEATURE:
<223> OTHER INFORMATION: Synthetic

<400> SEQUENCE: 1009 ttacg 5

<210> SEQ ID NO 1010
<211> LENGTH: 23
<212> TYPE: DNA
<213> ORGANISM: Artificial Sequence
<220> FEATURE:
<223> OTHER INFORMATION: Synthetic

<400> SEQUENCE: 1010
gaagcgctac ctgattccaa ttc 23

<210> SEQ ID NO 1011
<211> LENGTH: 23
<212> TYPE: DNA
<213> ORGANISM: Artificial Sequence
<220> FEATURE:
<223> OTHER INFORMATION: Synthetic

<400> SEQUENCE: 1011
tggcagttag gaaggttgta tcg 23

<210> SEQ ID NO 1012
<211> LENGTH: 118
<212> TYPE: DNA
<213> ORGANISM: Artificial Sequence
<220> FEATURE:
<223> OTHER INFORMATION: Synthetic

<400> SEQUENCE: 1012
atggctacct cagagctgag ctgcgaggtg tcgaggtgtc ggaggagaac tgtgagcgcc 60
gggaggcctt ctgggcagaa tggaaggatc tgacactgtc cacacggccc gaggaggg 118

<210> SEQ ID NO 1013
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (18)..(18)
<223> OTHER INFORMATION: n is a, c, g, or t

<400> SEQUENCE: 1013
agctgagctg cgaggtgntc gaggtgt 27

<210> SEQ ID NO 1014
<211> LENGTH: 151
<212> TYPE: DNA
<213> ORGANISM: Artificial Sequence
<220> FEATURE:
<223> OTHER INFORMATION: Synthetic

<400> SEQUENCE: 1014
gctgctccag gcatgtggga agctgaagcg gcagctctgc gccatgtacc ggctgaactt 60
tctgaccaca gcccccagca ggggaggccc ccagcagggg aggcccacac ctgccccagc 120
acctgcagga ccaagtgcag aggctcatgc g 151

<210> SEQ ID NO 1015
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(19)
<223> OTHER INFORMATION: n is a, c, g, or t

<400> SEQUENCE: 1015
ccagcagggg aggcccccna gcaggggagg ccc 33

<210> SEQ ID NO 1016
<211> LENGTH: 49
<212> TYPE: DNA
<213> ORGANISM: Artificial Sequence
<220> FEATURE:
<223> OTHER INFORMATION: Synthetic

<400> SEQUENCE: 1016
cacagttctc ctccgacacc tcgagacctc gcagctcagc tctgaggta 49

<210> SEQ ID NO 1017
<211> LENGTH: 40
<212> TYPE: DNA
<213> ORGANISM: Artificial Sequence
<220> FEATURE:
<223> OTHER INFORMATION: Synthetic

<400> SEQUENCE: 1017
ttctcctccg acacctcgca gctcagctct gaggtagcca 40

<210> SEQ ID NO 1018
<211> LENGTH: 47
<212> TYPE: DNA
<213> ORGANISM: Artificial Sequence
<220> FEATURE:
<223> OTHER INFORMATION: Synthetic

<400> SEQUENCE: 1018
gttctcctcc gacacctcga cctcgaggtc cgaggcagag gtgagca 47

<210> SEQ ID NO 1019
<211> LENGTH: 43
<212> TYPE: DNA
<213> ORGANISM: Artificial Sequence
<220> FEATURE:
<223> OTHER INFORMATION: Synthetic

<400> SEQUENCE: 1019
ttctcctccg acacctcgaa cctcggatct gaggtatgag tga 43

<210> SEQ ID NO 1020
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(19)
<223> OTHER INFORMATION: n is a, c, g, or t

<400> SEQUENCE: 1020
ccagcagggg aggcccccna gcaggggagg ccc 33

<210> SEQ ID NO 1021
<211> LENGTH: 26
<212> TYPE: DNA
<213> ORGANISM: Artificial Sequence
<220> FEATURE:
<223> OTHER INFORMATION: Synthetic

<400> SEQUENCE: 1021
agctgagctg cgaggtgtcg aggtgt 26

<210> SEQ ID NO 1022
<211> LENGTH: 18
<212> TYPE: DNA
<213> ORGANISM: Artificial Sequence
<220> FEATURE:
<223> OTHER INFORMATION: Synthetic

<400> SEQUENCE: 1022
agctgagctg cgaggtgt 18

<210> SEQ ID NO 1023
<211> LENGTH: 43
<212> TYPE: DNA
<213> ORGANISM: Artificial Sequence
<220> FEATURE:
<223> OTHER INFORMATION: Synthetic

<400> SEQUENCE: 1023
cagcccccag caggggaggc ccccagcagg ggaggcccac acc 43

<210> SEQ ID NO 1024
<211> LENGTH: 43
<212> TYPE: DNA
<213> ORGANISM: Artificial Sequence
<220> FEATURE:
<223> OTHER INFORMATION: Synthetic

<400> SEQUENCE: 1024
cagcccccag caggggaggc ccccagcagg ggaggcccac acc 43

<210> SEQ ID NO 1025
<211> LENGTH: 43
<212> TYPE: DNA
<213> ORGANISM: Artificial Sequence
<220> FEATURE:
<223> OTHER INFORMATION: Synthetic

<400> SEQUENCE: 1025
cagcccccag caggggaggc ccccagcagg ggaggcccac acc 43

<210> SEQ ID NO 1026
<211> LENGTH: 43
<212> TYPE: DNA
<213> ORGANISM: Artificial Sequence
<220> FEATURE:
<223> OTHER INFORMATION: Synthetic

<400> SEQUENCE: 1026
cagcccccag caggggaggc ccccagcagg ggaggcccac acc 43

<210> SEQ ID NO 1027
<211> LENGTH: 43
<212> TYPE: DNA
<213> ORGANISM: Artificial Sequence
<220> FEATURE:
<223> OTHER INFORMATION: Synthetic

<400> SEQUENCE: 1027
cagcccccag caggggaggc ccccagcagg ggaggcccac acc 43

<210> SEQ ID NO 1028
<211> LENGTH: 43
<212> TYPE: DNA
<213> ORGANISM: Artificial Sequence
<220> FEATURE:
<223> OTHER INFORMATION: Synthetic

<400> SEQUENCE: 1028
cagcccccag caggggaggc ccccagcagg ggaggcccac acc 43

<210> SEQ ID NO 1029
<211> LENGTH: 27
<212> TYPE: DNA
<213> ORGANISM: Artificial Sequence
<220> FEATURE:
<223> OTHER INFORMATION: Synthetic

<400> SEQUENCE: 1029
cagcccccag caggggaggc ccacacc 27

<210> SEQ ID NO 1030
<211> LENGTH: 38
<212> TYPE: DNA
<213> ORGANISM: Artificial Sequence
<220> FEATURE:
<223> OTHER INFORMATION: Synthetic

<400> SEQUENCE: 1030
cccccagcag gggaggcccc cagcagggga ggcccaca 38

<210> SEQ ID NO 1031
<211> LENGTH: 22
<212> TYPE: DNA
<213> ORGANISM: Artificial Sequence
<220> FEATURE:
<223> OTHER INFORMATION: Synthetic

<400> SEQUENCE: 1031
cccccagcag gggaggccca ca 22

<210> SEQ ID NO 1032
<211> LENGTH: 38
<212> TYPE: DNA
<213> ORGANISM: Artificial Sequence
<220> FEATURE:
<223> OTHER INFORMATION: Synthetic

<400> SEQUENCE: 1032
cccccagcag gggaggcccc cagcagggga ggcccaca 38

<210> SEQ ID NO 1033
<211> LENGTH: 37
<212> TYPE: DNA
<213> ORGANISM: Artificial Sequence
<220> FEATURE:
<223> OTHER INFORMATION: Synthetic

<400> SEQUENCE: 1033
cccccagcag gggaggcccc agcaggggag ccccaca 37

<210> SEQ ID NO 1034
<211> LENGTH: 27
<212> TYPE: DNA
<213> ORGANISM: Artificial Sequence
<220> FEATURE:
<223> OTHER INFORMATION: Synthetic

<400> SEQUENCE: 1034
cccccagcag gggaggggag gcccaca 27

<210> SEQ ID NO 1035
<211> LENGTH: 32
<212> TYPE: DNA
<213> ORGANISM: Artificial Sequence
<220> FEATURE:
<223> OTHER INFORMATION: Synthetic

<400> SEQUENCE: 1035
cccccagcag gggagagcag gggaggccca ca 32

<210> SEQ ID NO 1036
<211> LENGTH: 38
<212> TYPE: DNA
<213> ORGANISM: Artificial Sequence
<220> FEATURE:
<223> OTHER INFORMATION: Synthetic

<400> SEQUENCE: 1036
cccccagcag gggaggcccc cagcagggga ggcccaca 38

<210> SEQ ID NO 1037
<211> LENGTH: 35
<212> TYPE: DNA
<213> ORGANISM: Artificial Sequence
<220> FEATURE:
<223> OTHER INFORMATION: Synthetic

<400> SEQUENCE: 1037
cccccagcag gggaggccag caggggaggc ccaca 35

<210> SEQ ID NO 1038
<211> LENGTH: 34
<212> TYPE: DNA
<213> ORGANISM: Artificial Sequence
<220> FEATURE:
<223> OTHER INFORMATION: Synthetic

<400> SEQUENCE: 1038
cccccagcag gggaggcagc aggggaggcc caca 34

<210> SEQ ID NO 1039
<211> LENGTH: 30
<212> TYPE: DNA
<213> ORGANISM: Artificial Sequence
<220> FEATURE:
<223> OTHER INFORMATION: Synthetic

<400> SEQUENCE: 1039
cccccagcag gggagcaggg gaggcccaca 30

<210> SEQ ID NO 1040
<211> LENGTH: 36
<212> TYPE: DNA
<213> ORGANISM: Artificial Sequence
<220> FEATURE:
<223> OTHER INFORMATION: Synthetic

<400> SEQUENCE: 1040
cccccagcag gggaggccca gcaggggagg cccaca 36

<210> SEQ ID NO 1041
<211> LENGTH: 35
<212> TYPE: DNA
<213> ORGANISM: Artificial Sequence
<220> FEATURE:
<223> OTHER INFORMATION: Synthetic

<400> SEQUENCE: 1041
cccccagcag gggaggcccc ccaggggagg ccaca 35

<210> SEQ ID NO 1042
<211> LENGTH: 37
<212> TYPE: DNA
<213> ORGANISM: Artificial Sequence
<220> FEATURE:
<223> OTHER INFORMATION: Synthetic

<400> SEQUENCE: 1042
cccccagcag gggaggcccc cgcaggggag gcccaca 37

<210> SEQ ID NO 1043
<211> LENGTH: 31
<212> TYPE: DNA
<213> ORGANISM: Artificial Sequence
<220> FEATURE:
<223> OTHER INFORMATION: Synthetic

<400> SEQUENCE: 1043
cccccagcag gggaagcagg ggaggcccac a 31

<210> SEQ ID NO 1044
<211> LENGTH: 28
<212> TYPE: DNA
<213> ORGANISM: Artificial Sequence
<220> FEATURE:
<223> OTHER INFORMATION: Synthetic

<400> SEQUENCE: 1044
ataggtgcct atatgtgatg gatgggtg 28

<210> SEQ ID NO 1045
<211> LENGTH: 28
<212> TYPE: DNA
<213> ORGANISM: Artificial Sequence
<220> FEATURE:
<223> OTHER INFORMATION: Synthetic

<400> SEQUENCE: 1045
ctagccccag caaagccaag ccaaggtg 28

<210> SEQ ID NO 1046
<211> LENGTH: 28
<212> TYPE: DNA
<213> ORGANISM: Artificial Sequence
<220> FEATURE:
<223> OTHER INFORMATION: Synthetic

<400> SEQUENCE: 1046
catggtgctg gccggcgtgg gcgtggag 28

<210> SEQ ID NO 1047

<211> LENGTH: 28
<212> TYPE: DNA
<213> ORGANISM: Artificial Sequence
<220> FEATURE:
<223> OTHER INFORMATION: Synthetic

<400> SEQUENCE: 1047
tttgggtcag aagaaaaggg aaaaggga 28

<210> SEQ ID NO 1048
<211> LENGTH: 51
<212> TYPE: DNA
<213> ORGANISM: Artificial Sequence
<220> FEATURE:
<223> OTHER INFORMATION: Synthetic

<400> SEQUENCE: 1048
tttgggacat aggtacaaac atagtggacc ataggtacaa acatagtgga c 51

<210> SEQ ID NO 1049
<211> LENGTH: 54
<212> TYPE: DNA
<213> ORGANISM: Artificial Sequence
<220> FEATURE:
<223> OTHER INFORMATION: Synthetic

<400> SEQUENCE: 1049
cattggcctt tggggtgcac ttctgagcat tggcctttgg ggtgcacttc tgag 54

<210> SEQ ID NO 1050
<211> LENGTH: 58
<212> TYPE: DNA
<213> ORGANISM: Artificial Sequence
<220> FEATURE:
<223> OTHER INFORMATION: Synthetic

<400> SEQUENCE: 1050
aagtggatgt tatgtgctca cactacaata agtggatgtt atgtgctcac actacaat 58

<210> SEQ ID NO 1051
<211> LENGTH: 64
<212> TYPE: DNA
<213> ORGANISM: Artificial Sequence
<220> FEATURE:
<223> OTHER INFORMATION: Synthetic

<400> SEQUENCE: 1051
tctagggagt aaacatgcaa agattttgga actctaggga gtaaacatgc aaagattttg 60
gaac 64

<210> SEQ ID NO 1052
<211> LENGTH: 72
<212> TYPE: DNA
<213> ORGANISM: Artificial Sequence
<220> FEATURE:
<223> OTHER INFORMATION: Synthetic

<400> SEQUENCE: 1052
aaggggctta taattcaata tccatacatg acatagaagg ggcttataat tcaatatcca 60
tacatgacat ag 72

<210> SEQ ID NO 1053
<211> LENGTH: 75
<212> TYPE: DNA
<213> ORGANISM: Artificial Sequence
<220> FEATURE:
<223> OTHER INFORMATION: Synthetic

<400> SEQUENCE: 1053
ggttccacta tgtagaaatc cttccagtca gggccatagg atagatatac ggttcaggta 60
ccagggggca gagag 75

<210> SEQ ID NO 1054
<211> LENGTH: 75
<212> TYPE: DNA
<213> ORGANISM: Artificial Sequence
<220> FEATURE:
<223> OTHER INFORMATION: Synthetic

<400> SEQUENCE: 1054
ccaaggtgat acatctttag gaaggtcagt cccggtatcc tatctatatg ccaagtccat 60
ggtcccccgt ctctc 75

<210> SEQ ID NO 1055
<211> LENGTH: 70
<212> TYPE: DNA
<213> ORGANISM: Artificial Sequence
<220> FEATURE:
<223> OTHER INFORMATION: Synthetic

<400> SEQUENCE: 1055
cccttctctc tgccccctgg tacctgaacc gtatatctat cctatggccc tgactggaag 60
gatttctacg 70

<210> SEQ ID NO 1056
<211> LENGTH: 60
<212> TYPE: DNA
<213> ORGANISM: Artificial Sequence
<220> FEATURE:
<223> OTHER INFORMATION: Synthetic

<400> SEQUENCE: 1056
ccccctggta cctgaaccgt atatctatcc tatggccctg actggaagga tttctacgta 60

<210> SEQ ID NO 1057
<211> LENGTH: 61
<212> TYPE: DNA
<213> ORGANISM: Artificial Sequence
<220> FEATURE:
<223> OTHER INFORMATION: Synthetic

<400> SEQUENCE: 1057
cccctggtac ctgaaccgta tatctatcct atggccctga ctggaaggat ttctacgtag 60
t 61

<210> SEQ ID NO 1058
<211> LENGTH: 66
<212> TYPE: DNA
<213> ORGANISM: Artificial Sequence
<220> FEATURE:
<223> OTHER INFORMATION: Synthetic

<400> SEQUENCE: 1058
cccttctctc tgccccctgg tacctgaacc gtatatctat cctatggccc tgactggaag 60
gatttc 66

<210> SEQ ID NO 1059

<211> LENGTH: 38
<212> TYPE: DNA
<213> ORGANISM: Artificial Sequence
<220> FEATURE:
<223> OTHER INFORMATION: Synthetic

<400> SEQUENCE: 1059
tttatctgtc ccctccaccc cacagtgggg ccactagg 38

<210> SEQ ID NO 1060
<211> LENGTH: 39
<212> TYPE: DNA
<213> ORGANISM: Artificial Sequence
<220> FEATURE:
<223> OTHER INFORMATION: Synthetic

<400> SEQUENCE: 1060
tttatctgtc ccctccaccc cacaagtggg gccactagg 39

<210> SEQ ID NO 1061
<211> LENGTH: 36
<212> TYPE: DNA
<213> ORGANISM: Artificial Sequence
<220> FEATURE:
<223> OTHER INFORMATION: Synthetic

<400> SEQUENCE: 1061
tttatctgtc ccctccaccc cagtggggcc actagg 36

<210> SEQ ID NO 1062
<211> LENGTH: 22
<212> TYPE: DNA
<213> ORGANISM: Artificial Sequence
<220> FEATURE:
<223> OTHER INFORMATION: Synthetic

<400> SEQUENCE: 1062
tttatctgtc ccctccacta gg 22

<210> SEQ ID NO 1063
<211> LENGTH: 33
<212> TYPE: DNA
<213> ORGANISM: Artificial Sequence
<220> FEATURE:
<223> OTHER INFORMATION: Synthetic

<400> SEQUENCE: 1063
tttatctgtc ccctccacag tggggccact agg 33

<210> SEQ ID NO 1064
<211> LENGTH: 27
<212> TYPE: DNA
<213> ORGANISM: Artificial Sequence
<220> FEATURE:
<223> OTHER INFORMATION: Synthetic

<400> SEQUENCE: 1064
tttatctgtc ccctccaccc cactagg 27

<210> SEQ ID NO 1065
<211> LENGTH: 34
<212> TYPE: DNA
<213> ORGANISM: Artificial Sequence
<220> FEATURE:
<223> OTHER INFORMATION: Synthetic

<400> SEQUENCE: 1065
tttatctgtc ccctccaccc catgggccac tagg 34

<210> SEQ ID NO 1066
<211> LENGTH: 37
<212> TYPE: DNA
<213> ORGANISM: Artificial Sequence
<220> FEATURE:
<223> OTHER INFORMATION: Synthetic

<400> SEQUENCE: 1066
tttatctgtc ccctccaccc caagtggggc cactagg 37

<210> SEQ ID NO 1067
<211> LENGTH: 34
<212> TYPE: DNA
<213> ORGANISM: Artificial Sequence
<220> FEATURE:
<223> OTHER INFORMATION: Synthetic

<400> SEQUENCE: 1067
tttatctgtc ccctccacca gtggggccac tagg 34

<210> SEQ ID NO 1068
<211> LENGTH: 30
<212> TYPE: DNA
<213> ORGANISM: Artificial Sequence
<220> FEATURE:
<223> OTHER INFORMATION: Synthetic

<400> SEQUENCE: 1068
tttatctgtc ccctcagtgg ggccactagg 30

<210> SEQ ID NO 1069
<211> LENGTH: 37
<212> TYPE: DNA
<213> ORGANISM: Artificial Sequence
<220> FEATURE:
<223> OTHER INFORMATION: Synthetic

<400> SEQUENCE: 1069
tttatctgtc ccctccaccc cacatggggc cactagg 37

<210> SEQ ID NO 1070
<211> LENGTH: 32
<212> TYPE: DNA
<213> ORGANISM: Artificial Sequence
<220> FEATURE:
<223> OTHER INFORMATION: Synthetic

<400> SEQUENCE: 1070
tttatctgtc ccctccaagt ggggccacta gg 32

<210> SEQ ID NO 1071
<211> LENGTH: 37
<212> TYPE: DNA
<213> ORGANISM: Artificial Sequence
<220> FEATURE:
<223> OTHER INFORMATION: Synthetic

<400> SEQUENCE: 1071
tttatctgtc ccctccaccc ccagtggggc cactagg 37

<210> SEQ ID NO 1072
<211> LENGTH: 29
<212> TYPE: DNA

<213> ORGANISM: Artificial Sequence
<220> FEATURE:
<223> OTHER INFORMATION: Synthetic

<400> SEQUENCE: 1072
tttatctgtc ccctagtggg gccactagg 29

<210> SEQ ID NO 1073
<211> LENGTH: 48
<212> TYPE: DNA
<213> ORGANISM: Artificial Sequence
<220> FEATURE:
<223> OTHER INFORMATION: Synthetic

<400> SEQUENCE: 1073
ggcggcgggg agcagcatgg agccggcggc ggggagcagc atggagcc 48

<210> SEQ ID NO 1074
<211> LENGTH: 48
<212> TYPE: DNA
<213> ORGANISM: Artificial Sequence
<220> FEATURE:
<223> OTHER INFORMATION: Synthetic

<400> SEQUENCE: 1074
ggcggcgggg agcagcatgg agccggcggc ggggagcagc atggagcc 48

<210> SEQ ID NO 1075
<211> LENGTH: 48
<212> TYPE: DNA
<213> ORGANISM: Artificial Sequence
<220> FEATURE:
<223> OTHER INFORMATION: Synthetic

<400> SEQUENCE: 1075
ggcggcgggg agcagcatgg agccggcggc ggggagcagc atggagcc 48

<210> SEQ ID NO 1076
<211> LENGTH: 54
<212> TYPE: DNA
<213> ORGANISM: Artificial Sequence
<220> FEATURE:
<223> OTHER INFORMATION: Synthetic

<400> SEQUENCE: 1076
cattggcctt tggggtgcac ttctgagcat tggcctttgg ggtgcacttc tgag 54

<210> SEQ ID NO 1077
<211> LENGTH: 54
<212> TYPE: DNA
<213> ORGANISM: Artificial Sequence
<220> FEATURE:
<223> OTHER INFORMATION: Synthetic

<400> SEQUENCE: 1077
cattggcctt tggggtgcac ttctgagcat tggcctttgg ggtgcacttc tgag 54

<210> SEQ ID NO 1078
<211> LENGTH: 34
<212> TYPE: DNA
<213> ORGANISM: Artificial Sequence
<220> FEATURE:
<223> OTHER INFORMATION: Synthetic

<400> SEQUENCE: 1078
agctgagctg cgaggtgtcg gaggagaact gtga 34

<210> SEQ ID NO 1079
<211> LENGTH: 40
<212> TYPE: DNA
<213> ORGANISM: Artificial Sequence
<220> FEATURE:
<223> OTHER INFORMATION: Synthetic

<400> SEQUENCE: 1079
agctgagctg cgaggtcgag gtgtcggagg agaactgtga 40

<210> SEQ ID NO 1080
<211> LENGTH: 25
<212> TYPE: DNA
<213> ORGANISM: Artificial Sequence
<220> FEATURE:
<223> OTHER INFORMATION: Synthetic

<400> SEQUENCE: 1080
agctgagctg cgaggtgaac tgtga 25

<210> SEQ ID NO 1081
<211> LENGTH: 42
<212> TYPE: DNA
<213> ORGANISM: Artificial Sequence
<220> FEATURE:
<223> OTHER INFORMATION: Synthetic

<400> SEQUENCE: 1081
agctgagctg cgaggtgtcg aggtgtcgga ggagaactgt ga 42

<210> SEQ ID NO 1082
<211> LENGTH: 43
<212> TYPE: DNA
<213> ORGANISM: Artificial Sequence
<220> FEATURE:
<223> OTHER INFORMATION: Synthetic

<400> SEQUENCE: 1082
agctgagctg cgaggtgttc gaggtgtcgg aggagaactg tga 43

<210> SEQ ID NO 1083
<211> LENGTH: 44
<212> TYPE: DNA
<213> ORGANISM: Artificial Sequence
<220> FEATURE:
<223> OTHER INFORMATION: Synthetic

<400> SEQUENCE: 1083
agctgagctg cgaggtgtgt cgaggtgtcg gaggagaact gtga 44

<210> SEQ ID NO 1084
<211> LENGTH: 41
<212> TYPE: DNA
<213> ORGANISM: Artificial Sequence
<220> FEATURE:
<223> OTHER INFORMATION: Synthetic

<400> SEQUENCE: 1084
agctgagctg cgaggttcga ggtgtcggag gagaactgtg a 41

<210> SEQ ID NO 1085
<211> LENGTH: 39
<212> TYPE: DNA
<213> ORGANISM: Artificial Sequence
<220> FEATURE:

<223> OTHER INFORMATION: Synthetic

<400> SEQUENCE: 1085
agctgagctg cgagtcgagg tgtcggagga gaactgtga 39

<210> SEQ ID NO 1086
<211> LENGTH: 35
<212> TYPE: DNA
<213> ORGANISM: Artificial Sequence
<220> FEATURE:
<223> OTHER INFORMATION: Synthetic

<400> SEQUENCE: 1086
agctgagctg cgaggtgttc ggaggagaac tgtga 35

<210> SEQ ID NO 1087
<211> LENGTH: 36
<212> TYPE: DNA
<213> ORGANISM: Artificial Sequence
<220> FEATURE:
<223> OTHER INFORMATION: Synthetic

<400> SEQUENCE: 1087
agctgagctg ctcgaggtgt cggaggagaa ctgtga 36

<210> SEQ ID NO 1088
<211> LENGTH: 28
<212> TYPE: DNA
<213> ORGANISM: Artificial Sequence
<220> FEATURE:
<223> OTHER INFORMATION: Synthetic

<400> SEQUENCE: 1088
agctgagctg cgaggaggag aactgtga 28

<210> SEQ ID NO 1089
<211> LENGTH: 34
<212> TYPE: DNA
<213> ORGANISM: Artificial Sequence
<220> FEATURE:
<223> OTHER INFORMATION: Synthetic

<400> SEQUENCE: 1089
agctgagctg cgaggtgtcg gaggagaact gtga 34

<210> SEQ ID NO 1090
<211> LENGTH: 42
<212> TYPE: DNA
<213> ORGANISM: Artificial Sequence
<220> FEATURE:
<223> OTHER INFORMATION: Synthetic

<400> SEQUENCE: 1090
agctgagctg cgaggtgtcg aggtgtcgga ggagaactgt ga 42

<210> SEQ ID NO 1091
<211> LENGTH: 40
<212> TYPE: DNA
<213> ORGANISM: Artificial Sequence
<220> FEATURE:
<223> OTHER INFORMATION: Synthetic

<400> SEQUENCE: 1091
agctgagctg cgaggtcgag gtgtcggagg agaactgtga 40

<210> SEQ ID NO 1092
<211> LENGTH: 43
<212> TYPE: DNA
<213> ORGANISM: Artificial Sequence
<220> FEATURE:
<223> OTHER INFORMATION: Synthetic

<400> SEQUENCE: 1092
agctgagctg cgaggtgttc gaggtgtcgg aggagaactg tga 43

<210> SEQ ID NO 1093
<211> LENGTH: 25
<212> TYPE: DNA
<213> ORGANISM: Artificial Sequence
<220> FEATURE:
<223> OTHER INFORMATION: Synthetic

<400> SEQUENCE: 1093
agctgagctg cgaggtgaac tgtga 25

<210> SEQ ID NO 1094
<211> LENGTH: 35
<212> TYPE: DNA
<213> ORGANISM: Artificial Sequence
<220> FEATURE:
<223> OTHER INFORMATION: Synthetic

<400> SEQUENCE: 1094
agctgagctg cgaggtgttc ggaggagaac tgtga 35

<210> SEQ ID NO 1095
<211> LENGTH: 44
<212> TYPE: DNA
<213> ORGANISM: Artificial Sequence
<220> FEATURE:
<223> OTHER INFORMATION: Synthetic

<400> SEQUENCE: 1095
agctgagctg cgaggtgtgt cgaggtgtcg gaggagaact gtga 44

<210> SEQ ID NO 1096
<211> LENGTH: 41
<212> TYPE: DNA
<213> ORGANISM: Artificial Sequence
<220> FEATURE:
<223> OTHER INFORMATION: Synthetic

<400> SEQUENCE: 1096
agctgagctg cgaggttcga ggtgtcggag gagaactgtg a 41

<210> SEQ ID NO 1097
<211> LENGTH: 36
<212> TYPE: DNA
<213> ORGANISM: Artificial Sequence
<220> FEATURE:
<223> OTHER INFORMATION: Synthetic

<400> SEQUENCE: 1097
agctgagctg ctcgaggtgt cggaggagaa ctgtga 36

<210> SEQ ID NO 1098
<211> LENGTH: 39
<212> TYPE: DNA
<213> ORGANISM: Artificial Sequence
<220> FEATURE:
<223> OTHER INFORMATION: Synthetic

<400> SEQUENCE: 1098
agctgagctg cgagtcgagg tgtcggagga gaactgtga 39

<210> SEQ ID NO 1099
<211> LENGTH: 28
<212> TYPE: DNA
<213> ORGANISM: Artificial Sequence
<220> FEATURE:
<223> OTHER INFORMATION: Synthetic

<400> SEQUENCE: 1099
agctgagctg cgaggaggag aactgtga 28

<210> SEQ ID NO 1100
<211> LENGTH: 56
<212> TYPE: DNA
<213> ORGANISM: Artificial Sequence
<220> FEATURE:
<223> OTHER INFORMATION: Synthetic

<400> SEQUENCE: 1100
gtgatcatgg ctacctcagc tgagctgcga ggtgtcgagg tgtcggagga gaactg 56

<210> SEQ ID NO 1101
<211> LENGTH: 56
<212> TYPE: DNA
<213> ORGANISM: Artificial Sequence
<220> FEATURE:
<223> OTHER INFORMATION: Synthetic

<400> SEQUENCE: 1101
gtgatcatgg ctacctcagc tgagctgcga ggtgtcgagg tgtcggagga gaactg 56

<210> SEQ ID NO 1102
<211> LENGTH: 35
<212> TYPE: DNA
<213> ORGANISM: Artificial Sequence
<220> FEATURE:
<223> OTHER INFORMATION: Synthetic

<400> SEQUENCE: 1102
gtgatcatgg ctacctcagc tgagctgcga ggtgt 35

<210> SEQ ID NO 1103
<211> LENGTH: 36
<212> TYPE: DNA
<213> ORGANISM: Artificial Sequence
<220> FEATURE:
<223> OTHER INFORMATION: Synthetic

<400> SEQUENCE: 1103
gtgatcatgg ctaccggagg tgtcggagga gaactg 36

<210> SEQ ID NO 1104
<211> LENGTH: 35
<212> TYPE: DNA
<213> ORGANISM: Artificial Sequence
<220> FEATURE:
<223> OTHER INFORMATION: Synthetic

<400> SEQUENCE: 1104
gtgatcatgg ctacctcagc tgagctgcga ggtgt 35

<210> SEQ ID NO 1105
<211> LENGTH: 35

-continued

```
<212> TYPE: DNA
<213> ORGANISM: Artificial Sequence
<220> FEATURE:
<223> OTHER INFORMATION: Synthetic

<400> SEQUENCE: 1105

gtgatcatgg ctacctcagc tgagctgcga ggtgt                        35


<210> SEQ ID NO 1106
<211> LENGTH: 48
<212> TYPE: DNA
<213> ORGANISM: Artificial Sequence
<220> FEATURE:
<223> OTHER INFORMATION: Synthetic

<400> SEQUENCE: 1106

gtgatcatgg ctacctcagc tgagctgcga ggtgtcggag gagaactg          48


<210> SEQ ID NO 1107
<211> LENGTH: 37
<212> TYPE: DNA
<213> ORGANISM: Artificial Sequence
<220> FEATURE:
<223> OTHER INFORMATION: Synthetic

<400> SEQUENCE: 1107

gtgatcatgg ctacctcgag gtgtcggagg agaactg                      37
```